US009988684B2

(12) United States Patent
Modlin

(10) Patent No.: US 9,988,684 B2
(45) Date of Patent: Jun. 5, 2018

(54) PREDICTING GASTROENTEROPANCREATIC NEUROENDOCRINE NEOPLASMS (GEP-NENS)

(71) Applicant: Yale University, New Haven, CT (US)

(72) Inventor: Irvin M. Modlin, Woodbridge, CT (US)

(73) Assignee: Yale University, New Haven, CT (US)

( * ) Notice: Subject to any disclaimer, the term of this patent is extended or adjusted under 35 U.S.C. 154(b) by 0 days. days.

(21) Appl. No.: 14/017,258

(22) Filed: Sep. 3, 2013

(65) Prior Publication Data

US 2014/0066328 A1 Mar. 6, 2014

Related U.S. Application Data

(63) Continuation of application No. PCT/US2012/027351, filed on Mar. 1, 2012.

(60) Provisional application No. 61/448,137, filed on Mar. 1, 2011.

(51) Int. Cl.
*C12Q 1/68* (2018.01)
*G01N 33/574* (2006.01)

(52) U.S. Cl.
CPC ...... *C12Q 1/6886* (2013.01); *C12Q 2600/112* (2013.01); *C12Q 2600/118* (2013.01); *C12Q 2600/158* (2013.01); *G01N 33/57438* (2013.01)

(58) Field of Classification Search
CPC ............ C12Q 1/6886; C12Q 2600/118; C12Q 2600/112; C12Q 2600/158; G01N 33/57438
See application file for complete search history.

(56) References Cited

U.S. PATENT DOCUMENTS

2005/0084883 A1* 4/2005 Maitra et al. ..................... 435/6

FOREIGN PATENT DOCUMENTS

WO WO-2005/020795 3/2005
WO WO-2005/031001 4/2005

OTHER PUBLICATIONS

Furey et al. (Bioinformatics, 2000, 16:906-914).*
Affymetrix GeneChip Human Genome U133 Array Set HG-U133A, GEO, Mar. 11, 2002, retrieved from the Internet on Jan. 2, 2014, 3 pages.
Affymetrix GeneChip Human Genome U133 Array Set HG-U133A, GEO, Aug. 22, 2012, pp. 1-2.
Affymetrix Platform GPL96, GEO, Aug. 22, 2012, pp. 1-3.
Arnold et al., "Placebo-controlled, double-blind, prospective, randomized study of the effect of octreotide LAR in the control of tumor growth in patients with metastatic neuroendocrine midgut tumors: A report from the PROMID study group," J Clin Oncol (2009) 27(28):4656-4663.

(Continued)

*Primary Examiner* — Jeremy C Flinders
(74) *Attorney, Agent, or Firm* — Saul Ewing Arnstein & Lehr LLP; Kathryn Doyle

(57) ABSTRACT

Described are embodiments related to gastroenteropancreatic neuroendocrine neoplasms (GEP-NEN) biomarkers and agents, systems, and kits for detecting the same, and associated GEP-NEN diagnostic, prognostic, and predictive methods and uses thereof, such as detection, prediction, staging, profiling, classification, and monitoring treatment efficacy and other outcomes.

7 Claims, 69 Drawing Sheets

(56) References Cited

OTHER PUBLICATIONS

Arvidsson et al., "Amyloid precursor-like protein 1 is differentially unregulated in neuroendocrine tumours of the gastrointestinal tract," Endocrine Related Cancer (2008) 15(2):569-581.
Boom et al., "Rapid and simple method for purification of nucleic acids," J Clin Microbiol. (1990) 28:495-503.
Cai et al., "Cytokeratin 7 and 20 and thyroid transcription factor 1 can help distinguish pulmonary from gastrointestinal carcinoid and pancreatic endocrine tumors," Hum Patho (2001) 32(10):1087-1093.
Cappellen et al., "Transcriptional program of mouse osteoclast differentiation governed by the macrophage colony-stimulating factor and the ligand for the receptor activator of NFkappa B.," J Biol Chem (2002) 277(24):21971-21982.
Chomczynski et al., "The single-step method of RNA isolation by acid guanidinium thiocyanate-phenol-chloroform extraction: twenty-something years on," Nat Protoc. (2006) 1(2):581-585.
Cohen et al., "Isolation and characterization of circulating tumor cells in patients with metastatic colorectal cancer," Clin Colorectal Cancer (2006) 6(2):125-132.
Cristofanilli et al., "Circulating tumor cells, disease progression, and survival in metastatic breast cancer," N Engl J Med (2004) 351(8):781-791.
Danila et al., "Circulating tumor cell number and prognosis in progressive castration-resistant prostate cancer," Clin Cancer Res (2007) 13(23):7053-7058.
Dhawan et al., "Application of committee kNN classifiers for gene expression profile classification," Int J Bioinform Res Appl. (2010) 6(4):344-352.
Drozdov, "Genome-wide expression patterns in physiological cardiac hypertrophy," BMC Genomics (2010) 11(557):1-13.
Drozdov et al., "High Efficacy of Gene Expression Profiling and Regularized Discriminant Analysis in the Prediction of Neuroendocrine Tumor Subtypes and Their Metastases," Gastroenterology (2009) 136(5):A-7.
Drozdov et al., "Predicting neuroendocrine tumor (carcinoid) neoplasia using gene expression profiling and supervised machine learning," Cancer (2009) 115(8):1638-1650.
Duerr et al., "Defining molecular classifications and targets in gastroenteropancreatic neuroendocrine tumors through DNA microarray analysis," Endocrine Related Cancer (2008) 15(1):243-256.
Evgeniou et al., "Regularization Networks and Support Vector Machines," Advances in Computational Math (2000) 13(1):1-50.
Freeman et al., "Construction, visualisation, and clustering of transcription networks from microarray expression data," PLoS Comput Biol (2007) 3(10):2032-2042.
Gabriel, "The biplot graphic display of matrices with application to principal component analysis," Biometrika (1971) 58(3):453-467.
Gallant, "Perceptron-based learning algorithms," IEEE Trans Neural Networks (1990) 1(2):179-191.
Glotsos et al., "Automated diagnosis of brain tumours astrocytomas using probabilistic neural network clustering and support vector machines," Int J Neural Syst (2005) 15(1-2):1-11.
Godfrey et al., "Quantitative mRNA expression analysis from formalin-fixed, paraffin-embedded tissues using 5' nuclease quantitative reverse transcription-polymerase chain reaction," J Mol Diagn. (2000) 2(2):84-91.
Havens et al., "The role of CD164 in metastatic cancer," University of Michigan Undergraduate Research Forum (2004) 1:20-25.
Hod, "A simplified ribonuclease protection assay," Biotechniques (1992) 13(6):852-854.
Hofsli, "Genes involved in neuroendocrine tumor biology," Pituitary (2006) 9(3):165-178.
Hofsli et al., "Identification of novel neuroendocrine-specific tumour genes," British J of Cancer (2008) 99(8):1330-1339.
International Preliminary Report on Patentability for PCT/US2012/027351, dated Sep. 3, 2013, 13 pages.
International Search Report and Written Opinion for PCT/US2012/027351, dated Jul. 26, 2012, 19 pages.
Ji et al., "Kernel Uncorrelated and Regularized Discriminant Analysis: A Theoretical and Computational Study," IEEE Transactions on Knowledge and Data Engineering (2008) 20(10):1311-1321.
Kawarazaki et al., "Conversion of a molecular classifier obtained by gene expression profiling into a classifier based on real-time PCR: a prognosis predictor for gliomas," BMC Med Genomics (2010) 3(52):1-8.
Khan et al., "Circulating Tumor Cells and EpCAM Expression in Neuroendrocrine Tumors," Clinical Cancer Research (2011) 17(2):337-345.
Kidd et al., "CTGF, intestinal stellate cells and carcinoid fibrogenesis," World J Gastroenterol (2007) 13(39):5208-5216.
Kidd et al., "GeneChip, geNorm, and gastrointestinal tumors: novel reference genes for real-time PCR," Physiol Genomics (2007) 30(3):363-370.
Kidd et al., "Isolation, functional characterization and transcriptome of *Mastomys* ileal enterochromaffin cells," Am J Physiol Gastrointest Liver Physiol (2006) 291:G778-G791.
Kidd et al., "Microsatellite instability and gene mutations in transforming growth factor-beta type II receptor are absent in small bowel carcinoid tumors," Cancer (2005) 103(2):229-236.
Kidd et al., "Q RT-PCR detection of chromogranin A: a new standard in the identification of neuroendocrine tumor disease," Ann Surg (2006) 243(2):273-280.
Kidd, et al., "The role of genetic markers, NAP1L1, MAGE-D2 and MTA1, in defining small intestinal carcinoid neoplasia," Ann Surg Oncol (2006) 13(2):253-262.
Kohavi, "A study of cross-validation and bootstrap for accuracy estimation and model selection.," Proc. of the Fourteenth Intl Joint Conf. on Artificial Intelligence (1995) 2(12):1137-1143.
Lawlor et al., "Increased Peripheral Blood GATA-3 Expression in Asymptomatic Patients With Active Ulcerative Colitis at Colonoscopy," Gastroenterology (2011) 140(5):S-842.
Leja et al., "Novel markers for enterochromaffin cells and gastrointestinal neuroendocrine carcinomas," Modern Pathology (2009) 22:261-272.
Lilien et al., "Probabilistic disease classification of expression-dependent proteomic data from mass spectrometry of human serum," J Comput Bio (2003) 10(6):925-946.
Liu et al., "Heterogeneity in primary and metastatic prostate cancer as defined by cell surface CD profile," Am J Pathol (2004) 165(5):1543-1556.
Maitra et al., "Global expression analysis of well-differentiated pancreatic endocrine neoplasms using oligonucleotide microarrays," Clinical Cancer Research, the American Association for Cancer Research, US (2003) 9:5988-5995.
Markey et al., "Perceptron error surface analysis: a case study in breast cancer diagnosis," Comput Bioi Med (2002) 32(2):99-109.
Mattfeldt et al., "Classification of prostatic carcinoma with artificial neural networks using comparative genomic hybridization and quantitative stereological data.," Pathol Res Pract (2003) 199(12):773-784.
Mazzaglia et al., "Laparoscopic radiofrequency ablation of neuroendocrine liver metastases: a 10-year experience evaluating predictors of survival," Surgery (2007) 142(1):10-19.
Michiels et al., "Interpretation of microarray data in cancer," Br J Cancer (2007) 96(8):1155-1158.
Mimori et al., "A large-scale study of MTI-MMP as a marker for isolated tumor cells in peripheral blood and bone marrow in gastric cancer cases," Ann Surg Onco (2008) 15(10):2934-2942.
Modlin et al., "Chromogranin A—Biological Function and Clinical Utility in Neuro Endocrine Tumor Disease," Ann Surg Oncol (2010) 17(9):2427-2443.
Modlin et al., "The functional characterization of normal and neoplastic human enterochromaffin cells," J Clin Endocrinol Metab (2006) 91(6):2340-2348.
Modlin et al., "Gastroenteropancreatic neuroendocrine tumours," Lancet Oncol (2008) 9(1):61-72.
Modlin et al., "Genetic differentiation of appendiceal tumor malignancy: a guide for the perplexed," Ann Surg (2006) 244(1):52-60.
Modlin et al., "Principal component analysis, hierarchical clustering, and decision tree assessment of plasma mRNA and hormone

(56) References Cited

OTHER PUBLICATIONS levels as an early detection strategy for small intestinal neuroendocrine (carcinoid) tumors," Ann Surg Oncol (2009) 16(2):487-498.
Modlin et al., "Priorities for improving the management of gastroenteropancreatic neuroendocrine tumors," J Natl Cancer Inst (2008) 100:1282-1289.
Nadler, "Discussion of 'On consistency and sparsity for principal component analysis in high dimensions,'" Journal of the American Statistical Association (2009) 104:694-697.
Noble, "What is a support vector machine?" Nat Biotechnol (2006) 24(12):1565-1567.
Parker et al., "mRNA: detection by in situ and northern hybridization," Methods Mol Biol. (1999) 106:247-283.
Peng et al., "Feature selection based on mutual information: criteria of max-dependency, max-relevance, and min-redundancy," IEEE Transactions on Pattern Analysis and Machine Intelligence (2005) 27(8):1226-1238.
Picon et al., "A subset of metastatic human colon cancers expresses elevated levels of transforming growth factor beta 1," Cancer Epidemiol Biomarkers Prey (1998) 7(6):497-504.
Pima et al., "Regularized discriminant analysis for face recognition," Pattern Recognition (2003) 37(9):1945-1948.
Pimentel et al., "Validating a New Genomic Test for Irritable Bowel Syndrome," Gastroenterology (2011) 140 (Suppl 1):S-798.
Pirooznia et al., "A comparative study of different machine learning methods on microarray gene expression data," BMC Genomics (2008) 9(Suppl 1):S13.
Ross et al., "Detection and viability of tumor cells in peripheral blood stem cell collections from breast cancer patients using immunocytochemical and clonogenic assay techniques," Blood (1993) 82(9):2605-2610.
Sieuwerts et al., "Molecular characterization of circulating tumor cells in large quantities of contaminating leukocytes by a multiplex real-time PCR," Breast Cancer Res Treat (2009) 118(3):455-468.
Specht et al., "Quantitative gene expression analysis in microdissected archival formalin-fixed and paraffin-embedded tumor tissue," Am J Pathol. (2001) 158(2):419-429.
Tannapfel et al., "BRAF gene mutations are rare events in gastroenteropancreatic neuroendocrine tumors," Am J Clin Pathol (2005) 123(2):256-260.
Urgard et al., "Metagenes associated with survival in non-small cell lung cancer," Cancer Inform (2011) 10:175-183.
Van Eeden et al., "Classification of low-grade neuroendocrine tumors of midgut and unknown origin," Hum Patho (2002) 33(11):1126-1132.
Vandebriel et al., "Altered cytokine (receptor) mRNA expression as a tool in immunotoxicology," Toxicology (1998) 130(1):43-67.
Vandesompele et al., "Accurate normalization of real-time quantitative RT-PCR data by geometric averaging of multiple internal control genes," Genome Biol (2002) 3(7):Research0034.1-0034.11.
Weis et al., "Detection of rare mRNAs via quantitative RT-PCR," Trends Genet. (1992) 8(8):263-264.
Yu et al., "TGF-beta receptor-activated p38 MAP kinase mediates Smad-independent TGF-beta responses," Embo J (2002) 21(14):3749-3759.
Zampetaki et al., "Plasma microRNA profiling reveals loss of endothelial miR-126 and other microRNAs in type 2 diabetes," Circ Res. (2010) 107(6):810-817.
Zhang et al., "Recursive partitioning for tumor classification with gene expression microarray data," Proc Natl Acad Sci USA (2001) 98(12):6730-6735.

* cited by examiner

PREDICTING GASTROENTEROPANCREATIC NEUROENDOCRINE NEOPLASMS (GEP-NENS)

CROSS-REFERENCE TO RELATED APPLICATIONS

This application is a continuation of international application PCT/US2012/27351 having an international filing date of Mar. 1, 2012, which claims benefit of U.S. provisional application Ser. No. 61/448,137, filed Mar. 1, 2011. The contents of the above patent applications are hereby incorporated by reference in their entirety for all purposes.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 6691012000101SeqList.txt, date recorded: Sep. 3, 2013, size: 447,739 bytes).

TECHNICAL FIELD

The invention described herein relates to gastroenteropancreatic neuroendocrine neoplasm (GEP-NEN) biomarkers and agents, systems, and kits for detecting the same, and associated GEP-NEN diagnostic and prognostic methods, such as detection, prediction, staging, profiling, classification, and monitoring treatment efficacy and other outcomes.

BACKGROUND ART

Gastroenteropancreatic neuroendocrine neoplasm (GEP-NEN, also called Gastroenteropancreatic (GEP) neuroendocrine tumor and neuoroendocrine tumor (NET)) is the second most prevalent malignant tumor of the gastrointestinal (GI) tract in the U.S., more prevalent than gastric, esophageal, pancreatic, and hepatobiliary neoplasms, with an incidence of about 2.5-5 cases per 100,000. Incidence and prevalence have increased between 100 and 600 percent in the U.S. over the last thirty years, with no increase in survival.

Heterogeneity and complexity of GEP-NENs has made diagnosis, treatment, and classification difficult. These neoplasms lack several mutations commonly associated with other cancers; microsatellite instability is largely absent. See Tannapfel A, Vomschloss S, Karhoff D, et al., "BRAF gene mutations are rare events in gastroenteropancreatic neuroendocrine tumors," *Am J Clin Pathol* 2005; 123(2):256-60; Kidd M, Eick G, Shapiro M D, et al. Microsatellite instability and gene mutations in transforming growth factor-beta type II receptor are absent in small bowel carcinoid tumors," *Cancer* 2005; 103(2):229-36. Individual histopathologic subtypes associate with distinct clinical behavior, yet there is no definitive, generally accepted pathologic classification or prediction scheme, hindering treatment development.

Existing diagnostic and prognostic approaches include imaging (e.g., CT and MRI), histology, and detection of some gene products. Available methods are limited, for example, by low sensitivity and/or specificity, and inability to detect early-stage disease. GEP-NENs often go undiagnosed until they are metastatic and often untreatable.

There is a need for specific and sensitive methods and agents for detection of GEP-NENs, including early-stage GEP-NENs, for example, for use in diagnosis, prognosis, prediction, staging, classification, treatment, monitoring, and risk assessment, and for investigating and understanding molecular factors of pathogenesis, malignancy, and aggressiveness of this disease. For example, such methods and agents are needed that can be performed simply, rapidly, and at relatively low cost. Provided herein are methods, compositions, and combinations that meet these needs.

SUMMARY

In one aspect, the present invention relates to gastroenteropancreatic neuroendocrine neoplasm (GEP-NEN) biomarkers, the detection of which may be used in diagnostic, prognostic and predictive methods. Among the provided objects are GEP-NEN biomarkers, panels of the biomarkers, agents for binding and detecting the biomarkers, kits and systems containing such agents, and methods and compositions for detecting the biomarkers, for example, in biological samples, as well as prognostic, predictive, diagnostic, and therapeutic uses thereof.

Provided are agents, sets of agents, and systems containing the agents for GEP-NEN prognosis, detection and diagnosis. Typically, the systems include a plurality of agents (e.g., set of agents), where the plurality specifically binds to and/or detects a plurality of GEP-NEN biomarkers in a panel of GEP-NEN biomarkers. Typically, the agents are isolated polypeptides or polynucleotides which specifically bind to one or more GEP-NEN biomarkers. For example, provided are sets of isolated polynucleotides and polypeptides that bind to a panel of GEP-NEN biomarkers, and methods and uses of the same.

Also provided are prognostic, diagnostic and predictive methods and uses of the agents, compositions, systems, and kits for GEP-NEN and associated conditions, syndromes and symptoms. For example, provided are methods and uses for detection, diagnosis, classification, prediction, therapeutic monitoring, prognosis, or other evaluation of GEP-NEN or an outcome, stage or level of aggressiveness or risk thereof, or associated condition. In some embodiments, the methods are performed by determining the presence, absence, expression levels, or expression profile of a GEP-NEN biomarker, more typically a plurality of GEP-NEN biomarkers, such as a panel of biomarkers, and/or comparing such information with normal or reference expression levels or profiles or standards. Thus, in some embodiments, the methods are carried out by obtaining a biological test sample and detecting the presence, absence, expression levels, or expression profile of a GEP-NEN biomarker as described herein, more typically of a panel of at least two of the provided GEP-NEN biomarkers. For example, the methods can be performed with any of the systems of agents, e.g., polynucleotides or polypeptides, provided herein. For example, the methods generally are carried out using one or more of the provided systems.

Provided are methods, agents and compositions for detection of and distinguishing between a number of different GEP-NEN types, stages, and sites (for example, pancreatic vs. small intestine GEP-NEN). In one aspect, differentiating between sites can provide prognostic information or help identify the GEP-NEN. Thus, in some embodiments, the methods distinguish between small intestine NENs (SI-NENs) and pancreatic NENs (PI-NENs). Exemplary GEP-NEN types and stages include metastatic and primary GEP-NEN, GEP-NENs that are or are not responsive to various treatment approaches, and various GEP-NENs sub-types, including well-differentiated NET (WDNET), primary well differentiated neuroendocrine carcinoma (WDNEC), primary poorly differentiated neuroendocrine tumor (PDNET), primary poorly differentiated NEC (PDNEC), metastatic WDNET (WDNET MET), metastatic WDNEC (WDNEC MET) metastatic PDNEC (PDNEC MET) and metastatic PDNET (PDNET MET).

In one aspect, the provided methods and compositions may be used to specifically and sensitively detect GEP-NENs, such as early-stage, primary, or asymptomatic GEP-NENs; in some aspects, the methods and compositions may be used to predict disease progression, treatment response, and metastasis. Methods and compositions provided herein are useful for diagnosis, prognosis, prediction (i.e., prediction of metastases in early-stage and primary GEP-NENs), staging, classification, treatment, monitoring, assessing risk, and investigating molecular factors associated with GEP-NEN disease.

Provided are such methods capable of being carried out quickly, simply, and at relatively low cost, as compared to other diagnostic and prognostic methods.

Provided are methods and compositions that are useful for defining gene expression-based classification of GEP-NENs, and thus are useful for allowing the prediction of malignancy and metastasis, such as in early stage disease or using histologically negative samples, providing accurate staging, facilitating rational therapy, and in developing large validated clinical datasets for GEP-NEN-specific therapeutics.

The GEP-NEN biomarkers include biomarkers, the expression of which is different in or is associated with the presence or absence of GEP-NEN, or is different in or is associated with a particular classification, stage, aggressiveness, severity, degree, metastasis, symptom, risk, treatment responsiveness or efficacy, or associated syndrome. The panel of GEP-NEN biomarkers typically includes at least 2 GEP-NEN biomarkers, typically at least 3 biomarkers. In some embodiments, the panel of biomarkers includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, or includes at or about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 GEP-NEN biomarkers, or more.

For example, in some aspects, the panel of biomarkers includes at least 3, at least 11, at least 21, or at least 29 biomarkers, at least 51 biomarkers, or at least 75 more biomarkers. In a particular example, the panel contains at least 51 biomarkers or about 51 biomarkers or 51 biomarkers. Because the systems contain a plurality of agents (generally polypeptides or polynucleotides) that specifically bind to or hybridize to the biomarkers in the panel, the number of biomarkers generally relates to the number of agents in a particular system. For example, among the provided systems is a system that contains 51 agents, which specifically hybridize to or bind to a panel of 51 GEP-NEN biomarkers, respectively.

In some aspects, the panel of biomarkers includes at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following groups of gene products, including polynucleotides (e.g., transcripts) and polypeptides:

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, ZZZ3, APLP2, CD59, ARAF1, BRAF1, KRAS, and RAF1 gene products;

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3 gene products; and APLP2, ARAF1, BRAF, CD59, CTGF, FZD7, Ki67, KRAS, NAP1L1, PNMA2, RAF1, TPH1, VMAT1, and VMAT2 gene products.

In some examples, the panel of biomarkers includes AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3 gene products.

In some examples, the panel of biomarkers includes APLP2, ARAF1, BRAF, CD59, CTGF, FZD7, Ki67, KRAS, NAP1L1, PNMA2, RAF1, TPH1, VMAT1, and VMAT2 gene products.

In some examples, the panel of biomarkers includes AKAP8L, APLP2, ARAF1, ATP6V1H, BNIP3L, BRAF, C21orf7, CD59, COMMD9, CTGF, ENPP4, FAM131A, FLJ10357, FZD7, GLT8D1, HDAC9, HSF2, Ki67, KRAS, LEO1, MORF4L2, NAP1L1, NOL3, NUDT3, OAZ2, PANK2, PHF21A, PKD1, PLD3, PNMA2, PQBP1, RAF1, RNF41, RSF1, RTN2, SMARCD3, SPATA7, SST1, SST3, SST4, SST5, TECPR2, TPH1, TRMT112, VMAT1, VMAT2, VPS13C, WDFY3, ZFHX3, ZXDC, and ZZZ3 gene products.

In some examples, the panel of biomarkers includes an APLP2 gene product, a CD59 gene product, an ARAF1 gene product, a BRAF1 gene product, a KRAS gene product, or a RAF1 gene product.

In some examples, the panel of GEP-NEN biomarkers includes APLP2, ARAF1, BRAF, CD59, CTGF, FZD7, Ki67, KRAS, NAP1L1, PNMA2, RAF1, TPH1, and VMAT2 gene products; or the panel of GEP-NEN biomarkers includes APLP2, ARAF1, BRAF1, CD59, KRAS, RAF1, CXCL14, GRIA2, HOXC6, NKX2-3, OR51E1, PNMA2, PTPRN2, SCG5, SPOCK1, X2BTB48, CgA, CTGF, FZD7, Ki-67, Kiss1, MAGE-D2, MTA1, NAP1L1, NRP2, Tph1, VMAT1, VMAT2 and Survivin gene products.

In some examples, it further includes further includes a gene product selected from the group consisting of MAGE-D2, MTA1, Survivin, Kiss1, HOXC6, NRP2, X2BTB48, CXCL14, GRIA2, NKX2-3, OR51E1, CTGF, PTPRN2, SPOCK1, and SCG5 gene products.

In other examples, the panel of GEP-NEN biomarkers includes at least 2, 3, 4, 5, 6, 7, 8, 9, 10, 11, 12, 13, 14, 15, 16, 17, 18, 19, 20, 21, 22, 23, 24, 25, 26, 27, 28, 29 of, or includes each of, the biomarkers in one, more, or all of the following groups of gene products, including polynucleotides (e.g., transcripts) and polypeptides:

(a) APLP2, ARAF1, BRAF1, CD59, KRAS, RAF1, CXCL14, GRIA2, HOXC6, NKX2-3, OR51E1, PNMA2, PTPRN2, SCG5, SPOCK1, X2BTB48, CgA, CTGF, FZD7, Ki-67, Kiss1, MAGE-D2, MTA1, NAP1L1, NRP2, Tph1, VMAT1, VMAT2, and Survivin gene products; (b) MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph gene products; (c) ARAF1, BRAF, CTGF, FZD7, Ki67, KRAS, NAP1L1, PNMA2, RAF1, TPH1, and VMAT2 gene products; (d) CXCL14, GRIA2, HOXC6, Ki-67, Kiss1, MAGE-D2, MTA1, NAP1L1, NKX2-3, OR51E1, PTPRN2, SCG5, SPOCK1, and X2BTB48 gene products; (e) CXCL14, GRIA2, HOXC6, NKX2-3, OR51E1, PNMA2, PTPRN2, SCG5, SPOCK1, and X2BTB48 gene products; (f) APLP2, ARAF1, BRAF, CD59, CTGF, FZD7, Ki67, KRAS, NAP1L1, PNMA2, RAF1, TPH1, and VMAT2 gene products; (g) APLP2, ARAF1, BRAF1, CD59, KRAS, and RAF1 gene products; and/or (h) ARAF1, BRAF1, CD59, KRAS, RAF1, CXCL14, GRIA2, HOXC6, NKX2-3, OR51E1, PNMA2, PTPRN2, SCG5, SPOCK1, X2BTB48, CgA, CTGF, FZD7, Ki-67, Kiss1, MAGE-D2, MTA1, NAP1L1, NRP2, Tph1, VMAT1, VMAT2 and Survivin gene products.

In some examples, the biomarkers include at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51 of the following gene products (the term gene product including, for example, polynucleotides (e.g., transcripts) and polypeptides): AKAP8L, APLP2, ARAF1, ATP6V1H, BNIP3L, BRAF, C21orf7, CD59, COMMD9, CTGF, ENPP4, FAM131A, FLJ10357, FZD7, GLT8D1, HDAC9, HSF2, Ki67, KRAS, LEO1, MORF4L2, NAP1L1, NOL3, NUDT3, OAZ2, PANK2, PHF21A, PKD1, PLD3, PNMA2, PQBP1, RAF1, RNF41, RSF1, RTN2, SMARCD3, SPATA7, SST1, SST3, SST4, SST5, TECPR2, TPH1, TRMT112, VMAT1, VMAT2, VPS13C, WDFY3, ZFHX3, ZXDC, and ZZZ3 gene products.

In some aspects, the biomarkers include AKAP8L, APLP2, ARAF1, ATP6V1H, BNIP3L, BRAF, C21orf7, CD59, COMMD9, CTGF, ENPP4, FAM131A, FLJ10357, FZD7, GLT8D1, HDAC9, HSF2, Ki67, KRAS, LEO1, MORF4L2, NAP1L1, NOL3, NUDT3, OAZ2, PANK2, PHF21A, PKD1, PLD3, PNMA2, PQBP1, RAF1, RNF41, RSF1, RTN2, SMARCD3, SPATA7, SST1, SST3, SST4, SST5, TECPR2, TPH1, TRMT112, VMAT1, VMAT2, VPS13C, WDFY3, ZFHX3, ZXDC, and ZZZ3 gene products.

In some examples, the biomarkers include at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, or 38 of the following gene products (the term gene product including, for example, polynucleotides (e.g., transcripts) and polypeptides): AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3 gene products.

In some aspects, the biomarkers include AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3.

In some examples, the biomarkers include at least two GEP-NEN biomarkers selected from among APLP2, ARAF1, BRAF1, CD59, KRAS, RAF1, CXCL14, GRIA2, HOXC6, NKX2-3, OR51E1, PNMA2, PTPRN2, SCG5, SPOCK1, X2BTB48, CgA, CTGF, FZD, Ki-67, Kiss1, MAGE-D2, MTA1, NAP1L1, NRP2, Tph1, VMAT1, VMAT2, and Survivin gene products.

In one embodiment, the plurality of GEP-NEN biomarkers includes an APLP2 gene product or a CD59 gene product. In one embodiment, the GEP-NEN biomarkers include an APLP2 gene product. In one embodiment, they include a CD59 gene product.

In one embodiment, the GEP-NEN biomarkers include an APLP2, CD59, ARAF1, BRAF1, KRAS or RAF1 gene product.

In some embodiments, the panel of GEP-NEN biomarkers includes an APLP2, ARAF1, BRAF, CD59, KRAS, or RAF1 gene product or a GTGF, FZD7, Ki67, NAP1L1, PNMA2, TPH1, or VMAT2 gene product. In some embodiments, the panel of GEP-NEN biomarkers includes a PNMA2 gene product. In some embodiments, the panel of GEP-NEN biomarkers includes a VMAT2 gene product. In some embodiments, the panel of GEP-NEN biomarkers includes a CgA, CXCL14, GRIA2, HOXC6, Kiss1, MAGE-D2, MTA1, NKX2-3, NRP2, OR51E1, PTPRN2, SCG5, SPOCK1, survivin, VMAT1, or X2BTB48 gene product. In other embodiments, the panel includes a PNMA2 biomarker. In some embodiments, the panel includes a VMAT2 biomarker.

In some embodiments, the panel includes APLP2, ARAF1, BRAF, CD59, CTGF, FZD7, Ki67, KRAS, NAP1L1, PNMA2, RAF1, TPH1, and VMAT2 gene products; or includes MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, CgA, and Tph gene products. In one aspect, the biomarkers includes at least one of or includes each of the following biomarkers: APLP2, ARAF1, BRAF1, CD59, KRAS, RAF1, CXCL14, GRIA2, HOXC6, NKX2-3, OR51E1, PNMA2, PTPRN2, SCG5, SPOCK1, X2BTB48, CTGF, FZD7, Ki-67, Kiss1, MAGE-D2, MTA1, NAP1L1, NRP2, Tph1, VMAT1, VMAT2, Survivin and X2BTB48 gene products. In one such embodiment, the biomarkers further include a CgA gene product.

In one embodiment, the GEP-NEN biomarkers include one or more gene products having a nucleotide sequence with at least at or about or at or about 90, 91, 92, 93, 94, 95, 96, 97, 98, 99% identity to or 100% identity to (i.e., having a nucleotide sequence of) SEQ ID NO: 1, or to SEQ ID NO: 1, from nucleotide residues 158-2449; SEQ ID NO: 2, or to SEQ ID NO: 2 from nucleotide residues 195-2015 SEQ ID NO: 3 or to SEQ ID NO: 3, from nucleotide residues 62-2362; SEQ ID NO: 4 or to SEQ ID NO: 4, from nucleotide residues 278-664; SEQ ID NO: 5, or to SEQ ID NO: 5 from nucleotide residues 1 to 1374; SEQ ID NO: 6, or to SEQ ID NO: 6 from nucleotide residues 207-1256; SEQ ID NO: 7, or to SEQ ID NO: 7 from nucleotide residues 466-801; SEQ ID NO: 8, or to SEQ ID NO: 8 from nucleotide residues 62-1786; SEQ ID NO: 9, or to SEQ ID NO: 9 from nucleotide residues 460-3111; SEQ ID NO: 10, or to SEQ ID NO: 10 from nucleotide residues 113-820; SEQ ID NO: 11, or to SEQ ID NO: 11 from nucleotide residues 196-9966; SEQ ID NO: 12, or to SEQ ID NO: 12 from nucleotide residues 155-571; SEQ ID NO: 13, or to SEQ ID NO: 13 from nucleotide residues 182-751; SEQ ID NO: 14, or to SEQ ID NO: 14 from nucleotide residues 100-1920; SEQ ID NO: 15, or to SEQ ID NO: 15 from nucleotide residues 188-2335; SEQ ID NO: 16, or to SEQ ID NO: 16 from nucleotide residues 413-1588; SEQ ID NO: 17, or to SEQ ID NO: 17 from nucleotide residues 200-1294; SEQ ID NO: 18, or to SEQ ID NO: 18 from nucleotide residues 792-3587; SEQ ID NO: 19, or to SEQ ID NO: 19 from nucleotide residues 145-1101; SEQ ID NO: 20, or to SEQ ID NO: 20 from nucleotide residues 771-1865; SEQ ID NO: 21, or to SEQ ID NO: 21 from nucleotide residues 122-3169; SEQ ID NO: 22, or to SEQ ID NO: 22 from nucleotide residues 416-2362; or to SEQ ID NO: 22 SEQ ID NO: 23, or to SEQ ID NO: 23 from nucleotide residues 118-756; SEQ ID NO: 24, or to SEQ ID NO: 24 from nucleotide residues 152-1471; SEQ ID NO: 25, or to SEQ ID NO: 25 nucleotide residues 2811-2921, 3174-3283, 5158-5275, 11955-12044, or to SEQ ID NO: 34; SEQ ID NO: 26, or to SEQ ID NO: 26 from nucleotide residues 27-1361; SEQ ID NO: 27, or to SEQ ID NO: 27 from nucleotide residues 472-2049; SEQ ID NO: 28, or to SEQ ID NO: 28 from nucleotide residues 32-1576; SEQ ID NO: 29, or to SEQ ID NO: 29 from nucleotide residues 467-1801; SEQ ID NO: 105, or to SEQ ID NO: 105 from nucleotide residues 122-1456; SEQ ID NO: 201, or to SEQ ID NO: 201 from nucleotide residues 100-2040; SEQ ID NO: 204, or to SEQ ID NO: 240, from nucleotide residues 293-1744; SEQ ID NO: 205, or to SEQ ID NO: 205, from nucleotide residues 125-784; SEQ ID NO: 206, or to SEQ ID NO: 206 from nucleotide residues 278-1006; SEQ ID NO: 207, or to SEQ ID NO: 207 from nucleotide residues 38-508; SEQ ID NO: 208, or to SEQ ID NO: 208 from nucleotide residues 260-1621; SEQ ID NO: 209, or to SEQ ID NO: 209 from nucleotide residues 281-1126; SEQ ID NO: 210, or to SEQ ID NO: 210 from nucleotide residues 30-4589; SEQ ID NO: 211, or to SEQ ID NO: 211 from nucleotide residues 852-1967; SEQ ID NO: 212, or to SEQ ID NO: 212 from nucleotide residues 362-2128; SEQ ID NO: 213, or to SEQ ID NO: 213 from nucleotide residues 188-1798; SEQ ID NO: 215, or to SEQ ID NO: 215 from nucleotide residues 17-2017; SEQ ID NO: 217, or to SEQ ID NO: 217 from nucleotide residues 505-1371; SEQ ID NO: 218, or to SEQ ID NO: 218 from nucleotide residues 194-853; SEQ ID NO: 219, or to SEQ ID NO: 219 from nucleotide residues 319-837; SEQ ID NO: 220, or to SEQ ID NO: 220 from nucleotide residues 216-311 and 313-786; SEQ ID NO: 221, or to SEQ ID NO: 221 from nucleotide residues 312-1151; SEQ ID NO: 222, or to SEQ ID NO: 222 from nucleotide residues 625-2667; SEQ ID NO: 223, or to SEQ ID NO: 223 from nucleotide residues 210-13117, or to the sequence referenced at GenBank gi Number 205360961 or to that sequence from nucleotide residues 210-13118; SEQ ID NO: 224, or to SEQ ID NO: 224 from nucleotide residues 399-1871; SEQ ID NO: 225, or to SEQ ID NO: 225 from nucleotide residues 122-919; SEQ ID NO: 227, or to SEQ ID NO: 227 from nucleotide residues 320-1273; SEQ ID NO: 228, or to SEQ ID NO: 228 from nucleotide residues 121-4446; SEQ ID NO: 229, or to SEQ ID NO: 229 from nucleotide residues 229-1866; SEQ ID NO: 232, or to SEQ ID NO: 232 from nucleotide residues 102-1553; SEQ ID NO: 233, or to SEQ ID NO: 233 from nucleotide residues 176-1879; SEQ ID NO: 234, or to SEQ ID NO: 234 from nucleotide residues 618-1793; SEQ ID NO: 235, or to SEQ ID NO: 235 from nucleotide residues 526-1782; SEQ ID NO: 236, or to SEQ ID NO: 236 from nucleotide residues 65-1231; SEQ ID NO: 237, or to SEQ ID NO: 237 from nucleotide residues 89-1183; SEQ ID NO: 238, or to SEQ ID NO: 238 from nucleotide residues 227-4030; SEQ ID NO: 239, or to SEQ ID NO: 239 from nucleotide residues 104-1969; SEQ ID NO: 240, or to SEQ ID NO: 240 from nucleotide residues 94-612, SEQ ID NO: 243, or to SEQ ID NO: 243 from nucleotide residues 409-10988, SEQ ID NO: 244, or to SEQ ID NO: 244 from nucleotide residues 130-8499, SEQ ID NO: 245, or to SEQ ID NO: 245 from nucleotide residues 55-2187, and/or SEQ ID NO: 246, or to SEQ ID NO: 246 from nucleotide residues 477-3188.

Among the provided methods, agents, and systems are those that are able to classify or detect a GEP-NEN in a human blood sample. In some embodiments, the provided systems and methods can identify or classify a GEP-NEN in a human blood sample; in some embodiments, it can differentiate between a subject with GEP-NEN and a subject with another type of gastrointestinal (GI) cancer (or other cancer) or can determine the site of a GEP-NEN, e.g., by differentiating between a subject with small intestinal NEN and a subject with a pancreatic NEN. In some examples, the systems can provide such information with a specificity, sensitivity, and/or accuracy of at least 75%, 80%, 85%, 90%, 91%, 92%, 93%, 94%, 95%, 96%, 97%, 98%, 99% or 100%, e.g., at least 80%.

In some embodiments, the system can predict treatment responsiveness to, or determine whether a patient has become clinically stable following, or is responsive or non-responsive to, a GEP-NEN treatment, such as a surgical intervention or drug therapy (for example, somatostatin analog therapy). In some cases, the methods and systems do so with a specificity, sensitivity, and/or accuracy of at least 75%, 80%, 85%, 90%, 91%, 92%, 93%, 94%, 95%, 96%, 97%, 98%, 99% or 100%, e.g., with at least 90% accuracy. In some cases, it can differentiate between treated and untreated GEP-NEN with a specificity, sensitivity, and/or accuracy of at least 75%, 80%, 85%, 90%, 91%, 92%, 93%, 94%, 95%, 96%, 97%, 98%, 99% or 100%, e.g., with a sensitivity and specificity of at least 85%.

In some cases, it can determine diagnostic or prognostic information regarding a subject previously diagnosed with GEP-NEN, for example, whether the subject has stable disease, progressive disease, or is in complete remission (for example, would be clinically categorized as having stable disease, progressive disease, or being in complete remission).

In some embodiments, the agents for detecting the biomarkers (e.g., the sets of polynucleotide or polypeptide agents), and uses thereof, are capable of distinguishing between the presence and absence of GEP-NEN in a biological sample, between GEP-NEN and other intestinal and mucosal samples, such as enterochromaffin (EC) and small intestinal (SI) mucosal samples and GEP-NEN samples, between metastatic or aggressive and primary GEP-NEN samples, and/or between specific classes or subtypes of GEP-NENs.

In some embodiments, the methods distinguish between GEP-NEN and other cancers, such as adenocarcinomas, including gastrointestinal adenocarcinoma or one of the breast, prostate, or pancreas, or a gastric or hepatic cancer, such as esophageal, pancreatic, gallbladder, colon, or rectal cancer. In other embodiments, the methods and systems differentiate between GEP-NENs of different sites, such as between GEP-NENs of the small intestine and those of the pancreas.

In one embodiment, the set of agents distinguishes between enterochromaffin (EC) and small intestinal (SI) mucosa. In one aspect, the panel of GEP-NEN biomarkers comprises CTGF, CXCL14, FZD7, Kiss1, FZD, Kiss1, NKX2-3, PNMA2, PTPRN2, SCG5, SPOCK1, and X2BTB48 gene products. In another embodiment, the system or set of agents distinguishes between Adenocarcinoma and GEP-NEN, such as an adenocarcinoma and a GEP-NEN sample. In one aspect, the panel of GEP-NEN biomarkers comprises at least sixteen GEP-NEN biomarkers, including a CgA gene product. In another embodiment, the system or set of agents distinguishes between primary and metastatic GEP-NEN disease. In one aspect of this embodiment, the panel of GEP-NEN biomarkers includes at least eighteen GEP-NEN biomarkers.

In some embodiments, the system or set of agents or use of the same distinguishes between one or more various sub-types of GEP-NEN, and/or contains agents that bind to or detect a set of biomarkers the expression profile of which or the summed expression (e.g. vectorally summed expression) of which differs significantly between the various sub-types. In one aspect of this embodiment, the system distinguishes between primary PDNEC and primary WDNET; in one example, the panel of biomarkers includes CXCL14 and MAGE-D2 gene products. In another embodiment, the system distinguishes between primary PDNEC and primary WDNEC; in one example, the panel of GEP-NEN biomarkers includes three biomarkers, including a PTPRN2 gene product. In another embodiment, the system distinguishes between primary PDNEC and primary PDNET; in one example, the panel of biomarkers includes MTA1 and PNMA2 gene products. In another embodiment, the system distinguishes between primary PDNET and primary WDNET; in one example, the panel of NE biomarkers includes at least four biomarkers. In another embodiment, the system distinguishes between primary WDNEC and primary WDNET; in one example, the set contains at least 21 biomarkers.

In another embodiment, the system distinguishes between metastatic sub-types of GEP-NEN, such as between metastatic WDNEC and metastatic WDNET, for example, where the panel contains at least three biomarkers, including a CXCL14 gene product; between metastatic PDNEC and metastatic WDNEC, for example, where the set of biomarkers includes at least four biomarkers, including a NAP1L1 gene product; between metastatic PDNEC and metastatic WDNET, for example, where the panel of GEP-NEN biomarkers includes at least six biomarkers, for example, including a NRP2 gene product.

In one aspect, the system is able to classify or detect a GEP-NEN in a human blood sample or human saliva sample. In one aspect, the human sample is whole blood or nucleic acid or protein prepared from whole blood, without first sorting or enriching for any particular population of cells. In one aspect, the system includes agents that bind to biomarkers in a panel of at least 29 GEP-NEN biomarkers.

In some aspects, the methods and systems provide such diagnostic, differentiation, detection, predictive, or prognostic information or determination as described above with a greater sensitivity, specificity, or accuracy compared with another diagnostic method, such as available detection or diagnosis method, such as the detection of circulating CgA levels.

In some embodiments, in addition to the agents that bind the GEP-NEN biomarkers, the provided systems contain one or more agents that bind to gene products for use in normalization or as controls, for example, housekeeping gene products, including any one or more of: ACTB, TOX4, TPT1 and TXNIP gene products;

housekeeping gene products, including any one or more of: 18S, GAPDH, ALG9, SLC25A3, VAPA, TXNIP, ADD3, DAZAP2, ACTG1, ACTB, ACTG4B, ARF1, HUWE1, MORF4L1 RHOA, SERP1, SKP1, TPT1, TOX4, TFCP2, and ZNF410, gene products;

housekeeping genes including any one or more of 18S, GAPDH, ALG9, SLC25A3, VAPA, TXNIP, ADD3, DAZAP2, ACTG1, ACTB, ACTG4B, ARF1, HUWE1, MORF4L1 RHOA, SERP1, SKP1, TPT1, and TOX4 gene products; or housekeeping genes including any one or more of: ALG9, TFCP2, ZNF410, 18S, and GAPDH gene products.

In some embodiments, the system distinguishes between enterochromaffin (EC) and small intestinal (SI) mucosa and the panel of GEP-NEN biomarkers further includes CTGF, CXCL14, FZD7, Kiss1, FZD, Kiss1, NKX2-3, PNMA2, PTPRN2, SCG5, SPOCK1, and X2BTB48 gene products. In another embodiment, the panel of GEP-NEN biomarkers includes MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CgA, CTGF, PTPRN2, SCG5, and Tph1 gene products. In another embodiment, the system distinguishes between Adenocarcinoma and GEP-NEN and includes a set of polynucleotides or polypeptides that specifically hybridize to a panel of sixteen or more GEP-NEN biomarkers, including a CgA gene product.

In some embodiments, the methods and systems determine the presence, absence, expression levels, or expression profile indicates the presence, absence, classification, prognosis, risk, responsiveness to treatment, aggressiveness, severity, or metastasis of the GEP-NEN. For example, in one aspect, the presence, absence, expression levels, or expression profile detected in the test sample indicates the efficacy of a GEP-NEN treatment. In one aspect, the detected presence, absence, expression levels, or expression profile distinguishes between primary PDNEC and primary WDNET and the panel of biomarkers includes CXCL14 and MAGE-D2 gene products; in other aspects, it distinguishes between primary PDNEC and primary WDNEC and the panel of biomarkers includes three biomarkers, including a PTPRN2 gene product; in another aspect, it distinguishes between primary PDNEC and primary PDNET, and the panel of biomarkers includes MTA1 and PNMA2 gene products; in another aspect, it distinguishes between primary PDNET and primary WDNET or in primary PDNET and primary WDNEC, and the panel of biomarkers includes at least four biomarkers; in another aspect, it distinguishes between primary WDNEC and primary WDNET, the panel of biomarkers includes twenty-one biomarkers; in another aspect, it distinguishes between metastatic WDNEC and metastatic WDNET and the panel of biomarkers includes at least three biomarkers, including a CXCL14 gene product; in another aspect, it distinguishes between metastatic PDNEC and metastatic WDNEC and the panel comprises at least four biomarkers, including a NAP1L1 gene product; in another aspect, it distinguishes between metastatic PDNEC and metastatic WDNET and the panel comprises at least six biomarkers, including a NRP2 gene product.

The biological test sample used with the methods can be any biological sample, such as tissue, biological fluid, or other sample, including blood samples, such as plasma, serum, whole blood, buffy coat, or other blood sample, tissue, saliva, serum, urine, or semen sample. In some aspects, the sample is obtained from blood. Often, the test sample is taken from a GEP-NEN patient.

In some embodiments, the methods further include comparing the expression levels or expression profile or presence or absence of the biomarkers detected in the test sample to a normal or reference level of expression or a normal or reference expression profile, or a standard value of expression level, amount, or expression profile, or the presence (or more typically the absence) of detection in a reference or normal sample.

In some such embodiments, the methods include a step of obtaining a normal or reference sample and detecting the presence, absence, expression levels, or expression profile of the panel of GEP-NEN biomarkers in the normal sample, typically carried out prior to the comparison step. In one aspect, this further step determines a normal or reference level of expression or a normal or reference expression profile, which can be compared to the expression level or profile detected in the test biological sample.

In some cases, statistical analysis is performed to determine whether there is a difference, such as a significant difference, between the expression levels detected in the test biological sample and the normal or reference sample, or other standard or reference expression level. For example, a difference may be considered significant where there is a p value of less than 0.05 or where there is a ±2 standard deviation. Other methods for determining significance are known in the art.

The normal or reference sample may be from a healthy patient or a patient who has GEP-NEN. Where the test sample is from a patient with GEP-NEN, the normal or reference sample or level may be from the same or a different patient. For example, the normal or reference sample may be from the GEP-NEN patient from a tissue, fluid or cell not expected to contain GEP-NEN or GEP-NEN cells. On another aspect, the normal or control sample is from the GEP-NEN patient before or after therapeutic intervention, such as after surgery or chemical intervention. In another aspect, the reference or normal sample is from a tissue or fluid that corresponds to the GEP-NEN or metastasis of the test sample, from a healthy individual, such as normal EC or SI sample, or normal liver, lung, bone, blood, saliva, or other bodily fluid, tissue, or biological sample. In another embodiment, the test sample is from a metastatis, plasma, or whole blood or other fluid of a GEP-NEN patient and the reference sample is from primary tumor or sorted tumor cells.

In one aspect, the test biological sample is from a GEP-NEN patient prior to treatment and the normal or reference sample is from the GEP-NEN patient after treatment. In another aspect, the normal or reference sample is from a non-metastatic tissue of the GEP-NEN patient.

In other aspects, the test sample is from blood and the test biological sample is from the GEP-NEN patient after treatment and the reference sample is from the same GEP-NEN patient as the test biological sample, prior to treatment; the reference sample is from a tissue or fluid not containing GEP-NEN cells; the reference sample is from a healthy individual; the reference sample is from a cancer other than GEP-NEN; the reference sample is from an EC cell or SI tissue; the test biological sample is from a metastatic GEP-NEN and the reference sample is from a non-metastatic GEP-NEN; or the reference sample is from a GEP-NEN of a different classification compared to the GEP-NEN patient from which the test biological sample is obtained.

The agents can be any agents for detection of biomarkers, and typically are isolated polynucleotides or isolated polypeptides or proteins, such as antibodies, for example, those that specifically hybridize to or bind to a panel of GEP-NEN biomarkers including at least 21 GEP-NEN biomarkers.

In some embodiments, the methods are performed by contacting the test sample with one of the provided agents, more typically with a plurality of the provided agents, for example, one of the provided systems, such as a set of polynucleotides that specifically bind to the panel of GEP-NEN biomarkers. In some embodiments, the set of polynucleotides includes DNA, RNA, cDNA, PNA, genomic DNA, or synthetic oligonucleotides. In some embodiments, the methods include the step of isolating RNA from the test sample prior to detection, such as by RT-PCR, e.g., QPCR. Thus, in some embodiments, detection of the GEP-NEN biomarkers, such as expression levels thereof, includes detecting the presence, absence, or amount of RNA. In one example, the RNA is detected by PCR or by hybridization.

In one aspect, the polynucleotides include sense and antisense primers, such as a pair of primers that is specific to each of the GEP-NEN biomarkers in the panel of biomarkers. In one aspect of this embodiment, the detection of the GEP-NEN biomarkers is carried out by PCR, typically quantitative or real-time PCR. For example, in one aspect, detection is carried out by producing cDNA from the test sample by reverse transcription; then amplifying the cDNA using the pairs of sense and antisense primers that specifically hybridize to the panel of GEP-NEN biomarkers, and detecting products of the amplification. In some embodiments, the GEP-NEN biomarkers include mRNA, cDNA, or protein.

In some embodiments, the methods are capable of detecting low-volume GEP-NENs, early-stage GEP-NENs, micrometastes, circulating GEP-NEN cells, and/or other instances of GEP-NEN that are difficult to detect by available methods, such as imaging or detection of available biomarkers such as GEP-NEN. For example, in some embodiments, the sample is a blood sample, such as a whole blood sample, and the method detects at least at or about three GEP-NEN cells per milliliter (mL) of whole blood.

In some aspects the methods further comprise statistical analysis and analysis using predictive models such as mathematical algorithms. In one example, the methods include computing a mean expression level for the panel of GEP-NEN biomarkers in the test biological sample. In one aspect of this embodiment, the computing is carried out by vectorally summing the detected expression levels for each of the plurality of GEP-NEN biomarkers. In some aspects, the mean expression level is compared to a reference mean expression level, such as one obtained by performing the methods on a reference or normal sample. Often the comparison reveals a significant difference in the mean expression levels in the test sample compared to the mean reference expression levels. In some aspects, the detected expression or expression profiles are sufficiently different, such as significantly different or sufficiently up or down-regulated, where there is a p value of less than at or about 0.05, or a difference of +standard deviation, or an S value of ±0.4, with $S<-0.4$ or $S>0.4$, or other known method, such as those described herein. In some aspects, the expression, such as mean expression, mean summed expression or expression profile detected and/or determined in the test biological sample correlates with that of another GEP-NEN sample, such as where the test sample is a whole blood or other biological fluid sample, and the amount correlates with that of a GEP-NEN tissue or purified cell population. For example, with an $R^2$ of at least about 0.4, 0.5, 0.6, 0.7, 0.8, 0.9, or 1.

In one embodiment, the method identifies the presence or absence, classification, or stage of GEP-NEN with between 80% to 100%, such as at or about or at least at or about 80, 81, 82, 83, 84, 85, 86, 87, 88, 89, 90, 91, 92, 93, 94, 95, 96, 97, 98, 99, or 100% predictive value, sensitivity, or specificity. In some embodiments, the methods include a step of compressing the detected expression levels of the biomarkers from the test biological sample. Typically, the compression is carried out to determine the expression profile of the panel of biomarkers.

In some embodiments, the test biological sample is a whole blood or saliva sample from a GEP-NEN patient and expression levels or expression profile detected or determined for the test biological sample correlate(s) with the expression levels or expression profile for the same GEP-NEN biomarkers for a GEP-NEN tissue sample or purified GEP-NEN cell sample obtained from the same patient, with an $R^2$ of at least about 0.4.

In some embodiments, the methods include steps for analyzing the data using a predictive algorithm, model, and/or topographical analysis. In some examples, the predictive algorithm is support vector machines (SVM), linear discriminant analysis (LDA), K-nearest neighbor (KNN) or naïve Bayes (NB). In some examples, the predictive algorithm is support vector machines (SVM), linear discriminant analysis (LDA), or K-nearest neighbor (KNN). In other examples, the algorithm is decision tree, SVM, RDA, or Perceptron, or other model known in the art or described herein. In one aspect, the model or algorithm determines the presence, absence, metastatic or non-metastatic nature of a GEP-NEN, or distinguishes between two or more classes of GEP-NEN with a misclassification rate of between 0.05 to 0.

Also among the provided are methods are methods for detecting neuroendocrine tumor cells in blood, by obtaining a blood sample; and contacting the blood sample with one or more agents, which specifically binds to a panel of GEP-NEN biomarkers, which includes at least two GEP-NEN biomarkers, wherein the method detects at least at or about one, two, three, four, or five cells per mL of blood. GEP-NEN cells per mL blood.

Also among the provided embodiments are methods for enriching or isolating GEP-NEN cells from fluids and mixtures of cells, such as plasma, blood, buffy coat, cell culture, biological fluid, or other cell preparation. In one aspect of this embodiment the method is carried out by contacting the mixture of cells with an agent that specifically binds to a GEP-NEN biomarker and purifying cells which bind to the agent. In one aspect of this embodiment, the biomarker is CD164. In one aspect, the biomarker is a polypeptide biomarker. In one such aspect, the agent is an antibody that specifically binds to the biomarker, such as a CD164 antibody. In some embodiments, the purification is by FACS or column purification or any other known method for purifying cells based on affinity. In one aspect, the contacting further includes contacting the cells with another GEP-NEN-specific agent. In some aspects, the method enriches or isolates at least at or about one, two, three, four, or five cells per mL of blood.

Also provided are methods and uses of the provided biomarkers, agents, systems and detection methods for use in GEP-NEN treatment and treatment monitoring. For example, provided are methods using the diagnostic, predictive, and detection methods described above in conjunction with GEP-NEN treatment, such as to assay a sample obtained from a subject undergoing treatment or who was previously undergoing treatment for GEP-NEN. In one embodiment, such methods are carried out by obtaining a sample from such a patient and detecting or determining the presence or absence of expression, expression levels, or expression profile of a GEP-NEN biomarker, typically a panel of GEP-NEN biomarkers, in the sample. In one aspect, the method includes first providing a treatment to the patient. In such methods, the biomarker or panels generally is or are detected using an agent or system as provided herein, such as those described above. In some aspects, the method further includes, prior to providing the treatment, determining a pre-treatment amount, presence, absence, expression levels, or expression profile in a sample from the patient of the biomarker or panel of biomarkers. Thus, in some examples, the pre-treatment amount, presence, absence, expression levels, or expression profile is or are compared to the amount, presence, absence, expression levels, or expression profile determined or detected in the patient after treatment.

In some cases, this analysis determines that there is a difference in expression levels between the pre-treatment expression levels and the post-treatment expression levels, which can indicate the efficacy of the treatment. In some cases, the method further includes determining expression amount, presence, absence, levels, or profiles of the biomarkers in the patient or a sample from the patient at a later time. Such methods can further include comparing the information from the later time to that originally detected or determined. This information, for example, a difference between the expression amounts, presence, absence, levels, or profiles levels can indicate information about whether the individual has been responsive to treatment, for example, can indicate recurrence, lack of treatment responsiveness, stable disease, or progressive disease.

In some embodiments, such methods provide the advantage of providing more sensitive, specific, or accurate information compared to available diagnostic methods, such as detection of CgA levels in the serum or other sample. Thus, in one example, the methods provide the indicated diagnostic, prognostic, or predictive information in a case where the CgA expression levels are not significantly different in the samples assayed, for example, between the pre-treatment and post-treatment samples and/or the sample taken at a later timepoint, or between the test sample and the normal sample.

In some cases, the treatment is discontinued or modified based on the determination from the methods. The methods may be performed in an iterative fashion, with treatment reevaluated or modified according to the expression levels or profiles or comparisons. Thus, in some embodiments, the methods further include discontinuing the treatment or modifying the treatment provided to the patient, for example, based on the information determined by the diagnostic approach. In some cases, the comparison and/or expression amount, presence, absence, levels, or profile indicates the presence of a GEP-NEN micrometastasis in the patient. In one example, one or more of the samples taken from the patient is or was determined to be free of GEP-NEN, GEP-NEN metastases, or GEP-NEN recurrence by another diagnostic method, such as by histology or detection of CgA alone.

In other embodiments, the treatment methods are carried out by obtaining a first sample from a GEP-NEN patient and detecting expression levels of a panel of GEP-NEN biomarkers in the first sample; providing a treatment to the patient; obtaining a second sample from the GEP-NEN patient and detecting expression levels of the panel of GEP-NEN biomarkers in the second sample; and comparing the expression levels detected in the first sample to those detected in the second sample. In one aspect, the method further includes determining whether there is a difference in expression levels between the first and second samples, for example, determining that there is such a difference. In one example the difference indicates the efficacy of the treatment. In a further embodiment, the method further includes obtaining a third sample from the patient, detecting the expression levels in the third sample and comparing them to the expression levels in the first or second sample. In some cases, the comparison indicates the presence of a metastasis, such as micrometastasis. In some embodiments, one or more of the samples is taken from a patient determined to be free of GEP-NEN, GEP-NEN metastases, or GEP-NEN recurrence by another assay, such as detection of CgA alone, imaging, or histology, yet the methods detect the presence of GEP-NEN, GEP-NEN metastases, or GEP-NEN recurrence in the same sample.

In one example, the method further includes determining that there is a difference between expression levels detected in the second and third samples, where the difference indicates a recurrence or lack of treatment responsiveness. In some aspects, the levels of CgA expression in the second sample are not significantly different compared to those in the first sample or the third sample.

DETAILED DESCRIPTION

A. Definitions

Figure 1A:
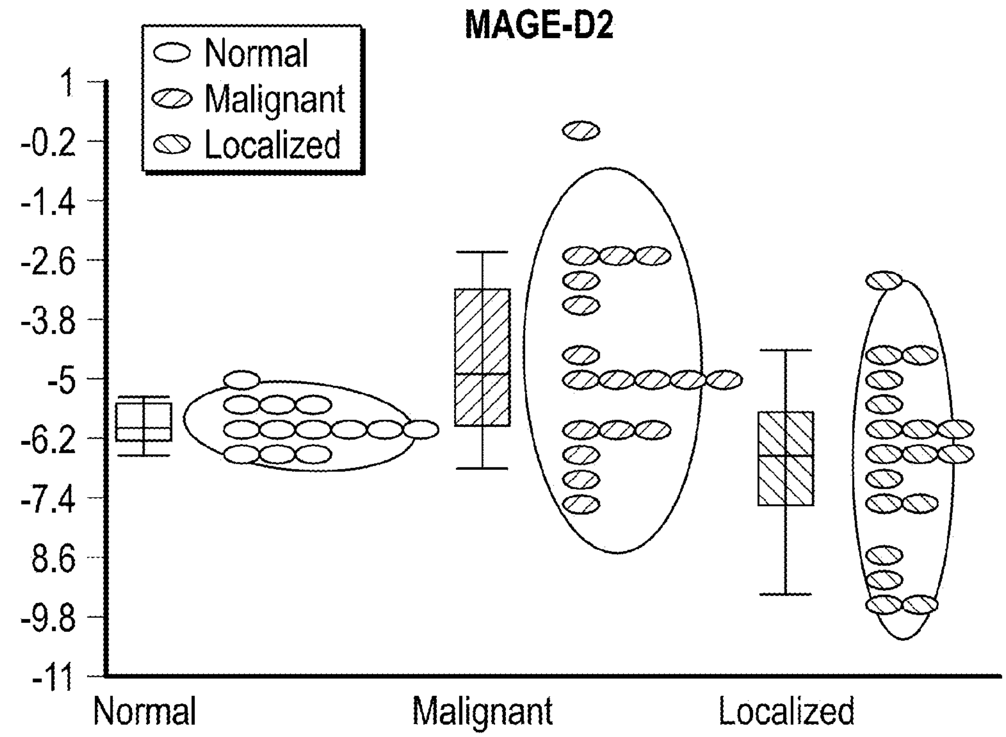
FIGS. 1A-I. Gene expression distribution across Normal, Localized and Malignant tissues. Expression of individual genes (listed above individual graphs) across samples was compared to average expression in the normal enterochomaffin (EC) cell and assigned to Upregulated, Downregulated, or Baseline class. Each graph shows results for normal, malignant, and localized tissues, from left to right. Ellipsoids correspond to a ±2 Standard Deviations (SD) threshold. All p-values: $p<0.05$.
Figure 1B:
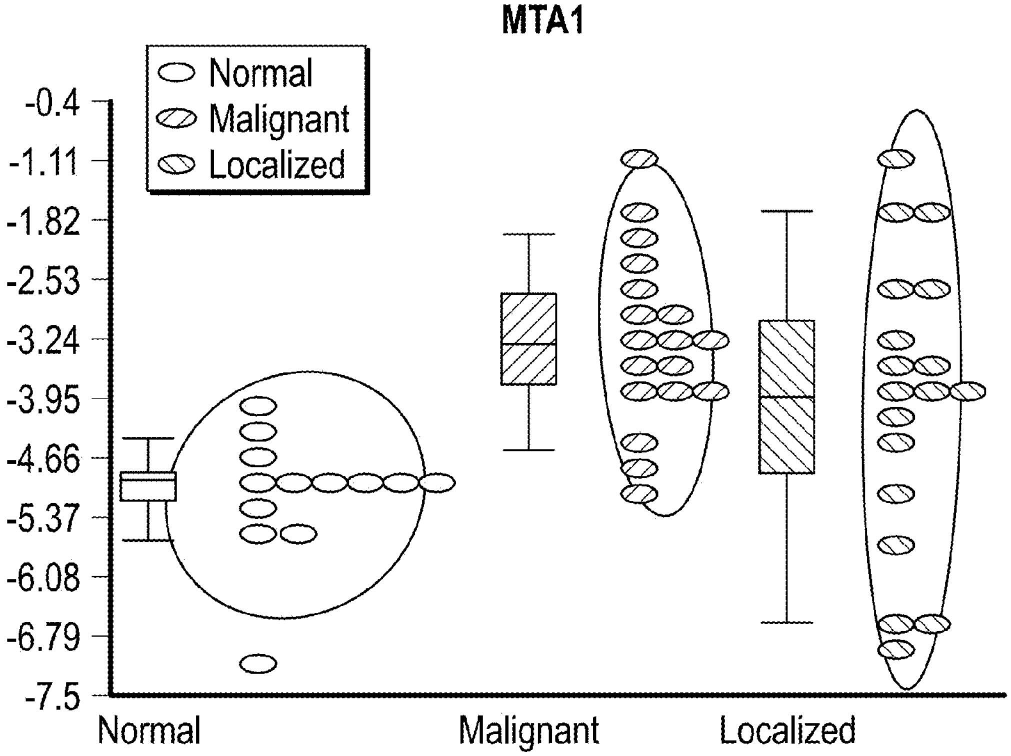
Figure 1C:
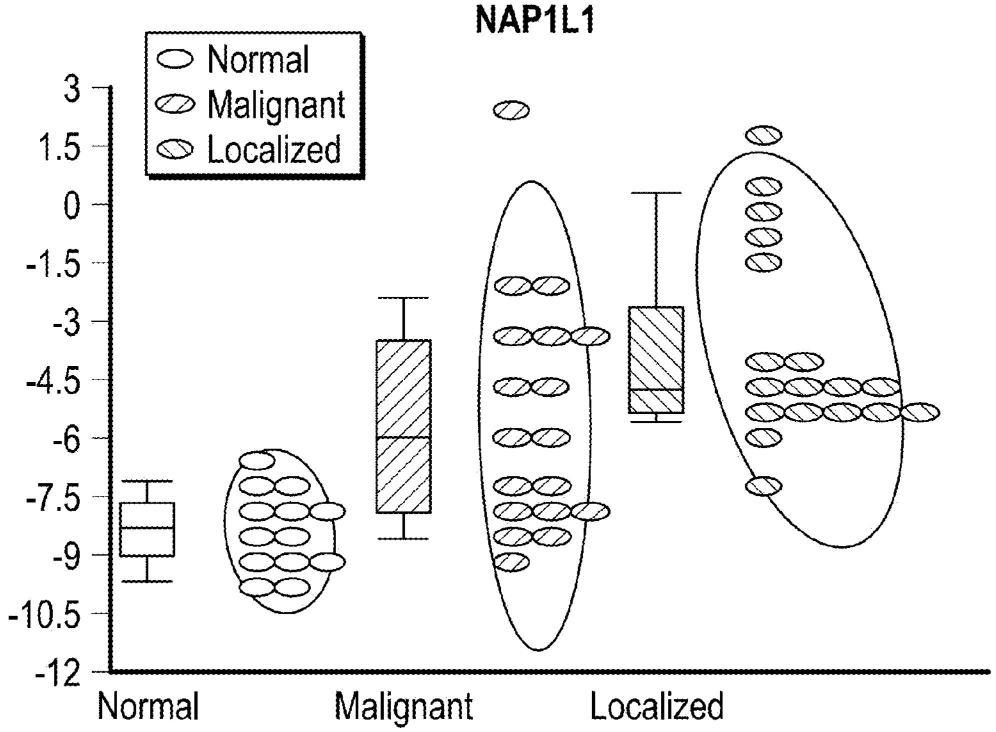
Figure 1D:
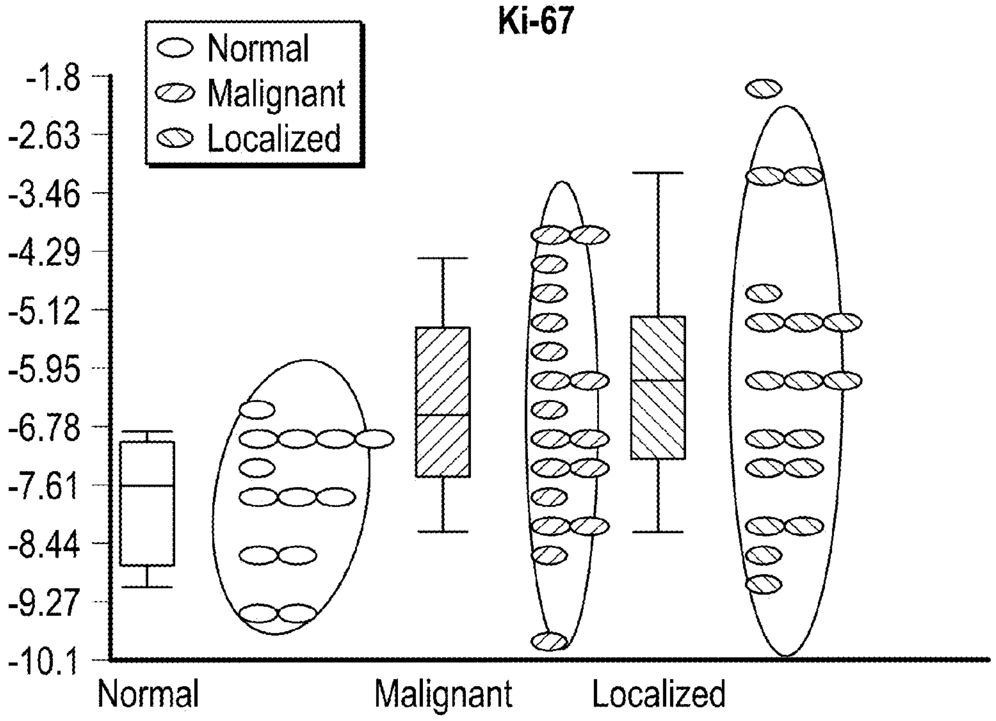
Figure 1E:
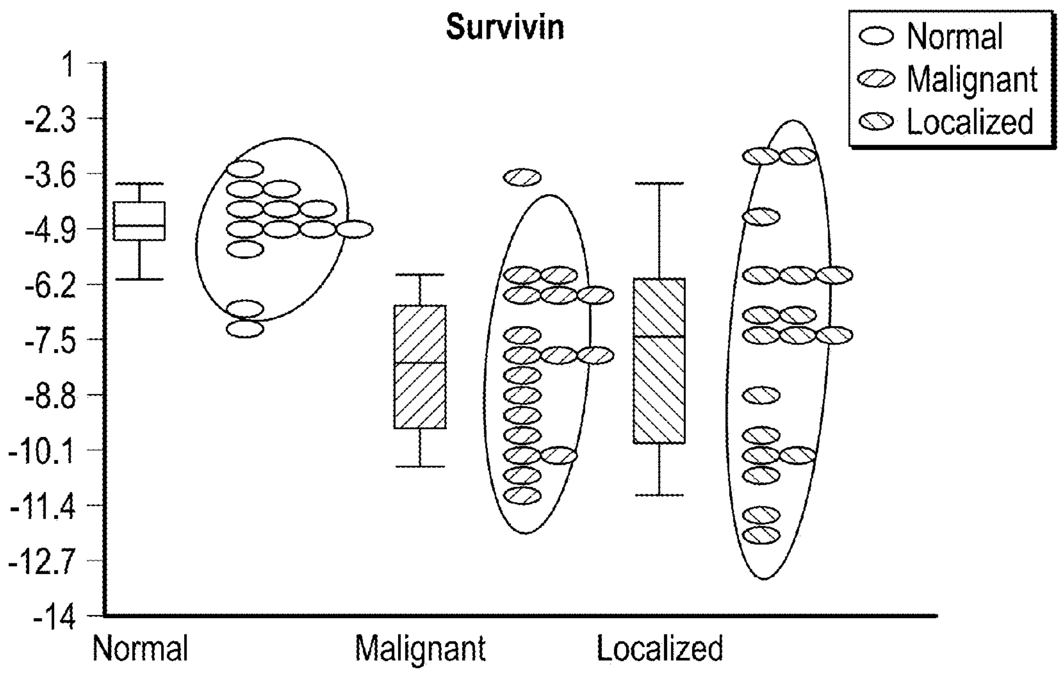
Figure 1F:
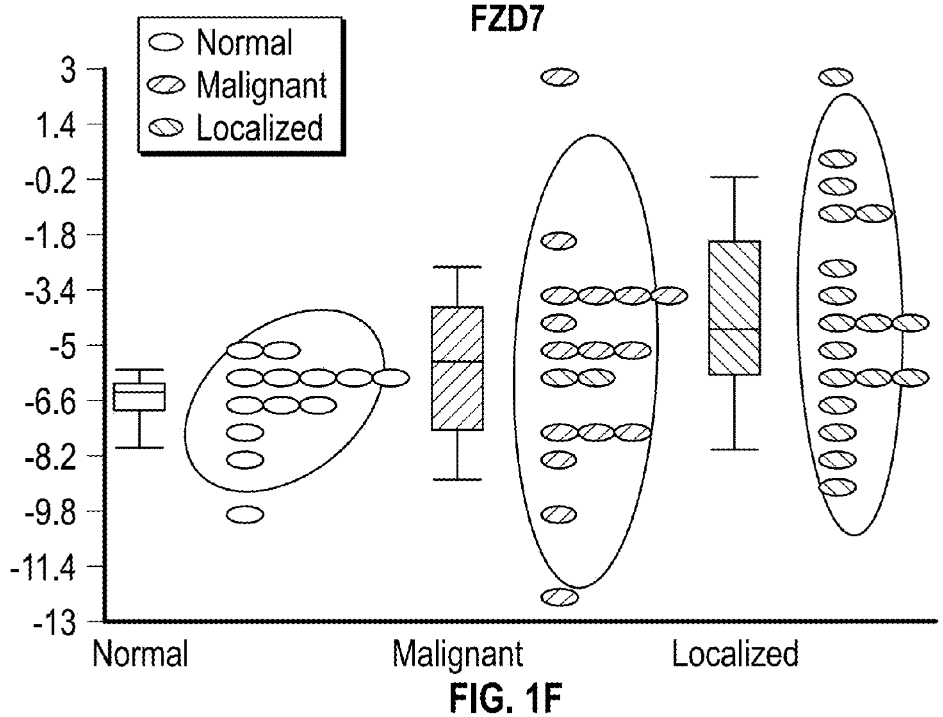
Figure 1G:
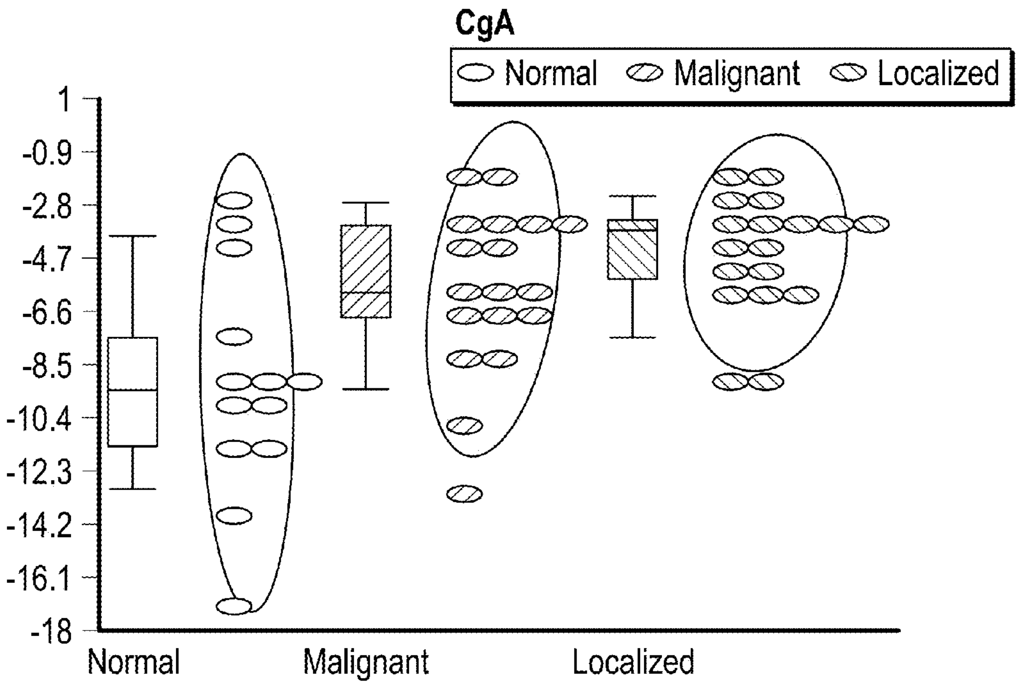
Figure 1H:
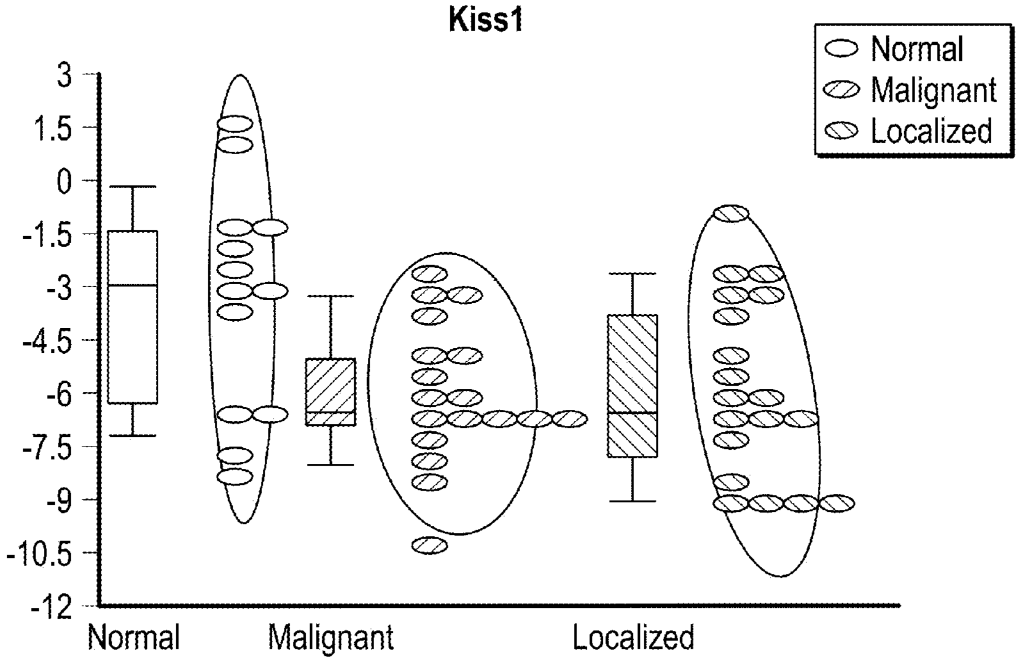
Figure 1I:
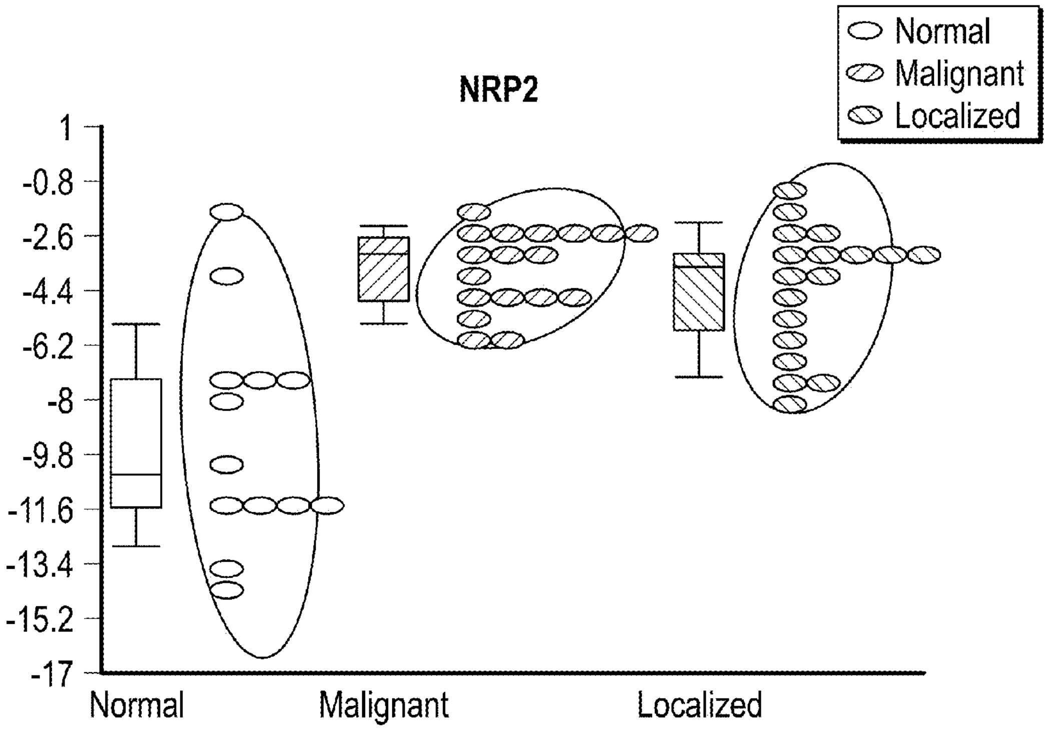

Unless otherwise defined, all terms of art, notations and other scientific terminology used herein are intended to have the meanings commonly understood by those of skill in the art to which this invention pertains. In some cases, terms with commonly understood meanings are defined herein for clarity and/or for ready reference, and the inclusion of such definitions herein should not necessarily be construed to represent a substantial difference over what is generally understood in the art. The techniques and procedures described or referenced herein are generally well understood and commonly employed using conventional methodology by those skilled in the art, such as, for example, the widely utilized molecular cloning methodologies described in Sambrook et al., Molecular Cloning: A Laboratory Manual 2nd. edition (1989) Cold Spring Harbor Laboratory Press, Cold Spring Harbor, N.Y. As appropriate, procedures involving the use of commercially available kits and reagents are generally carried out in accordance with manufacturer defined protocols and/or parameters unless otherwise noted.

As used herein, the term "GEP-NEN biomarker" and "NET biomarker" refer synonymously to a biological molecule, such as a gene product, the expression or presence of which (e.g., the expression level or expression profile) on its own or as compared to one or more other biomarkers (e.g., relative expression) differs (i.e., is increased or decreased) depending on the presence, absence, type, class, severity, metastasis, location, stage, prognosis, associated symptom, outcome, risk, likelihood of treatment responsiveness, or prognosis of GEP-NEN disease, or is associated positively or negatively with such factors or the prediction thereof.

As used herein, the term "polynucleotide" or nucleic acid molecule means a polymeric form of nucleotides of at least 10 bases or base pairs in length, either ribonucleotides or deoxynucleotides or a modified form of either type of nucleotide, and is meant to include single and double stranded forms of DNA. As used herein, a nucleic acid molecule or nucleic acid sequence of the invention that serves as a probe in a microarray analysis preferably comprises a chain of nucleotides, more preferably DNA and/or RNA. In other embodiments a nucleic acid molecule or nucleic acid sequence of the invention comprises other kinds of nucleic acid structures such as for instance a DNA/RNA helix, peptide nucleic acid (PNA), locked nucleic acid (LNA) and/or a ribozyme. Hence, as used herein the term "nucleic acid molecule" also encompasses a chain comprising non-natural nucleotides, modified nucleotides and/or non-nucleotide building blocks which exhibit the same function as natural nucleotides.

As used herein, the term "polypeptide" means a polymer of at least 10 amino acids. Throughout the specification, standard three letter or single letter designations for amino acids are used.

As used herein, the terms "hybridize," "hybridizing," "hybridizes," and the like, used in the context of polynucleotides, are meant to refer to conventional hybridization conditions, preferably such as hybridization in 50% formamide/6×SSC/0.1% SDS/100 μg/ml ssDNA, in which temperatures for hybridization are above 37 degrees C. and temperatures for washing in 0.1×SSC/0.1% SDS are above 55 degrees C., and most preferably to stringent hybridization conditions.

In the context of amino acid sequence comparisons, the term "identity" is used to express the percentage of amino acid residues at the same relative position which are the same. Also in this context, the term "homology" is used to express the percentage of amino acid residues at the same relative positions which are either identical or are similar, using the conserved amino acid criteria of BLAST analysis, as is generally understood in the art. Further details regarding amino acid substitutions, which are considered conservative under such criteria, are provided below.

Additional definitions are provided throughout the subsections which follow.

B. GEP-NEN Disease and Biomarkers

Diagnosis and prognosis of GEP-NEN has been difficult, in part due to the prosaic symptoms and syndromes of the disease, such as carcinoid syndrome, diarrhea, flushing, sweating, bronchioconstruction, GI bleeding, cardiac disease, intermittent abdominal pain, which often remain silent for years. Available diagnostic methods include anatomical localization, such as by imaging, e.g., X-ray, gastrointestinal endoscopy, abdominal computed tomography (CT), combined stereotactic radiosurgery (SRS)/CT, and MRI, and detection of some gene products. Known methods are limited, for example by low specificity and/or sensitivity and/or in the ability to detect early-stage disease. Detection of single biomarkers has not been entirely satisfactory, for example, to identify malignancy in human blood samples and predict complex outcomes like fibrosis and metastasis. See Michiels S, Koscielny S, Hill C, "Interpretation of microarray data in cancer," *Br J Cancer* 2007; 96(8):1155-8. Limitations in available methods have contributed to difficulties in pathological classification, staging, and prediction, treatment developing and monitoring therapeutic effects. Among the embodiments provided herein are methods and compositions that address these limitations.

In one aspect, the provided invention relates to the detection and identification of GEP-NEN biomarkers and panels of such biomarkers, for example, in biological samples. Provided are methods and compositions (e.g., agents, such as polynucleotides), for detecting, determining expression levels of, and recognizing or binding to the biomarkers, in biological samples, typically blood samples, and for detecting and analyzing expression profiles (signatures) of panels of biomarkers. Also provided are compositions and combinations containing the agents, including sets (panels) of agents, systems, and kits, for use in the provided methods.

Also provided are methods and compositions for the detection, enrichment, isolation, and purification of GEP-NEN cells, e.g., circulating GEP-NEN cells (CNCs), for example, from a blood sample, culture, cell mixture, fluid, or other biological sample, based on the expression of one or more of the GEP-NEN biomarkers.

Also provided are models and biomathematical algorithms, e.g., supervised learning algorithms, and methods using the same, for prediction, classification, and evaluation of GEP-NEN and associated outcomes, for example, predicting degree of risk, responsiveness to treatment, metastasis or aggressiveness, and for determining GEP-NEN sub-type.

Detection of the biomarkers using the provided embodiments is useful for improving GEP-NEN diagnostics and prognostics, and to inform treatment protocols. In some aspects, detection of the biomarkers and/or expression levels by the provided embodiments confirms or indicates the presence, absence, stage, class, location, sub-type, aggressiveness, malignancy, metastasis, prognosis, or other outcome of GEP-NEN, or a GEP-NEN cell, such as a circulating GEP-NEN cell (CNC). The provided methods and compositions may be used for tumor localization, and for predicting or detecting metastases, micrometastases, and small lesions, and/or for determining degree of risk, likelihood of recurrence, treatment responsiveness or remission, and informing appropriate courses of treatment. For example, detecting the biomarkers, e.g., in circulation may be used to detect early-stage and primary GEP-NENs (e.g., to identify GEP-NEN disease or metastases in a patient previously deemed "negative" by another approach, such as anatomic localization).

The provided methods and compositions may be used for designing, implementing, and monitoring treatment strategies, including patient-specific treatment strategies. In one example, detected expression levels of the GEP-NEN biomarkers serve as surrogate markers for treatment efficacy, e.g., to monitor the effects of surgical therapy (e.g., removal of tumors), targeted medical therapy (e.g., inhibition of tumor secretion/proliferation), and other therapeutic approaches, by detecting remission or recurrence of tumors, even in the form of small micrometastases. The methods also may be used in evaluating clinical symptoms and outcomes, and for histological grading and molecular characterization of GEP-NENs.

C. GEP-NEN Biomarkers

The provided biomarkers including GEP-NEN biomarkers, and panels (sets) of the same. Among the provided GEP-NEN biomarkers are gene products, such as DNA, RNA, e.g., transcripts, and protein, which are differentially expressed in GEP-NEN disease, and/or in different stages or sub-types of GEP-NEN, or in different GEP-NEN tumors, such as gene products differentially expressed in metastatic versus primary tumors, tumors with different degrees of aggressiveness, high versus low-risk tumors, responsive versus non-responsive tumors, tumors exhibiting different pathological classifications and/or likelihood of response to particular courses of treatment, as well as those associated with features of GEP-NEN disease, stage, or type, or with neuroendocrine cells or related cell-types.

For example, the biomarkers include gene products whose expression is associated with or implicated in tumorogenicity, metastasis, or hormone production, or a phenotype of primary or metastatic GEP-NEN, such as adhesion, migration, proliferation, apoptosis, metastasis, and hormone secretion, and those associated with neoplasia or malignancy in general. The biomarkers also include gene products expressed in related normal tissues, such as neuroendocrine cells, the small intestine (SI) mucosa, and enterochromaffin (EC) cells.

Among the biomarkers are GEP-NEN cell secretion products, including hormones and amines, e.g., gastrin, ghrelin, pancreatic polypeptide, substance P, histamine, and serotonin, and growth factors such as tumor growth factor-beta (TGF-β) and connective tissue growth factor (CTGF), which are detectable in the circulation. Secretion products can vary with tumor sub-type and origin.

In one example, the biomarkers are gene products associated with regulatory genotypes (i.e., adhesion, migration, proliferation, apoptosis, metastasis, and/or hormone secretion) that underlay various GEP-NEN subtypes, stages, degrees of aggressiveness, or treatment responsiveness.

Also among the GEP-NEN biomarkers are gene products differentially expressed in primary GEP-NENs and hepatic metastases as compared to normal small bowel mucosa and pure preparations of EC cells See Modlin et al., "Genetic differentiation of appendiceal tumor malignancy: a guide for the perplexed," *Ann Surg* 2006; 244(1):52-60; Kidd M, et al., "The role of genetic markers, NAP1L1, MAGE-D2 and MTA1, in defining small intestinal carcinoid neoplasia," *Annals of Surgical Oncology* 2006; 13:253-62; Kidd M et al., "Q RT-PCR detection of Chromogranin A: A new standard in the identification of neuroendocrine tumor disease," *Annals of Surgery* 2006; 243:273-80.

The GEP-NEN biomarkers include: AKAP8L (A kinase (PRKA) anchor protein 8-like), ATP6V1H (ATPase, H+ transporting, lysosomal 50/57 kDa, V1 subunit H), BNIP3L (BCL2/adenovirus E1B 19 kDa interacting protein 3-like), C21orf7 (chromosome 21 open reading frame 7), COMMD9 (COMM domain containing 9), ENPP4 (ectonucleotide pyrophosphatase/phosphodiesterase 4). FAM131A (family with sequence similarity 13, member A), FLJ10357 (Rho guanine nucleotide exchange factor 40), GLT8D1 (glycosyltransferase 8 domain containing 1), HDAC9 (histone deacetylase 9), HSF2 (heat shock transcription factor 2), LEO1 (Paf1/RNA polymerase II complex component, homolog (*S. cerevisiae*)), MORF4L2 (MORF4L2 mortality factor 4 like 2), NOL3 (nucleolar protein 3 (apoptosis repressor with CARD domain)), NUDT3 (nudix (nucleoside diphosphate linked moiety X)-type motif 3), OAZ2 (ornithine decarboxylase antizyme 2), PANK2 (pantothenate kinase 2), PHF21A (PHD finger protein 21A), PKD1 (polycystic kidney disease 1 (autosomal dominant)), PLD3 (phospholipase D family, member 3), PQBP1 (polyglutamine binding protein 1), RNF41 (polyglutamine binding protein 1), RSF1 (remodeling and spacing factor 1), RTN2 (reticulon 2), SMARCD3 (SWI/SNF related, matrix associated, actin dependent regulator of chromatin, subfamily d, member 3p), SPATA7 (spermatogenesis associated 7), SST1 (somatostatin receptor 1), SST3 (somatostatin receptor 3), SST4 (somatostatin receptor 4), SST5 (somatostatin receptor 5), TECPR2 (tectonin beta-propeller repeat containing 2), TRMT112 (tRNA methyltransferase 11-2 homolog (*S. cerevisiae*)), VPS13C (vacuolar protein sorting 13 homolog C (*S. cerevisiae*)), WDFY3 (WD repeat and FYVE domain containing 3), ZFHX3 (zinc finger homeobox 3), ZXDC (ZXD family zinc finger C), ZZZ3 (zinc finger, ZZ-type containing 3), Amyloid beta (A4) precursor-like protein 2 (APLP2); v-raf murine sarcoma 3611 viral oncogene homolog (ARAF1); v-raf murine sarcoma viral oncogene homolog B1 (BRAF1); CD59; Chromogranin A (CgA, also called parathyroid secretory protein 1, CHGA); connective tissue growth factor (CTGF); chemokine (C-X-C motif) ligand 14 (CXCL14); frizzled homolog 7 (FZD7); glutamate receptor, ionotropic, AMPA 2 (GRIA2); homeobox C6 (HOXC6); Ki-67; KiSS-1 metastasis-suppressor (Kiss1); v-Ki-ras2 Kirsten rat sarcoma viral oncogene homolog (KRAS); melanoma antigen family D, 2 (MAGE-D2); metastasis associated 1 (MTA1); nucleosome assembly protein 1-like 1 (NAP1L1); NK2 transcription factor related, locus 3 (e.g., Homo Sapiens NK2 transcription factor related, locus 3 (Drosophila)) (NKX2-3); neuropilin 2 (NRP2); olfactory receptor, family 51, subfamily E, member 1 (OR51E1); paraneoplastic antigen MA2 (PNMA2); protein tyrosine phosphatase, receptor type, N polypeptide 2 (PTPRN2); v-raf-1 murine leukemia viral oncogene homolog 1 (RAF1); secretogranin V (7B2 protein) (SCG5); sparc/osteonectin, cwcv and kazal-like domains proteoglycan (testican) 1 (SPOCK1); apoptosis inhibitor survivin gene (BIRC5; API4; EPR-1) (Survivin); tryptophan hydroxylase 1 (TPH1), solute carrier family 18 (vesicular monoamine), member 1 (VMAT1); solute carrier family 18 (vesicular monoamine), member 2 (VMAT2); and X2BTB48 (serpin peptidase inhibitor, Glade A (alpha-1 antiproteinase, antitrypsin), member 10), including gene products typically human gene products, including transcripts, mRNA, cDNA, coding sequences, proteins and polypeptides, as well as polynucleotides (nucleic acids) encoding the proteins and polypeptides, including naturally occurring variants, e.g., allelic variants, splice variants, transcript variants, and single nucleotide polymorphism (SNP) variants. For example, the biomarkers include polynucleotides, proteins, and polypeptides having the sequences disclosed herein, and naturally occurring variants thereof.

The GEP-NEN biomarkers further include CD164. In another aspect, the biomarkers include NALP, e.g., products of the caspase-3 activating apoptosis gene and apoptotic marker, NALP.

APLP2 biomarkers include human APLP2 gene products, including natural variants, e.g., allelic variants, and homologs and analogs thereof. In one example, the APLP2 biomarker is a polynucleotide having the nucleotide sequence set forth in SEQ ID NO: 1 (referenced at GenBank gi number 214010177) or containing a protein-coding portion thereof, (e.g., the open reading frame at nucleotides 158-2449 of SEQ ID NO: 1), a natural variant thereof, or a protein encoded by such a polynucleotide.

The ARAF1 biomarkers include human ARAF1 gene products, including natural variants, e.g., allelic variants, and homologs and analogs thereof. In one example, the ARAF1 biomarker is a polynucleotide having the nucleotide sequence set forth in SEQ ID NO: 2 (referenced at GenBank gi number 283484007), or containing a protein-coding portion thereof, (e.g., the open reading frame at nucleotides 195-2015 of SEQ ID NO: 2), a natural variant thereof, or a protein encoded by such a polynucleotide.

The BRAF1 biomarkers include BRAF1 gene products, including natural variants, e.g., allelic variants, and homologs and analogs thereof. In one example, the BRAF1 biomarker is a polynucleotide having the nucleotide sequence set forth in SEQ ID NO: 3 (referenced at GenBank gi number 187608632), or containing a protein-coding portion thereof, (e.g., the open reading frame at nucleotides 62-2362 of SEQ ID NO: 3), a natural variant thereof, or a protein encoded by such a polynucleotide.

The CD59 biomarkers include human CD59 gene products, including natural variants, e.g., allelic variants, and homologs and analogs thereof. In one example, the CD59 biomarker is a polynucleotide having the nucleotide sequence set forth in SEQ ID NO: 4 (referenced at GenBank gi number 187829037), or containing a protein-coding portion thereof, (e.g., the open reading frame at nucleotides 278-664 of SEQ ID NO: 4), a natural variant thereof, or a protein encoded by such a polynucleotide.

The CgA biomarkers include human CGA or CHGA gene products, including natural variants, e.g., allelic variants, and homologs and analogs thereof. In one example, the CgA biomarker is a polynucleotide having the nucleotide sequence set forth in SEQ ID NO: 5 (referenced at GenBank gi number 33990769), or containing a protein-coding portion thereof, (e.g., the open reading frame at nucleotides 1 to 1374 of SEQ ID NO: 5), a natural variant thereof, or a protein encoded by such a polynucleotide. Human CgA encodes a water soluble acidic glycoprotein stored in the secretory granules of neuroendocrine cells and detectable in plasma.

The CTGF biomarkers include human CTGF gene products, including natural variants, e.g., allelic variants, and homologs and analogs thereof. In one example, the CTGF biomarker is a polynucleotide having the nucleotide sequence set forth in SEQ ID NO: 6 (referenced at GenBank gi number 98986335), or containing a protein-coding portion thereof, (e.g., the open reading frame at nucleotides 207-1256 of SEQ ID NO: 6), a natural variant thereof, or a protein encoded by such a polynucleotide.

The CXCL14 biomarkers include human CXCL14 gene products, including natural variants, e.g., allelic variants, and homologs and analogs thereof. In one example, the CXCL14 biomarker is a polynucleotide having the nucleotide sequence set forth in SEQ ID NO: 7 (referenced at GenBank gi number 208022628), or containing a protein-coding portion thereof, (e.g., the open reading frame at nucleotides 466-801 of SEQ ID NO: 7), a natural variant thereof, or a protein encoded by such a polynucleotide.

The FZD7 biomarkers include human FZD7 gene products, e.g., Homo sapiens frizzled homolog 7 (Drosophila) (FDZ7), including natural variants, e.g., allelic variants, and homologs and analogs thereof. In one example, the FDZ7 biomarker is a polynucleotide having the nucleotide sequence set forth in SEQ ID NO: 8 (referenced at GenBank gi number 4503832), or containing a protein-coding portion thereof, (e.g., the open reading frame at nucleotides 62-1786 of SEQ ID NO: 8 a natural variant thereof, or a protein encoded by such a polynucleotide.

The GRIA2 biomarkers include human GRIA2 gene products, including natural variants, e.g., allelic variants, and homologs and analogs thereof. In one example, the GRIA2 biomarker is a polynucleotide having the nucleotide sequence set forth in SEQ ID NO: 9 (referenced at GenBank gi number 134304849), or containing a protein-coding portion thereof, (e.g., the open reading frame at nucleotides 460-3111 of SEQ ID NO: 9), a natural variant thereof, or a protein encoded by such a polynucleotide.

The homeobox C6 (HOXC6) biomarkers include human HOXC6 gene products, including natural variants, e.g., allelic variants, and homologs and analogs thereof. In one example, the HOXC6 biomarker is a polynucleotide having the nucleotide sequence set forth in SEQ ID NO: 10 (referenced at GenBank gi number 93141222) or containing a protein-coding portion thereof, (e.g., the open reading frame at nucleotides 113-820 of SEQ ID NO: 10), a natural variant thereof, or a protein encoded by such a polynucleotide.

The Ki67 biomarkers include human Ki67 gene products, including natural variants, e.g., allelic variants, and homologs and analogs thereof. In one example, the Ki67 biomarker is a polynucleotide having the nucleotide sequence set forth in SEQ ID NO: 11 (referenced at GenBank gi number 225543213) or containing the coding region thereof (e.g., nucleotides 196-9966) of SEQ ID NO: 11), a natural variant thereof, or a protein encoded by such a polynucleotide.

The Kiss1 biomarkers include human KISS1 gene products, including natural variants, e.g., allelic variants, and homologs and analogs thereof. In one example, the KISS1 biomarker is a polynucleotide having the nucleotide sequence set forth in SEQ ID NO: 12 (referenced at GenBank gi number 116829963), or containing a protein-coding portion thereof, (e.g., the open reading frame at nucleotides 155-571 of SEQ ID NO: 12), a natural variant thereof, or a protein encoded by such a polynucleotide.

The KRAS biomarkers include human KRAS gene products, including natural variants, e.g., allelic variants, and homologs and analogs thereof. In one example, the KRAS biomarker is a polynucleotide having the nucleotide sequence set forth in SEQ ID NO: 13 (referenced at GenBank gi number 34485724) or containing the coding region thereof (e.g., nucleotides 182-751 of SEQ ID NO: 13), a natural variant thereof, or a protein encoded by such a polynucleotide.

The MAGE-D2 biomarkers include human MAGE-D2 gene products, including natural variants, e.g., allelic variants, and homologs and analogs thereof. In one example, the MAGE-D2 biomarker is a polynucleotide having the nucleotide sequence set forth in SEQ ID NO: 14 (referenced at GenBank gi number 29171703) or containing a protein-coding portion thereof, (e.g., the open reading frame at nucleotides 100-1920 of SEQ ID NO: 14), a natural variant thereof, or a protein encoded by such a polynucleotide. MAGE-D2 encodes an adhesion-associated protein.

The MTA1 biomarkers include human MTA1 gene products, including natural variants, e.g., allelic variants, and homologs and analogs thereof. In one example, the MTA1 biomarker is a polynucleotide having the nucleotide sequence set forth in SEQ ID NO: 15 (referenced at GenBank gi number 115527079) or containing the coding region thereof (e.g., nucleotides 188-2335 of SEQ ID NO: 15), a natural variant thereof, or a protein encoded by such a polynucleotide. MTA, an estrogen-antagonistic breast cancer malignancy gene, has been used to identify progressive (metastatic) disease in other tumors including breast, hepatocellular, esophageal, gastric, and colorectal carcinomas.

The NAP1L1 biomarkers include human NAP1L1 gene products, including natural variants, e.g., allelic variants, and homologs and analogs thereof. In one example, the NAP1L1 biomarker is a polynucleotide having the nucleotide sequence set forth in SEQ ID NO: 16 (referenced at GenBank gi number 219842231) or containing a protein-coding portion thereof, (e.g., the open reading frame at nucleotides 413-1588 of SEQ ID NO: 16), a natural variant thereof, or a protein encoded by such a polynucleotide. NAP1L1 is a mitosis-regulatory gene encoding a nuclear protein involved in chromatin assembly and DNA replication.

The NKX2-3 biomarkers include human NKX2-3 gene products, including natural variants, e.g., allelic variants, and homologs and analogs thereof. In one example, the NKX2-3 biomarker is a polynucleotide having the nucleotide sequence set forth in SEQ ID NO: 17 (referenced at GenBank gi number 148746210) or containing a protein-coding portion thereof, (e.g., the open reading frame at nucleotides 200-1294 of SEQ ID NO: 17), a natural variant thereof, or a protein encoded by such a polynucleotide.

The NRP2 biomarkers include human NRP2 gene products, including natural variants, e.g., allelic variants, and homologs and analogs thereof. In one example, the NRP2 biomarker is a polynucleotide having the nucleotide sequence set forth in SEQ ID NO: 18 (referenced at GenBank gi number 41872561) or containing a protein-coding portion thereof, (e.g., the open reading frame at nucleotides 792-3587 of SEQ ID NO: 18), a natural variant thereof, or a protein encoded by such a polynucleotide.

The OR51E1 biomarkers include human OR51E1 gene products, including natural variants, e.g., allelic variants, and homologs and analogs thereof. In one example, the OR51E1 biomarker is a polynucleotide having the nucleotide sequence set forth in SEQ ID NO: 19 (referenced at GenBank gi number 205277377) or containing a protein-coding portion thereof, (e.g., the open reading frame at nucleotides 145-1101 of SEQ ID NO: 19), a natural variant thereof, or a protein encoded by such a polynucleotide.

The PNMA2 biomarkers include human PNMA2 gene products, including natural variants, e.g., allelic variants, and homologs and analogs thereof. In one example, the PNMA2 biomarker is a polynucleotide having the nucleotide sequence set forth in SEQ ID NO: 20 (referenced at GenBank gi number 156766040) or containing a protein-coding portion thereof, (e.g., the open reading frame at nucleotides 771-1865 of SEQ ID NO: 20), a natural variant thereof, or a protein encoded by such a polynucleotide.

The PTPRN2 biomarkers include human PTPRN2 gene products, including natural variants, e.g., allelic variants, and homologs and analogs thereof. In one example, the PTPRN2 biomarker is a polynucleotide having the nucleotide sequence set forth in SEQ ID NO: 21 (referenced at GenBank gi number 194097439) or containing a protein-coding portion thereof, (e.g., the open reading frame at nucleotides 122-3169 of SEQ ID NO: 21), a natural variant thereof, or a protein encoded by such a polynucleotide.

The RAF1 biomarkers include human RAF1 gene products, including natural variants, e.g., allelic variants, and homologs and analogs thereof. In one example, the RAF1 biomarker is a polynucleotide having the nucleotide sequence set forth in SEQ ID NO: 22 (referenced at GenBank gi number 189458830) or containing a protein-coding portion thereof, (e.g., the open reading frame at nucleotides 416-2362 of SEQ ID NO: 22), a natural variant thereof, or a protein encoded by such a polynucleotide.

The SCG5 biomarkers include human SCG5 gene products, including natural variants, e.g., allelic variants, and homologs and analogs thereof. In one example, the SCG5 biomarker is a polynucleotide having the nucleotide sequence set forth in SEQ ID NO: 23 (referenced at GenBank gi number 221139784) or containing a protein-coding portion thereof, (e.g., the open reading frame at nucleotides 118-756 of SEQ ID NO: 23), a natural variant thereof, or a protein encoded by such a polynucleotide.

The SPOCK1 biomarkers include human SPOCK1 gene products, including natural variants, e.g., allelic variants, and homologs and analogs thereof. In one example, the SPOCK1 biomarker is a polynucleotide having the nucleotide sequence set forth in SEQ ID NO: 24 (referenced at GenBank gi number 82659117) or containing a protein-coding portion thereof, (e.g., the open reading frame at nucleotides 152-1471 of SEQ ID NO: 24), a natural variant thereof, or a protein encoded by such a polynucleotide.

The Survivin biomarkers include human Survivin gene products, including natural variants, e.g., allelic variants, and homologs and analogs thereof. In one example, the Survivin biomarker is a polynucleotide having the nucleotide sequence set forth in SEQ ID NO: 25 (referenced at GenBank gi number 59859877) or containing a protein-coding portion thereof, (e.g., the open reading frame at nucleotides 122-550 of SEQ ID NO: 25) or a polynucleotide having the protein-coding sequence (SEQ ID NO: 34) of nucleotides 2811-2921, 3174-3283, 5158-5275, 11955-12044 of GenBank gi number 2315862), a natural variant thereof, or a protein encoded by such a polynucleotide.

The TPH1 biomarkers include human TPH1 gene products, including natural variants, e.g., allelic variants, and homologs and analogs thereof. In one example, the TPH1 biomarker is a polynucleotide having the nucleotide sequence set forth in SEQ ID NO: 26 (referenced at GenBank gi number 226342925) or containing a protein-coding portion thereof (e.g., the open reading frame at nucleotides 27-1361 of SEQ ID NO: 26), a natural variant thereof, or a protein encoded by such a polynucleotide. TPH1 encodes an enzyme produced by enterochromaffin (EC) cells of the GI tract, important for the production of serotonin.

The VMAT1 biomarkers include human VMAT1 gene products, including natural variants, e.g., allelic variants, and homologs and analogs thereof. In one example, the VMAT1 biomarker is a polynucleotide having the nucleotide sequence set forth in SEQ ID NO: 27 (referenced at GenBank gi number 215272388) or containing the coding region thereof (e.g., nucleotides 472-2049 of SEQ ID NO: 27), a natural variant thereof, or a protein encoded by such a polynucleotide.

The VMAT2 biomarkers include human VMAT2 gene products, including natural variants, e.g., allelic variants, and homologs and analogs thereof. In one example, the VMAT2 biomarker is a polynucleotide having the nucleotide sequence set forth in SEQ ID NO: 28 (referenced at GenBank gi number 141803164) or containing the coding region thereof (e.g., nucleotides 32-1576 of SEQ ID NO: 28), a natural variant thereof, or a protein encoded by such a polynucleotide.

The X2BTB48 biomarkers include human serpin peptidase inhibitor, Glade A (alpha-1 antiproteinase, antitrypsin), member 10) gene products, including natural variants, e.g., allelic variants, and homologs and analogs thereof. In one example, the X2BTB48 biomarker is a polynucleotide having the nucleotide sequence set forth in SEQ ID NO: 29 (referenced at GenBank gi number 154759289) or containing the coding region thereof (e.g., nucleotides 467-1801 of SEQ ID NO: 29), a natural variant thereof, such as the nucleotide sequence referenced at GenBank gi number 154759290 (SEQ ID NO: 105) or a coding sequence thereof, e.g., the coding sequence thereof at nucleotides 122-1456, or a protein encoded by such polynucleotides, such as the protein having the amino acid sequence referenced at GenBank gi number 7705879.

The AKAP8L (A kinase (PRKA) anchor protein 8-like) biomarkers include human AKAP8L gene products, including natural variants, e.g., allelic variants, and homologs and analogs thereof. In one example, the AKAP8L biomarker is a polynucleotide having the nucleotide sequence set forth in SEQ ID NO: 201 (referenced at GenBank gi number 49472840), or containing a protein-coding portion thereof, e.g., the coding sequence thereof of nucleotides 100-2040 of SEQ ID NO: 201, a natural variant thereof, or a protein encoded by such a polynucleotide.

The ATP6V1H (ATPase, H+ transporting, lysosomal 50/57 kDa, V1 subunit H) biomarkers include human ATP6V1H gene products, including natural variants, e.g., allelic variants, and homologs and analogs thereof. In one example, the ATP6V1H biomarker is a polynucleotide having the nucleotide sequence set forth in SEQ ID NO: 204 (referenced at GenBank gi number 47717103), or containing a protein-coding portion thereof, e.g., the coding sequence thereof of nucleotides 293-1744, a natural variant thereof, or a protein encoded by such a polynucleotide.

The BNIP3L (BCL2/adenovirus E1B 19 kDa interacting protein 3-like) biomarkers include human BNIP3L gene products, including natural variants, e.g., allelic variants, and homologs and analogs thereof. In one example, the BNIP3L biomarker is a polynucleotide having the nucleotide sequence set forth in SEQ ID NO: 205 (referenced at GenBank gi number 47078259), or containing a protein-coding portion thereof, e.g., the coding sequence thereof at nucleotides 125-784 of SEQ ID NO: 205, a natural variant thereof, or a protein encoded by such a polynucleotide.

The C21orf7 (chromosome 21 open reading frame 7) biomarkers include human C21orf7 gene products, including natural variants, e.g., allelic variants, and homologs and analogs thereof. In one example, the C21orf7 biomarker is a polynucleotide having the nucleotide sequence set forth in SEQ ID NO: 206 (referenced at GenBank gi number 31542267), or containing a protein-coding portion thereof, e.g., the coding sequence thereof at nucleotides 278-1006 of SEQ ID NO: 206, a natural variant thereof, or a protein encoded by such a polynucleotide.

The COMMD9 (COMM domain containing 9) biomarkers include human ATP6V1H gene products, including natural variants, e.g., allelic variants, and homologs and analogs thereof. In one example, the COMMD9 biomarker is a polynucleotide having the nucleotide sequence set forth in SEQ ID NO: 207 (referenced at GenBank gi number 156416006), or containing a protein-coding portion thereof, e.g., the coding sequence thereof at nucleotides 38-508 of SEQ ID NO: 207, a natural variant thereof, or a protein encoded by such a polynucleotide.

The ENPP4 (ectonucleotide pyrophosphatase/phosphodiesterase 4) biomarkers include human ENPP4 gene products, including natural variants, e.g., allelic variants, and homologs and analogs thereof. In one example, the ENPP4 biomarker is a polynucleotide having the nucleotide sequence set forth in SEQ ID NO: 208 (referenced at GenBank gi number 194688140), or containing a protein-coding portion thereof, e.g., the coding sequence thereof of nucleotides 260-1621 of SEQ ID NO: 208, a natural variant thereof, or a protein encoded by such a polynucleotide.

The FAM131A (family with sequence similarity 13, member A) biomarkers include human FAM131A gene products, including natural variants, e.g., allelic variants, and homologs and analogs thereof. In one example, the FAM131A biomarker is a polynucleotide having the nucleotide sequence set forth in SEQ ID NO: 209 (referenced at GenBank gi number 283806631), or containing a protein-coding portion thereof, e.g., the coding sequence thereof at nucleotides 281-1126 of SEQ ID NO: 209, a natural variant thereof, or a protein encoded by such a polynucleotide.

The FLJ10357 (Rho guanine nucleotide exchange factor 40) biomarkers include human ARHGEF40 gene products, including natural variants, e.g., allelic variants, and homologs and analogs thereof. In one example, the FLJ10357 biomarker is a polynucleotide having the nucleotide sequence set forth in SEQ ID NO: 210 (referenced at GenBank gi number 50843836), or containing a protein-coding portion thereof, e.g., the coding sequence thereof of nucleotides 30-4589 of SEQ ID NO: 210, a natural variant thereof, or a protein encoded by such a polynucleotide.

The GLT8D1 (glycosyltransferase 8 domain containing 1) biomarkers include human GLT8D1 gene products, including natural variants, e.g., allelic variants, and homologs and analogs thereof. In one example, the GLT8D1 biomarker is a polynucleotide having the nucleotide sequence set forth in SEQ ID NO: 211 (referenced at GenBank gi number 58331224), or containing a protein-coding portion thereof, e.g., the coding sequence thereof of nucleotides 852-1967 of SEQ ID NO: 211, a natural variant thereof, or a protein encoded by such a polynucleotide.

The HDAC9 (histone deacetylase 9) biomarkers include human HDAC9 gene products, including natural variants, e.g., allelic variants, and homologs and analogs thereof. In one example, the HDAC9 biomarker is a polynucleotide having the nucleotide sequence set forth in SEQ ID NO: 212 (referenced at GenBank gi number 323423043), or containing a protein-coding portion thereof, e.g., the coding sequence thereof at nucleotides 362-2128 of SEQ ID NO: 212, a natural variant thereof, or a protein encoded by such a polynucleotide.

The HSF2 (heat shock transcription factor 2) biomarkers include human HSF2 gene products, including natural variants, e.g., allelic variants, and homologs and analogs thereof. In one example, the HSF2 biomarker is a polynucleotide having the nucleotide sequence set forth in SEQ ID NO: 213 (referenced at GenBank gi number 207113145), or containing a protein-coding portion thereof, e.g., the coding sequence thereof of nucleotides 188-1798 of SEQ ID NO: 213, a natural variant thereof, or a protein encoded by such a polynucleotide.

The LEO1 (Paf1/RNA polymerase II complex component, homolog (*S. cerevisiae*)) biomarkers include human LEO1 gene products, including natural variants, e.g., allelic variants, and homologs and analogs thereof. In one example, the LEO1 biomarker is a polynucleotide having the nucleotide sequence set forth in SEQ ID NO: 215 (referenced at GenBank gi number 37059738), or containing a protein-coding portion thereof, e.g., the coding sequence thereof at nucleotides 17-2017 of SEQ ID NO: 215, a natural variant thereof, or a protein encoded by such a polynucleotide.

The MORF4L2 (MORF4L2 mortality factor 4 like 2) biomarkers include human MORF4L2 gene products, including natural variants, e.g., allelic variants, and homologs and analogs thereof. In one example, the MORF4L2 biomarker is a polynucleotide having the nucleotide sequence set forth in SEQ ID NO: 217 (referenced at GenBank gi number 215490020, or containing a protein-coding portion thereof, e.g., the coding sequence thereof at nucleotides 505-1371, a natural variant thereof, or a protein encoded by such a polynucleotide.

The NOL3 (nucleolar protein 3 (apoptosis repressor with CARD domain)) biomarkers include human NOL3 gene products, including natural variants, e.g., allelic variants, and homologs and analogs thereof. In one example, the NOL3 biomarker is a polynucleotide having the nucleotide sequence set forth in SEQ ID NO: 218 (referenced at GenBank gi number 297632351), or containing a protein-coding portion thereof, e.g., the coding sequence thereof at nucleotides 194-853, a natural variant thereof, or a protein encoded by such a polynucleotide.

The NUDT3 (nudix (nucleoside diphosphate linked moiety X)-type motif 3) biomarkers include human NUDT3 gene products, including natural variants, e.g., allelic variants, and homologs and analogs thereof. In one example, the NUDT3 biomarker is a polynucleotide having the nucleotide sequence set forth in SEQ ID NO: 219 (referenced at GenBank gi number 322302838), or containing a protein-coding portion thereof, e.g., the coding sequence thereof at nucleotides 319-837 of SEQ ID NO: 219, a natural variant thereof, or a protein encoded by such a polynucleotide.

The OAZ2 (ornithine decarboxylase antizyme 2) biomarkers include human OAZ2 gene products, including natural variants, e.g., allelic variants, and homologs and analogs thereof. In one example, the OAZ2 biomarker is a polynucleotide having the nucleotide sequence set forth in SEQ ID NO: 220 (referenced at GenBank gi number 161377456), or containing a protein-coding portion thereof, e.g., the coding sequence thereof at nucleotides 216-311 and 313-786, or a natural variant thereof, or a protein encoded by such a polynucleotide.

The PANK2 (pantothenate kinase 2) biomarkers include human PANK2 gene products, including natural variants, e.g., allelic variants, and homologs and analogs thereof. In one example, the PANK2 biomarker is a polynucleotide having the nucleotide sequence set forth in SEQ ID NO: 221 (referenced at GenBank gi number 85838514), or containing a protein-coding portion thereof, e.g., the coding sequence thereof at nucleotides 312-1151, a natural variant thereof, or a protein encoded by such a polynucleotide.

The PHF21A (PHD finger protein 21A) biomarkers include human PHF21A gene products, including natural variants, e.g., allelic variants, and homologs and analogs thereof. In one example, the PHF21A biomarker is a polynucleotide having the nucleotide sequence set forth in SEQ ID NO: 222 (referenced at GenBank gi number 156546893), or containing a protein-coding portion thereof, e.g., the coding sequence thereof at nucleotides 625-2667, a natural variant thereof, or a protein encoded by such a polynucleotide.

The PKD1 (polycystic kidney disease 1 (autosomal dominant)) biomarkers include human PKD1 gene products, including natural variants, e.g., allelic variants, and homologs and analogs thereof. In one example, the PKD1 biomarker is a polynucleotide having the nucleotide sequence set forth in SEQ ID NO: 223, or the sequence referenced at GenBank gi Number 205360961, or containing a protein-coding portion thereof of such a sequence, e.g., the coding sequence thereof at nucleotides 210-13118 or nucleotides 210-13117 of GenBank gi Number 205360961 or SEQ ID NO: 223, a natural variant thereof, or a protein encoded by such a polynucleotide.

The PLD3 (phospholipase D family, member 3) biomarkers include human PLD3 gene products, including natural variants, e.g., allelic variants, and homologs and analogs thereof. In one example, the PLD3 biomarker is a polynucleotide having the nucleotide sequence set forth in SEQ ID NO: 224 (referenced at GenBank gi number 166197669), or containing a protein-coding portion thereof, e.g., the coding sequence thereof at nucleotides 399-1871 of SEQ ID NO: 224, a natural variant thereof, or a protein encoded by such a polynucleotide.

The PQBP1 (polyglutamine binding protein 1) biomarkers include human PQBP1 gene products, including natural variants, e.g., allelic variants, and homologs and analogs thereof. In one example, the PQBP1 biomarker is a polynucleotide having the nucleotide sequence set forth in SEQ ID NO: 225 (referenced at GenBank gi number 74027246), or containing a protein-coding portion thereof, e.g., the coding sequence thereof at nucleotides 122-919, a natural variant thereof, or a protein encoded by such a polynucleotide.

The RNF41 (polyglutamine binding protein 1) biomarkers include human RNF41 gene products, including natural variants, e.g., allelic variants, and homologs and analogs thereof. In one example, the RNF41 biomarker is a polynucleotide having the nucleotide sequence set forth in SEQ ID NO: 227 (referenced at GenBank gi number 338827617), or containing a protein-coding portion thereof, e.g., the coding sequence thereof at nucleotides 320-1273 of SEQ ID NO: 227, a natural variant thereof, or a protein encoded by such a polynucleotide.

The RSF1 (remodeling and spacing factor 1) biomarkers include human RSF1 gene products, including natural variants, e.g., allelic variants, and homologs and analogs thereof. In one example, the RSF1 biomarker is a polynucleotide having the nucleotide sequence set forth in SEQ ID NO: 228 (referenced at GenBank gi number 38788332), or containing a protein-coding portion thereof, e.g., the coding sequence thereof at nucleotides 121-4446 of SEQ ID NO: 228, a natural variant thereof, or a protein encoded by such a polynucleotide.

The RTN2 (reticulon 2) biomarkers include human RTN2 gene products, including natural variants, e.g., allelic variants, and homologs and analogs thereof. In one example, the RTN2 biomarker is a polynucleotide having the nucleotide sequence set forth in SEQ ID NO: 229 (referenced at GenBank gi number 46255010), or containing a protein-coding portion thereof, e.g., the coding sequence thereof at nucleotides 229-1866 of SEQ ID NO: 229, a natural variant thereof, or a protein encoded by such a polynucleotide.

The SMARCD3 (SWI/SNF related, matrix associated, actin dependent regulator of chromatin, subfamily d, member 3p) biomarkers include human SMARCD3 gene products, including natural variants, e.g., allelic variants, and homologs and analogs thereof. In one example, the SMARCD3 biomarker is a polynucleotide having the nucleotide sequence set forth in SEQ ID NO: 232 (referenced at GenBank gi number 51477701), or containing a protein-coding portion thereof, e.g., the coding sequence thereof at nucleotides 102-1553, a natural variant thereof, or a protein encoded by such a polynucleotide.

The SPATA7 (spermatogenesis associated 7) biomarkers include human SPATA7 gene products, including natural variants, e.g., allelic variants, and homologs and analogs thereof. In one example, the SPATA7 biomarker is a polynucleotide having the nucleotide sequence set forth in SEQ ID NO: 233 (referenced at GenBank gi number 295789142), or containing a protein-coding portion thereof, e.g., the coding sequence thereof at nucleotides 176-1879 of SEQ ID NO: 233, a natural variant thereof, or a protein encoded by such a polynucleotide.

The SST1 (somatostatin receptor 1) biomarkers include human SST1 gene products, including natural variants, e.g., allelic variants, and homologs and analogs thereof. In one example, the SST1 biomarker is a polynucleotide having the nucleotide sequence set forth in SEQ ID NO: 234 (referenced at GenBank gi number 33946330), or containing a protein-coding portion thereof, e.g., the coding sequence thereof at nucleotides 618-1793 of SEQ ID NO: 234, a natural variant thereof, or a protein encoded by such a polynucleotide.

The SST3 (somatostatin receptor 3) biomarkers include human SST3 gene products, including natural variants, e.g., allelic variants, and homologs and analogs thereof. In one example, the SST3 biomarker is a polynucleotide having the nucleotide sequence set forth in SEQ ID NO: 235 (referenced at GenBank gi number 44890055), or containing a protein-coding portion thereof, e.g., the coding sequence thereof at nucleotides 526-1782 of SEQ ID NO: 235, a natural variant thereof, or a protein encoded by such a polynucleotide.

The SST4 (somatostatin receptor 4) biomarkers include human SST3 gene products, including natural variants, e.g., allelic variants, and homologs and analogs thereof. In one example, the SST3 biomarker is a polynucleotide having the nucleotide sequence set forth in SEQ ID NO: 236 (referenced at GenBank gi number 149944553), or containing a protein-coding portion thereof, e.g., the coding sequence thereof at nucleotides 65-1231, a natural variant thereof, or a protein encoded by such a polynucleotide.

The SST5 (somatostatin receptor 5) biomarkers include human SST3 gene products, including natural variants, e.g., allelic variants, and homologs and analogs thereof. In one example, the SST3 biomarker is a polynucleotide having the nucleotide sequence set forth in SEQ ID NO: 237 (referenced at GenBank gi number 289547751), or containing a protein-coding portion thereof, e.g., the coding sequence thereof at nucleotides 89-1183, a natural variant thereof, or a protein encoded by such a polynucleotide.

The TECPR2 (tectonin beta-propeller repeat containing 2) biomarkers include human TECPR2 gene products, including natural variants, e.g., allelic variants, and homologs and analogs thereof. In one example, the TECPR2 biomarker is a polynucleotide having the nucleotide sequence set forth in SEQ ID NO: 238 (referenced at GenBank gi number 289547516), or containing a protein-coding portion thereof, e.g., the coding sequence thereof at nucleotides 227-4030 of SEQ ID NO: 238, a natural variant thereof, or a protein encoded by such a polynucleotide.

The TRMT112 (tRNA methyltransferase 11-2 homolog (*S. cerevisiae*)) biomarkers include human TRMT112 gene products, including natural variants, e.g., allelic variants, and homologs and analogs thereof. In one example, the TRMT112 biomarker is a polynucleotide having the nucleotide sequence set forth in SEQ ID NO: 241 (referenced at GenBank gi number 7705476), or containing a protein-coding portion thereof, e.g., the coding sequence thereof at nucleotides 36-413 of SEQ ID NO: 241, a natural variant thereof, or a protein encoded by such a polynucleotide.

The VPS13C (vacuolar protein sorting 13 homolog C (*S. cerevisiae*)) biomarkers include human VPS13C gene products, including natural variants, e.g., allelic variants, and homologs and analogs thereof. In one example, the VPS13C biomarker is a polynucleotide having the nucleotide sequence set forth in SEQ ID NO: 242 (referenced at GenBank gi number 308081495), or containing a protein-coding portion thereof, e.g., the coding sequence thereof at nucleotides 92-10978, a natural variant thereof, or a protein encoded by such a polynucleotide.

The WDFY3 (WD repeat and FYVE domain containing 3) biomarkers include human WDFY3 gene products, including natural variants, e.g., allelic variants, and homologs and analogs thereof. In one example, the WDFY3 biomarker is a polynucleotide having the nucleotide sequence set forth in SEQ ID NO: 243, or the sequence referenced at GenBank gi number 195972885, or containing a protein-coding portion thereof, e.g., the coding sequence at nucleotides 409-10988 of SEQ ID NO: 243 or GenBank gi number 195972885, a natural variant thereof, or a protein encoded by such a polynucleotide.

The ZFHX3 (zinc finger homeobox 3) biomarkers include human ZFHX3 gene products, including natural variants, e.g., allelic variants, and homologs and analogs thereof. In one example, the ZFHX3 biomarker is a polynucleotide having the nucleotide sequence set forth in SEQ ID NO: 244 (referenced at GenBank gi number 258613986), or containing a protein-coding portion thereof, e.g., the coding sequence thereof at nucleotides 130-8499 of SEQ ID NO: 244, a natural variant thereof, or a protein encoded by such a polynucleotide.

The ZXDC (ZXD family zinc finger C) biomarkers include human ZXDC gene products, including natural variants, e.g., allelic variants, and homologs and analogs thereof. In one example, the ZXDC biomarker is a polynucleotide having the nucleotide sequence set forth in SEQ ID NO: 245 (referenced at GenBank gi number 217035098), or containing a protein-coding portion thereof, e.g., the coding sequence thereof at nucleotides 55-2187 of SEQ ID NO: 245, a natural variant thereof, or a protein encoded by such a polynucleotide.

The ZZZ3 (zinc finger, ZZ-type containing 3) biomarkers include human ZZZ3 gene products, including natural variants, e.g., allelic variants, and homologs and analogs thereof. In one example, the ZZZ3 biomarker is a polynucleotide having the nucleotide sequence set forth in SEQ ID NO: 246 (referenced at GenBank gi number 141803158), or containing a protein-coding portion thereof, e.g., the coding sequence thereof at nucleotides 477-3188 of SEQ ID NO: 246, a natural variant thereof, or a protein encoded by such a polynucleotide.

In some aspects, the provided methods and compositions detect a GEP-NEN biomarker; in some examples, the provided methods and compositions detect panels of GEP-NEN biomarkers, including two or more GEP-NEN biomarkers, such as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers.

For example, provided are methods and compositions that detect at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following sets of biomarkers:

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, ZZZ3, APLP2, CD59, ARAF1, BRAF1, KRAS, and RAF1 gene products;

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3 gene products; and APLP2, ARAF1, BRAF, CD59, CTGF, FZD7, Ki67, KRAS, NAP1L1, PNMA2, RAF1, TPH1, VMAT1, and VMAT2 gene products.

Also provided are methods and compositions that detect at least 2, 3, 4, 5, 6, 7, 8, 9, 10, 11, 12, 13, 14, 15, 16, 17, 18, 19, 20, 21, 22, 23, 24, 25, 26, 27, 28, or 29 of the following sets of biomarkers:

APLP2, ARAF1, BRAF1, CD59, CgA, CTGF, CXCL14, FZD7, GRIA2, HOXC6, Ki-67; Kiss1, KRAS, MAGE-D2, MTA1, NAP1L1, NKX2-3, NRP2, OR51E1, PNMA2, PTPRN2, RAF1, SCG5, SPOCK1, Survivin, TPH1, VMAT1, VMAT2); and X2BTB48;

APLP2, ARAF1, BRAF1, CD59, KRAS, RAF1, CXCL14, GRIA2, HOXC6, NKX2-3, OR51E1, PNMA2, PTPRN2, SCG5, SPOCK1, and X2BTB48;

CXCL14, GRIA2, HOXC6, NKX2-3, OR51E1, PNMA2, PTPRN2, SCG5, SPOCK1, and X2BTB48; or CgA (chromogranin A), CTGF, FZD7 (frizzled homolog 7), Ki-67 (a marker of proliferation), Kiss1 (Kiss1 metastasis suppressor), MAGE-D2 (melanoma antigen family D2), MTA1 (metastasis-associated 1), NAP1L1, NRP2 (neuropilin 2), Tph1, VMAT1, VMAT2, and Survivin.

In some aspects, the panels further include CD164.

In some aspects, they further include NALP or other known biomarkers.

In some embodiments, the panel of polynucleotides further includes one or more polynucleotide able to specifically hybridize to "housekeeping," or reference genes, for example, genes for which differences in expression is known or not expected to correlate with differences in the variables analyzed, for example, with the presence or absence of GEP-NEN or other neoplastic disease, differentiation of various GEP-NEN sub-types, metastasis, mucosal or other tissue types, prognostic indications, and/or other phenotype, prediction, or outcome. In some aspects, expression levels of such housekeeping genes are detected and used as an overall expression level standards, such as to normalize expression data obtained for GEP-NEN biomarkers across various samples.

Housekeeping genes are well known in the art. Typically, the housekeeping genes include one or more genes characterized as particularly appropriate for analyzing GEP-NEN samples, such as ALG9, TFCP2 and ZNF410. See Kidd M, et al., "GeneChip, geNorm and Gastrointestinal tumors: novel reference genes for real-time PCR." Physiol Genomics 2007; 30:363-70. Other housekeeping genes and polynucleotides are well known in the art and include glyceraldehyde-3-phosphate dehydrogenase (GAPDH), hypoxanthine phosphoribosyltransferase (HPRT) and 18S RNA.

The ALG9 housekeeping genes include human ALG9 (asparagine-linked glycosylation 9, alpha-1,2-mannosyltransferase homolog) gene products, including natural variants, e.g., allelic variants, and homologs and analogs thereof. In one example, the ALG9 housekeeper is a polynucleotide having the nucleotide sequence set forth in SEQ ID NO: 35 and referenced at GenBank gi no.: 118026920 or containing the coding region thereof of nucleotides 100-1956 of SEQ ID NO: 35, a natural variant thereof, or a protein encoded by such a polynucleotide.

The TFCP2 housekeeping genes include human TFCP2 (transcription factor CP2) gene products, including natural variants, e.g., allelic variants, and homologs and analogs thereof. In one example, the TFCP2 housekeeper is a polynucleotide having the nucleotide sequence set forth in SEQ ID NO: 36 and referenced at GenBank gi no. 291219872, or containing the coding region thereof at nucleotides 722-2230 of SEQ ID NO: 36, a natural variant thereof, or a protein encoded by such a polynucleotide.

The ZNF410 housekeeping genes include human ZNF410 (zinc finger protein 410) gene products, including natural variants, e.g., allelic variants, and homologs and analogs thereof. In one example, the ZNF410 housekeeper is a polynucleotide having the nucleotide sequence set forth in SEQ ID NO: 37 and referenced at GenBank gi no. 10863994, or containing the coding region thereof at nucleotides 183-1619 of SEQ ID NO: 37, a natural variant thereof, or a protein encoded by such a polynucleotide.

The GAPDH housekeeping genes include human GAPDH (glyceraldehyde-3-phosphate dehydrogenase) gene products, including natural variants, e.g., allelic variants, and homologs and analogs thereof. In one example, the GAPDH housekeeper is a polynucleotide having the nucleotide sequence set forth in SEQ ID NO: 38 and referenced at GenBank gi number 83641890 or containing the coding region thereof at nucleotides 103-1110 of SEQ ID NO: 38, a natural variant thereof, or a protein encoded by such a polynucleotide.

The 18S housekeeping genes include human 18S (Eukaryotic 18S rRNA), including natural variants, e.g., allelic variants, and homologs and analogs thereof. In one example, the 18S housekeeper is a polynucleotide having the nucleotide sequence set forth in SEQ ID NO: 39 and referenced at GenBank gi number 36162 or a natural variant thereof.

The HPRT housekeeping genes include human HPRT gene products, including natural variants, e.g., allelic variants, and homologs and analogs thereof. In one example, the HPRT housekeeper is a polynucleotide having the nucleotide sequence set forth in SEQ ID NO: 40, and referenced at GenBank gi no. 164518913, or containing the coding region thereof at nucleotides 168-824 of SEQ ID NO: 40, a natural variant thereof, or a protein encoded by such a polynucleotide.

The SLC25A3 housekeeping genes include human SLC25A3 (solute carrier family 25 (mitochondrial carrier; phosphate carrier), member 3) gene products, including natural variants, e.g., allelic variants, and homologs and analogs thereof. In one example, the SLC25A3 housekeeper is a polynucleotide having the nucleotide sequence set forth in SEQ ID NO: 247 and referenced at GenBank gi no.: 223718119, or containing a coding region thereof, e.g., the coding sequence thereof at nucleotides 121-1209 of SEQ ID NO: 247, a natural variant thereof, or a protein encoded by such a polynucleotide.

The VAPA housekeeping genes include human VAPA ((vesicle-associated membrane protein)-associated protein A) gene products, including natural variants, e.g., allelic variants, and homologs and analogs thereof. In one example, the VAPA housekeeper is a polynucleotide having the nucleotide sequence set forth in SEQ ID NO: 248 and referenced at GenBank gi no.: 94721249, or containing a coding region thereof, e.g., the coding sequence thereof at nucleotides 300-1184 of SEQ ID NO: 248, a natural variant thereof, or a protein encoded by such a polynucleotide.

The TXNIP housekeeping genes include human TXNIP (thioredoxin interacting protein) gene products, including natural variants, e.g., allelic variants, and homologs and analogs thereof. In one example, the TXNIP housekeeper is a polynucleotide having the nucleotide sequence set forth in SEQ ID NO: 249 and referenced at GenBank gi no.: 171184420, or containing a coding region thereof, e.g., the coding sequence thereof at nucleotides 342-1517 of SEQ ID NO: 249, a natural variant thereof, or a protein encoded by such a polynucleotide.

The ADD3 housekeeping genes include human ADD3 (adducin 3 (gamma)) gene products, including natural variants, e.g., allelic variants, and homologs and analogs thereof. In one example, the ADD3 housekeeper is a polynucleotide having the nucleotide sequence set forth in SEQ ID NO: 250 and referenced at GenBank gi no.: 62912451, or containing a coding region thereof, e.g., the coding sequence thereof at nucleotides 377-2497 of SEQ ID NO: 250, a natural variant thereof, or a protein encoded by such a polynucleotide.

The DAZAP2 housekeeping genes include human DAZAP2 (DAZ-associatod protein 2) gene products, including natural variants, e.g., allelic variants, and homologs and analogs thereof. In one example, the DAZAP2 housekeeper is a polynucleotide having the nucleotide sequence set forth in SEQ ID NO: 251 and referenced at GenBank gi no.: 211904132 or containing a coding region thereof, e.g., the coding sequence thereof at nucleotides 185-691, a natural variant thereof, or a protein encoded by such a polynucleotide.

The ACTG1 housekeeping genes include human ACTG1 (actin, gamma 1) gene products, including natural variants, e.g., allelic variants, and homologs and analogs thereof. In one example, the ACTG1 housekeeper is a polynucleotide having the nucleotide sequence set forth in SEQ ID NO: 252 and referenced at GenBank gi no.: 316659408, or containing a coding region thereof, e.g., the e.g., the coding sequence thereof at nucleotides 259-1386 of SEQ ID NO: 252, a natural variant thereof, or a protein encoded by such a polynucleotide.

The ACTB housekeeping genes include human ACTB (actin, beta) gene products, including natural variants, e.g., allelic variants, and homologs and analogs thereof. In one example, the ACTB housekeeper is a polynucleotide having the nucleotide sequence set forth in SEQ ID NO: 200 and referenced at GenBank gi no.: 168480144, or containing a coding region thereof, e.g., the coding sequence thereof at nucleotides 85-1212 of SEQ ID NO: 200, a natural variant thereof, or a protein encoded by such a polynucleotide.

The ATG4B housekeeping genes include human ACG4B (autophagy related 4 homolog B (*S. cerevisiae*)) gene products, including natural variants, e.g., allelic variants, and homologs and analogs thereof. In one example, the ACTG4B housekeeper is a polynucleotide having the nucleotide sequence set forth in SEQ ID NO: 203, or containing a coding region thereof, e.g., the coding sequence thereof at nucleotides 104-1285 of SEQ ID NO: 203, or the sequence referenced at GenBank gi no.: 47132610, a natural variant thereof, or a protein encoded by such a polynucleotide.

The ARF1 housekeeping genes include human ARF1 (ADP-ribosylation factor 1) gene products, including natural variants, e.g., allelic variants, and homologs and analogs thereof. In one example, the ARF1 housekeeper is a polynucleotide having the nucleotide sequence set forth in SEQ ID NO: 202 and referenced at GenBank gi no.: 66879659 or containing a coding region thereof, e.g., the coding sequence thereof at nucleotide residues 229-774, a natural variant thereof, or a protein encoded by such a polynucleotide.

The HUWE1 housekeeping genes include human HUWE1 (HECT, UBA and WWE domain containing 1) gene products, including natural variants, e.g., allelic variants, and homologs and analogs thereof. In one example, the HUWE1 housekeeper is a polynucleotide having the nucleotide sequence set forth in SEQ ID NO: 214 and referenced at GenBank gi no.: 195963314, or containing the coding region thereof, e.g., the coding sequence thereof at nucleotides 403-13527, a natural variant thereof, or a protein encoded by such a polynucleotide.

The MORF4L1 housekeeping genes include human MORF4L1 (mortality factor 4 like 1) gene products, including natural variants, e.g., allelic variants, and homologs and analogs thereof. In one example, the MORF4L1 housekeeper is a polynucleotide having the nucleotide sequence set forth in SEQ ID NO: 216 and referenced at GenBank gi no.: 45643136, or containing a coding region thereof, e.g., the coding sequence at nucleotides 189-1160, a natural variant thereof, or a protein encoded by such a polynucleotide.

The RHOA housekeeping genes include human RHOA (ras homolog gene family, member A) gene products, including natural variants, e.g., allelic variants, and homologs and analogs thereof. In one example, the RHOA housekeeper is a polynucleotide having the nucleotide sequence set forth in SEQ ID NO: 226 and referenced at GenBank gi no.: 50593005, or containing a coding region thereof, e.g., the coding sequence thereof at nucleotides 277-858, a natural variant thereof, or a protein encoded by such a polynucleotide.

The SERP1 housekeeping genes include human SERP1 (stress-associated endoplasmic reticulum protein 1) gene products, including natural variants, e.g., allelic variants, and homologs and analogs thereof. In one example, the SERP1 housekeeper is a polynucleotide having the nucleotide sequence set forth in SEQ ID NO: 230 and referenced at GenBank gi no.: 109809760, or containing a coding region thereof, e.g., the coding sequence thereof at nucleotides 507-707, a natural variant thereof, or a protein encoded by such a polynucleotide.

The SKP1 housekeeping genes include human SKP1 (S-phase kinase-associated protein 1) gene products, including natural variants, e.g., allelic variants, and homologs and analogs thereof. In one example, the SKP1 housekeeper is a polynucleotide having the nucleotide sequence set forth in SEQ ID NO: 231 and referenced at GenBank gi no.: 160420325, or containing a coding region thereof, e.g., the coding sequence thereof at nucleotides 180-662, a natural variant thereof, or a protein encoded by such a polynucleotide.

The TOX4 housekeeping genes include human TOX4 (TOX high mobility group box family member 4) gene products, including natural variants, e.g., allelic variants, and homologs and analogs thereof. In one example, the TOX4 housekeeper is a polynucleotide having the nucleotide sequence set forth in SEQ ID NO: 239 and referenced at GenBank gi no.: 99077116, or containing a coding region thereof, e.g., the coding sequence thereof at nucleotides 104-1969, a natural variant thereof, or a protein encoded by such a polynucleotide.

The TPT1 housekeeping genes include human TPT1 (tumor protein, translationally-controlled 1) gene products, including natural variants, e.g., allelic variants, and homologs and analogs thereof. In one example, the TPT1 housekeeper is a polynucleotide having the nucleotide sequence set forth in SEQ ID NO: 240 and referenced at GenBank gi no.: 141801911, or containing a coding region thereof, e.g., the coding sequence thereof at nucleotides 94-612, a natural variant thereof, or a protein encoded by such a polynucleotide.

D. Methods and Agents for Detecting the GEP-NEN Biomarkers, Tumors, and Cells Also provided are methods, compositions, and systems, for the detection of the GEP-NEN biomarkers and for identifying, isolating, and enriching tumors and cells that express the GEP-NEN biomarkers. For example, provided are agents, sets of agents, and systems for detecting the GEP-NEN biomarkers and methods for use of the same, including for diagnostic and prognostic uses.

1. Agents and Systems for Detecting the Biomarkers

In one embodiment, the agents are proteins, polynucleotides or other molecules which specifically bind to or specifically hybridize to the GEP-NEN biomarkers. The agents include polynucleotides, such as probes and primers, e.g. sense and antisense PCR primers, having identity or complementarity to the polynucleotide biomarkers, such as mRNA, and proteins, such as antibodies, which specifically bind to such biomarkers. Sets and kits containing the agents, such as agents specifically hybridizing to or binding the panel of biomarkers, also are provided.

Thus, the systems, e.g., microarrays, sets of polynucleotides, and kits, provided herein include those with nucleic acid molecules, typically DNA oligonucleotides, such as primers and probes, the length of which typically varies between 15 bases and several kilo bases, such as between 20 bases and 1 kilobase, between 40 and 100 bases, and between 50 and 80 nucleotides or between 20 and 80 nucleotides. In one aspect, most (i.e. at least 60% of) nucleic acid molecules of a nucleotide microarray, kit, or other system, are capable of hybridizing to GEP-NEN biomarkers.

In one example, systems containing polynucleotides that specifically hybridize to the biomarkers, e.g., nucleic acid microarrays, are provided to detect and measure changes in expression levels and determine expression profiles of the biomarkers according to the provided methods. Among such systems, e.g., microarrays, are those comprising polynucleotides able to hybridize to at least as at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, and/or all of the following sets of biomarkers:

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, ZZZ3, APLP2, CD59, ARAF1, BRAF1, KRAS, and RAF1 gene products;

AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, and ZZZ3 gene products; and APLP2, ARAF1, BRAF, CD59, CTGF, FZD7, Ki67, KRAS, NAP1L1, PNMA2, RAF1, TPH1, VMAT1, and VMAT2 gene products; or at least 2, 3, 4, 5, 6, 7, 8, 9, 10, 11, 12, 13, 14, 15, 16, 17, 18, 19, 20, 21, 22, 23, 24, 25, 26, 27, 28, or 29 of APLP2, ARAF1, BRAF1, CD59, CgA, CTGF, CXCL14, FZD7, GRIA2, HOXC6, Ki-67; Kiss1, KRAS, MAGE-D2, MTA1, NAP1L1, NKX2-3, NRP2, OR51E1, PNMA2, PTPRN2, RAF1, SCG5, SPOCK1, Survivin, TPH1, VMAT1, VMAT2); and X2BTB48; or of the biomarkers APLP2, ARAF1, BRAF1, CD59, KRAS, RAF1, CXCL14, GRIA2, HOXC6, NKX2-3, OR51E1, PNMA2, PTPRN2, SCG5, SPOCK1, and X2BTB48; or of the biomarkers CXCL14, GRIA2, HOXC6, NKX2-3, OR51E1, PNMA2, PTPRN2, SCG5, SPOCK1, and X2BTB48.

In some aspects, at least 60%, or at least 70%, at least 80%, or more, of the nucleic acid molecules of the system, e.g., microarray, are able to hybridize to biomarkers in the panel of biomarkers. In one example, probes immobilized on such nucleotide microarrays comprise at least 2, and typically at least 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more nucleic acid molecules able to hybridize to at least 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 80, 85, 90, 95, or 100 or more biomarkers, such as to at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, or 51, or more of the biomarkers, where each of the nucleic acid molecules is capable of specifically hybridizing to a different one of the biomarkers, such that at least that many different biomarkers can be bound.

In one example, the remaining nucleic acid molecules, such as 40% or at most 40% of the nucleic acid molecules on the microarray or in the set of polynucleotides are able to hybridize to a set of reference genes or a set of normalization genes (such as housekeeping genes), for example, for normalization in order to reduce systemic bias. Systemic bias results in variation by inter-array differences in overall performance, which can be due to for example inconsistencies in array fabrication, staining and scanning, and variation between labeled RNA samples, which can be due for example to variations in purity. Systemic bias can be introduced during the handling of the sample in a microarray experiment. To reduce systemic bias, the determined RNA levels are preferably corrected for background non-specific hybridization and normalized.

The use of such reference probes is advantageous but not mandatory. In one embodiment a set of polynucleotides or system, e.g., microarray, is provided wherein at least 90% of the nucleic acid sequences are able to hybridize to the GEP-NEN biomarkers; further embodiments include such systems and sets in which at least 95% or even 100% of the polynucleotides hybridize to the biomarkers.

Disclosed in the Examples are exemplary suitable polynucleotides, such as PCR primers. Other nucleic acid probes and primers, able to hybridize to different regions of the biomarkers are of course also suitable for use in connection with the provided systems, kits and methods.

2. Detection of the Biomarkers

Also provided are methods for detecting and quantifying the biomarkers, including detecting the presence, absence, amount or relative amount, such as expression levels or expression profile of the biomarkers. Typically, the methods are nucleic acid based methods, for example, measuring the presence, amount or expression levels of biomarker mRNA expression. Such methods typically are carried out by contacting polynucleotide agents to biological samples, such as test samples and normal and reference samples, for example, to quantify expression levels of nucleic acid biomarkers (e.g., mRNA) in the samples.

Detection and analysis of biomarkers according to the provided embodiments can be performed with any suitable method known in the art. For example, where the biomarkers are RNA biomarkers, RNA detection and quantification methods are used.

Exemplary methods for quantifying or detecting nucleic acid expression levels, e.g., mRNA expression, are well known, and include northern blotting and in situ hybridization (Parker and Barnes, *Methods in Molecular Biology* 106:247-283, 1999); RNAse protection assays (Hod, *Biotechniques* 13:852-854, 1992); and quantitative or semi-quantitative reverse transcription polymerase chain reaction (RT-PCR) (Weis et al., *Trends in Genetics* 8:263-264, 1992), representative methods for sequencing-based gene expression analysis include Serial Analysis of Gene Expression (SAGE), and gene expression analysis by massively parallel signature sequencing (MPSS).

Therefore, in one embodiment, expression of the biomarker or biomarker panel includes RNA expression; the methods include determining levels of RNA of the biomarkers, such as RNA obtained from and/or present in a sample of a patient, and performing analysis, diagnosis, or predictive determinations based upon the RNA expression levels determined for the biomarkers or panel of biomarkers.

RNA samples can be processed in numerous ways, as is known to those in the art. Several methods are well known for isolation of RNA from samples, including guanidinium thiocyanate-phenol-chloroform extraction, which may be carried out using the TRIZOL® reagent, a proprietary formulation (see Chomczynski P, Sacchi N (2006). "The single-step method of RNA isolation by acid guanidinium thiocyanate-phenol-chloroform extraction: twenty-something years on". *Nat Protoc* 1 (2): 581-5). In this method, TRIZOL® is used to extract RNA and DNA; chloroform and centrifugation are used to separate RNA from other nucleic acids, followed by a series of washes with ethanol for cleanup of the RNA sample.

The RNA samples can be freshly prepared from cells or tissues at the moment of harvesting; alternatively, they can be prepared from samples that stored at −70° C. until processed for sample preparation. Alternatively, tissues or cell samples can be stored under and/or subjected to other conditions known in the art to preserve the quality of the RNA, including fixation for example with formalin or similar agent; and incubation with RNase inhibitors such as RNAsin® (Pharmingen) or RNasecure® (Ambion); aqueous solutions such as RNAlater® (Assuragen), Hepes-Glutamic acid buffer mediated Organic solvent Protection Effect (HOPE), and RCL2 (Alphelys); and non-aqueous solutions such as Universal Molecular Fixative (Sakura Finetek USA Inc.). A chaotropic nucleic acid isolation lysis buffer (Boom method, Boom et al. J Clin Microbiol. 1990; 28:495-503) may also be used for RNA isolation.

In one embodiment, RNA is isolated from buffy coat by incubating samples with TRIZOL®, followed by RNA clean-up. RNA is dissolved in diethyl pyrocarbonate water and measured spectrophotometrically, and an aliquot analyzed on a Bioanalyzer (Agilent Technologies, Palo Alto, Calif.) to assess the quality of the RNA (Kidd M, et al. "The role of genetic markers—NAP1L1, MAGE-D2, and MTA1—in defining small-intestinal carcinoid neoplasia," *Ann Surg Oncol* 2006; 13(2):253-62). In another embodiment, RNA is isolated from plasma using the QIAamp RNA Blood Mini Kit; in some cases, this method allows better detection by real-time PCR of significantly more housekeeping genes from plasma compared to the TRIZOL® approach. In another embodiment, RNA is isolated directly from whole blood, for example, using the QIAamp RNA Blood Mini Kit in a similar manner.

Methods for isolating RNA from fixed, paraffin-embedded tissues as the RNA source are well-known and generally include mRNA isolation, purification, primer extension and amplification (for example: T. E. Godfrey et al., *J. Molec. Diagnostics* 2: 84-91 [2000]; K. Specht et al., *Am. J. Pathol.* 158: 419-29 [2001]). In one example, RNA is extracted from a sample such as a blood sample using the QIAamp RNA Blood Mini Kit RNA. Typically, RNA is extracted from tissue, followed by removal of protein and DNA and analysis of RNA concentration. An RNA repair and/or amplification step may be included, such as a step for reverse transcription of RNA for RT-PCR.

Expression levels or amounts of the RNA biomarkers may be determined or quantified by any method known in the art, for example, by quantifying RNA expression relative to housekeeping gene or with relation to RNA levels of other genes measured at the same time. Methods to determine RNA levels of genes are known to a skilled person and include, but are not limited to, Northern blotting, (quantitative) PCR, and microarray analysis.

Northern blotting may be performed for quantification of RNA of a specific biomarker gene or gene product, by hybridizing a labeled probe that specifically interacts with the RNA, following separation of RNA by gel electrophoresis. Probes are for example labeled with radioactive isotopes or chemiluminescent substrates. Quantification of the labeled probe that has interacted with said nucleic acid expression product serves as a measure for determining the level of expression. The determined level of expression can be normalized for differences in the total amounts of nucleic acid expression products between two separate samples with for instance an internal or external calibrator by comparing the level of expression of a gene that is known not to differ in expression level between samples or by adding a known quantity of RNA before determining the expression levels.

For RT-PCR, biomarker RNA is reverse transcribed into cDNA. Reverse transcriptase polymerase chain reaction (RT-PCR) is, for example, performed using specific primers that hybridize to an RNA sequence of interest and a reverse transcriptase enzyme. Furthermore, RT-PCR can be performed with random primers, such as for instance random hexamers or decamers which hybridize randomly along the RNA, or oligo d(T) which hybridizes to the poly(A) tail of mRNA, and reverse transcriptase enzyme.

In some embodiments, RNA expression levels of the biomarkers in a sample, such as one from a patient suffering from or suspected of suffering from GEP-NEN or associated symptom or syndrome, are determined using quantitative methods such as by real-time rt-PCR (qPCR) or microarray analysis. In some embodiments, quantitative Polymerase Chain Reaction (QPCR) is used to quantify the level of expression of nucleic acids. In one aspect, detection and determining expression levels of the biomarkers is carried out using RT-PCR, GeneChip analysis, quantitative real-time PCR (Q RT-PCR), or carcinoid tissue microarray (TMA) immunostaining/quantitation, for example, to compare biomarker RNA, e.g., mRNA, or other expression product, levels in different sample populations, characterize patterns of gene expression, to discriminate between closely related mRNAs, and to analyze RNA structure.

In one example, QPCR is performed using real-time PCR (RTPCR), where the amount of product is monitored during the amplification reaction, or by end-point measurements, in which the amount of a final product is determined. As is known to a skilled person, rtPCR is for instance performed by the use of a nucleic acid intercalator, such as for example ethidium bromide or SYBR® Green I dye, which interacts which all generated double stranded products resulting in an increase in fluorescence during amplification, or for instance by the use of labeled probes that react specifically with the generated double stranded product of the gene of interest. Alternative detection methods that can be used are provided by amongst other things dendrimer signal amplification, hybridization signal amplification, and molecular beacons.

In one embodiment, reverse transcription on total RNA is carried out using the High Capacity cDNA Archive Kit (Applied Biosystems (ABI), Foster City, Calif.) following the manufacturer's suggested protocol (briefly, using 2 micrograms of total RNA in 50 microliters water, mixing with 50 uL of 2×RT mix containing Reverse Transcription Buffer, deoxynucleotide triphosphate solution, random primers, and Multiscribe Reverse Transcriptase). RT reaction conditions are well known. In one example, the RT reaction is performed using the following thermal cycler conditions: 10 mins, 25° C.; 120 min., 37° C. (see Kidd M, et al., "The role of genetic markers—NAP1L1, MAGE-D2, and MTA1—in defining small-intestinal carcinoid neoplasia," *Ann Surg Oncol* 2006; 13(2):253-62).

For measurement of individual transcript levels, in one embodiment, Assays-on-Demand™ products are used with the ABI 7900 Sequence Detection System according to the manufacturer's suggestions (see Kidd M, Eick G, Shapiro M D, et al. Microsatellite instability and gene mutations in transforming growth factor-beta type II receptor are absent in small bowel carcinoid tumors. *Cancer* 2005; 103(2):229-36). In one example, cycling is performed under standard conditions, using the TaqMan® Universal PCR Master Mix Protocol, by mixing cDNA in 7.2 uL water, 0.8 uL 20•Assays-on-Demand primer and probe mix and 8 uL of 2× TaqMan Universal Master mix, in a 384-well optical reaction plate, under the following conditions: 50° C., 2 min.; 95° C.; 10 min.; 50 cycles at 95° C. for 15 min., 60° for 1 min (see Kidd M, et al., "The role of genetic markers—NAP1L1, MAGE-D2, and MTA1—in defining small-intestinal carcinoid neoplasia," *Ann Surg Oncol* 2006; 13(2):253-62).

Typically, results from real-time PCR are normalized, using internal standards and/or by comparison to expression levels for housekeeping genes. For example, in one embodiment, Raw $\Delta C_T$ (delta $C_T$=change in cycle time as a function of amplification) data from QPCR as described above is normalized using well-known methods, such as geNorm (see Vandesompele J, De Preter K, Pattyn F, et al. Accurate normalization of real-time quantitative RT-PCR data by geometric averaging of multiple internal control genes. *Genome Biol* 2002; 3(7):RESEARCH0034). Normalization by house-keeping gene expression levels is also well-known. See Kidd M, et al., "GeneChip, geNorm, and gastrointestinal tumors: novel reference genes for real-time PCR," *Physiol Genomics* 2007; 30(3):363-70.

Microarray analysis involves the use of selected nucleic acid molecules that are immobilized on a surface. These nucleic acid molecules, termed probes, are able to hybridize to nucleic acid expression products. In a preferred embodiment the probes are exposed to labeled sample nucleic acid, hybridized, washed and the (relative) amount of nucleic acid expression products in the sample that are complementary to a probe is determined. Microarray analysis allows simultaneous determination of nucleic acid expression levels of a large number of genes. In a method according to the invention it is preferred that at least 5 genes according to the invention are measured simultaneously.

Background correction can be performed for instance according to the "offset" method that avoids negative intensity values after background subtraction. Furthermore, normalization can be performed in order to make the two channels on each single array comparable for instance using global loess normalization, and scale normalization which ensures that the log-ratios are scaled to have the same median-absolute-deviation (MAD) across arrays.

Protein levels may, for example, be measured using antibody-based binding assays. Enzyme labeled, radioactively labeled or fluorescently labeled antibodies may be used for detection of protein. Exemplary assays include enzyme-linked immunosorbent assays (ELISA), radio-immuno assays (RIA), Western Blot assays and immunohistochemical staining assays. Alternatively, in order to determine the expression level of multiple proteins simultaneously protein arrays such as antibody-arrays are used.

Typically, the biomarkers and housekeeping markers are detected in a biological sample, such as a tissue or fluid sample, such as a blood, such as whole blood, plasma, serum, stool, urine, saliva, tears, serum or semen sample, or a sample prepared from such a tissue or fluid, such as a cell preparation, including of cells from blood, saliva, or tissue, such as intestinal mucosa, tumor tissue, and tissues containing and/or suspected of containing GEP-NEN metastases or shed tumor cells, such as liver, bone, and blood. In one embodiment, a specific cell preparation is obtained by fluorescence-activated cell sorting (FACS) of cell suspensions or fluid from tissue or fluid, such as mucosa, e.g., intestinal mucosa, blood or buffy coat samples.

In some embodiments, the sample is taken from a GEP-NEN patient, a patient suspected of having GEP-NEN, a patient having and/or suspected of having cancer generally, a patient exhibiting one or more GEP-NEN symptoms or syndromes or determined to be at-risk for GEP-NEN, or a GEP-NEN patient undergoing treatment or having completed treatment, including patients whose disease is and/or is thought to be in remission.

In other embodiments, the sample is taken from a human without GEP-NEN disease, such as a healthy individual or an individual with a different type of cancer, such as an adenocarcinoma, for example, a gastrointestinal adenocarcinoma or one of the breast, prostate, or pancreas, or a gastric or hepatic cancer, such as esophageal, pancreatic, gallbladder, colon, or rectal cancer.

In some examples, the methods and systems distinguish between GEP-NEN and other cancers, such as adenocarcinomas, including gastrointestinal adenocarcinoma or one of the breast, prostate, or pancreas, or a gastric or hepatic cancer, such as esophageal, pancreatic, gallbladder, colon, or rectal cancer. In other embodiments, the methods and systems differentiate between GEP-NENs of different sites, such as between GEP-NENs of the small intestine and those of the pancreas. Such embodiments are useful, for example, to determine the primary location of a tumor where it is unknown and to determine prognosis (particularly because GEP-NEN tumors can exhibit significantly different prognosis depending upon site of origin). In some embodiments, the methods and systems differentiate between GEP-NENs of different sites, e.g., pancreatic and small intestinal tumors, with at least 80, 85, 90, 91, 92, or greater accuracy. In other embodiments, the methods can diagnose or detect adenocarcinomas with neuroendocrine components.

In some embodiments, the sample is taken from the GEP-NEN tumor or metastasis. In other embodiments, the sample is taken from the GEP-NEN patient, but from a tissue or fluid not expected to contain GEP-NEN or GEP-NEN cells; such samples may be used as reference or normal samples. Alternatively, the normal or reference sample may be a tissue or fluid or other biological sample from a patient without GEP-NEN disease, such as a corresponding tissue, fluid or other sample, such as a normal blood sample, a normal small intestinal (SI) mucosa sample, a normal enterochromaffin (EC) cell preparation.

In some embodiments, the sample is a whole blood sample. As neuroendocrine tumors metastasize, they typically shed cells into the blood. Accordingly, detection of the panels of GEP-NEN biomarkers provided herein in plasma and blood samples may be used for identification of GEP-NENs at an early time point and for predicting the presence of tumor metastases, e.g., even if anatomic localization studies are negative. Accordingly, the provided agents and methods are useful for early diagnosis.

Thus, in some embodiments, the methods can identify a GEP-NEN molecular signature or expression profile in 1 mL or about 1 mL of whole blood. In some aspects, the molecular signature or expression profile is stable for up to four hours (for example, when samples are refrigerated 4-8° C. following phlebotomy) prior to freezing. In one aspect, the approach able to diagnose, prognose or predict a given GEP-NEN-associated outcome using a sample obtained from tumor tissue is also able to make the same diagnosis, prognosis, or prediction using a blood sample.

A number of existing detection and diagnostic methodologies require 7 to 10 days to produce a possible positive result, and can be costly. Thus, in one aspect, the provided methods and compositions are useful in improving simplicity and reducing costs associated with GEP-NEN diagnosis, and make early-stage diagnosis feasible.

Thus in one example, the biomarkers are detected in circulation, for example by detection in a blood sample, such as a serum, plasma, cells, e.g., peripheral blood mononuclear cells (PBMCs), obtained from buffy coat, or whole blood sample.

Tumor-specific transcripts have been detected in whole blood in some cancers. See Sieuwerts A M, et al., "Molecular characterization of circulating tumor cells in large quantities of contaminating leukocytes by a multiplex real-time PCR," *Breast Cancer Res Treat* 2009; 118(3):455-68 and Mimori K, et al., "A large-scale study of MT1-MMP as a marker for isolated tumor cells in peripheral blood and bone marrow in gastric cancer cases," *Ann Surg Oncol* 2008; 15(10):2934-42.

The CellSearch™ CTC Test (Veridex LLC) (described by Kahan L., "Medical devices; immunology and microbiology devices; classification of the immunomagnetic circulating cancer cell selection and enumeration system. Final rule," *Fed Regist* 2004; 69:26036-8) uses magnetic beads coated with EpCAM-specific antibodies that detects epithelial cells (CK-8/18/19) and leukocytes (CD45), as described by Sieuwerts A M, Kraan J, Bolt-de Vries J, et al., "Molecular characterization of circulating tumor cells in large quantities of contaminating leukocytes by a multiplex real-time PCR," *Breast Cancer Res Treat* 2009; 118(3):455-68. This method has been used to detect circulating tumor cells (CTCs), and monitoring disease progression and therapy efficacy in metastatic prostate (Danila D C, Heller G, Gignac G A, et al. Circulating tumor cell number and prognosis in progressive castration-resistant prostate cancer. *Clin Cancer Res* 2007; 13(23):7053-8), colorectal (Cohen S J, Alpaugh R K, Gross S, et al. Isolation and characterization of circulating tumor cells in patients with metastatic colorectal cancer. *Clin Colorectal Cancer* 2006; 6(2):125-32. and breast (Cristofanilli M, Budd G T, Ellis M J, et al., Circulating tumor cells, disease progression, and survival in metastatic breast cancer. *N Engl J Med* 2004; 351(8):781-91).

This and other existing approaches have not been entirely satisfactory for detection of GEP-NEN cells, which can exhibit variable expression and/or not express cytokeratin (See Van Eeden S, et al, Classification of low-grade neuroendocrine tumors of midgut and unknown origin," *Hum Pathol* 2002; 33(11):1126-32; Cai Y C, et al., "Cytokeratin 7 and 20 and thyroid transcription factor 1 can help distinguish pulmonary from gastrointestinal carcinoid and pancreatic endocrine tumors," *Hum Pathol* 2001; 32(10):1087-93, and studies described herein, detecting EpCAM transcript expression in two of twenty-nine GEP-NEN samples).

Factors to consider in the available detection methods for circulating tumor cells are relatively low numbers of the cells in peripheral blood, typically about 1 per $10^6$ peripheral blood mononuclear cells (PBMCs) (see Ross A A, et al. "Detection and viability of tumor cells in peripheral blood stem cell collections from breast cancer patients using immunocytochemical and clonogenic assay techniques," *Blood* 1993; 82(9):2605-10), and the potential for leukocyte contamination. See Sieuwerts A M, et al. "Molecular characterization of circulating tumor cells in large quantities of contaminating leukocytes by a multiplex real-time PCR," *Breast Cancer Res Treat* 2009; 118(3):455-68; Mimori K, et al) and technical complexity of available approaches. These factors can render available methods not entirely satisfactory for use in the clinical laboratory.

In some embodiments, Neuroendocrine cells are FACS-sorted to heterogeneity, using known methods, following acridine orange (AO) staining and uptake, as described Kidd M, et al., "Isolation, Purification and Functional Characterization of the Mastomys EC cell," *Am J Physiol* 2006; 291:G778-91; Modlin I M, et al., "The functional characterization of normal and neoplastic human enterochromaffin cells," *J Clin Endocrinol Metab* 2006; 91(6):2340-8.

In some embodiments, the provided detection methods are used to detect, isolate, or enrich for the GEP-NEN cells and/or biomarkers in two to three mL of blood or less. The methods are performed using standard laboratory apparatuses and thus are easily performed in the clinical laboratory setting. In one example, a readout is obtained within 12 hours, at an average cost of approximately 20-30 per sample.

E. Diagnostic, Prognostic, and Predictive Uses

Also provided are diagnostic, prognostic, and predictive uses for the agents and detection methods provided herein, such as for the diagnosis, prognosis, and prediction of GEP-NEN, associated outcomes, and treatment responsiveness. For example, available GEP-NEN classification methods are limited, in part due to incorrect classifications and that individual lesions or tumors can evolve into different GEP-NEN sub-types or patterns, and/or contain more than one GEP-NEN sub-type. Known classification frameworks are limited, for example, in the ability to predict response to treatment or discriminate accurately between tumors with similar histopathologic features that may vary substantially in clinical course and treatment response, and to predict treatment responsiveness.

For example, the World Health Organization (WHO) classification criteria, adopted in 2000, distinguish between well differentiated NETs (WDNETs) (benign behavior or uncertain malignant potential), well differentiated neuroendocrine carcinomas (low-grade malignancy) (WDNECs), poorly differentiated neuroendocrine tumors (PDNETs) (medium grade malignancy), and poorly differentiated (usually small cell) NECs (PDNECs) (high-grade malignancy), based on size, proliferative rate, localization, differentiation, and hormone production. Metastatic sub-types follow the same nomenclature and classification strategy (MET-WDNET; MET-WDNEC, MET-PDNET, MET-PDNEC). Proposed alternatives to classification can be subjective. There is a need for molecular or gene-based classification schemes. The provided methods and systems, including GEP-NEN-specific predictive gene-based models, address these issues, and may be used in identifying and analyzing molecular parameters that are predictive of biologic behavior and prediction based on such parameters.

Among the provided diagnostic, prognostic, and predictive methods are those which employ statistical analysis and biomathematical algorithms and predictive models to analyze the detected information about expression of GEP-NEN biomarkers and other markers such as housekeeping genes. In some embodiments, expression levels, detected binding or other information is normalized and assessed against reference value(s), such as expression levels in normal samples or standards. Provided embodiments include methods and systems for classification and prediction of GEP-NENs using the detected and measured information about the expression of the GEP-NEN biomarkers, for example, in classification, staging, prognosis, treatment design, evaluation of treatment options, and prediction of GEP-NEN disease outcomes, e.g., predicting development of metastases.

Detection and Diagnosis of GEP-NEN

In some embodiments, the methods are used to establish GEP-NEN diagnosis, such as diagnosis or detection of early-stage disease or metastasis, define or predict the extent of disease, identify early spread or metastasis, predict outcome or prognosis, predict progression, classify disease, monitor treatment responsiveness, detect or monitor for recurrence, and to facilitate early therapeutic intervention. For example, among the provided methods and algorithms are those for use in classification, staging, prognosis, treatment design, evaluation of treatment options, and prediction of GEP-NEN disease outcomes, e.g., predicting development of metastases.

In one embodiment, the methods, algorithms and models are useful for diagnostic surveillance, such as routine surveillance. In some embodiments, the methods, algorithms and models provide for early diagnosis; in one aspect, the methods are capable of detection of low-volume tumors, and detection of circulating tumor cells, including at early stages of disease, such as detection of as few as at or about 3 circulating GEP-NEN cells per milliliter of blood. In some embodiments, early detection allows early therapeutic intervention, at a time when therapies are more effective, which can improve survival rates and disease outcomes.

For example, in one embodiment, the methods useful for early detection of the recurrence and/or metastasis of GEP-NEN, such as after treatment for example following surgical or chemical intervention. In some aspect, the methods are performed weekly or monthly following therapeutic intervention, for example, on human blood samples. In some aspects, the methods are capable of detecting micrometastases that are too small to be detected by conventional means, such as by imaging methods. For example, in one aspect the methods are capable of detecting metastases less than one centimeter (cm), such as at or about 1, 0.9, 0.8, 0.7, 0.6, 0.5, 0.4, 0.3, 0.2, or 0.1 cm metastases, such as in the liver.

For example, among the provided methods and systems are those that determine the presence or absence (or both) of a GEP-NEN in a subject or sample with a correct call rate of between 56 and 92%, such as at least or at least about a 65, 70, 75, 80, 81, 82, 83, 84, 85, 86, 87, 88, 89, 90, 91, 92, 93, 94, 95, 96, 97, 98, 99, or 100% correct call rate. In some cases, the methods are useful for diagnosis with a specificity or sensitivity of at least or at least about 70, 75, 80, 81, 82, 83, 84, 85, 86, 87, 88, 89, 90, 91, 92, 93, 94, 95, 96, 97, 98, 99, or 100%.

In other aspects, the methods are capable of detecting the recurrence, metastasis, or spread of GEP-NEN following treatment or during initial disease progression at an earlier stage as compared with other diagnostic methods, such as imaging and detection of available biomarkers. In some aspects, the detected expression levels and/or expression signature of the biomarkers correlate significantly with the progression of disease, disease severity or aggressiveness, lack of responsiveness of treatment, reduction in treatment efficacy, GEP-NEN-associated events, risk, prognosis, type or class of GEP-NEN or disease stage.

For example, in some embodiments, the methods are capable of predicting or monitoring the effects of therapeutic intervention. In one aspect, the methods provide are capable of detecting an improvement in disease as a result of treatment sooner or more effectively than available methods for detection and diagnosis, such as detection of tumors and metastasis by imaging and detection of available biomarkers, such as CgA.

Development and Monitoring of Treatment and Therapeutic Uses

Among the provided embodiments are methods that use the provided biomarkers and detection thereof in treatment development, strategy, and monitoring, including evaluation of response to treatment and patient-specific or individualized treatment strategies that take into consideration the likely natural history of the tumor and general health of the patient.

GEP-NEN management strategies include surgery—for cure (rarely achieved) or cytoreduction—radiological intervention—for example, by chemoembolisation or radiofrequency ablation—chemotherapy, cryoablation, and treatment with somatostatin and somatostatin analogues (such as Sandostatin LAR® (Octreotide acetate injection)) to control symptoms caused by released peptides and neuroamines, CTET-CT, and met resection. Biological agents, including interferon, and hormone therapy, and somatostatin-tagged radionucleotides are under investigation.

In one example, Cryoablation liberates GEP-NEN tissue for entry into the blood, which in turn induces symptoms, as described by Mazzaglia P J, et al., "Laparoscopic radiofrequency ablation of neuroendocrine liver metastases: a 10-year experience evaluating predictors of survival," *Surgery* 2007; 142(1):10-9.

Chemotherapeutic agents, e.g., systemic cytotoxic chemotherapeutic agents, include etoposide, cisplatin, 5-fluorouracil, streptozotocin, doxorubicin; vascular endothelial growth factor inhibitors, receptor tyrosine kinase inhibitors (e.g., sunitinib, sorafenib, and vatalanib), and mammalian target of rapamycin (mTOR) inhibitors (e.g., temsirolimus and everolimus), and combinations thereof, for example to treat disseminated and/or poorly differentiated disease. Other treatment approaches are well known.

In some embodiments, the detection and diagnostic methods are used in conjunction with treatment, for example, by performing the methods weekly or monthly before and/or after treatment. In some aspects, the expression levels and profiles correlate with the progression of disease, ineffectiveness or effectiveness of treatment, and/or the recurrence or lack thereof of disease. In some aspects, the expression information indicates that a different treatment strategy is preferable. Thus, provided herein are therapeutic methods, in which the GEP-NEN biomarker detection methods are performed prior to treatment, and then used to monitor therapeutic effects.

At various points in time after initiating or resuming treatment, significant changes in expression levels or expression profiles of the biomarkers (e.g., as compared to expression or expression profiles before treatment, or at some other point after treatment, and/or in a normal or reference sample) indicates that a therapeutic strategy is or is not successful, that disease is recurring, or that a different therapeutic approach should be used. In some embodiments, the therapeutic strategy is changed following performing of the detection methods, such as by adding a different therapeutic intervention, either in addition to or in place of the current approach, by increasing or decreasing the aggressiveness or frequency of the current approach, or stopping or reinstituting the treatment regimen.

In another aspect, the detected expression levels or expression profile of the biomarkers identifies the GEP-NEN disease for the first time or provides the first definitive diagnosis or classification of GEP-NEN disease. For example, in some aspects the method distinguishes between one or more of GEP-NEN classifications, such as WDNEC, WDNET, PDNEC, PDNET, and metastatic forms thereof, and/or distinguishes between GEP-NEN and other cancers, including other intestinal cancers. In some aspects of this embodiment, a treatment approach is designed based upon the expression levels or expression profiles, and/or the determined classification. The methods include iterative approaches, whereby the biomarker detection methods are followed by initiation or shift in therapeutic intervention, followed by continued periodic monitoring, reevaluation, and change, cessation, or addition of a new therapeutic approach, optionally with continued monitoring.

In some aspects, the methods and systems determine whether or not the assayed subject is responsive to treatment, such as a subject who is clinically categorized as in complete remission or exhibiting stable disease. In some aspects, the methods and systems determine whether or not the subject is untreated (or treatment-naïve, i.e., has not received treatment) or is non-responsive (i.e., clinically categorized as "progressive." For example, methods are provided for distinguishing treatment-responsive and non-responsive patients, and for distinguishing patients with stable disease or those in complete remission, and those with progressive disease. In various aspects, the methods and systems make such calls with at least at or about 65, 70, 75, 80, 81, 82, 83, 84, 85, 86, 87, 88, 89, 90, 91, 92, 93, 94, 95, 96, 97, 98, 99, or 100% correct call rate (i.e., accuracy), specificity, or sensitivity.

In some aspects, the sensitivity or correct call rate for the diagnostic or predictive or prognostic outcome is greater than, e.g., significantly greater than, that obtained using a known diagnosis or prognostic method, such as detection and measurement of circulating CgA or other single protein.

Statistical Analysis, Mathematical Algorithms and Predictive Models

Typically, the diagnostic, prognostic, and predictive methods include statistical analysis and mathematical modeling. Thus, provided are supervised learning algorithms useful for the construction of predictive models, based on the GEP-NEN biomarkers identified herein, and methods and uses thereof for the prediction and classification of GEP-NENs.

Any of a number of well-known methods for evaluating differences in gene expression may be used. Such methods range from simple comparisons of mean expression levels in each population e.g., using ANOVA (which is limited as the relevance of changes are complex to quantify) to mathematical analyses that are based on topographic, pattern-recognition based protocols e.g., support vector machines (SVM) (Noble W S. What is a support vector machine? Nat Biotechnol. 2006; 24(12): 1565-7). Machine-learning based techniques are typically desirable for developing sophisticated, automatic, and/or objective algorithms for analyzing high-dimensional and multimodal biomedical data.

In some examples, SVM—a variant of the supervised learning algorithm—is used in connection with the provided methods and systems. SVMs have been used to predict the grading of astrocytomas with a >90% accuracy, and prostatic carcinomas with an accuracy of 74-80% (Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11; Glotsos D, Tohka J, Ravazoula P, Cavouras D, Nikiforidis G. Automated diagnosis of brain tumours astrocytomas using probabilistic neural network clustering and support vector machines. Int J Neural Syst 2005; 15(1-2): 1-11).

Other algorithms for use with the provided methods and systems include linear discriminant analysis (LDA), naïve Bayes (NB), and K-nearest neighbor (KNN) protocols. Such approaches are useful for identifying individual or multivariable alterations in neoplastic conditions (Drozdov I, Tsoka S, Ouzounis C A, Shah A M. Genome-wide expression patterns in physiological cardiac hypertrophy. BMC Genomics. 2010; 11: 55; Freeman T C, Goldovsky L, Brosch M, et al. Construction, visualisation, and clustering of transcription networks from microarray expression data. PLoS Comput Biol 2007; 3(10): 2032-42; Zampetaki A, Kiechl S, Drozdov I, et al. Plasma microRNA profiling reveals loss of endothelial miR-126 and other microRNAs in type 2 diabetes. Circ Res. 2010; 107(6): 810-7. Epub 2010 Jul. 22; Dhawan M, Selvaraja S, Duan Z H. Application of committee kNN classifiers for gene expression profile classification. Int J Bioinform Res Appl. 2010; 6(4): 344-52; Kawarazaki S, Taniguchi K, Shirahata M, et al. Conversion of a molecular classifier obtained by gene expression profiling into a classifier based on real-time PCR: a prognosis predictor for gliomas. BMC Med Genomics. 2010; 3: 52; Vandebriel R J, Van Loveren H, Meredith C. Altered cytokine (receptor) mRNA expression as a tool in immunotoxicology. Toxicology. 1998; 130(1): 43-67; Urgard E, Vooder T, Vosa U, et al. Metagenes associated with survival in non-small cell lung cancer. Cancer Inform. 2011; 10: 175-83. Epub 2011 Jun. 2; Pimentel M, Amichai M, Chua K, Braham L. Validating a New Genomic Test for Irritable Bowel Syndrome Gastroenterology 2011; 140 (Suppl 1): S-798; Lawlor G, Rosenberg L, Ahmed A, et al. Increased Peripheral Blood GATA-3 Expression in Asymptomatic Patients With Active Ulcerative Colitis at Colonoscopy. Gastroenterology 2011; 140 (Suppl 1)).

In some embodiments, the provided methods and systems analyze expression of the GEP-NEN biomarkers as a group, with outputs dependent on an expression signature, such as expression signatures or profiles that are distinct between normal or reference samples and samples obtained from a subject with a "GEP-NEN." In such embodiments, pattern recognition protocols generally are used. Such approaches are useful, for example, to identify malignant signatures and signaling pathways in GEP-NEN tumor tissue (such as those described in Drozdov I, Kidd M, Nadler B, et al. Predicting neuroendocrine tumor (carcinoid) neoplasia using gene expression profiling and supervised machine learning. Cancer. 2009; 115(8): 1638-50) and determining whether individual plasma samples were obtained from normal control or GEP-NENs (for example, as described in Modlin I M, Gustafsson B I, Drozdov I, Nadler B, Pfragner R, Kidd M. Principal component analysis, hierarchical clustering, and decision tree assessment of plasma mRNA and hormone levels as an early detection strategy for small intestinal neuroendocrine (carcinoid) tumors. Ann Surg Oncol 2009; 16(2): 487-98).

Methods using the predictive algorithms and models use statistical analysis and data compression methods, such as those well known in the art. For example, expression data may be transformed, e.g., ln-transformed, and imported into a statistical analysis program, such as Partek® Genomic Suite ("Partek," Partek® Genomics Suite™, ed. Revision 6.3 St. Louis: Partek Inc, 2008) or similar program, for example. Data are compressed and analyzed for comparison.

Statistical analyses include determining mean (M), e.g., geometric mean, of gene expression levels for individual sample types, standard deviations (SD) among types of samples, Geometric Fold Change (FC) between different sample types or conditions, calculated as the ratio of geometric means for two groups of samples or values, comparison of expression levels by 2-tailed Fisher's test, or two-sample t-test, e.g., to identify biomarker genes differentially expressed between various samples and tissue types. Analysis of Variance (ANOVA) is used to evaluate differences in biomarker expression levels between expression in different samples and/or values. In one example, a two-class unpaired algorithm is implemented, such as by expression levels from a test and normal sample or reference value defining the two groups.

Whether differences in expression levels, amounts, or values are deemed significant may be determined by well-known statistical approaches, and typically is done by designating a threshold for a particular statistical parameter, such as a threshold p-value (e.g., $p<0.05$), threshold S-value (e.g., ±0.4, with $S<-0.4$ or $S>0.4$), or other value, at which differences are deemed significant, for example, where expression of a biomarker is considered significantly down- or up-regulated, respectively, among two different samples, for example, representing two different GEP-NEN subtypes, tumors, stages, localizations, aggressiveness, or other aspect of GEP-NEN or normal or reference sample.

In one aspect, the algorithms, predictive models, and methods are based on biomarkers expressed from genes associated with regulatory genotypes (i.e., adhesion, migration, proliferation, apoptosis, metastasis, and hormone secretion) underlying various GEP-NEN subtypes.

In one aspect, the methods apply the mathematical formulations, algorithms or models identify specific cutoff points, for example, expression levels or amounts, which distinguish between normal and GEP-NEN samples, between GEP-NEN and other cancers, and between various sub-types, stages, and other aspects of disease or disease outcome. In another aspect, the methods are used for prediction, classification, prognosis, and treatment monitoring and design. In one aspect, the predictive embodiments are useful for identifying molecular parameters predictive of biologic behavior, and prediction of various GEP-NEN-associated outcomes using the parameters. In one aspect of these embodiments, machine learning approaches are used, e.g., to develop sophisticated, automatic and objective algorithms for the analysis of high-dimensional and multimodal biomedical data.

Compression of Data and Determining Expression Profiles

For the comparison of expression levels or other values, and to identify expression profiles (expression signatures) or regulatory signatures based on GEP-NEN biomarker expression, data are compressed. Compression typically is by Principal Component Analysis (PCA) or similar technique for describing and visualizing the structure of high-dimensional data. PCA allows the visualization and comparison of GEP-NEN biomarker expression and determining and comparing expression profiles (expression signatures, expression patterns) among different samples, such as between normal or reference and test samples and among different tumor types.

In some embodiments, expression level data are acquired, e.g., by real-time PCR, and reduced or compressed, for example, to principal components.

PCA is used to reduce dimensionality of the data (e.g., measured expression values) into uncorrelated principal components (PCs) that explain or represent a majority of the variance in the data, such as about 50, 60, 70, 75, 80, 85, 90, 95 or 99% of the variance.

In one example, the PCA is 3-component PCA, in which three PCs are used that collectively represent most of the variance, for example, about 75%, 80%, 85%, 90%, or more variance in the data (Jolliffe I T, "Principle Component Anlysis," Springer, 1986).

PCA mapping, e.g., 3-component PCA mapping is used to map data to a three dimensional space for visualization, such as by assigning first ($1^{st}$), second ($2^{nd}$) and third ($3^{rd}$) PCs to the x-, y-, and z-axes, respectively.

PCA may be used to determine expression profiles for the biomarkers in various samples. For example, reduced expression data for individual sample types (e.g., each tumor type, sub-type or grade, or normal sample type) are localized in a PCA coordinate system and localized data used to determine individual transcript expression profiles or signatures.

In one aspect, the expression profile is determined for each sample by plotting or defining a centroid (center of mass; average expression), corresponding to or representing the sample's individual transcript expression profile (regulatory signature), as given by the principal component vector, as determined by PCA for the panel of biomarkers.

Generally, two centroids or points of localization separated by a relatively large distance in this coordinate system represent two relatively distinct transcript expression profiles. Likewise, relatively close centroids represent relatively similar profiles. In this representation, the distance between centroids is inversely equivalent to the similarity measure (greater distance=less similarity) for the different samples, such that large distances or separation between centroids indicates samples having distinct transcript expression signatures. Proximity of centroids indicates similarity between samples. For example, the relative distance between centroids for different GEP-NEN tumor samples represents the relative similarity of their regulatory signatures or transcript expression profiles.

Correlation, Linear Relationships and Regulatory Clusters

In one aspect, the statistical and comparative analysis includes determining the inverse correlation between expression levels or values for two biomarkers. In one example, this correlation and the cosine of the angle between individual expression vectors (greater angle=less similarity), is used to identify related gene expression clusters (Gabriel K R, "The biplot graphic display of matrices with application to principal component analysis," *Biometrika* 1971; 58(3):453).

In some embodiments, there is a linear correlation between expression levels of two or more biomarkers, and/or the presence or absence of GEP-NEN, sub-type, stage, or other outcome. In one aspect, there is an expression-dependant correlation between the provided GEP-NEN biomarkers and characteristics of the biological samples, such as between biomarkers (and expression levels thereof) and various GEP-NEN sub-types (primary or metastatic), normal versus GEP-NEN samples, and/or primary versus metastatic or aggressive disease.

Pearson's Correlation (PC) coefficients ($R^2$) may be used to assess linear relationships (correlations) between pairs of values, such as between expression levels of a biomarker for different biological samples (e.g., tumor sub-types) and between pairs of biomarkers. This analysis may be used to linearly separate distribution in expression patterns, by calculating PC coefficients for individual pairs of the biomarkers (plotted on x- and y-axes of individual Similarity Matrices). Thresholds may be set for varying degrees of linear correlation, such as a threshold for highly linear correlation of ($R^2>0.50$, or 0.40). Linear classifiers can be applied to the datasets. In one example, the correlation coefficient is 1.0.

In one embodiment, regulatory clusters are determined by constructing networks of correlations using statistical analyses, for example, to identify regulatory clusters composed of subsets of the panel of biomarkers. In one example, PC correlation coefficients are determined and used to construct such networks of correlations. In one example, the networks are identified by drawing edges between transcript pairs having $R^2$ above the pre-defined threshold. Degree of correlation can provide information on reproducibility and robustness.

Predictive Models and Supervised Learning Algorithms

Also provided herein are objective algorithms, predictive models, and topographic analytical methods, and methods using the same, to analyze high-dimensional and multimodal biomedical data, such as the data obtained using the provided methods for detecting expression of the GEP-NEN biomarker panels. As discussed above, the objective algorithms, models, and analytical methods include mathematical analyses based on topographic, pattern-recognition based protocols e.g., support vector machines (SVM) (Noble W S. What is a support vector machine? Nat Biotechnol. 2006; 24(12): 1565-7), linear discriminant analysis (LDA), naïve Bayes (NB), and K-nearest neighbor (KNN) protocols, as well as other supervised learning algorithms and models, such as Decision Tree, Perceptron, and regularized discriminant analysis (RDA), and similar models and algorithms well-known in the art (Gallant S I, "Perceptron-based learning algorithms," *Perceptron-based learning algorithms* 1990; 1(2):179-91).

In some embodiments, biomarker expression data is analyzed in biological samples, using feed-forward neural networks; best transcripts-predictors are selected.

In some embodiments, Feature Selection (FS) is applied to remove the most redundant features from a dataset, such as a GEP-NEN biomarker expression dataset. FS enhances the generalization capability, accelerates the learning process, and improves model interpretability. In one aspect, FS is employed using a "greedy forward" selection approach, selecting the most relevant subset of features for the robust learning models. (Peng H, Long F, Ding C, "Feature selection based on mutual information: criteria of max-dependency, max-relevance, and min-redundancy," *IEEE Transactions on Pattern Analysis and Machine Intelligence,* 2005; 27(8):1226-38).

In some embodiments, Support Vector Machines (SVM) algorithms are used for classification of data by increasing the margin between the n data sets (Cristianini N, Shawe-Taylor J. An Introduction to Support Vector Machines and other kernel-based learning methods. Cambridge: Cambridge University Press, 2000).

In some embodiments, the predictive models include Decision Tree, which maps observations about an item to a conclusion about its target value (Zhang H, Singer B. "Recursive Partitioning in the Health Sciences," (Statistics for Biology and Health): Springer, 1999.). The leaves of the tree represent classifications and branches represent conjunctions of features that devolve into the individual classifications. It has been used effectively (70-90%) to predict prognosis of metastatic breast cancer (Yu L et al "TGF-beta receptor-activated p38 MAP kinase mediates Smad-independent TGF-beta responses.," *Embo J* 2002; 21(14):3749-59), as well as colon cancer (Zhang H et al "Recursive partitioning for tumor classification with gene expression microarray data.," *Proc Natl Acad Sci USA* 2001; 98(12): 6730-5.), to predict the grading of astrocytomas (Glotsos D et al "Automated diagnosis of brain tumours astrocytomas using probabilistic neural network clustering and support vector machines.," *Int J Neural Syst* 2005; 15(1-2):1-11.) with a >90% accuracy, and prostatic carcinomas with an accuracy of 74-80% (Mattfeldt T et al. "Classification of prostatic carcinoma with artificial neural networks using comparative genomic hybridization and quantitative stereological data.," *Pathol Res Pract* 2003; 199(12):773-84.). The efficiency of this technique has been measured by 10-fold cross-validation (Pirooznia M et al "A comparative study of different machine learning methods on microarray gene expression data.," *BMC Genomics* 2008; 9 Suppl 1:S13.).

The predictive models and algorithms further include Perceptron, a linear classifier that forms a feed forward neural network and maps an input variable to a binary classifier (Gallant S I. "Perceptron-based learning algorithms," *Perceptron-based learning algorithms* 1990; 1(2): 179-91). It has been used to predict malignancy of breast cancer (Markey M K et al. "Perceptron error surface analysis: a case study in breast cancer diagnosis.," *Comput Biol Med* 2002; 32(2):99-109). In this model, the learning rate is a constant that regulates the speed of learning. A lower learning rate improves the classification model, while increasing the time to process the variable (Markey M K et al. "Perceptron error surface analysis: a case study in breast cancer diagnosis.," *Comput Biol Med* 2002; 32(2):99-109). In one example, a learning rate of 0.05 is used. In one aspect, a Perceptron algorithm is used to distinguish between localized or primary tumors and corresponding metastatic tumors. In one aspect, three data scans are used to generate decision boundaries that explicitly separate data into classes.

The predictive models and algorithms further include Regularized Discriminant Analysis (RDA), which can be used as a flexible alternative to other data mining techniques, including Linear and Quadratic Discriminant Analysis (LDA, QDA) (Lilien R H, Farid H, Donald B R. "Probabilistic disease classification of expression-dependent proteomic data from mass spectrometry of human serum.," *J Comput Biol* 2003; 10(6):925-46.; Cappellen D, Luong-Nguyen N H, Bongiovanni S, et al. "Transcriptional program of mouse osteoclast differentiation governed by the macrophage colony-stimulating factor and the ligand for the receptor activator of NFkappa B.," *J Biol Chem* 2002; 277(24):21971-82.). RDA's regularization parameters, $\gamma$ and $\lambda$, are used to design an intermediate classifier between LDA and QDA. QDA is performed when $\gamma=0$ and $\lambda=0$ while LDA is performed when $\gamma=0$ and $\lambda=1$ (Picon A, Gold L I, Wang J, Cohen A, Friedman E. A subset of metastatic human colon cancers expresses elevated levels of transforming growth factor beta1. *Cancer Epidemiol Biomarkers Prev* 1998; 7(6):497-504).

To reduce over-fitting, RDA parameters are selected to minimize cross-validation error while not being equal 0.0001, thus forcing RDA to produce a classifier between LDA, QDA, and L2 (Pima I, Aladjem M., "Regularized discriminant analysis for face recognition," *Pattern Recognition* 2003; 37(9):1945-48). Finally, regularization itself has been used widely to overcome over-fitting in machine learning (Evgeniou T, Pontil M, Poggio T. "Regularization Networks and Support Vector Machines.," *Advances in Computational Math* 2000; 13(1):1-50.; Ji S, Ye J. Kernel "Uncorrelated and Regularized Discriminant Analysis: A Theoretical and Computational Study.," *IEEE Transactions on Knowledge and Data Engineering* 2000; 20(10): 1311-21.).

In one example, regularization parameters are defined as $\gamma=0.002$ and $\lambda=0$. In one example, for each class pair, S-values are assigned to all transcripts which are then arranged by a decreasing S-value. RDA is performed, e.g., 21 times, such that the $N^{th}$ iteration consists of top N scoring transcripts. Error estimation can be carried out by a 10-fold cross-validation of the RDA classifier. This can be done by partitioning the tissue data set into complementary subsets, performing the analysis on one subset (called the training set), and validating the analysis on the other subset (called the validation set or testing set).

Calculating Misclassification Error

In one example, misclassification error is averaged to reduce variability in the overall predictive assessment, which can provide a more accurate approach to error estimation compared to other approaches, including bootstrapping and leave-one-out cross-validation (Kohavi R. "A study of cross-validation and bootstrap for accuracy estimation and model selection.," *Proceedings of the Fourteenth International Joint Conference on Artificial Intelligence,* 1995; 2(12):1137-43.).

In one example, selection for tissue classification is performed, for example, by computing the rank score (S) for each gene and for each class pair as:

$$S = \frac{|\mu_{C2} - \mu_{C1}|}{\sigma_{C1} + \sigma_{C2}}$$

where $\mu_{C1}$ and $\mu_{C2}$ represent means of first and second class respectively and $\sigma_{C1}$ and $\sigma_{C2}$ are inter-class standard deviations. A large S value is indicative of a substantial differential expression ("Fold Change") and a low standard deviation ("transcript stability") within each class. Genes may be sorted by a decreasing S-value and used as inputs for the regularized discriminant analysis algorithm (RDA).

The algorithms and models may be evaluated, validated and cross-validated, for example, to validate the predictive and classification abilities of the models, and to evaluate specificity and sensitivity. In one example, radial basis function is used as a kernel, and a 10-fold cross-validation used to measure the sensitivity of classification (Cristianini N, Shawe-Taylor J. "An Introduction to Support Vector Machines and other kernel-based learning methods.," Cambridge: Cambridge University Press, 2000.). Various classification models and algorithms may be compared by the provided methods, for example, using training and cross-validation, as provided herein, to compare performance of the predictive models for predicting particular outcomes.

Embodiments of the provided methods, systems, and predictive models are reproducible, with high dynamic range, can detect small changes in data, and are performed using simple methods, at low cost, e.g., for implementation in a clinical laboratory.

F. Kits

For use in the diagnostic, prognostic, predictive, and therapeutic applications described or suggested above, kits and other articles of manufacture are provided. In some embodiments, the kits include a carrier, package, or packaging, compartmentalized to receive one or more containers such as vials, tubes, plates, and wells, in which each of the containers includes one of the separate elements for use in the methods provided herein, and in some aspects further include a label or insert with instructions for use, such as the uses described herein. In one example, the individual containers include individual agents for detection of the GEP-NEN biomarkers as provided herein; in some examples, individual containers include agents for detection of housekeeping genes and/or normalization.

For example, the container(s) can comprise an agent, such as a probe or primer, which is or can be detectably labeled. Where the method utilizes nucleic acid hybridization for detection, the kit can also have containers containing nucleotide(s) for amplification of the target nucleic acid sequence. Kits can comprise a container comprising a reporter, such as a biotin-binding protein, such as avidin or streptavidin, bound to a reporter molecule, such as an enzymatic, fluorescent, or radioisotope label; such a reporter can be used with, e.g., a nucleic acid or antibody.

The kits will typically comprise the container(s) described above and one or more other containers associated therewith that comprise materials desirable from a commercial and user standpoint, including buffers, diluents, filters, needles, syringes; carrier, package, container, vial and/or tube labels listing contents and/or instructions for use, and package inserts with instructions for use.

A label can be present on or with the container to indicate that the composition is used for a specific therapeutic or non-therapeutic application, such as a prognostic, prophylactic, diagnostic or laboratory application, and can also indicate directions for either in vivo or in vitro use, such as those described herein. Directions and or other information can also be included on an insert(s) or label(s) which is included with or on the kit. The label can be on or associated with the container. A label a can be on a container when letters, numbers or other characters forming the label are molded or etched into the container itself; a label can be associated with a container when it is present within a receptacle or carrier that also holds the container, e.g., as a package insert. The label can indicate that the composition is used for diagnosing, treating, prophylaxing or prognosing a condition, such as GEP-NEN.

In another embodiment, an article(s) of manufacture containing compositions, such as amino acid sequence(s), small molecule(s), nucleic acid sequence(s), and/or antibody(s), e.g., materials useful for the diagnosis, prognosis, or therapy of GEP-NEN is provided. The article of manufacture typically comprises at least one container and at least one label. Suitable containers include, for example, bottles, vials, syringes, and test tubes. The containers can be formed from a variety of materials such as glass, metal or plastic. The container can hold amino acid sequence(s), small molecule(s), nucleic acid sequence(s), cell population(s) and/or antibody(s). In one embodiment, the container holds a polynucleotide for use in examining the mRNA expression profile of a cell, together with reagents used for this purpose. In another embodiment a container comprises an antibody, binding fragment thereof or specific binding protein for use in evaluating protein expression of GEP-NEN biomarkers in cells and tissues, or for relevant laboratory, prognostic, diagnostic, prophylactic and therapeutic purposes; indications and/or directions for such uses can be included on or with such container, as can reagents and other compositions or tools used for these purposes.

The article of manufacture can further comprise a second container comprising a pharmaceutically-acceptable buffer, such as phosphate-buffered saline, Ringer's solution and/or dextrose solution. It can further include other materials desirable from a commercial and user standpoint, including other buffers, diluents, filters, stirrers, needles, syringes, and/or package inserts with indications and/or instructions for use.

EXAMPLES

Various aspects of the invention are further described and illustrated by way of the several examples which follow, none of which are intended to limit the scope of the invention.

Example 1: Detection and Determining Expression Levels of Biomarkers in GEP-NEN and Normal Samples Sample Preparation, RNA Extraction, Real-Time PCR Normal and neoplastic samples were obtained for detection and determination of GEP-NEN biomarker expression levels by real-time PCR. Normal samples included twenty-seven (27) normal small intestinal (SI) mucosa samples (NML), and thirteen (13) normal human enterochromaffin (EC) cell preparations (NML_EC; obtained through fluorescence-activated cell sorting (FACS) of normal mucosa; >98% pure EC cells (Modlin I M et al., "The functional characterization of normal and neoplastic human enterochromaffin cells," *J Clin Endocrinol Metab* 2006; 91(6): 2340-8).

Neoplastic samples included fifty-three (53) primary SI GEP-NENs and twenty-one (21) corresponding liver metastases collected from a frozen biobank (all tissues microdissected). The GEP-NEN samples were obtained from patients enrolled according to protocols approved by the Institutional Review Board of Yale University. Each was classified as functional, with greater than 80% pure neoplastic cells and as positive for TPH1, confirming it was EC cell-derived (Modlin I M et al., "The functional characterization of normal and neoplastic human enterochromaffin cells," *J Clin Endocrinol Metab* 2006; 91(6):2340-8). Patient samples also were collected from adenocarcinomas of the breast (n=53), colon (n=21), and pancreas (n=16).

Primary GEP-NENs were classified pathologically according to the 2000 World Health Organization (WHO) standard, as well differentiated NETs ((WDNETs) (n=26) (benign behavior or uncertain malignant potential)); well differentiated neuroendocrine carcinomas ((WDNECs) (n=20) (low-grade malignancy)); poorly differentiated neuroendocrine tumors ((PDNETs) (n=5) (medium grade malignancy)); and poorly-differentiated (typically small-cell) neuroendocrine carcinomas ((PDNECs) (n=2) (high grade malignancy)). Metastatic GEP-NEN tissue samples (metastases; MET) (collected from liver resections from corresponding tumor types), were classified using a similar standard, as: WDNET MET (n=6), WDNEC MET (n=12), and PDNEC MET (n=3). Metastatic PDNETs (PDNET METs) are classified using the same method.

For real-time PCR, RNA was extracted from various normal and neoplastic samples (27 samples of normal SI mucosa, 13 preparations of normal human EC cells, 53 primary SI GEP-NENs, 21 corresponding liver metastases, and 53 adenocarcinoma samples) using TRIzol® reagent (ready-to-use, monophasic solution of phenol and guanidine isothiocyanate; Invitrogen™, Carlsbad, Calif.).

Transcript expression levels were measured by real-time PCR using Assays-on-Demand™ gene expression products and the ABI 7900 Sequence Detection System (both from Applied Biosystems) according to the manufacturer's suggestions (Kidd M et al, "Microsatellite instability and gene mutations in transforming growth factor-beta type II receptor are absent in small bowel carcinoid tumors," *Cancer* 2005; 103(2):229-36). Cycling was performed under standard conditions using the TaqMan® Universal PCR Master Mix Protocol (Applied Biosystems).

GEP-NEN biomarkers were detected and expression levels measured by real-time PCR, using sets of polynucleotide primer pairs, where each set contained primer pairs designed to specifically bind to and amplify a panel of GEP-NEN biomarkers. The GEP-NEN biomarker panel included products (transcripts) of genes implicated in typical primary and metastatic GEP-NEN phenotypes, for example, genes involved in adhesion, migration, proliferation, apoptosis, metastasis, and hormone secretion, and neuroendocrine marker genes. Housekeeping gene (ALG9, TFCP2 and ZNF410) expression levels also were measured. Raw $\Delta C_T$ values for biomarker expression were normalized using the geNorm algorithm (Vandesompele J et al., "Accurate normalization of real-time quantitative RT-PCR data by geometric averaging of multiple internal control genes," *Genome Biol* 2002; 3(7):RESEARCH0034) and the housekeeping expression levels.

Normalized data were natural log (ln)-transformed for compression and imported into Partek® Genomic Suite (Partek, "Partek® Genomics Suite™," ed. Revision 6.3 St. Louis: Partek Inc, 2008). Mean gene expression levels (M) of the various biomarker transcripts and Standard Deviations (SD) were calculated. All statistical computations were carried out using R 2.9 language for statistical computing (R Development Core Team. R, "A language and environment for statistical computing," Vienna, Austria: R Foundation for Statistical Computing, 2008).

Detection and Determination of Transcript Expression Levels of a 9-Biomarker Panel Expression levels were determined by real-time PCR as described above using a set of primer pairs specific for a panel of nine GEP-NEN biomarkers (MAGE-D2, MTA1, NAP1L1, Ki-67, Survivin, FZD7, Kiss1, NRP2, and CgA (see Kidd M et al., "The role of genetic markers—NAP1L1, MAGE-D2, and MTA1—in defining small-intestinal carcinoid neoplasia," *Ann Surg Oncol* 2006; 13(2):253-62; Kidd M et al., "Q RT-PCR detection of chromogranin A: a new standard in the identification of neuroendocrine tumor disease," *Ann Surg* 2006; 243(2):273-80) transcripts. The sequences of the primer pairs are listed in Table 1A, below, with other information about primer pairs listed in Table 1B. Expression of the nine biomarkers (transcripts) was measured in samples from primary SI GEP-NEN (AKA SI NET) (n=53), corresponding liver metastases (n=21), and normal EC cell preparations (n=13). Expression levels in the tumor samples were compared for each biomarker to corresponding average expression levels in the normal enterochomaffin (EC) cell preparations. Based on this comparison, expression levels in the tumor samples were classified as Upregulated, Downregulated, or Baseline.

Table 1: Sets of Primers for GEP-NEN Biomarkers and Housekeeping Genes

TABLE 1A

| Primer sequences | | | | |
|---|---|---|---|---|
| GEP-NEN Biomarker or Housekeeping Gene | Forward Primer sequence | SEQ ID NO: | Reverse Primer sequence | SEQ ID NO: |
| AKAP8L | 5'-gaagcatctgaagaccatgg-3' | 106 | 5'-atgagggaggacttcttgga-3' | 107 |
| APLP2 | 5'-cggtgccgaagagaaagtga-3' | 41 | 5'-ctctctcggcattgaaaatc-3' | 42 |
| ARAF1 | 5'-ctcatcgacgtggcccggca-3' | 43 | 5'-gtggatgatgttcttggcat-3' | 44 |
| ATP6V1H | 5'-caggtccgctataatgctct-3' | 108 | 5'-ggcagcggtctggggctgct-3' | 109 |
| BNIP3L | 5'-cagagtagttccagaggcag-3' | 110 | 5'-aaacatgatctgcccatcttc-3' | 111 |
| BRAF1 | 5'-cctcttcggctgcggaccct-3 | 45 | 5'-gtgtcaacttaatcatttgt-3' | 46 |
| C21ORF7 | 5'-attactgtgcccgtggaaat-3' | 112 | 5'-gaaagaccaaaggaatggag-3' | 113 |
| CD59 | 5'-ggctgctgctcgtcctggct-3' | 47 | 5'-ttgggttaggacagttgtag-3' | 48 |
| CgA | 5'-aacggatcctttccattctg-3' | 49 | 5'-ctgagagttcatcttcaaaa-3' | 50 |
| COMMD9 | 5'-ctcaaaaacctgctgacaaa-3' | 114 | 5'-gtggcagagagatctgattt-3' | 115 |

TABLE 1A-continued

| Primer sequences | | | | |
|---|---|---|---|---|
| GEP-NEN Biomarker or Housekeeping Gene | Forward Primer sequence | SEQ ID NO: | Reverse Primer sequence | SEQ ID NO: |
| CTGF | 5'-tgcgaagctgacctggaaga-3' | 51 | 5'-ttttgggagtacggatgcac-3' | 52 |
| CXCL14 | 5'-aagcgcttcatcaagtggta-3' | 53 | 5'-tgaggtttttcaccctattc-3' | 54 |
| ENPP4 | 5'-gctggacaattgtgctaaatg-3' | 116 | 5'-aaatggatgcatactaggca-3' | 117 |
| FAM131A | 5'-tcagcgagggcgaacaagag-3' | 118 | 5'-tccgcgatggcaaactgctc-3' | 119 |
| FLJ10357 | 5'-acacaaactggagaatggtc-3' | 120 | 5'-tgttccagaggctgctgcag-3' | 121 |
| FZD7 | 5'-gatgcgggaccccggcgcgg-3' | 55 | 5'-cagcagcgccagcaccaggg-3' | 56 |
| GLT8D1 | 5'-aacttcctcagcttgagcag-3' | 122 | 5'-atttgggacaaagtctatag-3' | 123 |
| GRIA2 | 5'-aagtttgcatacctctatga-3' | 57 | 5'-tttcagcagcagaatccagca-3' | 58 |
| HDAC9 | 5'-gcagaagcaataccagcagc-3' | 124 | 5'-tgcttcagttgttcaataga-3' | 125 |
| HOXC6 | 5'-ccagatttaccccctggatgc-3' | 59 | 5'-cgagtagatctggcggccgc-3' | 60 |
| HSF2 | 5'-aggaagacaatttagcatag-3' | 126 | 5'-gatgtaatctgtgggattca-3' | 127 |
| Ki-67 | 5'-gcacgtcgtgtctcaagatc-3' | 61 | 5'-gacacacgccttcttttcaa-3' | 62 |
| Kiss1 | 5'-gtggcctctgtggggaattc-3' | 63 | 5'-ctccccgggggccaggaggc-3' | 64 |
| KRAS | 5'-tcaggacttagcaagaagtt-3' | 65 | 5'-tcatcttttctttatgtttt-3' | 66 |
| LEO1 | 5'-ggaaggcgaggagtccatca-3' | 128 | 5'-gagctttatcttcttctgat-3' | 129 |
| MAGE-D2 | 5'-gaatcaggatactcggccca-3' | 67 | 5' actctgatcactgctgccat-3' | 68 |
| MORF4L2 | 5'-gcaaagaattctgcatctct-3' | 130 | 5'-aattttacaagaaaaagact-3' | 131 |
| MTA1 | 5'-ggcggtacgcaagccgctgg-3' | 69 | 5'-ggacacgcttttcacgggtc-3' | 70 |

TABLE 1A-continued

| Primer sequences | | | | |
|---|---|---|---|---|
| GEP-NEN Biomarker or Housekeeping Gene | Forward Primer sequence | SEQ ID NO: | Reverse Primer sequence | SEQ ID NO: |
| NAP1L1 | 5'-ggtctaccttctgcttccct-3' | 71 | 5'-tcttgtaagaactaaaattg-3' | 72 |
| NKX2-3 | 5'-aaggaacatgaagaggagcc-3' | 73 | 5'-ccgccttgcagtctccggccg-3' | 74 |
| NOL3 | 5'-ccgtgttggcctccaggtcc-3' | 132 | 5'-ggcgtttccgctcgcggtcg-3' | 133 |
| NRP2 | 5'-agccctctacttttcaagaca-3' | 75 | 5'-agccagcatctttggaattca-3' | 76 |
| NUDT3 | 5'-tggcagcagttcgtgaagtc-3' | 134 | 5'-aactaatcttcccaatgtcc-3' | 135 |
| OAZ2 | 5'-ctcccaccctgagcagagcc-3' | 136 | 5'-gtgcctgcagcactggag-3' | 137 |
| OR51E1 | 5'-ctggaggaagactggacaaag-3' | 77 | 5'-caccatcatgaagaagctgaa-3' | 78 |
| PANK2 | 5'-agtacgagatatttatggag-3' | 138 | 5'-ctggccaggtcctctttact-3' | 139 |
| PHF21A | 5'-ggaagaagcaattccatggc-3' | 140 | 5'-ttgtcgttcttgttttaaat-3' | 141 |
| PKD1 | 5'-agcctgaccgtgtggaaggc-3' | 142 | 5'-gccttgcaggacacacactc-3' | 143 |
| PLD3 | 5'-accctcaccaacaatgacac-3' | 144 | 5'-cggacgttcacgccct-3' | 145 |
| PNMA2 | 5'-gggtccaagccgccctgctg-3' | 79 | 5'-ccttccactctgggacccag-3' | 80 |
| PQB1 | 5'-caagagaggcatcctcaaac-3' | 146 | 5'-cgtcatagtcctcggcaatg-3' | 147 |
| PTPRN2 | 5'-gcagcgcctgcgcgtggcgt-3' | 81 | 5'-tcacatactgagtatagtca-3' | 82 |
| RAF1 | 5'-gacatccacacctaatgtcca-3' | 83 | 5'-ctgattcgctgtgacttcgaa-3' | 84 |
| RNF41 | 5'-gaacagggaacctgcccccc-3' | 148 | 5'-gttacatcataccccatgtc-3' | 149 |
| RSF1 | 5'-aaaaatgtggccttccaaac-3' | 150 | 5 '-cactatcgcaagagtc-3' | 151 |

TABLE 1A-continued

Primer sequences

| GEP-NEN Biomarker or Housekeeping Gene | Forward Primer sequence | SEQ ID NO: | Reverse Primer sequence | SEQ ID NO: |
|---|---|---|---|---|
| RTN2 | 5'-gtgattggtctattc accat-3' | 152 | 5'-aactgattggttcaccaac ccc-3' | 153 |
| SMARCD3 | 5' gctgcaggactccc atgaca-3' | 154 | 5'-ggctgtgaggcgctggg gaa-3' | 155 |
| SPATA7 | 5'-tgcaagaggactaa gcatgg-3' | 156 | 5'-aaataggcacggtggacc at-3' | 157 |
| SCG5 | 5'-ctcctttacgagaa gatgaa-3' | 85 | 5'-acattatccagtctctgtcc-3' | 86 |
| SPOCK1 | 5'-cctgtgtgtcagcc gcaagc-3' | 87 | 5'-gtgtttctgggccacgttc c-3' | 88 |
| SST1 | 5'-acggcatggagga gccaggg-3' | 158 | 5'-atgaaagagatcaggatg gc-3' | 159 |
| SST3 | 5'-gcagggctggccg tcagtgg-3' | 160 | 5'-gaccagcgagttacccag ca-3' | 161 |
| SST4 | 5'-cgggggcgagga agggctgg-3' | 162 | 5'-cccgcgcgtccccgggc ccc-3' | 163 |
| SST5 | 5'-cctctggggagcg acttttc-3' | 164 | 5'-caagcgctttcgggtgtct t-3' | 165 |
| Survivin | 5'-ctggactttcctcca ggagtt-3' | 89 | 5'-ccgcagtttcctcaaattct-3' | 90 |
| TECPR2 | 5'-aggcgagcagtgg aagtgtg-3' | 166 | 5'-ttatgcagacgggttctaa a-3' | 167 |
| Tph1 | 5'-gaagagcaagtctc attttttc-3' | 91 | 5'-aacaaaaatctcaaattct g-3' | 92 |
| TRMT112 | 5'-cttacccacaatctg ctgagct-3' | 168 | 5'-ggcagatacggacctcg gtg-3' | 169 |
| VMAT1 | 5'-ctaacagctgccaa tacctca-3' | 93 | 5'-ctgcagcctttatggaaga gg-3' | 94 |
| VMAT2 | 5'-ctgaaggacccgta catcct-3' | 95 | 5'-gcgatgcccatgtttgcaa ag-3' | 96 |
| VPS13C | 5'-aagtttaagggcca ggttgt-3' | 170 | 5'-cagggaacattgcacctg gt-3' | 171 |
| WDFY3 | 5'-aagtcctagaaatg caggaa-3' | 172 | 5'-cttctgaatcactgctgtcc-3' | 173 |
| X2BTB48 | 5'-gtgaactctcagct actgga-3' | 97 | 5'-tgcccctttcatcaacttca-3' | 98 |

TABLE 1A-continued

| Primer sequences | | | | |
|---|---|---|---|---|
| GEP-NEN Biomarker or Housekeeping Gene | Forward Primer sequence | SEQ ID NO: | Reverse Primer sequence | SEQ ID NO: |
| ZFHX3 | 5'-gaggagcttgctaaggacca-3' | 174 | 5'-gaatctgtcagctccttctc-3' | 175 |
| ZXDC | 5'-gcgcccttacaagtgtgact-3' | 176 | 5'-gaaaacagggcactcactgt-3' | 177 |
| ZZZ3 | 5'-gaaagtggatttgtgcaaca-3' | 178 | 5'-tggatgggttctatgccaca-3' | 179 |
| ALG9 | 5'-tttgtgagctgtatttgtga-3' | 99 | 5'-caacccaaacttcttgcaca-3' | 100 |
| TFCP2 | 5'-aatctgtggccctgcagatgg-3' | 101 | 5'-gattcctgacaaacataaatg-3' | 102 |
| ZNF410 | 5'-cgttcctttgctgagtattc-3' | 103 | 5'-ccactctgagagaaggtcttcc-3' | 104 |
| 18S | 5'-tacctggttgatcctgccag-3' | 30 | 5'-cgcccgtcggcatgtattag-3' | 31 |
| GAPDH | 5'-atttggtcgtattgggcgcc-3' | 32 | 5'-gaatcatattggaacatgta-3' | 33 |
| ACTB | 5'-accgccgagaccgcgtccgc-3' | 180 | 5'-gcccgggggcatcgtcgcc-3' | 181 |
| ARF1 | 5'-ggagaccccgcctagcatag-3' | 182 | 5'-tgaccatgcagaattgatcg-3' | 183 |
| ATG4B | 5'-gagctccttggcggtccaca-3' | 184 | 5'-ctgcaggaaacgcagtggcg-3' | 185 |
| HUWE1 | 5'-cacgttttggatacactcat-3' | 186 | 5'-ttggtccgctgctgtgtgaa-3' | 187 |
| MORF4L1 | 5'-gtgctgtgaggtctgcgggc-3' | 188 | 5' tcaggcactgccagctctac-3' | 189 |
| RHOA | 5'-gcacacaaggcgggagctag-3' | 190 | 5'-ctctgccttcttcaggtttc-3' | 191 |
| SERP1 | 5'-ctggttattggctctcttca-3' | 192 | 5'-catgcccatcctgatact-3' | 193 |
| SKP1 | 5'-ctaggatgtcttccagcctc-3' | 194 | 5'-gcaatatatttaaaactaag-3' | 195 |
| TOX4 | 5'-gaactcagtatagtgccaac-3' | 196 | 5'-gtgccacccccctaggctcaa-3' | 197 |
| TPT1 | 5'-atggtcagtaggacagaagg-3' | 198 | 5'-atggttcatgacaatatcga-3' | 199 |

TABLE 1B

| other information | | | | | | | | | |
|---|---|---|---|---|---|---|---|---|---|
| GEP-NEN Biomarker or Housekeeping Gene | | NCBI Chromosome | UniGene | | Primer Pair SEQ ID NO: | | Amplicon produced using forward and reverse | Exon | |
| Symbol | Name | location | ID | RefSeq | Fwd | Rev | primers Length | Boundary | Position |
| 18S | Eukaryotic 18S rRNA | | | X03205.1 | 30 | 31 | 187 | 1-1 | 1-187 |
| ACTB | Actin, beta | Chr.7: 5566779-5570232 | Hs.520640 | NM_001101 | 180 | 181 | 170 | 1-1 | 1-170 |
| ALG9 | asparagine-linked glycosylation 9, alpha-1,2-mannosyltransferase homolog | Chr. 11-111652919-111742305 | Hs.503850 | NM_024740.2 | 99 | 100 | 68 | 4-5 | 541-600 |
| AKAP8L | A kinase (PRKA) anchor protein 8-like | Chr.19: 15490859-15529833 | Hs.399800 | NM_014371 | 106 | 107 | 75 | 12-13 | 1596-1670 |
| APLP2 | amyloid beta (A4) precursor-like protein 2 | Chr. 11-129939716-130014706 | Hs.370247 | NM_001142276.1 | 41 | 42 | 102 | 14-15 | 2029-2132 |
| ARAF1 | v-raf murine sarcoma 3611 viral oncogene homolog | Chr. X-47420578-47431320 | Hs.446641 | NM_001654.3 | 43 | 44 | 74 | 10-11 | 1410-1475 |
| ARF1 | ADP-ribosylation factor 1, transcript variant 3 | Chr.1: 228270361-228286913 | Hs.286221 | NM_001024226 | 182 | 183 | 122 | 5-5 | 1231-1352 |
| ATG4B | ATG4 autophagy related 4 homolog B (*S. cerevisiae*), transcript variant 1 | Chr.2: 242577027-242613272 | Hs.283610 | NM_013325 | 184 | 185 | 110 | 7-8 | 586-695 |
| ATP6V1H | ATPase, H+ transporting, lysosomal 50/57 kDa, V1, Subunit H | Chr.8: 54628115-54755850 | Hs.491737 | NM_015941 | 108 | 109 | 102 | 13-14 | 1631-1732 |
| Survivin (BIRC5) | baculoviral IAP repeat-containing 5 (Survivin) | Chr. 17-76210277-76221716 | Hs.514527 | AB154416.1 | 89 | 90 | 78 | 3-4 | 473-551 |
| BNIP3L | BCL2/adenovirus E1B 19 kDa interacting protein 3-like | Chr.8: 26240523-26270644 | Hs.131226 | NM_004331 | 110 | 111 | 69 | 2-3 | 374-342 |
| BRAF | v-raf murine sarcoma viral oncogene homolog B1 | Chr. 7-140433812-140624564 | Hs.550061 | NM_004333.4 | 45 | 46 | 77 | 1-2 | 165-233 |
| C21ORF7 | chromosome 21 open reading frame 7 | Chr.21: 30452873-30548204 | Hs.222802 | NM_020152 | 112 | 113 | 76 | — | 611-686 |
| CD59 | CD59 molecule, complement regulatory protein | Chr. 11-33724556-33758025 | Hs.278573 | NM_203331.2 | 47 | 48 | 70 | 3-4 | 193-264 |
| CgA | chromogranin A (parathyroid secretory protein 1) | Chr. 14-93389445-93401638 | Hs.150793 | NM_001275.3 | 49 | 50 | 115 | 4-5 | 451-557 |
| COMMD9 | COMM domain containing 9 | Chr.11: 36293842-36310999 | Hs.279836 | NM_001101653 | 114 | 115 | 85 | 2-3 | 191-275 |
| CTGF | connective tissue growth factor | Chr. 6-132269316-132272518 | Hs.410037 | NM_001901.2 | 51 | 52 | 60 | 4-5 | 929-990 |

TABLE 1B-continued other information

| GEP-NEN Biomarker or Housekeeping Gene Symbol | Name | NCBI Chromosome location | UniGene ID | RefSeq | Primer Pair SEQ ID NO: Fwd | Primer Pair SEQ ID NO: Rev | Amplicon produced using forward and reverse primers Length | Exon Boundary | Position |
|---|---|---|---|---|---|---|---|---|---|
| CXCL14 | chemokine (C—X—C motif) ligand 14 | Chr. 5-134906369-134914969 | Hs.483444 | NM_004887.4 | 53 | 54 | 73 | 3-4 | 742-816 |
| ENPP4 | ectonucleotide pyrophosphatase/phosphodiesterase 4 | Chr.6: 46097701-46114436 | Hs.643497 | NM_014936 | 116 | 117 | 82 | 3-4 | 1221-1303 |
| FAM131A | family with sequence similarity 131, member A, transcript variant 2 | Chr.3: 184053717-184064063 | Hs.591307 | NM_001171093 | 118 | 119 | 64 | 4-5 | 498-561 |
| FLJ10357 | Rho guanine nucleotide exchange factor (GEF) 40 (ARHGEF40) | Chr.14: 21538527-21558036 | Hs.35125 | NM_018071 | 120 | 121 | 102 | 16-17 | 3557-3658 |
| FZD7 | frizzled homolog 7 (*Drosophila*) | Chr. 2-202899310-202903160 | Hs.173859 | NM_003507.1 | 55 | 56 | 70 | 1-1 | 1-70 |
| GAPDH | glyceraldehyde-3-phosphate dehydrogenase | Chr. 12-6643657-6647536 | Hs.544577 | NM_002046.3 | 32 | 33 | 122 | 3-4 | 132-254 |
| GLT8D1 | glycosyltransferase 8 domain containing 1, transcript variant 3 | Chr.3: 52728504-52740048 | Hs.297304 | NM_001010983 | 122 | 123 | 87 | 4-5 | 924-1010 |
| GRIA2 | glutamate receptor, ionotropic, AMPA 2 | Chr. 4-158141736-158287227 | Hs.32763 | NM_001083619.1 | 57 | 58 | 71 | 3-4 | 898-970 |
| HDAC9 | histone deacetylase 9, transcript variant 6 | Chr.7: 18535369-19036993 | Hs.196054 | NM_001204144 | 124 | 125 | 69 | 11-12 | 1777-1845 |
| HOXc6 | homeobox C6 | Chr. 12-54410642-54424607 | Hs.549040 | NM_153693.3 | 59 | 60 | 87 | 2-3 | 863-951 |
| HSF2 | heat shock transcription factor 2, transcript variant 1 | Chr.6: 122720696-122754264 | Hs.158195 | NM_004506 | 126 | 127 | 82 | 10-11 | 1324-1405 |
| HUWE1 | HECT, UBA and WWE domain containing 1 | Chr.X: 53559063-53713673 | Hs.136905 | NM_031407 | 186 | 187 | 68 | 67-68 | 10405-10472 |
| Ki-67 | antigen identified by monoclonal antibody Ki-67 | Chr. 10-129894923-129924655 | Hs.689823 | NM_001145966.1 | 61 | 62 | 78 | 6-7 | 556-635 |
| KISS1 | KiSS-1 metastasis-suppressor | Chr. 1-204159469-204165619 | Hs.95008 | NM_002256.3 | 63 | 64 | 71 | 2-3 | 227-299 |
| KRAS | v-Ki-ras2 Kirsten rat sarcoma viral oncogene homolog | Chr. 12-25358180-25403854 | Hs.505033 | NM_004985.3 | 65 | 66 | 130 | 4-5 | 571-692 |
| LEO1 | Leo1, Paf1/RNA polymerase II complex component homolog (*S. cerevisiae*) | Chr.15: 52230222-52263958 | Hs.567662 | NM_138792 | 128 | 129 | 122 | 10-11 | 1753-1874 |

TABLE 1B-continued

| other information | | | | | | | | | |
|---|---|---|---|---|---|---|---|---|---|
| GEP-NEN Biomarker or Housekeeping Gene | | NCBI Chromosome | UniGene | | Primer Pair SEQ ID NO: | | Amplicon produced using forward and reverse | Exon | |
| Symbol | Name | location | ID | RefSeq | Fwd | Rev | primers Length | Boundary | Position |
| MAGE-D2 | melanoma antigen family D, 2 | Chr. X-54834171-54842445 | Hs.522665 | NM_014599.4 | 67 | 68 | 90 | 3-4 | 591-682 |
| MORF4L1 | mortality factor 4 like 1, transcript variant 1 | Chr.15: 79165172-79190075 | Hs.374503 | NM_006791 | 188 | 189 | 62 | 1-1 | 35-96 |
| MORF4L2 | mortality factor 4 like 2, transcript variant 1 | Chr.X: 102930426-102943086 | Hs.326387 | NM_001142418 | 130 | 131 | 153 | 5-5 | 1294-1447 |
| MTA1 | metastasis associated 1 | Chr. 14-105886186-105937062 | Hs.525629 | NM_004689.3 | 60 | 70 | 86 | 16-17 | 1771-1838 |
| NAP1L1 | nucleosome assembly protein 1-like 1 | Chr. 12-76438672-76478738 | Hs.524599 | NM_139207.2 | 71 | 72 | 139 | 16-16 | 1625-1764 |
| NKX2-3 | NK2 transcription factor related, locus 3 (*Drosophila*) | Chr. 10-101292690-101296281 | Hs.243272 | NM_145285.2 | 73 | 74 | 95 | 1-2 | 512-608 |
| NOL3 | nucleolar protein 3 (apoptosis repressor with CARD domain), transcript variant 3 | Chr.16: 67204405-67209643 | Hs.513667 | NM_001185057 | 132 | 133 | 118 | 1-2 | 131-248 |
| NRP2 | neuropilin 2 | Chr. 2-206547224-206662857 | Hs.471200 | NM_018534.3 | 75 | 76 | 81 | 1-2 | 824-906 |
| NUDT3 | nudix (nucleoside diphosphate linked moiety X)-type motif 3 | Chr.6: 34255997-34360441 | Hs.188882 | NM_006703 | 134 | 135 | 62 | 2-3 | 500-561 |
| OAZ2 | ornithine decarboxylase antizyme 2 | Chr.15: 64979773-64995462 | Hs.713816 | NM_002537 | 136 | 137 | 96 | 1-2 | 189-284 |
| OR51E1 | olfactory receptor, family 51, subfamily E, member 1 | Chr. 11-4665156-4676718 | Hs.470038 | NM_152430.3 | 77 | 78 | 97 | 1-2 | 55-153 |
| PANK2 | pantothenate kinase 2 | Chr.20: 3869486-3904502 | Hs.516859 | NM_024960 | 138 | 139 | 126 | 4-5 | 785-910 |
| PHF21A | PHD finger protein 21A, transcript variant 1 | Chr.11: 45950870-46142985 | Hs.502458 | NM_001101802 | 140 | 141 | 127 | 16-17 | 2241-2367 |
| PKD1 | polycystic kidney disease 1 (autosomal dominant), transcript variant 2 | Chr.16: 2138711-2185899 | Hs.75813 | NM_000296 | 142 | 143 | 110 | 16-17 | 7224-7333 |
| PLD3 | phospholipase D family, member 3, transcript variant 1 | Chr.19: 40854332-40884390 | Hs.257008 | NM_001031696 | 144 | 145 | 104 | 6-7 | 780-883 |
| PQB1 | polyglutamine binding protein 1, transcript variant 2 | Chr.X: 48755195-48760422 | Hs.534384 | NM_001032381 | 146 | 147 | 68 | 2-3 | 157-224 |
| PNMA2 | paraneoplastic antigen MA2 | Chr. 8-26362196-26371483 | Hs.591838 | NM_007257.5 | 79 | 80 | 60 | 3-3 | 283-343 |

TABLE 1B-continued other information

| GEP-NEN Biomarker or Housekeeping Gene Symbol | Name | NCBI Chromosome location | UniGene ID | RefSeq | Primer Pair SEQ ID NO: Fwd | Rev | Amplicon produced using forward and reverse primers Length | Exon Boundary | Position |
|---|---|---|---|---|---|---|---|---|---|
| PTPRN2 | protein tyrosine phosphatase, receptor type, N polypeptide 2 | Chr. 7-157331750-158380482 | Hs.490789 | NM_130842.2 | 81 | 82 | 75 | 2-3 | 307-383 |
| RAF1 | v-raf-1 murine leukemia viral oncogene homolog 1 | Chr. 3-12625100-12705700 | Hs.159130 | NM_002880.3 | 83 | 84 | 90 | 7-8 | 1186-1277 |
| RHOA | ras homolog gene family, member A | Chr.3: 49396578-49449526 | Hs.247077 | NM_001664 | 190 | 191 | 62 | 4-5 | 651-712 |
| RNF41 | ring finger protein 41, transcript variant 4 | Chr.12: 56598285-56615735 | Hs.524502 | NM_001242826 | 148 | 149 | 72 | 2-3 | 265-336 |
| RSF1 | remodeling and spacing factor 1 | Chr.11: 77377274-77531880 | Hs.420229 | NM_016578 | 150 | 151 | 60 | 7-8 | 2804-2863 |
| RTN2 | reticulon 2, transcript variant 1 | Chr.19: 45988550-46000313 | Hs.47517 | NM_005619 | 152 | 153 | 87 | 9-10 | 1681-1766 |
| SCG5 | secretogranin V (7B2 protein) | Chr. 15-32933870-32989298 | Hs.156540 | NM_001144757.1 | 85 | 86 | 84 | 5-6 | 616-701 |
| SERP | stress-associated endoplasmic reticulum protein 1 | Chr.3: 150259780-150264428 | Hs.518326 | NM_014445 | 192 | 193 | 79 | 2-3 | 626-704 |
| SKP1 | S-phase kinase-associated protein 1, transcript variant 1 | Chr.5: 133492082-133512724 | Hs.171626 | NM_006930 | 194 | 195 | 140 | 5-5 | 1821-1960 |
| SMARCD3 | SWI/SNF related, matrix associated, actin dependent regulator of chromatin, subfamily d, member 3, transcript variant 3 | Chr.7: 150936059-150974231 | Hs.647067 | NM_001003801 | 154 | 155 | 109 | 8-9 | 986-1094 |
| SPATA7 | spermatogenes is associated 7, transcript variant 2 | Chr.14: 88851988-88904804 | Hs.525518 | NM_001040428 | 156 | 157 | 81 | 1-2 | 160-241 |
| SPOCK1 | sparc/osteonectin, cwcv and kazal-like domains proteoglycan (testican) 1 | Chr. 5-136310987-136835018 | Hs.596136 | NM_004598.3 | 87 | 88 | 63 | 4-5 | 465-529 |
| SST1 | somatostatin receptor 1 | Chr.14: 38677204-38682268 | Hs.248160 | NM_001049 | 158 | 159 | 85 | 3-3 | 724-808 |
| SST3 | somatostatin receptor 3 | Chr.22: 37602245-37608353 | Hs.225995 | NM_001051 | 160 | 161 | 84 | 2-2 | 637-720 |
| SST4 | somatostatin receptor 4 | Chr.20: 23016057-23017314 | Hs.673846 | NM_001052 | 162 | 163 | 104 | 1-1 | 91-194 |
| SST5 | somatostatin receptor 5, transcript variant 1 | Chr.16: 1122756-1131454 | Hs.449840 | NM_001053 | 164 | 165 | 157 | 1-1 | 1501-1657 |

TABLE 1B-continued

| other information | | | | | | | | | | |
|---|---|---|---|---|---|---|---|---|---|---|
| GEP-NEN Biomarker or Housekeeping Gene | | NCBI Chromosome | UniGene | | Primer Pair SEQ ID NO: | | Amplicon produced using forward and reverse | Exon | |
| Symbol | Name | location | ID | RefSeq | Fwd | Rev | primers Length | Boundary | Position |
| TECPR2 | tectonin beta-propeller repeat containing 2, transcript variant 2 | Chr.14: 102829300-102968818 | Hs.195667 | NM_001172631 | 166 | 167 | 61 | 12-13 | 3130-3191 |
| TFCP2 | transcription factor CP2 | Chr. 12-51488620-51566664 | Hs.48849 | NM_005653.3 | 101 | 102 | 91 | 11-12 | 1560-1652 |
| TOX4 | TOX high mobility group box family member 4 | Chr.14: 21945335-21967319 | Hs.555910 | NM_014828 | 196 | 197 | 145 | 5-5 | 441-585 |
| TPH1 | tryptophan hydroxylase 1 | Chr. 11-18042538-18062309 | Hs.591999 | NM_004179.2 | 91 | 92 | 145 | 1-2 | 73-219 |
| TPT1 | tumor protein, translationally-controlled 1 | Chr.13: 45911304-45915297 | Hs.374596 | NM_003295 | 198 | 199 | 131 | 3-3 | 196-321 |
| TRMT112 | tRNA methyltransferase 11-2 homolog (*S. cerevisiae*) | Chr.11: 64084163-64085033 | Hs.333579 | NM_016404 | 168 | 169 | 91 | 1-2 | 45-135 |
| VMAT1 | solute carrier family 18 (vesicular monoamine), member 1 | Chr. 8-20002366-20040717 | Hs.158322 | NM_003053.3 | 93 | 94 | 102 | 1-2 | 93-196 |
| VMAT2 | solute carrier family 18 (vesicular monoamine), member 2 | Chr. 10-119000716-119037095 | Hs.596992 | NM_003054.3 | 95 | 96 | 60 | 9-10 | 896-957 |
| VPS13C | vacuolar protein sorting 13 homolog C (*S. cerevisiae*), transcript variant 2B | Chr.15: 62144588-62352647 | Hs.511668 | NM_001018088 | 170 | 171 | 65 | 69-70 | 9685-9749 |
| WDFY3 | WD repeat and FYVE domain containing 3 | Chr.4: 85590690-85887544 | Hs.480116 | NM_014991 | 172 | 173 | 81 | 64-65 | 10190-10270 |
| X2BTB48 | serpin peptidase inhibitor, clade A (alpha-1 antiproteinase, antitrypsin), member 10 | Chr. 14-94749650-94759596 | Hs.118620 | NM_001100607.1 | 97 | 98 | 80 | 4-5 | 1305-1224 |
| ZFHX3 | zinc finger homeobox 3, transcript variant B | Chr.16: 72816784-73092534 | Hs.598297 | NM_001164766 | 174 | 175 | 68 | 5-6 | 886-953 |
| ZNF410 | zinc finger protein 410 | Chr. 14-74353586-74398803 | Hs.270869 | NM_021188.1 | 103 | 104 | 102 | 7-8 | 1134-1237 |
| ZXDC | zinc finger C, transcript variant 2 | Chr.3: 126156444-126194762 | Hs.440049 | NM_001040653 | 176 | 177 | 61 | 1-2 | 936-1001 |
| ZZZ3 | zinc finger, ZZ-type containing 3 | Chr.1: 78030190-78148343 | Hs.480506 | NM_015534 | 178 | 179 | 62 | 13-14 | 2909-2971 |

The results are presented in FIG. 1, with each of the figures nine panels showing average expression levels for an individual biomarker in normal EC (left), malignant/metastatic (center) and localized (right) samples. Ellipsoids correspond to a ±2 Standard Deviation (SD) threshold. All p-values: $p<0.05$. The results demonstrate significantly higher expression levels of MAGE-D2. MTA1, NAP1L1, Ki-67. FZD7, CgA and NRP2, and reduced levels of survivin and Kiss1 in SI GEP-NEN (AKA SI NETs), confirming differential expression of these GEP-NEN biomarkers in GEP-NEN samples compared to normal cells, and between different GEP-NEN tumor grades.

Detection and Expression Level Determination for Transcripts of 21-Biomarker Panel Quantitative real-time PCR (QPCR) was carried out as described above, using a set of primer pairs to measure expression levels of transcripts from a 21-gene GEP-NEN biomarker panel (including MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph1). The primer sequences and information are listed in Tables 1A and 1B, above. Expression of the 21 biomarkers was measured in 167 human tissue samples, including normal EC cell (n=13) normal SI mucosa (n=27), and primary (n=53) and metastatic (n=21 liver METs) GEP-NEN subtype and 53 adenocarcinoma (colon, breast, and pancreatic) samples. This study demonstrated that each of the 21 biomarkers is significantly differentially expressed in GEP-NEN tumor samples.

For each of the 21 biomarkers, the proportion of GEP-NEN samples versus adenocarcinoma samples in which transcript levels were detected was calculated and compared using a 2-tailed Fisher's test (GraphPad Prizm 4; FIG. 8B: *$p<0.002$ SI GEP-NENs versus adenocarcinomas (Fisher's exact test)). As shown in FIG. 8B, a significantly higher proportion (>95%) of the GEP-NEN samples in this study expressed (i.e., were positive for) 16 of the 21 GEP-NEN biomarker genes (76%), as compared to adenocarcinomas ($p<0.002$). Genes highly expressed in both tumor types included CTGF, FZD7, NRP2, PNMA2 and survivin.

In contrast to different GEP-NEN sub-types, the various normal EC cell samples exhibited homogeneous transcript expression, with low transcript variation (57%) between samples. Different neoplastic SI GEP-NEN (a.k.a. SI NET) subtypes showed heterogeneity at the transcript level, indicating that different GEP-NEN sub-types could be differentiated by detecting and determining expression levels of transcripts in the 21-biomarker panel.

Example 2: Principal Component Analysis (PCA)

After natural log (ln)-transformation, and importation into Partek® Genomic Suite, Principal Component Analysis (PCA) was performed to describe the structure of the high-dimensional expression data. PCA allowed visualization and comparison of transcript expression patterns among various samples (e.g., normal, neoplastic, GEP-NEN vs. other tumor, GEP-NEN subtypes, primary vs. metastatic/malignant). PCA reduced dimensionality of the expression data—obtained with each of the nine-biomarker and twenty-one biomarker panels—to three uncorrelated principal components (PCs), which explained most variations (Jolliffe I T, "Principle Component Anlysis," Springer, 1986.). PCA mapping was visualized in a 3-dimensional space, with the first ($1^{st}$), second ($2^{nd}$) and third ($3^{rd}$) PCs assigned to the x-, y-, and z-axes, respectively.

For the nine and the twenty-one gene panels, average expression data for various samples were superimposed in this PCA coordinate system. The centroid (center of mass (average expression)) of each sample represented its individual transcript expression profile (regulatory signature) as given by the principal component vector. In this representation, the distance between centroids inversely equivalent to the similarity measure (greater distance=less similarity). Thus, large distances or separation between centroids indicated samples with distinct transcript expressions signatures; proximity of centroids indicated similarity between samples. For example, distance between centroids for different tumor type samples represented the relative similarity of their regulatory signatures (transcript expression levels).

9-Biomarker Panel

PCA was carried out, as described above, for the real-time PCR expression data for the nine-gene biomarker panel (MAGE-D2, MTA1, NAP1L1, Ki-67, Survivin, FZD7, Kiss1, NRP2, and CgA). Three PCs (PC#1, PC#2, PC#3) reflected most of the expression variance between primary SI GEP-NENs, normal EC cell preparations, and respective metastases. Reduced data were mapped to a three dimensional space (FIG. 2). As shown in FIG. 2, for primary SI GEP-NENs and normal EC cell preparations, PC#1, PC#2, and PC#3 represented 31.7%, 26.5%, and 17.4% of the variance, respectively; overall, the three PCs represented 75.6% of the variance.

Figure 2A:
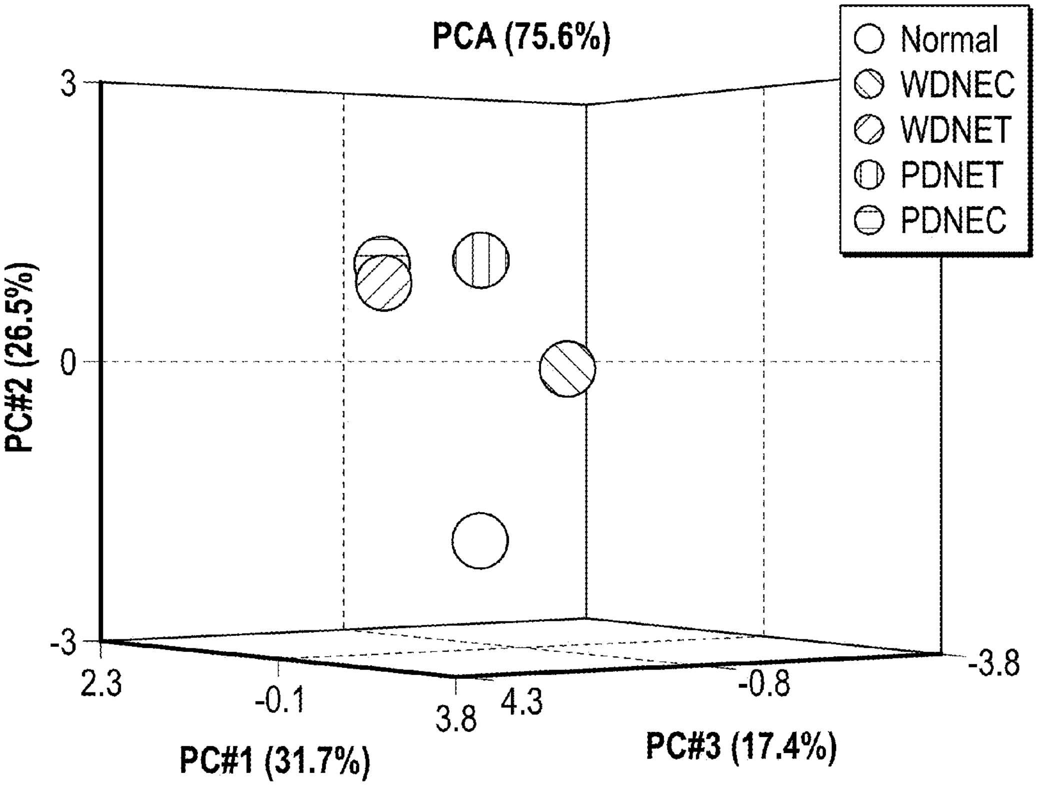
FIGS. 2A-D. Principal Component (PC) Analysis of primary Small Intestinal Neuroendocrine Tumors, metastases and normal EC cells. Ln-normalized real-time PCR expression levels of indicated biomarkers, reduced to 3 PCs, representing 75.6% variance in primary tumor subtypes and normal EC cell preparations (2A) and 73.2% variance in primary tumor subtypes and corresponding metastases (2C). For primary tumors and normal EC cells, three groups of genes with similar expression patterns were observed (2B), with two groups identified in corresponding metastases (2D).
Figure 2B:
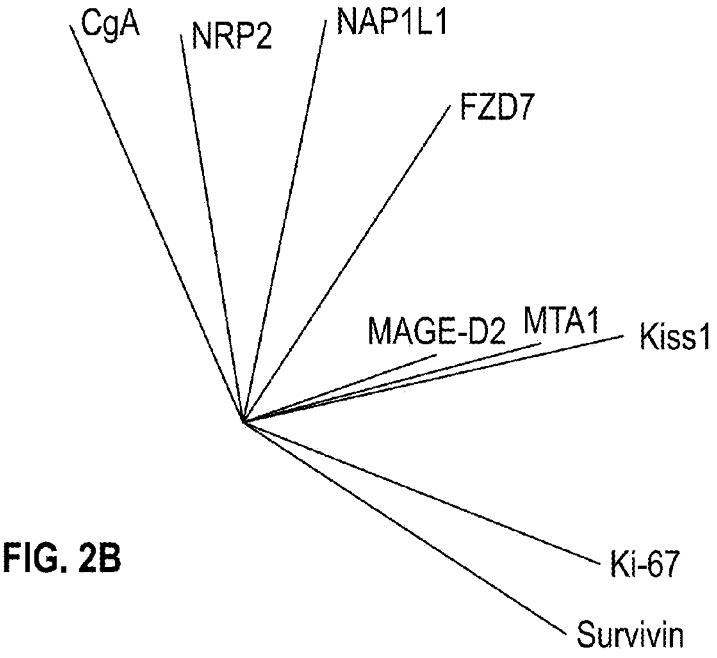
Figure 2C:
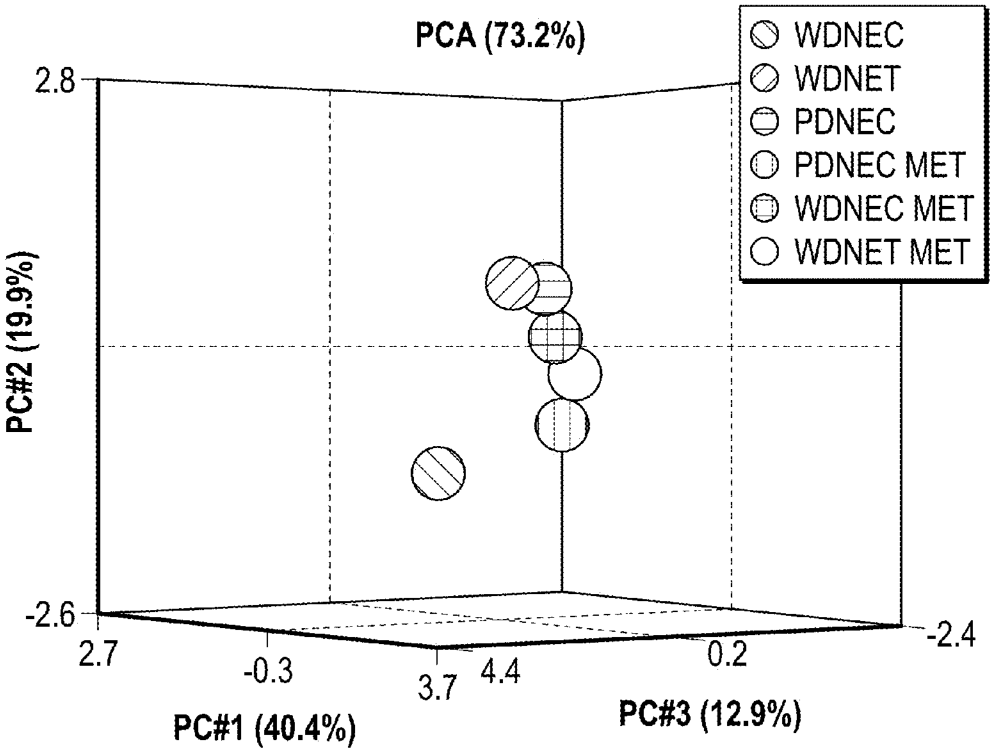
Figure 2D:
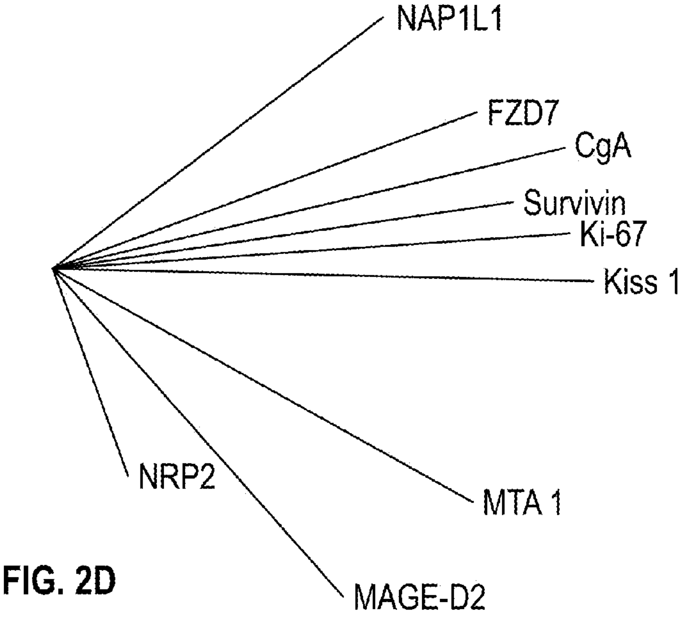

The three PCs represented 75.6% of variance for primary tumor subtypes and normal EC cell preparations (FIG. 2A), and 73.2% of variance for primary GEP-NEN tumor subtypes and corresponding metastases (FIG. 2C). For metastases, PC#1, PC#2, and PC#3 represented 40.4%, 19.9%, and 12.9% of the variance, respectively; overall 73.2% of the variance in the data was represented by all 3 PCs (FIG. 2C).

The inverse correlation between biomarker expression levels and the cosine of the angle between individual expression vectors (greater angle=less similarity) was used to identify related gene expression clusters. The clusters are shown in FIG. 2B for primary SI GEP-NENs ((1) CgA, NRP2, NAP1L1, FZD7; (2) MAGE-D2, MTA1, Kiss1; and (3) Ki-67, Survivin)) and in FIG. 2D for corresponding metastases ((1) NAP1L1, FZD7, CgA, Survivin, Ki-67, Kiss1; (2) MTA1, MAGE-D2, NRP2) (Gabriel K R, "The biplot graphic display of matrices with application to principal component analysis," *Biometrika* 1971; 58(3):453).

21-Biomarker Panel PCA

PCA also was carried out as described above for the 21-biomarker panel (MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph1). Three principal components captured most of the variance (83%) within the dataset. Reduced data were mapped to a three dimensional space.

Figure 8A:
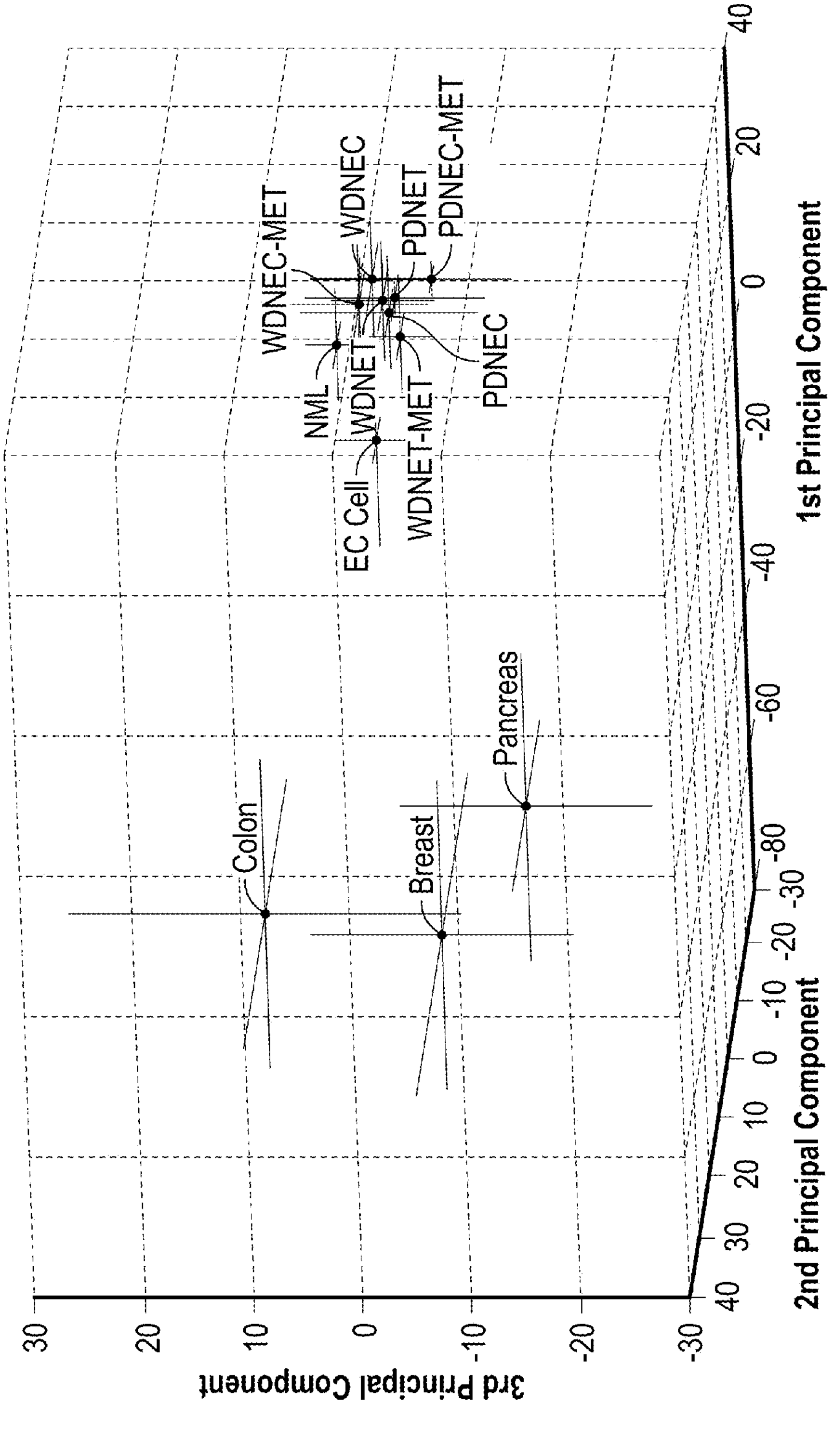
FIGS. 8A-B: Principal component analysis (PCA) and expression of marker genes in NETs, adenocarcinomas and normal tissues. 8A. Transcript expressions of the 21 marker gene panel reduced to 3 principal components that capture most of the variance (83%) within the dataset. Each centroid (average expression) corresponds to the transcript expression profile of the sample as given by its principal component vector. In this representation, proximity of separation between centroids is indicative of the degree of similarity. Thus, the marker gene panel can successfully distinguish adenocarcinomas (breast, colon, pancreas), normal SI mucosa, normal EC cells, and primary and metastatic NET subtypes. Of note, normal EC cells have a substantially different genetic profile to normal SI mucosa and neoplastic tissue. 8B. An analysis of the proportion of samples that express each of the marker genes, demonstrated that significantly more NET samples (>95%) were positive for 16 of the marker genes compared to adenocarcinomas (AC). Genes highly expressed in both tumor types included CTGF, FZD7, NRP2, PNMA2 and survivin. NML=normal SI mucosa, NML_EC=normal EC cell, MET=metastasis, WDNET=well differentiated NET; WDNEC=well differentiated neuroendocrine carcinoma; PDNET=poorly differentiated NET; PDNEC=poorly differentiated NEC. *p<0.002 SI NETs versus adenocarcinomas (Fisher's exact test).
Figure 8B:
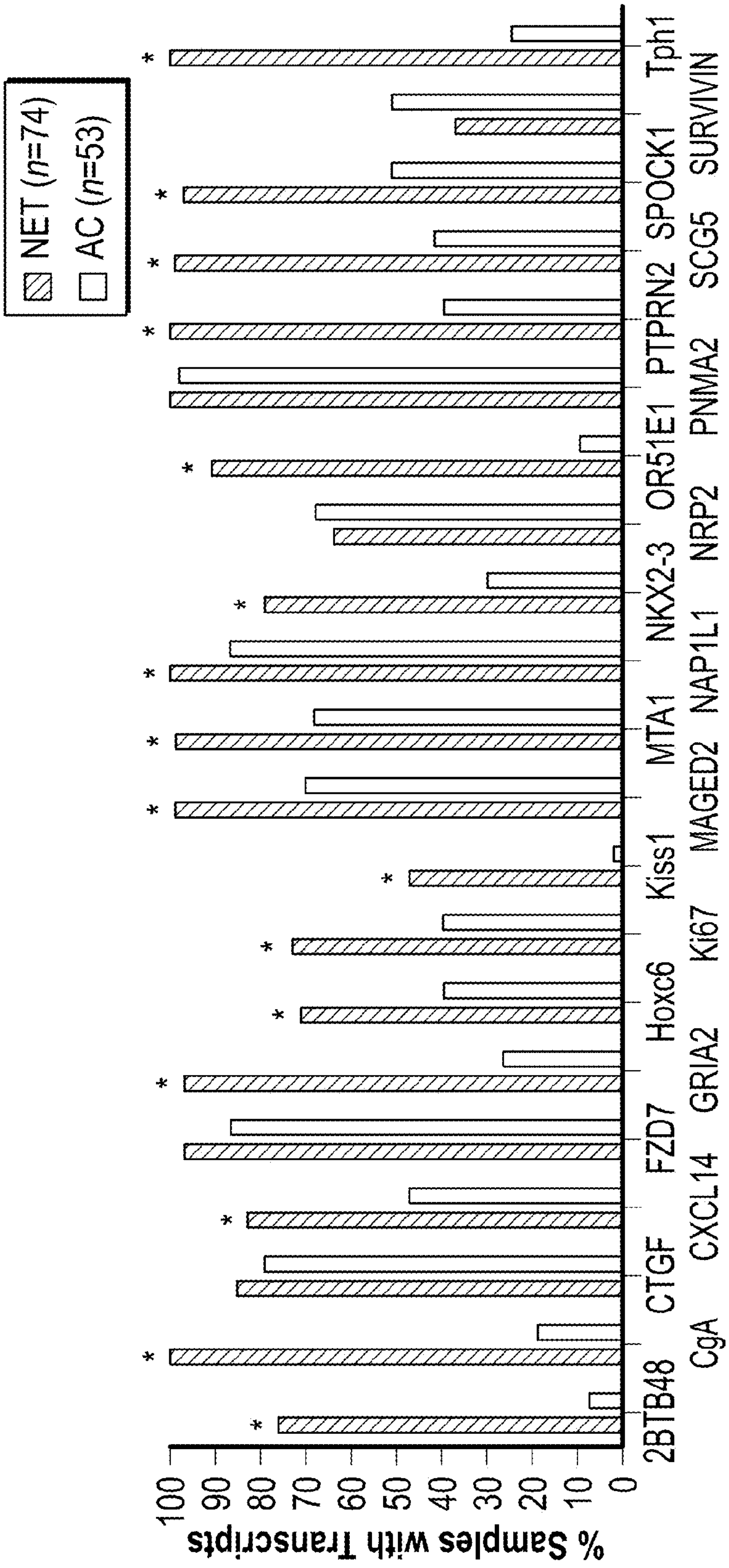

FIG. 8A shows a comparison of expression profiles for GEP-NENs (including various primary and metastatic subtypes), adenocarcinomas (sub-types), and normal tissues (EC and SI). As shown, centroids for the three adenocarcinoma types were separate from those for both normal SI mucosa and neoplastic GEP-NEN tissue subtypes. This observation confirms significant difference in expression levels in this other (epithelial) tumor type, shown using the Fisher's exact test, described above (FIG. 8B). The various neoplastic (SI GEP-NEN) subtypes displayed heterogeneous expression profiles, showing they could be distinguished using this panel of biomarkers.

All normal EC preparations displayed homogeneous transcript expression (with low variation (57%) within samples). Further, the normal sample expression profiles were substantially different compared to those of other tissue types, including normal SI mucosa. The genetic profile for normal EC cells was substantially different compared to normal SI mucosa and neoplastic tissue.

The results demonstrate differences in expression profiles for the GEP-NEN biomarkers and distinct regulatory expression signatures for primary SI GEP-NEN tumor subtypes, normal EC cell preparations, and SI GEP-NEN metastases. This study confirms that measuring expression of the 21 biomarkers can successfully distinguish between GEP-NEN sub-types, adenocarcinoma types, normal SI mucosa, normal EC cells, and between primary and metastatic GEP-NEN subtypes.

Example 3: Tumor Profiling and Analysis

Statistical analyses and tumor profiling were performed on transformed expression data obtained with the nine- and twenty-one biomarker panels described above.

9-Biomarker Panel

Mean (M) transcript expression levels and standard deviations (SD) were calculated for the nine-biomarker panel, for primary tumor subtypes and normal EC cell preparations. Mean normal expression of CgA ($M_{Normal}$=−9.2, SD=4.2), Ki-67 ($M_{Normal}$=−4.5, $SD_{Normal}$=1.1), Kiss1 ($M_{Normal}$=−4.0, $SD_{Normal}$=3.2), NAP1L1 ($M_{Normal}$=−8.3, $SD_{Normal}$=1.1), NRP2 ($M_{Normal}$=−9.3, SD=3.8), and Survivin ($M_{Normal}$=−6.0, $SD_{Normal}$=1.0) was significantly different compared to mean expression in primary tumors, both overall (All Tumors) and among individual subtypes. Seep values and Fold Change (FC), listed in Table 2, below. Transcript expression level measurements were reevaluated in a subset of samples (n=35). The data were highly correlated ($R^2$=0.93, p=0.001), demonstrating this approach was both highly reproducible and robust.

Analysis of Variance (ANOVA) was carried out to evaluate differences in biomarker expression levels between tumor and normal samples, and between normal samples and individual tumor subtype samples. Specifically, ANOVA compared expression between normal EC cell preparations and primary tumor tissues, and between normal EC cell preparations and individual primary tumor types (Table 2). A two-class unpaired algorithm was implemented, with tumor sample data (total or individual sub-type) and normal sample expression data defining the two groups. As there were no missing values in the datasets, imputation was unnecessary. For each biomarker transcript, geometric Fold Change (FC) was calculated as the ratio of geometric means for the Tumor Group and the Normal Group.

Biomarker genes calculated to have differences in expression between normal and tumor groups, with p<0.05, were considered significantly changed. Transcripts with p<0.05 and absolute FC≥2.0 were considered differentially expressed between groups. CgA, FZD7, Ki-67, NAP1L1, NRP2, and Survivin were significantly altered in WDNETs compared to normal EC cell preparations. Transcript levels of CgA, Ki-67, MAGE-D2, and NRP2 were significantly changed in WDNECs. PDNETs displayed alternatively expressed levels of CgA, Ki-67, NAP1L1, NRP2, and Survivin. Finally, PDNECs were different only in expressions of NAP1L1 and NRP2.

TABLE 2

ANOVA comparing biomarker expression levels in SI-GEP-NENs, and individual SI-GEP-NEN sub-types, to expression levels in normal EC cell samples

| Gene | All Tumors vs. Normal | | WDNET vs. Normal | | WDNEC vs. Normal | | PDNET vs. Normal | | PDNEC vs. Normal | |
|---|---|---|---|---|---|---|---|---|---|---|
| | p | FC | p | FC | p | FC | p | FC | p | FC |
| CgA | $1.3 \times 10^{-4}$ | 17.7 | $1.05 \times 10^{-4}$ | 28.3 | 0.03 | 8.3 | 0.01 | 13.5 | NS | 20.5 |
| FZD7 | 0.05 | 3.6 | 0.02 | 5.9 | NS | −1.1 | NS | 5.5 | NS | 6.9 |
| Ki-67 | $1.1 \times 10^{-3}$ | −3.5 | 0.01 | −3.0 | 0.02 | −3.5 | $2.7 \times 10^{-3}$ | −5.5 | NS | −3.7 |
| Kiss1 | 0.02 | −3.9 | 0.05 | −3.7 | NS | −4.5 | NS | −4.4 | NS | −1.8 |
| MAGE-D2 | NS | 1.2 | NS | −1.6 | $6.4 \times 10^{-4}$ | 5.3 | NS | 1.6 | NS | −1.8 |
| MTA1 | NS | −1.2 | NS | −1.5 | NS | 1.1 | NS | 1.1 | NS | −1.6 |
| NAP1L1 | $4.7 \times 10^{-5}$ | 13.7 | $4.1 \times 10^{-6}$ | 24.8 | NS | 2.9 | $7.4 \times 10^{-4}$ | 17.3 | 0.01 | 26.9 |
| NRP2 | $2.2 \times 10^{-8}$ | 39.5 | $1.6 \times 10^{-6}$ | 31.5 | $2.3 \times 10^{-5}$ | 33.7 | $1.9 \times 10^{-6}$ | 82.08 | $5.0 \times 10^{-3}$ | 47.1 |
| Survivin | 0.01 | −3.5 | 0.04 | −3.1 | NS | −3.1 | 0.02 | −5.1 | NS | −5.07 |

Figure 3:
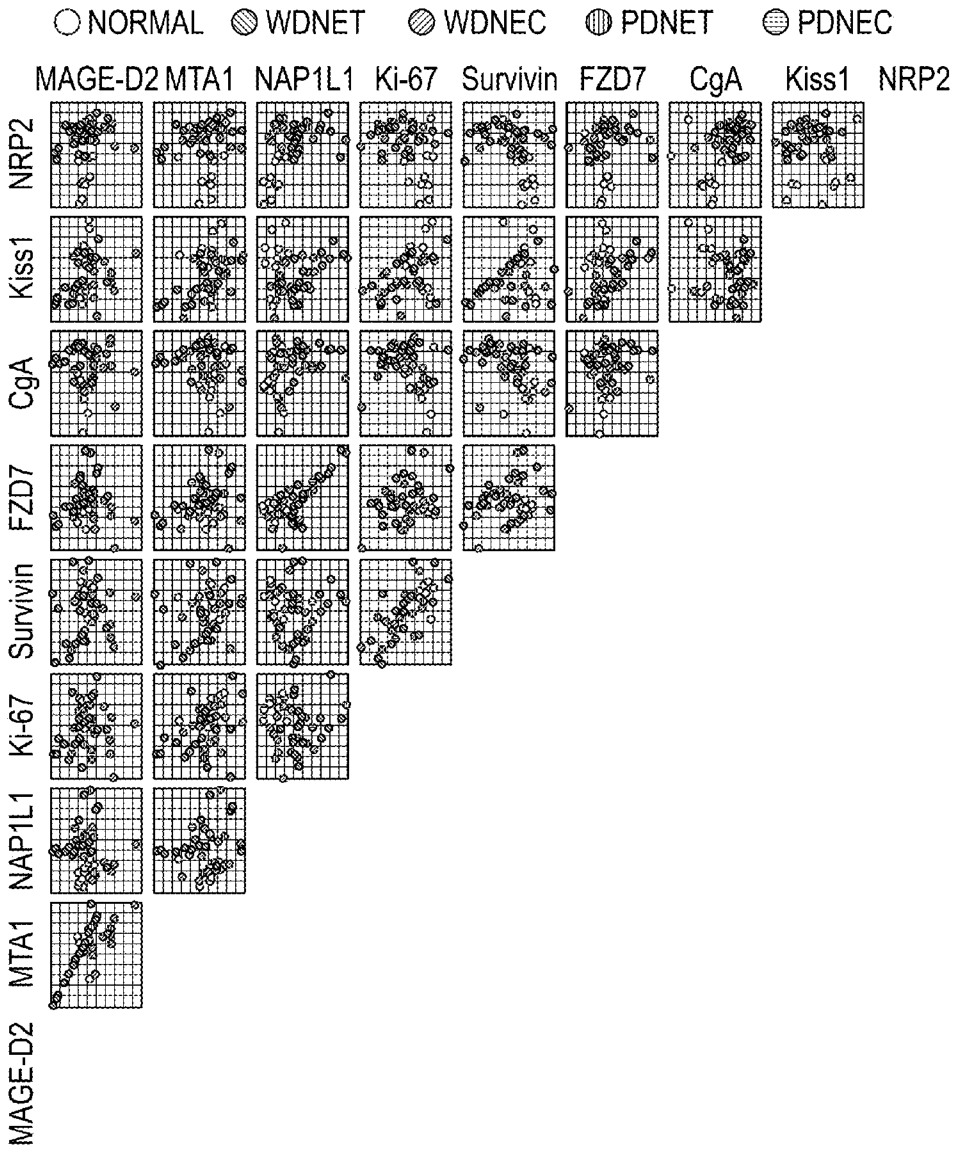
FIG. 3: Similarity Matrix using Pearson Correlation of the marker gene expressions in primary Small Intestinal Neuroendocrine Tumors and normal EC cells. Ln-normalized real-time PCR expression levels of indicated genes plotted onto X- and Y-axis.

WDNET = Well Differentiated Neuroendocrine Tumors,
WDNEC = Well Differentiated Neuroendocrine Carcinomas,
PDNET = Poorly Differentiated Neuroendocrine Tumors,
PDNEC = Poorly Differentiated Neuroendocrine Carcinomas;
NS = p ≥ 0.05,
FC = Fold Change Pearson's Correlation (PC) coefficients ($R^2$) were calculated for the nine-biomarker panel to assess linear relationships between pairs of biomarkers and between tumor sub-type differentiation and expression of the biomarkers. The distribution of biomarker expression among primary GEP-NEN subtypes and normal EC samples was linearly separated by calculating PC coefficients for individual pairs of the biomarkers (plotted on x- and y-axes of individual Similarity Matrices shown in FIG. 3). The study determined highly linear ($R^2$>0.50) correlation of expression for four pairs of biomarkers (MTA1:MAGE-D2, MTA1:Kiss1, FZD7:NAP1L1, and Survivin: Ki-67 (highly correlated ($R^2$>0.50)). Additionally, distribution of expression profiles for WDNETs, WDNEC, and PDNETs was linearly correlated to pair-wise expressions of Kiss1: Survivin, FZD7: NAP1L1, Survivin:MTA1, and MTA1:MAGE-D2, indicating a linear classifier could be applied to the dataset. The data further suggest an expression-dependant correlation between the biomarkers and primary tumor subtypes.

21-Biomarker Panel

Figure 9A:
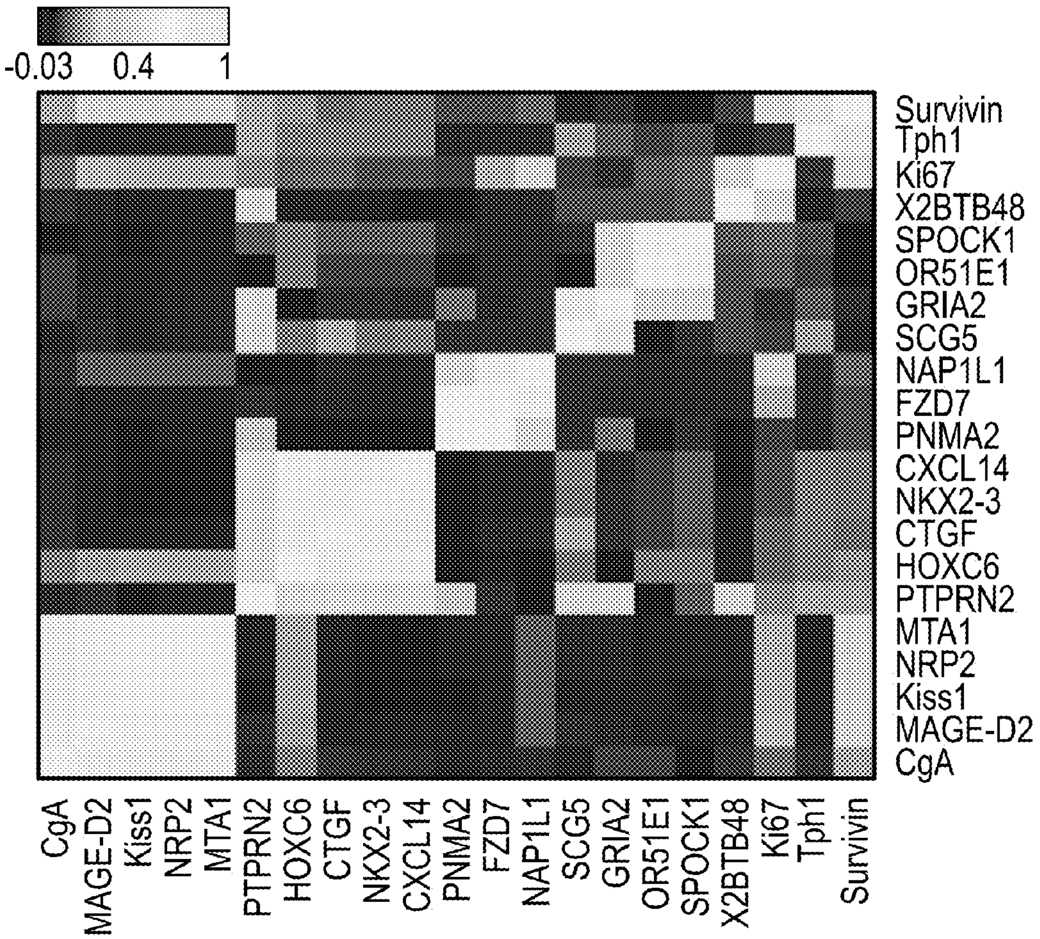
FIGS. 9A-B: Heatmap of correlation coefficients and relationship network of highly correlated gene pairs. 9A. Pearson's correlation coefficients ($R^2$) for each gene across all tissue types were calculated and represented as a heatmap with the lowest value (−0.03) represented in black, medium (0.4) in dark grey, and highest (1) in light grey. 9B. A network of co-expression was constructed such that transcript pairs with $R^2>0.40$ were connected by an edge. Actual $R^2$ values are superimposed on every edge.

Pearson's Correlation (PC) coefficients were used to identify linear relationships between expression levels of biomarkers in the 21-gene panel. PC coefficients were calculated for each pair of the 21 biomarkers, across all tissue types (FIG. 9A). FIG. 9 shows the results in a heatmap, with the pairs with the lowest (−0.03), medium (0.4), and highest (1) correlations indicated in black, dark grey, and light grey, respectively. The 21-biomarker panel contained 27 highly correlated ($R^2$>0.40) transcript pairs, with the highest correlation coefficient ($R^2$=1.00) between MTA1, NRP2, and Kiss1.

Figure 9B:
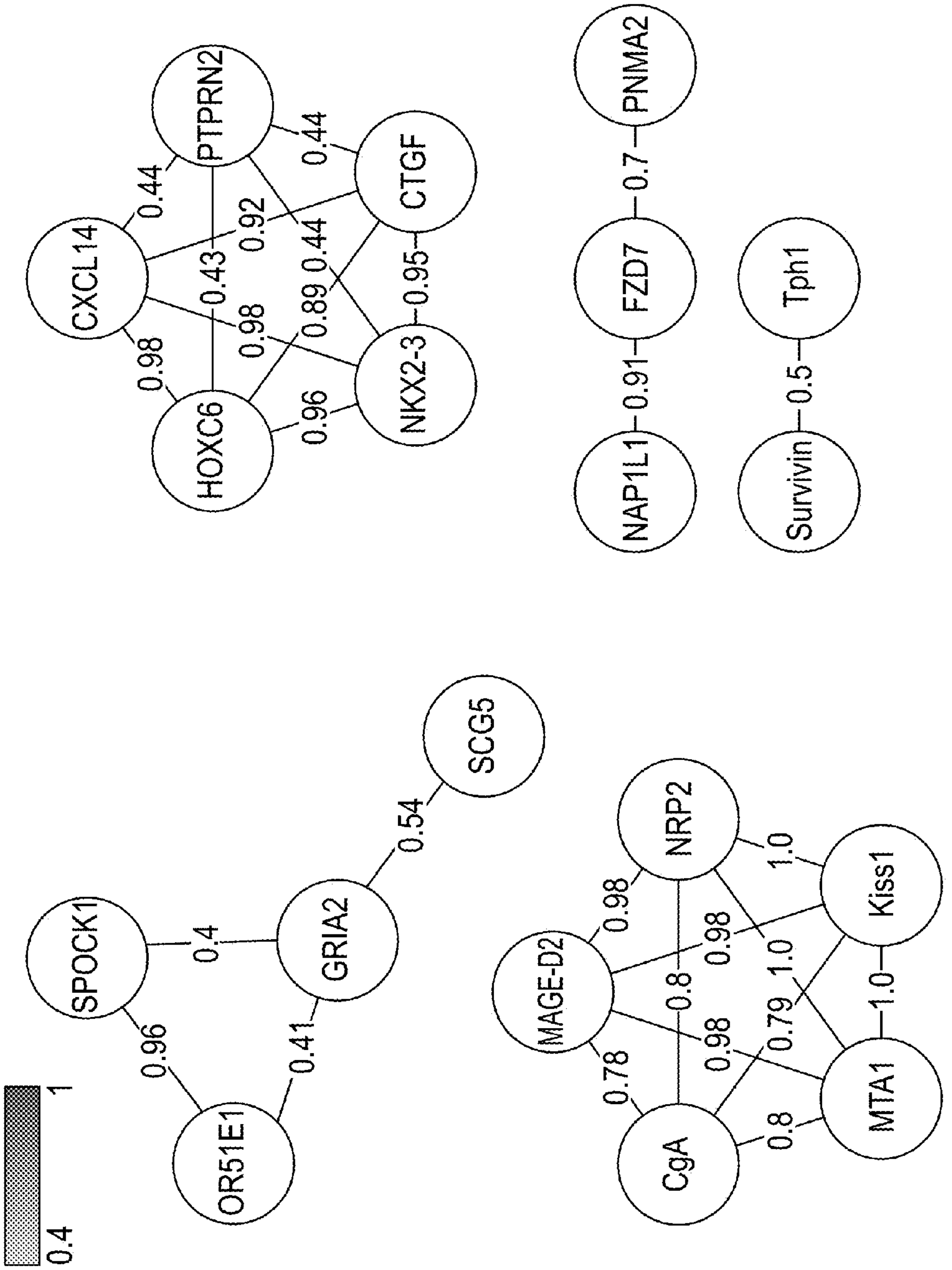

From these data, a network of correlations was constructed by drawing an edge between any transcript pair having an $R^2$ above a pre-defined threshold ($R^2$>0.40) (FIG. 9B, with actual $R^2$ values superimposed on each edge). As shown in FIG. 9B, five distinct regulatory clusters were identified within the network, each having a unique set of biomarkers: (1) MAGE-D2, NRP2, Kiss1, MTA1, and CgA (most tightly-connected cluster (every $R^2$-value>0.79)); (2) GRIA2, OR51E1, SPOCK1, and SCG5; (3), CXCL14, NKX2-3, HOXC6, CTGF, PTPRN2; (4) NAP1L1, FZD7, and PNMA2; and (5) Survivin and Tph1. In FIG. 9B, the R2 values are superimposed on individual edges. The lowest $R^2$-value is 0.40 within each cluster; the highest value is 1.0. The results demonstrate expression levels of the panel of biomarkers are biologically relevant to GEP-NEN.

A two-sample t-test computation was used to identify biomarker genes that are differentially expressed between: 1) EC cells, normal SI mucosa, and primary and metastatic tissues; 2) primary GEP-NEN subtypes; and 3) metastatic GEP-NEN subtypes (FIG. 10).

Calculated S-values for each subset ranged from −1.4 to 1.1. Based on the number of genes (n=21) and the sample size (n=114), the threshold for statistical significance for the S-value was set at ±0.4 (Nadler B, "Discussion of "On consistency and sparsity for principal component analysis in high dimensions,"" *Journal of the American Statistical Association* 2009; 104:694-97). Transcripts with S<−0.4 or S>0.4, and p<0.05, were considered significantly down- or up-regulated, respectively. Results are presented in FIG. 10, with volcano plots of gene ranks and significance (p) values for the t-test.

Figure 10A:
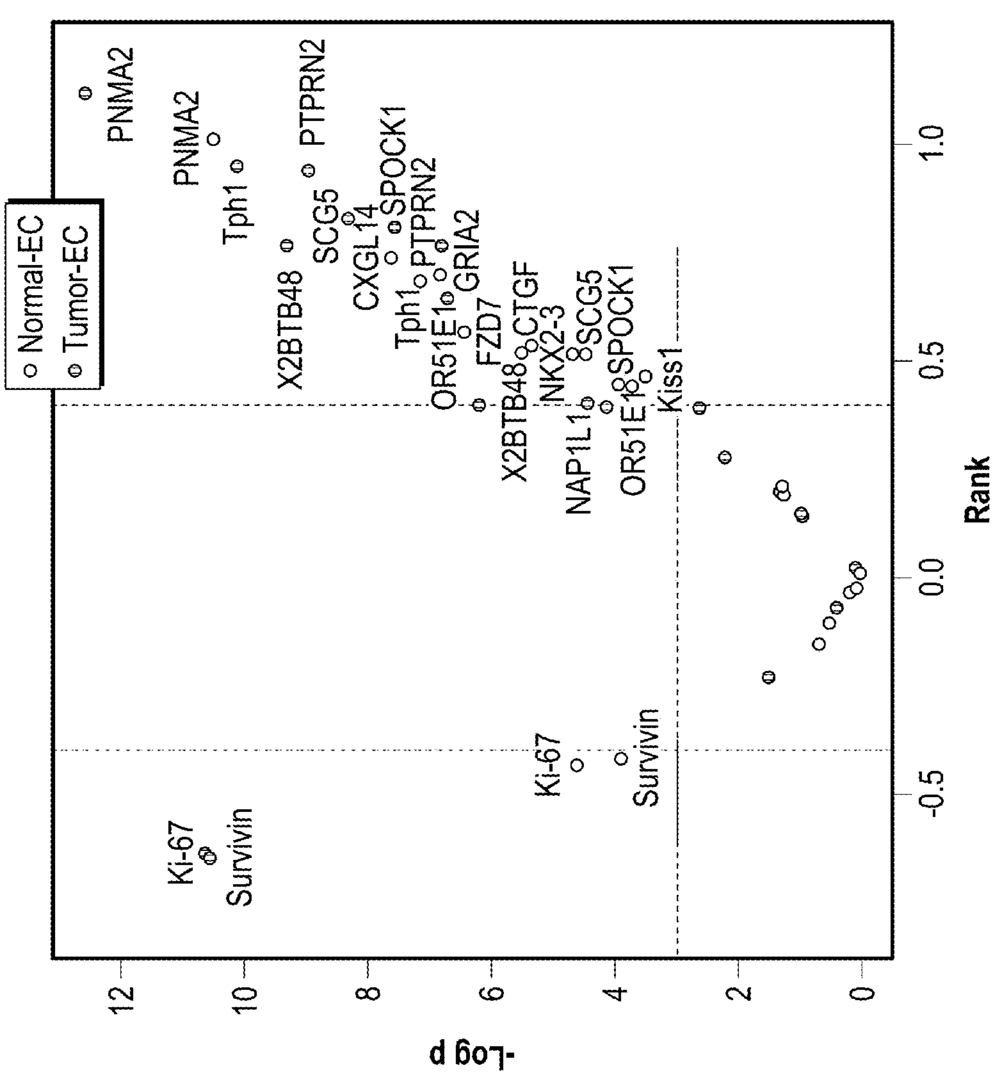
FIGS. 10A-D: Volcano plots of gene ranks and significance (p) values for a t-test. 10A. A two-sample t-test was computed to identify differentially expressed genes in 1) EC cells, normal SI mucosa, and primary and metastatic tissues; 2) primary NET subtypes; 3) metastatic NET subtypes. In normal EC cells compared to normal SI mucosa, transcript expression of the classic neuroendocrine marker Tph1, was significantly higher (p<0.001, S=0.7). 10B. Compared to normal SI mucosa, neoplastic tissue expressed higher transcript levels of CgA and GRIA-2, however CgA expression was not significantly altered (p=0.07, S=0.39) between neoplastic tissue and normal EC cells. 10C. There were no differentially expressed genes between all metastases as a group and all the different primary NET subtypes when analyzed as a group. 10D. There were no differentially expressed transcripts between PDNET-PDNEC and WDNET-PDNEC, and in WDNEC-PDNEC, MAGE-D2 was the only significant marker (p=0.009, S=1.03). CgA, Kiss1, NRP2, and Tph1 were differentially expressed between all metastasis subtypes.

FIG. 10A shows the comparison between normal SI mucosa, normal EC cells and SI GEP-NENs. Compared to normal mucosa, transcript expression of the classic neuroendocrine marker Tph1, was significantly higher (p<0.001, S=0.7; FIG. 10A) in SI GEP-NEN samples. Compared to normal SI mucosa, neoplastic tissue expressed higher transcript levels of CgA and GRIA2 (FIG. 10B); expression of CgA was not significantly altered (p=0.07, S=0.39) between neoplastic tissue and normal EC cells.

Figure 10B:
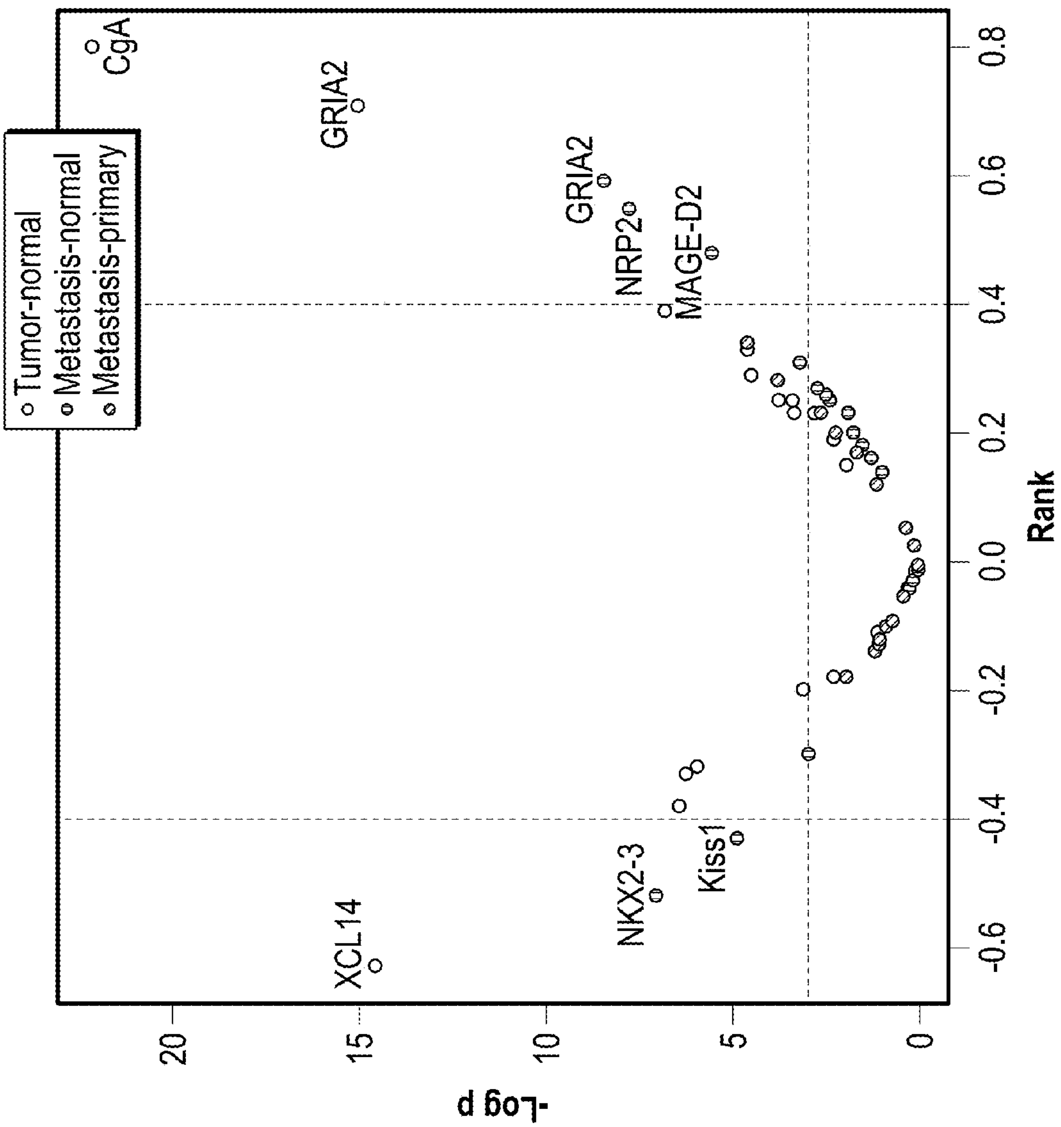

FIG. 10B shows the comparison between all GEP-NEN (tumor) samples and all normal samples, all metastatic GEP-NEN samples and all normal samples, and all metastatic GEP-NEN samples and all primary GEP-NEN samples. None of the biomarker transcripts were differentially expressed in the collective metastatic GEP-NEN samples, when analyzed as an entire group, compared to the collective primary GEP-NEN samples, analyzed as a group.

Figure 10C:
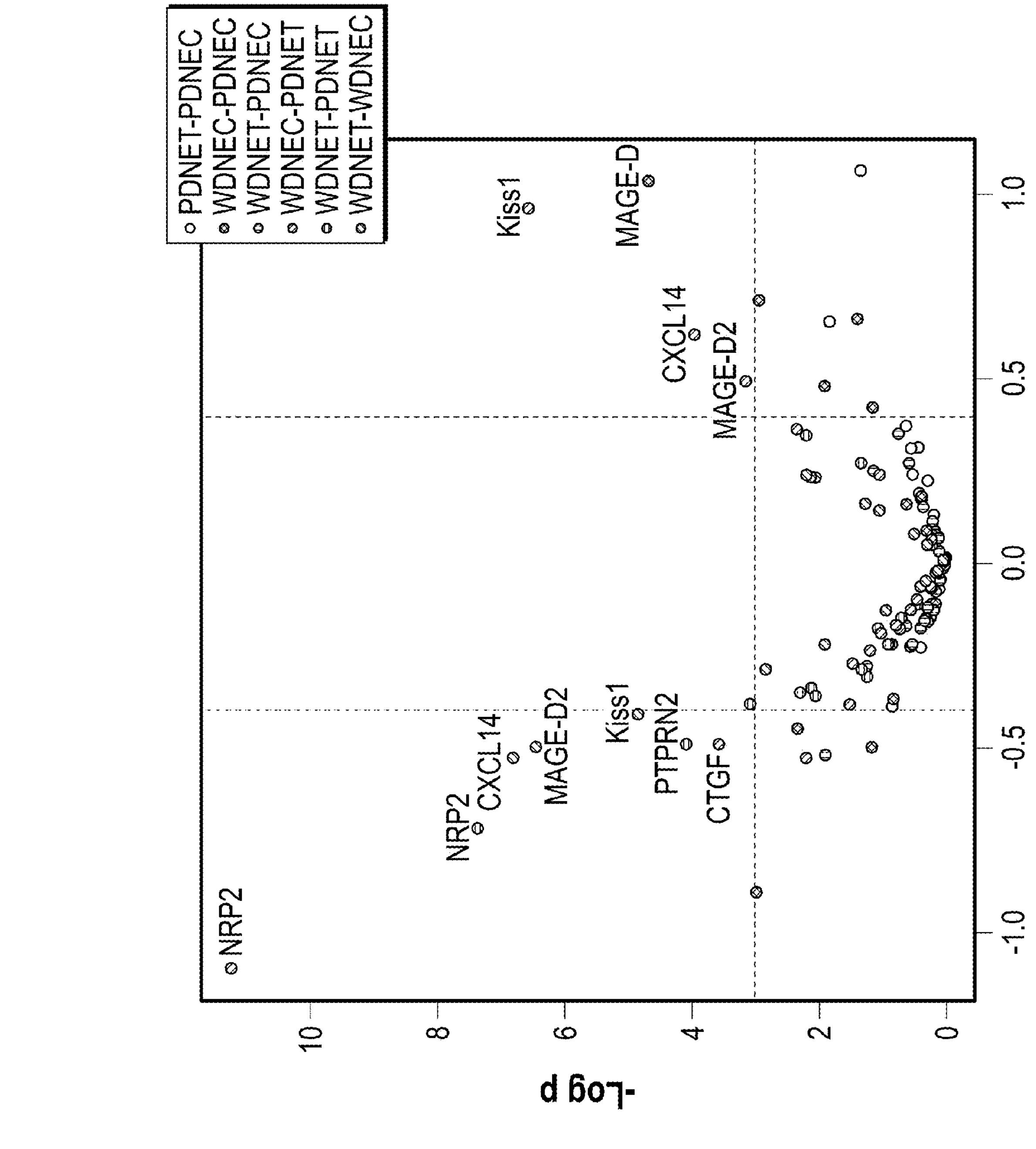

FIG. 10C shows the comparison between primary GEP-NEN subtypes and all metastases as a group. No biomarker transcripts were differentially expressed in PDNET samples as compared to PDNEC samples (PDNET-PDNEC), or WDNET samples as compared to PDNEC (WDNET-PDNEC) samples. Between WDNEC and PDNEC (WDNEC-PDNEC), MAGE-D2 was the only significant differentiating marker (p=0.009, S=1.03; FIG. 10C).

Figure 10D:
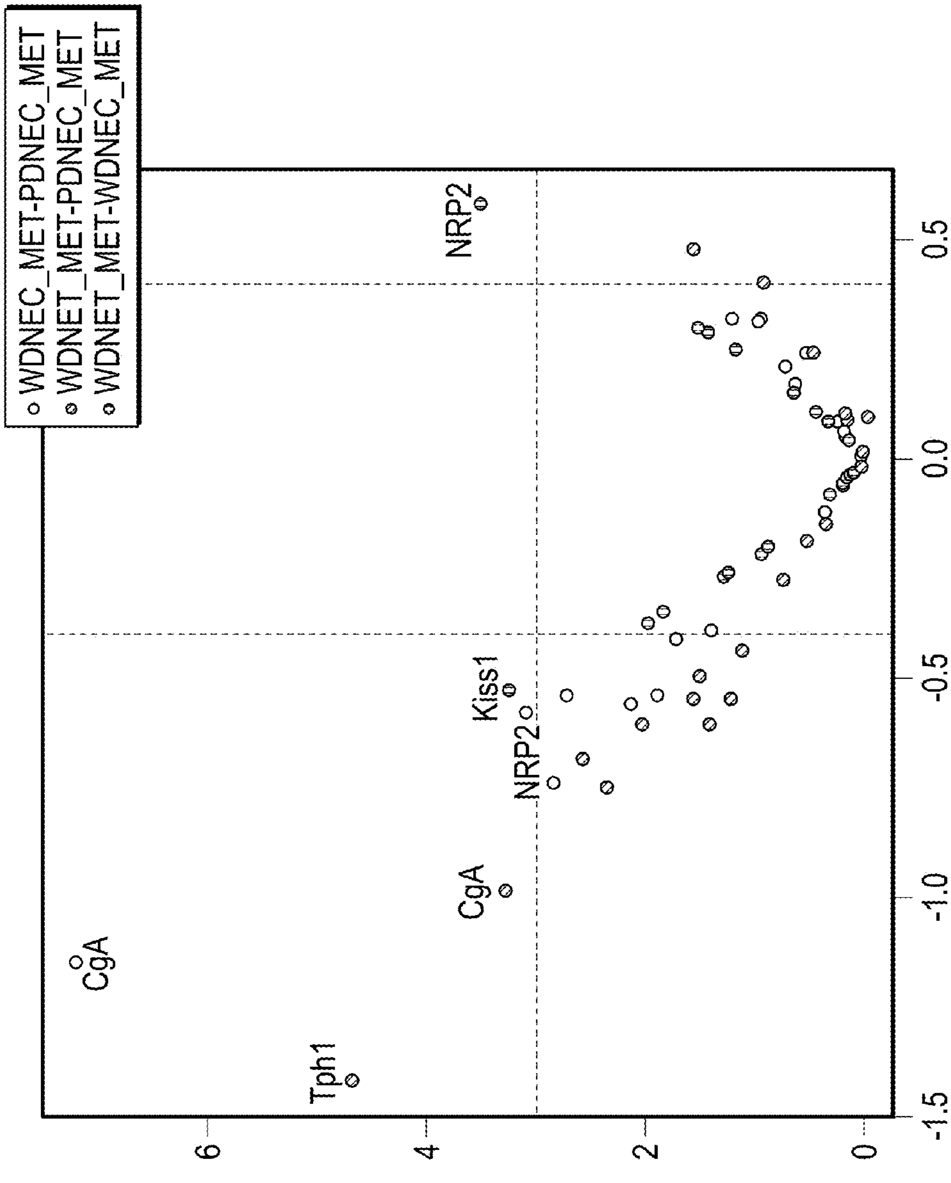

FIG. 10D shows comparison between primary tumors and metastatic subtypes. CgA, Kiss1, NRP2, and Tph1 were differentially expressed between all metastasis subtypes (FIG. 10D).

Example 4: Predictive Models for Classifying GEP-NENs

Expression levels of GEP-NEN biomarkers obtained in the studies in Examples 1-4 were further analyzed with supervised learning algorithms and models, including Support Vector Machines (SVM), Decision Tree, Perceptron, and regularized discriminant analysis RDA (Gallant S I, "Perceptron-based learning algorithms," *Perceptron-based learning algorithms* 1990; 1(2):179-91)).

Example 4A: Prediction and Modeling with Detected Expression of the Nine-Biomarker Panel Expression data obtained in the nine-biomarker study were analyzed using the Feature Selection (FS) classification model. The model was employed using a "greedy forward" selection approach, selecting the most relevant subset of features for the robust learning models, as described by Peng H, Long F, Ding C, "Feature selection based on mutual information: criteria of max-dependency, max-relevance, and min-redundancy," *IEEE Transactions on Pattern Analysis and Machine Intelligence,* 2005; 27(8):1226-38.

FS determined that for this study, expression levels of NAP1L1, FZD7, Kiss1 and MAGE-D2 were the best variables (of the nine biomarkers) for SVM classification. Thus, SVM was carried out by comparing expression levels for these biomarkers in normal EC cell preparations (n=13) and primary SI-GEP-NENs (n=36). For SVM, radial basis function was used as a kernel and a 10-fold cross-validation was used to measure the sensitivity of classification. See Cristofanilli M et al. "Circulating tumor cells, disease progression, and survival in metastatic breast cancer," *N Engl J Med* 2004. The results are shown in Table 3, below, and in FIG. 4. As shown, SMV predicted SI GEP-NENs in this study with 100% sensitivity, and 92% class specificity; normal EC cell preparations were accurately predicated with 77% sensitivity, with a class specificity of 100%.

TABLE 3

Class predictions produced by the Support Vector Machines classification model using transcript expression levels of NAP1L1, FZD7, Kiss1, and MAGE-D2

| | True Normal | True Tumor | Class Precision |
|---|---|---|---|
| Predicted Normal | 10 | 0 | 100% |
| Predicted Tumor | 3 | 36 | 92% |
| Class Recall | 77% | 100% | |

Figure 4:
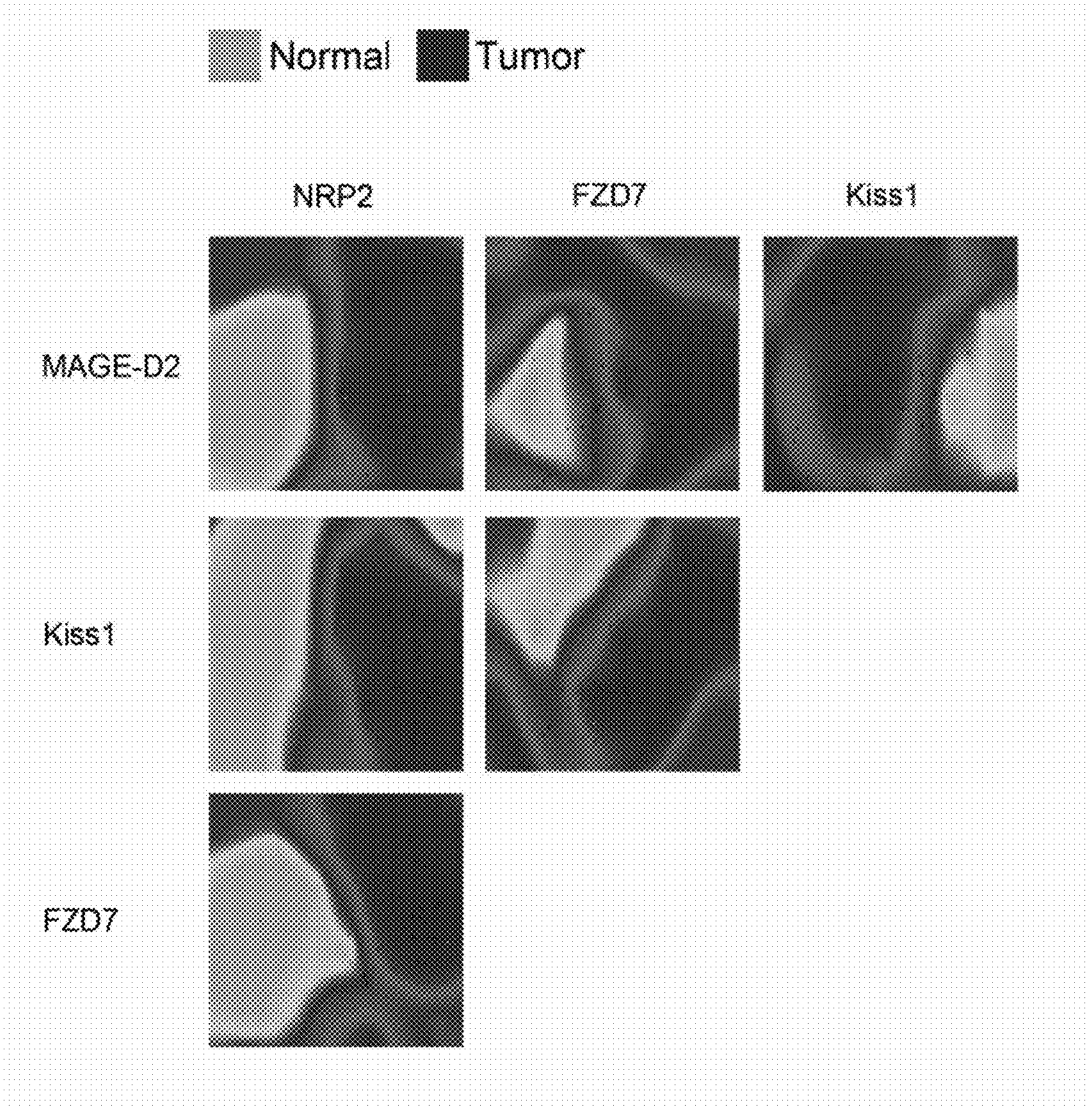
FIG. 4: Density Map of distributions between normal EC cells and Small Intestinal Neuroendocrine Tumors. Expression levels of indicated transcripts as identified by FS plotted on X- and Y-axes, with normal and neoplastic samples scattered according to respective gene pair expressions, distribution densities based on average Euclidean distance (difference in expression) between samples were colorized green (normal) and red (neoplastic). Blue areas indicate a region of transition between normal and neoplastic groups.

Density maps in FIG. 4 display distributions between SI GEP-NENs and normal EC cells, colorized to the density of the samples produced differential zones that depended on the individual gene expressions. Expression levels of NRP2, MAGE-D2, Kiss1, and FZD7 transcripts as identified by the Feature Selection algorithm were plotted on the X- and Y-axis. Normal and neoplastic sample data were scattered according to their respective gene pair expressions. Distribution densities based on average Euclidean distance (difference in expression) between samples were colorized green (normal) and red (neoplastic). Blue areas indicate a region of transition between normal and neoplastic groups.

The distinct separation between normal EC cells and primary small intestinal tumors indicates the utility of the selected transcripts as malignancy markers.

Figure 5:
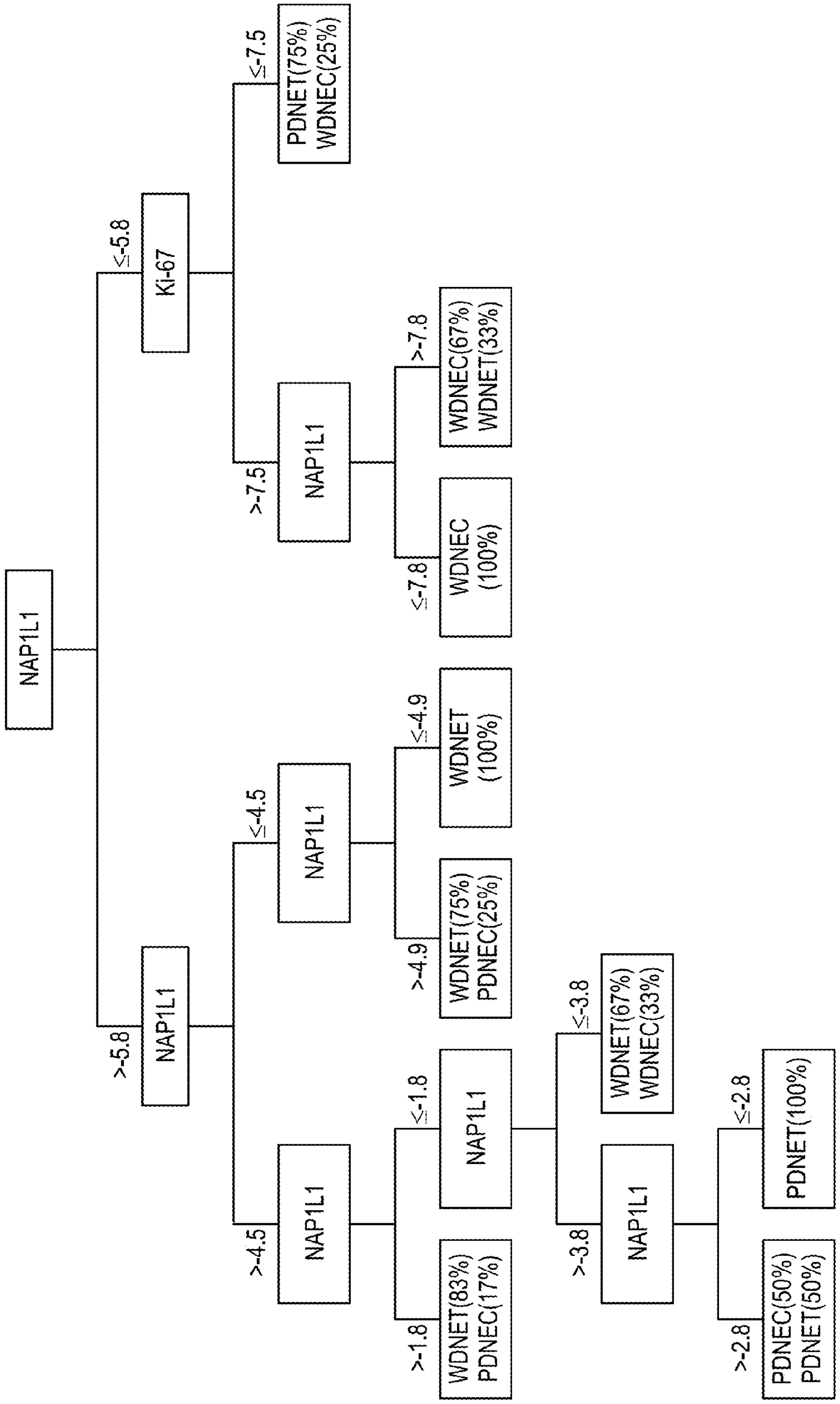
FIG. 5: Decision Tree classifying primary Small Intestinal Neuroendocrine Tumors. Expression levels of NAP1L1 and Ki-67 were identified as principle discriminators in the Decision Tree classifier using Feature Selection. The model was constructed by correlating values of NAP1L1 and Ki-67 to primary tumor subtypes. Percentages in parenthesis indicate the occurrence frequencies of primary small intestinal neuroendocrine tumor subtypes.

Feature Selection identified NAP1L1 and Ki-67 expression levels as principle discriminators in the Decision Tree classifier. Based on this result, Decision Trees classification model was constructed on expression data for individual primary SI GEP-NEN subtypes by correlating NAP1L1 and Ki-67 expression level values to the corresponding expression levels for primary tumor subtypes, as determined above. The results are displayed in FIG. 5, with the leaves of the tree representing classifications and branches representing conjunctions of features that devolve into the individual classifications. A 10-fold cross-validation was used to measure the efficiency of this technique, as described by Pirooznia M, et al., "A comparative study of different machine learning methods on microarray gene expression data," *BMC Genomics* 2008; 9 Suppl 1:S13. Percentages shown in parenthesis in FIG. 5 indicate the occurrence frequencies of primary SI GEP-NEN subtypes. As shown in Table 4, below, Decision Trees classification predicted WDNETs in this study with 78% sensitivity and 82%; predicted WDNECs in this study with 78% sensitivity and 64%; and predicted PDNETs in this study with 71% sensitivity and 63% specificity. With the nine biomarker panel, PDNECs were misclassified in this study as either WDNETs or PDNETs. (FIG. 5; Table 4).

TABLE 4

Class predictions produced by the Decision Trees classification model using transcript expression of Ki-67 and NAP1L1.

| | True WDNET | True WDNEC | True PDNET | True PDNEC | Class Precision |
|---|---|---|---|---|---|
| Predicted WDNET | 14 | 1 | 1 | 1 | 82% |
| Predicted WDNEC | 3 | 7 | 1 | 0 | 64% |
| Predicted PDNET | 1 | 1 | 5 | 1 | 63% |
| Predicted PDNEC | 0 | 0 | 0 | 0 | 0% |
| Class Recall | 78% | 78% | 78% | 0% | |

ANOVA was performed to identify transcripts differentially expressed in primary SI GEP-NEN subtypes and corresponding metastases (Table 5). Significant gain of Kiss1 ($p<0.005$) was associated with metastasis in all tumor subtypes.

TABLE 5

ANOVA results across Small Intestinal Neuroendocrine Tumor subtypes and corresponding metastases.

| | WDNET vs. WDNET MET | | WDNEC vs. WDNEC MET | | PDNEC vs. PDNEC MET | |
|---|---|---|---|---|---|---|
| Gene | p | FC | p | FC | p | FC |
| Kiss1 | $5.7 \times 10^{-7}$ | 52.8 | $1.2 \times 10^{-7}$ | 81.2 | 0.004 | 41.6 |
| MAGE-D2 | $5.2 \times 10^{-3}$ | 5.6 | NS | −1.04 | 0.03 | 10.4 |
| CgA | 0.02 | 9.08 | 0.01 | 12.4 | 0.08 | 21.1 |
| Ki-67 | NS | 2.7 | 0.02 | 3.7 | NS | 1.5 |
| MTA1 | 0.02 | 2.8 | NS | 1.1 | NS | 4.4 |
| Survivin | NS | 4.02 | 0.05 | 4.4 | NS | 6.1 |
| FZD7 | NS | 1.7 | $1.8 \times 10^{-3}$ | 27.2 | NS | 1.2 |

TABLE 5-continued

ANOVA results across Small Intestinal Neuroendocrine Tumor subtypes and corresponding metastases.

| | WDNET vs. WDNET MET | | WDNEC vs. WDNEC MET | | PDNEC vs. PDNEC MET | |
|---|---|---|---|---|---|---|
| Gene | p | FC | p | FC | p | FC |
| NAP1L1 | NS | 1.1 | 0.01 | 12.05 | NS | −1.9 |
| NRP2 | NS | 1.2 | NS | −1.6 | NS | −1.4 |

MET = Metastasis;
FC = Fold Change;
"p" = p value;
NS = $p \geq 0.05$

Figure 6A:
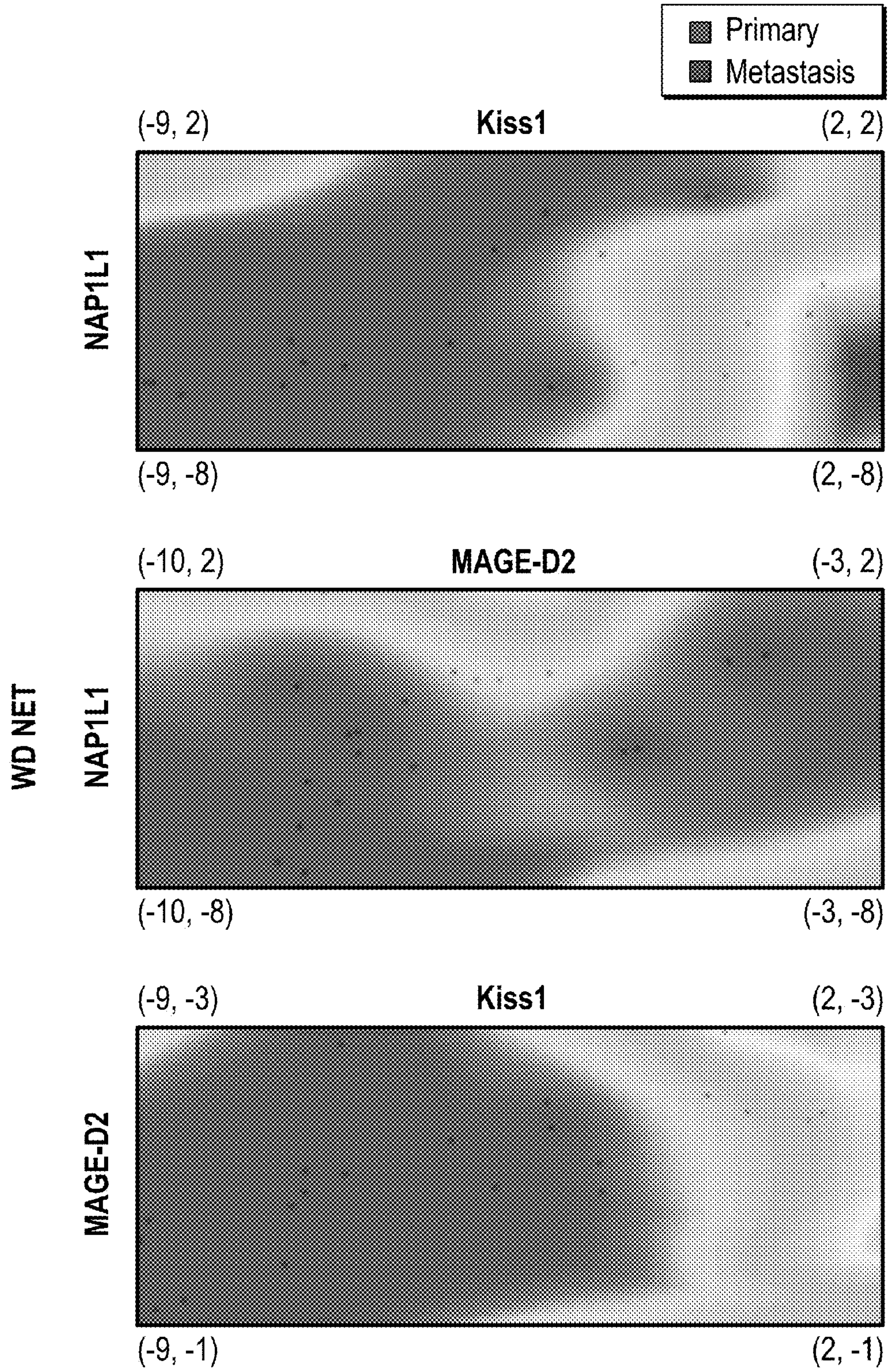
FIGS. 6A-C: Density Map of distributions between primary Small Intestinal Neuroendocrine Tumors and their metastases. Expression levels of Kiss1, NAP1L1, MAGE-D2, and CgA transcripts as identified by the FS algorithm plotted on X- and Y-axis. Primary Small Intestinal Neuroendocrine tumor subtypes (WDNETs, WDNECs, PDNECs) and respective metastases (METs) scattered according to their respective gene pair expressions (6A-C). Distribution densities based on the average Euclidean distance (difference in expression) between samples were colorized blue (primary tumors) and red (metastases). Green areas indicate a region of transition between primary tumor subtypes and respective metastases.

Detected expression levels of MAGE-D2, NAP1L1, and Kiss1 (as identified by FS) were analyzed in primary and corresponding metastatic WDNETs, using SVM to construct a classifier. To evaluate expression of biomarkers as compared to metastatic potential of primary tumors, samples were plotted in correlation with the selected gene expression levels and distribution densities were colorized to outline the separation of primary and metastatic samples (FIG. 6A).

WDNETs and metastatic WDNET results scattered according to their respective gene pair expressions, with distribution densities based on the average Euclidean distance (difference in expression) between samples colorized blue (primary tumors) and red (metastases), green areas indicating a region of transition between primary and metastatic tumors). As shown, WDNETs and WDNET METs were predicted with 100% sensitivity and specificity. WDNET could be predicted to metastasize if transcript levels of 1) NAP1L1>−2.71 and Kiss1>−2.50; 2) NAP1L1>−3.82 and MAGE-D2>−4.42; 3) MAGE-D2>−3.21 and Kiss1>−2.12.

A perceptron classifier (Markey M K et al., "Perceptron error surface analysis: a case study in breast cancer diagnosis," *Comput Biol Med* 2002; 32(2):99-109) of 0.05 was used to distinguish between localized tumors and the corresponding metastases. This methodology has been shown to effectively predict malignancy of breast cancer (Markey M K et al., "Perceptron error surface analysis: a case study in breast cancer diagnosis" *Comput Biol Med* 2002; 32(2): 99-109). A Perceptron classifier (using three data scans to generate the decision boundaries that explicitly separate data into classes, with a learning rate of 0.05) was used to predict metastases of WDNECs and PDNECs.

Figure 6B:
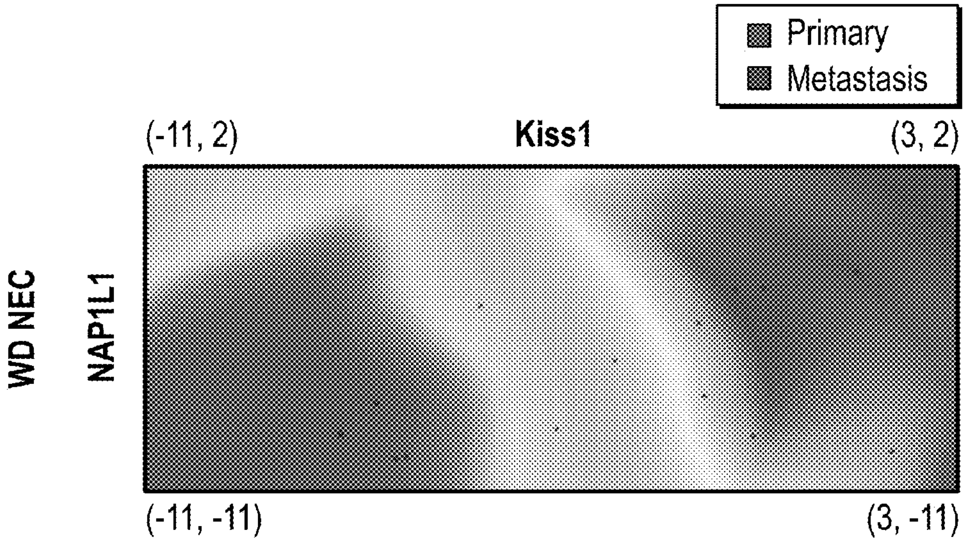
Figure 6C:
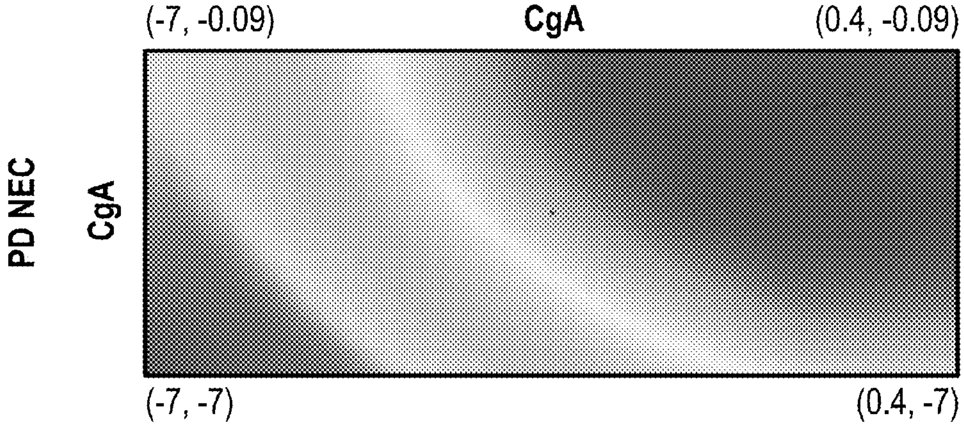

The FS algorithm predicted that NAP1L1 and Kiss1 were highly expressed specifically in WDNEC METs and that CgA was highly expressed specifically in PDNEC METs. Metastatic potential of primary tumors was visualized by plotting expressions of featured genes and colorizing the distribution densities of primary tumors and their metastases. Data are presented in FIG. 6B and FIG. 6C, showing data from primary tumor subtypes and respective metastases scattered according to their respective gene pair expressions, with distribution densities based on the average Euclidean distance (difference in expression) between samples colorized blue (primary tumors) and red (metastases), and green areas indicating regions of transition between primary tumor subtypes and respective metastases. WDNECs were predicted to metastasize with values of NAP1L1>−5.28 and Kiss1>−2.83, while PDNECs could be predicted to metastasize when CgA>−3.5. These results show distinct separation of primary SI GEP-NEN subtypes and the respective metastases, demonstrating the utility of the provided biomarkers as metastasis markers.

Example 4B: Evaluating Classification and Predictive Capabilities of the Nine-Biomarker Panel To evaluate classification and predictive capabilities using the nine-biomarker panel, real-time PCR was performed on samples obtained from an independent set of SI GEP-NEN tissues (n=37), including normal EC cell preparations (n=17), localized SI GEP-NENs (n=8), and malignant SI GEP-NENs (n=12), to measure the marker gene transcript expression. All WDNETs were considered as "localized" while other tumor subtypes were considered "malignant". Assessment of linearly correlated transcript pairs identified a pattern similar to the training set whereas MTA1:MAGE-D2, MTA1:Kiss1, FZD7:NAP1L1, and Survivin:Ki-67 transcript pairs were highly correlated (R2>0.50). The trained SVM model was applied to differentiate normal EC cell preparations from neoplasia with 76% accuracy.

Figure 7:
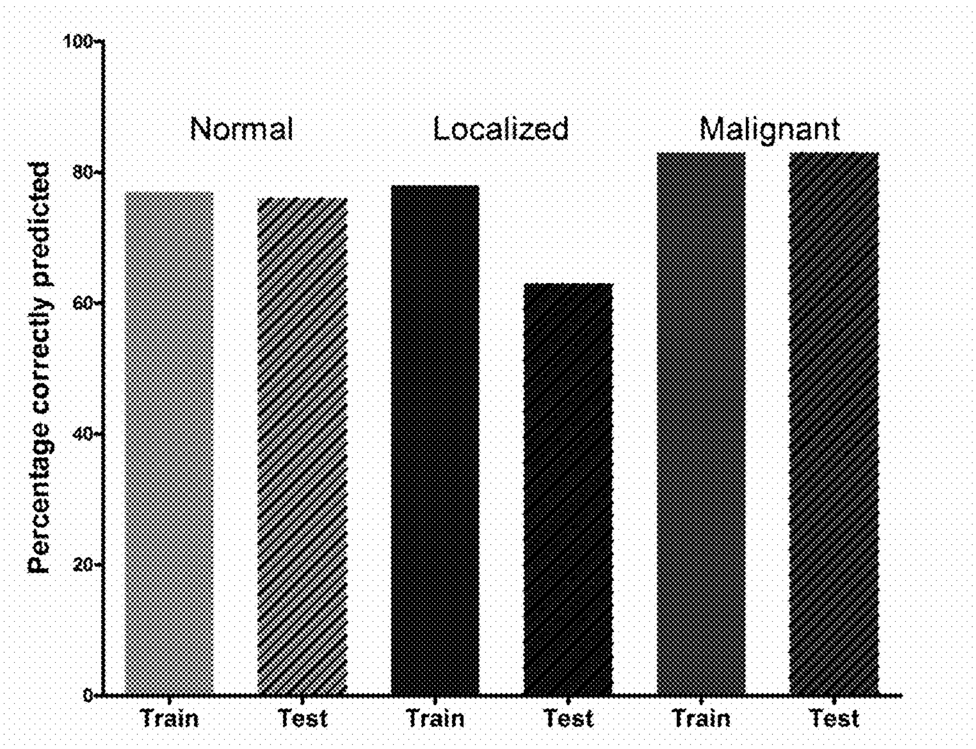
FIG. 7: Evaluation of the classifier performance in the test and training sets. Graph shows percentage of correctly-validated samples in training and test sets, showing Normal EC cells cross-validated with the 77% accuracy and predicted in an independent test set with 76% accuracy (p=0.84). Localized NETs were cross-validated with 78% accuracy and predicted with 63% accuracy in the test set (p=0.25). Malignant NETs were cross-validated with 83% accuracy and predicted with 83% accuracy in an independent set (p=0.80)

The results (shown in FIG. 7) indicated that in this study (using subsets of the nine-biomarker panel), normal EC cells were cross-validated with only 77% accuracy and predicted in an independent test set with 76% accuracy (p=0.84). Localized GEP-NENs were cross-validated with only 78% accuracy and predicted with 63% accuracy in the test set (p=0.25). Malignant GEP-NENs were cross-validated with only 83% accuracy and predicted with 83% accuracy in an independent set (p=0.80). The Decision tree model could predict localized and malignant GEP-NENs with only 63% and 83% accuracy respectively (FIG. 7). The F-test statistic was computed to confirm that the classification results of the training and the independent sets were not significantly different. The p-values for normal, localized, and malignant subgroups were 0.84, 0.25, and 0.80 respectively.

Example 4C: Prediction and Modeling Using Expression Levels from the 21-Biomarker Panel A regularized discriminant analysis (RDA) algorithm was designed and applied to expression data for the twenty-one biomarker panel (MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph1), described above. Gene selection for tissue classification was performed by computing the rank score (S) for each gene and for each class pair as:

$$S = \frac{|\mu_{C2} - \mu_{C1}|}{\sigma_{C1} + \sigma_{C2}}$$

where $\mu_{C1}$ and $\mu_{C2}$ represent means of first and second class respectively and $\sigma_{C1}$ and $\sigma_{C2}$ are inter-class standard deviations. A large S value was indicative of a substantial differential expression ("Fold Change") and a low standard deviation ("transcript stability") within each class. Genes were sorted by a decreasing S-value and used as inputs for the RDA.

RDA's regularization parameters, $\gamma$ and $\lambda$ were used to design an intermediate classifier between LDA (performed when $\gamma$=0 and $\lambda$=1) and QDA (performed when $\gamma$=0 and $\lambda$=0) (Picon A, Gold L I, Wang J, Cohen A, Friedman E. A subset of metastatic human colon cancers expresses elevated levels of transforming growth factor beta1. Cancer Epidemiol Biomarkers Prev 1998; 7(6):497-504). To reduce overfitting, RDA parameters were selected to minimize cross-validation error while not being equal 0.0001, thus forcing RDA to produce a classifier between LDA, QDA, and L2 (Pima I, Aladjem M. Regularized discriminant analysis for face recognition. Pattern Recognition 2003; 37(9):1945-48).

Regularization parameters were defined as $\gamma$=0.002 and $\lambda$=0. For each class pair, S-values were assigned to expression data for individual transcripts, which were then arranged by a decreasing S-value. RDA was performed 21 times, such that the $N^{th}$ iteration consisted of top N scoring transcripts. Error estimation was done by a 10-fold cross-validation of the RDA classifier, by partitioning the tissue data set into complementary subsets, performing the analysis on one subset (called the training set), and validating the analysis on the other subset (called the validation set or testing set). This operation was performed for all permutations of test-train sets and misclassification error was averaged to reduce variability in the overall predictive assessment.

Example 4D: Sensitive, Accurate Mathematical Classification of Unknown Tissues and GEP-NENs, Differentiation of GEP-NEN Sub-Types and Staging of GEP-NENs Using Expression Data from a Twenty-One-Biomarker Panel This RDA algorithm was applied to expression data obtained as described above for the panel of 21-biomarkers (MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph1). The algorithm was used to distinguish samples of unknown tissue types (ECs (normal enterochromaffin cells); "Normal" (normal small intestinal mucosa); "Tumor" (aggregation of primary and metastatic GEP-NENs and carcinomas (NET/NEC)); and primary WDNET; WDNEC; PDNET; PDNEC), for mathematical classification of GEP-NENs, as follows.

For each sample, it first was determined whether the tissue was normal or neoplastic. Tissues deemed neoplastic then were assessed to determine whether they were primary or metastatic. GEP-NEN subtypes (primary or metastatic) then were characterized. The RDA algorithm was applied in every step using the same set of learning parameters ($\gamma$=0.002 and $\lambda$=0). Performance of the classifier was measured by calculating misclassification rate (overall proportion of false-positives between any two classes).

Results are shown in Tables 6A-C (listing misclassification rate versus numbers of gene (biomarker) transcripts detected, beginning with the highest ranked transcript for each distinction).

TABLE 6A

Misclassification Rates versus number of transcripts detected (normal vs. GEP-NEN; primary vs. Metastasis)

| | Misclassification Rates | | |
|---|---|---|---|
| Number of Transcripts | EC Cells vs. Tumor | Normal SI Mucosa vs. Tumor | Primary vs. Metastasis |
| 1 | 0.08 | 0.21 | 0.28 |
| 2 | 0.06 | 0.15 | 0.27 |
| 3 | 0.06 | 0.16 | 0.22 |
| 4 | 0.05 | 0.17 | 0.23 |
| 5 | 0.02 | 0.17 | 0.18 |
| 6 | 0.01 | 0.12 | 0.19 |
| 7 | 0.01 | 0.07 | 0.18 |
| 8 | 0 | 0.09 | 0.14 |
| 9 | 0 | 0.06 | .14. |
| 10 | 0 | 0.07 | 0.11 |
| 11 | 0.01 | 0.05 | 0.12 |

TABLE 6A-continued

Misclassification Rates versus number of transcripts detected (normal vs. GEP-NEN; primary vs. Metastasis)

| Number of Transcripts | Misclassification Rates EC Cells vs. Tumor | Normal SI Mucosa vs. Tumor | Primary vs. Metastasis |
|---|---|---|---|
| 12 | 0.01 | 0.04 | 0.07 |
| 13 | 0 | 0.03 | 0.08 |
| 14 | 0.01 | 0.03 | 0.05 |
| 15 | 0 | 0.02 | 0.03 |
| 16 | 0 | 0.01 | 0.02 |
| 17 | 0 | 0.01 | 0.02 |
| 18 | 0 | 0.01 | 0 |
| 19 | 0 | 0.01 | 0 |
| 20 | 0 | 0 | 0.02 |
| 21 | 0 | 0 | 0.02 |

TABLE 6B

Misclassification rates versus number of transcripts detected (primary GEP-NENs)

| Number of Transcripts 1 | Misclassification Rates PDNEC vs. WDNET | PDNEC vs. WDNEC | PDNEC vs. PDNET | PDNET vs. WDNET | PDNET vs. WDNEC |
|---|---|---|---|---|---|
| 2 | 0.07 | 0.09 | 0.14 | 0.16 | 0.2 |
| 3 | 0.04 | 0 | 0 | 0.29 | 0.2 |
| 4 | 0 | 0 | 0 | 0.16 | 0.08 |
| 5 | 0 | 0 | 0 | 0.04 | 0.05 |
| 6 | 0 | 0 | 0 | 0 | 0 |
| 7 | 0 | 0 | 0 | 0 | 0 |
| 8 | 0 | 0 | 0 | 0 | 0 |
| 9 | 0 | 0 | 0 | 0 | 0 |
| 10 | 0 | 0 | 0 | 0 | 0 |
| 11 | 0 | 0 | 0 | 0 | 0 |
| 12 | 0 | 0 | 0 | 0 | 0 |
| 13 | 0 | 0 | 0 | 0 | 0 |
| 14 | 0 | 0 | 0 | 0 | 0 |
| 15 | 0 | 0 | 0 | 0 | 0 |
| 16 | 0 | 0 | 0 | 0 | 0 |
| 17 | 0 | 0 | 0 | 0 | 0 |
| 18 | 0 | 0 | 0 | 0 | 0 |
| 19 | 0 | 0 | 0 | 0 | 0 |
| 20 | 0 | 0 | 0 | 0 | 0 |
| 21 | 0 | 0 | 0 | 0 | 0 |

TABLE 6C

Misclassification rates versus number of transcripts detected (metastatic GEP-NENs)

| Number of Transcripts | Misclassification Rates WDNEC MET vs. WDNET MET | PDNEC MET vs. WDNEC MET | PDNEC MET vs. WDNET MET |
|---|---|---|---|
| 1 | 0.17 | 0.2 | 0.22 |
| 2 | 0.28 | 0.27 | 0.22 |
| 3 | 0.06 | 0 | 0.11 |
| 4 | 0.06 | 0 | 0 |
| 5 | 0.06 | 0 | 0 |
| 6 | 0 | 0 | 0 |
| 7 | 0 | 0 | 0 |
| 8 | 0 | 0 | 0 |
| 9 | 0 | 0 | 0 |
| 10 | 0 | 0 | 0 |
| 11 | 0 | 0 | 0 |
| 12 | 0 | 0 | 0 |
| 13 | 0 | 0 | 0 |

TABLE 6C-continued

Misclassification rates versus number of transcripts detected (metastatic GEP-NENs)

| Number of Transcripts | Misclassification Rates WDNEC MET vs. WDNET MET | PDNEC MET vs. WDNEC MET | PDNEC MET vs. WDNET MET |
|---|---|---|---|
| 14 | 0 | 0 | 0 |
| 15 | 0 | 0 | 0 |
| 16 | 0 | 0 | 0 |
| 17 | 0 | 0 | 0 |
| 18 | 0 | 0 | 0 |
| 19 | 0 | 0 | 0 |
| 20 | 0 | 0 | 0 |
| 21 | 0 | 0 | 0 |

As shown in Tables 6A-C, the methods and RDA algorithm was able to detect the presence, stage, and classification (sub-type), with zero misclassification rates across pair-wise iterations of normal EC cells, normal small intestinal mucosa, and GEP-NEN subtypes.

As shown in Table 6A, the RDA algorithm distinguished normal EC cells from neoplastic tissue. Detection and analysis of expression levels of just the single highest ranked biomarker transcript (PNMA2) was able to make this distinction with a misclassification rate of 0.08; detection and analysis of the respective single highest ranked biomarker (CgA) was able to make the distinction between normal SI mucosa from neoplastic tissue with a misclassification rate of 0.21 (Table 6A).

Applying the method to data for pluralities of biomarkers (detecting expression of levels of biomarker panels and applying the RDA algorithm to the data) was able to detect and distinguish GEP-NENs from normal samples with zero misclassification. Distinguishing EC cells from tumor tissue with a misclassification rate of zero was achieved using a panel of eight (8) biomarker transcripts. Distinguishing normal SI mucosa from tumor tissue with a misclassification rate of zero was achieved using a panel of twenty (20) biomarker transcripts (Table 7). In this study, misclassification rates were higher with fewer transcripts. These results demonstrate the biomarker specificity for different tissue groups and confirm the ability of the present methods to detect GEP-NEN disease and distinguish GEP-NEN tissue from different normal tissue types, with high specificity.

Likewise, applying the RDA algorithm to expression levels of panels of biomarkers could determine with 100% accuracy whether an unknown tissue sample was primary or metastatic. For this determination, expression levels were detected for eighteen (18) biomarker transcripts and the data included in the RDA model (Table 7), with higher misclassification rates using fewer transcripts. Detecting expression of and applying the algorithm to only the highest ranked transcript (MAGE-D2) distinguished primary and metastatic samples with a 0.28 misclassification rate. (Table 6A).

Primary GEP-NEN subtypes also could be differentiated with 100% accuracy using the RDA algorithm. Misclassification rates when only the single highest ranked transcripts were detected ranged from 0.07 (PTPRN2, for distinguishing between PDNEC and WDNEC) to 0.37 (NRP2, for distinguishing between WDNEC and WDNET). Applying the RDA algorithm to expression levels of all 21 biomarker transcripts, the methods distinguished between WDNETs and WDNECs with a zero misclassification rate (Table 6B), with higher misclassification rates using fewer biomarkers.

As shown in Table 6C the RDA algorithm also was used to distinguish with 100% accuracy between metastatic GEP-NEN subtypes. Misclassification rates with only the single highest ranked transcripts were 0.22 (CXCL14, for distinguishing between WDNET MET and WDNEC MET), 0.2 (NAP1L1, for distinguishing between PDNEC MET and WDNEC MET), and 0.17 (NRP2, for distinguishing between PDNEC MET and WDNET MET), respectively (Table 6C).

TABLE 7

Misclassification rates with detection of various numbers of transcripts; achieving minimal misclassification; SVM, decision trees (DT), and multi-layer perceptron (MLP) classifiers.

| | Lowest misclassification rate in this example | | | Number of transcripts to achieve lowest misclassification rate in this example | | |
|---|---|---|---|---|---|---|
| Sample/Class Distinguished | SVM | DT | MLP | SVM | DT | MLP |
| EC vs. Normal SI Mucosa | 0.02 | 0.05 | 0 | 14 | 21 | 8 |
| EC vs. Tumor | 0.01 | 0.03 | 0 | 18 | 3 | 5 |
| Normal SI Mucosa vs. Tumor | 0.14 | 0.14 | 0.01 | 16 | 21 | 13 |
| Primary vs. Metastasis | 0.19 | 0.19 | 0.14 | 3 | 2 | 7 |
| PDNEC vs. WDNET | 0.07 | 0.07 | 0 | 21 | 21 | 4 |
| PDNEC vs. WDNEC | 0.09 | 0.09 | 0 | 21 | 21 | 2 |
| PDNEC vs. PDNET | 0.14 | 0.28 | 0.14 | 21 | 21 | 3 |
| PDNET vs. WDNET | 0.16 | 0.16 | 0.03 | 21 | 1 | 11 |
| PDNET vs. WDNEC | 0 | 0.20 | 0 | 19 | 21 | 10 |
| WDNEC vs. WDNET | 0.02 | 0.26 | 0.02 | 21 | 21 | 16 |
| WDNEC MET vs. WDNET MET | 0.11 | 0.33 | 0.11 | 3 | 21 | 12 |
| PDNEC MET vs. WDNEC MET | 0.20 | 0.20 | 0 | 21 | 21 | 12 |
| PDNEC MET vs. WDNET MET | 0.22 | 0.33 | 0 | 21 | 21 | 14 |

"Normal" = normal small intestinal mucosa;
"Tumor" = aggregation of primary and metastatic NETs and carcinomas (NET/NEC)

Table 8 summarizes the numbers of in NET biomarkers able to distinguish between indicated samples using the RDA algorithm in this example. In this example, all 21 biomarkers distinguished WDNEC from WDNET with zero misclassification (higher misclassification with fewer transcripts). By contrast, as few as two biomarkers could differentiate between PDNEC and WDNET (MAGE-D2, CXCL14), and between PDNEC and PDNET (PTPRN2, MTA1) with zero misclassification. In this example, 11 biomarkers distinguished normal enterochromaffin (EC) cells from normal SI mucosa with zero misclassification (PNMA2, CXCL14, PTPRN2, Tph1, FZD7, CTGF, X2BTB48, NKX2-3, SCG5, Kiss1, SPOCK1, with a higher misclassification rate using fewer biomarkers). Fewer transcripts were able to distinguish normal EC cells from neoplastic tissue (n=8, PNMA2, Tph1, PTPRN2, SCG5, SPOCK1, X2BTB48, GRIA2, OR51E1). Expression of twenty of the biomarkers (with the exception of CXCL14) could differentiate normal SI mucosa from neoplastic tissue with zero misclassification (higher misclassification rates with fewer transcripts).

TABLE 8

Numbers of biomarker transcripts used for pairwise distinctions with zero classification rate by RDA

| Distinction | Number of Transcripts that achieved a Zero Misclassification Rate |
|---|---|
| EC vs. Normal | 11 |
| EC vs. Tumor | 8 |
| Normal vs. Tumor | 20 |
| Primary vs. Metastasis | 18 |
| PDNEC vs. WDNET | 3 |
| PDNEC vs. WDNEC | 2 |
| PDNEC vs. PDNET | 2 |
| PDNET vs. WDNET | 4 |
| PDNET vs. WDNEC | 4 |
| WDNEC vs. WDNET | 21 |
| WDNEC MET vs. WDNET MET | 3 |
| PDNEC MET vs. WDNEC MET | 4 |
| PDNEC MET vs. WDNET MET | 6 |

Finally, SVM, decision trees (DT), and MLP classifiers were applied, as described above, using data for transcripts of the twenty-one biomarker panel, in a similar fashion as RDA. The performance of RDA was compared to performance of SVM, decision trees, and multi-layer perceptron (MLP), for classification of GEP-NEN subtypes by detecting expression of the twenty-one biomarker panel. All classifiers were subject to the training and cross-validation protocol outlined in Example 4A. Misclassification rates were calculated (Table 7). SVM was able to achieve a zero misclassification to distinguish PDNET from WDNEC. Decision trees distinguished with misclassification rates ranging from 0.03 (between EC and Tumor sample) to 0.33 (between WDNEC MET and WDNET MET, and between PDNEC MET and WDNET MET). Somewhat comparable to RDA, the MLP classifier produced zero misclassification rates with 7/13 iterations, with a high overall accuracy. The RDA approach was most reliable in this example with the 21 marker gene panel, achieving zero misclassification rates in all iterations.

Example 5: Detection of Circulating GEP-NEN Cells (CNC) and Identification of Biomarker Transcripts (mRNA) from Plasma Circulating GEP-NEN cells (CNCs) were detected in human blood using the provided methods and biomarkers. For this process, human blood samples (plasma, buffy coat, and whole blood) were obtained and subjected to staining, cell sorting, and real-time PCR (to detect GEP-NEN biomarkers and housekeeping genes).

Example 5A: Sample Preparation and RNA Isolation from Plasma, Buffy Coat, and Whole Blood In the following studies for detection of biomarkers in human plasma and buffy coat, human blood samples were obtained from a blood databank, with samples from healthy controls (n=85) or patients (n=195) who had been treated for GEP-NEN disease, at Yale New Haven Hospital, Uppsala or Berlin. See Kidd M, et al., "CTGF, intestinal stellate cells and carcinoid fibrogenesis," *World J Gastroenterol* 2007; 13(39):5208-16. Five mL of blood were collected in tubes containing ethylenediaminetetraacetic acid (EDTA). Plasma was separated from buffy coat following 2 spin cycles (5 min at 2,000 rpm) and then stored at −80° C. prior to nucleic acid isolation and/or hormone (CgA) analysis.

RNA Isolation from Various Blood Samples

For isolation of RNA from buffy coat, samples were incubated with TRIZOL®, followed by RNA clean-up. RNA was dissolved in diethyl pyrocarbonate water and measured spectrophotometrically, and an aliquot analyzed on a Bioanalyzer (Agilent Technologies, Palo Alto, Calif.) to assess the quality of the RNA (Kidd M, et al. "The role of genetic markers—NAP1L1, MAGE-D2, and MTA1—in defining small-intestinal carcinoid neoplasia," *Ann Surg Oncol* 2006; 13(2):253-62).

Figure 11A:
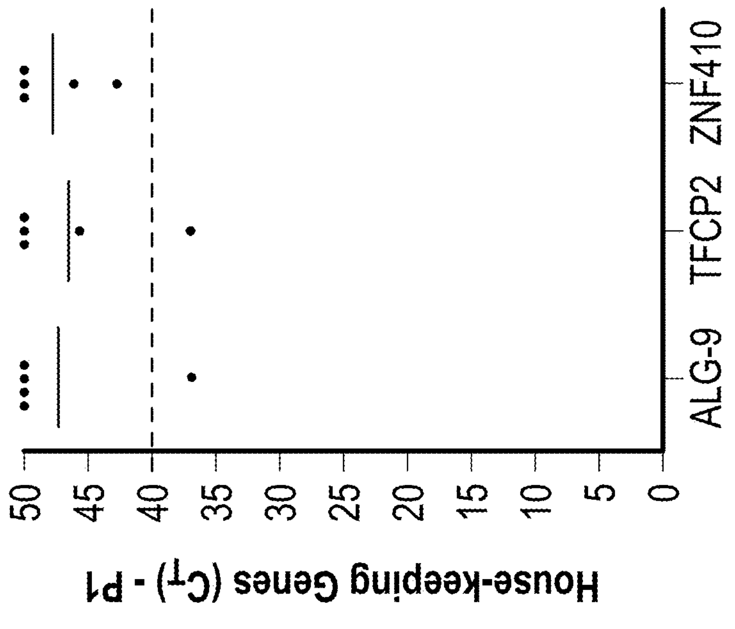
FIGS. 11A-C: Transcript expression in whole blood. Housekeeping genes (ALG-9, TFCP2, ZNF410) identified in plasma after Trizol mRNA isolation (11A) and the QIAamp RNA Blood Mini Kit approach (11B), showing identification of housekeeping genes in significantly more samples (8/15 versus 2/15, p=0.05) after isolation with the QIAamp RNA Blood Mini Kit approach. Transcript expression levels of the same 3 housekeeping genes and 11 NET biomarker genes were evaluated by PCR in mRNA prepared from whole blood from 3 healthy donors (normal samples), showing highly correlated detected gene expression levels across samples (11C).
Figure 11B:
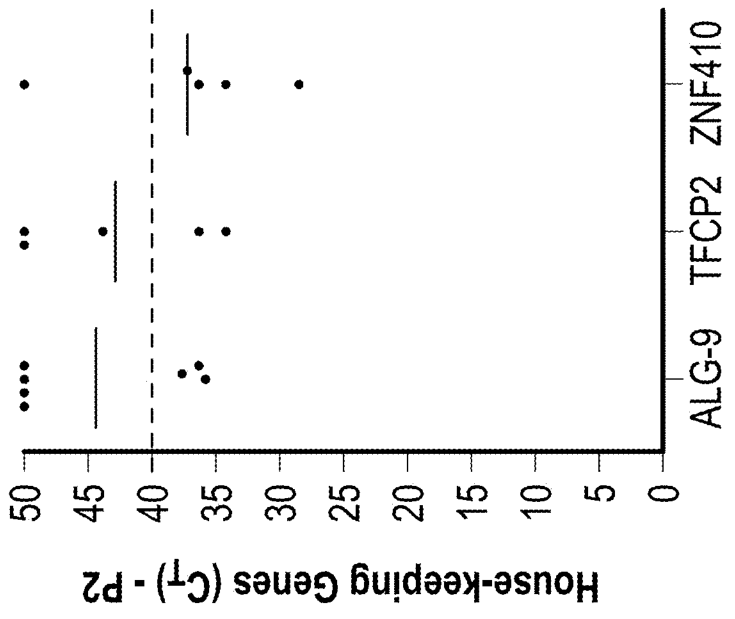

For isolation of RNA from GEP-NEN patient and control plasma, the QIAamp RNA Blood Mini Kit was used (FIG. 11A), which in this study allowed real-time PCR detection of housekeeping genes in significantly more samples compared to the TRIZOL® approach (FIG. 11B) (8/15 versus 2/15, p=0.05). For isolation of RNA directly from whole blood, the QIAamp RNA Blood Mini Kit was used, following the manufacturer's guidelines.

Stability and Reproducibility of Samples

The blood test is based on identifying the GEP-NEN molecular signature in 1 ml of whole blood, collected in an EDTA-tube. It was determined that the gene signature is stable for up to four hours (refrigeration at 4-8° C., following phlebotomy) prior to freezing (FIG. 13). It is unaffected by fasting/feeding. Analysis of inter-assay reproducibility (same samples processed on separate days) ranged from 98.8-99.6% while intra-assay reproducibility was 99.1-99.6%.

These studies identify that the gene signature is highly reproducible (~99%), is stable for up to four hours in refrigeration (prior to freezing) and is unaffected by fasting/feeding.

Real-Time PCR

Total RNA obtained from plasma, buffy coat, and whole blood as described above was subjected to reverse transcription with the High Capacity cDNA Archive Kit (Applied Biosystems (ABI), Foster City, Calif.) following the manufacturer's suggested protocol. Briefly, 2 micrograms of total RNA in 50 microliters of water was mixed with 50 uL of 2×RT mix containing Reverse Transcription Buffer, deoxynucleotide triphosphate solution, random primers, and Multiscribe Reverse Transcriptase. The RT reaction was performed in a thermal cycler for 10 mins at 25° C. followed by 120 mins at 37° C., as described by Kidd M, et al., "The role of genetic markers—NAP1L1, MAGE-D2, and MTA1—in defining small-intestinal carcinoid neoplasia," *Ann Surg Oncol* 2006; 13(2):253-62. Transcript levels of the marker genes were measured using Assays-on-Demand™ products and the ABI 7900 Sequence Detection System according to the manufacturer's suggestions (see Kidd M, Eick G, Shapiro M D, et al. Microsatellite instability and gene mutations in transforming growth factor-beta type II receptor are absent in small bowel carcinoid tumors. *Cancer* 2005; 103(2):229-36).

Cycling was performed under standard conditions, using the TaqMan® Universal PCR Master Mix Protocol. Briefly, complementary DNA in 7.2 uL of water was mixed with 0.8 uL of 20•Assays-on-Demand primer and probe mix and 8 uL of 2× TaqMan Universal Master mix in a 384-well optical reaction plate. The following PCR conditions were used: 50° C. for 2 mins and then 95° C. for 10 mins, followed by 50 cycles at 95° C. for 15 mins and 60° for 1 min, as described by Kidd M, et al., "The role of genetic markers—NAP1L1, MAGE-D2, and MTA1—in defining small-intestinal carcinoid neoplasia," *Ann Surg Oncol* 2006; 13(2):253-62. Raw $\Delta C_T$ (delta $C_T$=change in cycle time as a function of amplification) normalized using geNorm (see Vandesompele J, De Preter K, Pattyn F, et al. Accurate normalization of real-time quantitative RT-PCR data by geometric averaging of multiple internal control genes. *Genome Biol* 2002; 3(7):RESEARCH0034), and expression of the house-keeping genes ALG9, TFCP2 and ZNF410. See Kidd M, et al., "GeneChip, geNorm, and gastrointestinal tumors: novel reference genes for real-time PCR," *Physiol Genomics* 2007; 30(3):363-70. Normalized data were natural log (ln)-transformed for compression. ALG-9 was used as the housekeeping gene, its expression detected and used to normalize GEP-NEN biomarker expression data.

For statistical analysis, all computations were carried out using R 2.9 language for statistical computing. See R Development Core Team. R: A language and environment for statistical computing Vienna, Austria: R Foundation for Statistical Computing, 2008. GraphPad (Prizm 4) and SPSS16.0 were used for all statistical analyses, by receiver-operator characteristic (ROC) curves, Fisher's exact test and/or ANOVA, using 2-tailed tests, with $p<0.05$, considered significant.

Example 5B: Detection of Housekeeping Genes and Detection in Whole Blood

Transcript expression levels of three (3) housekeeping genes (ALG9, TFCP2 and ZNF410) were determined in mRNA isolated using the TRIZOL® approach, described above, from buffy coat from five healthy donors. All three genes were detected with $\Delta C_T$ levels between 30 and 35. Sequences and information for exemplary primer pairs are listed in Tables 1A and 1B.

Figure 11C:
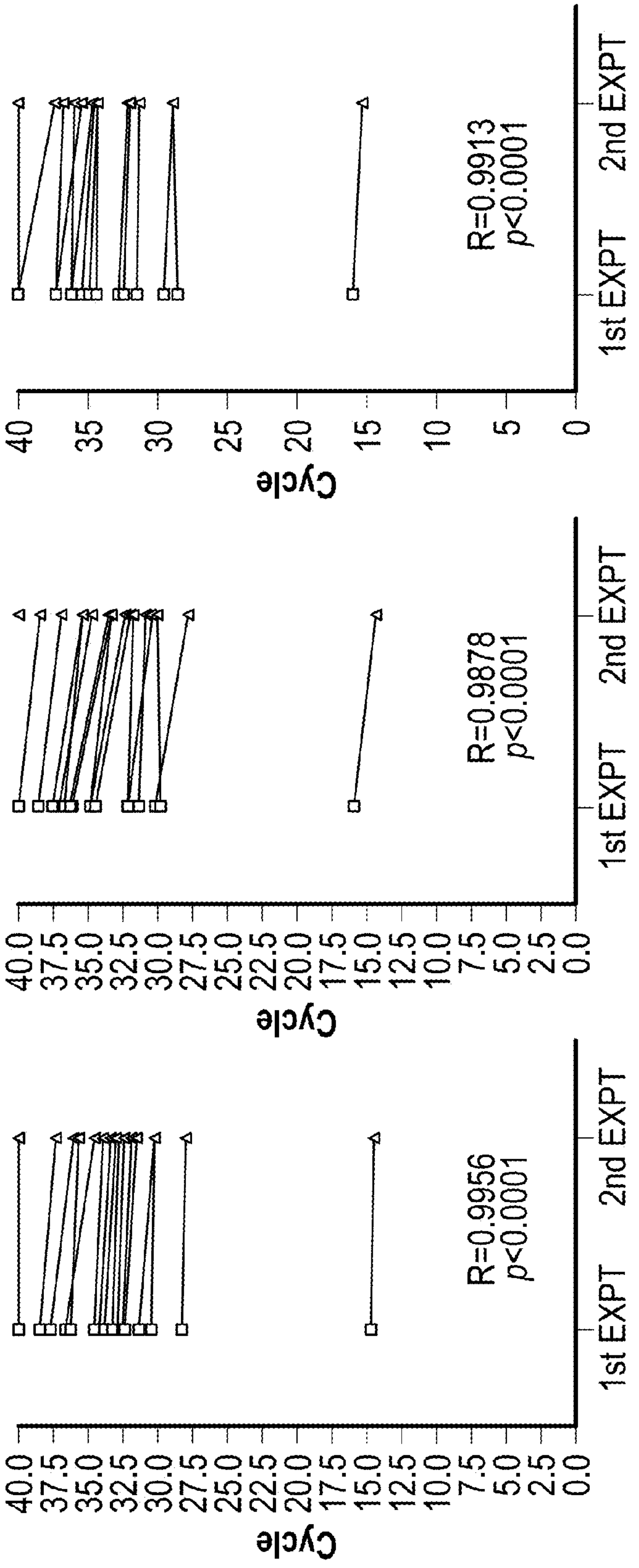
Figure 12A:
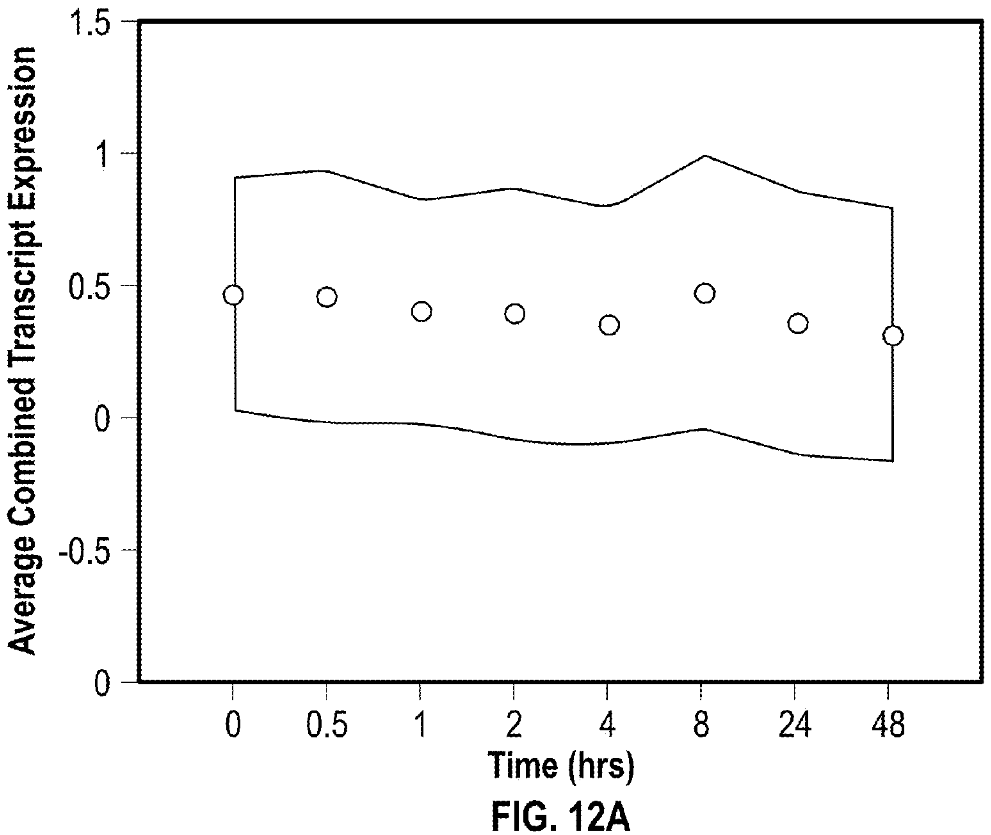
FIGS. 12A-B. Average combined transcript expression of each gene (12A). Transcripts exhibited a low variability: 0.04-0.45 (median 0.12). Principal component analysis of average marker gene expression for all samples (12B). The mathematical algorithms (SVM, LDA, KNN and NB) identified that the correct calls were made for times 0, 30 mins, 1 hr, 2 hr and 4 hr. Inconsistent call rates occurred between 8-48 hrs indicating the optimal time for storage in a refrigerator prior to freezing is 0-4 hrs.
Figure 12B:
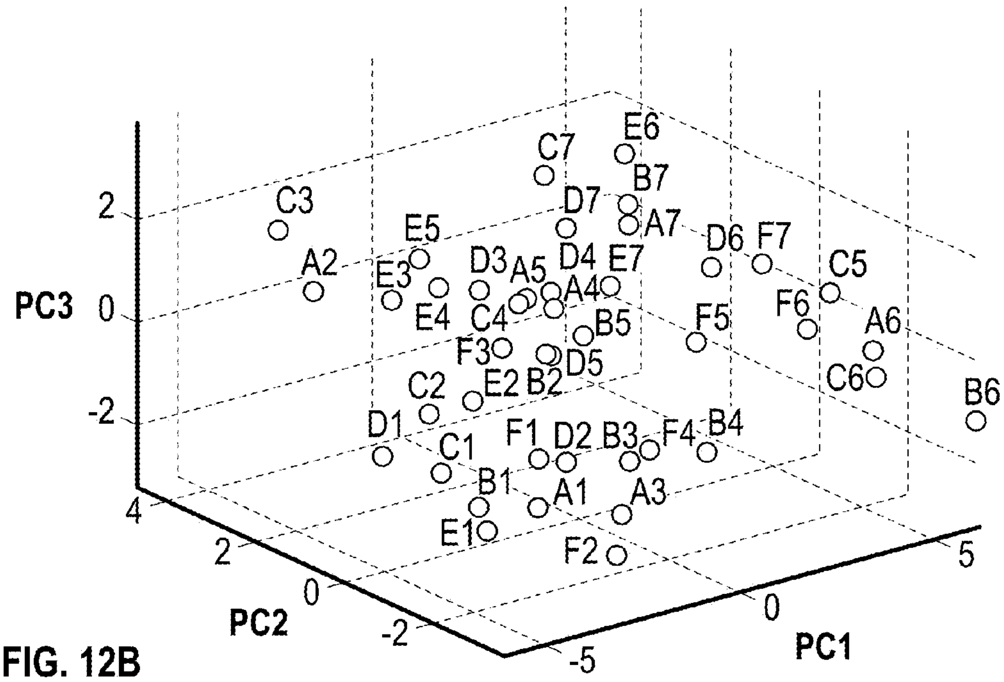

Transcript expression levels of the same 3 housekeeping genes and 11 GEP-NEN biomarker genes were evaluated in mRNA prepared from whole blood from 3 healthy donors (normal samples). For this process, mRNA was isolated, cDNA synthesized, and PCR performed by different people on different days, on separate plates, using independently-prepared reagents, made on different days. Detected gene expression levels across samples were highly correlated (FIG. 11C; $R>0.99$, $p<0.0001$).

Figure 13B:
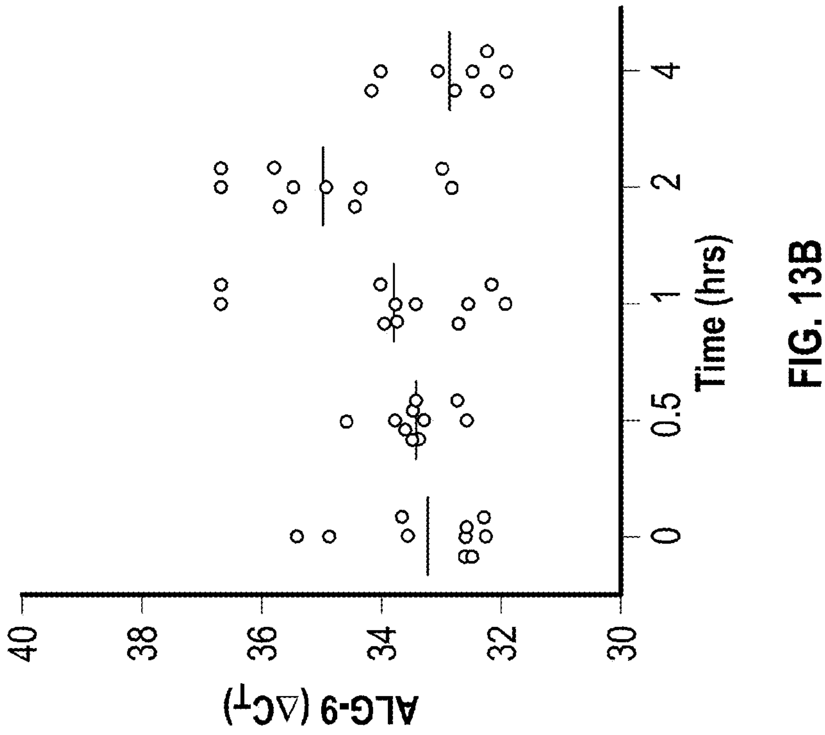
FIGS. 13A-B: Identification of the most appropriate housekeeping gene and determination of the effect of feeding on ALG-9 transcripts in whole blood. Transcript expression of 5 housekeeping genes was evaluated in 5 healthy controls. ALG-9 was identified to have the least variation (13A). ALG-9 expression was measured as a function of time after feeding, showing no significant alteration after feeding (up to 4 hrs) (13B).
Figure 13A:
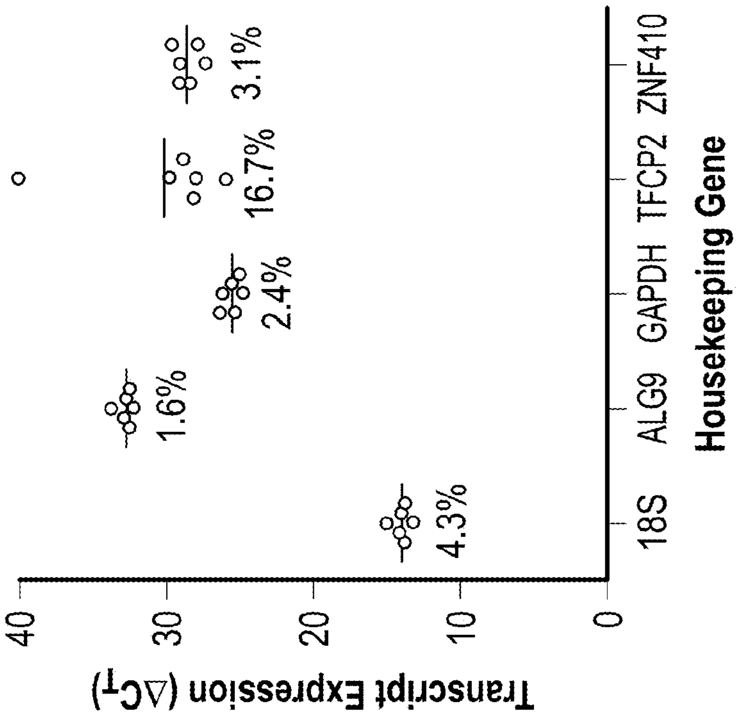

Expression of 5 housekeeping genes (18S, ALG9, GAPDH, TFCP2 and ZNF410) was detected by real-time PCR on mRNA isolated using TRIZOL®, from whole blood samples, from 5 healthy donors. Primer pairs are listed in Tables 1A and 1B. In this study, ALG9 expression was the least variable between samples (coefficient of variation=1.6%) (FIG. 13A). ALG9 transcript levels were determined by real-time PCR on RNA isolated from whole blood from five healthy control patients, before and at thirty-minute intervals after feeding. The results showed that expression levels of ALG9 were not significantly altered up to 4 hours postprandially (as determined by nANOVA: $p>0.05$) (FIG. 13B). These results demonstrate that detection of gene products according to the provided methods produces consistent results and is useful for comparison of data from patient samples acquired and prepared on different days by distinct investigators.

Delineation of a House-Keeping Gene

To identify the most useful house-keeping genes for normalization, a panel (n=19) of candidate markers was examined that comprised those identified from GEP-NEN tissue (n=9), and those through screening of the GEP-NEN blood transcriptomes (n=10). In order to select "housekeeper" markers, a number of criteria were used including: topological importance when mapped to the blood interactome (7,000 genes, 50,000 interactions)_ENREF_3, stability (M-value) following real-time PCR, and efficiency of transcription in the blood. In addition, the presence of efficiencies between the target genes and the house-keeping gene were examined. Such a correlation supports a relative quantitation-based algorithm for calculation. The 19 genes included in the analysis were tissue-derived: 18S, GAPDH, ALG9, SLC25A3, VAPA, TXNIP, ADD3, DAZAP2, ACTG1, and blood microarray-derived: ACTB, ACTG4B, ARF1, HUWE1, MORF4L1 RHOA, SERP1, SKP1, TPT1, and TOX4. Targets that were considered appropriate house-keepers exhibited ≥3 characteristics.

Topological Importance in Blood Microarray

Figure 14A:
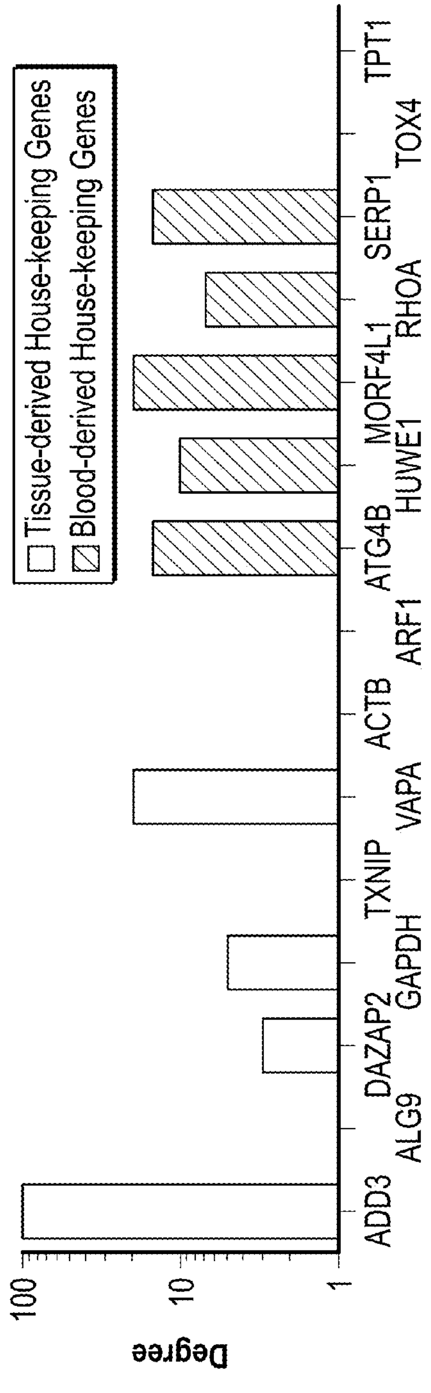
FIGS. 14A-C: Topological analysis of candidate housekeeping genes mapped to the blood interactome (7,000 genes, 50,000 interactions): Degree (14A), Betweeness (14B) and Clustering (14C). Genes with the lowest values in each category included TXNIP, ACTB, TOX4 and TPT1. Analysis of blood- and tissue-associated house-keeping genes identified potential candidate genes for normalization protocols.
Figure 14B:
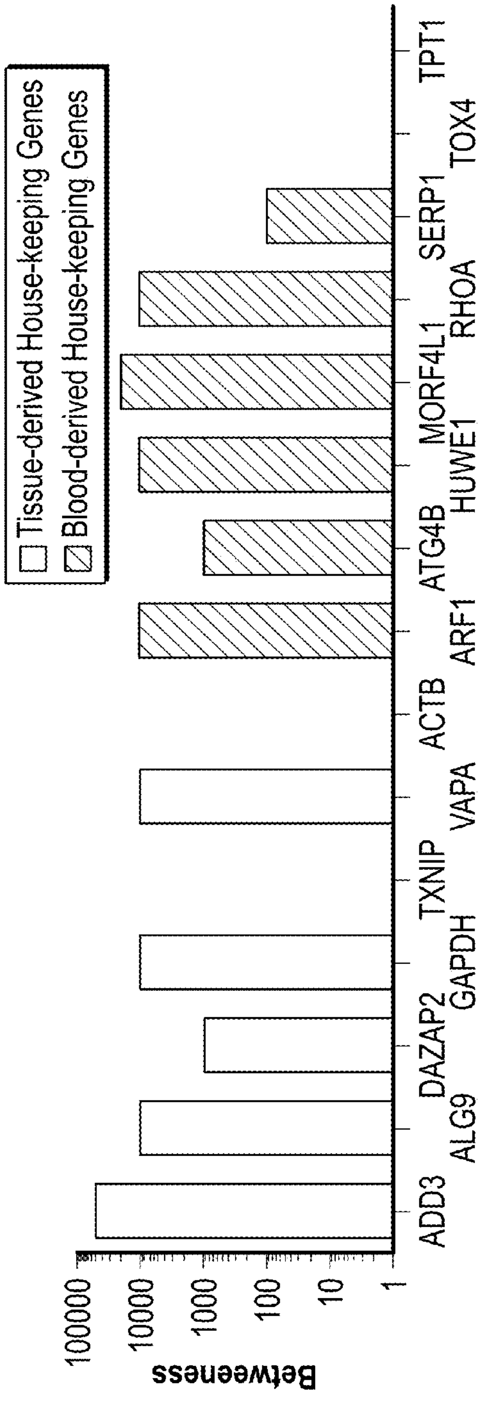
Figure 14C:
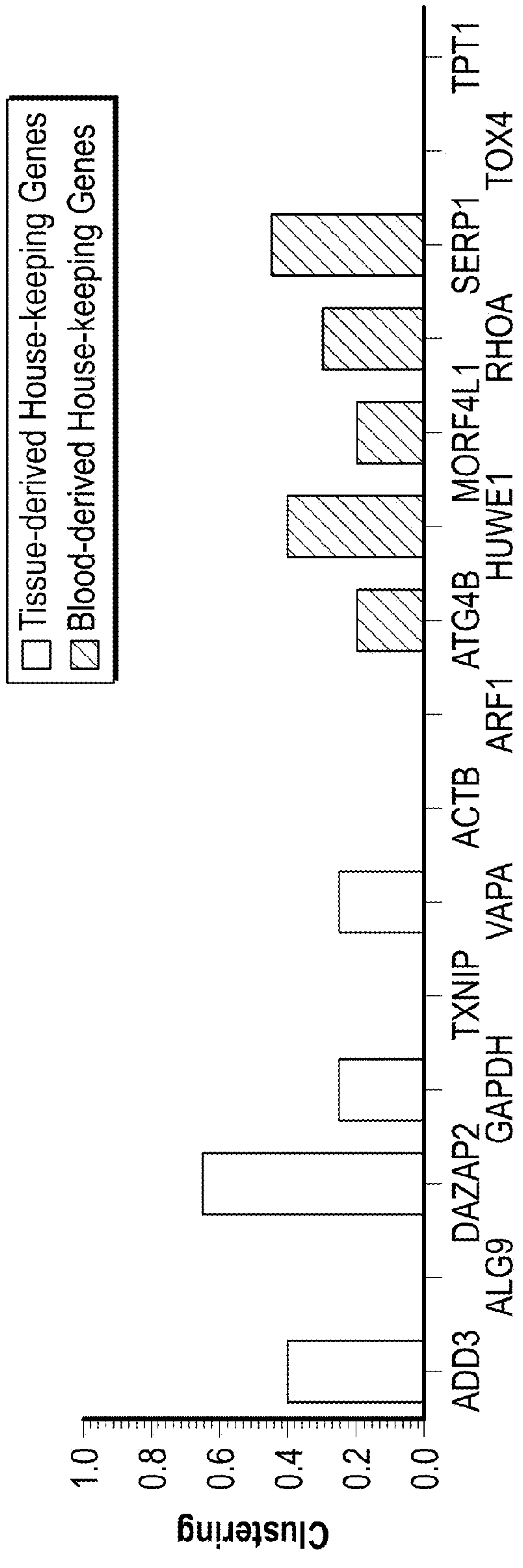

Three topological features were examined: "Degree"=number of connections in each gene; "Betweenness"=importance of a gene in signal transduction, and "Clustering"=clustering coefficient or the extent to which a gene's neighbors are interconnected. A high "degree" indicates many connections per gene, a high "betweenness" indicates a more critical role in the information flow within the interactome while a "high" clustering coefficient means that more of a gene's neighbors are connected to each other. The most appropriate gene would have low values for Degree, Betweeness and Clustering. Genes that fulfill all these characteristics include ACTB, TOX4, TPT1 and TXNIP (FIG. 14A-C). The order of genes is:

TXNIP=ACTB=TOX4=TPT1>ALG9=ARF1>GAPDH>DAZAP2>VAPA=ATG4B=HUWE1=MORF4L1=RHOA=SERP1>ADD3.

Variability (Coefficient of Variation and M-Value)

Figure 15:
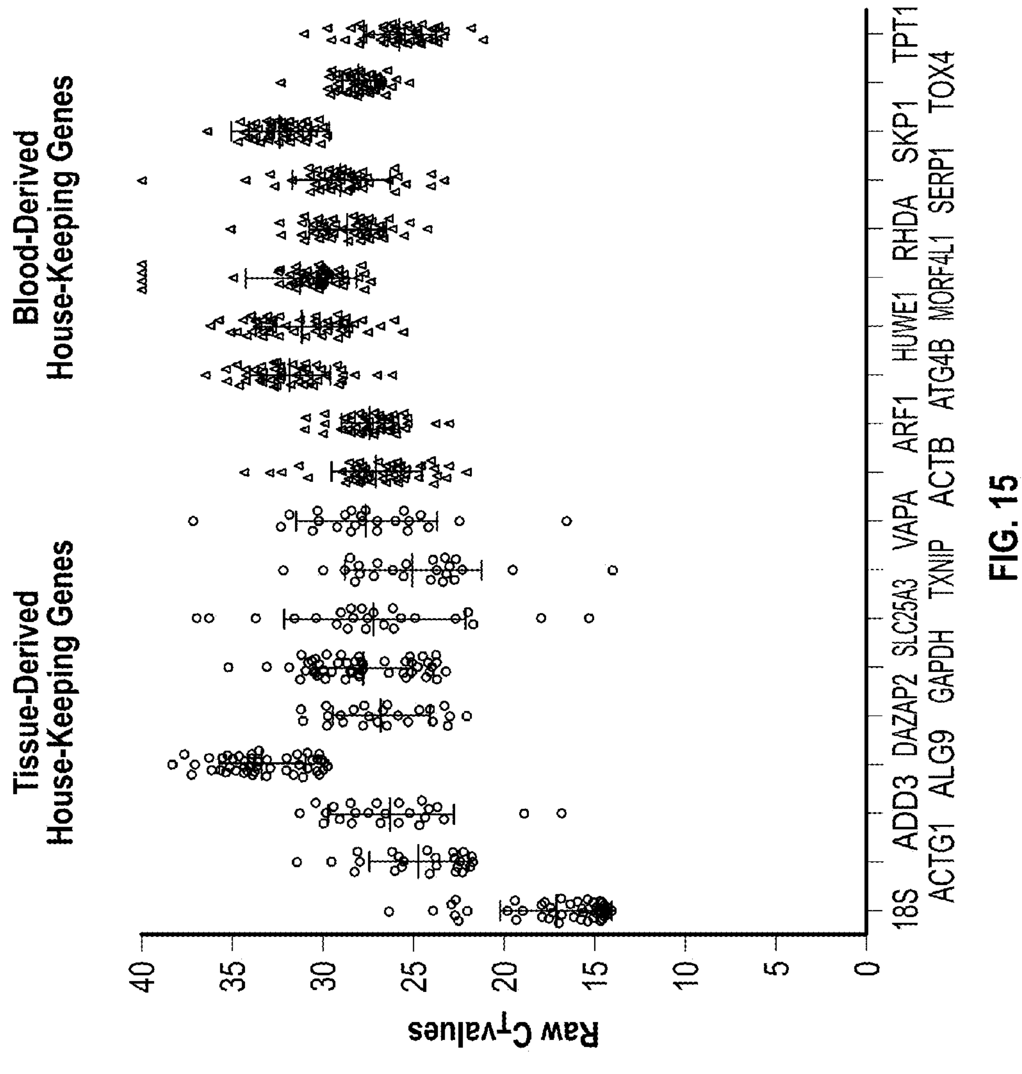
FIG. 15: Raw $C_T$ values plotted as a function of either tissue-derived or blood-derived candidate house-keeping genes. Genes with the least variation included ALG9, ARF1, ATG4B, RHDA, and SKP1. Mean and SD are included. A value of 40 was assigned to samples with no amplification. Samples with no gene expression are given a value of 40 (e.g., 4 samples amplified using MORF4L1). Analysis of candidate house-keeping genes identified a relatively small number (n=6) that exhibited low variability and were candidates for development of normalization protocols.

Two approaches were used to assess variation in house-keeping gene expression, firstly variability and secondly robustness (the "M" value) measured by geNorm. Raw CT values were examined for variation (FIG. 15) and whether expression passed the D'Agostino and Pearson normality test (Table 9).

TABLE 9

Candidate House-keeping genes and normality of expression

| | 18S | ACTG1 | ADD3 | ALG9 | DAZAP2 | GAPDH | SLC25A3 | TXNIP | VAPA |
|---|---|---|---|---|---|---|---|---|---|
| CV | 17.9% | 11.03% | 13.21% | 6.93% | 10.01% | 10.36% | 18.43% | 15.09% | 14.09% |
| DP test | N | Y | N | Y | Y | Y | Y | N | Y |

| | ACTB | ARF1 | ATGB4 | HUWE1 | MORF4L1 | RHDA | SERP1 | SKP1 | TOX4 | TPT1 |
|---|---|---|---|---|---|---|---|---|---|---|
| CV | 9.27% | 5.81% | 6.9% | 8.39% | 9.76% | 7.14% | 9.33% | 4.36% | 4.34% | 7.65% |
| DP test | N | Y | Y | Y | N | Y | N | Y | N | Y |

CV = coefficient of variation,
DP = D' Agostino and Pearson omnibus normality test.
N = not normally distributed,
Y = passed the normality test.

Figure 16:
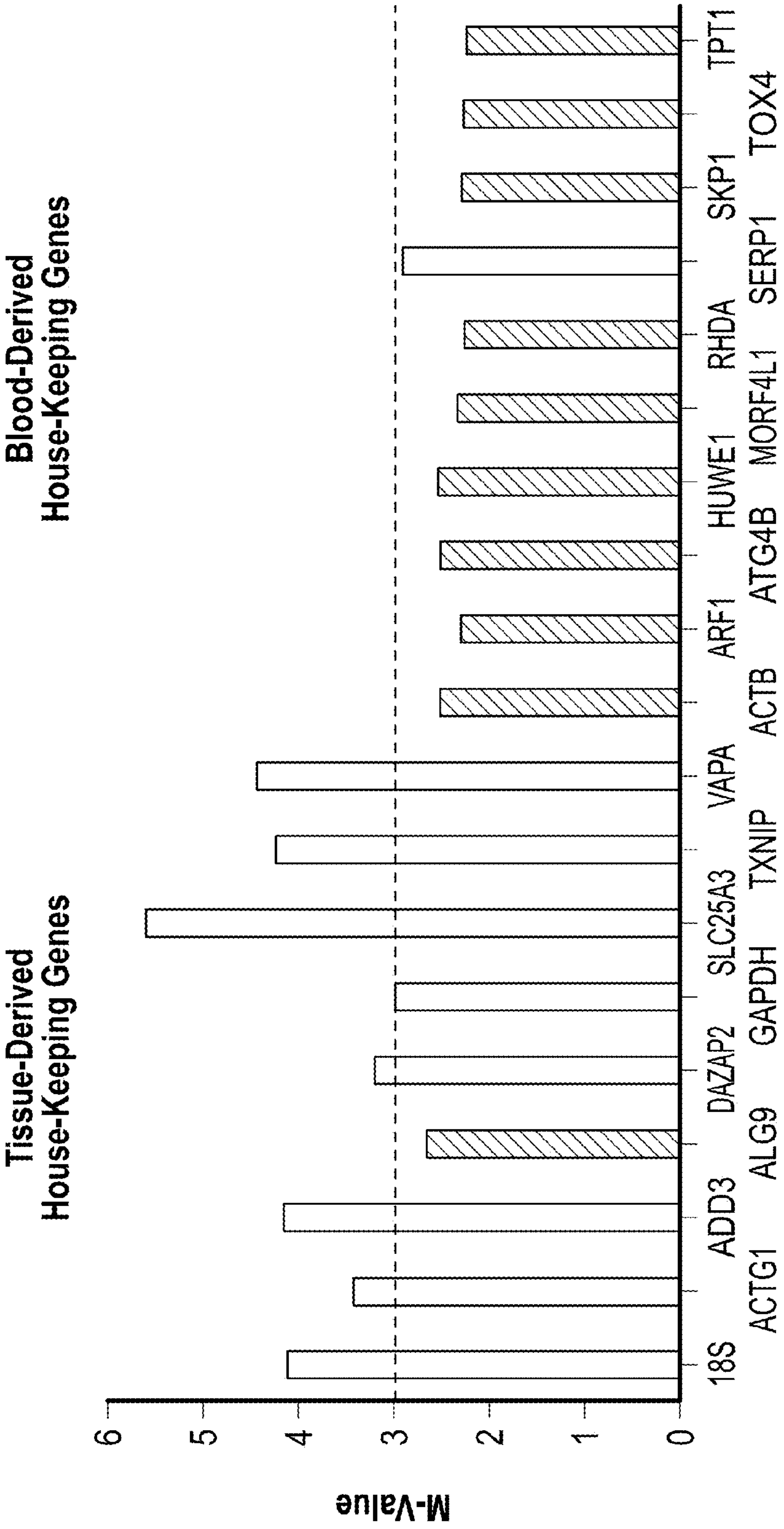
FIG. 16: M-values for each of the candidate housekeeping genes calculated using the geNorm program. ALG9 was the most stable of the tissue-derived genes. Nine of the 10 blood-derived genes (except SERP1) were considered robust. Robust markers (dotted boxes).

Variability analysis identified that ALG9, ARF1, ATG4B, RHDA and SKP1 were the least variable genes. Genes selected by geNorm as showing the least variation between samples (and hence the greatest stability or robust expression) are indicated in FIG. 16. The "M"-value is a measure of gene stability and defined as the average pair-wise variation of a particular gene with all other potential reference genes. The most stable genes included: ALG9, ACTB, ARF1, ATG4B, HUWE4, MORF4L1, RHDA, SKP1, TPT1 and TOX4.

PCR Efficiency

PCR efficiency was examined to evaluate which candidate house-keeping genes fulfilled adequate amplification criteria. This was undertaken in two independent samples using a standard curve (dilution: 2000-0.01 ng/ul). The PCR efficiency was calculated using the Fink equation:

$$\text{Efficiency}=10\hat{}(-1/\text{slope})-1$$

Figure 17:
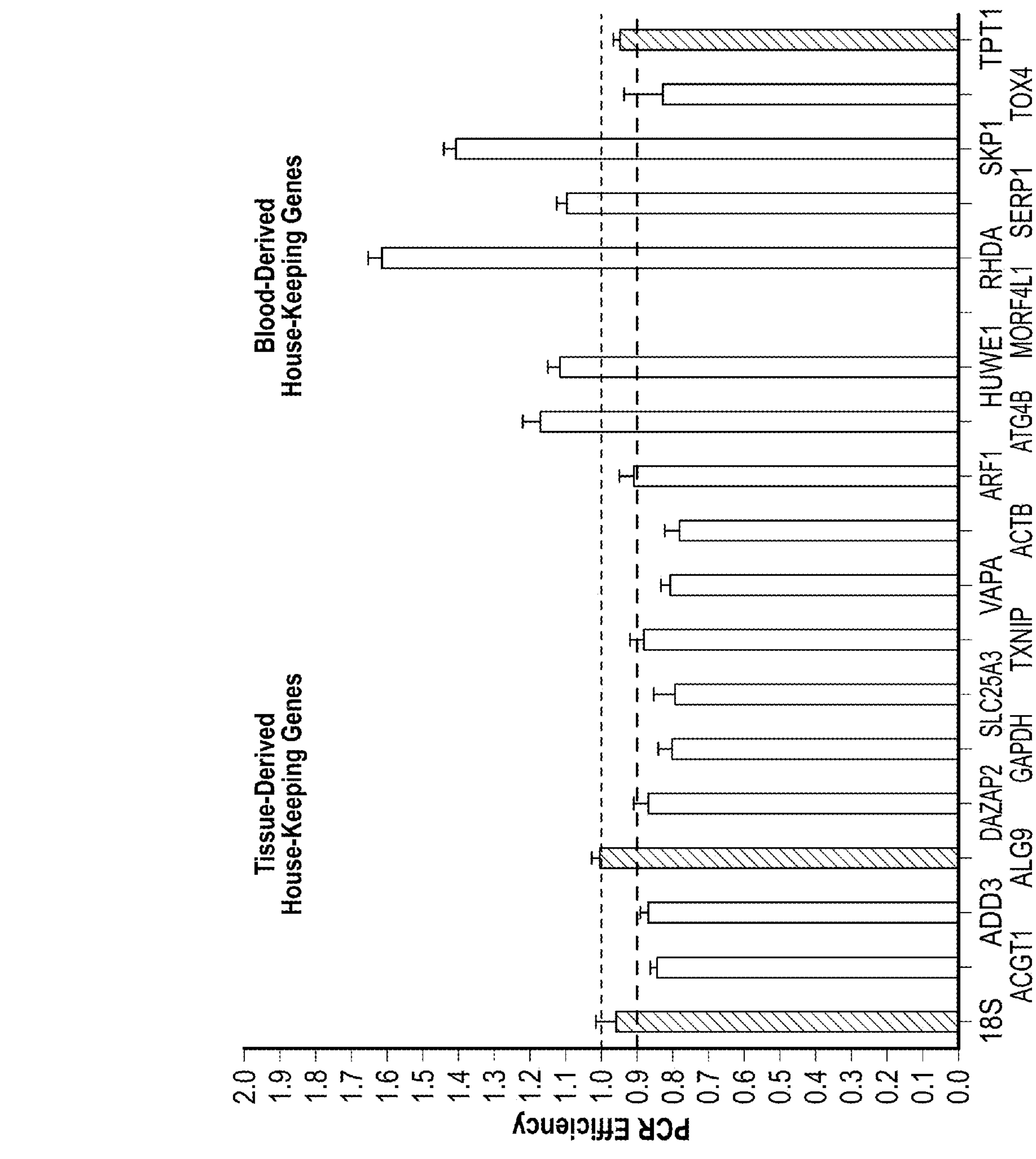
FIG. 17: PCR efficiency curves plotted for each of the candidate house-keeping genes. Efficient amplification occurs between 0.9-1.0. Values lower than 0.9 indicate sub-optimal primer binding and inefficient amplification. Values above 1.0 identify over-amplification, presumably through less than specific primer binding. Genes with appropriate efficiency included 18S, ALG9, and TPT1. Mean±SD, n=3. A small number of candidates (n=3) exhibited efficacy as house-keeping genes.

Analysis identified that 18S and ALG9 were the most efficiently transcribed tissue-derived genes while TPT1 was the most efficiently transcribed blood-derived candidate house-keeping gene (FIG. 17).

Efficacy of Amplification Compared to Target Genes

Finally, the amplification kinetics of the target and reference genes were examined for similarities. This is a necessary pre-requisite for any appropriate PCR amplification protocol otherwise a correction factor is required in quantitation algorithms to deal with over-estimated expression calculations. It is also important for any comparative $C_T$ method e.g., $\Delta\Delta C_T$ particularly as estimations from raw data are more accurate than from standard curves.

Figure 18:
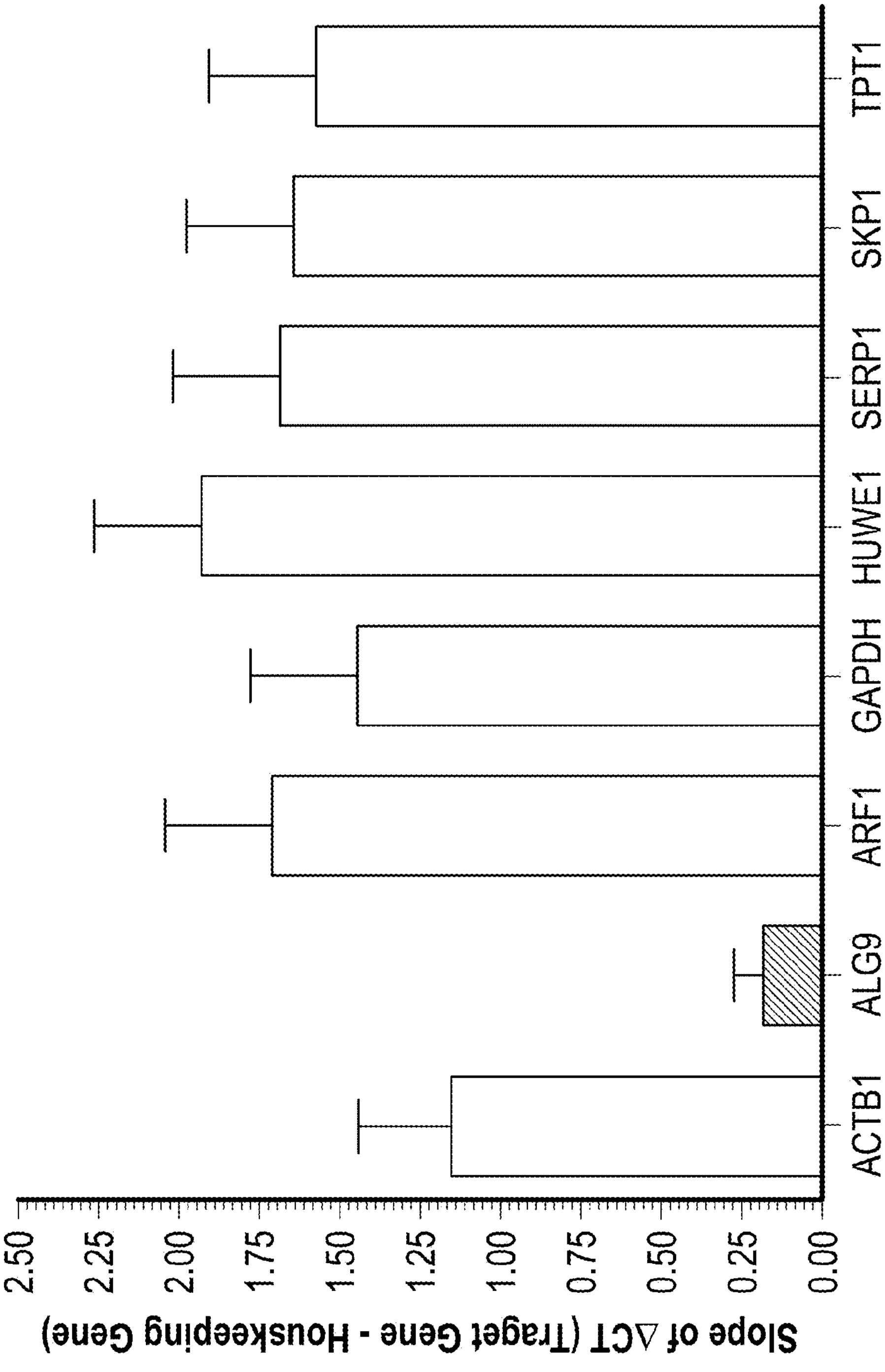
FIG. 18: Variance in amplification kinetics for the housekeeping and target genes. Values ~0.1 demonstrate similar PCR efficiencies and indicate the house-keeper can be used in comparative $C_T$ methods. ALG9 was the only housekeeping gene to exhibit an acceptable efficiency for normalization protocols.

In general, a house-keeping gene is considered appropriate if the difference in $C_T$ for the target-reference gene across a series of dilutions is ≤0.1. One house-keeping gene identified that shared similar PCR efficacies with target genes was ALG9 (FIG. 18).

None of the blood-microarray derived candidate house-keeping genes exhibited the appropriate features necessary to act as a house-keeping gene. ALG9, the tissue-derived candidate house-keeping gene, in contrast, exhibited low variability (M-value and DP test), appropriate topological features, was efficiently transcribed and shared similar amplification features with the target genes of interest. This gene was therefore selected as an appropriate house-keeping gene to normalize circulating tumor transcripts.

Target Normalization

Figure 19:
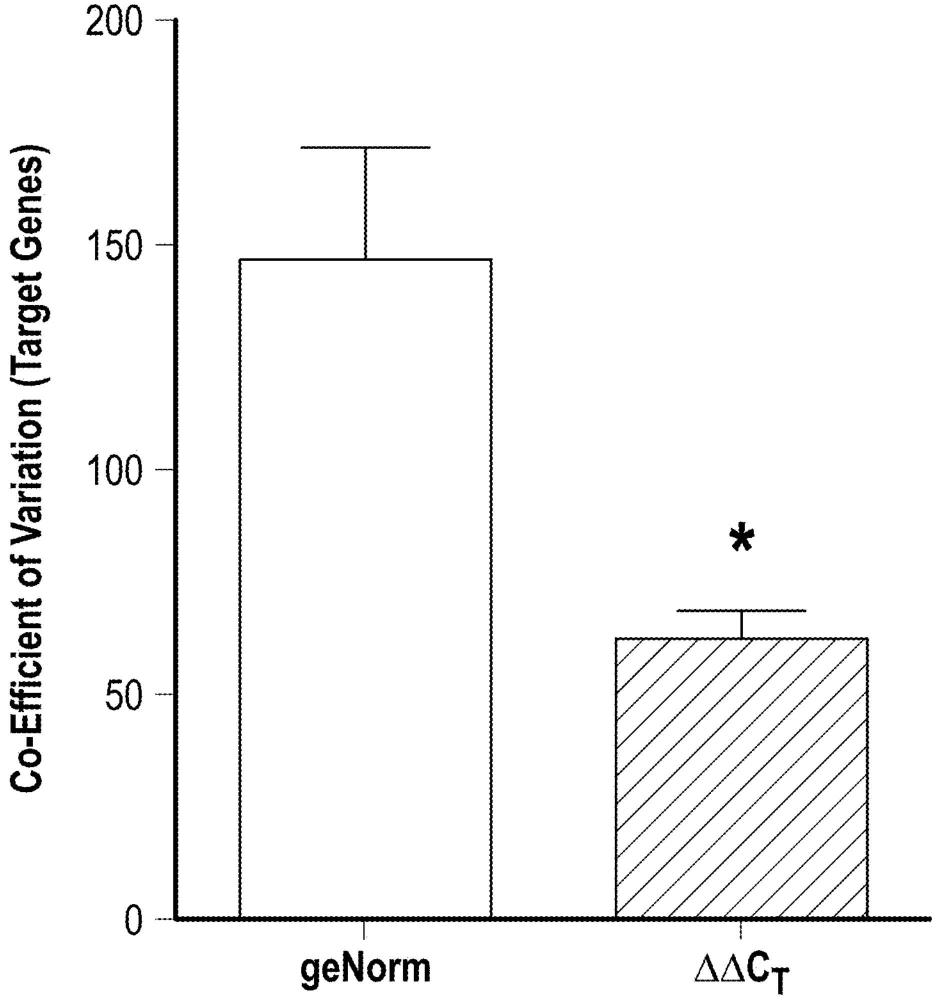
FIG. 19: Variance in target gene expression in normal samples using either a geNorm protocol (using 18S, ALG9 and GAPDH as house-keeping genes) or $\Delta\Delta C_T$ with ALG9. The latter exhibited a significantly lower co-efficient of variation for each of the target genes and ~60% of genes exhibited a normal distribution. *p<0.004 (Mann-Whitney test). The optimal method for normalization was $\Delta\Delta C_T$.

There are a two major methods for normalizing target gene expression: absolute and relative quantitation. The former requires a standard curve (and therefore uses up plate space), is more labor-intensive and is less accurate than protocols based on raw $C_T$ values. This study focused on relative quantitation approaches. A number of algorithms have been developed for relative quantification including the Gentle model, the Pfaffl model, models based on amplification plots, Q-Gene and geNorm. The majority of methods include mechanisms to estimate for differences in PCR efficiencies, use multiple house-keepers e.g., geNorm, or can only be commercially acquired (e.g., qBase$^{PLUS}$ from Biogazelle). One method that is easy to use and does not require estimation factors is the $\Delta\Delta C_T$ protocol. This is a mathematical model that calculates changes in gene expression as a relative fold difference between an experimental and calibrator sample. It is dependent on similar amplification efficiencies for the house-keeper and target genes (a feature identified for ALG9), requires the amplification of small PCR products (<150 bprs—a feature of Applied Biosystems Taqman), and a PCR method that has been optimized (e.g., starting concentration of target has been established). The $\Delta\Delta C_T$ approach was selected for normalization of the 51 candidate genes in peripheral blood. The utility of this approach was demonstrated when this method ($\Delta\Delta C_T$ normalization with ALG9) was compared to geNorm (normalization with 18S, ALG9 and GAPDH) (FIG. 19).

The variation in target gene expression was significantly lower in control samples using a $\Delta\Delta C_T$ protocol ($p<0.004$ vs. geNorm) while the majority of targets exhibited a normal distribution (62% versus 0%, D'Agostino and Pearson omnibus normality test) following normalization with ALG9. A $\Delta\Delta C_T$ protocol (with ALG9) has been shown to successfully normalize target expression in GEP-NEN tumor tissue. A $\Delta\Delta C_T$ approach using ALG9 as a housekeeping gene was identified to be the most appropriate normalization protocol for the 51 candidate GEP-NEN marker genes. Accordingly, this approach was selected to profile transcript expression in blood samples.

Identification of Candidate Tumor Marker Genes

To identify potential marker genes, both tissue- and blood-based tissue microarrays were from GEP-NEN samples as resources to detect candidate marker genes. Gene selection was optimized by applying and developing a number of biomathematical algorithms.

Initially, GEP-NEN (obtained from the small intestine) transcriptomes were analyzed and compared this to normal small intestinal mucosa (U133A chips, n=8 tumors and n=4 controls). Using dCHIP (lower bound fold change ≥1.2-fold, unpaired t-test, and hierarchical clustering based on Pearson correlation) 1,451 up-regulated genes in tumor samples were identified. Thirty-two candidate markers were chosen based on level of up-regulation (>3-fold, e.g., NAP1L1), known biological processes (proliferation e.g., Ki67; survival e.g., survivin), and clinical significance (e.g., somatostatin receptor expression, CgA). In a separate study, PCR-based expression in tumor tissue of nine of these candidate markers were confirmed as predictive of GEP-NEN malignancy. In the current study, the 32 candidate genes were examined further and 17 were included in the final gene panel.

Figure 20A:
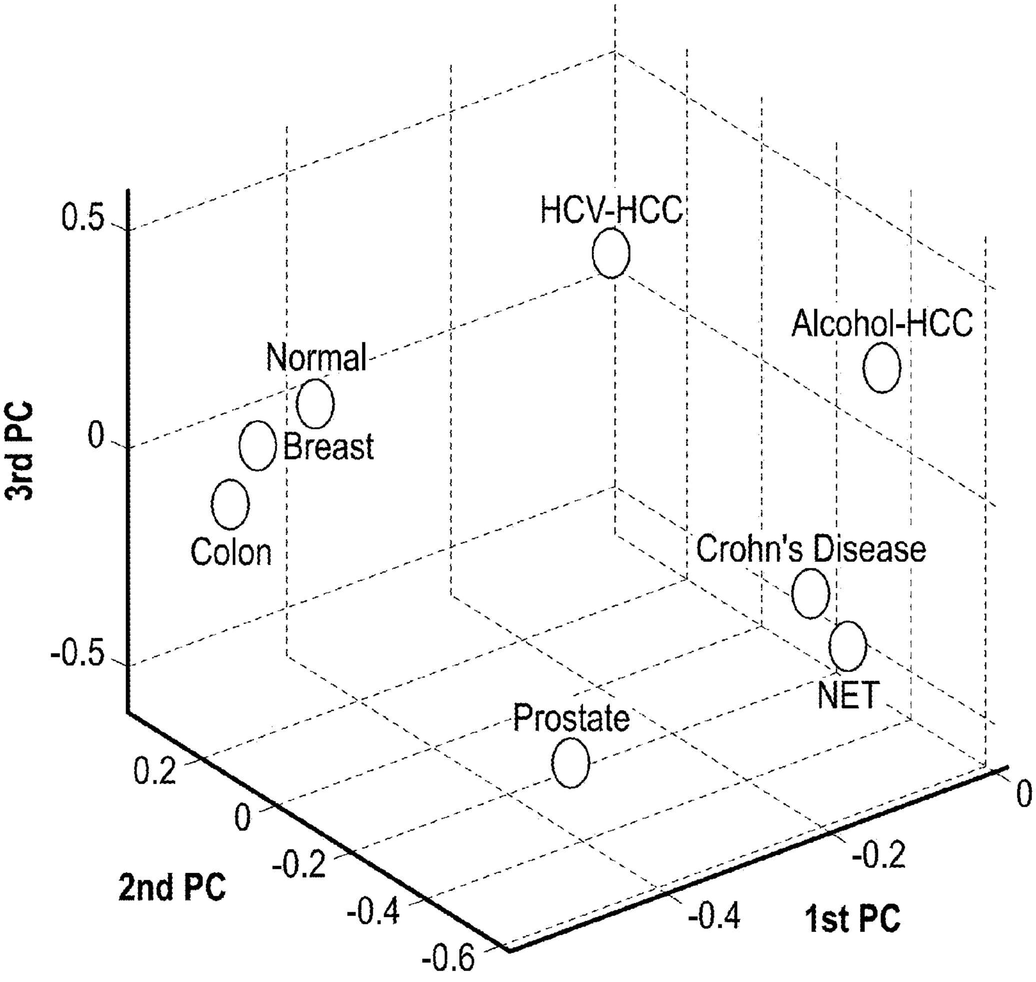
FIGS. 20A-D: Identification of tissue-associated genes from U133A and HUGE arrays. PCA of GEP-NENs compared to other neoplasia (breast, colon, prostate and liver) identified the transcriptome was most similar to Crohn's Disease (20A). Subtraction of transcript expression associated with other neoplasia identified a specific GEP-NEN gene signature (modeled as an interactome —20B). Back-analysis to the tissue arrays identified 21 novel markers which differentiated control from GEP-NENs both by hierarchical cluster analysis (20C) and principal component analysis (PCA) (20D). SI-NENs exhibit a different transcript spectrum to other cancers. A NEN-specific gene signature is identifiable, which can differentiate these tumors from control samples.

As a second strategy, two microarray data sets of tumor tissue (HUGE and U133A, a total of n=30 tumors and n=10 controls) were utilized, and compared GEP-NENs (obtained from small intestinal sites) to other tumors (breast, colon, prostate and liver cancers) from publicly available databases. Small bowel material from Crohn's disease, which is known to perturb local neuroendocrine cell activity and is associated with SI-NEN risk, was also assessed to further delineate the overall GEP-NEN gene landscape and help identify candidate markers. In order to assess the relationships of the genes involved, a graphic theoretical analysis of gene co-expression networks was constructed. This approach determined that the "GEP-NEN" gene network (generated by integrating the two platforms, U133A and HUGE) consisted of 6,244 genes and 46,948 links. The gene network was highly modular (i.e. genes tended to organize into interconnected communities) and therefore contained genes that were functionally related (as they occurred within the same community). An unbiased community detection algorithm identified 20 communities (collections of related genes) with >20 genes each. Enrichment of each gene community for biological processes identified terms including 'Oxidation reduction' (Cluster 1/2), 'Immune response' (Cluster 5), and 'Cell cycle' (Cluster 18). Of importance was identification that the GEP-NEN gene network was topologically distinct from other common cancers (but shared similarity) to Crohn's disease (FIG. 20A). The latter may reflect the known proliferation of neuroendocrine cells in Crohn's disease.

Figure 20B:
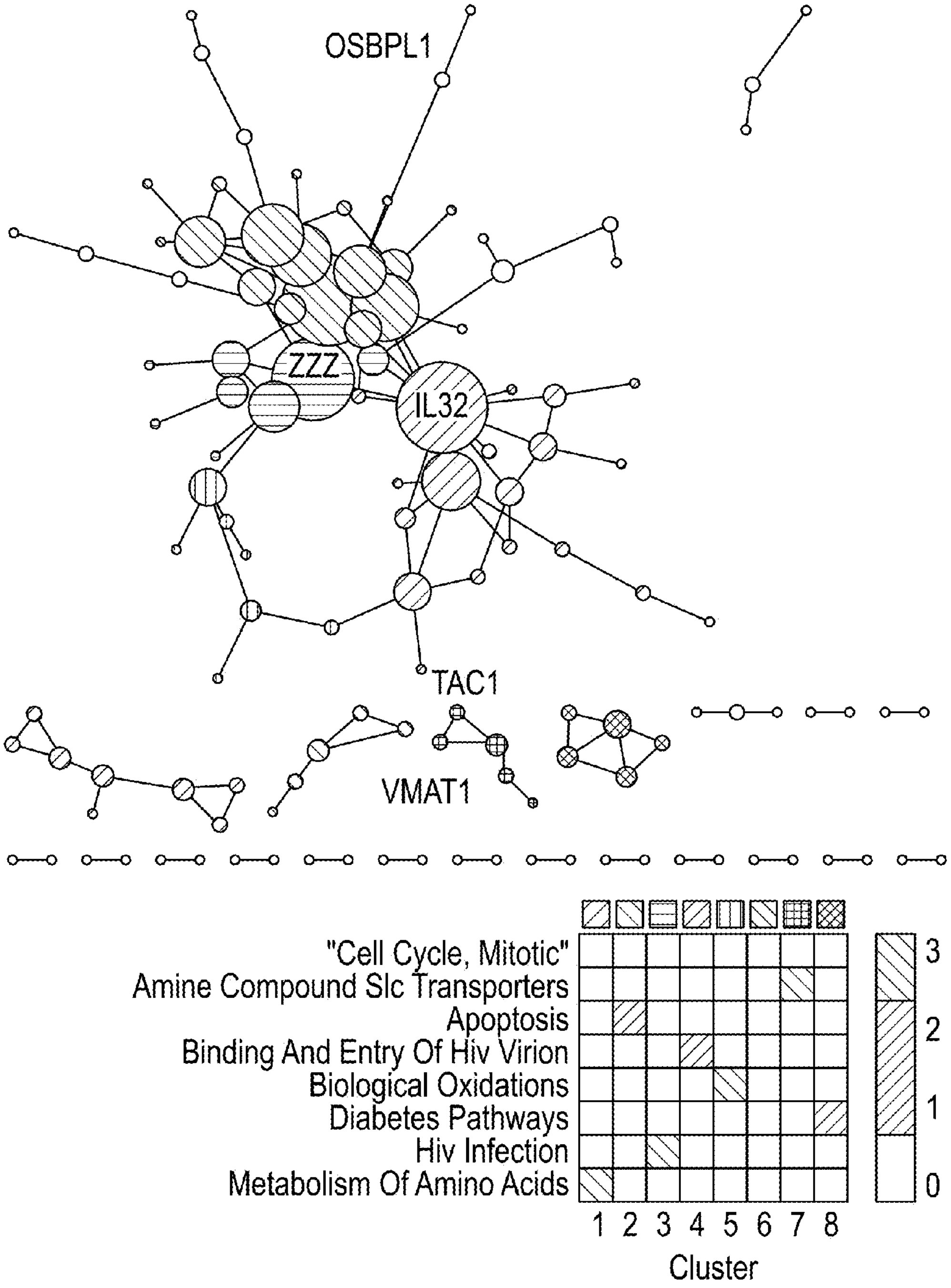

The topological distinction reflected unique connectivity patterns around each gene in the interactome providing information that a panel of genes or gene-interactions may be specific to the tumor (GEP-NEN). Such a tumor-specific signature was generated by eliminating gene-gene interactions found in breast, colon, prostate, and liver cancer gene networks from the GEP-NEN gene network. The resulting GEP-NEN-specific signature yielded 124 genes and 150 interactions (FIG. 20B).

Figure 20C:
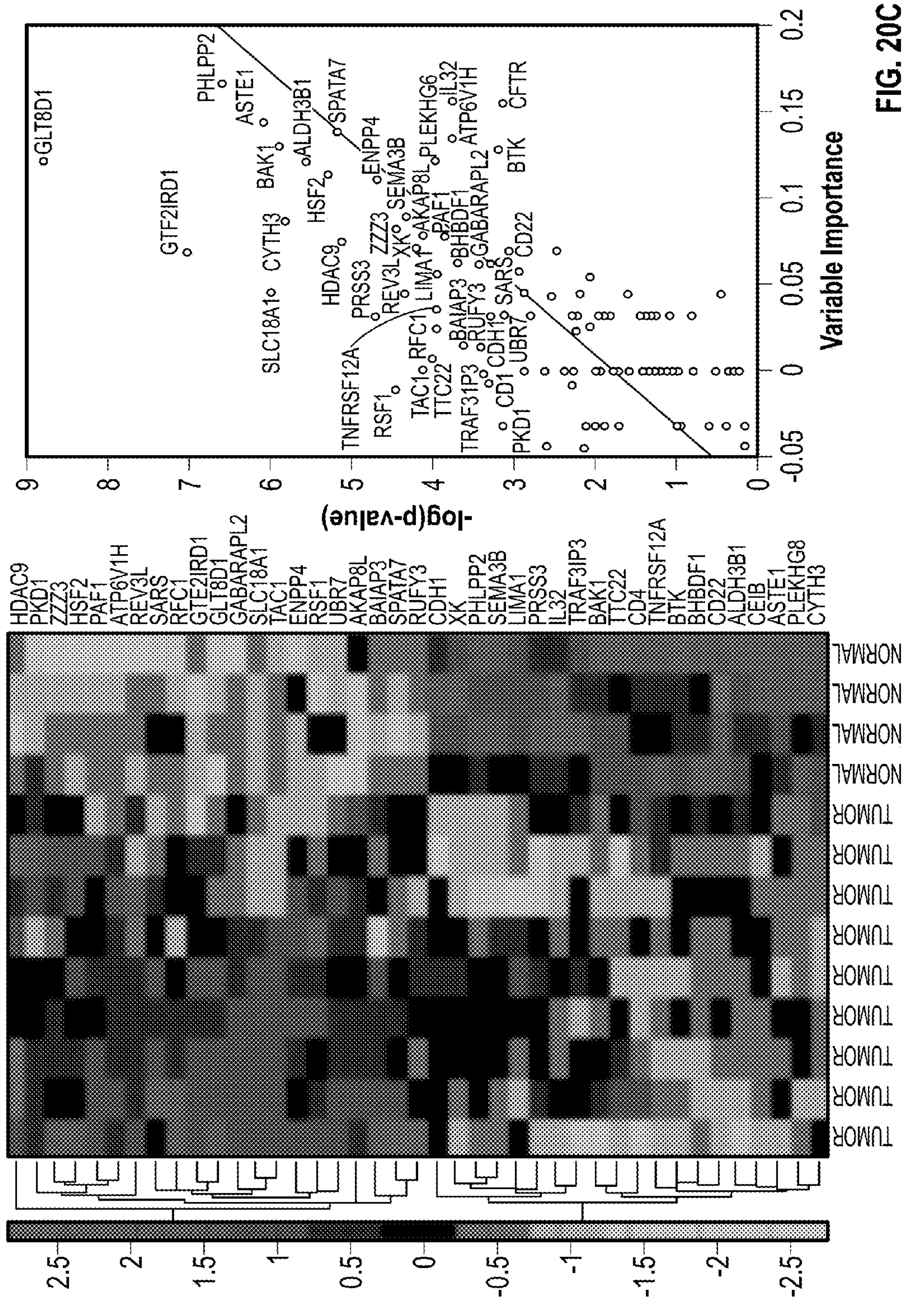
Figure 20D:
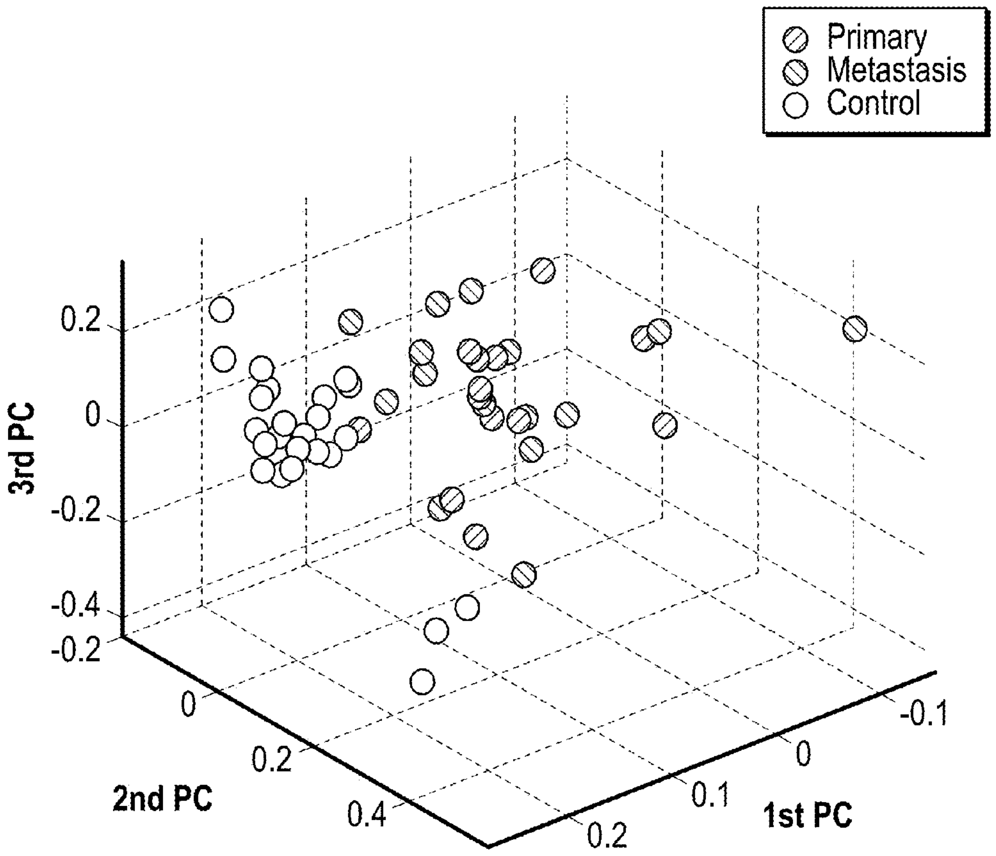

Mapping these 124 GEP-NEN-specific genes back to the U133A tissue-based microarray identified that 41 genes were differentially expressed, of which 21 were up-regulated (FIG. 20C) and could differentiate between GEP-NENs and controls (FIG. 20D). These 21 up-regulated genes were examined further, and 12 were included in the final gene panel.

As a third strategy, circulating GEP-NEN transcriptomes were examined to identify additional candidate markers. For these studies, peripheral blood transcriptomes (n=7 controls, n=7 GEP-NENs) were compared to the "In-house" tissue array (n=3 controls, n=9 GEP-NENs [from the small intestine]) and one published array from the ArrayExpress database (accession number: E-TABM-389: n=6 controls, n=3 primary midgut NENs, and n=3 GEP-NEN metastases [METs]).

Figure 21A:
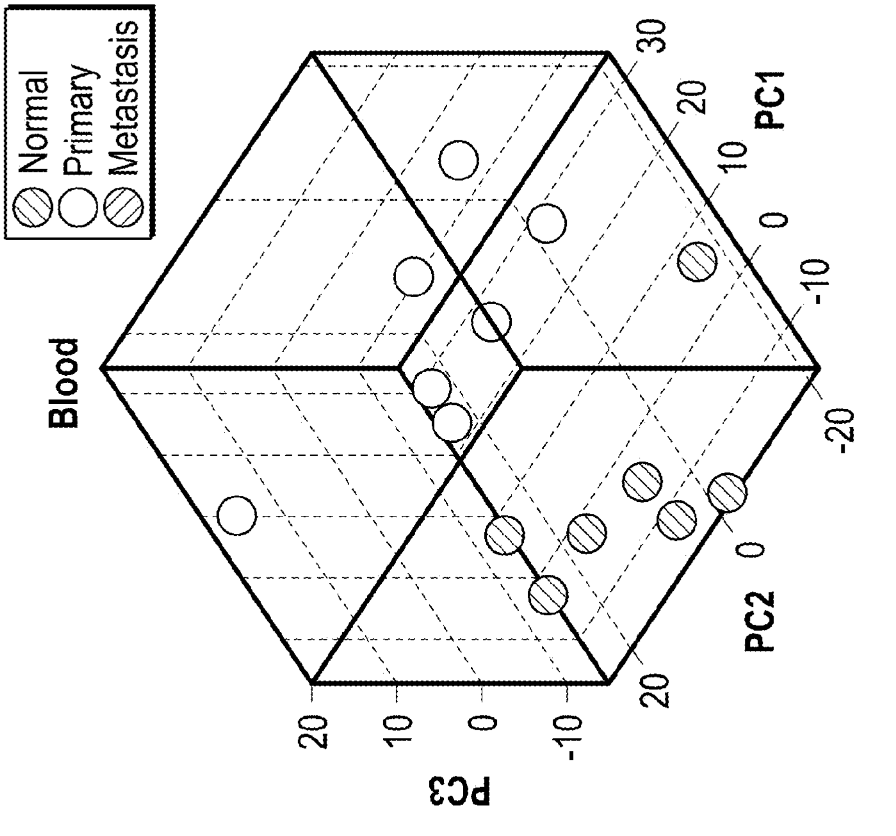
FIGS. 21A-F: Gene expression profiles in the Blood (21A,D), "In-house" (21B, E), and Public datasets (21C, F). Analysis of transcript expression identified that samples from both GEP-NEN tissue and blood could be differentiated from controls. This indicates that each of these compartments contain a definable GEP-NEN molecular fingerprint that can be measured and used to distinguish tumors from controls.
Figure 21B:
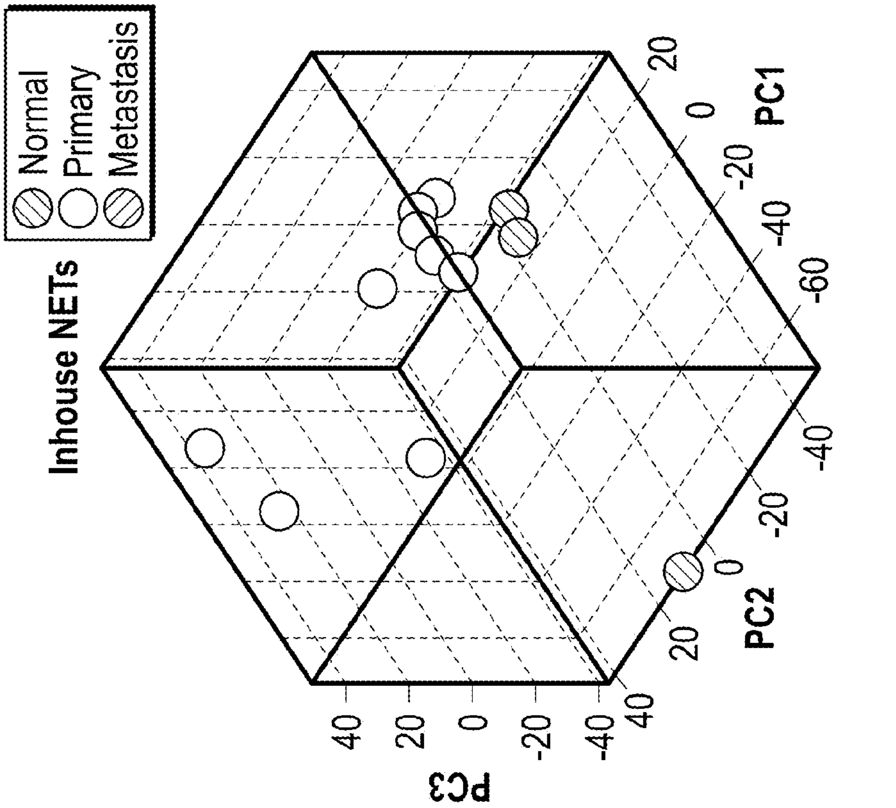
Figure 21C:
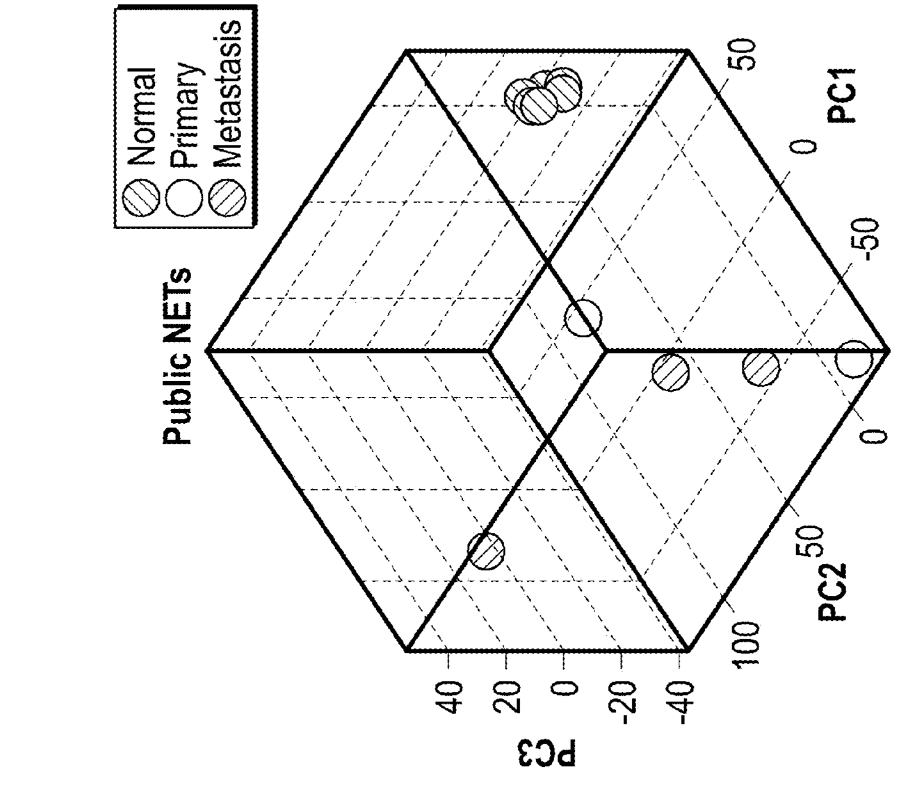
Figure 21D:
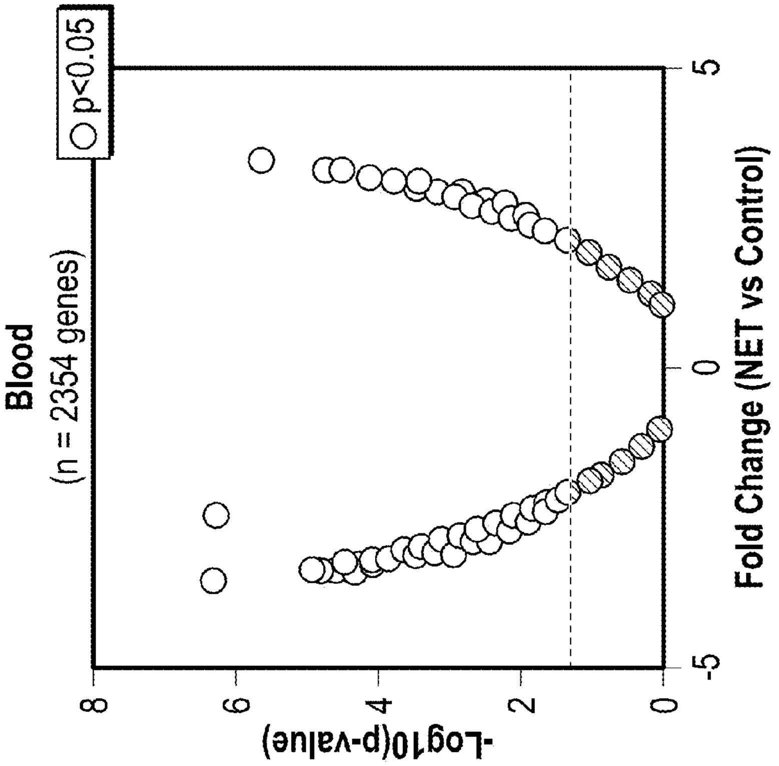
Figure 21E:
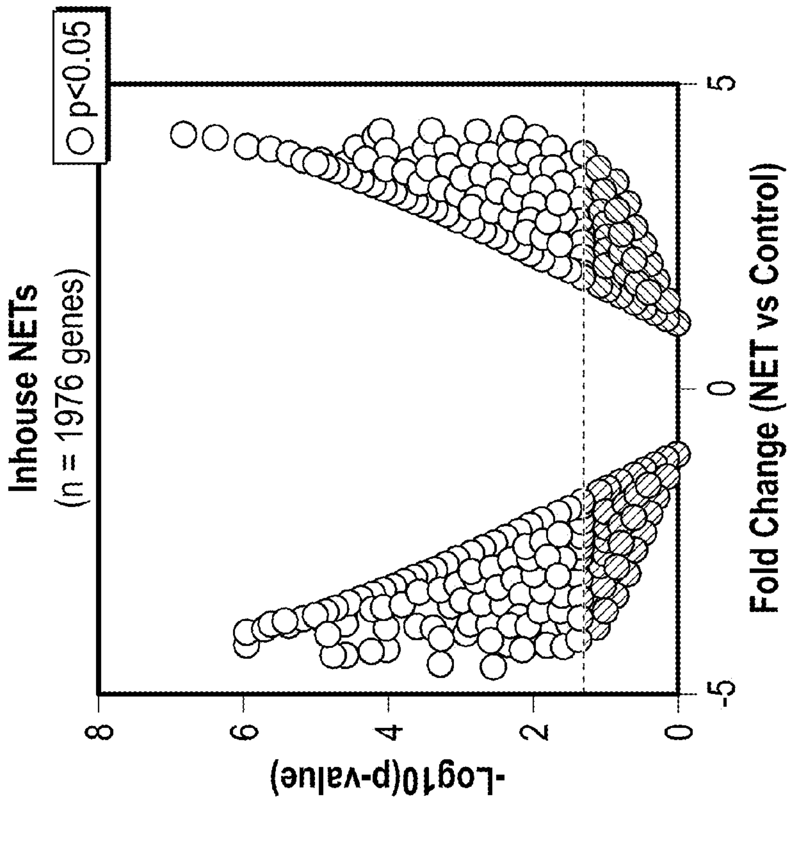
Figure 21F:
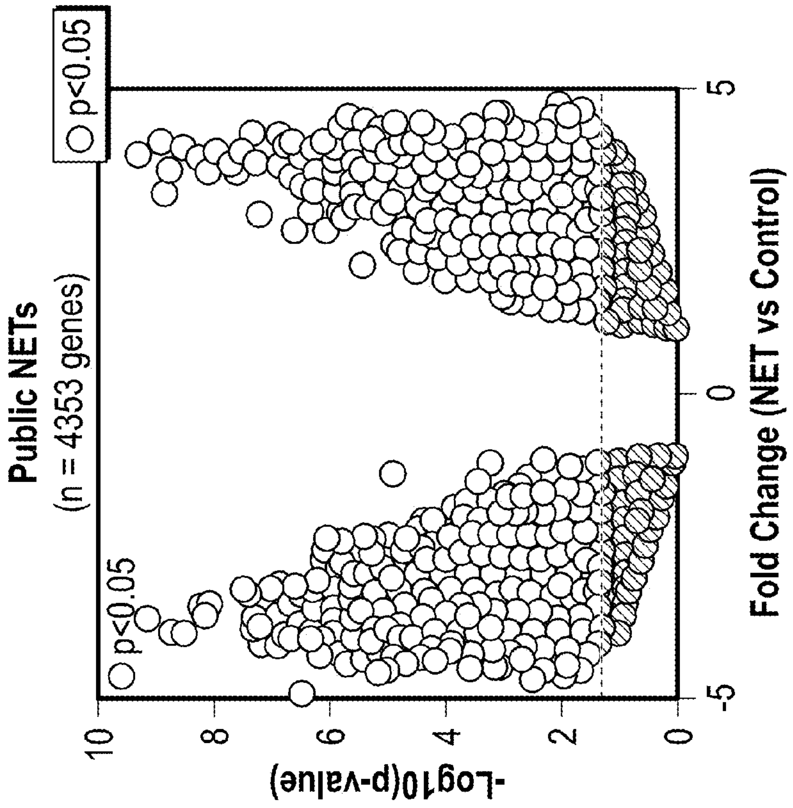

Tumor samples were clearly differentiated from controls (FIG. 21A-C) and differentially expressed genes were identified for each of the groups: Blood (n=2,354), "In-house" (n=1,976) and Public datasets (n=4,353) (FIG. 21D-F).

Figure 22A:
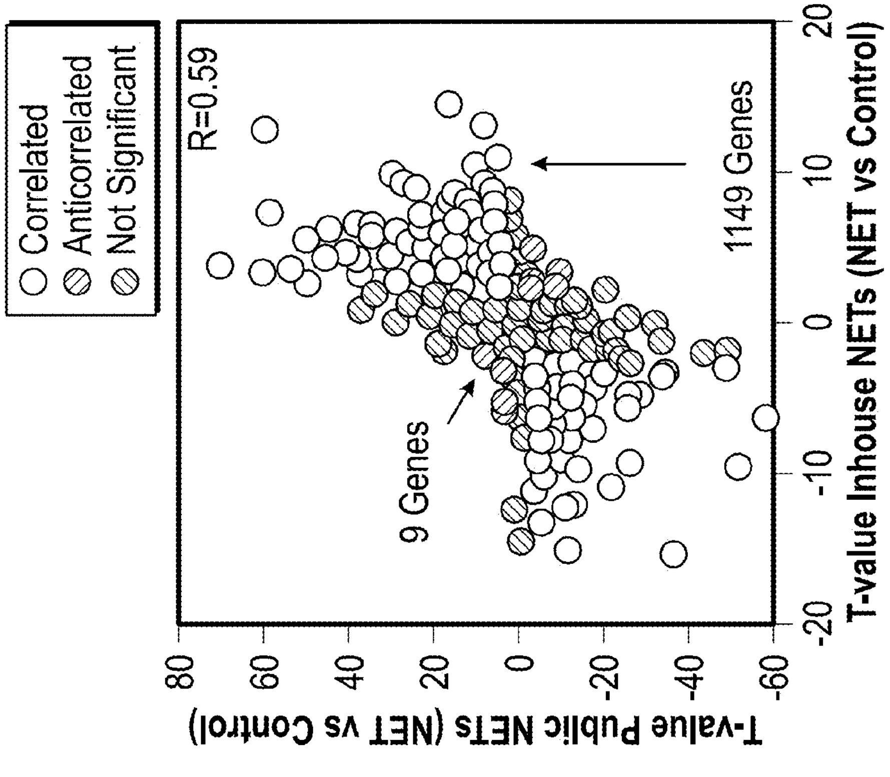
FIGS. 22A-C: Correlation profiles of transcript changes in blood and tissue samples. Both tissue databases were highly correlated (R=0.59, 22A) but lower correlations were noted between blood transcriptomes and either the "In-house" dataset (R=−0.11, 22B) or the Public dataset (R=−0.05, 22C). The common genes identified in both the tissue and blood samples provided a group of candidate marker transcripts which we then examined in blood.
Figure 22B:
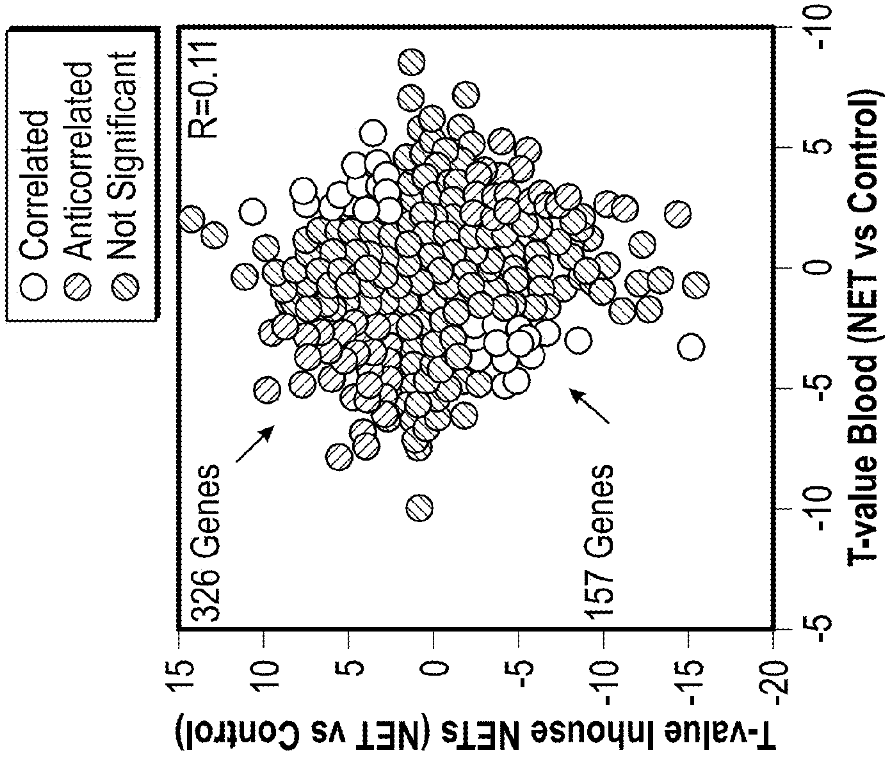

As expected, there was a large correlation between changes in gene expression for the "In-house" and Public tissue datasets (R=0.59, FIG. 22A). While the correlation between the Blood and "In-house" and Public datasets was low (R=−0.11 and −0.05, respectively) (FIG. 22A,B), 157 (33%) of the 483 significantly changed genes ("In-house"/blood) and 423 (45%) of the 947 significantly changed genes (Public/blood), were positively correlated.

Figure 23A:
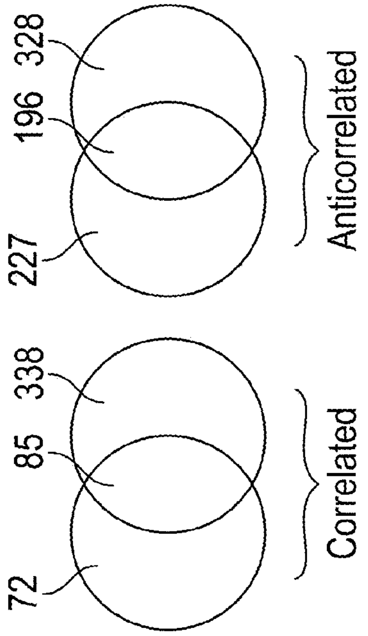
FIGS. 23A-C: A: Correlated and anti-correlated biological processes in GEP-NEN transcriptomes from peripheral blood and tumor tissue samples. B & C: Eighty-five genes associated with tumor function (intracellular signaling and transcription and regulation of cell death), were up-regulated in both tissue and blood samples. This group was considered to represent evaluable candidate circulating biomarkers.
Figure 22C:
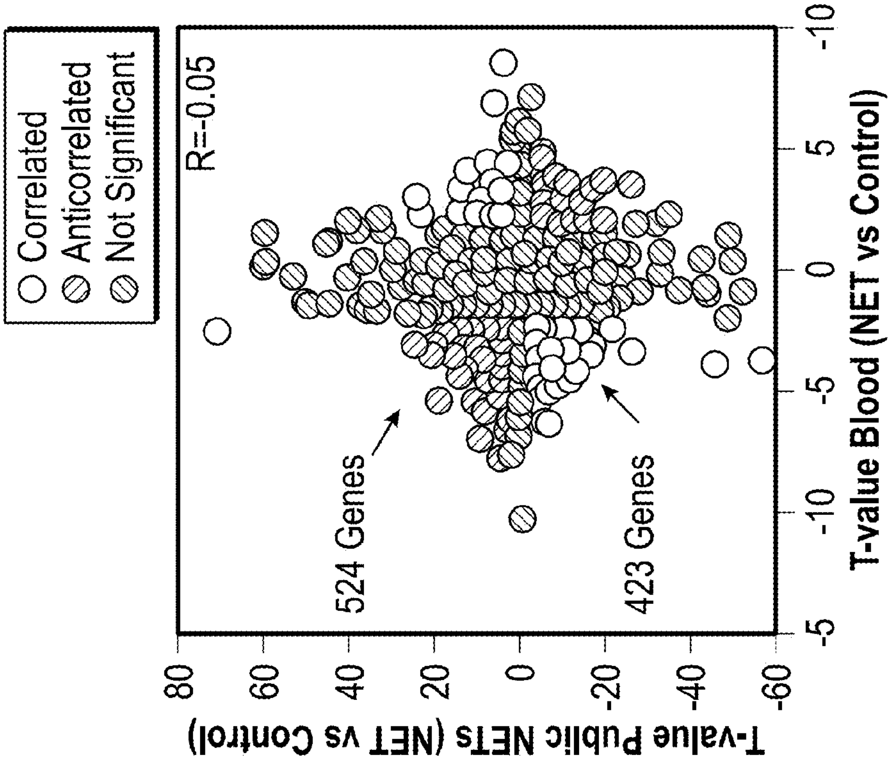
Figure 23B:
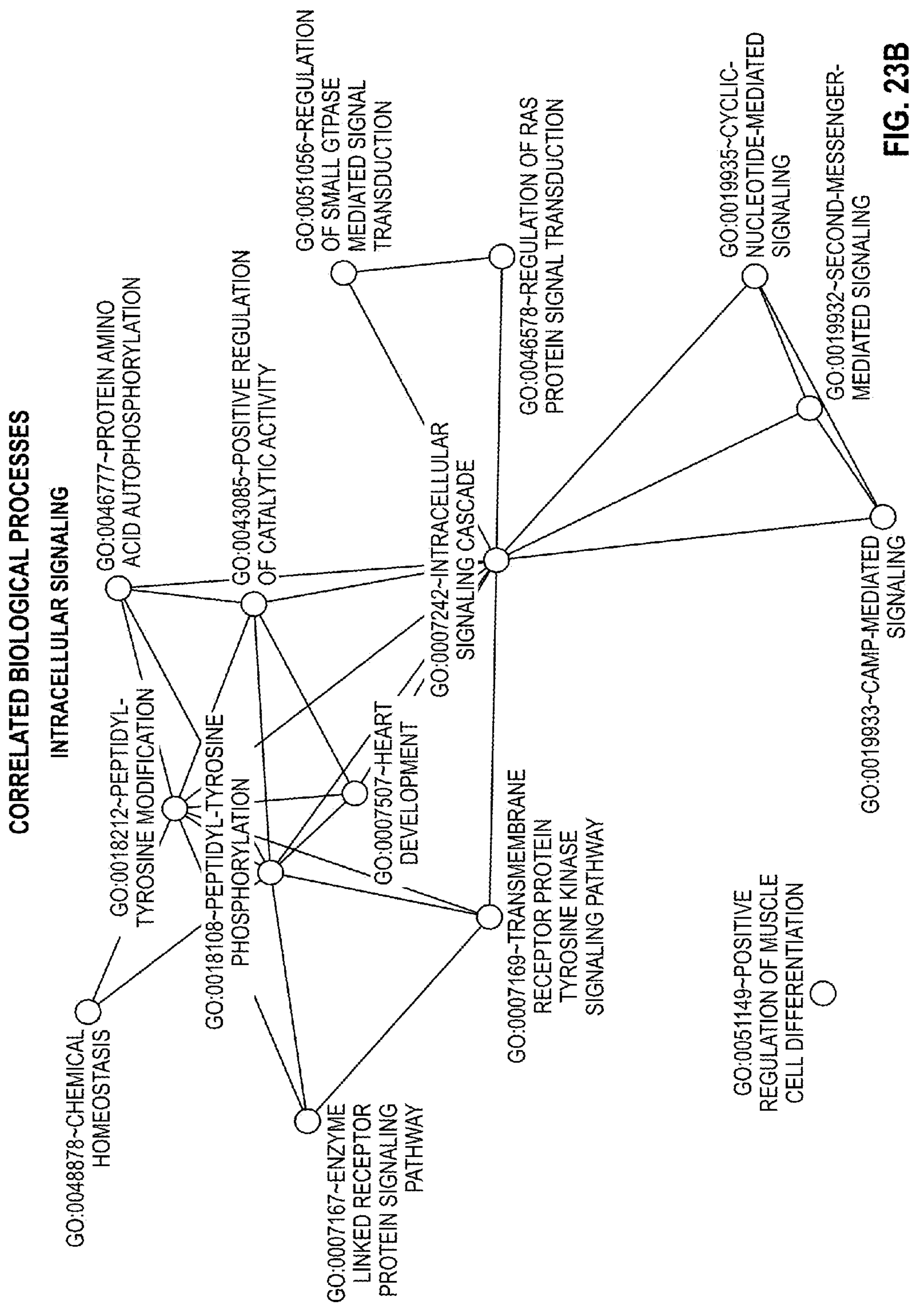
Figure 23B:
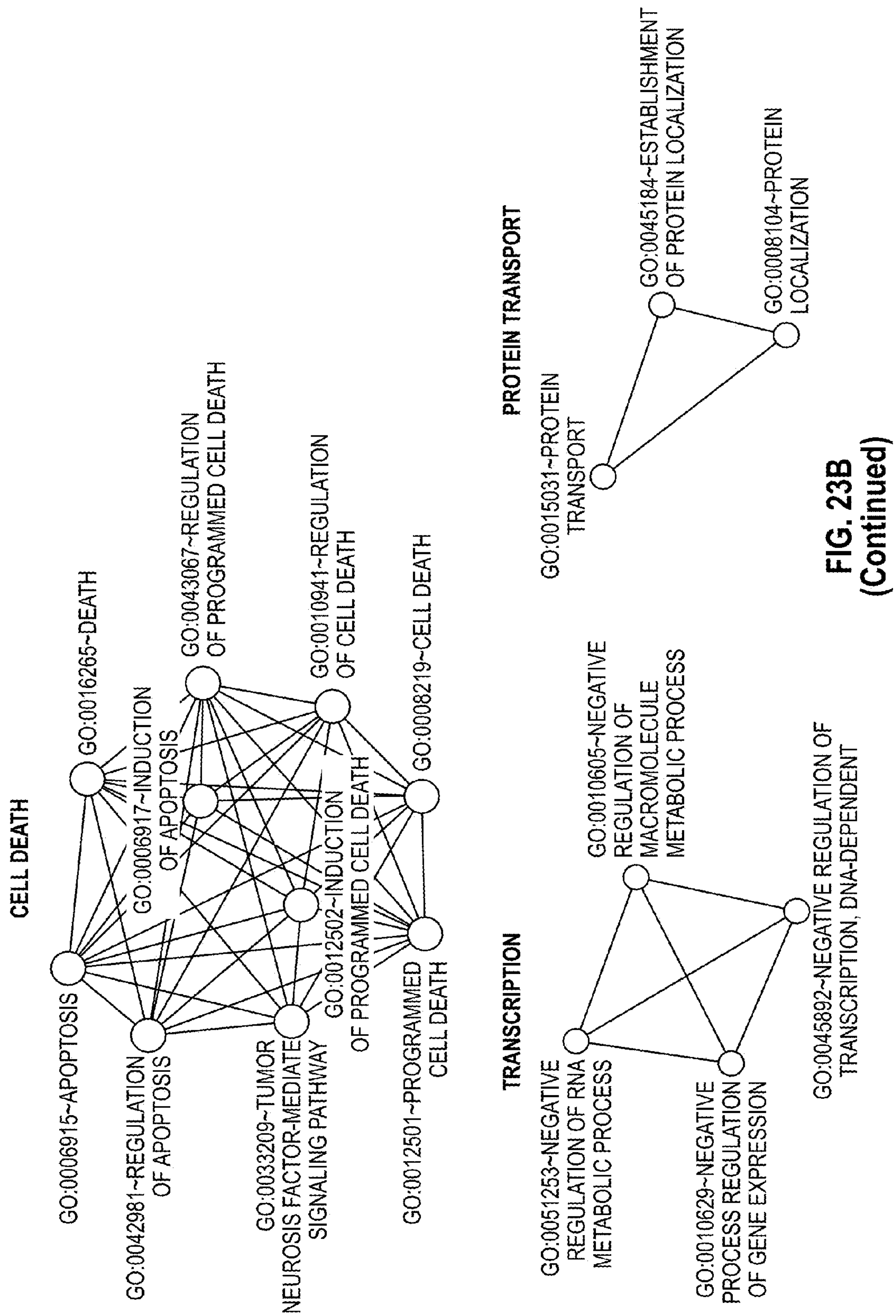
Figure 23C:
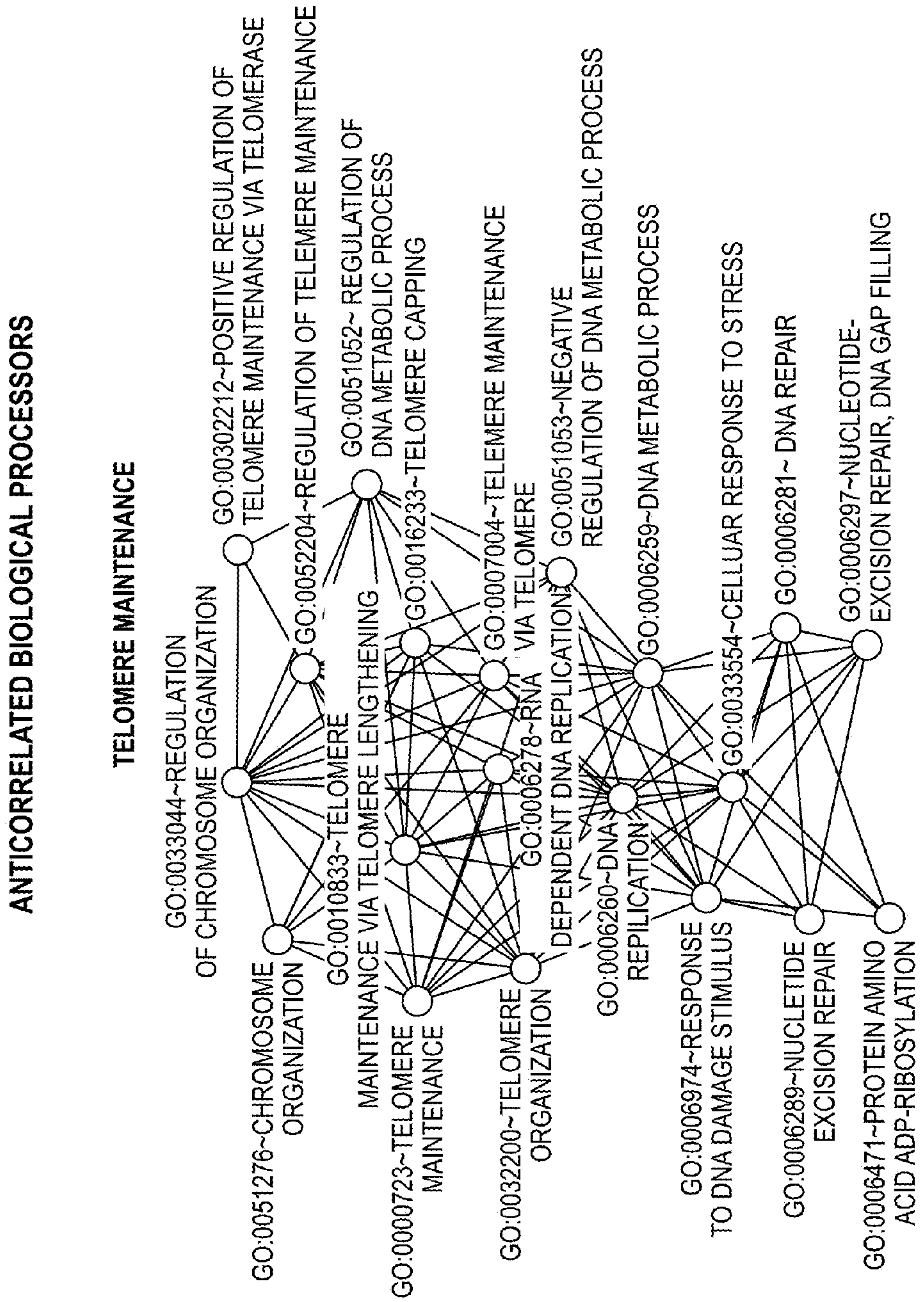
Figure 23C:
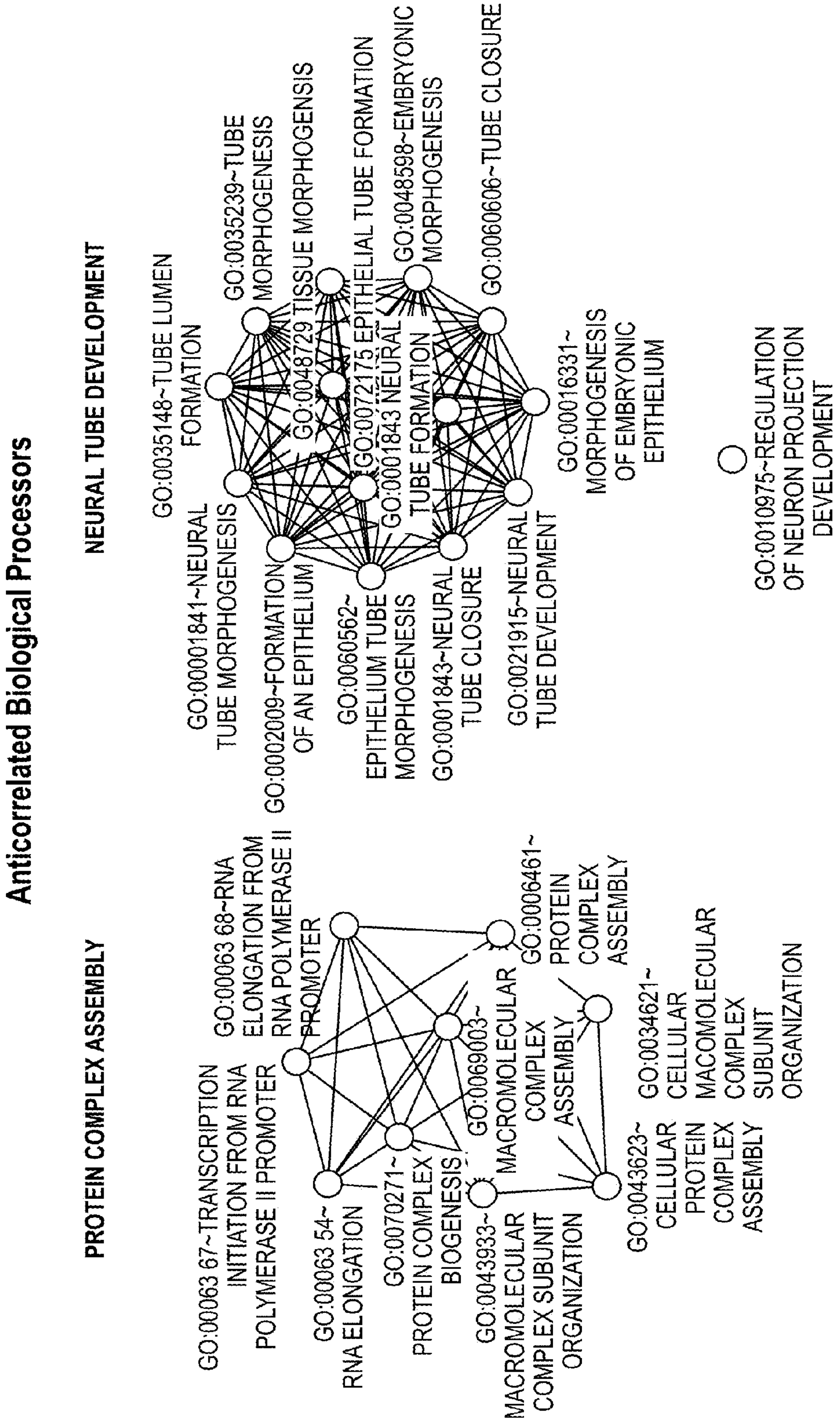

Overall, between the Blood, "In-house", and Public datasets, 85 genes were correlated in blood and tissue, while 196 were inversely or anti-correlated (FIG. 23A). The correlated genes encoded processes such as intracellular signaling, cell death, and regulation of transcription (FIG. 23B) while the anti-correlated genes encoded processes such as telomere maintenance, neural tube development, and protein complex assembly (FIG. 23C).

Figure 24:
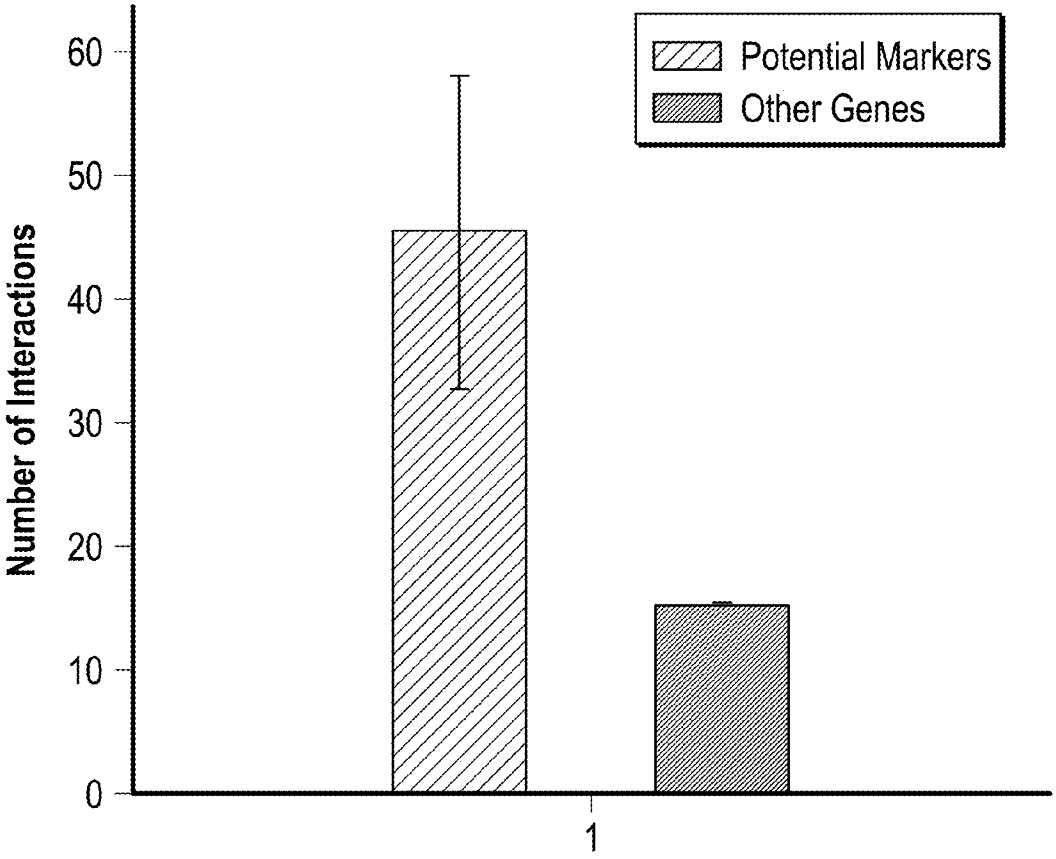
FIG. 24: Expression of the 22 genes with low paralog numbers (0-3) are ~3 times more central in the blood interactome compared to all other genes (6,000 genes). This group of specific genes, with few relatives, is present in blood and can be considered as potential markers of neuroendocrine neoplasia.

Thirty-nine of the 85 (46%) concordantly expressed genes in both blood and tissue were up-regulated and 46 transcripts are down-regulated. An analysis of the up-regulated genes identified that 22 had 0-3 paralogs and were expressed at levels >3-fold. Integration of these genes with the blood interactome confirmed that they were highly inter-connected (more central in the interactome), demonstrating their "putative" biological relevance in the context of GEP-NENs (FIG. 24).

These approaches, including analysis and integration of tumor tissue and circulating peripheral blood transcripts, enabled identification of a panel of 75 candidate marker genes associated with GEP-NENs. The utility of these genes to identify GEP-NENs was then studied in peripheral blood samples.

The Circulating GEP-NEN Fingerprint (51 Marker Gene Panel)

In order to develop a useable marker panel, transcript levels of each of the 75 candidate markers in mRNA isolated from 77 blood samples (controls: n=49; GEP-NENs: n=28) were measured. A 2-step protocol (RNA isolation, cDNA production and PCR) was developed as this is more accurate than 1-step protocols. The reproducibility of 2-step protocols is high (Pearson's correlation >0.97; for the 2-step approach, the correlation is 0.987-0.996). In preliminary studies, the preferred method for mRNA isolation from blood samples was the mini blood kit (Qiagen: RNA quality >1.8 $A_{260:280}$ ratio, RIN>5.0, appropriate for PCR applications [37]) with cDNA produced using the High Capacity Reverse transcriptase kit (Applied Biosystems: cDNA production 2000-2500 ng/ul). Real-time PCR was consistently performed with 200 ng/ul of cDNA on a HT-7900 machine using 384-well plates and 16 ul of reagents/well (Fast Universal PCR master mix, Applied Biosystems). The limit of detection for PCR was determined as 40 cycles (200 ng/ul cDNA positively amplified in 95.3±0.2% of cases). Increasing the number of cycles to 45-50 cycles identified positive expression in <1% of target samples; the false negative rate was calculated using a $C_T$ cut-off of 40 to be 0.8%. This cycle number is more stringent than the accepted European approach for leukemia detection, but is consistent with other PCR-based detection protocols. Primers were exon spanning to minimize genomic DNA amplification and were <150 bprs. Commercially available Applied Biosystems primers (5'-nuclease assay) were used. The consistent parameters for RNA isolation, cDNA synthesis and real-time PCR provide a stable platform for target and house-keeping gene analysis.

51 of the 75 candidate markers were as identified as producing detectable product ($C_T$<40 cycles) in blood. This 51 gene panel included: AKAP8L, APLP2, ARAF1, ATP6V1H, BNIP3L, BRAF, C21orf7, CD59, COMMD9, CTGF, ENPP4, FAM131A, FLJ10357, FZD7, GLT8D1, HDAC9, HSF2, Ki67, KRAS, LEO1, MORF4L2, NAP1L1, NOL3, NUDT3, OAZ2, PANK2, PHF21A, PKD1, PLD3, PNMA2, PQBP1, RAF1, RNF41, RSF1, RTN2, SMARCD3, SPATA7, SST1, SST3, SST4, SST5, TECPR2, TPH1, TRMT112, VMAT1, VMAT2, VPS13C, WDFY3, ZFHX3, ZXDC, ZZZ3. Thirteen of these 51 marker genes have previously been associated with GEP-NENs, either of the previous studies, or in those of others.

Having defined a potentially useful marker gene panel, the GEP-NEN transcriptomic resources were examined to identify preferred house-keeping genes and determine preferred methods for normalization of the data. Identifying appropriate house-keeping genes and applying normalization protocols would facilitate quantification of each of the 51 candidate transcripts and determine whether they represented a panel of GEP-NEN marker genes.

Example 5C: Detection of Circulating GEP-NEN Cells and Biomarker Expression in Whole Blood Using real-time PCR, flow cytometry, and florescence-activated cell sorting (FACS)-sorting, CD164 was identified as a marker capable of detecting circulating GEP-NEN cells in whole blood. Detection of CD164 transcript expression levels by real-time PCR demonstrated that this biomarker is consistently overexpressed (300-10,000×) in GEP-NEN patient samples (29/29 GEP-NEN cells and 4 GEP-NEN cell lines) compared to normal EC cells and leukocytes, demonstrating CD164 is useful as a biomarker for identification of GEP-NEN cells in human samples, e.g., whole blood.

Figure 25A:
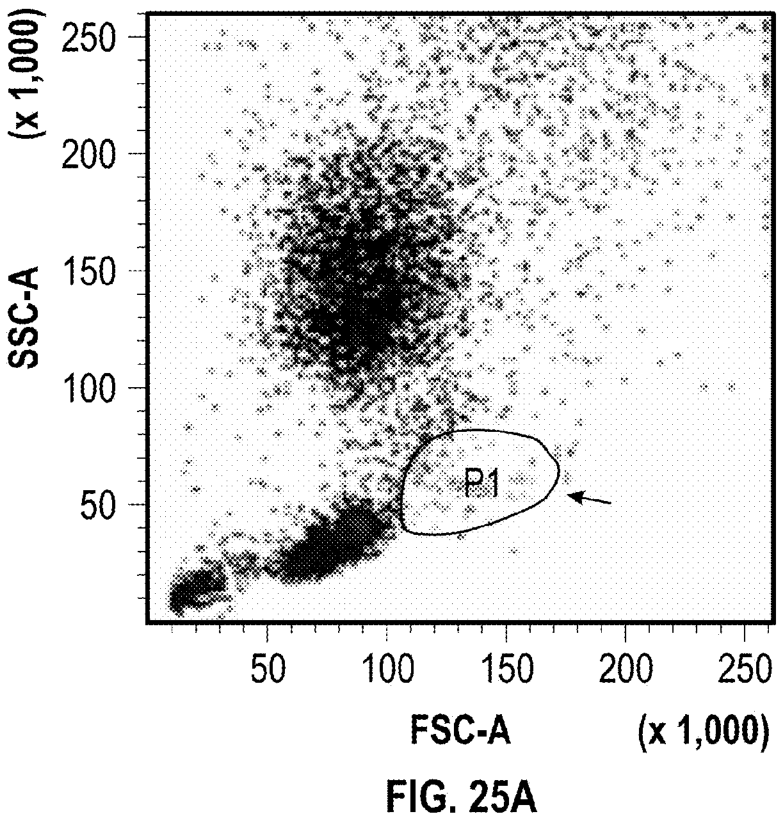
FIGS. 25A-C: FACS of AO/APC-CD164 dual stained whole blood from a patient with metastatic NETs. Flow cytometric analysis following AO (acridine orange)/APC-CD164 dual-staining of whole blood from a patient with metastatic NET showed a distinct population of cells consistent in size with NET cells (P1, arrow: 25A) exhibiting the characteristic AO/APC positivity of NETs (25B). This population of cells was collected (25C); immunostaining with anti-TPH confirmed that the cells were NET cells (25C—inset).
Figure 25B:
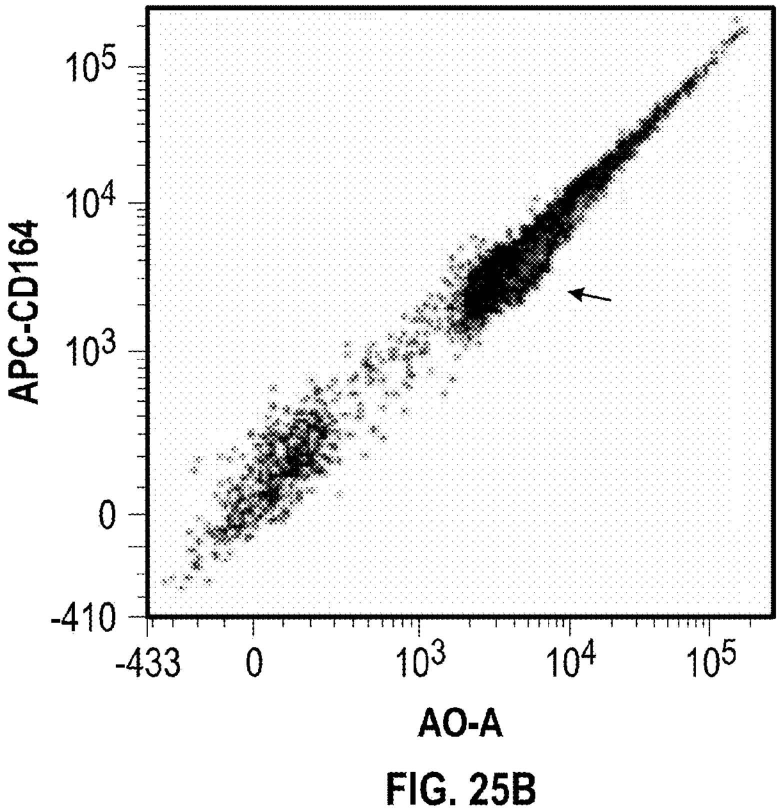
Figure 25C:
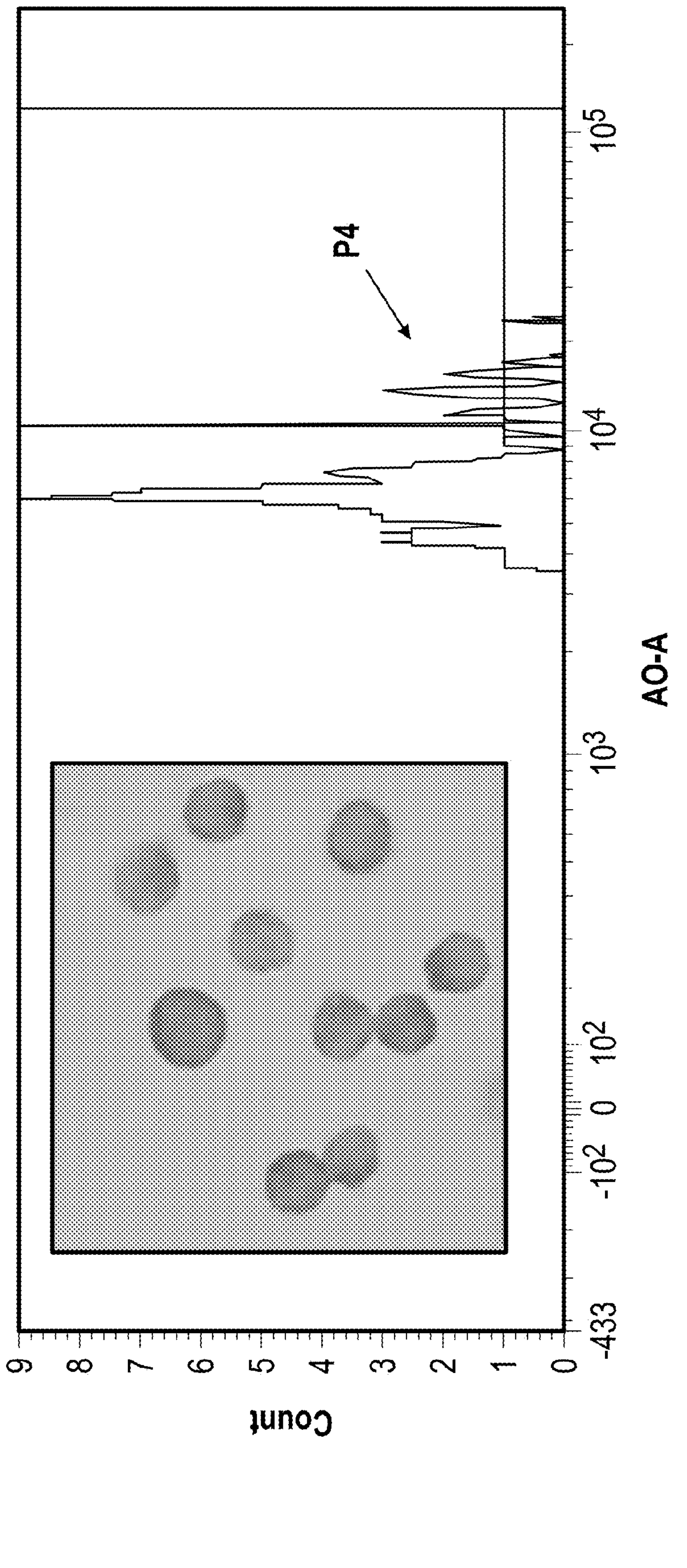

Multi-parameter flow cytometry was performed on whole blood samples obtained from 10 GEP-NEN patients and 10 age- and sex-matched controls. A population of GEP-NEN cell-sized cells (FIG. 25A), which was double-positive for acridine orange (AO)-PE-CY7 and CD164-APC was detected in GEP-NEN samples, but absent in normal control samples (FIG. 25B). Collection and immunostaining of these cells for TPH expression confirmed they were serotonin-positive GEP-NEN cells (FIG. 25C, inset).

After dual labeling with A0 and CD164, 3-12 GEP-NEN cells, per mL of blood, were sorted by FACS and collected. Real-time PCR identified elevated (>2-fold, p<0.03) expression levels of the 21 GEP-NEN biomarkers described above (MAGE-D2, MTA1, NAP1L1, Ki67, Survivin, FZD7, Kiss1, NRP2, X2BTB48, CXCL14, GRIA2, NKX2-3, OR51E1, PNMA2, SPOCK1, HOXC6, CTGF, PTPRN2, SCG5, and Tph1), normalized to house-keeping genes compared to normal whole blood samples, confirming that these cells were GEP-NEN tumor cells. Significantly higher expression levels (3-5 fold, p<0.05) were identified in samples obtained from six patients with metastatic disease, as compared to four patients with local disease.

Figure 26A:
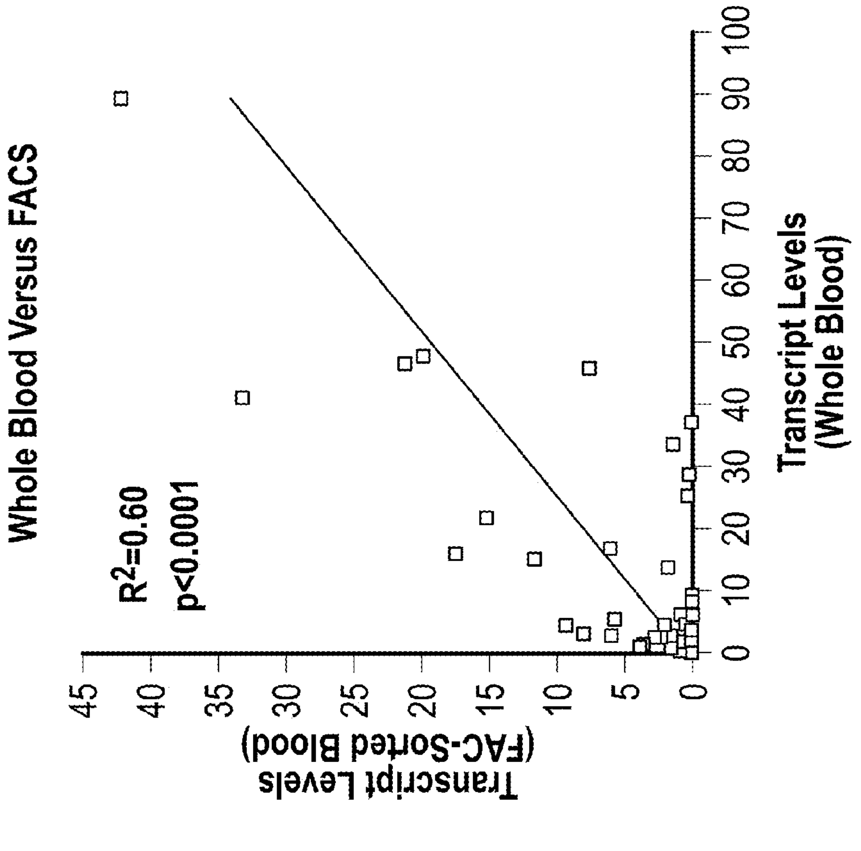
FIGS. 26A-B: Relationship between whole blood PCR marker levels and FACS-collected circulating NETs and tissue. Whole blood expression levels of biomarker transcripts were highly correlated ($p<0.0001$) with FACS-sorted samples (representing circulating tumor cells (26A)) and with tissue (26B), confirming that whole blood is an appropriate compartment for measuring NET transcripts.
Figure 26B:
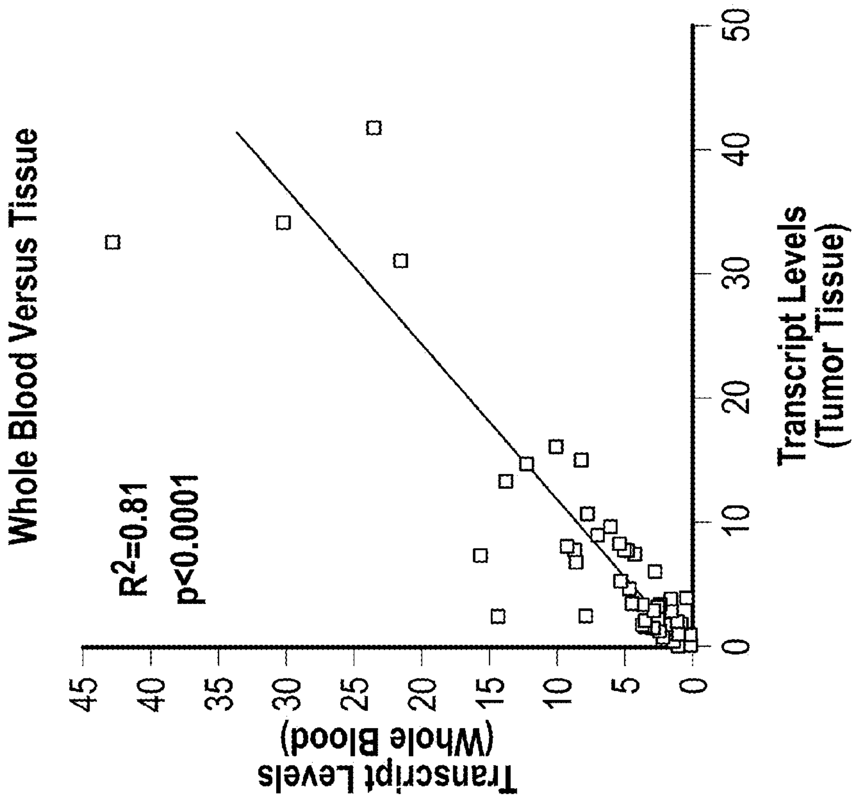
Figure 27A:
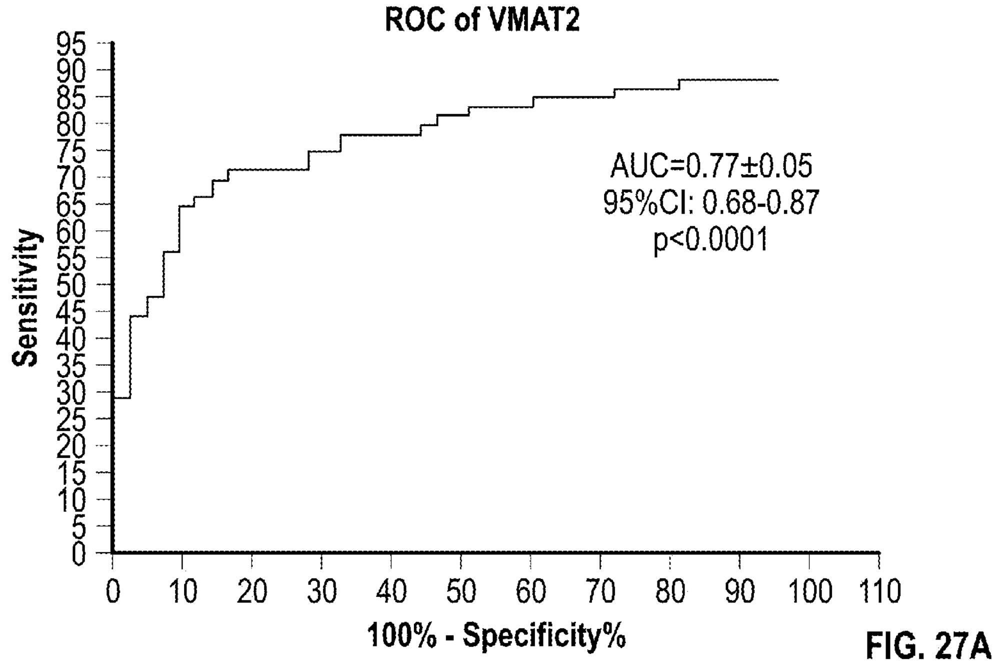
FIGS. 27A-F: ROCs and sensitivity and specificities for predicting NETs. ROCs and AUCs for selected genes and summed transcripts (V1) were calculated in Yale samples (NETs and controls) as described in Example 5D. Use of predicted cut-offs were tested in NETs from Berlin and Uppsala and sensitivities and specificities are provided.
Figure 27B:
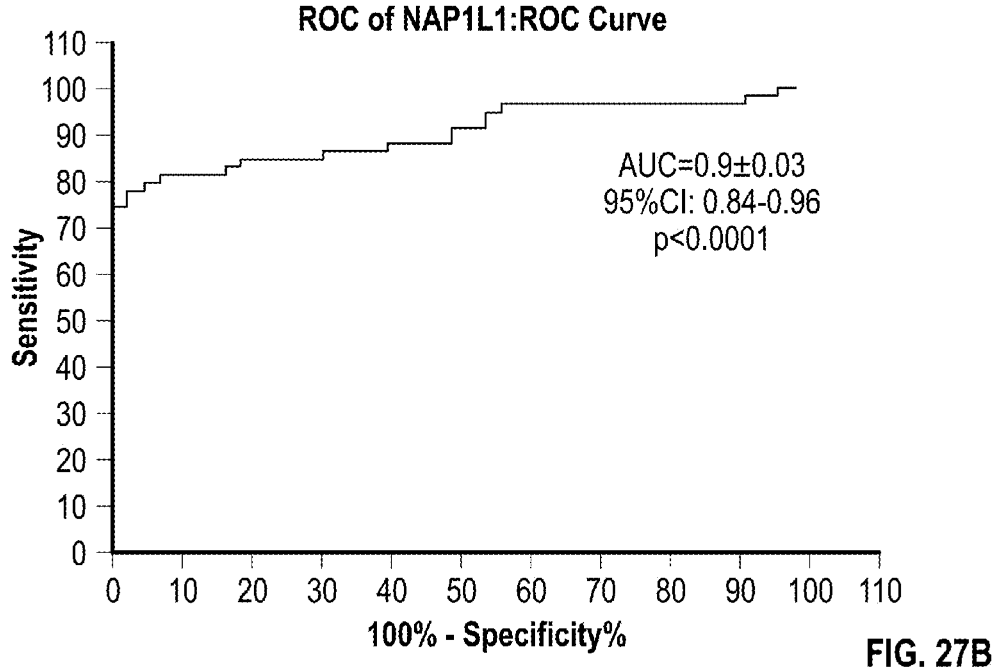
Figure 27C:
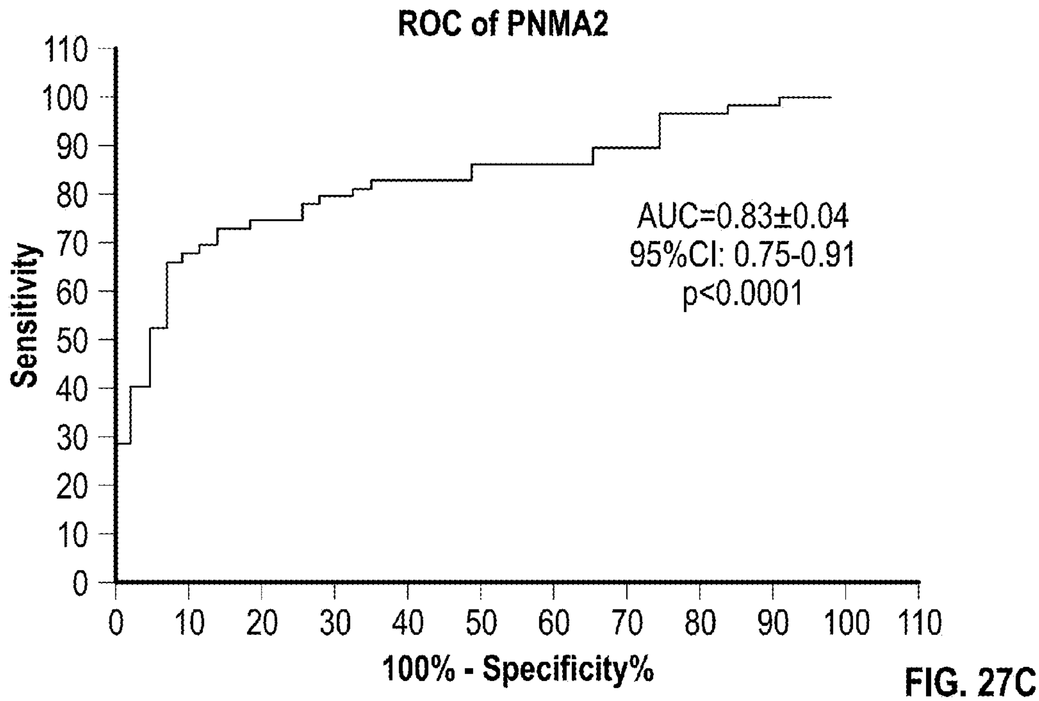
Figure 27D:
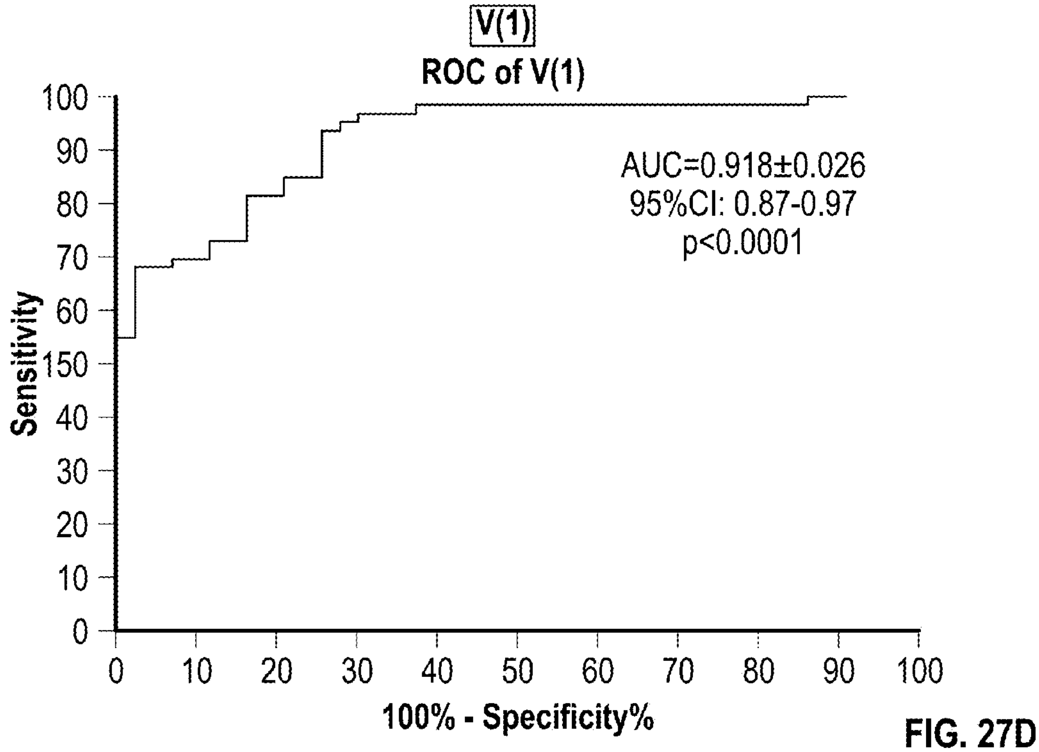
Figure 27F:
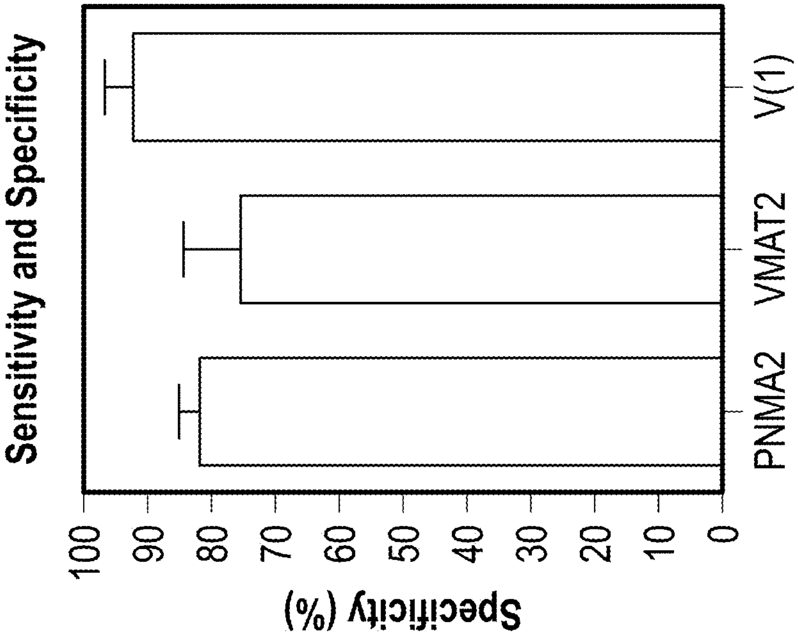
Figure 27E:
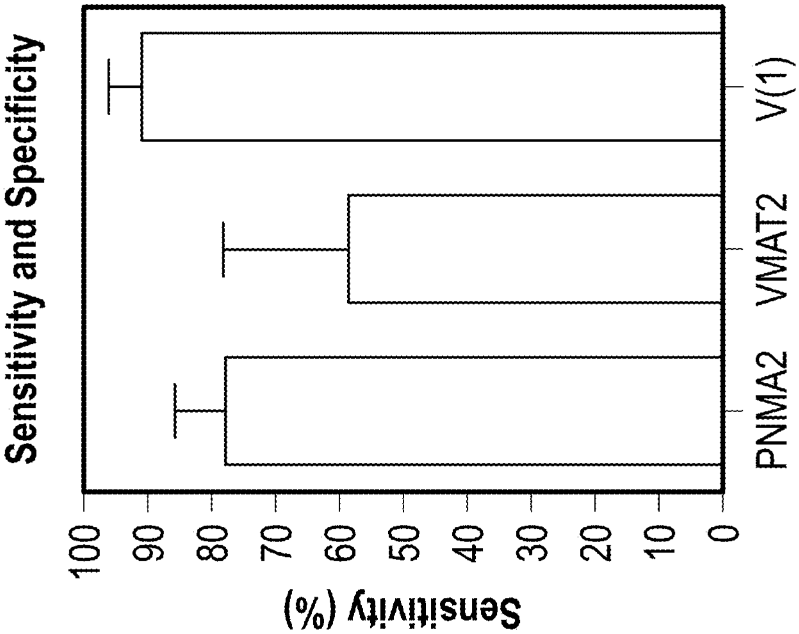

Expression of a thirteen GEP-NEN biomarker panel was detected by real-time PCR on RNA prepared directly from whole blood obtained from 12 patients. For comparison, PCR was performed in parallel on RNA purified from FACS-purified circulating blood GEP-NEN cells (as described above), and tumor mucosa from 12 patients from same study. The expression levels of the biomarker transcripts detected in whole blood were highly correlated with levels detected in purified circulating GEP-NEN cells ($R^2$=0.6, p<0.0001) (FIG. 26A) and in tumor tissue ($R^2$=0.81, p<0.0001) (FIG. 26B).

These results confirm that circulating GEP-NEN cells (CNCs) exist in blood and can be detected by PCR using RNA prepared from whole blood and other blood samples for the detection, staging, prognosis and prediction with the methods and compositions provided herein.

Example 5D: Detection of GEP-NEN Biomarker Expression and Statistical Analysis Using Whole Blood Samples Expression levels of individual biomarker transcripts (VMAT2, NAP1L1, and PNMA2), as well as the summed expression levels of a panel of thirteen (13) GEP-NEN biomarkers (APLP2, ARAF1, BRAF, CD59, CTGF, FZD7, Ki67, KRAS, NAP1L1, PNMA2, RAF1, TPH1, VMAT2) were determined by real-time PCR as described above, on whole blood samples from 3 groups of human samples obtained from: 1) a training group from Yale New Haven Hospital, including 55 GEP-NEN patients (all comers, including patients with high level disease as well as those considered disease-free) and 47 control patients, 2) an independent test group from Berlin (n=144 (n=120 patients, n=24 controls)) and 3) an independent test group from Uppsala (n=34 (n=20 patients; n=14 controls))), respectively. The primer pair sequences and other information about primers are listed in Tables 1A and 1B.

To facilitate representation, detected expression levels of the 13 biomarker transcripts were vectorally summed (>+1=Σ over-expressed genes; >−1=Σ genes whose expression is decreased) and plotted.

An ROC curve strategy was employed for identification of GEP-NENs, in group (1) samples. Results demonstrated areas under the curve (AUCs) for the three individual biomarker transcripts ranging from 0.66 to 0.90 (0.92 for summed transcripts (V1: p<0.0001)) in GEP-NEN patient samples (FIG. 27, showing ROCs for each). The sensitivity, specificity, positive predictive value and negative predictive value for determining GEP-NEN disease using the summed transcript expression levels were 96.1%; 90.2%; 83.3%, and 97.9%, respectively. Use of predicted cutoffs was tested in the two independent test sets (2) and (3). The sensitivities and specificities for V1 ranged from 95-97% and 81-87%. It was also observed that gender was not associated with transcript expression (Mann Whitney score=0.11, p=0.19) levels detected in blood. Storage at −80° C. had no significant effect on the transcript expression levels of the detected 13 biomarkers (R=0.987-0.996, p<0.0001).

Figure 28A:
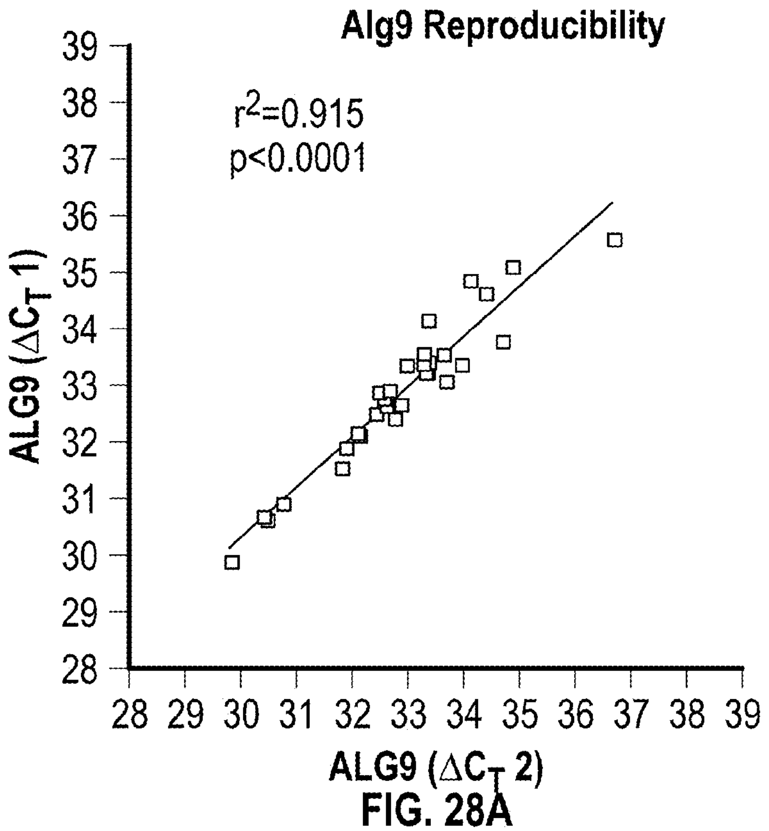
FIGS. 28A-D: Reproducibility studies of target genes in blood. The reproducibility of the marker gene ALG9 and the target gene, FZD7, demonstrated high correlation: $R^2$: 0.92-0.97, $p<0.0001$ (28A-B). Intra- and inter-assay reproducibilities were high for normalized FDZ7 (28C-D, CV=2.28-3.95%); no differences were noted between normalized FZD7 in controls and tumor samples (28D), demonstrating the significant reproducibility of blood measurements.
Figure 28B:
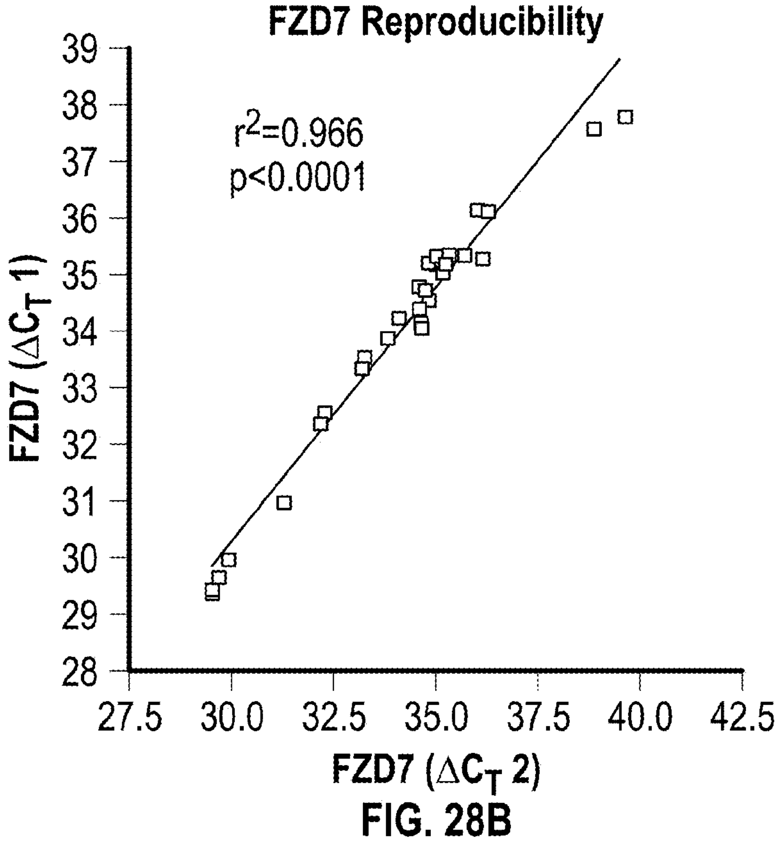
Figure 28C:
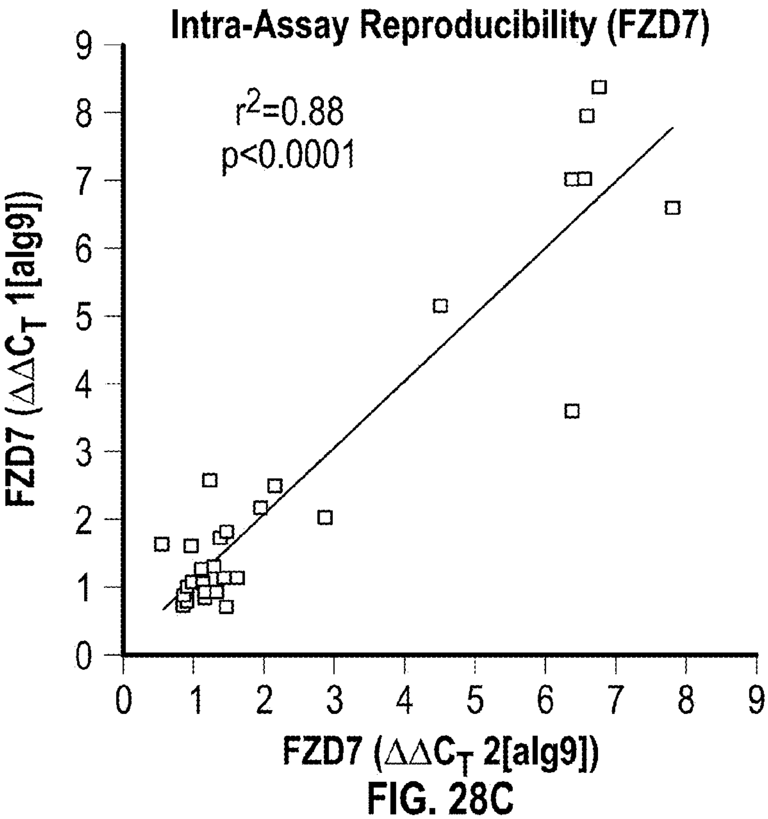
Figure 28D:
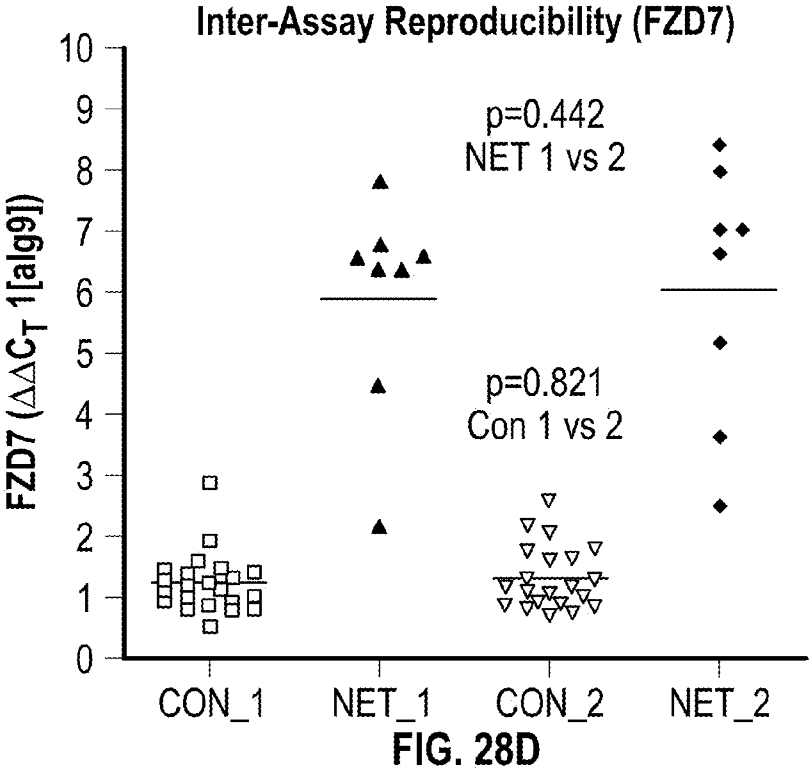

Housekeeping and summed GEP-NEN biomarker transcript expression levels were detected in 29 control and patient samples (Yale and Berlin), assayed on separate days in two separate PCR runs. Expression of the ALG9 housekeeping gene and the FZD7 GEP-NEN marker were each highly correlated when assayed on separate days: $R^2$: 0.92-0.97, p<0.0001 in two separate runs (FIG. 28A-B) and no significant differences were noted between normalized FZD7 in controls and tumor samples on separate days (FIG. 28C-D). Intra- and inter-assay reproducibility was high for FDZ7 (C.V.=2.28-3.95%) demonstrating that blood measurements of target genes are highly reproducible. The results demonstrate intra- and inter-assay reproducibility for housekeeping and GEP-NEN biomarker detection using real-time PCR on RNA obtained from whole blood.

These data demonstrated that detection of GEP-NEN biomarker transcript expression levels in whole blood can be used to identify circulating GEP-NEN cells (CNCs), that the detected expression levels in whole blood correlate well with tissue expression levels and can identify GEP-NEN patients with high sensitivity and specificity, and with high reproducibility.

Example 5E: Detection of Lesions and Treatment Response

To evaluate the utility of the 51 marker gene panel both as a technique as a circulating GEP-NEN signature to detect these lesions as well as treatment response, a test set of 130 samples (controls: n=67, GEP-NENs: n=63 [untreated disease, n=28, treated, n=35]) was established. PCR was performed on all markers, and values normalized to ALG9 ($\Delta\Delta C_T$), using the control group as the population control (calibrator sample). The work-flow for identifying the utility of the marker panel included normalization (ANOVA identified 39 of 51 genes to be differentially expressed in all 3 sets) and the support-machine bases mathematical assessments of gene expression.

Figure 29:
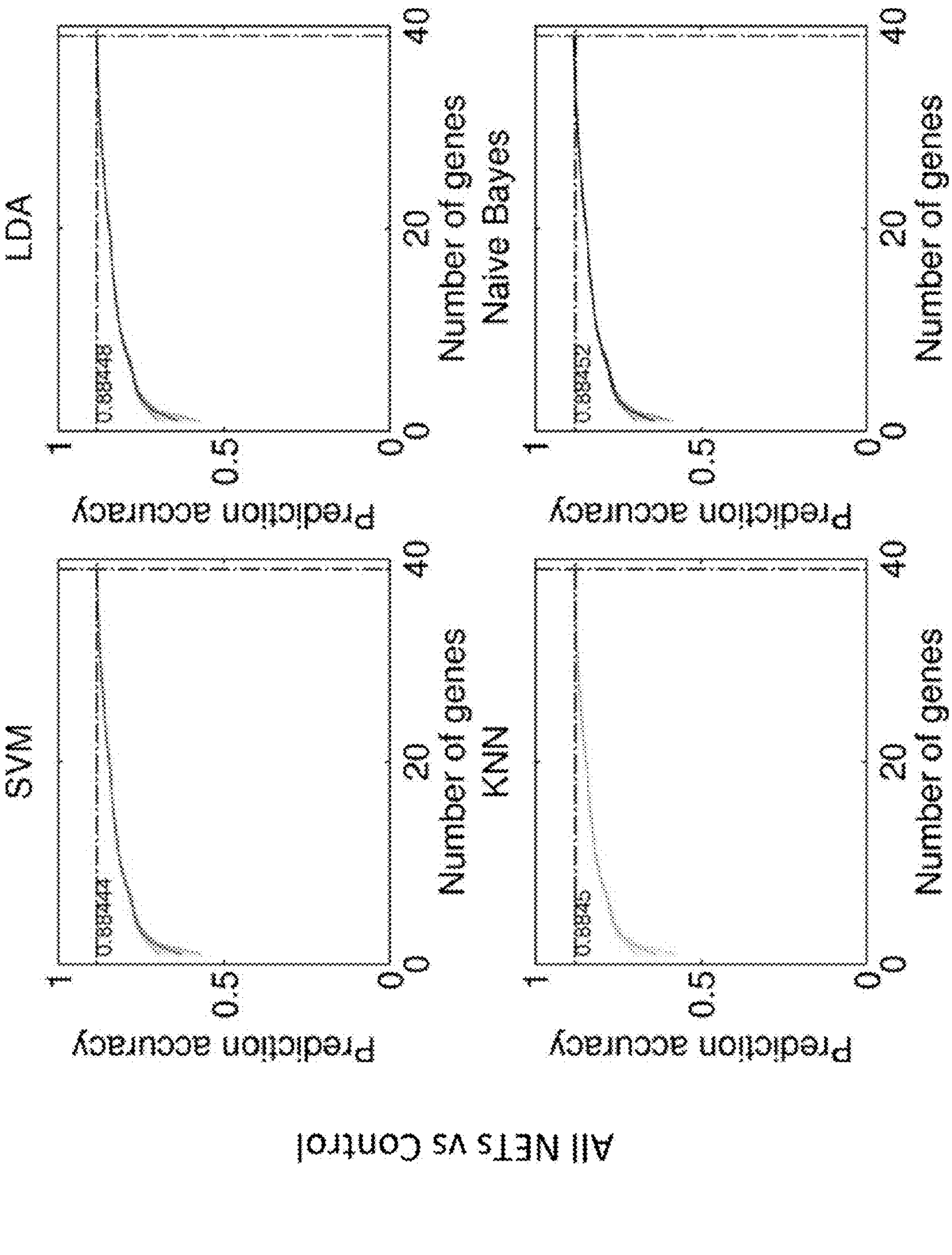
FIG. 29: Performance of the marker gene panel in differentiating Normal tissue from GEP-NENs (Treated and Untreated). All four mathematical algorithms exhibited similar performance metrics of ~88%.

Using the four algorithms, an average 88% correct call rate was determined (FIG. 29), while the performance metrics are included in Table 10. The data of the molecular test for differentiating normal samples from GEP-NENs (both treated and untreated) are as follows: overall sensitivity (94.0%), specificity (85.7%), positive predictive value (PPV) (87.5%) and negative predictive value (NPV) (93.1%).

TABLE 10

Performance evaluation of distinguishing normal samples from GEP-NENs.

| | Normal (True) | GEP-NENs (True) |
|---|---|---|
| Normal (Predicted) | 63 | 9 |
| GEP-NENs (Predicted) | 4 | 54 |

Using the same gene panel, it was determined that treated and un-treated GEP-NENs could be distinguished with the following performance metrics (Table 11): Sensitivity=85.7%, Specificity=85.7%, PPV=88.2% and NPV=82.8%.

TABLE 11

Performance evaluation of distinguishing Treated from Untreated GEP-NENs.

| | Treated GEP-NENs (True) | Untreated GEP-NENs (True) |
|---|---|---|
| Treated GEP-NENs (Predicted) | 30 | 4 |
| Untreated GEP-NENs (Predicted) | 5 | 24 |

For overall performance as a test to differentiate NENs from controls, the call rate was 94%, while the ability to identify treated samples was 85%.

These results indicate that pattern recognition protocols which enable analysis of expression of 51 candidate markers (as a group) have utility for differentiating between "normal" or "GEP-NENs". This confirmed that approaches e.g., SVM used in tumor tissue, are applicable to peripheral blood transcript analysis and identification of neuroendocrine tumor disease.

Example 5F: Evaluation of the Molecular Fingerprint as a Predictor of GEP-NENs The efficacy of this 51 marker gene panel as a potential test was examined in four independent datasets to establish whether it could correctly identify GEP-NENs versus controls. Four independent sets were constructed: Independent set 1 included 35 GEP-NENs and 36 controls; Independent set 2 included 33 GEP-NENs and 31 controls; Independent set 3 included 47 GEP-NENs and 24 controls; and Independent set 4 included 89 GEP-NENs and no controls.

The four algorithms were assessed: SVM, LDA, KNN and Bayes for utility in determining whether a blood sample was a GEP-NEN or a control in each of the independent sets. Tabulated results identified that overall correct call rates (identifying both GEP-NENs and controls correctly) ranged from 56-68% in independent set 1, 53-78% in set 2, 82-92% in set 3 and 48-74% in set 4 (Table 12). The average rates over all sets were 67-69% for SVM, LDA and Bayes; KNN scored higher: 73%.

TABLE 12

Overall call rates (percentage) for each of the algorithms in each of the independent sets

| | SVM | LDA | KNN | Bayes |
|---|---|---|---|---|
| Set 1 | 56 | 57 | 68 | 59 |
| Set 2 | 78 | 77 | 70 | 53 |

TABLE 12-continued

Overall call rates (percentage) for each of the algorithms in each of the independent sets

| | SVM | LDA | KNN | Bayes |
|---|---|---|---|---|
| Set 3 | 90 | 92 | 89 | 82 |
| Set 4 | 48 | 48 | 65 | 74 |
| AVE (%) | 68 | 69 | 73 | 67 |

Further analysis of the calls identified whether the correct call rates corresponded to identifying controls or tumor samples (Table 13). Most consistent correct calls for controls were the SVM (90% overall) and LDA (91%) algorithms. The highest correct call rates for GEP-NENs were identified with the Bayes algorithm (85%).

TABLE 13

Call rates (percentage) for each of the groups, control or GEP-NENs, in each of the independent sets

| | SVM | | LDA | | KNN | | Bayes | |
|---|---|---|---|---|---|---|---|---|
| | CON | NEN | CON | NEN | CON | NEN | CON | NEN |
| Set 1 | 97 | 14 | 97 | 17 | 97 | 37 | 33 | 86 |
| Set 2 | 73 | 70 | 77 | 76 | 58 | 82 | 3 | 100 |
| Set 3 | 100 | 85 | 100 | 87 | 100 | 83 | 88 | 79 |
| Set 4 | NA | 48 | NA | 48 | NA | 65 | NA | 74 |
| AVE (%) | 90 | 54 | 91 | 57 | 85 | 67 | 41 | 85 |

NA = not applicable (no controls included in this set)

Sensitivities, specificities, positive predictive values and negative predictive values calculated for each of the algorithms in the 3 independent sets are included in Table 14.

TABLE 14

Performance metrics for each of the algorithms in each of the independent sets

| | SVM | | | | LDA | | | | KNN | | | | Bayes | | | |
|---|---|---|---|---|---|---|---|---|---|---|---|---|---|---|---|---|
| | A | B | C | D | A | B | C | D | A | B | C | D | A | B | C | D |
| Set 1 | 14 | 97 | 83 | 54 | 17 | 97 | 86 | 54 | 37 | 97 | 93 | 61 | 86 | 33 | 55 | 70 |
| Set 2 | 70 | 87 | 85 | 73 | 76 | 77 | 78 | 75 | 81 | 58 | 68 | 75 | 100 | 3 | 52 | 100 |
| Set 3 | 85 | 100 | 100 | 77 | 87 | 100 | 100 | 80 | 83 | 100 | 100 | 75 | 79 | 88 | 93 | 68 |

A = sensitivity,
B = specificity,
C = positive predictive value,
D = negative predictive value. Set 4 had no controls.

The Bayes algorithm performed best for detecting GEP-NENs (sensitivity=83%), while the SVM algorithm performed best for determining controls (specificity=96%). The weakness of Bayes is a high false-positive; the weakness of SVM is that it does not perform adequately in sample sets that exhibit a majority of well-treated (complete remission/stable disease) samples.

For overall performance as a test to differentiate NENs from controls, algorithms SVM, LDA and KNN had positive predictive values of ~90% and negative predictive values of 70%.

Example 5G: 51 Marker Gene Panel for GEP-NEN Identification

Figure 30:
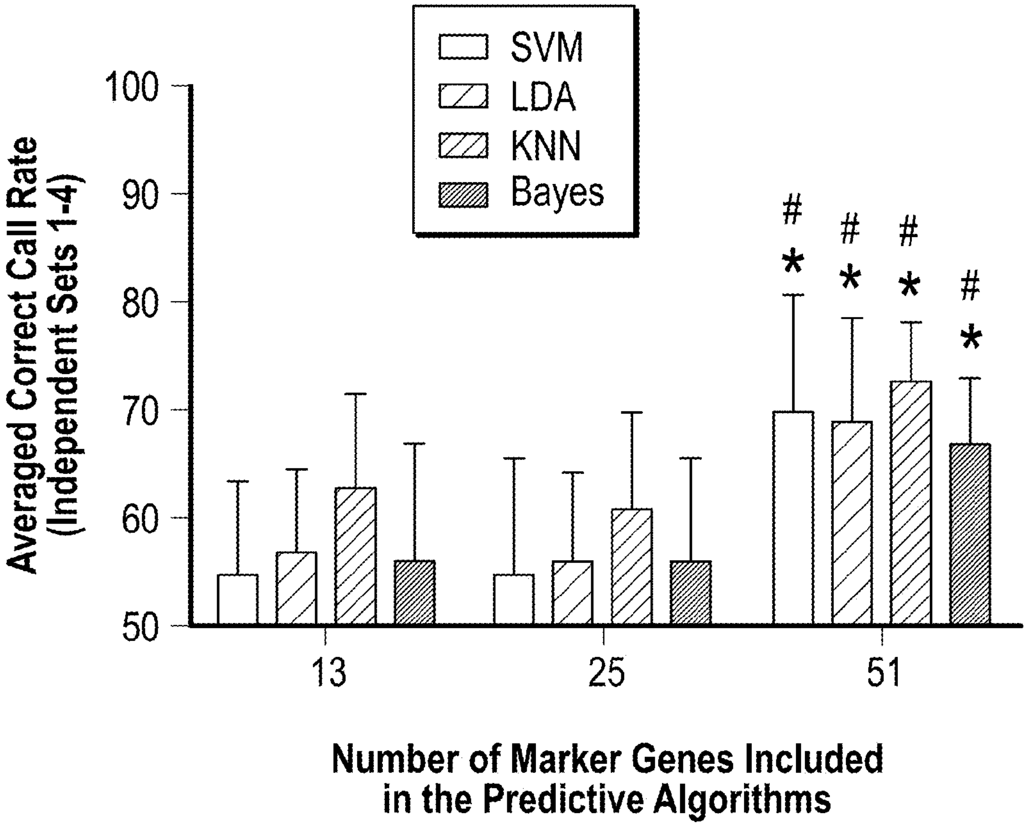
FIG. 30: Correct call rates for each of the mathematical algorithms (SVM, LDA, KNN and Bayes) in each of the four independent sets. The 51 marker panel had significantly more correct calls (20% better) than either the 25 or 13 panel subsets. Increasing the number of the marker genes increased the sensitivity of detecting GEP-NENs in blood. Mean±SEM. *$p<0.008$ vs. 13 and 25 panels (Yates value 6.8-14.7; $^{\#}$Fishers 2-tailed exact probability test <0.005).

To confirm that the 51 marker gene panel was effective, correct call rates for the panel were compared in each of the independent sets (Table 12) and compared this with a 13 marker and 25 marker subsets. The 13 marker subset was limited to genes confirmed as predictive of GEP-NEN malignancy in tissue; the 25 marker panel included these genes as well as an additional 12 GEP-NEN specific genes identified in FIG. 20D. Examining correct calls in each of the 4 independent sets identified that the 51 marker panel performed significantly better than either the 13 or 25 marker panel (FIG. 30).

These results indicate that a number of pattern recognition protocols based on the 51 candidate marker genes can distinguish between control samples and GEP-NENs with high efficiency and sensitivity.

Example 5H: Detection of GEP-NEN-Biomarker Expression Levels in Whole Blood, for Evaluation of Therapeutic Responsiveness and Prediction of Metastases (Comparison to CgA)

Detection of summed GEP-NEN biomarker transcript expression levels (13-biomarker panel) in whole blood, before and following therapeutic intervention (resection and Octreotide LAR) was carried out, demonstrating the clinical utility of embodiments of the provided methods and systems. Moreover, comparison to detection of CgA expression alone demonstrated improved sensitivity of the provided methods in GEP-NEN detection, risk determination, and monitoring of therapeutic responses. CgA is an SI GEP-NEN marker present in 60-80% of GEP NETs, as described by Modlin I M et al., Chromogranin A-Biological Function and Clinical Utility in Neuro Endocrine Tumor Disease, *Ann Surg Oncol.* 2010 September; 17(9):2427-43. Epub 2010 Mar. 9.

Detection of GEP-NEN Biomarkers Following Surgical Intervention:

Nine patients underwent small bowel and hepatic met resection (resulting in an approximately 90% reduction in tumor volume). Expression levels of the 13 summed GEP-NEN biomarker transcripts (APLP2, ARAF1, BRAF, CD59, CTGF, FZD7, Ki67, KRAS, NAP1L1, PNMA2, RAF1, TPH1, VMAT2) were determined as described above using real-time PCR on samples prepared from whole blood samples, taken one day before surgery and then two weeks post-operatively.

Figure 31B:
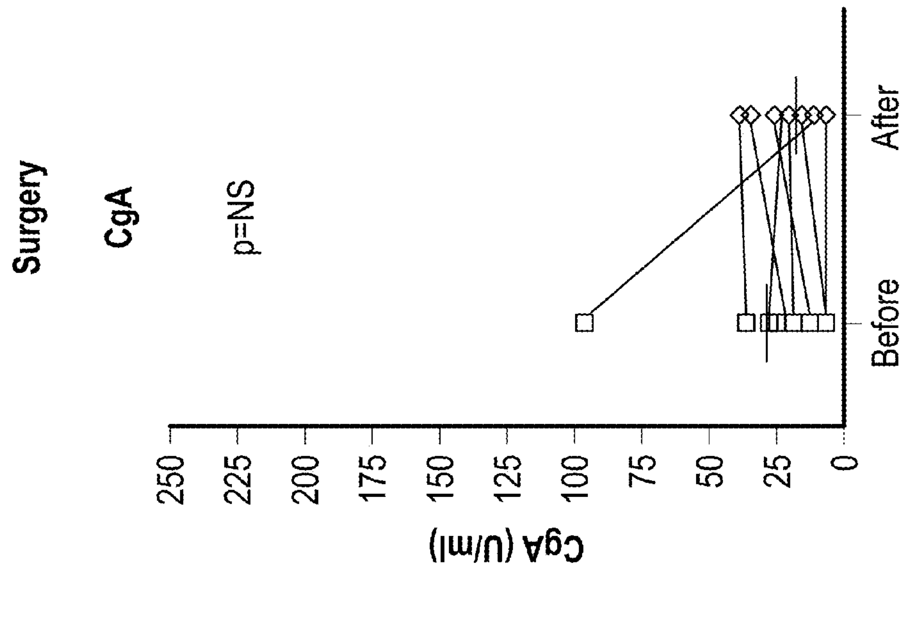
FIGS. 31A-B: Alterations in blood PCR marker levels and CgA during surgical resection. Tumor excision significantly reduced expression levels of a panel of biomarkers ("PCR") as described in Example 5H, when measured 2 weeks post-operation (31A). CgA levels were variable (31B). horizontal=mean. n=9 patients.
Figure 31A:
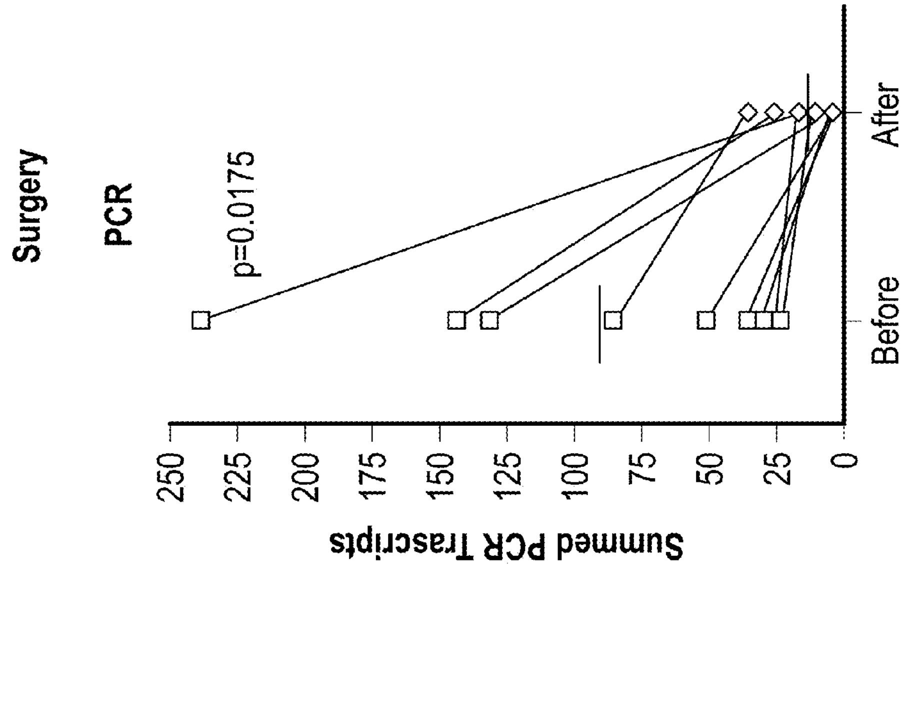

The results are shown in FIG. 31 (horizontal bars representing mean expression levels pre and post surgery). Two weeks following surgery, summed expression levels (as described above) of the GEP-NEN Biomarkers levels were significantly decreased (from a mean of 84 before surgery to a mean of 19 after surgery, greater than 75% reduction, with $p<0.02$) (FIG. 31A). As shown in FIG. 31B, detection of CgA expression levels alone did not show a significant decrease (20% reduction in mean expression).

These results demonstrate that biomarker expression levels detected with the provided methods and systems accurately reflect tumor removal and can be used to evaluate responsiveness and efficacy of surgical intervention.

Figure 32B:
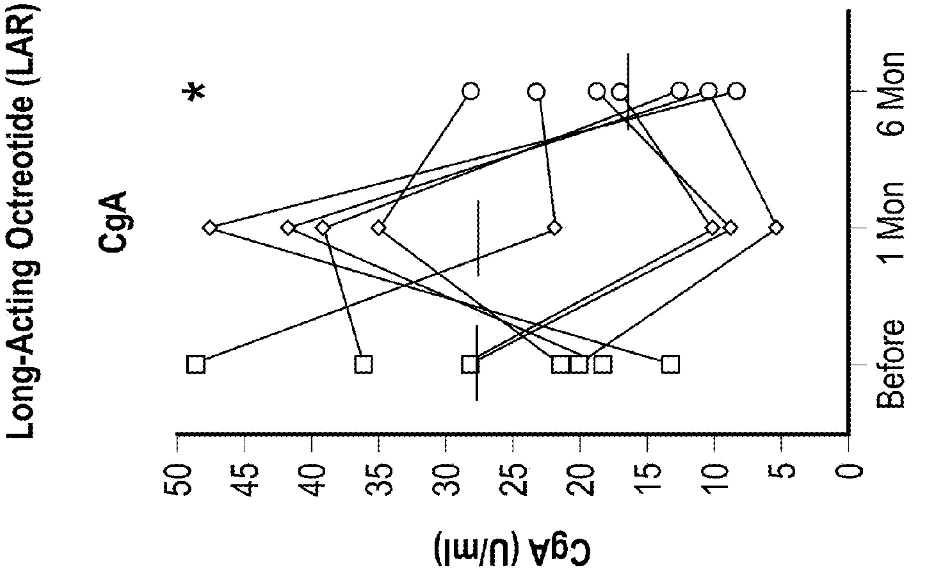
FIGS. 32A-B: Alterations in blood PCR marker levels and CgA during Octreotide LAR therapy. Octreotide LAR significantly reduced blood expression levels of the panel of biomarkers ("PCR") as described in Example 5H; expression remained suppressed over the time course (32A). CgA levels were variable before being reduced by 6 months (32B). *$p<0.02$ versus BEFORE. #p=0.06 vs. 1 MONTH. Horizontal line=mean. MON=month. n=8 patients.

Detection of GEP-NEN-Biomarkers Following Somatostatin Analogue (Sandostatin LAR® (Octreotide Acetate Injection)) Drug Therapy Summed expression levels (as described above) for the thirteen biomarkers also were detected in eight patient samples by real-time PCR, before, one month after, and two months after treatment with Sandostatin LAR® (Octreotide acetate injection), a somatostatin analog. The results are shown in FIG. 32.

Figure 32A:
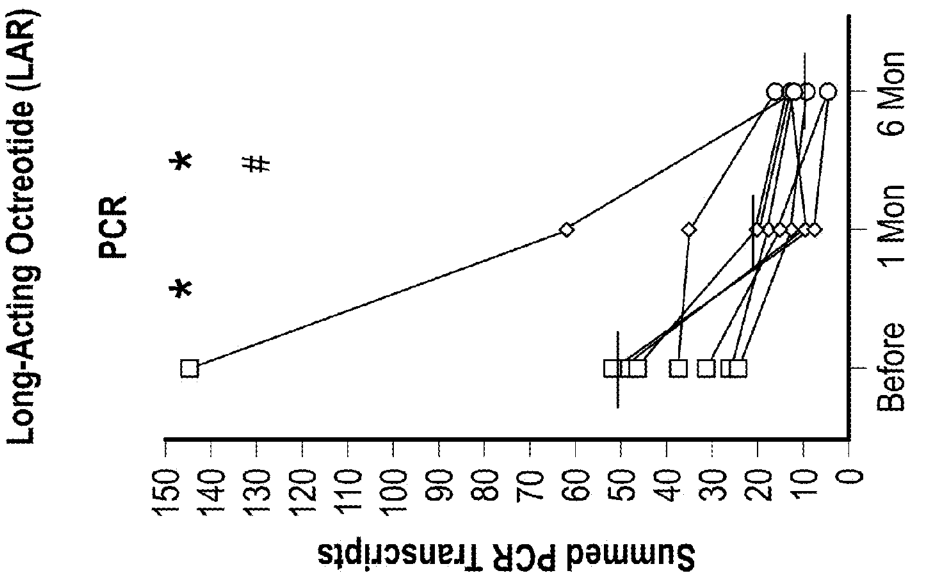

Results showed a significant (p=0.017) reduction in expression of the summed biomarker transcripts one month after continuous treatment. After six months of continued treatment, transcript levels were reduced by an additional 50% (p=0.06 vs. 1 month) and were in the normal range (FIG. 32A). In contrast, no significant change in CgA expression levels, alone, was observed at one month post-LAR® treatment (FIG. 32B); in this study, detected levels of CgA expression alone decreased only at the 6 month time-point. These results show that as for surgical intervention, the provided systems and methods for biomarker detection can be used to monitor LAR® treatment, providing a higher sensitivity as compared to detection of a single GEP-NEN biomarker alone, e.g. CgA.

Early Detection of Low Volume Micrometastasis and Evaluation of Treatment Efficacy in Individual Patients The summed 13 GEP-NEN biomarker expression levels (as described above) were monitored to evaluate treatment efficacy and predict risk in two individual patients, treated with CryoAblation and hepatic met resection, respectively.

Figure 33:
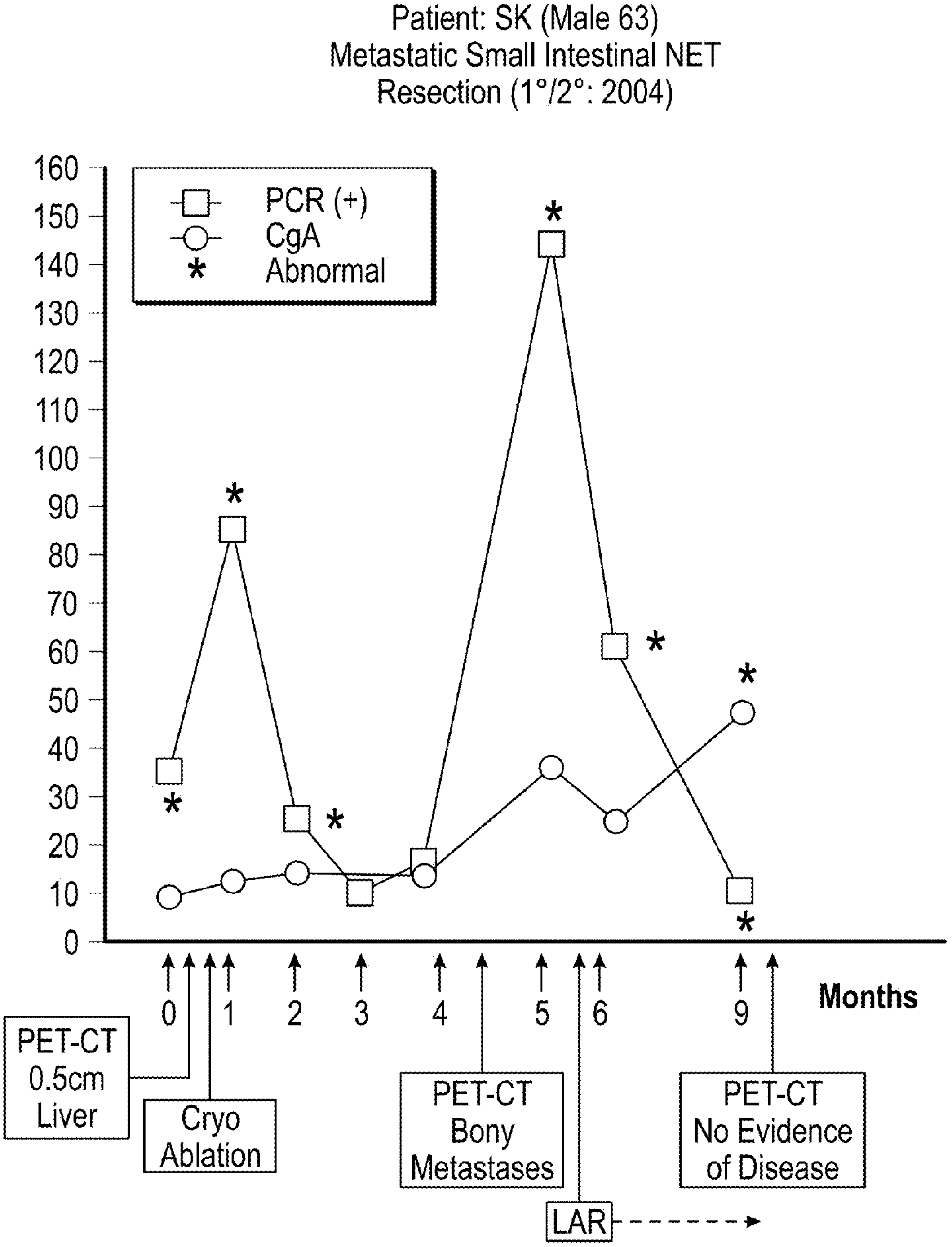
FIG. 33: Alterations in blood PCR marker levels and CgA after CryoAblation. Expression levels of CgA and a 13-biomarker panel (PCR+) in patient SK before and at various times following cryoablation, as described in Example 5H, with changes in biomarker expression correlating with the appearance of micrometastases.

Patient SK, a male of 63 yrs, with metastatic small intestinal (SI) GEP-NEN was evaluated as normal by stereotactic radiosurgery (SRS)/computed tomography (CT), and was considered disease free. Summed expression of transcripts in whole blood was evaluated using real-time PCR as described above. The results, presented in FIG. 33, showed normal expression levels of CgA. In contrast, summed expression levels of the panel of 13 GEP-NEN biomarkers (APLP2, ARAF1, BRAF, CD59, CTGF, FZD7, Ki67, KRAS, NAP1L1, PNMA2, RAF1, TPH1, VMAT2) ("PCR(+)") were elevated (FIG. 33). Based on this information, the patient underwent $^{11}$CPET-CT in Sweden, demonstrating he had a liver metastasis of approximately 0.5 cm. Subsequently, the patient underwent cryoablation, which liberates GEP-NEN tissue for entry into the blood, inducing symptoms, as described by Mazzaglia P J, et al., "Laparoscopic radiofrequency ablation of neuroendocrine liver metastases: a 10-year experience evaluating predictors of survival," *Surgery* 2007; 142(1):10-9.

Expression levels were monitored monthly for six months following cryoablation, by real-time PCR on RNA prepared from whole blood. The results demonstrated elevated expression levels of the biomarker panel, but not of CgA alone, after cryoablation. Between four and five months following cryoablation, bone micrometastases were identified; PCR demonstrated the appearance of these micrometastases correlated with elevated GEP-NEN biomarker panel transcript expression levels; CgA expression alone was detected as normal. Following LAR® therapy (which blocks secretion and proliferation of GEP-NEN cells), biomarker panel expression levels in the blood were determined to normalize (real-time PCR).

This study demonstrates that detection of GEP-NEN biomarker panels by the provided methods can accurately reflect acute GEP-NEN-associated events, demonstrating the improved sensitivity of the provided methods (e.g., as compared to detection of an available biomarker, CgA alone) and systems for detecting GEP-NEN biomarkers in prognostic and predictive analysis and evaluation of treatment efficacy and detection of relapse or early-stage disease, particularly when disease is limited to rare micrometastases.

Figure 34:
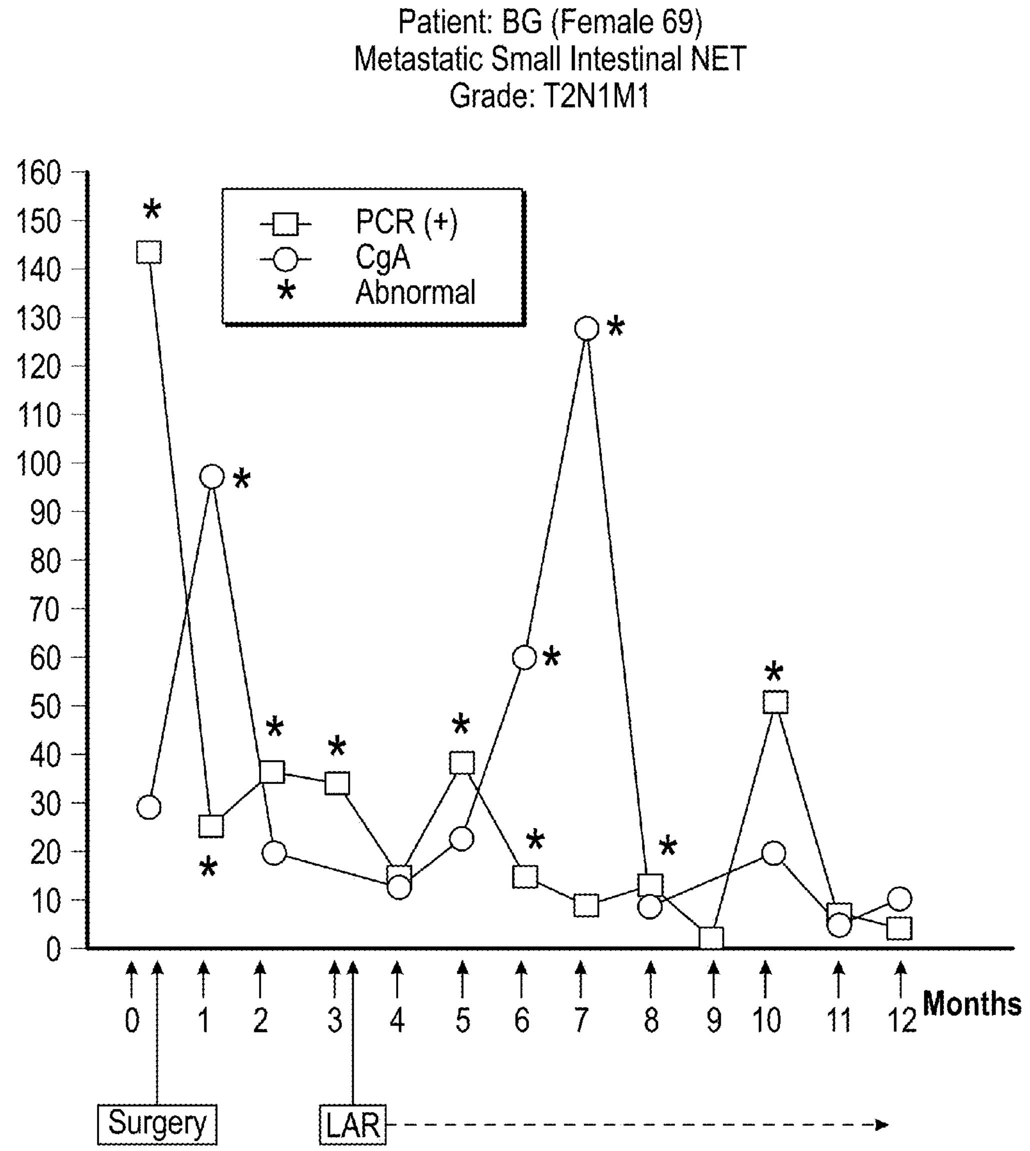
FIG. 34: Alterations in blood PCR marker levels and CgA during surgical resection and Octreotide LAR therapy. Expression levels of CgA and an NET biomarker panel levels in patient BG, as described in Example 5H, measured out to 2 weeks post-operation and following Octreotide LAR.

Patient BG, a 69-year old female with metastatic small intestinal GEP-NEN, Grade T2N1M1, underwent surgical small bowel and hepatic met resection, followed by 9 months of treatment with Octreotide LAR®. Expression levels of CgA and the 13-GEP-NEN biomarkers ("PCR(+)") were monitored by real-time PCR on whole blood samples as described above, prior to surgery, two weeks post-op, and monthly for twelve months. All symptoms resolved after twelve months of treatment. As shown in FIG. 34, detection of CgA expression levels alone revealed dramatic fluctuations, not correlating with treatment or symptom reduction. Biomarker panel expression levels ("PCR(+)"), by contrast, were detected as significantly reduced following surgical tumor excision, measured two weeks post-op, and significantly reduced following LAR® treatment, remaining reduced out to twelve months (at which point all symptoms remained resolved).

This study demonstrates that detection of GEP-NEN biomarker panels by the provided methods can sensitively reflect disease severity and responsiveness to treatment, providing an improvement over available biomarker detection methods. The provided methods and systems are useful for monitoring treatment responsiveness and relapse, and can detect both the presence (FIG. 33) and the absence (FIG. 34) of GEP-NEN disease with high fidelity. These results demonstrate that detection of the provided biomarkers in blood provides added diagnostic and treatment value, for example, as surrogate markers for treatment efficacy to monitor the effects of surgery (removal of tumors) or targeted medical therapy (inhibition of tumor secretion/proliferation). See Arnold R, et al., "Placebo-controlled, double-blind, prospective, randomized study of the effect of octreotide LAR in the control of tumor growth in patients with metastatic neuroendocrine midgut tumors: A report from the PROMID study group," *ASCO* 2009*, Gastrointestinal Cancers Symposium, Abstract* #121. 2009.

Example 6: Evaluation of the Molecular Fingerprint as an Indicator of Treatment Efficacy The efficacy of this 51 marker gene panel as a potential test was examined in the four independent datasets to establish whether it could differentiate between treatment-responsive (those that were clinically categorized as in complete remission or as exhibiting stable disease) and untreated (treatment-naïve) or non-responsive (clinically categorized as "progressive") tumors. In addition, a 13 marker subset of the 51 marker gene panel was evaluated to determine if it could be used to provide additional information regarding response to therapy, specifically if it could provide more specific information in progressive, untreated disease compared to stable disease.

Independent set 1 included 35 GEP-NENs. Full clinical details were available for all patients; 33 of the samples were considered in complete remission or had stable disease. Sixty percent of samples were under treatment (predominantly LAR: 96%).

Independent set 2 included 32 GEP-NENs. Full clinical details were available for all; 28 of the samples were considered in complete remission or had stable disease. Eighty-four percent of samples were under treatment (LAR: ~40%, surgery ~25%).

Independent set 3 included 47 NENs. Full clinical details were available for all; 30 of the samples were considered in complete remission or had stable disease. Fifty-six percent of samples were under treatment (LAR: ~75%).

Independent set 4 included 89 GEP-NENs. Full clinical details were available for all patients; 71 of the samples were considered in complete remission or had stable disease. Forty-six percent of samples were under treatment (predominantly LAR: 85%).

The four algorithms were assessed: SVM, LDA, KNN and Bayes for utility in determining whether a blood sample was associated with a "treated" phenotype (clinically responsive/stable disease) or could identify untreated/progressive disease. Tumor samples that were called "normal" or "treated" were considered to exhibit a "treated" or clinically responsive ("responder") phenotype. Those considered "untreated" were classified as being non-responsive (or "non-responders"). The algorithms as a group ("voting" algorithm) were examined for utility and include correct call rates from best 3 of 4 algorithms.

Tabulated results indicate that overall correct call rates (identifying both appropriately treated and non-responsive samples) was 73-94% in independent set 1, 81-89% in set 2, 82-94% in set 3 and 72-94% in set 4 (Table 15). The average rates were 83-88% for each of the algorithms. A combination, best "3 of 4", resulted in similar (88%) correct call rate.

TABLE 15

Overall call rates (%) for each of the algorithms in each of the independent sets

| | SVM | LDA | KNN | Bayes | Best 3 of 4 |
|---|---|---|---|---|---|
| Set 1 | 89 | 89 | 94 | 94 | 94 |
| Set 2 | 88 | 88 | 88 | 88 | 88 |
| Set 3 | 83 | 85 | 89 | 72 | 88 |
| Set 4 | 73 | 81 | 82 | 82 | 82 |
| AVE (%) | 83 | 86 | 88 | 84 | 88 |

Further analysis of the calls identified whether the correct call rates corresponded to identifying clinically responsive patients or samples from those individuals that were not responding to treatment (Table 16).

TABLE 16

Call rates (%) for each of the groups, clinically responsive or non-responders, in each of the independent sets

| | SVM | | LDA | | KNN | | Bayes | |
|---|---|---|---|---|---|---|---|---|
| | RESP | NON | RESP | NON | RESP | NON | RESP | NON |
| Set 1 | 94 | 0* | 94 | 0* | 100 | 0* | 100 | 0* |
| Set 2 | 100 | 0* | 100 | 0* | 100 | 0* | 100 | 0* |
| Set 3 | 91 | 73 | 94 | 80 | 97 | 73 | 75 | 67 |
| Set 4 | 83 | 83 | 82 | 77 | 90 | 50 | 96 | 39 |
| AVE (%) | 92 | 78 | 90 | 79 | 97 | 62 | 93 | 53 |

*= excluded from analysis as only two and four patients were classified as "non-responders" in each of these two sets.

The most consistent correct calls for "responders" were identified with the KNN algorithm (~97%). The highest correct call rates for "non-responders" were the SVM and LDA algorithms (~80%).

Sensitivities, specificities, positive predictive values and negative predictive values calculated for each of the algorithms in the 3 independent sets are included in Table 17.

TABLE 17

Performance metrics for each of the algorithms in each of the independent sets

| | SVM | | | | LDA | | | | KNN | | | | Bayes | | | |
|---|---|---|---|---|---|---|---|---|---|---|---|---|---|---|---|---|
| | A | B | C | D | A | B | C | D | A | B | C | D | A | B | C | D |
| Set 1 | 97 | 0 | 97 | 0 | 97 | 0 | 97 | 0 | 100 | 0 | 100 | 0 | 100 | 0 | 100 | 0 |
| Set 2 | 88 | * | 100 | 0 | 88 | * | 100 | 0 | 88 | * | 100 | 0 | 88 | * | 100 | 0 |
| Set 3 | 100 | 62 | 86 | 100 | 96 | 86 | 94 | 92 | 97 | 85 | 94 | 92 | 89 | 55 | 76 | 77 |
| Set 4 | 95 | 56 | 83 | 83 | 94 | 52 | 82 | 77 | 88 | 56 | 90 | 50 | 85 | 88 | 98 | 39 |
| AVE | 95 | 39 | 92 | 46 | 94 | 46 | 93 | 42 | 93 | 47 | 96 | 36 | 90 | 48 | 94 | 29 |

SENS = sensitivity,
SPEC = specificity,
PPV = positive predictive value,
NPV = negative predictive value,
* no value (cannot be calculated)

The SVM, LDA and KNN algorithms performed best for detecting patients that were considered to be either in complete remission or exhibiting stable disease (sensitivity=93-95%). The SVM algorithm was also the most sensitive algorithm for detecting individuals with untreated or progressive disease (80%). The combination, best "3 of 4", resulted in an average 99% correct call rate for determining remission/disease stability and 75% for detecting untreated or progressive disease.

The best algorithms to differentiate treatment-responsive samples from those classified as non-responders were LDA and KNN with PPVs of ~98% and NPVs of ~92%.

Thereafter, the association between clinical description and PCR-based scores was examined. To delineate individual groups, the following descriptors were used:

"Complete remission"=all investigations negative;

"Stable disease after surgery"=abnormal investigations but no change in serial evaluation; and "Stable disease after surgery+LAR"=abnormal investigations but no change in serial evaluation.

Figure 35:
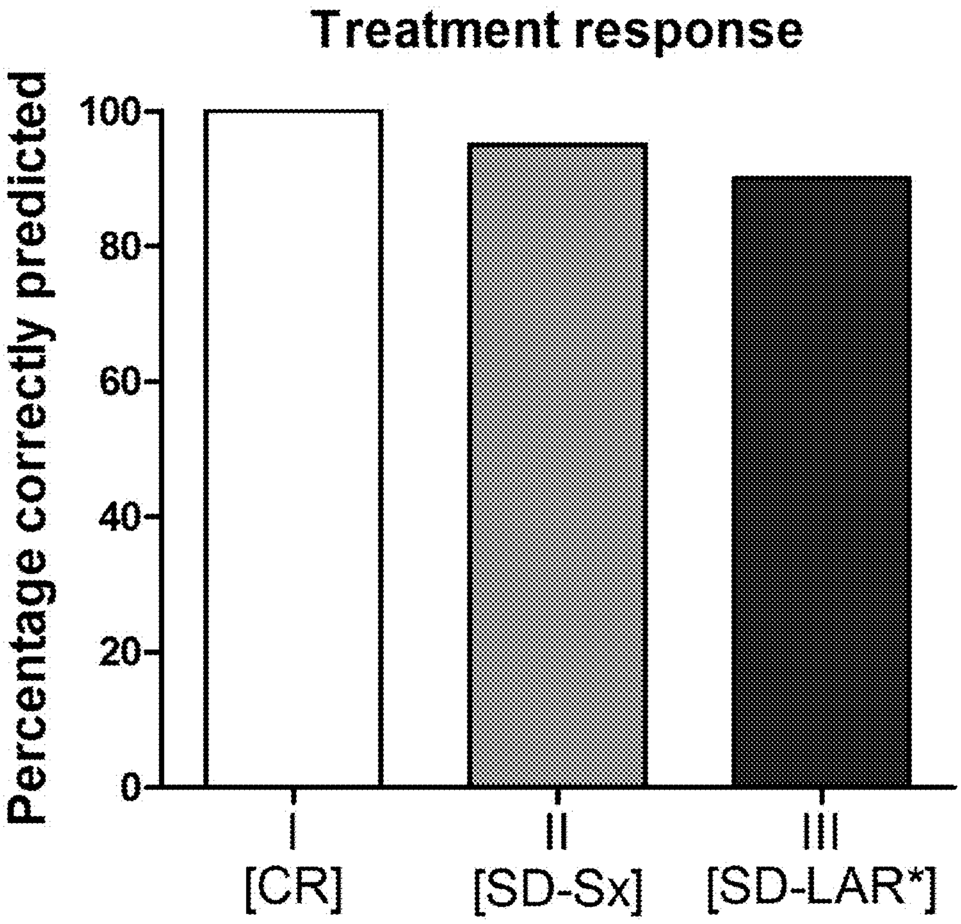
FIG. 35: Overall percentage correct calls for patients in complete remission (Group I: complete responders [CR], n=12), considered clinically as exhibiting stable disease (SD) following surgery (n=42, Group II—SD-Sx) or after treatment with long-acting somatostatin analogs (LAR: n=78, Group III—SD-LAR). *This includes pasireotide: n=1 and everolimus: n=4). The PCR test exhibited between 90-100% correct call rates for treated samples.

Analysis by clinical criteria (examination, biochemistry, scanning) of all treated samples in the 4 independent sets as a group identified:

1) Patients considered in complete remission (i.e. following surgery for removal of an appendiceal tumor (n=3) or a hemicolectomy for a <1.5 cm ileo-cecal NEN with no lymph node metastases (n=8) or <2 lymph node metastases (n=2) were correctly identified in 100% of cases by the algorithms (FIG. 35). All 13 samples were called "normal" by the algorithm.

2) Patients considered as stable disease (following surgery for removal of tumor (hemicolectomy: n=24, gastrectomy: n=1, appendectomy: n=3, hemicolectomy and liver resection: n=7, ileal/colonic resection: n=3, hemicolectomy, liver resection and lymph node dissection: n=2, embolization: n=2) were correctly called (called tumor "treated" by the mathematical algorithms) in 95% of cases (40/42) (FIG. 35).

3) Patients considered as stable disease following drug therapy (long-acting somatostatin analog (SI-NENs=72, PNENs=13, rectal NENs=2, gastric NENs=2), pasireotide (SI-NEN=1) or RAD001 (SI-NEN=4) were correctly called in 90% of cases (70/78) (FIG. 35).

Example 7: Use of a 13 Marker Panel Gene Panel Subset to Evaluate Disease Responses A subset of genes that were highly correlated with untreated, progressive disease was evaluated to determine if they could be used to further define patient groups and be used to provide additional information regarding response to therapy, particularly in patients undergoing treatment but considered to be "progressive".

Figure 36:
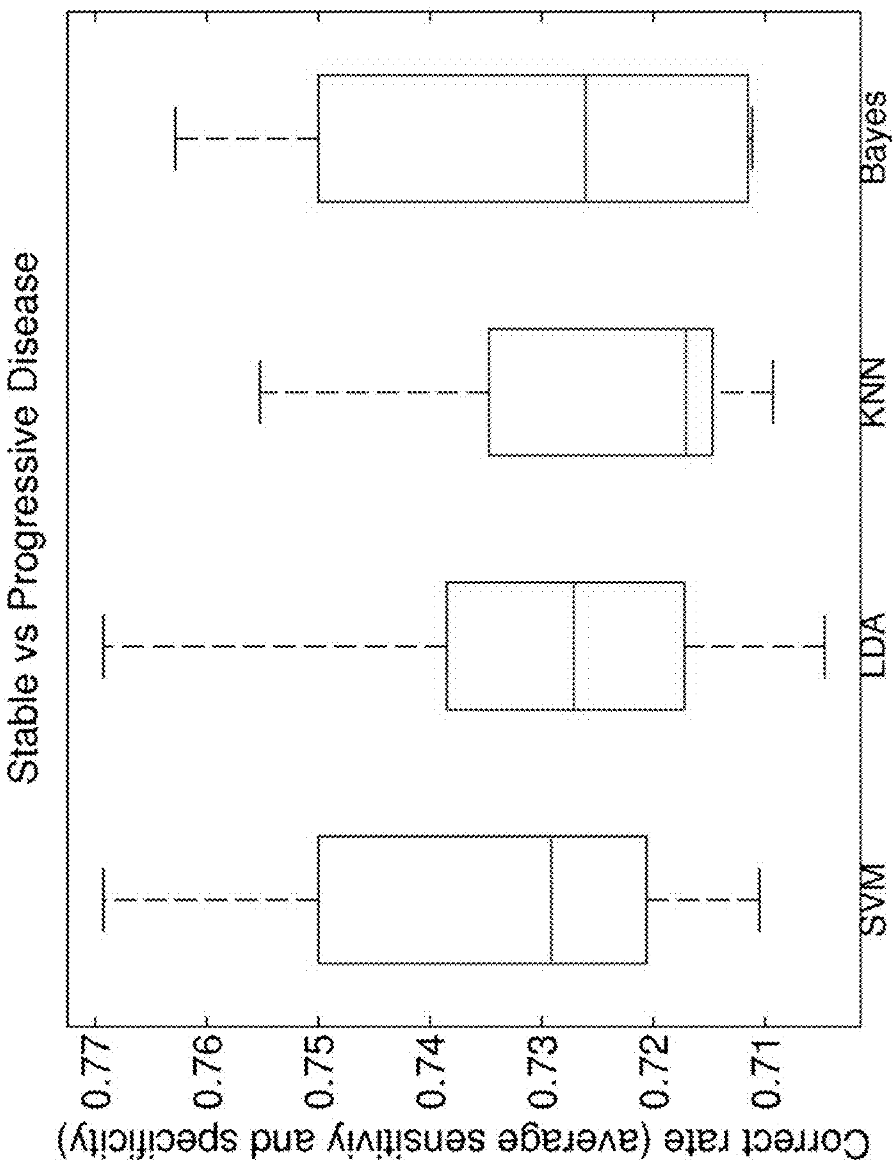
FIG. 36: Mathematical analyses including SVM, LDA, KNN and Bayes demonstrated that the 13 marker panel could differentiate between stable and progressive disease with sensitivities of ~73%.

An analysis of clinical samples in the test set identified 13 genes selectively over-expressed in the untreated, progressive group compared to those considered to exhibit stable disease. The genes identified were: AKAP8L, BRAF, CD59, COMMD9, Ki67, MORF4L2, OAZ2, RAF1, SST1, SST3, TECPR2, ZFHX3 and ZXDC. Inclusion of these genes in an algorithm resulted in correct call rates to differentiate stable from progressive disease in ~73% of cases in the test set (FIG. 36).

An analysis of this gene panel in independent sets 1-4 (as a group; progressive disease—irrespective of treatment: n=26 [50% of patients on treatment, 50% treatment stopped because considered untreatable]; stable disease: n=143) identified that the correct call rate for samples from patients considered to exhibit "progressive" disease was 65% (KNN). The sensitivities, specificities, PPV and NPV for the four different algorithms in this group were 34-65%, 96-100%, 64-100%, and 89-94% respectively. The best algorithm to detect "progressive" disease was KNN; the best algorithm for detecting "stable" disease was SVM. This indicates that a 13 marker panel subset is useful as an adjunct to the 51 marker panel particularly for identifying GEP-NENs that are not responding to therapy and are considered clinically "progressive".

These approaches demonstrate that treatment responsiveness can be accurately defined by the 51 marker panel in 90-100%. Samples that are considered clinically progressive and therefore not responsive to therapy (e.g., LAR or everolimus) can be identified in 65-80%.

Example 8: Comparison of the 51-Marker Gene Panel with Plasma Chromogranin a Levels for Disease Prediction The utility of the PCR-based approach was compared to Chromogranin A levels measured in plasma for identifying GEP-NENs and differentiating between treated and untreated samples.

CgA is widely utilized as a generalized NEN marker and elevated levels are generally considered to be a sensitive, ~70-90% accurate as a marker for GEP-NENs. Measurements of this peptide, however, are non-specific (10-35% specificity) as it is also elevated in other neoplasia e.g., pancreatic and small cell lung neoplasia and prostate carcinomas as well as in a variety of cardiac and inflammatory diseases, by proton pump inhibitor usage and in renal failure. CgA is a component of neuroendocrine cell secretion, not proliferation, and therefore its use as a surrogate for tumor growth has obvious significant limitations. In general, the sensitivity of this biomarker for predicting GEP-NENs is dependent on the degree of differentiation of the tumor, the location of the tumor and whether it is metastatic or not. Despite modest correlations between CgA levels and hepatic tumor burden, the low (<60%) sensitivity for detecting metastases, the absence of a standardization of measurement in the USA, as well as that the FDA does not accept CgA as a supportable biomarker, it is currently the only marker "routinely" used to evaluate treatment efficacy (surgery, liver transplantation, bio-/chemo-therapy, chemo-/embolization, radiofrequency ablation). CgA levels were therefor used as the best available equivalent of a "gold-standard" against which to assess the PCR-based test.

CgA values were measured using the DAKO ELISA kit in the initial test set of 130 samples (controls: n=67, GEP-NENs: n=63 [untreated disease, n=28, treated, n=35]) used to develop the 51 marker gene panel. The DAKO kit is art recognized to detect CgA in plasma samples from GEP-NENs.

Figure 37B:
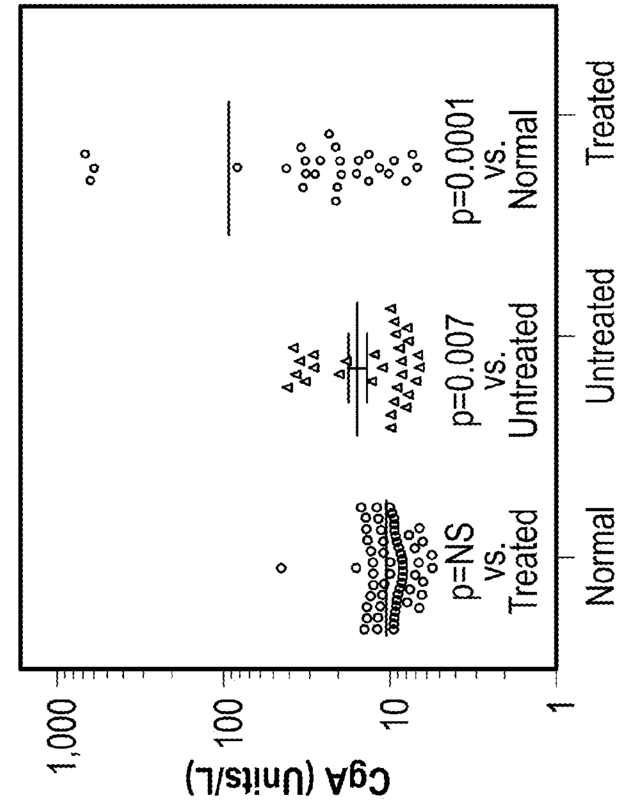
FIGS. 37A-B: Comparison of CgA DAKO levels across control and GEP-NEN (both untreated and treated) blood samples (n=130). Differences were noted between untreated and treated samples using the Student's t-test (37A) or non-parametric analyses (37B). Red crosses represent outliers (37A) and the y-scale is transformed logarithmically for visualization purposes (37A, B). CgA levels can consistently distinguish between normal and untreated groups but exhibit significant overlap with treated samples.
Figure 37A:
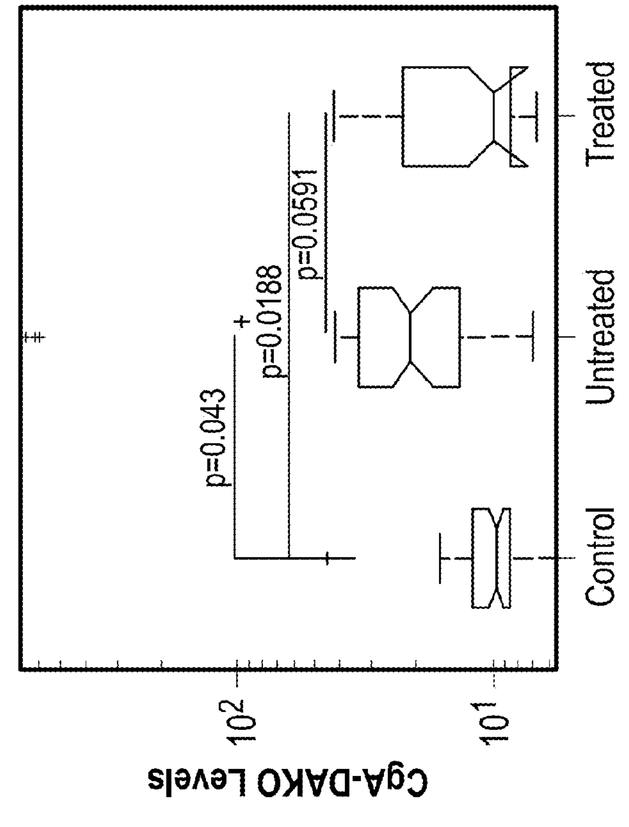

CgA levels were elevated ($p<0.05$) in both untreated (63%) and treated GEP-NENs (32%) using either the Student's t-test (FIG. 37A) or non-parametric tests (FIG. 37B).

The efficacy of CgA to identify GEP-NENs compared to controls identified a correct call rate of 74% (Table 18). The efficacy for correctly identifying a GEP-NEN, irrespective of treatment, was lower at ~45%.

TABLE 18

Diagnostic capacity of CgA levels to discriminate controls from all GEP-NENs (treated and untreated).

| | Normal (True) | GEP-NENs (True) |
|---|---|---|
| Normal (Predicted) | 65 | 30 |
| GEP-NENs (Predicted) | 2 | 26 |

The performance metrics of this test were: Sensitivity = 97%, Specificity = 46%, PPV = 68% and NPV = 93%.

Figure 38:
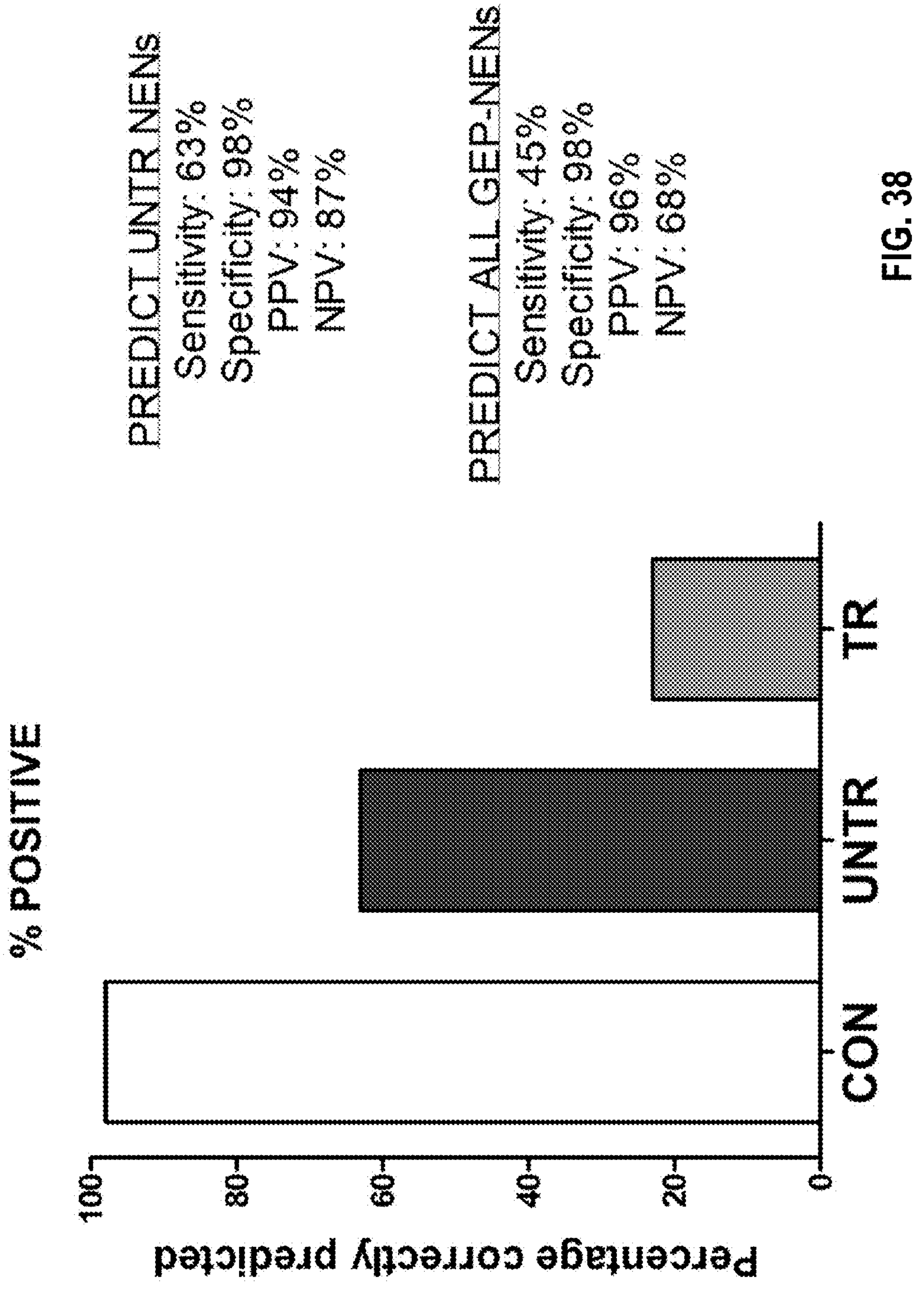
FIG. 38: Utility of CgA ELISA for correctly detecting GEP-NENs and differentiating treated from untreated samples. Using 19 U/L as a cut-off (as per DAKO criteria), the overall percentage correct calls for GEP-NENs and controls was 70%, and the performance metrics were better in untreated patients compared to treated patients (sensitivity 63% vs. 45%). CgA levels best identify untreated patients and samples from individuals with no disease (controls).

DAKO uses a cut-off of 19 Units/L as the upper limit of normal. Using this value, a total of 25 (45%) of 56 GEP-NENs were considered positive compared to 1 (1.4%) of 67 controls for performance metrics of Sensitivity=45%, Specificity=98%, PPV=96% and NPV=68% (FIG. 38). The correct call rate for this cut-off was 70%.

Figure 39A:
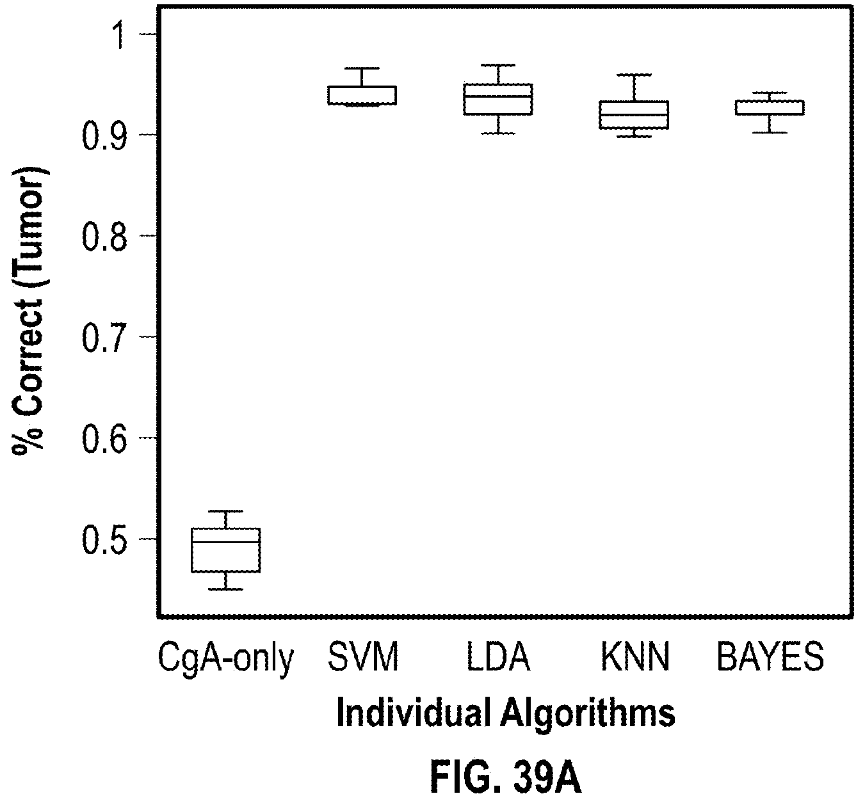
FIGS. 39A-B: Comparison of correct call rates for circulating CgA DAKO levels and the individual algorithms using the PCR-based approach across control and GEP-NEN (both untreated and treated) blood samples (n=130). Call rates were significantly higher for the PCR-based test (~90-95% for each of the algorithms) compared to ~50% of CgA (FIG. 39A). Inclusion of CgA values in the algorithm did not increase the correct call rates, and was associated with a decrease in correct calls for the KNN algorithm (FIG. 39B).
Figure 39B:
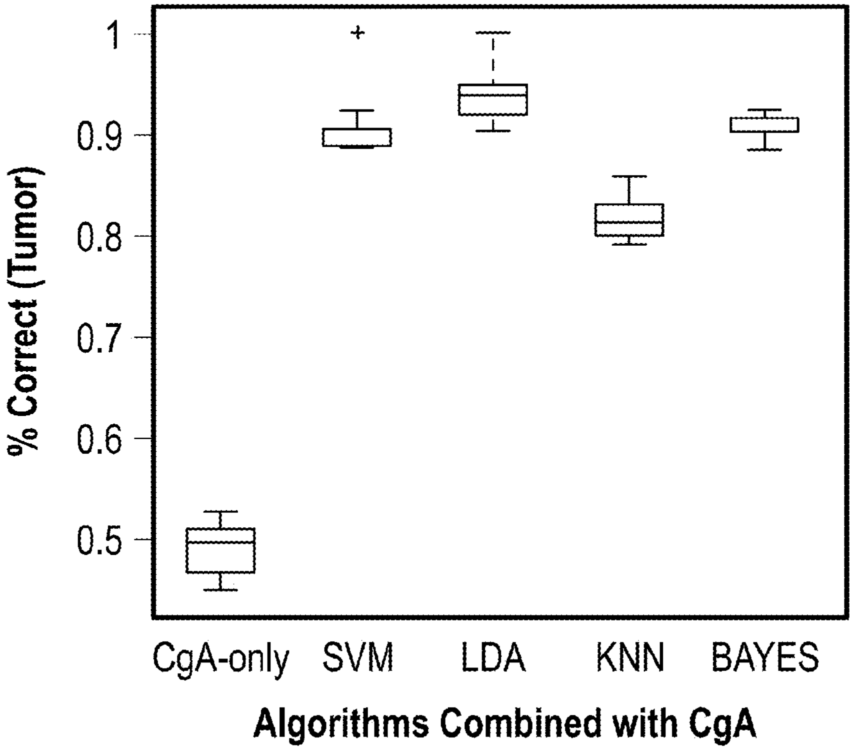

Using CgA levels with the PCR transcript expression (51 marker panel) was next evaluated for the ability to provide additional value to the predictions. Inclusion of CgA levels did not increase the prediction ability of the marker genes, and reduced the efficacy, particularly of the KNN classifier (FIG. 39A-B). It was conclude that inclusion of CgA levels do not improve the quality of the candidate marker gene panel.

These results demonstrate that quantification of a circulating multi-transcript molecular signature (tumor transcripts) is more sensitive than measurement of a single, circulating protein (CgA). Inclusion of CgA measurement in the molecular fingerprint provides no "added" predictive value.

Example 9: Comparison of the 51-Marker Gene Panel with Plasma Chromogranin a Levels for Assessment of Disease Efficacy The utility of the PCR-based approach was directly compared to CgA levels measured in plasma for identifying GEP-NENs and differentiating between treated and untreated samples. Analyses of the efficacy of CgA to differentiate between treated and untreated GEP-NENs identified that the correct call rate was 66% (Table 19). The performance metrics were: Sensitivity=69%, Specificity=63%, PPV=67% and NPV=65%.

TABLE 19

| Diagnostic capacity of CgA levels to discriminate between un-treated and treated GEP-NEN samples | | |
|---|---|---|
| | Treated (True) | Untreated (True) |
| Treated (Predicted) | 20 | 10 |
| Untreated (Predicted) | 9 | 17 |

Illustrative Cases

Figure 40:
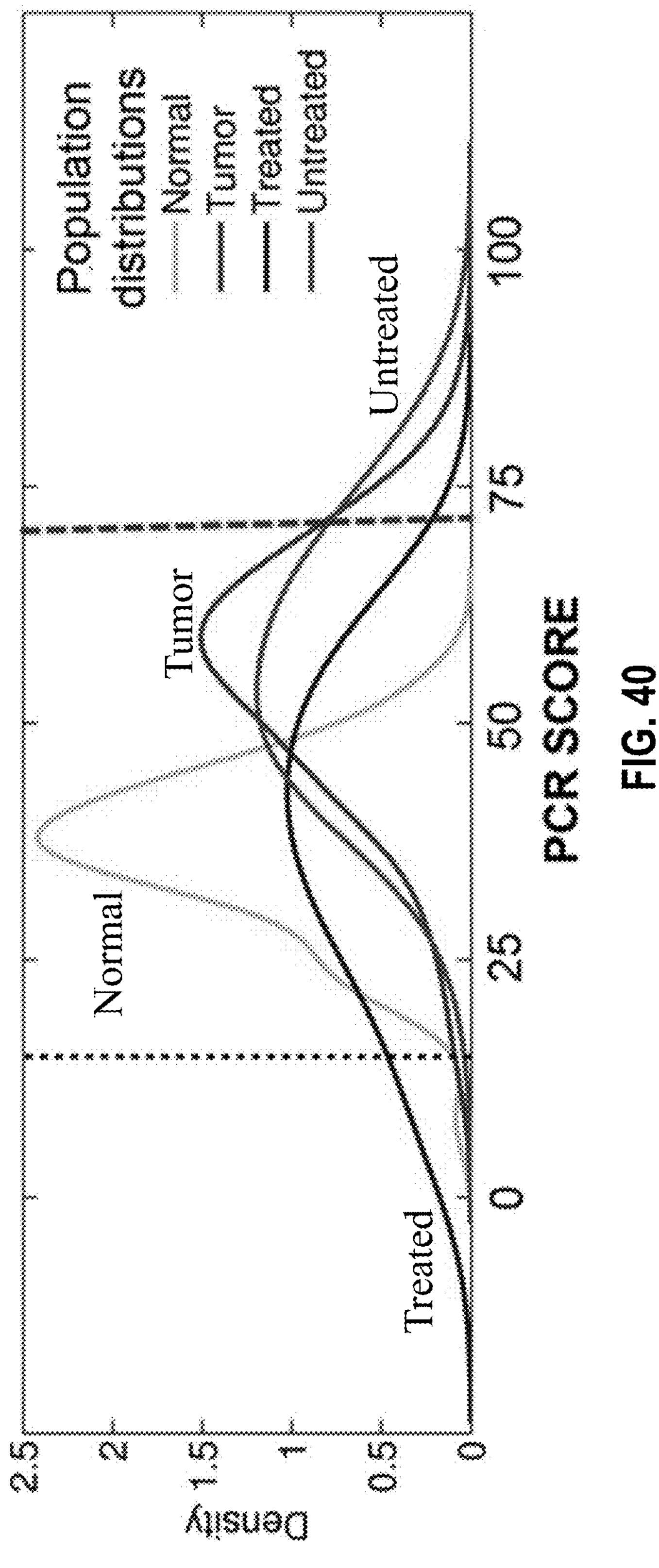
FIG. 40: PCR score for a blood sample obtained from a normal control (black dotted line: PCR Score=15, called "normal") and from Case 1 presenting with mesenteric metastases (red dotted line: PCR Score 68: called "tumor untreated". The population distributions are in solid lines. This provides an illustration of the relationship between the algorithm calls and a Score (Transcript index).

To facilitate clinical usage, a scoring system was developed based on the calls from the mathematical algorithm. This is a "Distance" score that measures the Euclidean distance of an unknown sample to gene expression profiles of the different calls "Normal" versus "Tumor", and "Treated" versus "Untreated". A low score: 0-25 converts to "normal", 26-50 is "tumor-treated" (or stable) and 51-100 is "tumor untreated". This provides a physician-friendly visualization since it is clear where an individual patient value falls in the disease spectrum (diagnosis of "normal" versus "tumor" and clinical interpretation of "treated" versus "untreated"). It also provides the opportunity to graph how treatment influences the transcript index of the disease. An example is provided in FIG. 40. These terms and scores are used for the individual, illustrative cases provided below.

Index Case 1: Incidentally Identified Appendiceal NEN, with Subsequent Development of a Mesenteric Metastasis JPP (45 yo male with hypertension and previous splenectomy [1998]), underwent left hemicolectomy for an abscess and perforation [December 2009]. At surgery, a well differentiated 0.8 cm NEN was identified with lymphatic invasion and extension to the meso-appendix [T?N1M1]. The tumor exhibited low proliferative capacity: Ki67<2% and mitotic count <1/10 HPF). A subsequent MRI scan (January 2010) identified residual mesenteric implants and repeat surgery (April 2010) was undertaken for colostomy closure. At this time a mesenteric lymph node metastasis (<1 cm) was removed (Ki67<2%).

TABLE 20

| | | Surgery Dec-09 | Jan-10 | Mar-10 | Surgery Apr-10 | Aug-10 | Apr-11 |
|---|---|---|---|---|---|---|---|
| PCR test | Score | | | 68 | | 40 | 45 |
| | Diagnosis | | | TUMOR | | TUMOR | TUMOR |
| | Interpretation | | | Untreated | | Treated | Treated |
| CgA ELISA | Value | | 6.5 U/L | 9.6 U/L | | 6.7 U/L | 7.8 U/L |
| | Call | | NML | NML | | NML | NML |
| PROCEDURE | | Left hemi-colectomy [<1 cm well-differentiated NEN, Ki67<2%] | MRI: Residual mesenteric Disease | | Surgery-colectomy 1 cm LN metastasis, Ki67<2% | | |

PCR score: 0-100 (0-25 = normal, 26-50 = treated; 51-100 = untreated disease);
Diagnosis = normal or tumor,
interpretation = treated versus untreated.
CgA values: Units/liter (U/L) (DAKO ELISA)
ABNML = abnormal (elevated);
NML = normal range The PCR test is more sensitive than CgA for identifying residual (untreated) disease (diagnosis="tumor", interpretation="untreated", PCR score 68) and for demonstrating surgical removal of the metastasis (diagnosis="tumor", interpretation="treated", PCR score 40). The identification that the blood PCR test did not revert to a call of "Normal" following surgical excision indicates the presence of residual metastatic disease (PCR score remains above normal: ~40). Since the PCR value has not changed between 2010 and 2011 to an "untreated" phenotype it is likely that the disease is clinically "stable".

Index Case 2: SI-NEN, Surgical Resection.

BA (65 yr female, history of coronary artery disease, type II diabetes and glaucoma exhibited with anemia in 1996 and 2006. Colonoscopy and CT scan identified a terminal ileal NEN [May 2009]. She underwent a right hemicolectomy (February 2010) for removal of a 1 cm SI-NEN which exhibited lymphatic invasion but no nodes were positive [T1N0M0]. Tumor exhibited low proliferative index: Ki67=2% and mitotic count <2/10 HPF).

TABLE 21

| | | May-09 | Nov-09 | Surgery Feb-10 | Mar-10 |
|---|---|---|---|---|---|
| PCR test | Score | | 61 | 30 | 26 |
| | Diagnosis | | TUMOR | TUMOR | TUMOR |
| | Interpretation | | Untreated | Treated | Treated |

TABLE 21-continued

| | | May-09 | Nov-09 | Surgery Feb-10 | Mar-10 |
|---|---|---|---|---|---|
| CgA ELISA | Value | | 15.5 U/L | 7.8 U/L | 17 U/L |
| | Call | | NML | NML | ABNML |
| PROCEDURE | | Endoscopy & CT Scan: ILEAL NEN | | Right hemi-colectomy 1 cm well-differentiated lesion, Ki67 < 2% | |

PCR score: 0-100 (0-25 = normal, 26-50 = treated; 51-100 = untreated disease);
Diagnosis = normal or tumor,
interpretation = treated versus untreated.
CgA values: Units/liter (U/L) (DAKO ELISA)
ABNML = abnormal (elevated);
NML = normal range The PCR test identifies a small mass, low proliferation small intestinal NEN (diagnosis="tumor", interpretation="untreated", PCR score 61). The identification that the blood PCR test did not revert to a call of "Normal" following surgical excision indicates the presence of residual disease (PCR score 26-30) suggesting incomplete resection (non-R0).

Index Case 3: Metastatic Rectal NEN (Endoscopically Removed), Pan-Segmental Liver Metastases, Treated with LAR AJ (47 yo male, with an incidentally identified rectal NEN (on endoscopy—May 2010)). Extensive pan-segmental liver metastases were noted on follow-up (CT/MRI scan June 2010). Sandostatin was initiated [July 2011]. Surgical resection for residual disease (primary and rectal lymph node metastasis) with removal of 2 liver metastases was undertaken [October 2010]. A 1.5 cm rectal lymph node metastasis), with a Ki67<15% was identified. The liver metastases had a Ki67~3% (T2N1M1). Subsequent surgery was undertaken [February 2011] to close the ileostomy and remove additional liver metastases. Serial MRI scans demonstrated no change in hepatic burden. Sandosatin continued.

The failure of the PCR test to revert to a call of "Normal" is consistent with the presence of liver metastases. The values have not changed between 2010 and 2011 to an "untreated" phenotype suggesting the disease is "stable". This finding (PCR score: 26-44) is consistent with current imaging protocols which demonstrate stable non progressive disease.

Index Case 4: Metastatic SI-NEN, Pan-Segmental Liver Metastases, Treated with Hemicolectomy, Lymph Node Dissection and Liver Resection and LAR BG (71 yo female, initially identified with hepatic nodules and ~4 cm mesenteric mass (positive by octreoscan) confirmed to be a well-differentiated neuroendocrine carcinoma (by liver biopsy) [September 2008]. Underwent an ileal and liver wedge resections [December 2008]. An 8 cm mesenteric nodule was removed as was a 1.5 cm NEN, while 6/9 lymph nodes were positive for metastasis. The tumor had a low proliferative capacity, mitotic count=2/10 hpf, Ki67<2% (T2N1M1). Octreotide was initiated February 2009 with some control of symptoms but increasing right upper quadrant discomfort was noted. Octreoscan [April 2010] identified several small liver lesions with additional lesions confirmed in February 2011 (Octreoscan). Underwent ERCP and sphincterotomy [April 2011] and cholecystectomy [June 2011].

TABLE 22

| | | May-10 | Jun-10 | Jul-10 | Oct-10 | Jan-11 | Jun-11 |
|---|---|---|---|---|---|---|---|
| PCR test | Score | | | 78 | 36 | 44 | 26 |
| | Diagnosis | | | TUMOR | TUMOR | TUMOR | TUMOR |
| | Interpretation | | | Untreated | Treated | Treated | Treated |
| CgA ELISA | Value | | | 9.5 U/L | 9 U/L | 10 U/L | 9.3 U/L |
| | Call | | | NML | NML | NML | NML |
| PROCEDURE | | Endoscopy & Polyp removal: RECTAL NEN (1 cm) | MRI/CT Scan: Extensive hepatic metastasis | Sandostatin initiated | Resection for residual disease, 1.5 cm LN, Ki67~15% | Closure, liver mets, Ki67<3%, CT/MRI no change in disease burden | CT/MRI no change in disease burden |

PCR score: 0-100 (0-25 = normal, 26-50 = treated; 51-100 = untreated disease);
Diagnosis = normal or tumor,
interpretation = treated versus untreated.
CgA values: Units/liter (U/L) (DAKO ELISA)
ABNML = abnormal (elevated);
NML = normal range The PCR test identifies liver metastases as well as residual disease from a non-functional (non-secreting) lesion (diagnosis="tumor", interpretation="untreated", PCR score 78). The PCR test is more effective than CgA for both identifying the disease and monitoring treatment response.

TABLE 23

| | | Sep-08 | Dec-08 | Feb-09 | Apr-10 | Feb-11 | Apr-11 | Jun-11 |
|---|---|---|---|---|---|---|---|---|
| PCR test | Score | | 70 | 32 | 27 | 32 | 35 | 33 |
| | Diagnosis | | TUMOR | TUMOR | TUMOR | TUMOR | TUMOR | TUMOR |
| | Interpretation | | Untreated | Treated | Treated | Treated | Treated | Treated |
| CgA ELISA | Value | 9.2 U/L | 10 U/L | 28.8 U/L | 9.1 U/L | 8 U/L | 8.2 U/L | 11 U/L |
| | Call | NML | NML | ABNML | NML | NML | NML | NML |
| PROCEDURE | | Octreoscan & Liver biospy: WD NEC | Ileal and hepatic resection, 1.5 cm NEN, Ki67 = 2% | Sandostatin initiated | Octreoscan: small liver lesions | Octreoscan: additional liver lesions | ERCP & sphincterotomy | Cholecystectomy |

PCR score: 0-100 (0-25 = normal, 26 50 = treated; 51-100 = untreated disease);
Diagnosis = normal or tumor,
interpretation = treated versus untreated.
CgA values: Units/liter (U/L) (DAKO ELISA)
ABNML = abnormal (elevated);
NML = normal range The PCR test identifies extensive disease (diagnosis="tumor", interpretation="untreated", PCR score 70). Since the blood PCR test (PCR Score 27-35) did not revert to "Normal" after surgery the result is consistent with residual metastases. CgA results performed less effectively than the PCR test for both identifying the disease and monitoring treatment response.

Index Case 5: Recurrent Liver Metastasis (Following Hepatectomy), Treated with LAR and Embolization SK (64 yo male, with a history of atrial fibrillation, hyperlipedemia and kidney stones). SI-NEN diagnosed [December 2001] after developing flushing. He underwent resection of the ileal tumor and hepatic mets. Subsequent surgeries included re-resection of a mesenteric lymph node mass [March 2005] and lymph nodes [September 2006]. In [December 2008] cryoablation for a liver met. PET scan [April 2009] identified small liver nodules and a bone lesion. Sandostatin begun [June 2009], repeat scans [PET and MRI] identify no new lesions.

TABLE 24

| | | Dec-01 | Mar-05 | Sep-06 | Jan-09 | Dec-09 | Apr-10 | Sep-10 | Mar-11 |
|---|---|---|---|---|---|---|---|---|---|
| PCR test | Score | | | | 63 | 26 | 49 | 33 | 35 |
| | Diagnosis | | | | TUMOR | TUMOR | TUMOR | TUMOR | TUMOR |
| | Interpretation | | | | Untreated | Treated | Treated | Treated | Treated |
| CgA ELISA | Value | | | | 8.1 U/L | 10 U/L | 8.2 U/L | 28.8 U/L | 8 U/L |
| | Call | | | | NML | NML | NML | ABNML | NML |
| PROCEDURE | | Ileal and hepatic resection for NEN with Liver Mets | Mesenteric LN Resection | Lymph node resection | | Cryoablation for liver metastasis | PET Scan: liver nodules and bone lesion | Somatostatin initiated | PET/MRI no lesions |

PCR score: 0-100 (0-25 = normal, 26-50 = treated; 51-100 = untreated disease);
Diagnosis = normal or tumor,
interpretation = treated versus untreated.
CgA values: Units/liter (U/L) (DAKO ELISA)
ABNML = abnormal (elevated);
NML = normal range The PCR test identified recurrence of the disease (diagnosis="tumor", interpretation="untreated", PCR score 63), demonstrated efficacy of cryoablation and detected residual disease. Because the blood PCR test did not revert to a call of "Normal", this result was considered evidence of metastases which were identified by 13C-PET (PCR score 49). CgA results were less effective than the PCR test for both identifying the disease and monitoring treatment response.

Example 10: Utility of the Molecular Signature to Differentiate GEP-NEN Subtypes (Small Intestine Versus Pancreatic NENs)

The 51 marker gene panel was used to examine the ability to distinguish GEP-NENs from controls and to differentiate whether a sample is from a patient responsive to treatment compared to a non-responder or treatment-naïve individual. The marker panel was developed around information derived from small intestinal NEN tissue and blood microarrays. While the performance metrics are significantly better than for CgA ELISA, it was a goal of this work to establish whether the test could differentiate between GEP-NENs from two different sites, namely the small intestine and the pancreas. This is relevant in the case of a tumor of unknown primary location and is also relevant since tumors exhibit significantly different prognoses depending on their site of origin. The 5-year survival of a SI-NEN is ~80% and ~50% of the mortality is not disease-specific. In contrast, the 5-year survival of a PNEN is ~40% and ~95% of patients die from the disease. Determining the location of an unknown primary can therefore be an important variable in determining therapy; somatostatin analogs have demonstrated utility in SI-NENs 9 while sunitinib and everolimus have efficacy in PNENs_ENREF_10.

Figure 41A:
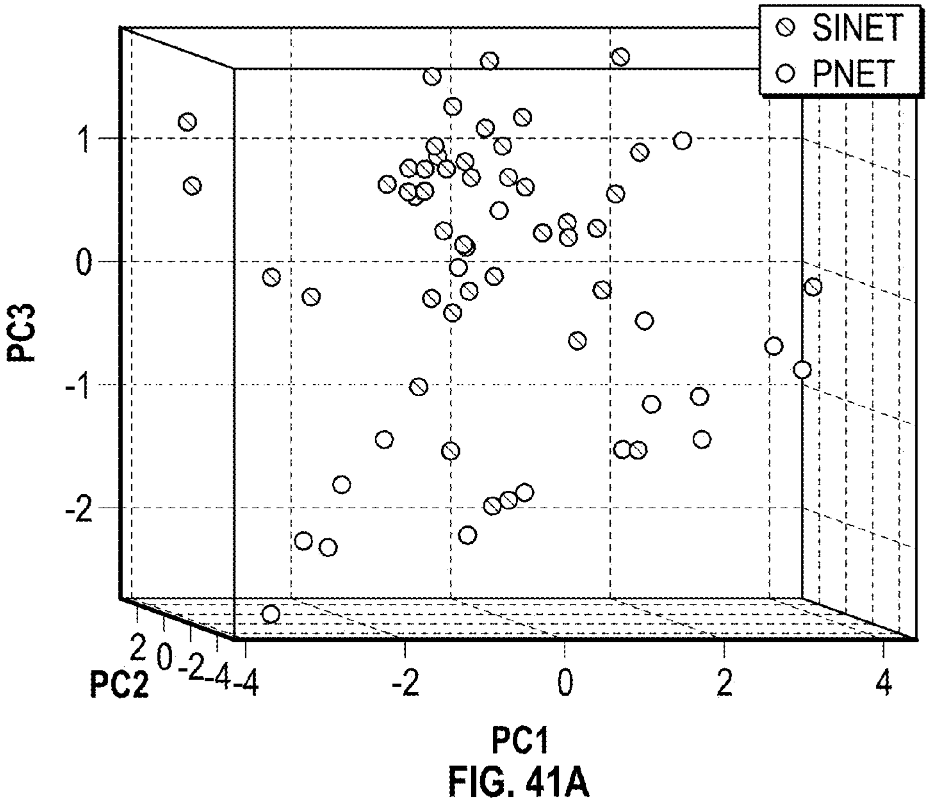
FIGS. 41A-B: PCA of SI-NENs (n=46) and PNENs (n=18) identified that the 51 marker panel could differentiate between pancreatic NENs and small bowel NENs. (41A). A variety of mathematical algorithms including SVM, LDA, KNN and Bayes demonstrated these two tumor groups could be differentiated with an overall sensitivity of ~92% (FIG. 41B). The signature for SI-NENs is different to PNENs.

Examination of the 51 marker gene panel identified that it exhibited a much larger expression variance (0.54±0.4 versus 0.38±0.14 in SI-NENs) indicating that the genes selected in the panel were not as specific for PNENs as for SI-NENs. Mapping expression identified that tumors were spatially separated (FIG. 41A).

Figure 41B:
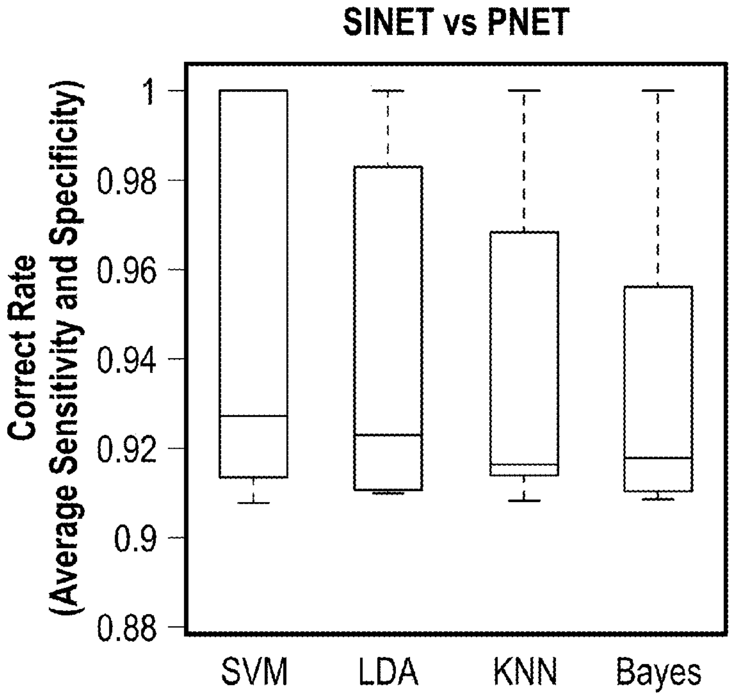

Furthermore, the expression in the panel could differentiate with 92% accuracy between the two tumor sites (FIG. 41B). The test can thus accurately differentiate between a pancreatic and a small bowel tumor.

Example 11: Ability of the 51-Marker Gene Panel to Discriminate Between GEP-NENs and GI Cancers To further evaluate the utility of this PCR-based approach, the molecular fingerprint in gastrointestinal adenocarcinomas, such as gastric and hepatic cancers (esophageal: n=2, pancreatic: n=11, gallbladder: n=3, colon: n=10, rectal: n=7 was examined. This was undertaken to assess whether some genes e.g., KRAS, BRAF, Ki67 over-expressed in GI adenocarcinoma and included in the panel, might perturb the accuracy.

Figure 42A:
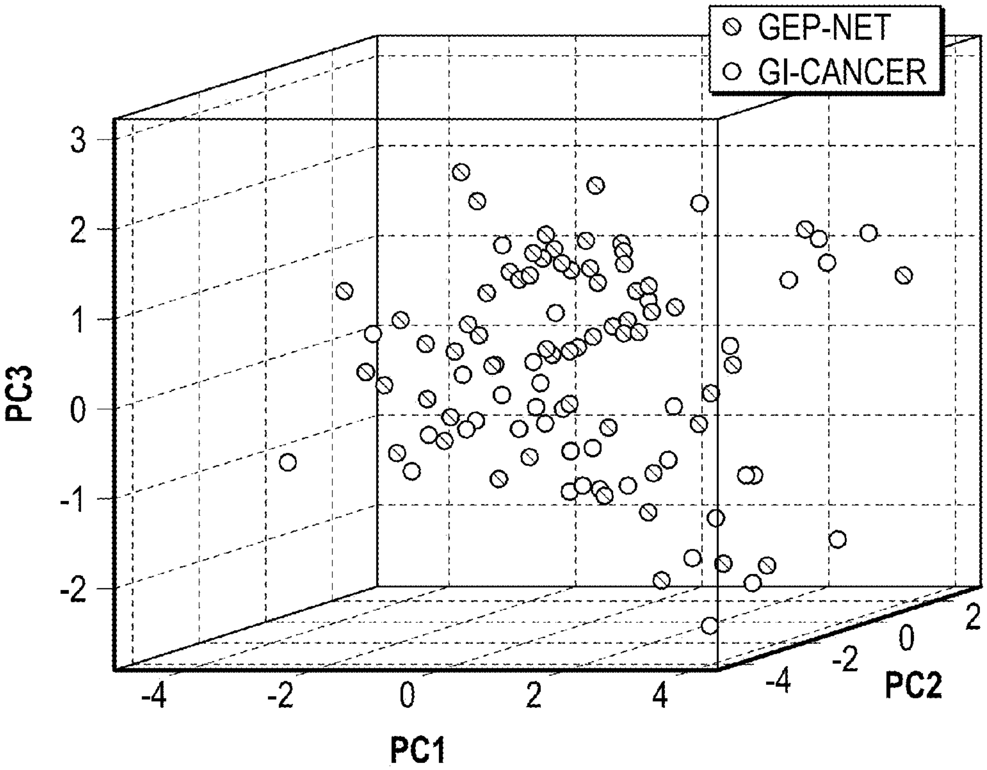
FIGS. 42A-B: PCA of GEP-NENs (n=64) and GI cancers (n=42) identified that the 51 marker panel could differentiate between the two neoplasia types (FIG. 42A). Mathematical analyses including SVM, LDA, KNN and Bayes demonstrated these two tumor types could be differentiated with sensitivities of ~83% (FIG. 42B). The signature for GEP-NENs is different to GI cancers.
Figure 42B:
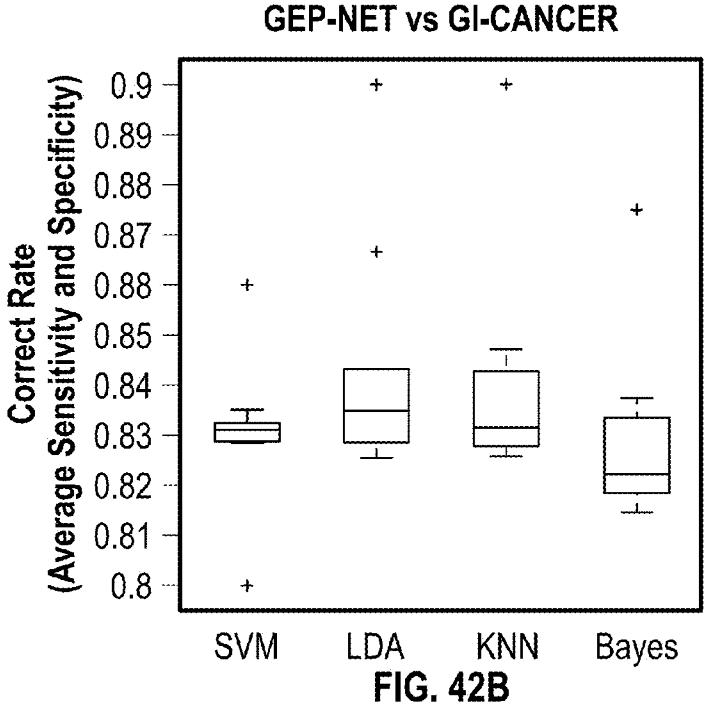

Examination of the 51 marker gene panel identified that it exhibited a larger expression variance (0.5±0.25 versus 0.44±0.17 in GEP-NENs) indicating that the NEN-specific genes selected in the panel were less specific for GI cancers than for GEP-NENs. PCA identified that tumors were spatially separated (FIG. 42A) and that the NEN panel could differentiate with 83% accuracy between GEP-NENs and GI cancers (FIG. 42B).

The test therefore has the power to differentiate between GEP-NENs and GI cancers and the circulating molecular signature of NENs is different to that of GI adenocarcinomas. The minor overlap is consistent with the observation that ~40% of GI adenocarcinomas exhibit neuroendocrine elements.

Figure 43:
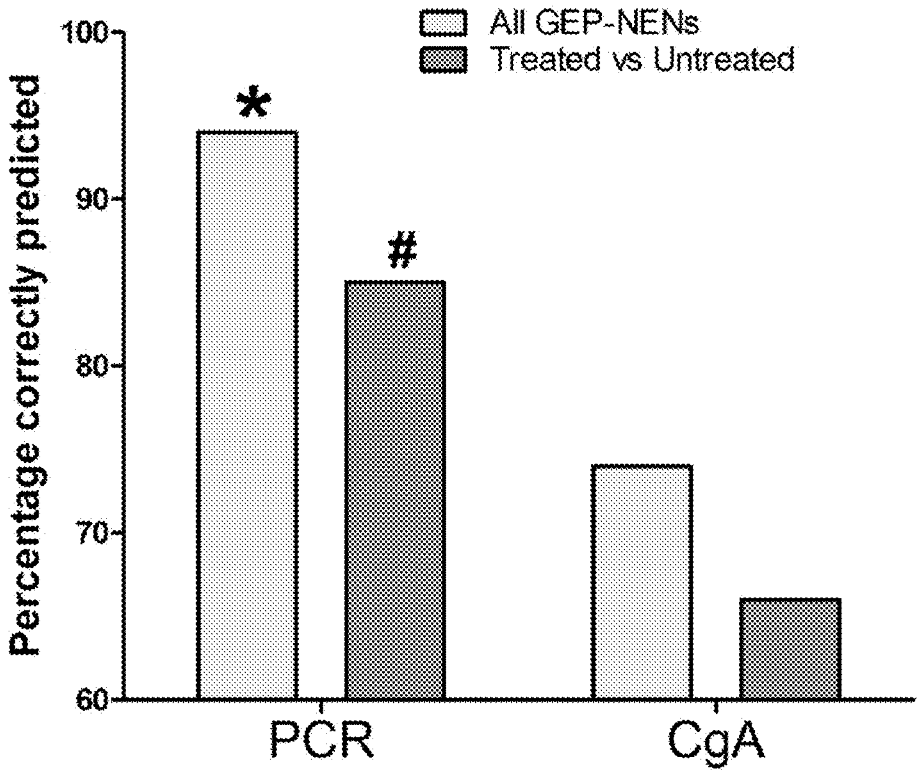
FIG. 43: Comparison of the PCR-based approach and CgA DAKO levels across control and GEP-NEN (both untreated and treated) blood samples (n=130). Call rates were significantly higher for the PCR-based test for identifying either a GEP-NEN or for differentiating between treated and untreated samples. *$p<0.0005$ vs. CgA, $^{\#}p<0.02$ vs. CgA. The PCR blood test is significantly more accurate than measurement of CgA levels to detect tumors and differentiate treated from non-treated patients.

A direct comparison of the molecular test and CgA ELISA identified that the PCR-based method had a significantly more accurate call rate compared to measurement of CgA levels ($\chi^2$=12.3, p<0.0005) (FIG. 43).

The sensitivities were similar for detecting a GEP-NEN (94% versus 97%) but the specificity of the PCR test was higher than CgA (85% versus 46%). For differentiating treated versus untreated samples, the PCR-based test exhibited higher performance metrics (85% versus ~65%).

CgA is less useful than the circulating molecular fingerprint for defining "treatment" in GEP-NENs. This reflects the fact that the protein (CgA) is a constitutive secretory product of all neuroendocrine cells and has no specific biological relationship to neuroendocrine tumors, their proliferation rate or their metastasis.

Throughout this application, various website data content, publications, patent applications and patents are referenced. (Websites are referenced by their Uniform Resource Locator, or URL, addresses on the World Wide Web.) The disclosures of each of these references are hereby incorporated by reference herein in their entireties.

The present invention is not to be limited in scope by the embodiments disclosed herein, which are intended as single illustrations of individual aspects of the invention, and any that are functionally equivalent are within the scope of the invention. Various modifications to the models and methods of the invention, in addition to those described herein, will become apparent to those skilled in the art from the foregoing description and teachings, and are similarly intended to fall within the scope of the invention. Such modifications or other embodiments can be practiced without departing from the true scope and spirit of the invention.

The invention claimed is:

1. A method of using a kit for determining treatment responsiveness in a subject with a gastroenteropancreatic neuroendocrine neoplasm (GEP-NEN), the method comprising:

(a) contacting a biological test sample from the subject with primers specific for at least three GEP-NEN biomarkers selected from the group consisting of: AKAP8L, ATP6V1H, BNIP3L, C21orf7, COMMD9, ENPP4, FAM131A, FLJ10357, GLT8D1, HDAC9, HSF2, LEO1, MORF4L2, NOL3, NUDT3, OAZ2, PANK2, PHF21A, PKD1, PLD3, PQBP1, RNF41, RSF1, RTN2, SMARCD3, SPATA7, SST1, SST3, SST4, SST5, TECPR2, TRMT112, VPS13C, WDFY3, ZFHX3, ZXDC, ZZZ3, APLP2, CD59, ARAF1, BRAF1, KRAS, and RAF1, wherein the length of the primers is at least 15 base pair (bp) and wherein the sequence of the primers comprises SEQ ID NOs: 106-179, 41-48, 65, 66, 83 or 84;

(b) performing a reverse-transcriptase polymerase chain reaction (RT-PCR) on the biological test sample from (a);

(c) measuring the amount of GEP-NEN biomarker complementary DNA molecule (cDNA) generated for each of the at least three GEP-NEN biomarkers so reverse transcribed;

(d) detecting whether the level of the at least three GEP-NEN biomarkers is elevated in a biological test sample from the subject as compared to a normal or a reference biomarker level;

(e) computing the differential in the level of the detected GEP-NEN biomarker cDNA to the level of the normal or the reference biomarker cDNA;

(f) diagnosing the subject with a GEP-NEN nonresponsive to treatment when the level of the least three GEP-NEN biomarkers is elevated in the biological test sample as compared to the normal or the reference biomarker level; and (g) recommending that GEP-NEN treatment of the subject is modified based on the elevated level so detected, wherein the treatment comprises at least one selected from the group consisting of surgical intervention, chemical therapy, hormonal therapy and somatostatin analog therapy.

2. The method of claim 1, wherein the biological test sample is a blood, plasma, serum, tissue, saliva, urine, or semen sample.

3. The method of claim 1, wherein the biological test sample is a blood sample and the method detects as few as three GEP-NEN cells per milliliter (mL) of whole blood.

4. The method of claim 1, wherein the method further comprises, prior to determining treatment responsiveness, detecting the level of the GEP-NEN biomarker cDNA in a normal or reference sample, thereby determining the normal or reference level of expression or expression profile of the GEP-NEN biomarker.

5. The method of claim 4, wherein: the biological test sample is from a GEP-NEN subject after treatment and the normal or reference level or profile is the from the same GEP-NEN subject prior to treatment; the reference sample is from a tissue or fluid not containing GEP-NEN cells; the reference sample is from a healthy subject; the reference sample is from a subject with a cancer other than GEP-NEN; the reference sample is from an EC cell or SI Tissue; the biological test sample is from a metastatic GEP-NEN subject and the reference sample is from a non-metastatic GEP-NEN subject; or the reference sample is from a GEP-NEN subject with a different classification compared to the GEP-NEN subject from which the biological test sample is obtained.

6. The method of claim 1, wherein the primers comprise sense and antisense primers, and wherein the method further comprises amplifying the cDNA so produced with pairs of sense and antisense primers, which specifically hybridize to the at least three GEP-NEN biomarkers and detecting products of the amplification.

7. The method of claim 1, further comprising analyzing data obtained by the method using a predictive algorithm, wherein the predictive algorithm comprises at least one selected from the group consisting of support vector machines (SVM), linear discriminant analysis (LDA), K-nearest neighbor (KNN), nave Bayes (NB), decision tree, regularized discriminant analysis (RDA) and Perceptron.

* * * * *

SEQUENCE LISTING

```
<160> NUMBER OF SEQ ID NOS: 252

<210> SEQ ID NO 1
<211> LENGTH: 3827
<212> TYPE: DNA
<213> ORGANISM: Homo sapiens

<400> SEQUENCE: 1

agaaggaggg cgtggtaata tgaagtcagt tccggttggt gtaaaacccc cggggcggcg      60

gcgaactggc tttagatgct tctgggtcgc ggtgtgctaa gcgaggagtc cgagtgtgtg     120

agcttgagag ccgcgcgcta gagcgacccg gcgagggatg gcggccaccg ggaccgcggc     180

cgccgcagcc acgggcaggc tcctgcttct gctgctggtg gggctcacgg cgcctgcctt     240

ggcgctggcc ggctacatcg aggctcttgc agccaatgcc ggaacaggat ttgctgttgc     300

tgagcctcaa atcgcaatgt tttgtgggaa gttaaatatg catgtgaaca ttcagactgg     360

gaaatgggaa cctgatccaa caggcaccaa gagctgcttt gaaacaaaag aagaagttct     420

tcagtactgt caggagatgt atccagagct acagatcaca aatgtgatgg aggcaaacca     480

gcgggttagt attgacaact ggtgccggag ggacaaaaag caatgcaaga gtcgctttgt     540

tacacctttc aagtgtctcg tgggtgaatt tgtaagtgat gtcctgctag ttccagaaaa     600

gtgccagttt ttccacaaag agcggatgga ggtgtgtgag aatcaccagc actggcacac     660

ggtagtcaaa gaggcatgtc tgactcaggg aatgacctta tatagctacg gcatgctgct     720
```

-continued

```
cccatgtggg gtagaccagt tccatggcac tgaatatgtg tgctgccctc agacaaagat    780
tattggatct gtgtcaaaag aagaggaaga ggaagatgaa gaggaagagg aagaggaaga    840
tgaagaggaa gactatgatg tttataaaag tgaatttcct actgaagcag atctggaaga    900
cttcacagaa gcagctgtgg atgaggatga tgaggatgag gaagaagggg aggaagtggt    960
ggaggaccga gattactact atgacacctt caaaggagat gactacaatg aggagaatcc   1020
tactgaaccc ggcagcgacg gcaccatgtc agacaaggaa attactcatg atgtcaaagc   1080
tgtctgctcc caggaggcga tgacggggcc ctgccgggcc gtgatgcctc gttggtactt   1140
cgacctctcc aagggaaagt gcgtgcgctt tatatatggt ggctgcggcg gcaacaggaa   1200
caattttgag tctgaggatt attgtatggc tgtgtgtaaa gcgatgattc ctccaactcc   1260
tctgccaacc aatgatgttg atgtgtattt cgagacctct gcagatgata atgagcatgc   1320
tcgcttccag aaggctaagg agcagctgga gattcggcac cgcaaccgaa tggacagggt   1380
aaagaaggaa tgggaagagg cagagcttca agctaagaac ctccccaaag cagagaggca   1440
gactctgatt cagcacttcc aagccatggt taaagcttta gagaaggaag cagccagtga   1500
gaagcagcag ctggtggaga cccacctggc ccgagtggaa gctatgctga atgaccgccg   1560
tcggatggct ctggagaact acctggctgc cttgcagtct gacccgccac ggcctcatcg   1620
cattctccag gccttacggc gttatgtccg tgctgagaac aaagatcgct tacataccat   1680
ccgtcattac cagcatgtgt tggctgttga cccagaaaag gcggcccaga tgaaatccca   1740
ggtgatgaca catctccacg tgattgaaga aaggaggaac caaagcctct ctctgctcta   1800
caaagtacct tatgtagccc aagaaattca agaggaaatt gatgagctcc ttcaggagca   1860
gcgtgcagat atggaccagt tcactgcctc aatctcagag acccctgtgg acgtccgggt   1920
gagctctgag gagagtgagg agatcccacc gttccacccc ttccacccct tcccagccct   1980
acctgagaac gaagacactc agccggagtt gtaccaccca atgaaaaaag gatctggagt   2040
gggagagcag gatgggggac tgatcggtgc cgaagagaaa gtgattaaca gtaagaataa   2100
agtggatgaa aacatggtca ttgacgagac tctggatgtt aaggaaatga ttttcaatgc   2160
cgagagagtt ggaggcctcg aggaagagcg ggaatccgtg ggcccactgc gggaggactt   2220
cagtctgagt agcagtgctc tcattggcct gctggtcatc gcagtggcca ttgccacggt   2280
catcgtcatc agcctggtga tgctgaggaa gaggcagtat ggcaccatca gccacgggat   2340
cgtggaggtt gatccaatgc tcaccccaga agagcgtcac ctgaacaaga tgcagaacca   2400
tggctatgag aaccccacct acaaatacct ggagcagatg cagatttagg tggcagggag   2460
cgcggcagcc ctggcggagg gatgcaggtg ggccggaaga tcccacgatt ccgatcgact   2520
gccaagcagc agccgctgcc aggggctgcg tctgacatcc tgacctcctg gactgtagga   2580
ctatataaag tactactgta gaactgcaat ttccattctt ttaaatgggt gaaaaatggt   2640
aatataacaa tatatgatat ataaacctta aatgaaaaaa atgatctatt gcagatattt   2700
gatgtagttt tctttttttaa attaatcaga aaccccactt ccattgtatt gtctgacaca   2760
tgctctcaat atataataaa tgggaaatgt cgattttcaa taatagactt atatgcaggc   2820
tgtcgttccg gttatgttgt gtaagtcaac tcttcagcct cattcactgt cctggctttt   2880
atttaaagaa aaaaaaggca gtattccctt tttaaatgag ctttcaggaa gttgctgaga   2940
aatggggtgg aatagggaac tgtaatggcc actgaagcac gtgagagacc ctcgcaaaat   3000
gatgtgaaag gaccagtttc ttgaagtcca gtgtttccac ggctggatac ctgtgtgtct   3060
```

```
ccataaaagt cctgtcacca aggacgttaa aggcatttta ttccagcgtc ttctagagag   3120

cttagtgtat acagatgagg gtgtccgctg ctgctttcct tcggaatcca gtgcttccac   3180

agagattagc ctgtagctta tatttgacat tcttcactgt ctgttgttta cctaccgtag   3240

ctttttaccg ttcacttccc cttccaacta tgtccagatg tgcaggctcc tcctctctgg   3300

actttctcca aaggcactga ccctcggcct ctactttgtc ccctcacctc cacccccctcc  3360

tgtcaccggc cttgtgacat tcactcagag aagaccacac caaggaggcg gccgctggcc   3420

caggagagaa cacggggagg tttgtttgtg tgaaaggaaa gtagtccagg ctgtccctga   3480

aactgagtct gtggacactg tggaaagctt tgaacaattg tgttttcgtc acaggagtct   3540

ttgtaatgct tgtacagttg atgtcgatgc tcactgcttc tgctttttct ttctttttat   3600

tttaaatctg aaggttctgg taacctgtgg tgtattttta ttttcctgtg actgtttttg   3660

ttttgttttt ttcctttttc ctccccttttg accctattca tgtctctacc cactatgcac  3720

agattaaact tcacctacaa actccttaat atgatctgtg gagaatgtac acagtttaaa   3780

cacatcaata aatactttaa cttccaccga gaaaaaaaaa aaaaaaa                 3827
```

<210> SEQ ID NO 2
<211> LENGTH: 2503
<212> TYPE: DNA
<213> ORGANISM: Homo sapiens

<400> SEQUENCE: 2

```
tgacccaata agggtggaag gctgagtccc gcagagccaa taacgagagt ccgagaggcg     60

acggaggcgg actctgtgag gaaacaagaa gagaggccca agatggagac ggcggcggct    120

gtagcggcgt gacaggagcc ccatggcacc tgcccagccc cacctcagcc catcttgaca    180

aaatctaagg ctccatggag ccaccacggg gcccccctgc caatggggcc gagccatccc    240

gggcagtggg caccgtcaaa gtatacctgc ccaacaagca acgcacggtg gtgactgtcc    300

gggatggcat gagtgtctac gactctctag acaaggccct gaaggtgcgg ggtctaaatc    360

aggactgctg tgtggtctac cgactcatca agggacgaaa gacggtcact gcctgggaca    420

cagccattgc tcccctggat ggcgaggagc tcattgtcga ggtccttgaa gatgtcccgc    480

tgaccatgca caattttgta cggaagacct tcttcagcct ggcgttctgt gacttctgcc    540

ttaagtttct gttccatggc ttccgttgcc aaacctgtgg ctacaagttc caccagcatt    600

gttcctccaa ggtccccaca gtctgtgttg acatgagtac caaccgccaa cagttctacc    660

acagtgtcca ggatttgtcc ggaggctcca gacagcatga ggctccctcg aaccgccccc    720

tgaatgagtt gctaaccccc cagggtccca gcccccgcac ccagcactgt gacccggagc    780

acttcccctt ccctgcccca gccaatgccc ccctacagcg catccgctcc acgtccactc    840

ccaacgtcca tatggtcagc accacggccc ccatggactc caacctcatc cagctcactg    900

gccagagttt cagcactgat gctgccggta gtagaggagg tagtgatgga accccccggg    960

ggagccccag cccagccagc gtgtcctcgg ggaggaagtc cccacattcc aagtcaccag   1020

cagagcagcg cgagcggaag tccttggccg atgacaagaa gaaagtgaag aacctggggt   1080

accgggactc aggctattac tgggaggtac cacccagtga ggtgcagctg ctgaagagga   1140

tcgggacggg ctcgtttggc accgtgtttc gagggcggtg gcatggcgat gtggccgtga   1200

aggtgctcaa ggtgtcccag cccacagctg agcaggccca ggctttcaag aatgagatgc   1260

aggtgctcag gaagacgcga catgtcaaca tcttgctgtt tatgggcttc atgacccggc   1320

cgggatttgc catcatcaca cagtggtgtg agggctccag cctctaccat cacctgcatg   1380
```

```
tggccgacac acgcttcgac atggtccagc tcatcgacgt ggcccggcag actgcccagg   1440
gcatggacta cctccatgcc aagaacatca tccaccgaga tctcaagtct aacaacatct   1500
tcctacatga ggggctcacg gtgaagatcg gtgactttgg cttggccaca gtgaagactc   1560
gatggagcgg ggcccagccc ttggagcagc cctcaggatc tgtgctgtgg atggcagctg   1620
aggtgatccg tatgcaggac ccgaacccct acagcttcca gtcagacgtc tatgcctacg   1680
gggttgtgct ctacgagctt atgactggct cactgcctta cagccacatt ggctgccgtg   1740
accagattat ctttatggtg ggccgtggct atctgtcccc ggacctcagc aaaatctcca   1800
gcaactgccc caaggccatg cggcgcctgc tgtctgactg cctcaagttc cagcgggagg   1860
agcggcccct cttcccccag atcctggcca caattgagct gctgcaacgg tcactcccca   1920
agattgagcg gagtgcctcg gaaccctcct tgcaccgcac ccaggccgat gagttgcctg   1980
cctgcctact cagcgcagcc cgccttgtgc cttaggcccc gcccaagcca ccagggagcc   2040
aatctcagcc ctccacgcca aggagccttg cccaccagcc aatcaatgtt cgtctctgcc   2100
ctgatgctgc ctcaggatcc cccattcccc accctgggag atgagggggt ccccatgtgc   2160
ttttccagtt cttctggaat tgggggaccc ccgccaaaga ctgagccccc tgtctcctcc   2220
atcatttggt ttcctcttgg ctttggggat acttctaaat tttgggagct cctccatctc   2280
caatggctgg gatttgtggc agggattcca ctcagaacct ctctggaatt tgtgcctgat   2340
gtgccttcca ctggattttg gggttcccag caccccatgt ggattttggg ggtccctttt   2400
tgtgtctccc ccgccattca aggactcctc tctttcttca ccaagaagca cagaattctg   2460
ctgggccttt gcttgtttaa aaaaaaaaaa aaaaaaaaaa aaa                    2503

<210> SEQ ID NO 3
<211> LENGTH: 2949
<212> TYPE: DNA
<213> ORGANISM: Homo sapiens

<400> SEQUENCE: 3

cgcctccctt cccccctccc gcccgacagc ggccgctcgg gccccggctc tcggttataa     60
gatggcggcg ctgagcggtg gcggtggtgg cggcgcggag ccgggccagg ctctgttcaa    120
cggggacatg gagcccgagg ccggcgccgg cgccggcgcc gcggcctctt cggctgcgga    180
ccctgccatt ccggaggagg tgtggaatat caaacaaatg attaagttga cacaggaaca    240
tatagaggcc ctattggaca aatttggtgg ggagcataat ccaccatcaa tatatctgga    300
ggcctatgaa gaatacacca gcaagctaga tgcactccaa caaagagaac aacagttatt    360
ggaatctctg gggaacggaa ctgatttttc tgtttctagc tctgcatcaa tggataccgt    420
tacatcttct tcctcttcta gcctttcagt gctaccttca tctctttcag tttttcaaaa    480
tcccacagat gtggcacgga gcaaccccaa gtcaccacaa aaacctatcg ttagagtctt    540
cctgcccaac aaacagagga cagtggtacc tgcaaggtgt ggagttacag tccgagacag    600
tctaaagaaa gcactgatga tgagaggtct aatcccagag tgctgtgctg tttacagaat    660
tcaggatgga gagaagaaac caattggttg ggacactgat atttcctggc ttactggaga    720
agaattgcat gtggaagtgt tggagaatgt tccacttaca acacacaact ttgtacgaaa    780
aacgtttttc accttagcat tttgtgactt ttgtcgaaag ctgcttttcc agggtttccg    840
ctgtcaaaca tgtggttata aatttcacca gcgttgtagt acagaagttc cactgatgtg    900
tgttaattat gaccaacttg atttgctgtt tgtctccaag ttctttgaac accacccaat    960
```

-continued accacaggaa gaggcgtcct tagcagagac tgccctaaca tctggatcat cccctttccgc 1020 acccgcctcg gactctattg ggccccaaat tctcaccagt ccgtctcctt caaaatccat 1080
tccaattcca cagcccttcc gaccagcaga tgaagatcat cgaaatcaat ttgggcaacg 1140
agaccgatcc tcatcagctc ccaatgtgca tataaacaca atagaacctg tcaatattga 1200
tgacttgatt agagaccaag gatttcgtgg tgatggagga tcaaccacag gtttgtctgc 1260
taccccccct gcctcattac ctggctcact aactaacgtg aaagccttac agaaatctcc 1320
aggacctcag cgagaaagga agtcatcttc atcctcagaa gacaggaatc gaatgaaaac 1380
acttggtaga cgggactcga gtgatgattg ggagattcct gatgggcaga ttacagtggg 1440
acaaagaatt ggatctggat catttggaac agtctacaag ggaaagtggc atggtgatgt 1500
ggcagtgaaa atgttgaatg tgacagcacc tacacctcag cagttacaag ccttcaaaaa 1560
tgaagtagga gtactcagga aaacacgaca tgtgaatatc ctactcttca tgggctattc 1620
cacaaagcca caactggcta ttgttaccca gtggtgtgag ggctccagct tgtatcacca 1680
tctccatatc attgagacca aatttgagat gatcaaactt atagatattg cacgacagac 1740
tgcacagggc atggattact tacacgccaa gtcaatcatc cacagagacc tcaagagtaa 1800
taatatattt cttcatgaag acctcacagt aaaaataggt gattttggtc tagctacagt 1860
gaaatctcga tggagtgggt cccatcagtt tgaacagttg tctggatcca ttttgtggat 1920
ggcaccagaa gtcatcagaa tgcaagataa aaatccatac agctttcagt cagatgtata 1980
tgcatttgga attgttctgt atgaattgat gactggacag ttaccttatt caaacatcaa 2040
caacagggac cagataattt ttatggtggg acgaggatac ctgtctccag atctcagtaa 2100
ggtacggagt aactgtccaa aagccatgaa gagattaatg gcagagtgcc tcaaaaagaa 2160
aagagatgag agaccactct ttccccaaat tctcgcctct attgagctgc tggcccgctc 2220
attgccaaaa attcaccgca gtgcatcaga accctccttg aatcgggctg gtttccaaac 2280
agaggatttt agtctatatg cttgtgcttc tccaaaaaca cccatccagg caggggggata 2340 tggtgcgttt cctgtccact gaaacaaatg agtgagagag ttcaggagag tagcaacaaa 2400
aggaaaataa atgaacatat gtttgcttat atgttaaatt gaataaaata ctctcttttt 2460
ttttaaggtg aaccaaagaa cacttgtgtg gttaaagact agatataatt tttccccaaa 2520
ctaaaattta tacttaacat tggattttta acatccaagg gttaaaatac atagacattg 2580
ctaaaaattg gcagagcctc ttctagaggc tttactttct gttccgggtt tgtatcattc 2640
acttggttat tttaagtagt aaacttcagt ttctcatgca acttttgttg ccagctatca 2700
catgtccact agggactcca gaagaagacc ctacctatgc ctgtgtttgc aggtgagaag 2760
ttggcagtcg gttagcctgg gttagataag gcaaactgaa cagatctaat ttaggaagtc 2820
agtagaattt aataattcta ttattattct taataatttt tctataacta tttcttttta 2880
taacaatttg gaaaatgtgg atgtctttta tttccttgaa gcaataaact aagtttcttt 2940
ttataaaaa 2949

<210> SEQ ID NO 4
<211> LENGTH: 7796
<212> TYPE: DNA
<213> ORGANISM: Homo sapiens

<400> SEQUENCE: 4
ggggccgggg ggcggagcct tgcgggctgg agcgaaagaa tgcgggggct gagcgcagaa 60
gcggctcgag gctggaagag gatcttgggc gccgccagtc tctctctgtt gcccaagctg 120

-continued

```
gagtgcagtg gcacagtctt ggctcactgc aacctccacc tcctgggtgc aagcgattct    180
cgtgtctcag cctctcaagt agctgggatt acagtcttta gcaccagttg gtgtaggagt    240
tgagacctac ttcacagtag ttctgtggac aatcacaatg ggaatccaag gagggtctgt    300
cctgttcggg ctgctgctcg tcctggctgt cttctgccat tcaggtcata gcctgcagtg    360
ctacaactgt cctaacccaa ctgctgactg caaaacagcc gtcaattgtt catctgattt    420
tgatgcgtgt ctcattacca aagctgggtt acaagtgtat aacaagtgtt ggaagtttga    480
gcattgcaat ttcaacgacg tcacaacccg cttgagggaa aatgagctaa cgtactactg    540
ctgcaagaag gacctgtgta actttaacga acagcttgaa aatggtggga catccttatc    600
agagaaaaca gttcttctgc tggtgactcc atttctggca gcagcctgga gccttcatcc    660
ctaagtcaac accaggagag cttctcccaa actccccgtt cctgcgtagt ccgctttctc    720
ttgctgccac attctaaagg cttgatattt tccaaatgga tcctgttggg aaagaataaa    780
attagcttga gcaacctggc taagatagag gggctctggg agactttgaa gaccagtcct    840
gtttgcaggg aagccccact tgaaggaaga agtctaagag tgaagtaggt gtgacttgaa    900
ctagattgca tgcttcctcc tttgctcttg ggaagaccag ctttgcagtg acagcttgag    960
tgggttctct gcagccctca gattattttt cctctggctc cttggatgta gtcagttagc   1020
atcattagta catctttgga gggtggggca ggagtatatg agcatcctct ctcacatgga   1080
acgctttcat aaacttcagg gatcccgtgt tgccatggag gcatgccaaa tgttccatat   1140
gtgggtgtca gtcagggaca acaagatcct taatgcagag ctagaggact tctggcaggg   1200
aagtggggaa gtgttccaga tagcagggca tgaaaactta gagaggtaca agtggctgaa   1260
aatcgagttt ttcctctgtc tttaaatttt atatgggctt tgttatcttc cactggaaaa   1320
gtgtaatagc atacatcaat ggtgtgttaa agctatttcc ttgccttttt tttattggaa   1380
tggtaggata tcttggcttt gccacacaca gttacagagt gaacactcta ctacatgtga   1440
ctggcagtat taagtgtgct tattttaaat gttactggta gaaaggcagt tcaggtatgt   1500
gtgtatatag tatgaatgca gtggggacac cctttgtggt tacagtttga gacttccaaa   1560
ggtcatcctt aataacaaca gatctgcagg ggtatgtttt accatctgca tccagcctcc   1620
tgctaactcc tagctgactc agcatagatt gtataaaata cctttgtaac ggctcttagc   1680
acactcacag atgtttgagg ctttcagaag ctcttctaaa aaatgataca cacctttcac   1740
aagggcaaac tttttccttt tccctgtgta ttctagtgaa tgaatctcaa gattcagtag   1800
acctaatgac atttgtattt tatgatcttg gctgtattta atggcatagg ctgacttttg   1860
cagatggagg aatttcttga ttaatgttga aaaaaaaccc ttgattatac tctgttggac   1920
aaaccgagtg caatgaatga tgcttttctg aaaatgaaat ataacaagtg ggtgaatgtg   1980
gttatggccg aaaaggatat gcagtatgct taatggtagc aactgaaaga agacatcctg   2040
agcagtgcca gctttcttct gttgatgccg ttccctgaac ataggaaaat agaaacttgc   2100
ttatcaaaac ttagcattac cttggtgctc tgtgttctct gttagctcag tgtctttcct   2160
tacatcaata ggtttttttt tttttttttg gcctgaggaa gtactgacca tgcccacagc   2220
caccggctga gcaaagaagc tcatttcatg tgagttctaa ggaatgagaa acaattttga   2280
tgaatttaag cagaaaatga atttctggga actttttttgg gggcgggggg gtggggaatt   2340
cagccacact ccagaaagcc aggagtcgac agttttggaa gcctctctca ggattgagat   2400
tctaggatga gattggctta ctgctatctt gtgtcatgta cccacttttt ggccagacta   2460
```

-continued

```
cactgggaag aaggtagtcc tctaaagcaa aatctgagtg ccactaaatg gggagatggg   2520
gctgttaagc tgtccaaatc aacaagggtc atataaatgg ccttaaactt tggggttgct   2580
ttctgcaaaa agttgctgtg actcatgcca tagacaaggt tgagtgcctg gacccaaagg   2640
caatactgta atgtaaagac atttatagta ctaggcaaac agcaccccag gtactccagg   2700
ccctcctggc tggagagggc tgtggcaata gaaaattagt gccaactgca gtgagtcagc   2760
ctaggttaaa tagagagtgt aagagtgctg gacaggaacc tccaccctca tgtcacattt   2820
cttcaatgtg acccttctgg cccctctcct cctgacagcg gaacaatgac tgccccgata   2880
ggtgaggctg gaggaagaat cagtcctgtc cttggcaagc tcttcactat gacagtaaag   2940
gctctctgcc tgctgccaag gcctgtgact ttctaacctg gcctcacgct gggtaagctt   3000
aaggtagagg tgcaggatta gcaagcccac ctggctacca ggccgacagc tacatcctcc   3060
aactgaccct gatcaacgaa gagggattca tgtgtctgtc tcagttggtt ccaaatgaaa   3120
ccagggagca ggggagttag gaatcgaaca ccagtcatgc ctactggctc tctgctcgag   3180
agccaatacc ctgtgccctc cactcatctg gatttacagg aactgtcata gtgttcagta   3240
ttgggtggtg ataagcccat tggattgtcc ccttgggggg atgagctagg ggtgcaagga   3300
acacctgatg agtagataag tggagctcat ggtatttcct gaaagatgct aatctatttg   3360
ccaaacttgg tcttgaatgt actgggggct tcaaggtatg ggtatatttt tcttgtgtcc   3420
ttgcagttag cccccatgtc ttatgtgtgt cctgaaaaaa taagagcctg cccaagactt   3480
tgggcctctt gacagaatta accactttta tacatctgag ttctcttggt aagttcttta   3540
gcagtgttca aagtctacta gctcgcatta gtttctgttg ctgccaacag atctgaacta   3600
atgctaacag atccccctga gggattcttg atgggctgag cagctggctg gagctagtac   3660
tgactgacat tcattgtgat gagggcagct ttctggtaca ggattctaag ctctatgttt   3720
tatatacatt ttcatctgta cttgcacctc actttacaca agaggaaact atgcaaagtt   3780
agctggatcg ctcaaggtca cttaggtaag ttggcaagtc catgcttccc actcagctcc   3840
tcaggtcagc aagtctactt ctctgcctat tttgtatact ctctttaata tgtgcctagc   3900
tttggaaagt ctagaatggg tccctggtgc ctttttactt tgaagaaatc agtttctgcc   3960
tctttttgga aaagaaaaca aagtgcaatt gtttttttact ggaaagttac ccaatagcat   4020
gaggtgaaca ggacgtagtt aggccttcct gtaaacagaa aatcatatca aaacactatc   4080
ttcccatctg tttctcaatg cctgctactt cttgtagata tttcatttca ggagagcagc   4140
agttaaaccc gtggattttg tagttaggaa cctgggttca aaccctcttc cactaattgg   4200
ctatgtctct ggacaagttt tttttttttt ttttttttaa accctttctg aactttcact   4260
ttctatgtct acctcaaaga attgttgtga ggcttgagat aatgcatttg taaagggtct   4320
gccagatagg aagatgctag ttatggattt acaaggttgt taaggctgta agagtctaaa   4380
acctacagtg aatcacaatg catttacccc cactgacttg gacataagtg aaaactagcc   4440
agaagtctct ttttcaaatt acttacaggt tattcaatat aaaatttttg taatggataa   4500
tcttatttat ctaaactaaa gcttcctgtt tatacacact cctgttattc tgggataaga   4560
taaatgacca cagtacctta atttctaggt gggtgcctgt gatggttcat tgtaggtaag   4620
gacattttct ctttttcagc agctgtgtag gtccagagcc tctgggagag gagggggggta   4680
gcatgcaccc agcaggggac tgaactggga aactcaaggt tctttttact gtggggtagt   4740
gagctgcctt tctgtgatcg gtttccctag ggatgttgct gttcccctcc ttgctattcg   4800
cagctacata caacgtggcc aaccccagta ggctgatcct atatatgatc agtgctggtg   4860
```

```
ctgactctca atagccccac ccaagctggc tataggttta cagatacatt aattaggcaa   4920
cctaaaatat tgatgctggt gttggtgtga cataatgcta tggccagaac tgaaacttag   4980
agttataatt catgtattag ggttctccag agggacagaa ttagtaggat atatgtatat   5040
atgaaaggga ggttattagg gagaactggc tcccacagtt agaaggcgaa gtcgcacaat   5100
aggccgtctg caagctgggt tagagagaag ccagtagtgg ctcagcctga gttcaaaaac   5160
ctcaaaactg gggaagctga cagtgcagcc agccttcagt ctgtggccaa aggcccaaga   5220
gcccctggca accaacccac tggtgcaagt cctagattcc aaaggctgaa gaacctggag   5280
tctgatgtcc aagagcagga agagtggaag aaagccagaa gactcagcaa acaaggtaga   5340
cagtgtctac caccatagtg gccataccaa agaggctacc gattccttcc tgctacctgg   5400
atccctgaag ttgccctggt ctctgcacct tctaaaccta gttcttaaga gctttccatt   5460
acatgagctg tctcaaagcc ctccaataaa ttctcagtgt aagcttctgt tgcttgtgga   5520
cagaaaattc tgacagacct accctataag tgttactgtc aggataacat gagaacgcac   5580
aacagtaagt ggtcactaag tgttagctac ggttattttg cccaaggtag catggctagt   5640
tgatgccggt tgatggggct taaacccagc tccctcatct tccaggcctc tgtactccct   5700
attccactaa actacctctc aggtttattt ttttaaattc ttactctgca agtacatagg   5760
accacattta cctgggaaaa caagaataaa ggctgctctg catttttttag aaacttttttt   5820
gaaagggaga tgggaatgcc tgcacccccca agtccagacc aacacaatgg ttaattgaga   5880
tgaataataa aggaaagact gttctgggct tcccagaata gcttggtcct taaattgtgg   5940
cacaaacaac ctcctgtcag agccagcctc ctgccaggaa gaggggtagg agactagagg   6000
ccgtgtgtgc agccttgccc tgaaggctag ggtgacaatt tggaggctgt ccaaacaccc   6060
tggcctctag agctggcctg tctatttgaa atgccggctc tgatgctaat cggcgaccct   6120
caggcaagtt acttaacctt acatgcctca gttttctcat ctggaaaatg agaaccctag   6180
gtttagggtt gttagaaaag ttaaatgagt taagacaagt gcctgggaca cagtagcctc   6240
ttgtgtgtgt ttatcattat gtcctcagca ggtcgtagaa gcagcttctc aggtgtgagg   6300
ctggcgcgat tatctggagt gggttgggtt ttctaggatg gaccccctgc tgcattttcc   6360
tcattcatcc accagggctt aatggggaat caaggaatcc atgtgtaact gtataataac   6420
tgtagccaca ctccaatgac cacctactag ttgtccctgg cactgcttat acatatgtcc   6480
atcaaatcaa tcctatgaag tagatactgt cttcatttta tagatcagag acaattgggg   6540
ttcagagagc tgatgtgatt ttcccagggt cacagagagt cccagattca ggcacaactc   6600
ttgtattcca agacacaacc actacatgtc caaaggctgc ccagagccac cgggcacggc   6660
aaattgtgac atatccctaa agaggctgag cacctggtca ggatctgatg gctgacagtg   6720
tgtccagatg cagagctgga gtgggggagg ggaaggggggg ctccttggga cagagaaggc   6780
tttctgtgct ttctctgaag ggagcagtct gaggaccaag ggaacccggc aaacagcacc   6840
tcaggtactc caggccctcc tggctggaga gggctgtggc aatggaaaat tagtgccaac   6900
tgcaatgagt cagcctcggt taaatagaga gtgaagaatg ctggacagga acctccaccc   6960
tcatgtcaca tttcttcagt gtgacccttc tggcccctct cctcctgaca gcggaacaat   7020
gactgccccg ataggtgagg ctggaggaag aatcagtcct gtccttggca agctcttcac   7080
tatgacagta aaggctctct gcctgctgcc aaggcctgtg actttctaac ctggcctcac   7140
gctgggtaag cttaaggtag aggtgcagga ttagcaagcc cacctggcta ccaggccgac   7200
```

-continued

```
agctacatct ttcaactgac cctgatcaac gaagagggac ttgtgtctct cagttggttc   7260
caaatgaaac cagggagcag gggcgttagg aagctccaac aggatggtac ttaatggggc   7320
atttgagtgg agaggtaggt gacatagtgc tttggagccc agggagggaa aggttctgct   7380
gaagttgaat tcaagactgt tctttcatca caaacttgag tttcctggac atttgtttgc   7440
agaaacaacc gtagggtttt gccttaacct cgtgggttta ttattacctc atagggactt   7500
tgcctcctga cagcagttta tgggtgttca ttgtggcact tgagttttct tgcatacttg   7560
ttagagaaac caagtttgtc atcaacttct tatttaaccc cctggctata acttcatgga   7620
ttatgttata attaagccat ccagagtaaa atctgtttag attatcttgg agtaaggggg   7680
aaaaaatctg taattttttc tcctcaacta gatatataca taaaaaatga ttgtattgct   7740
tcatttaaaa aatataacgc aaaatctctt ttccttctaa aaaaaaaaaa aaaaaa       7796
```

<210> SEQ ID NO 5
<211> LENGTH: 1885
<212> TYPE: DNA
<213> ORGANISM: Homo sapiens

<400> SEQUENCE: 5

```
ctcgcccggt gcctaggtgc ccggccccac accgccagct gctcggcgcc cgggtccgcc     60
atgcgctccg ccgctgtcct ggctcttctg ctctgcgccg ggcaagtcac tgcgctccct    120
gtgaacagcc ctatgaataa aggggatacc gaggtgatga aatgcatcgt tgaggtcatc    180
tccgacacac tttccaagcc cagccccatg cctgtcagcc aggaatgttt tgagacactc    240
cgaggagatg aacggatcct ttccattctg agacatcaga atttactgaa ggagctccaa    300
gacctcgctc tccaaggcgc caaggagagg gcacatcagc agaagaaaca cagcggtttt    360
gaagatgaac tctcagaggt tcttgagaac cagagcagcc aggccgagct gaaagaggcg    420
gtggaagagc catcatccaa ggatgttatg gagaaaagag aggattccaa ggaggcagag    480
aaaagtggtg aagccacaga cggagccagg ccccaggccc tcccggagcc catgcaggag    540
tccaaggctg aggggaacaa tcaggcccct ggggaggaag aggaggagga ggaggaggcc    600
accaacaccc accctccagc cagcctcccc agccagaaat acccaggccc acaggccgag    660
ggggacagtg agggcctctc tcagggtctg gtggacagag agaagggcct gagtgcagag    720
ccagggtggc aggcaaagag agaagaggag gaggaggagg aggaggaggc tgaggctgga    780
gaggaggctg tccccgagga agaaggcccc actgtagtgc tgaacccccca cccgagcctt    840
ggctacaagg agatccggaa aggcgagagt cggtcggagg ctctggctgt ggatggagct    900
gggaagcctg gggctgagga ggctcaggac cccgaaggga agggagaaca ggagcactcc    960
cagcagaaag aggaggagga ggagatggca gtggtcccgc aaggcctctt ccggggtggg   1020
aagagcggag agctggagca ggaggaggag cggctctcca aggagtggga ggactccaaa   1080
cgctggagca agatggacca gctggccaag gagctgacgg ctgagaagcg gctggagggg   1140
caggaggagg aggaggacaa ccgggacagt tccatgaagc tctccttccg ggcccgggcc   1200
tacggcttca ggggccctgg gccgcagctg cgacgaggct ggaggccatc ctcccgggag   1260
gacagccttg aggcgggcct gcccctccag gtccgaggct accccgagga gaagaaagag   1320
gaggagggca gcgcaaaccg cagaccagag gaccaggagc tggagagcct gtcggccatt   1380
gaggcagagc tggagaaagt ggcccaccag ctgcaggcac tacggcgggg ctgagacacc   1440
gactggcagg gctggcccca gggcaccctg tggccctggc tctgctgtcc ccttggcagg   1500
tcctggccag atggcccgga cgctgcttcc ggtagggagg cagcctccag cctgcccaag   1560
```

```
cccaggccac cctatcgccc cctacgcgcc ttgtctccta ctcctgactc ctacctgccc   1620

tggaacatcc tttgcagggc agccccacaa ctttaaacat tgacgattcc ttctctgaac   1680

acaggcagct ttctagaagt ttcccttcct ccatcctatc cactgggcac aactgcaata   1740

acttctgacc ttttggtgaa agctgagaac tcctgactgt aacatattct gtatgaactt   1800

tatctaaaga aaaataaatc tgttctgggc tctttaaaaa aaaaaaaaaa aaaaaaaaaa   1860

aaaaaaaaaa aaaaaaaaaa aaaaa                                          1885
```

<210> SEQ ID NO 6
<211> LENGTH: 2358
<212> TYPE: DNA
<213> ORGANISM: Homo sapiens

<400> SEQUENCE: 6

```
aaactcacac aacaactctt ccccgctgag aggagacagc cagtgcgact ccaccctcca     60

gctcgacggc agccgccccg gccgacagcc ccgagacgac agcccggcgc gtcccggtcc    120

ccacctccga ccaccgccag cgctccaggc cccgccgctc cccgctcgcc gccaccgcgc    180

cctccgctcc gcccgcagtg ccaaccatga ccgccgccag tatgggcccc gtccgcgtcg    240

ccttcgtggt cctcctcgcc ctctgcagcc ggccggccgt cggccagaac tgcagcgggc    300

cgtgccggtg cccggacgag ccggcgccgc gctgcccggc gggcgtgagc ctcgtgctgg    360

acggctgcgg ctgctgccgc gtctgcgcca agcagctggg cgagctgtgc accgagcgcg    420

acccctgcga cccgcacaag ggcctcttct gtgacttcgg ctccccggcc aaccgcaaga    480

tcggcgtgtg caccgccaaa gatggtgctc cctgcatctt cggtggtacg gtgtaccgca    540

gcggagagtc cttccagagc agctgcaagt accagtgcac gtgcctggac ggggcggtgg    600

gctgcatgcc cctgtgcagc atggacgttc gtctgcccag ccctgactgc cccttcccga    660

ggagggtcaa gctgcccggg aaatgctgcg aggagtgggt gtgtgacgag cccaaggacc    720

aaaccgtggt tgggcctgcc ctcgcggctt accgactgga agacacgttt ggcccagacc    780

caactatgat tagagccaac tgcctggtcc agaccacaga gtggagcgcc tgttccaaga    840

cctgtgggat gggcatctcc acccgggtta ccaatgacaa cgcctcctgc aggctagaga    900

agcagagccg cctgtgcatg gtcaggcctt gcgaagctga cctggaagag aacattaaga    960

agggcaaaaa gtgcatccgt actcccaaaa tctccaagcc tatcaagttt gagctttctg   1020

gctgcaccag catgaagaca taccgagcta aattctgtgg agtatgtacc gacggccgat   1080

gctgcacccc ccacagaacc accaccctgc cggtggagtt caagtgccct gacggcgagg   1140

tcatgaagaa gaacatgatg ttcatcaaga cctgtgcctg ccattacaac tgtcccggag   1200

acaatgacat ctttgaatcg ctgtactaca ggaagatgta cggagacatg gcatgaagcc   1260

agagagtgag agacattaac tcattagact ggaacttgaa ctgattcaca tctcattttt   1320

ccgtaaaaat gatttcagta gcacaagtta tttaaatctg tttttctaac tgggggaaaa   1380

gattcccacc caattcaaaa cattgtgcca tgtcaaacaa atagtctatc aaccccagac   1440

actggtttga agaatgttaa gacttgacag tggaactaca ttagtacaca gcaccagaat   1500

gtatattaag gtgtggcttt aggagcagtg ggagggtacc agcagaaagg ttagtatcat   1560

cagatagcat cttatacgag taatatgcct gctatttgaa gtgtaattga gaaggaaaat   1620

tttagcgtgc tcactgacct gcctgtagcc ccagtgacag ctaggatgtg cattctccag   1680

ccatcaagag actgagtcaa gttgttcctt aagtcagaac agcagactca gctctgacat   1740
```

```
tctgattcga atgacactgt tcaggaatcg gaatcctgtc gattagactg gacagcttgt   1800

ggcaagtgaa tttgcctgta acaagccaga ttttttaaaa tttatattgt aaatattgtg   1860

tgtgtgtgtg tgtgtgtata tatatatata tgtacagtta tctaagttaa tttaaagttg   1920

tttgtgcctt tttatttttg tttttaatgc tttgatattt caatgttagc ctcaatttct   1980

gaacaccata ggtagaatgt aaagcttgtc tgatcgttca aagcatgaaa tggatactta   2040

tatggaaatt ctgctcagat agaatgacag tccgtcaaaa cagattgttt gcaaagggga   2100

ggcatcagtg tccttggcag gctgatttct aggtaggaaa tgtggtagcc tcacttttaa   2160

tgaacaaatg gcctttatta aaaactgagt gactctatat agctgatcag ttttttcacc   2220

tggaagcatt tgtttctact ttgatatgac tgtttttcgg acagtttatt tgttgagagt   2280

gtgaccaaaa gttacatgtt tgcacctttc tagttgaaaa taaagtgtat atttttttcta  2340

taaaaaaaaa aaaaaaa                                                  2358
```

```
<210> SEQ ID NO 7
<211> LENGTH: 1989
<212> TYPE: DNA
<213> ORGANISM: Homo sapiens

<400> SEQUENCE: 7

aatgtgtgcg cgctgtggta tgggtgtgca agtgtgcgaa ggcggcgtgt tgtgtgagcg     60

agagggtagc ggatgtgtgt gtgcgtgtgc gcgcgtggct ccgggtgtgc gccgctgcga    120

tagcgggtcc tttcccgggg cgggcgacgg gcgggctggg aaggtctcct cccctcacca    180

cattgagaaa tctcagtgag tcaccgagtg gttctgcata ttaatgagct cgctcgctgc    240

gagggcagga gcggatttaa aagaggccag ggcgggcgga gggaggctgt ggagagagcg    300

cggagacaag cgcagagcgc agcgcacggc cacagacagc cctgggcatc caccgacggc    360

gcagccggag ccagcagagc cggaaggcgc gccccgggca gagaaagccg agcagagctg    420

ggtggcgtct ccgggccgcc gctccgacgg gccagcgccc tccccatgtc cctgctccca    480

cgccgcgccc ctccggtcag catgaggctc ctggcggccg cgctgctcct gctgctgctg    540

gcgctgtaca ccgcgcgtgt ggacgggtcc aaatgcaagt gctcccggaa gggacccaag    600

atccgctaca gcgacgtgaa gaagctggaa atgaagccaa agtacccgca ctgcgaggag    660

aagatggtta tcatcaccac caagagcgtg tccaggtacc gaggtcagga gcactgcctg    720

caccccaagc tgcagagcac caagcgcttc atcaagtggt acaacgcctg gaacgagaag    780

cgcagggtct acgaagaata gggtgaaaaa cctcagaagg gaaaactcca aaccagttgg    840

gagacttgtg caaaggactt tgcagattaa aaaaaaaaaa aaaaaaaaaa aaaaaaaaaa    900

aaaaaaaaaa agcctttctt tctcacaggc ataagacaca aattatatat tgttatgaag    960

cactttttac caacggtcag tttttacatt ttatagctgc gtgcgaaagg cttccagatg   1020

ggagacccat ctctcttgtg ctccagactt catcacaggc tgctttttat caaaaagggg   1080

aaaactcatg cctttccttt ttaaaaaatg cttttttgta tttgtccata cgtcactata   1140

catctgagct ttataagcgc ccgggaggaa caatgagctt ggtggacaca tttcattgca   1200

gtgttgctcc attcctagct tgggaagctt ccgcttagag gtcctggcgc ctcggcacag   1260

ctgccacggg ctctcctggg cttatggccg gtcacagcct cagtgtgact ccacagtggc   1320

ccctgtagcc gggcaagcag gagcaggtct ctctgcatct gttctctgag gaactcaagt   1380

ttggttgcca gaaaaatgtg cttcattccc ccctggttaa tttttacaca ccctaggaaa   1440

catttccaag atcctgtgat ggcgagacaa atgatcctta aagaaggtgt ggggtctttc   1500
```

-continued ccaacctgag gatttctgaa aggttcacag gttcaatatt taatgcttca gaagcatgtg 1560
aggttcccaa cactgtcagc aaaaacctta ggagaaaact taaaaatata tgaatacatg 1620
cgcaatacac agctacagac acacattctg ttgacaaggg aaaaccttca aagcatgttt 1680
ctttccctca ccacaacaga acatgcagta ctaaagcaat atatttgtga ttccccatgt 1740
aattcttcaa tgttaaacag tgcagtcctc tttcgaaagc taagatgacc atgcgccctt 1800
tcctctgtac atataccctt aagaacgccc cctccacaca ctgcccccca gtatatgccg 1860
cattgtactg ctgtgttata tgctatgtac atgtcagaaa ccattagcat tgcatgcagg 1920
tttcatattc tttctaagat ggaaagtaat aaaatatatt tgaaatgtac caaaaaaaaa 1980
aaaaaaaaa 1989

<210> SEQ ID NO 8
<211> LENGTH: 3851
<212> TYPE: DNA
<213> ORGANISM: Homo sapiens

<400> SEQUENCE: 8
ctctcccaac cgcctcgtcg cactcctcag gctgagagca ccgctgcact cgcggccggc 60
gatgcgggac cccggcgcgg ccgctccgct ttcgtccctg ggcctctgtg ccctggtgct 120
ggcgctgctg ggcgcactgt ccgcgggcgc cggggcgcag ccgtaccacg gagagaaggg 180
catctccgtg ccggaccacg gcttctgcca gcccatctcc atcccgctgt gcacggacat 240
cgcctacaac cagaccatcc tgcccaacct gctgggccac acgaaccaag aggacgcggg 300
cctcgaggtg caccagttct acccgctggt gaaggtgcag tgttctcccg aactccgctt 360
tttcttatgc tccatgtatg cgcccgtgtg caccgtgctc gatcaggcca tcccgccgtg 420
tcgttctctg tgcgagcgcg cccgccaggg ctgcgaggcg ctcatgaaca agttcggctt 480
ccagtggccc gagcggctgc gctgcgagaa cttcccggtg cacggtgcgg gcgagatctg 540
cgtgggccag aacacgtcgg acggctccgg gggcccaggc ggcggcccca ctgcctaccc 600
taccgcgccc tacctgccgg acctgccctt caccgcgctg cccccggggg cctcagatgg 660
cagggggcgt cccgccttcc ccttctcatg cccccgtcag ctcaaggtgc ccccgtacct 720
gggctaccgc ttcctgggtg agcgcgattg tggcgccccg tgcgaaccgg gccgtgccaa 780
cggcctgatg tactttaagg aggaggagag gcgcttcgcc cgcctctggg tgggcgtgtg 840
gtccgtgctg tgctgcgcct cgacgctctt taccgttctc acctacctgg tggacatgcg 900
gcgcttcagc tacccagagc ggcccatcat cttcctgtcg ggctgctact tcatggtggc 960
cgtggcgcac gtggccggct tccttctaga ggaccgcgcc gtgtgcgtgg agcgcttctc 1020
ggacgatggc taccgcacgg tggcgcaggg caccaagaag gagggctgca ccatcctctt 1080
catggtgctc tacttcttcg gcatggccag ctccatctgg tgggtcattc tgtctctcac 1140
ttggttcctg gcggccggca tgaagtgggg ccacgaggcc atcgaggcca actcgcagta 1200
cttccacctg gccgcgtggg ccgtgcccgc cgtcaagacc atcactatcc tggccatggg 1260
ccaggtagac ggggacctgc tgagcggggt gtgctacgtt ggcctctcca gtgtggacgc 1320
gctgcggggc ttcgtgctgg cgcctctgtt cgtctacctc ttcataggca cgtccttctt 1380
gctggccggc ttcgtgtccc tcttccgtat ccgcaccatc atgaaacacg acggcaccaa 1440
gaccgagaag ctggagaagc tcatggtgcg catcggcgtc ttcagcgtgc tctacacagt 1500
gcccgccacc atcgtcctgg cctgctactt ctacgagcag gccttccgcg agcactggga 1560

-continued

```
gcgcacctgg ctcctgcaga cgtgcaagag ctatgccgtg ccctgcccgc ccggccactt   1620
cccgcccatg agccccgact tcaccgtctt catgatcaag tacctgatga ccatgatcgt   1680
cggcatcacc actggcttct ggatctggtc gggcaagacc ctgcagtcgt ggcgccgctt   1740
ctaccacaga cttagccaca gcagcaaggg ggagactgcg gtatgagccc cggcccctcc   1800
ccacctttcc caccccagcc ctcttgcaag aggagaggca cggtagggaa aagaactgct   1860
gggtgggggc ctgtttctgt aactttctcc ccctctactg agaagtgacc tggaagtgag   1920
aagttctttg cagatttggg gcgaggggtg atttggaaaa gaagacctgg gtggaaagcg   1980
gtttggatga aaagatttca ggcaaagact tgcaggaaga tgatgataac ggcgatgtga   2040
atcgtcaaag gtacgggcca gcttgtgcct aatagaaggt tgagaccagc agagactgct   2100
gtgagtttct cccggctccg aggctgaacg gggactgtga gcgatccccc tgctgcaggg   2160
cgagtggcct gtccagaccc ctgtgaggcc ccgggaaagg tacagccctg tctgcggtgg   2220
ctgctttgtt ggaaagaggg agggcctcct gcggtgtgct tgtcaagcag tggtcaaacc   2280
ataatctctt ttcactgggg ccaaactgga gcccagatgg gttaatttcc agggtcagac   2340
attacggtct ctcctcccct gccccctccc gcctgttttt cctcccgtac tgctttcagg   2400
tcttgtaaaa taagcatttg gaagtcttgg gaggcctgcc tgctagaatc ctaatgtgag   2460
gatgcaaaag aaatgatgat aacattttga gataaggcca aggagacgtg gagtaggtat   2520
ttttgctact ttttcatttt ctggggaagg caggaggcag aaagacgggt gttttatttg   2580
gtctaatacc ctgaaaagaa gtgatgactt gttgcttttc aaaacaggaa tgcatttttc   2640
cccttgtctt tgttgtaaga gacaaaagag gaaacaaaag tgtctccctg tggaaaggca   2700
taactgtgac gaaagcaact tttataggca aagcagcgca aatctgaggt ttcccgttgg   2760
ttgttaattt ggttgagata aacattcctt tttaaggaaa agtgaagagc agtgtgctgt   2820
cacacaccgt taagccagag gttctgactt cgctaaagga aatgtaagag gttttgttgt   2880
ctgttttaaa taaatttaat tcggaacaca tgatccaaca gactatgtta aaatattcag   2940
ggaaatctct cccttcattt actttttctt gctataagcc tatatttagg tttcttttct   3000
atttttttct cccatttgga tcctttgagg taaaaaaaca taatgtcttc agcctcataa   3060
taaaggaaag ttaattaaaa aaaaaaagca aagagccatt ttgtcctgtt ttcttggttc   3120
catcaatctg tttattaaac atcatccata tgctgaccct gtctctgtgt ggttgggttg   3180
ggaggcgatc agcagatacc atagtgaacg aagaggaagg tttgaaccat gggccccatc   3240
tttaaagaaa gtcattaaaa gaaggtaaac ttcaaagtga ttctggagtt ctttgaaatg   3300
tgctggaaga cttaaattta ttaatcttaa atcatgtact ttttttctgt aatagaactc   3360
ggattctttt gcatgatggg gtaaagctta gcagagaatc atgggagcta acctttatcc   3420
cacctttgac actaccctcc aatcttgcaa cactatcctg tttctcagaa cagtttttaa   3480
atgccaatca tagagggtac tgtaaagtgt acaagttact ttatatatgt aatgttcact   3540
tgagtggaac tgctttttac attaaagtta aaatcgatct tgtgtttctt caaccttcaa   3600
aactatctca tctgtcagat ttttaaaact ccaacacagg ttttggcatc ttttgtgctg   3660
tatcttttaa gtgcatgtga aatttgtaaa atagagataa gtacagtatg tatattttgt   3720
aaatctccca tttttgtaag aaaatatata ttgtatttat acatttttac tttggatttt   3780
tgttttgttg gctttaaagg tctaccccac tttatcacat gtacagatca caaataaatt   3840
tttttaaata c                                                        3851
```

<210> SEQ ID NO 9
<211> LENGTH: 5755
<212> TYPE: DNA
<213> ORGANISM: Homo sapiens

<400> SEQUENCE: 9
gagtcgcgca cgcgcgcccg ggactgcctg cccctctctg tgacttgcct gtgtgtgtgc 60
gtgtgtgtat gtgtgtgtgt gtgtgtgtgt gcgcgcgcgc gtgagtgaga gaggagagag 120
ggagaagaga gcgcgagaga gggtgagtgt gtgtgagtgc atgggagggt gctgaatatt 180
ccgagacact gggaccacag cggcagctcc gctgaaaact gcattcagcc agtcctccgg 240
acttctggag cggggacagg gcgcagggca tcagcagcca ccagcaggac ctgggaaata 300
gggattcttc tgcctccact tcaggtttta gcagcttggt gctaaattgc tgtctcaaaa 360
tgcagaggat ctaatttgca gaggaaaaca gccaaagaag gaagaggagg aaaaggaaaa 420
aaaaaggggt atattgtgga tgctctactt ttcttggaaa tgcaaaagat tatgcatatt 480
tctgtcctcc tttctcctgt tttatgggga ctgatttttg gtgtctcttc taacagcata 540
cagatagggg ggctatttcc taggggcgcc gatcaagaat acagtgcatt tcgagtaggg 600
atggttcagt tttccacttc ggagttcaga ctgacacccc acatcgacaa tttggaggtg 660
gcaaacagct tcgcagtcac taatgctttc tgctcccagt tttcgagagg agtctatgct 720
atttttggat tttatgacaa gaagtctgta aataccatca catcattttg cggaacactc 780
cacgtctcct tcatcactcc cagcttccca acagatggca cacatccatt tgtcattcag 840
atgagacccg acctcaaagg agctctcctt agcttgattg aatactatca atgggacaag 900
tttgcatacc tctatgacag tgacagaggc ttatcaacac tgcaagctgt gctggattct 960
gctgctgaaa agaaatggca agtgactgct atcaatgtgg gaaacattaa caatgacaag 1020
aaagatgaga tgtaccgatc actttttcaa gatctggagt taaaaaagga acggcgtgta 1080
attctggact gtgaaaggga taaagtaaac gacattgtag accaggttat taccattgga 1140
aaacatgtta aagggtacca ctacatcatt gcaaatctgg gatttactga tggagaccta 1200
ttaaaaatcc agtttggagg tgcaaatgtc tctggatttc agatagtgga ctatgatgat 1260
tcgttggtat ctaaatttat agaaagatgg tcaacactgg aagaaaaaga ataccctgga 1320
gctcacacaa caacaattaa gtatacttct gctctgacct atgatgccgt tcaagtgatg 1380
actgaagcct tccgcaacct aaggaagcaa agaattgaaa tctcccgaag gggggaatgca 1440 ggagactgtc tggcaaaccc agcagtgccc tggggacaag gtgtagaaat agaaagggcc 1500
ctcaaacagg ttcaggttga aggtctctca ggaaatataa agtttgacca gaatggaaaa 1560
agaataaact atacaattaa catcatggag ctcaaaacta atgggccccg gaagattggc 1620
tactggagtg aagtggacaa aatggttgtt acccttactg agctcccttc tggaaatgac 1680
acctctgggc ttgagaataa gactgttgtt gtcaccacaa ttttggaatc tccgtatgtt 1740
atgatgaaga aaaatcatga aatgcttgaa ggcaatgagc gctatgaggg ctactgtgtt 1800
gacctggctg cagaaatcgc caaacattgt gggttcaagt acaagttgac aattgttggt 1860
gatggcaagt atggggccag ggatgcagac acgaaaattt ggaatgggat ggttggagaa 1920
cttgtatatg ggaaagctga tattgcaatt gctccattaa ctattaccct tgtgagagaa 1980
gaggtgattg acttctcaaa gcccttcatg agcctcggga tatctatcat gatcaagaag 2040
cctcagaagt ccaaaccagg agtgttttcc tttcttgatc ctttagccta tgagatctgg 2100
atgtgcattg tttttgccta cattggggtc agtgtagttt tattcctggt cagcagattt 2160

-continued

```
agcccctacg agtggcacac tgaggagttt gaagatggaa gagaaacaca aagtagtgaa   2220
tcaactaatg aatttgggat ttttaatagt ctctggtttt ccttgggtgc ctttatgcgg   2280
caaggatgcg atatttcgcc aagatccctc tctgggcgca ttgttggagg tgtgtggtgg   2340
ttctttaccc tgatcataat ctcctcctac acggctaact tagctgcctt cctgactgta   2400
gagaggatgg tgtctcccat cgaaagtgct gaggatcttt ctaagcaaac agaaattgct   2460
tatggaacat tagactctgg ctccactaaa gagtttttca ggagatctaa aattgcagtg   2520
tttgataaaa tgtggaccta catgcggagt gcggagccct ctgtgtttgt gaggactacg   2580
gccgaagggg tggctagagt gcggaagtcc aaagggaaat atgcctactt gttggagtcc   2640
acgatgaacg agtacattga gcaaaggaag ccttgcgaca ccatgaaagt tggtggaaac   2700
ctggattcca aaggctatgg catcgcaaca cctaaaggat cctcattaag aaccccagta   2760
aatcttgcag tattgaaact cagtgagcaa ggcgtcttag acaagctgaa aaacaaatgg   2820
tggtacgata aaggtgaatg tggagccaag gactctggaa gtaaggaaaa gaccagtgcc   2880
ctcagtctga gcaacgttgc tggagtattc tacatccttg tcgggggcct tggtttggca   2940
atgctggtgg ctttgattga gttctgttac aagtcaaggg ccgaggcgaa acgaatgaag   3000
gtggcaaaga atgcacagaa tattaaccca tcttcctcgc agaattcaca gaattttgca   3060
acttataagg aaggttacaa cgtatatggc atcgaaagtg ttaaaattta ggggatgacc   3120
ttgaatgatg ccatgaggaa caaggcaagg ctgtcaatta caggaagtac tggagaaaat   3180
ggacgtgtta tgactccaga atttcccaaa gcagtgcatg ctgtccctta cgtgagtcct   3240
ggcatgggaa tgaatgtcag tgtgactgat ctctcgtgat tgataagaac cttttgagtg   3300
ccttacacaa tggttttctt gtgtgtttat tgtcaaagtg gtgagaggca tccagtatct   3360
tgaagacttt tctttcagcc aagaattctt aaatatgtgg agttcatctt gaattgtaag   3420
gaatgattaa ttaaaacaca acatcttttt ctactcgagt tacagacaaa gcgtggtgga   3480
catgcacagc taacatggaa gtactataat ttacctgaag tctttgtaca gacaacaaac   3540
ctgtttctgc agccactatt gttagtctct tgattcataa tgacttaagc acacttgaca   3600
tcaactgcat caagatgtga catgttttat aaaaaaagga aaaaaaacat ttaaaactaa   3660
aaaatatttt taggtatttt cacaaacaaa ctggctttta aataaatttg cttccatatt   3720
ggttgaataa gacaaaaaca attaaactga gtgggaagtg aataaaaaaa ggctttaggt   3780
atcgattcca tatttttcaa agccaaatat gtaaatgcta aggaaagtaa acaaagagga   3840
gattccaatc ttgtaattta atattgttat taaaacttta atgtatccta ttctttaaca   3900
tttggtgtta atataaaatt acttggcaat gcttgacatt tgaaataaac atttttctat   3960
tgttttattg caagtggtcc aattaatttt gcttagctac agtttggtca taaatcaagt   4020
gagtttaaag acactaccaa gttgttaggt gcccagagaa aatttctccc ttttaaaaag   4080
gccaggtgat ttttcaaatg taatcttgcc cccaaagtaa tatctgaata tctttttgac   4140
atgtctaaat atatatatat ataaagaaat atttgttaac acaaaagcat ttgatctatg   4200
tagataaatg ctaatagatt taaaaagcta atattaacaa ataccagaat acgtgaagtt   4260
ccatttttaa agtgtttgag cttacagaag agaaacattc attttaaatg aagtaaaaaa   4320
tgccttgaaa gtaattcttt agatagttgc ccattgatta aattccaaaa actaaatatg   4380
tttttagctt taaaattata aaagctgtca taaactttat atattatgaa ttttaaaata   4440
tgtttgagtc tcctgcaata tagtttcatc ccattgacat caattaaaaa taaccctaat   4500
atattatttt tatatttatt cctcaggtgg aatggctatt ttaatatgcc cagtgtggat   4560
```

aaaatgtcac atttctgtaa cttttgacta aagagcctat atttatctag ttaatgaatt 4620
taaaggatct atctttccct tcataaaata cctcttattt ccattaaagc cccccaagtt 4680
taattaattt aggattttga atgattattg acatccaata gttattttta atatttgtat 4740
tcttgttatt tctggaagaa agcctttgtg tagcacttgg tattttgcaa agtgctttta 4800
aaacattctt acttaccgta tttcatagaa gggaaggaaa aatgtaaggt ttaacagtaa 4860
gcacttgcat tgaacatgga ggcatgtggt atcatgatat tcttcactaa atttagctgt 4920
ccctaatcac agatcctaag gtaatataat ataattttag tgcatttctc ctcatcagga 4980
atgctggagg tgcattttaa gttttaataa taagtgctag aatgaccaaa ttgcagacta 5040
attgtttcca tattgtactt aaaatgagtt tttaaaagtg aaaaagaaat gactatatac 5100
aatcaatgct atttattgta cctctgggcc tactcttcta aaaattgtag cttatcgatt 5160
tttctctgtc aagcttgaac taatgtaaat aattgaaata atgtaaagtt atattttcat 5220
gtttttatag atacaacatg acaagaatac ataatgtaag agtatttcaa ctatggataa 5280
tgttgattgg ataatgcaca tctcagttac aagcagtact catagtttaa tatccatgta 5340
acggtgcatc aatatattgc tatataaata tgtctgtgtg catataagtg aaaagtggtc 5400
aaacaagagt gatgacagct gtctaaaggt ttttttattc attttatata aaaactgtta 5460
tggaaagacc aaaatgttta tgaactattc ttatgtaaat ttacaattgt cctttactgt 5520 actttttgt ttacagtata gtaccttatt ttctgctgtg ttaagtgggt gtcaaactcc 5580
aagaagacat acactttcta taacttctat tgaagatatt ggaatttcca atttttcatg 5640
tgtactatgt cagaaaatgc tttcgatttt atttttaaat ctaacatcgg atggcttttc 5700
cggagtgttg taaaaacttc aatcatacat aaaacatgtt cttacaaaag gcaaa 5755

<210> SEQ ID NO 10
<211> LENGTH: 1681
<212> TYPE: DNA
<213> ORGANISM: Homo sapiens

<400> SEQUENCE: 10
ttttgtctgt cctggattgg agccgtccct ataaccatct agttccgagt acaaactgga 60
gacagaaata aatattaaag aaatcataga ccgaccaggt aaaggcaaag ggatgaattc 120
ctacttcact aacccttcct tatcctgcca cctcgccggg ggccaggacg tcctccccaa 180
cgtcgccctc aattccaccg cctatgatcc agtgaggcat ttctcgacct atggagcggc 240
cgttgcccag aaccggatct actcgactcc cttttattcg ccacaggaga atgtcgtgtt 300
cagttccagc cgggggccgt atgactatgg atctaattcc ttttaccagg agaaagacat 360
gctctcaaac tgcagacaaa acaccttagg acataacaca cagacctcaa tcgctcagga 420
ttttagttct gagcagggca ggactgcgcc ccaggaccag aaagccagta tccagattta 480
cccctggatg cagcgaatga attcgcacag tggggtcggc tacggagcgg accggaggcg 540
cggccgccag atctactcgc ggtaccagac cctggaactg gagaaggaat ttcacttcaa 600
tcgctaccta acgcggcgcc ggcgcatcga gatcgccaac gcgctttgcc tgaccgagcg 660
acagatcaaa atctggttcc agaaccgccg gatgaagtgg aaaaaagaat ctaatctcac 720
atccactctc tcggggggcg gcggaggggc caccgccgac agcctgggcg gaaaagagga 780
aaagcgggaa gagacagaag aggagaagca gaaagagtga ccaggactgt ccctgccacc 840
cctctctccc tttctccctc gctccccacc aactctcccc taatcacaca ctctgtattt 900

-continued

```
atcactggca caattgatgt gttttgattc cctaaaacaa aattagggag tcaaacgtgg    960
acctgaaagt cagctctgga ccccctccct caccgcacaa ctctctttca ccacgcgcct   1020
cctcctcctc gctcccttgc tagctcgttc tcggcttgtc tacaggccct tttccccgtc   1080
caggccttgg gggctcggac cctgaactca gactctacag attgccctcc aagtgaggac   1140
ttggctcccc cactccttcg acgcccccac ccccgccccc cgtgcagaga gccggctcct   1200
gggcctgctg gggcctctgc tccagggcct cagggcccgg cctggcagcc ggggagggcc   1260
ggaggcccaa ggagggcgcg ccttggcccc acaccaaccc ccagggcctc cccgcagtcc   1320
ctgcctagcc cctctgcccc agcaaatgcc cagcccaggc aaattgtatt taaagaatcc   1380
tgggggtcat tatggcattt tacaaactgt gaccgtttct gtgtgaagat ttttagctgt   1440
atttgtggtc tctgtattta tatttatgtt tagcaccgtc agtgttccta tccaatttca   1500
aaaaaggaaa aaaaagaggg aaaattacaa aaagagagaa aaaaagtgaa tgacgtttgt   1560
ttagccagta ggagaaaata aataaataaa taaatccctt cgtgttaccc tcctgtataa   1620
atccaacctc tgggtccgtt ctcgaatatt taataaaact gatattattt ttaaaacttt   1680
a                                                                   1681
```

```
<210> SEQ ID NO 11
<211> LENGTH: 12507
<212> TYPE: DNA
<213> ORGANISM: Homo sapiens

<400> SEQUENCE: 11
```

```
taccgggcgg aggtgagcgc ggcgccggct cctcctgcgg cggactttgg gtgcgacttg     60
acgagcggtg gttcgacaag tggccttgcg ggccggatcg tcccagtgga agagttgtaa    120
atttgcttct ggccttcccc tacggattat acctggcctt cccctacgga ttatactcaa    180
cttactgttt agaaaatgtg gcccacgaga cgcctggtta ctatcaaaag gagcggggtc    240
gacggtcccc actttcccct gagcctcagc acctgcttgt ttggaagggg tattgaatgt    300
gacatccgta tccagcttcc tgttgtgtca aaacaacatt gcaaaattga aatccatgag    360
caggaggcaa tattacataa tttcagttcc acaaatccaa cacaagtaaa tgggtctgtt    420
attgatgagc ctgtacggct aaaacatgga gatgtaataa ctattattga tcgttccttc    480
aggtatgaaa atgaaagtct tcagaatgga aggaagtcaa ctgaatttcc aagaaaaata    540
cgtgaacagg agccagcacg tcgtgtctca agatctagct tctcttctga ccctgatgag    600
aaagctcaag attccaaggc ctattcaaaa atcactgaag gaaaagtttc aggaaatcct    660
caggtacata tcaagaatgt caaagaagac agtaccgcag atgactcaaa agacagtgtt    720
gctcagggaa caactaatgt tcattcctca gaacatgctg gacgtaatgg cagaaatgca    780
gctgatccca tttctgggga ttttaaagaa atttccagcg ttaaattagt gagccgttat    840
ggagaattga agtctgttcc cactacacaa tgtcttgaca atagcaaaaa aaatgaatct    900
cccttttgga agctttatga gtcagtgaag aaagagttgg atgtaaaatc acaaaaagaa    960
aatgtcctac agtattgtag aaaatctgga ttacaaactg attacgcaac agagaaagaa   1020
agtgctgatg gtttacaggg ggagacccaa ctgttggtct cgcgtaagtc aagaccaaaa   1080
tctggtggga gcggccacgc tgtggcagag cctgcttcac ctgaacaaga gcttgaccag   1140
aacaagggga agggaagaga cgtggagtct gttcagactc ccagcaaggc tgtgggcgcc   1200
agctttcctc tctatgagcc ggctaaaatg aagacccctg tacaatattc acagcaacaa   1260
aattctccac aaaaacataa gaacaaagac ctgtatacta ctggtagaag agaatctgtg   1320
```

-continued

```
aatctgggta aaagtgaagg cttcaaggct ggtgataaaa ctcttactcc caggaagctt   1380
tcaactagaa atcgaacacc agctaaagtt gaagatgcag ctgactctgc cactaagcca   1440
gaaaatctct cttccaaaac cagaggaagt attcctacag atgtggaagt tctgcctacg   1500
gaaactgaaa ttcacaatga gccatttttta actctgtggc tcactcaagt tgagaggaag   1560
atccaaaagg attccctcag caagcctgag aaattgggca ctacagctgg acagatgtgc   1620
tctgggttac ctggtcttag ttcagttgat atcaacaact ttggtgattc cattaatgag   1680
agtgagggaa tacctttgaa aagaaggcgt gtgtcctttg gtgggcacct aagacctgaa   1740
ctatttgatg aaaacttgcc tcctaatacg cctctcaaaa ggggagaagc cccaaccaaa   1800
agaaagtctc tggtaatgca cactccacct gtcctgaaga aaatcatcaa ggaacagcct   1860
caaccatcag gaaaacaaga gtcaggttca gaaatccatg tggaagtgaa ggcacaaagc   1920
ttggttataa gccctccagc tcctagtcct aggaaaactc cagttgccag tgatcaacgc   1980
cgtaggtcct gcaaaacagc ccctgcttcc agcagcaaat ctcagacaga ggttcctaag   2040
agaggaggga gaaagagtgg caacctgcct tcaaagagag tgtctatcag ccgaagtcaa   2100
catgatattt tacagatgat atgttccaaa agaagaagtg gtgcttcgga agcaaatctg   2160
attgttgcaa aatcatgggc agatgtagta aaacttggtg caaaacaaac acaaactaaa   2220
gtcataaaac atggtcctca aaggtcaatg aacaaaaggc aaagaagacc tgctactcca   2280
aagaagcctg tgggcgaagt tcacagtcaa tttagtacag gccacgcaaa ctctccttgt   2340
accataataa tagggaaagc tcatactgaa aaagtacatg tgcctgctcg accctacaga   2400
gtgctcaaca acttcatttc caaccaaaaa atggacttta aggaagatct ttcaggaata   2460
gctgaaatgt tcaagacccc agtgaaggag caaccgcagt tgacaagcac atgtcacatc   2520
gctatttcaa attcagagaa tttgcttgga aaacagtttc aaggaactga ttcaggagaa   2580
gaacctctgc tccccacctc agagagtttt ggaggaaatg tgttcttcag tgcacagaat   2640
gcagcaaaac agccatctga taaatgctct gcaagccctc ccttaagacg gcagtgtatt   2700
agagaaaatg gaaacgtagc aaaaaacgcc aggaacacct acaaaatgac ttctctggag   2760
acaaaaaactt cagatactga gacagagcct tcaaaaacag tatccactgc aaacaggtca   2820
ggaaggtcta cagagttcag gaatatacag aagctacctg tggaaagtaa gagtgaagaa   2880
acaaatacag aaattgttga gtgcatccta aaaagaggtc agaaggcaac actactacaa   2940
caaaggagag aaggagagat gaaggaaata gaaagacctt ttgagacata taaggaaaat   3000
attgaattaa aagaaaacga tgaaaagatg aaagcaatga agagatcaag aacttggggg   3060
cagaaatgtg caccaatgtc tgacctgaca gacctcaaga gcttgcctga tacagaactc   3120
atgaaagaca cggcacgtgg ccagaatctc ctccaaaccc aagatcatgc caaggcacca   3180
aagagtgaga aaggcaaaat cactaaaatg ccctgccagt cattacaacc agaaccaata   3240
aacaccccaa cacacacaaa acaacagttg aaggcatccc tggggaaagt aggtgtgaaa   3300
gaagagctcc tagcagtcgg caagttcaca cggacgtcag gggagaccac gcacacgcac   3360
agagagccag caggagatgg caagagcatc agaacgttta aggagtctcc aaagcagatc   3420
ctggacccag cagcccgtgt aactggaatg aagaagtggc caagaacgcc taaggaagag   3480
gcccagtcac tagaagacct ggctggcttc aaagagctct tccagacacc aggtccctct   3540
gaggaatcaa tgactgatga gaaaactacc aaaatagcct gcaaatctcc accaccagaa   3600
tcagtggaca ctccaacaag cacaaagcaa tggcctaaga gaagtctcag gaaagcagat   3660
```

-continued

```
gtagaggaag aattcttagc actcaggaaa ctaacaccat cagcagggaa agccatgctt   3720
acgcccaaac cagcaggagg tgatgagaaa gacattaaag catttatggg aactccagtg   3780
cagaaactgg acctggcagg aactttacct ggcagcaaaa gacagctaca gactcctaag   3840
gaaaaggccc aggctctaga agacctggct ggctttaaag agctcttcca gactcctggt   3900
cacaccgagg aattagtggc tgctggtaaa accactaaaa taccctgcga ctctccacag   3960
tcagacccag tggacaccc aacaagcaca aagcaacgac ccaagagaag tatcaggaaa   4020
gcagatgtag agggagaact cttagcgtgc aggaatctaa tgccatcagc aggcaaagcc   4080
atgcacacgc ctaaaccatc agtaggtgaa gagaaagaca tcatcatatt tgtgggaact   4140
ccagtgcaga aactggacct gacagagaac ttaaccggca gcaagagacg gccacaaact   4200
cctaaggaag aggcccaggc tctggaagac ctgactggct ttaaagagct cttccagacc   4260
cctggtcata ctgaagaagc agtggctgct ggcaaaacta ctaaaatgcc ctgcgaatct   4320
tctccaccag aatcagcaga cacccaaca agcacaagaa ggcagcccaa gacacctttg   4380
gagaaaaggg acgtacagaa ggagctctca gccctgaaga agctcacaca gacatcaggg   4440
gaaaccacac acacagataa agtaccagga ggtgaggata aaagcatcaa cgcgtttagg   4500
gaaactgcaa aacagaaact ggacccagca gcaagtgtaa ctggtagcaa gaggcaccca   4560
aaaactaagg aaaaggccca acccctagaa gacctggctg gcttgaaaga gctcttccag   4620
acaccagtat gcactgacaa gcccacgact cacgagaaaa ctaccaaaat agcctgcaga   4680
tcacaaccag acccagtgga cacaccaaca agctccaagc cacagtccaa gagaagtctc   4740
aggaaagtgg acgtagaaga agaattcttc gcactcagga aacgaacacc atcagcaggc   4800
aaagccatgc acacacccaa accagcagta agtggtgaga aaaacatcta cgcatttatg   4860
ggaactccag tgcagaaact ggacctgaca gagaacttaa ctggcagcaa gagacggcta   4920
caaactccta aggaaaaggc ccaggctcta gaagacctgg ctggctttaa agagctcttc   4980
cagacacgag gtcacactga ggaatcaatg actaacgata aaactgccaa agtagcctgc   5040
aaatcttcac aaccagaccc agacaaaaac ccagcaagct ccaagcgacg gctcaagaca   5100
tccctgggga aagtgggcgt gaaagaagag ctcctagcag ttggcaagct cacacagaca   5160
tcaggagaga ctacacacac acacacagag ccaacaggag atggtaagag catgaaagca   5220
tttatggagt ctccaaagca gatcttagac tcagcagcaa gtctaactgg cagcaagagg   5280
cagctgagaa ctcctaaggg aaagtctgaa gtccctgaag acctggccgg cttcatcgag   5340
ctcttccaga caccaagtca cactaaggaa tcaatgacta acgaaaaaac taccaaagta   5400
tcctacagag cttcacagcc agacctagtg gacaccccaa caagctccaa gccacagccc   5460
aagagaagtc tcaggaaagc agacactgaa gaagaatttt tagcatttag gaaacaaacg   5520
ccatcagcag gcaaagccat gcacacaccc aaaccagcag taggtgaaga gaaagacatc   5580
aacacgtttt tgggaactcc agtgcagaaa ctggaccagc caggaaattt acctggcagc   5640
aatagacggc tacaaactcg taaggaaaag gcccaggctc tagaagaact gactggcttc   5700
agagagcttt tccagacacc atgcactgat aaccccacga ctgatgagaa aactaccaaa   5760
aaaatactct gcaaatctcc gcaatcagac ccagcggaca ccccaacaaa cacaaagcaa   5820
cggcccaaga gaagcctcaa gaaagcagac gtagaggaag aatttttagc attcaggaaa   5880
ctaacaccat cagcaggcaa agccatgcac acgcctaaag cagcagtagg tgaagagaaa   5940
gacatcaaca catttgtggg gactccagtg gagaaactgg acctgctagg aaatttacct   6000
ggcagcaaga gacggccaca aactcctaaa gaaaaggcca aggctctaga agatctggct   6060
```

```
ggcttcaaag agctcttcca gacaccaggt cacactgagg aatcaatgac cgatgacaaa   6120
atcacagaag tatcctgcaa atctccacaa ccagacccag tcaaaacccc aacaagctcc   6180
aagcaacgac tcaagatatc cttggggaaa gtaggtgtga aagaagaggt cctaccagtc   6240
ggcaagctca cacagacgtc agggaagacc acacagacac acagagagac agcaggagat   6300
ggaaagagca tcaaagcgtt taaggaatct gcaaagcaga tgctggaccc agcaaactat   6360
ggaactggga tggagaggtg gccaagaaca cctaaggaag aggcccaatc actagaagac   6420
ctggccggct tcaaagagct cttccagaca ccagaccaca ctgaggaatc aacaactgat   6480
gacaaaacta ccaaaatagc ctgcaaatct ccaccaccag aatcaatgga cactccaaca   6540
agcacaagga ggcggcccaa aacacctttg ggaaaaggg atatagtgga agagctctca   6600
gccctgaagc agctcacaca gaccacacac acagacaaag taccaggaga tgaggataaa   6660
ggcatcaacg tgttcaggga aactgcaaaa cagaaactgg acccagcagc aagtgtaact   6720
ggtagcaaga ggcagccaag aactcctaag ggaaaagccc aacccctaga agacttggct   6780
ggcttgaaag agctcttcca gacaccaata tgcactgaca agcccacgac tcatgagaaa   6840
actaccaaaa tagcctgcag atctccacaa ccagacccag tgggtacccc aacaatcttc   6900
aagccacagt ccaagagaag tctcaggaaa gcagacgtag aggaagaatc cttagcactc   6960
aggaaacgaa caccatcagt agggaaagct atggacacac ccaaaccagc aggaggtgat   7020
gagaaagaca tgaaagcatt tatgggaact ccagtgcaga aattggacct gccaggaaat   7080
ttacctggca gcaaaagatg gccacaaact cctaaggaaa aggcccaggc tctagaagac   7140
ctggctggct tcaaagagct cttccagaca ccaggcactg acaagcccac gactgatgag   7200
aaaactacca aaatagcctg caaatctcca caaccagacc cagtggacac cccagcaagc   7260
acaaagcaac ggcccaagag aaacctcagg aaagcagacg tagaggaaga atttttagca   7320
ctcaggaaac gaacaccatc agcaggcaaa gccatggaca caccaaaacc agcagtaagt   7380
gatgagaaaa atatcaacac atttgtggaa actccagtgc agaaactgga cctgctagga   7440
aatttacctg gcagcaagag acagccacag actcctaagg aaaaggctga ggctctagag   7500
gacctggttg gcttcaaaga actcttccag acaccaggtc acactgagga atcaatgact   7560
gatgacaaaa tcacagaagt atcctgtaaa tctccacagc cagagtcatt caaaacctca   7620
agaagctcca agcaaaggct caagataccc ctggtgaaag tggacatgaa agaagagccc   7680
ctagcagtca gcaagctcac acggacatca ggggagacta cgcaaacaca cacagagcca   7740
acaggagata gtaagagcat caaagcgttt aaggagtctc caaagcagat cctggaccca   7800
gcagcaagtg taactggtag caggaggcag ctgagaactc gtaaggaaaa ggcccgtgct   7860
ctagaagacc tggttgactt caaagagctc ttctcagcac caggtcacac tgaagagtca   7920
atgactattg acaaaaacac aaaaattccc tgcaaatctc cccccaccaga actaacagac   7980
actgccacga gcacaaagag atgccccaag acacgtccca ggaaagaagt aaaagaggag   8040
ctctcagcag ttgagaggct cacgcaaaca tcagggcaaa gcacacacac acacaaagaa   8100
ccagcaagcg gtgatgaggg catcaaagta ttgaagcaac gtgcaaagaa gaaaccaaac   8160
ccagtagaag aggaacccag caggagaagg ccaagagcac ctaaggaaaa ggcccaaccc   8220
ctggaagacc tggccggctt cacagagctc tctgaaacat caggtcacac tcaggaatca   8280
ctgactgctg gcaaagccac taaaataccc tgcgaatctc ccccactaga agtggtagac   8340
accacagcaa gcacaaagag gcatctcagg acacgtgtgc agaaggtaca agtaaaagaa   8400
```

-continued

```
gagccttcag cagtcaagtt cacacaaaca tcaggggaaa ccacggatgc agacaaagaa   8460
ccagcaggtg aagataaagg catcaaagca ttgaaggaat ctgcaaaaca gacaccggct   8520
ccagcagcaa gtgtaactgg cagcaggaga cggccaagag cacccaggga aagtgcccaa   8580
gccatagaag acctagctgg cttcaaagac ccagcagcag gtcacactga agaatcaatg   8640
actgatgaca aaaccactaa aataccctgc aaatcatcac cagaactaga agacaccgca   8700
acaagctcaa agagacggcc caggacacgt gcccagaaag tagaagtgaa ggaggagctg   8760
ttagcagttg gcaagctcac acaaacctca ggggagacca cgcacaccga caaagagccg   8820
gtaggtgagg gcaaaggcac gaaagcattt aagcaacctg caaagcggaa gctggacgca   8880
gaagatgtaa ttggcagcag gagacagcca agagcaccta aggaaaaggc ccaacccctg   8940
gaagatctgg ccagcttcca agagctctct caaacaccag gccacactga ggaactggca   9000
aatggtgctg ctgatagctt tacaagcgct ccaaagcaaa cacctgacag tggaaaacct   9060
ctaaaaatat ccagaagagt tcttcgggcc cctaaagtag aacccgtggg agacgtggta   9120
agcaccagag accctgtaaa atcacaaagc aaaagcaaca cttccctgcc cccactgccc   9180
ttcaagaggg gaggtggcaa agatggaagc gtcacgggaa ccaagaggct gcgctgcatg   9240
ccagcaccag aggaaattgt ggaggagctg ccagccagca agaagcagag ggttgctccc   9300
agggcaagag gcaaatcatc cgaacccgtg gtcatcatga agagaagttt gaggacttct   9360
gcaaaaagaa ttgaacctgc ggaagagctg aacagcaacg acatgaaaac caacaaagag   9420
gaacacaaat tacaagactc ggtccctgaa aataagggaa tatccctgcg ctccagacgc   9480
caaaataaga ctgaggcaga acagcaaata actgaggtct ttgtattagc agaaagaata   9540
gaaataaaca gaaatgaaaa gaagcccatg aagacctccc cagagatgga cattcagaat   9600
ccagatgatg gagcccggaa acccatacct agagacaaag tcactgagaa caaaaggtgc   9660
ttgaggtctg ctagacagaa tgagagctcc cagcctaagg tggcagagga gagcggaggg   9720
cagaagagtg cgaaggttct catgcagaat cagaaaggga aaggagaagc aggaaattca   9780
gactccatgt gcctgagatc aagaaagaca aaaagccagc ctgcagcaag cactttggag   9840
agcaaatctg tgcagagagt aacgcggagt gtcaagaggt gtgcagaaaa tccaaagaag   9900
gctgaggaca atgtgtgtgt caagaaaata agaaccagaa gtcataggga cagtgaagat   9960
atttgacaga aaaatcgaac tgggaaaaat ataataaagt tagttttgtg ataagttcta  10020
gtgcagtttt tgtcataaat tacaagtgaa ttctgtaagt aaggctgtca gtctgcttaa  10080
gggaagaaaa ctttggattt gctgggtctg aatcggcttc ataaactcca ctgggagcac  10140
tgctgggctc ctggactgag aatagttgaa caccgggggc tttgtgaagg agtctgggcc  10200
aaggtttgcc ctcagctttg cagaatgaag ccttgaggtc tgtcaccacc cacagccacc  10260
ctacagcagc cttaactgtg acacttgcca cactgtgtcg tcgtttgttt gcctatgtcc  10320
tccagggcac ggtggcagga acaactatcc tcgtctgtcc caacactgag caggcactcg  10380
gtaaacacga atgaatggat gagcgcacgg atgaatggag cttacaagat ctgtctttcc  10440
aatggccggg ggcatttggt ccccaaatta aggctattgg acatctgcac aggacagtcc  10500
tatttttgat gtcctttcct ttctgaaaat aaagttttgt gctttggaga atgactcgtg  10560
agcacatctt tagggaccaa gagtgacttt ctgtaaggag tgactcgtgg cttgccttgg  10620
tctcttggga atacttttct aactagggtt gctctcacct gagacattct ccacccgcgg  10680
aatctcaggg tcccaggctg tgggccatca cgacctcaaa ctggctccta atctccagct  10740
ttcctgtcat tgaaagcttc ggaagtttac tggctctgct cccgcctgtt ttctttctga  10800
```

```
ctctatctgg cagcccgatg ccacccagta caggaagtga caccagtact ctgtaaagca  10860
tcatcatcct tggagagact gagcactcag caccttcagc cacgatttca ggatcgcttc  10920
cttgtgagcc gctgcctccg aaatctcctt tgaagcccag acatctttct ccagcttcag  10980
acttgtagat ataactcgtt catcttcatt tactttccac tttgccccct gtcctctctg  11040
tgttccccaa atcagagaat agcccgccat cccccaggtc acctgtctgg attcctcccc  11100
attcacccac cttgccaggt gcaggtgagg atggtgcacc agacagggta gctgtccccc  11160
aaaatgtgcc ctgtgcgggc agtgccctgt ctccacgttt gtttccccag tgtctggcgg  11220
ggagccaggt gacatcataa atacttgctg aatgaatgca gaaatcagcg gtactgactt  11280
gtactatatt ggctgccatg atagggttct cacagcgtca tccatgatcg taagggagaa  11340
tgacattctg cttgagggag ggaatagaaa ggggcaggga ggggacatct gagggcttca  11400
cagggctgca aagggtacag ggattgcacc agggcagaac aggggagggt gttcaaggaa  11460
gagtggctct tagcagaggc actttggaag gtgtgaggca taaatgcttc cttctacgta  11520
ggccaacctc aaaactttca gtaggaatgt tgctatgatc aagttgttct aacactttag  11580
acttagtagt aattatgaac ctcacataga aaaatttcat ccagccatat gcctgtggag  11640
tggaatattc tgtttagtag aaaaatcctt tagagttcag ctctaaccag aaatcttgct  11700
gaagtatgtc agcacctttt ctcaccctgg taagtacagt atttcaagag cacgctaagg  11760
gtggttttca ttttacaggg ctgttgatga tgggttaaaa atgttcattt aagggctacc  11820
cccgtgttta atagatgaac accacttcta cacaaccctc cttggtactg gggagaggag  11880
agatctgaca aatactgccc attcccctag gctgactgga tttgagaaca aatacccacc  11940
catttccacc atggtatggt aacttctctg agcttcagtt tccaagtgaa tttccatgta  12000
ataggacatt cccattaaat acaagctgtt tttacttttt cgcctcccag ggcctgtggg  12060
atctggtccc ccagcctctc ttgggctttc ttacactaac tctgtaccta ccatctcctg  12120
cctcccttag gcaggcacct ccaaccacca cacactccct gctgttttcc ctgcctggaa  12180
ctttccctcc tgccccacca agatcatttc atccagtcct gagctcagct taagggaggc  12240
ttcttgcctg tgggttccct cacccccatg cctgtcctcc aggctggggc aggttcttag  12300
tttgcctgga attgttctgt acctctttgt agcacgtagt gttgtggaaa ctaagccact  12360
aattgagttt ctggctcccc tcctggggtt gtaagttttg ttcattcatg agggccgact  12420
gcatttcctg gttactctat cccagtgacc agccacagga gatgtccaat aaagtatgtg  12480
atgaaatggt cttaaaaaaa aaaaaaa                                      12507
```

<210> SEQ ID NO 12
<211> LENGTH: 731
<212> TYPE: DNA
<213> ORGANISM: Homo sapiens

<400> SEQUENCE: 12

```
gagaactctt gagaccggga gcccagctgc ccaccctctg gacattcacc cagccaggtg     60
gtctcgtcac ctcagaggct ccgccagact cctgcccagg ccaggactga ggcaagcctc    120
aaggcacttc taggacctgc ctcttctcac caagatgaac tcactggttt cttggcagct    180
actgcttttc ctctgtgcca cccactttgg ggagccatta gaaaaggtgg cctctgtggg    240
gaattctaga cccacaggcc agcagctaga atccctgggc ctcctggccc ccggggagca    300
gagcctgccg tgcaccgaga ggaagccagc tgctactgcc aggctgagcc gtcgggggac    360
```

-continued

```
ctcgctgtcc ccgccccccg agagctccgg gagcccccag cagccgggcc tgtccgcccc    420
ccacagccgc cagatccccg caccccaggg cgcggtgctg gtgcagcggg agaaggacct    480
gccgaactac aactggaact ccttcggcct gcgcttcggc aagcgggagg cggcaccagg    540
gaaccacggc agaagcgctg ggcggggctg agggcgcagg tgcggggcag tgaacttcag    600
accccaaagg agtcagagca tgcggggcgg gggcgggggg cggggacgta gggctaaggg    660
agggggcgct ggagcttcca acccgaggca ataaaagaaa tgttgcgtaa ctcaaaaaaa    720
aaaaaaaaaa a                                                          731
```

<210> SEQ ID NO 13
<211> LENGTH: 5436
<212> TYPE: DNA
<213> ORGANISM: Homo sapiens

<400> SEQUENCE: 13

```
ggccgcggcg gcggaggcag cagcggcggc ggcagtggcg gcggcgaagg tggcggcggc     60
tcggccagta ctcccggccc ccgccatttc ggactgggag cgagcgcggc gcaggcactg    120
aaggcggcgg cggggccaga ggctcagcgg ctcccaggtg cgggagagag gcctgctgaa    180
aatgactgaa tataaacttg tggtagttgg agctggtggc gtaggcaaga gtgccttgac    240
gatacagcta attcagaatc attttgtgga cgaatatgat ccaacaatag aggattccta    300
caggaagcaa gtagtaattg atggagaaac ctgtctcttg gatattctcg acacagcagg    360
tcaagaggag tacagtgcaa tgagggacca gtacatgagg actggggagg gctttctttg    420
tgtatttgcc ataaataata ctaaatcatt tgaagatatt caccattata gagaacaaat    480
taaaagagtt aaggactctg aagatgtacc tatggtccta gtaggaaata aatgtgattt    540
gccttctaga acagtagaca caaaacaggc tcaggactta gcaagaagtt atggaattcc    600
ttttattgaa acatcagcaa agacaagaca gagagtggag gatgcttttt atacattggt    660
gagggagatc cgacaataca gattgaaaaa aatcagcaaa gaagaaaaga ctcctggctg    720
tgtgaaaatt aaaaaatgca ttataatgta atctgggtgt tgatgatgcc ttctatacat    780
tagttcgaga aattcgaaaa cataaagaaa agatgagcaa agatggtaaa aagaagaaaa    840
agaagtcaaa gacaaagtgt gtaattatgt aaatacaatt tgtacttttt tcttaaggca    900
tactagtaca agtggtaatt tttgtacatt acactaaatt attagcattt gttttagcat    960
tacctaattt ttttcctgct ccatgcagac tgttagcttt taccttaaat gcttatttta   1020
aaatgacagt ggaagttttt ttttcctcta agtgccagta ttcccagagt tttggttttt   1080
gaactagcaa tgcctgtgaa aaagaaactg aatacctaag atttctgtct tggggttttt   1140
ggtgcatgca gttgattact tcttattttt cttaccaatt gtgaatgttg gtgtgaaaca   1200
aattaatgaa gcttttgaat catccctatt ctgtgtttta tctagtcaca taaatggatt   1260
aattactaat ttcagttgag accttctaat tggtttttac tgaaacattg agggaacaca   1320
aatttatggg cttcctgatg atgattcttc taggcatcat gtcctatagt ttgtcatccc   1380
tgatgaatgt aaagttacac tgttcacaaa ggttttgtct cctttccact gctattagtc   1440
atggtcactc tccccaaaat attatatttt ttctataaaa agaaaaaaat ggaaaaaaat   1500
tacaaggcaa tggaaactat tataaggcca tttccttttc acattagata aattactata   1560
aagactccta atagcttttc ctgttaaggc agacccagta tgaaatgggg attattatag   1620
caaccatttt ggggctatat ttacatgcta ctaaattttt ataataattg aaaagatttt   1680
aacaagtata aaaaattctc ataggaatta aatgtagtct ccctgtgtca gactgctctt   1740
```

-continued

```
tcatagtata actttaaatc ttttcttcaa cttgagtctt tgaagatagt tttaattctg   1800
cttgtgacat taaaagatta tttgggccag ttatagctta ttaggtgttg aagagaccaa   1860
ggttgcaagg ccaggccctg tgtgaacctt tgagctttca tagagagttt cacagcatgg   1920
actgtgtccc cacggtcatc cagtgttgtc atgcattggt tagtcaaaat ggggagggac   1980
tagggcagtt tggatagctc aacaagatac aatctcactc tgtggtggtc ctgctgacaa   2040
atcaagagca ttgcttttgt ttcttaagaa aacaaactct tttttaaaaa ttacttttaa   2100
atattaactc aaaagttgag attttggggt ggtggtgtgc caagacatta attttttttt   2160
taaacaatga agtgaaaaag ttttacaatc tctaggtttg gctagttctc ttaacactgg   2220
ttaaattaac attgcataaa cacttttcaa gtctgatcca tatttaataa tgctttaaaa   2280
taaaaataaa aacaatcctt ttgataaatt taaaatgtta cttattttaa aataaatgaa   2340
gtgagatggc atggtgaggt gaaagtatca ctggactagg aagaaggtga cttaggttct   2400
agataggtgt cttttaggac tctgattttg aggacatcac ttactatcca tttcttcatg   2460
ttaaaagaag tcatctcaaa ctcttagttt ttttttttta caactatgta atttatattc   2520
catttacata aggatacact tatttgtcaa gctcagcaca atctgtaaat ttttaaccta   2580
tgttacacca tcttcagtgc cagtcttggg caaaattgtg caagaggtga agtttatatt   2640
tgaatatcca ttctcgtttt aggactcttc ttccatatta gtgtcatctt gcctccctac   2700
cttccacatg ccccatgact tgatgcagtt ttaatacttg taattcccct aaccataaga   2760
tttactgctg ctgtggatat ctccatgaag ttttcccact gagtcacatc agaaatgccc   2820
tacatcttat ttcctcaggg ctcaagagaa tctgacagat accataaagg gatttgacct   2880
aatcactaat tttcaggtgg tggctgatgc tttgaacatc tctttgctgc ccaatccatt   2940
agcgacagta ggatttttca aacctggtat gaatagacag aaccctatcc agtggaagga   3000
gaatttaata aagatagtgc tgaaagaatt ccttaggtaa tctataacta ggactactcc   3060
tggtaacagt aatacattcc attgttttag taaccagaaa tcttcatgca atgaaaaata   3120
ctttaattca tgaagcttac tttttttttt tggtgtcaga gtctcgctct tgtcacccag   3180
gctggaatgc agtggcgcca tctcagctca ctgcaacctc catctcccag gttcaagcga   3240
ttctcgtgcc tcggcctcct gagtagctgg gattacaggc gtgtgccact acactcaact   3300
aatttttgta tttttaggag agacggggtt tcaccctgtt ggccaggctg gtctcgaact   3360
cctgacctca agtgattcac ccaccttggc ctcataaacc tgttttgcag aactcattta   3420
ttcagcaaat atttattgag tgcctaccag atgccagtca ccgcacaagg cactgggtat   3480
atggtatccc caaacaagag acataatccc ggtccttagg tagtgctagt gtggtctgta   3540
atatcttact aaggcctttg gtatacgacc cagagataac acgatgcgta ttttagtttt   3600
gcaaagaagg ggtttggtct ctgtgccagc tctataattg ttttgctacg attccactga   3660
aactcttcga tcaagctact ttatgtaaat cacttcattg ttttaaagga ataaacttga   3720
ttatattgtt tttttatttg gcataactgt gattctttta ggacaattac tgtacacatt   3780
aaggtgtatg tcagatattc atattgaccc aaatgtgtaa tattccagtt ttctctgcat   3840
aagtaattaa aatatactta aaaattaata gttttatctg ggtacaaata aacaggtgcc   3900
tgaactagtt cacagacaag gaaacttcta tgtaaaaatc actatgattt ctgaattgct   3960
atgtgaaact acagatcttt ggaacactgt ttaggtaggg tgttaagact tacacagtac   4020
ctcgtttcta cacagagaaa gaaatggcca tacttcagga actgcagtgc ttatgagggg   4080
```

```
atatttaggc ctcttgaatt tttgatgtag atgggcattt ttttaaggta gtggttaatt   4140
acctttatgt gaactttgaa tggtttaaca aaagatttgt ttttgtagag attttaaagg   4200
gggagaattc tagaaataaa tgttacctaa ttattacagc cttaaagaca aaaatccttg   4260
ttgaagtttt tttaaaaaaa gctaaattac atagacttag gcattaacat gtttgtggaa   4320
gaatatagca gacgtatatt gtatcatttg agtgaatgtt cccaagtagg cattctaggc   4380
tctatttaac tgagtcacac tgcataggaa tttagaacct aacttttata ggttatcaaa   4440
actgttgtca ccattgcaca attttgtcct aatatataca tagaaacttt gtggggcatg   4500
ttaagttaca gtttgcacaa gttcatctca tttgtattcc attgattttt tttttcttct   4560
aaacattttt tcttcaaaca gtatataact ttttttaggg gatttttttt tagacagcaa   4620
aaactatctg aagatttcca tttgtcaaaa agtaatgatt tcttgataat tgtgtagtaa   4680
tgttttttag aacccagcag ttaccttaaa gctgaattta tatttagtaa cttctgtgtt   4740
aatactggat agcatgaatt ctgcattgag aaactgaata gctgtcataa aatgaaactt   4800
tctttctaaa gaaagatact cacatgagtt cttgaagaat agtcataact agattaagat   4860
ctgtgtttta gtttaatagt ttgaagtgcc tgtttgggat aatgataggt aatttagatg   4920
aatttagggg aaaaaaaagt tatctgcaga tatgttgagg gcccatctct ccccccacac   4980
ccccacagag ctaactgggt tacagtgttt tatccgaaag tttccaattc cactgtcttg   5040
tgttttcatg ttgaaaatac ttttgcattt ttcctttgag tgccaatttc ttactagtac   5100
tatttcttaa tgtaacatgt ttacctggaa tgtattttaa ctatttttgt atagtgtaaa   5160
ctgaaacatg cacattttgt acattgtgct ttcttttgtg ggacatatgc agtgtgatcc   5220
agttgttttc catcatttgg ttgcgctgac ctaggaatgt tggtcatatc aaacattaaa   5280
aatgaccact cttttaattg aaattaactt ttaaatgttt ataggagtat gtgctgtgaa   5340
gtgatctaaa atttgtaata tttttgtcat gaactgtact actcctaatt attgtaatgt   5400
aataaaaata gttacagtga caaaaaaaaa aaaaaa                             5436
```

<210> SEQ ID NO 14
<211> LENGTH: 2080
<212> TYPE: DNA
<213> ORGANISM: Homo sapiens

<400> SEQUENCE: 14

```
ggagggcagt ctccgagttt cggaggggct tggagtgagt ggacgcactc gggaattgta     60
ggaggacgag gctcagctct tgccaggcca aattgagaca tgtctgacac aagcgagagt    120
ggtgcaggtc taactcgctt ccaggctgaa gcttcagaaa aggacagtag ctcgatgatg    180
cagactctgt tgacagtgac ccagaatgtg gaggtcccag agacaccgaa ggcctcaaag    240
gcactggagg tctcagagga tgtgaaggtc tcaaaagcct ctggggtctc aaaggccaca    300
gaggtctcaa agaccccaga ggctcgggag gcacctgcca cccaggcctc atctactact    360
cagctgactg atacccaggt tctggcagct gaaaacaaga gtctagcagc tgacaccaag    420
aaacagaatg ctgacccgca ggctgtgaca atgcctgcca ctgagaccaa aaaggtcagc    480
catgtggctg atacaaaggt caatacaaag gctcaggaga ctgaggctgc accctctcag    540
gccccagcag atgaacctga gcctgagagt gcagctgccc agtctcagga gaatcaggat    600
actcggccca aggtcaaagc caagaaagcc cgaaaggtga agcatctgga tggggaagag    660
gatggcagca gtgatcagag tcaggcttct ggaaccacag gtggccgaag ggtctcaaag    720
gccctaatgg cctcaatggc ccgcagggct tcaaggggtc ccatagcctt ttgggcccgc    780
```

-continued

```
agggcatcaa ggactcggtt ggctgcttgg gcccggagag ccttgctctc cctgagatca    840

cctaaagccc gtaggggcaa ggctcgccgt agagctgcca agctccagtc atcccaagag    900

cctgaagcac caccacctcg ggatgtggcc cttttgcaag ggagggcaaa tgatttggtg    960

aagtaccttt tggctaaaga ccagacgaag attcccatca agcgctcgga catgctgaag   1020

gacatcatca aagaatacac tgatgtgtac cccgaaatca ttgaacgagc aggctattcc   1080

ttggagaagg tatttgggat tcaattgaag gaaattgata agaatgacca cttgtacatt   1140

cttctcagca ccttagagcc cactgatgca ggcatactgg gaacgactaa ggactcaccc   1200

aagctgggtc tgctcatggt gcttcttagc atcatcttca tgaatggaaa tcggtccagt   1260

gaggctgtca tctgggaggt gctgcgcaag ttggggctgc gccctgggat acatcattca   1320

ctctttgggg acgtgaagaa gctcatcact gatgagtttg tgaagcagaa gtacctggac   1380

tatgccagag tccccaatag caatcccccct gaatatgagt tcttctgggg cctgcgctct   1440

tactatgaga ccagcaagat gaaagtcctc aagtttgcct gcaaggtaca aaagaaggat   1500

cccaaggaat gggcagctca gtaccgagag gcgatggaag cggatttgaa ggctgcagct   1560

gaggctgcag ctgaagccaa ggctagggcc gagattagag ctcgaatggg cattgggctc   1620

ggctcggaga atgctgccgg gccctgcaac tgggacgaag ctgatatcgg accctgggcc   1680

aaagcccgga tccaggcggg agcagaagct aaagccaaag cccaagagag tggcagtgcc   1740

agcactggtg ccagtaccag taccaataac agtgccagtg ccagtgccag caccagtggt   1800

ggcttcagtg ctggtgccag cctgaccgcc actctcacat ttgggctctt cgctggcctt   1860

ggtggagctg gtgccagcac cagtggcagc tctggtgcct gtggtttctc ctacaagtga   1920

gattttagat attgttaatc ctgccagtct ttctcttcaa gccagggtgc atcctcagaa   1980

acctactcaa cacagcactc taggcagcca ctatcaatca attgaagttg acactctgca   2040

ttaaatctat ttgccatttc aaaaaaaaaa aaaaaaaaaa                          2080


<210> SEQ ID NO 15
<211> LENGTH: 2856
<212> TYPE: DNA
<213> ORGANISM: Homo sapiens

<400> SEQUENCE: 15

gcggccctcc cgtccctgcg cggcctcggc ggcctcggcg gcggcggcgg cggcggcggc     60

ggcagcagcg cggccccttt aaacgcctgc ggcgcccccc gcccccgcca tcgcgcctcc    120

attttcccgg ccgcccgcgc cgagcgccgc gcccgccccg ggcccctccg ccgccgccgg    180

cccggacatg gccgccaaca tgtacagggt cggagactac gtctactttg agaactcctc    240

cagcaaccca tacctgatcc ggagaatcga ggagctcaac aagacggcca atgggaacgt    300

ggaggccaaa gtggtgtgct tctaccggag gcgggacatc tccagcaccc tcatcgccct    360

ggccgacaag cacgcaaccc tgtcagtctg ctataaggcc ggaccggggg cggacaacgg    420

cgaggaaggg gaaatagaag aggaaatgga gaatccggaa atggtggacc tgcccgagaa    480

actaaagcac cagctgcggc atcgggagct gttcctctcc cggcagctgg agtctctgcc    540

cgccacgcac atcaggggca agtgcagcgt caccctgctc aacgagaccg agtcgctcaa    600

gtcctacctg gagcgggagg atttcttctt ctattctcta gtctacgacc cacagcagaa    660

gaccctgctg gcagataaag gagagattcg agtaggaaac cggtaccagg cagacatcac    720

cgacttgtta aaagaaggcg aggaggatgg ccgagaccag tccaggttgg agacccaggt    780
```

```
gtgggaggcg cacaacccac tcacagacaa gcagatcgac cagttcctgg tggtggcccg    840
ctctgtgggc accttcgcac gggccctgga ctgcagcagc tccgtccgac agcccagcct    900
gcacatgagc gccgcagctg cctcccgaga catcaccctg ttccacgcca tggatactct    960
ccacaagaac atctacgaca tctccaaggc catctcggcg ctggtgccgc agggcgggcc   1020
cgtgctctgc agggacgaga tggaggagtg gtctgcatca gaggccaacc ttttcgagga   1080
agccctggaa aaatatggga aggatttcac ggacattcag caagattttc tcccgtggaa   1140
gtcgctgacc agcatcattg agtactacta catgtggaag accaccgaca gatacgtgca   1200
gcagaaacgc ttgaaagcag ctgaagctga gagcaagtta aagcaagttt atattcccaa   1260
ctataacaag ccaaatccga accaaatcag cgtcaacaac gtcaaggccg gtgtggtgaa   1320
cggcacgggg gcgccgggcc agagccctgg ggctggccgg gcctgcgaga gctgttacac   1380
cacacagtct taccagtggt attcttgggg tccccctaac atgcagtgtc gtctctgcgc   1440
atcttgttgg acatattgga agaaatatgg tggcttgaaa atgccaaccc ggttagatgg   1500
agagaggcca ggaccaaacc gcagtaacat gagtccccac ggcctcccag cccggagcag   1560
cgggagcccc aagtttgcca tgaagaccag gcaggctttc tatctgcaca cgacgaagct   1620
gacgcggatc gcccggcgcc tgtgccgtga gatcctgcgc ccgtggcacg ctgcgcggca   1680
cccctacctg cccatcaaca gcgcggccat caaggccgag tgcacggcgc ggctgcccga   1740
agcctcccag agcccgctgg tgctgaagca ggcggtacgc aagccgctgg aagccgtgct   1800
tcggtatctt gagacccacc cccgcccccc caagcctgac cccgtgaaaa gcgtgtccag   1860
cgtgctcagc agcctgacgc ccgccaaggt ggcccccgtc atcaacaacg gctcccccac   1920
catcctgggc aagcgcagct acgagcagca caacggggtg gacggcaaca tgaagaagcg   1980
cctcttgatg cccagtaggg gtctggcaaa ccacggacag gccaggcaca tgggaccaag   2040
ccggaacctc ctgctcaacg ggaagtccta ccccaccaaa gtgcgcctga tccggggggg   2100
ctccctgccc ccagtcaagc ggcggcggat gaactggatc gacgccccgg atgacgtgtt   2160
ctacatggcc acagaggaga ccaggaagat ccgcaagctg ctctcatcct cggaaaccaa   2220
gcgtgctgcc cgccggccct acaagcccat cgccctgcgc cagagccagg ccctgccgcc   2280
gcggccaccg ccacctgcgc ccgtcaacga cgagcccatc gtcatcgagg actaggggcc   2340
gcccccacct gcggccgccc cccgcccctc gcccgcccac acggcccctt cccagccagc   2400
ccgccgcccg cccctcagtt tggtagtgcc ccacctcccg ccctcacctg cagagaaacg   2460
cgctccttgg cggacactgg gggaggagag gaagaagcgc ggctaactta ttccgagaat   2520
gccgaggagt tgtcgttttt agctttgtgt ttactttttg gctggagcgg agatgagggg   2580
ccaccccgtg cccctgtgct gcggggcctt ttgcccggag gccgggccct aaggttttgt   2640
tgtgttctgt tgaaggtgcc attttaaatt ttatttttat tacttttttt gtagatgaac   2700
ttgagctctg taacttacac ctggaatgtt aggatcgtgc ggccgcggcc ggccgagctg   2760
cctggcgggg ttggcccttg tcttttcaag taattttcat attaaacaaa aacaaagaaa   2820
aaaaatctta taaaaaggaa aaaaaaaaaa aaaaaa                            2856
```

<210> SEQ ID NO 16
<211> LENGTH: 4451
<212> TYPE: DNA
<213> ORGANISM: Homo sapiens

<400> SEQUENCE: 16

```
aaaagatatg gtggggtgct taacagagga ggttagacac cggcgggaac cagaggagcc     60
```

-continued caagcgcggc gcctgggcct cggggctgca ggagtcctcg gtgggggtat ggaggtcgcc 120
ggggaaggag gacggttcag ttgctaggca acccggcctg gacccgcctc tcgctcgcgt 180
tgctgggaga ctacaaggcc gggaggaggg cggcgaaagg gccctacgtg ctgacgctaa 240
ttgtatatga gcgcgagcgg cgggctcttg ggtctttttt agcgccatct gctcgcggcg 300
ccgcctcctg ctcctcccgc tgctgctgcc gctgccgccc tgagtcactg cctgcgcagc 360
tccggccgcc tggctcccca tactagtcgc cgatatttgg agttcttaca acatggcaga 420
cattgacaac aaagaacagt ctgaacttga tcaagatttg gatgatgttg aagaagtaga 480
agaagaggaa actggtgaag aaacaaaact caaagcacgt cagctaactg ttcagatgat 540
gcaaaatcct cagattcttg cagcccttca agaaagactt gatggtctgg tagaaacacc 600
aacaggatac attgaaagcc tgcctagggt agttaaaaga cgagtgaatg ctctcaaaaa 660
cctgcaagtt aaatgtgcac agatagaagc caaattctat gaggaagttc acgatcttga 720
aaggaagtat gctgttctct atcagcctct atttgataag cgatttgaaa ttattaatgc 780
aatttatgaa cctacggaag aagaatgtga atggaaacca gatgaagaag atgagatttc 840
ggaggaattg aaagaaaagg ccaagattga agatgagaaa aaagatgaag aaaaagaaga 900
ccccaaagga attcctgaat tttggttaac tgtttttaag aatgttgact tgctcagtga 960
tatggttcag gaacacgatg aacctattct gaagcacttg aaagatatta aagtgaagtt 1020
ctcagatgct ggccagccta tgagttttgt cttagaattt cactttgaac ccaatgaata 1080
ttttacaaat gaagtgctga caaagacata caggatgagg tcagaaccag atgattctga 1140
tcccttttct tttgatggac cagaaattat gggttgtaca gggtgccaga tagattggaa 1200
aaaaggaaag aatgtcactt tgaaaactat taagaagaag cagaaacaca agggacgtgg 1260
gacagttcgt actgtgacta aaacagtttc caatgactct ttctttaact tttttgcccc 1320
tcctgaagtt cctgagagtg gagatctgga tgatgatgct gaagctatcc ttgctgcaga 1380
cttcgaaatt ggtcactttt tacgtgagcg tataatccca agatcagtgt tatattttac 1440
tggagaagct attgaagatg atgatgatga ttatgatgaa gaaggtgaag aagcggatga 1500
ggaaggggaa gaagaaggag atgaggaaaa tgatccagac tatgacccaa agaaggatca 1560
aaacccagca gagtgcaagc agcagtgaag caggatgtat gtggccttga ggataacctg 1620
cactggtcta ccttctgctt ccctggaaag gatgaattta catcatttga caagcctatt 1680
ttcaagttat ttgttgtttg tttgcttgtt tttgtttttg cagctaaaat aaaaatttca 1740
aatacaattt tagttcttac aagataatgt cttaattttg taccaattca ggtagaagta 1800
gaggcctacc ttgaattaag ggttatactc agtttttaac acattgttga agaaaaggta 1860
ccagctttgg aacgagatgc tatactaata agcaagtgta aaaaaaaaaa aaaaagagga 1920
agaaaatctt aagtgattga tgctgttttc ttttaaaaaa aaaaaaaaaa attcattttc 1980
tttgggttag agctagagag aaggccccaa gcttctatgg tttcttctaa ttcttattgc 2040
ttaaagtatg agtatgtcac ttacccgtgc ttctgtttac tgtgtaatta aaatgggtag 2100
tactgtttac ctaactacct catggatgtg ttaaggcata ttgagttaaa tctcatataa 2160
tgtttctcaa tcttgttaaa agctcaaaat tttgggccta tttgtaatgc cagtgtgaca 2220
ctaagcattt tgttcacacc acgctttgat aactaaactg gaaaacaaag gtgttaagta 2280
cctctgttct ggatctgggc agtcagcact ctttttagat ctttgtgtgg ctcctatttt 2340
tatagaagtg gagggatgca ctatttcaca aggtccaaga tttgttttca gatatttttg 2400

-continued

```
atgactgtat tgtaaatact acagggatag cactatagta ttgtagtcat gagacttaaa   2460

gtggaaataa gactattttt gacaaaagat gccattaaat ttcagactgt agagccacat   2520

ttacaatacc tcaggctaat tactgttaat tttggggttg aacttttttt tgacagtgag   2580

ggtggattat tggattgtca ttagaggaag gtctagattt cctgctctta ataaaattac   2640

attgaattga tttttagagg taatgaaaac ttcctttctg agaagttagt gttaaggtct   2700

tggaatgtga acacattgtt tgtagtgcta tccattcctc tcctgagatt ttaacttact   2760

actggaaatc cttaaccaat tataatagct ttttttcttt attttcaaaa tgatttcctt   2820

tgctttgatt agacactatg tgcttttttt ttttaaccat agttcatcga aatgcagctt   2880

tttctgaact tcaaagatag aatcccattt ttaatgaact gaagtagcaa aatcatcttt   2940

ttcattcttt aggaaatagc tattgccaaa gtgaaggtgt agataatacc tagtcttgtt   3000

acataaaggg gatgtggttt gcagaagaat tttctttata aaattgaagt tttaagggac   3060

gtcagtgttt atgccatttt tccagttcca aaatgattcc attccattct agaaatttga   3120

agtatgtaac ctgaaatcct taataaaatt tggatttaat tttataaaat gtactggtga   3180

tattttgggt gttttttttt aaatgaatgt atatactttt tttttgaaga gtggagagta   3240

gtgatgtcta gagggagcta ttttgtgctg aggccactat gttctgtaaa tatataattt   3300

taagagcaac ctcacaatcc ctgctaagtg gagtttatta tttgaagact aaaatggaat   3360

tccatagttc ctgataggtt atattctggg ttattattct gagttatcta caaacatttt   3420

tgagatttgt ctttacactc tgattgtagt ttccagcagc ccatgcacac tgccaagtaa   3480

gtctcatttt ttcctgttag aaatggtgaa atatcatata atcacttata aagaaaactg   3540

atatgaaaaa attttagagt tgtttgcttt atggtcactc aagtagggta agtgttccac   3600

aaattccaca agttgatagt ttaacatgga tgtctgaaag ccacatatat aatttcttag   3660

gattcttaaa ttagtaaatc tagcttactg aagcagtatt agcatcacta ttttagattg   3720

caaaaatacc ttaattgtgt ggaactggct tgtagagtgg tacttaagaa aaatgggatt   3780

ctacctctat ttctgtttta gcacacttaa tcaggaaagg atatattaac tttcataaaa   3840

atatttttgt tgtgtgaata ggttaatgat atggtaaggc ccctaaaata actgaattaa   3900

ttgtttattg taattgtagg ccattcccat tattaaaaat aaagacaaaa cttgaagtaa   3960

ctgaaaatct tatcgtgcta tgtagaaata ttgaactaat attcaaatat ttgaatgctt   4020

tggtttcagg gattggttta aaattggagt cctttttat gggttagtct tacaaaaatt   4080

taagccttta tatttttgac tttaaatcaa aacaaatgtt attttaaatg tacagaatag   4140

attggtagtg cagaagagtg taagttcttc ataggagctt tagaaaagag aaatatgtgc   4200

taattcagtt ttttttaat ctgcactgta catatatact tggtaattat gagcttgatt   4260

ttgtttttgg aaatatgtgt tcataattta ggtaatttgc tacttaaagc actaagtctc   4320

tgatacctga aaagtacatg taaatggtga tggtgaaata atactgcagt taacttaata   4380

gatgtatact ggtgattttt gtatgctgga ttaaaactcc agatattaaa atataacctg   4440

gataaaaagc c                                                        4451
```

<210> SEQ ID NO 17
<211> LENGTH: 2117
<212> TYPE: DNA
<213> ORGANISM: Homo sapiens

<400> SEQUENCE: 17

```
agtccctgca gtggctgtaa caaaacccag acccccaggt cccggccaat ggaggcgatt     60
```

-continued

```
tagactggag tgggaccgcg tctgtcaaaa gcccgactcg gcagcagcgg cggagtccag    120

gaggagagct ggagccgccg cgctgcctcc ccgcccccgc cgggatttat tatttggact    180

ggacaattaa gtggccctga tgatgttacc aagcccggtc acctccaccc ctttctcagt    240

caaagacatt ttgaatctgg agcagcagca ccagcacttc catggtgcgc acttgcaggc    300

ggacttggag caccacttcc actctgcgcc ctgcatgctg gccgccgctg aggggacgca    360

attttctgac ggaggggagg aggacgagga agacgagggc gagaaattgt cctatttgaa    420

ctcactagcc gcagcagacg gccacgggga ttcagggctg tgtccccagg gctatgtcca    480

cacggtcctg cgagactcgt gcagcgagcc caaggaacat gaagaggagc ccgaggtcgt    540

gagggaccgg agccaaaaaa gctgccagct gaagaagtct ctagagacgg ccggagactg    600

caaggcggcg gaggagagcg agaggccgaa gccacgcagc cgccggaagc cccgggtcct    660

cttctcgcaa gcccaggtct tcgagctgga acgcaggttc aagcagcagc ggtacctgtc    720

ggcacccgag cgcgagcacc tcgccagcag cctgaagctc acatccactc aggtgaaaat    780

ctggttccag aatcgcaggt acaagtgcaa gagacagcgg caggacaagt ctctggagct    840

tggcgcacac gcgcccccgc cgccgccgcg ccgcgtggct gtcccggtgc tggtgcggga    900

cggcaagccg tgcgtcacgc ccagcgcgca ggcctacggc gcgccctaca gcgtgggcgc    960

cagcgcctac tcctacaaca gcttccccgc ctacggctat gggaactcgg ccgcggccgc   1020

cgccgccgcc gccgccgccg ccgcagcagc ggcggcctac agcagcagct atggctgtgc   1080

gtacccggcg ggcggcggcg gcggcggcgg cgggacctcc gcggcgacca ctgccatgca   1140

gcccgcctgc agcgcggccg gaggcggccc ctttgtgaac gtgagcaacc taggaggctt   1200

cggcagcggc ggcagcgcac agccgttgca ccagggtact gcagccgggg ccgcgtgcgc   1260

tcagggcacc ttgcagggca tccgggcctg gtagggacgg ggcgggtcac gcggcgggca   1320

ccccagcgca gcctggcgcc gcgggactga agctcgagaa gggcctgacc taaaggtcag   1380

gtcccctcgt taaaaaaata tgtacgtcta gctcctcagg gcttcggatc gcagctcact   1440

cgaggcctgg ggaaggggac tcaggggcga ggaggatgac tgggtccggt cgccaggact   1500

gtctctgagg cagaaacgcc ggctgggcgc cggggaggac gatggccccg accctggcag   1560

cgagaggaga ccaggaggct aggaccctgg ccgcgcttgg ttcttccaaa gcgagaaggg   1620

cttctctccc tctgcctttc cgcggcctcc gcgaagcgtt ggcggggagc ccaaggacat   1680

aacaaattaa aagcatgaag gagagaaaaa tgggggtcgt ggcttgagaa attccaggcc   1740

ctaccgatcc tctgccccct ttgcgggcct ggagcgccat agcacagtcg atttcgtttc   1800

gcagctgtct cccctccgca gcagatacct cggtccagat ctccggattg tcgggggacg   1860

caggactctt cgaggaaaac cagccgaatg agatcaaaag ttgggggtgg ggggaggctg   1920

aacaaactca ggacctggtg gcccaccgga ggtgttaccg ggtttccttt ctgtttcgta   1980

ttctgtattc agcacatgtt atctatctat ctatctatat aactataacc acacgccgtg   2040

tagacacccg ctgccacaca ctacaggagt caataaacaa ggtgcaatat tttcaaaaaa   2100

aaaaaaaaaa aaaaaaa                                                  2117
```

<210> SEQ ID NO 18
<211> LENGTH: 6671
<212> TYPE: DNA
<213> ORGANISM: Homo sapiens

<400> SEQUENCE: 18

-continued

```
cagagatcgc gagcgaggca ccagcctgca gccggccccc agcacatcct cagccgcaca      60
gacactcggc gaggtggagg tgagggcggg cgccagcgaa ctcggagagg ggctcgctca     120
ctcccaggcg atcccagccg ccaccgccgc cgcaccagca gcagcaacag cagcagcagc     180
ttccttcctc agactcccct cgagaggctg gccaagcggg tgtagccgtt gggggaggct     240
cccgccgggg gaacccggcg aggacaagag cagggcggcc gccttccact cgggctgtcc     300
ggcggcggct gcctccgccc gtgtgtccgt caagggtgcc gcgggatgtg tgtcagttta     360
cgcctctgag atcacacagc tgcctggggg ccgtgtgatg cccaaggcaa gtcttggttt     420
taattattat tattatcatt attgttacgc ttggctttcg ggaaatactc gtgatatttg     480
taggataaag gaaatgacac tttgaggaac tggagagaac atatatgcgt tttgttttta     540
agaggaaaac cgtgttctct tcccggcttg ttccctcttt gctgatttca ggagctactc     600
tcctcctggt gaggtggaaa ttccagcaag aatagaggtg aagacaagcc accaggactc     660
aggagggaaa cgctgaccat tagaaacctc tgcataagac gttgtaagga ggaaaataaa     720
agagagaaaa acacaaagat ttaaacaaga aacctacgaa cccagctctg gaaagagcca     780
ccttctccaa aatggatatg tttcctctca cctgggtttt cttagccctc tacttttcaa     840
gacaccaagt gagaggccaa ccagacccac cgtgcggagg tcgtttgaat tccaaagatg     900
ctggctatat cacctctccc ggttaccccc aggactaccc ctcccaccag aactgcgagt     960
ggattgttta cgcccccgaa cccaaccaga agattgtcct caacttcaac cctcactttg    1020
aaatcgagaa gcacgactgc aagtatgact ttatcgagat tcgggatggg gacagtgaat    1080
ccgcagacct cctgggcaaa cactgtggga acatcgcccc gcccaccatc atctcctcgg    1140
gctccatgct ctacatcaag ttcacctccg actacgcccg gcagggggca ggcttctctc    1200
tgcgctacga gatcttcaag acaggctctg aagattgctc aaaaaacttc acaagcccca    1260
acgggaccat cgaatctcct gggtttcctg agaagtatcc acacaacttg gactgcacct    1320
ttaccatcct ggccaaaccc aagatggaga tcatcctgca gttcctgatc tttgacctgg    1380
agcatgaccc tttgcaggtg ggagaggggg actgcaagta cgattggctg gacatctggg    1440
atggcattcc acatgttggc cccctgattg gcaagtactg tgggaccaaa acaccctctg    1500
aacttcgttc atcgacgggg atcctctccc tgacctttca cacggacatg gcggtggcca    1560
aggatggctt ctctgcgcgt tactacctgg tccaccaaga gccactagag aactttcagt    1620
gcaatgttcc tctgggcatg gagtctggcc ggattgctaa tgaacagatc agtgcctcat    1680
ctacctactc tgatgggagg tggacccctc aacaaagccg gctccatggt gatgacaatg    1740
gctggacccc caacttggat tccaacaagg agtatctcca ggtggacctg cgctttttaa    1800
ccatgctcac ggccatcgca acacagggag cgatttccag ggaaacacag aatggctact    1860
atgtcaaatc ctacaagctg gaagtcagca ctaatggaga ggactggatg gtgtaccggc    1920
atggcaaaaa ccacaaggta tttcaagcca acaacgatgc aactgaggtg gttctgaaca    1980
agctccacgc tccactgctg acaaggtttg ttagaatccg ccctcagacc tggcactcag    2040
gtatcgccct ccggctggag ctcttcggct gccgggtcac agatgctccc tgctccaaca    2100
tgctggggat gctctcaggc ctcattgcag actcccagat ctccgcctct tccacccagg    2160
aatacctctg gagccccagt gcagcccgcc tggtcagcag ccgctcgggc tggttccctc    2220
gaatccctca ggcccagccc ggtgaggagt ggcttcaggt agatctggga acacccaaga    2280
cagtgaaagg tgtcatcatc cagggagccc gcggaggaga cagtatcact gctgtggaag    2340
ccagagcatt tgtgcgcaag ttcaaagtct cctacagcct aaacggcaag gactgggaat    2400
```

```
acattcagga ccccaggacc cagcagccaa agctgttcga agggaacatg cactatgaca   2460
cccctgacat ccgaaggttt gaccccattc cggcacagta tgtgcgggta tacccggaga   2520
ggtggtcgcc ggcggggatt gggatgcggc tggaggtgct gggctgtgac tggacagact   2580
ccaagcccac ggtagagacg ctgggaccca ctgtgaagag cgaagagaca accacccccct   2640
accccaccga agaggaggcc acagagtgtg ggagaactg cagctttgag gatgacaaag   2700
atttgcagct cccttcggga ttcaattgca acttcgattt cctcgaggag ccctgtggtt   2760
ggatgtatga ccatgccaag tggctccgga ccacctgggc cagcagctcc agcccaaacg   2820
accggacgtt tccagatgac aggaatttct tgcggctgca gagtgacagc cagagagagg   2880
gccagtatgc ccggctcatc agcccccctg tccacctgcc ccgaagcccg gtgtgcatgg   2940
agttccagta ccaggccacg ggcggccgcg gggtggcgct gcaggtggtg cgggaagcca   3000
gccaggagag caagttgctg tgggtcatcc gtgaggacca gggcggcgag tggaagcacg   3060
ggcggatcat cctgcccagc tacgacatgg agtaccagat tgtgttcgag ggagtgatag   3120
ggaaaggacg ttccggagag attgccattg atgacattcg gataagcact gatgtcccac   3180
tggagaactg catggaaccc atctcggctt ttgcaggtga gaattttaaa gtggacatcc   3240
cagaaataca tgagagagaa ggatatgaag atgaaattga tgatgaatac gaggtggact   3300
ggagcaattc ttcttctgca acctcagggt ctggcgcccc ctcgaccgac aaagaaaaga   3360
gctggctgta caccctggat cccatcctca tcaccatcat cgccatgagc tcactgggcg   3420
tcctcctggg ggccacctgt gcaggcctcc tgctctactg cacctgttcc tactcgggcc   3480
tgagctcccg aagctgcacc acactggaga actacaactt cgagctctac gatggcctta   3540
agcacaaggt caagatgaac caccaaaagt gctgctccga ggcatgacgg attgcacctg   3600
aatcctatct gacgtttcat tccagcaaga ggggctgggg aagattacat tttttttcc   3660
tttggaaact gaatgccata atctcgatca aaccgatcca gaataccgaa ggtatggaca   3720
ggacagaaaa gcgagtcgca ggaggaaggg agatgcagcc gcacagggga tgattaccct   3780
cctaggaccg cggtggctaa gtcattgcag gaacggggct gtgttctctg ctgggacaaa   3840
acaggagctc atctctttgg ggtcacagtt ctattttgtt tgtgagtttg tattattatt   3900
attattatta ttattattat attttatttc tttggtctgt gagcaactca aagaggcaga   3960
agaggagaat gacttttcca gaatagaagt ggagcagtga tcattattct ccgctttctc   4020
tttctaatca acacttgaaa agcaaagtgt cttttcagcc tttccatctt tacaaataaa   4080
actcaaaaaa gccgtccagc ttatcccatc ctctgattgt cttctgactt aagggattta   4140
ctgtggtgta ggttctgcca gccaacccta caagctgcca tttccagtcc tagcatttaa   4200
gtaggatgtt gttgccttta acttttctta tccaggggaa aattgccatt ttagggtcag   4260
catgaacagc tctttcttgt atgcgattta aaacaaactg gaaaggaaac ttcacacgtc   4320
aaaatccata gaagcgcctg gacgaggctt aaagtgcttt gtgagtgaat aggagccatt   4380
cgctaattct agacccacag tgtctggtgg tggggcttcc cttgtggggc ttctggtggt   4440
ggttttgcct tttcttttcc ctcctccatg ttcttctaaa acatatacat atatacatac   4500
acacatacac atattcttca ggtctctaag cccctggaag cagcattgtg tgatattctc   4560
agaggcaggg gaaaatagag ggaaaaatag agactattgg tatgttctcc ccatcagcga   4620
gttattgtaa ctggtcacca ctggacggga aggagaacag aggagaggga aagagaagcc   4680
caacctctgt gatcatatga gggccaaggc tgagcagtgt agacagagac cctttgaaat   4740
```

-continued gcatttgtct ctcaaataga ctagtaaaca ccgacttctc ctttgggtta caaacaccat 4800
ttcaaccttt cgggagagtc agagctagga tgtacaagaa ctgattctaa ccagaagtcc 4860
gcaagtactg tggacaagaa tgcttaacca tgctgcttca gccttgagag acctaggttc 4920
ttacacatat gcacacacgc atacacacat gcacgcacac acacatacac acatgcacgc 4980
acgcacgcat gcacaccaat ttatgttttt attaagtgcc ttgaaaaaat gaagaaaaat 5040
gtattttccc tttatgtaaa aattagtgaa tatcttatga attaaggcat tcctctttcc 5100
ctaaccccga tggctccatt cccaagtacc ccaactcact gctgatccta ttaaaggaat 5160
gagtcctgct acccgagtgg tagtcatagc cctagatgac tctcaactac tcttcaaagg 5220
gaggcatcag gaatagaatg aaactgtgtg aaggataaga ttgttcgcat caagatccaa 5280
atcttgattt catattaacg cctaaggatt gcctgtgtgc tggaaatata tttgaaactc 5340
aaccagtatg cccagcctat tgcatatcat tgtcagacca tttttgctgc tgtggtcacc 5400
cacgatttca tttgtcttat acccaggtga aaggggaagg gtgaatggga ctggctggtt 5460
cctttaaatg ttaacttatg gaaatgctag ttcaaatggt aatgtcacag tgttttgtat 5520
gcagagagca agagttcaac caacagctgt ttattcatgt gtgtgtgtct ttgctgcttt 5580
gagttctctg tatctactgt gtatgtgaat ggtcatgtgg gactcagtgg tggtgttgtg 5640
actttgacct agggtccgag tgtcacagct gatcttggca ctcggcactc attggcacag 5700
tggtagttag aggtgaaaag tagagctgtc aagcccaagg gcttagcttt agggctcctc 5760
ctgagttcgg cccacagtag aagcaagatt ttaactagcc ccttttcctc ttcaccctcc 5820
catgatgcgc agtgttcaga aagctggtaa gtcctaggga tttccagaag tagcctgcag 5880
aagaaggtaa gtttgaaagc cactccaggg gtcctgatgc tgtcatgctc agtgagccat 5940
tttacagttc tccaaagtct agccctgttt cggacctgca cttcacctct aagttatgta 6000
caactcaacc tgcatccctc taaaagtcct atatccatat tcaccattgg ctaatttgag 6060
gccctgagtg ggccttgaat gctaaaaaga agcagggtac gcagggctac atgtagatac 6120
cacaccaagg ctggaggctg gtctgtcata agacagaaag aaagacgctg ggcccaattt 6180
tgacttggcc aggggacacc ttggtgtgtt tgttatcttt atctgtgggt aggctagctg 6240
acccatctcc ttgagtcatt ccctttggga aaccccactg ccagtattga tctccttttt 6300
gccttgtact gaatgacaca ttacctccac actctcccgg actaggtggt caacagggcc 6360
acagggttgc tttctgtctt tggtggggca ggggagttga cagggatgag ggtccaagga 6420
ataagcatga atgacaagaa aacaagggaa agagttaacc tgtcacatag caggttaact 6480
ttttcagggt ttgcagttag aggtattcga ccattcactg gctgagccag atcacgggaa 6540
cttgagagct tttactgtga ttcttcaatg taaaaaataa acaacaatgt caaactgtgt 6600
ttatatgatt tgtataaagc ctttttaaga ttactattta aataaacatt ataccagaga 6660
taaaaaaaaa a 6671

<210> SEQ ID NO 19
<211> LENGTH: 3130
<212> TYPE: DNA
<213> ORGANISM: Homo sapiens

<400> SEQUENCE: 19
gggagtaggc ggagacagag aggctgtatt tcagtgcagc ctgccagacc tcttctggag 60
gaagactgga caaagggggt cacacattcc ttccatacgg ttgagcctct acctgcctgg 120
tgctggtcac agttcagctt cttcatgatg gtggatccca atggcaatga atccagtgct 180

-continued

```
acatacttca tcctaatagg cctccctggt ttagaagagg ctcagttctg gttggccttc    240
ccattgtgct ccctctacct tattgctgtg ctaggtaact tgacaatcat ctacattgtg    300
cggactgagc acagcctgca tgagcccatg tatatatttc tttgcatgct ttcaggcatt    360
gacatcctca tctccacctc atccatgccc aaaatgctgg ccatcttctg gttcaattcc    420
actaccatcc agtttgatgc ttgtctgcta cagatgtttg ccatccactc cttatctggc    480
atggaatcca cagtgctgct ggccatggct tttgaccgct atgtggccat ctgtcaccca    540
ctgcgccatg ccacagtact tacgttgcct cgtgtcacca aaattggtgt ggctgctgtg    600
gtgcgggggg ctgcactgat ggcacccctt cctgtcttca tcaagcagct gcccttctgc    660
cgctccaata tcctttccca ttcctactgc ctacaccaag atgtcatgaa gctggcctgt    720
gatgatatcc gggtcaatgt cgtctatggc cttatcgtca tcatctccgc cattggcctg    780
gactcacttc tcatctcctt ctcatatctg cttattctta agactgtgtt gggcttgaca    840
cgtgaagccc aggccaaggc atttggcact tgcgtctctc atgtgtgtgc tgtgttcata    900
ttctatgtac ctttcattgg attgtccatg gtgcatcgct ttagcaagcg gcgtgactct    960
ccgctgcccg tcatcttggc caatatctat ctgctggttc ctcctgtgct caacccaatt   1020
gtctatggag tgaagacaaa ggagattcga cagcgcatcc ttcgactttt ccatgtggcc   1080
acacacgctt cagagcccta ggtgtcagtg atcaaacttc ttttccattc agagtcctct   1140
gattcagatt ttaatgttaa cattttggaa gacagtattc agaaaaaaaa tttccttaat   1200
aaaaatacaa ctcagatcct tcaaatatga aactggttgg ggaatctcca ttttttcaat   1260
attattttct tctttgtttt cttgctacat ataattatta ataccctgac taggttgtgg   1320
ttggagggtt attacttttc attttaccat gcagtccaaa tctaaactgc ttctactgat   1380
ggtttacagc attctgagat aagaatggta catctagaga acatttgcca aaggcctaag   1440
cacggcaaag gaaaataaac acagaatata ataaaatgag ataatctagc ttaaaactat   1500
aacttcctct tcagaactcc caaccacatt ggatctcaga aaaatgctgt cttcaaaatg   1560
acttctacag agaagaaata atttttcctc tggacactag cacttaaggg gaagattgga   1620
agtaaagcct tgaaaagagt acatttacct acgttaatga aagttgacac actgttctga   1680
gagttttcac agcatatgga ccctgttttt cctatttaat tttcttatca accctttaat   1740
taggcaaaga tattattagt accctcattg tagccatggg aaaattgatg ttcagtgggg   1800
atcagtgaat taaatggggt catacaagta taaaaattaa aaaaaaaaga cttcatgccc   1860
aatctcatat gatgtggaag aactgttaga gagaccaaca gggtagtggg ttagagattt   1920
ccagagtctt acattttcta gaggaggtat ttaatttctt ctcactcatc cagtgttgta   1980
tttaggaatt tcctggcaac agaactcatg gctttaatcc cactagctat tgcttattgt   2040
cctggtccaa ttgccaatta cctgtgtctt ggaagaagtg atttctaggt tcaccattat   2100
ggaagattct tattcagaaa gtctgcatag ggcttatagc aagttattta tttttaaaag   2160
ttccataggt gattctgata ggcagtgagg ttagggagcc accagttatg atgggaagta   2220
tggaatggca ggtcttgaag ataacattgg ccttttgagt gtgactcgta gctggaaagt   2280
gagggaatct tcaggaccat gctttatttg gggctttgtg cagtatggaa cagggacttt   2340
gagaccagga aagcaatctg acttaggcat gggaatcagg catttttgct tctgaggggc   2400
tattaccaag ggttaatagg tttcatcttc aacaggatat gacaacagtg ttaaccaaga   2460
aactcaaatt acaaatacta aaacatgtga tcatatatgt ggtaagtttc atttctttt    2520
```

```
tcaatcctca ggttccctga tatggattcc tataacatgc tttcatcccc ttttgtaatg   2580

gatatcatat ttggaaatgc ctatttaata cttgtatttg ctgctggact gtaagcccat   2640

gagggcactg tttattattg aatgtcatct ctgttcatca ttgactgctc tttgctcatc   2700

attgaatccc ccagcaaagt gcctagaaca taatagtgct tatgcttgac accggttatt   2760

tttcatcaaa cctgattcct tctgtcctga acacatagcc aggcaatttt ccagccttct   2820

ttgagttggg tattattaaa ttctggccat tacttccaat gtgagtggaa gtgacatgtg   2880

caatttctat acctggctca taaaaccctc ccatgtgcag cctttcatgt tgacattaaa   2940

tgtgacttgg gaagctatgt gttacacaga gtaaatcacc agaagcctgg atttctgaaa   3000

aaactgtgca gagccaaacc tctgtcattt gcaactccca cttgtatttg tacgaggcag   3060

ttggataagt gaaaaataaa gtactattgt gtcaagtctc tgaaaaaaaa aaaaaaaaaa   3120

aaaaaaaaaa                                                          3130
```

<210> SEQ ID NO 20
<211> LENGTH: 4846
<212> TYPE: DNA
<213> ORGANISM: Homo sapiens

<400> SEQUENCE: 20

```
gagcggtgct caggggaggg ctggagggga gggaaggaga gagagagggg agggcggcac     60

cgcccctagc cccgcgctcc ggaagtgaag cggccagacc accagctaat ggatgcggag    120

cggagggccc gctgaccgct ctccgcgcct ggagcagctt ggcttggctg gagctaagag    180

ccagacacac cactgtgtgg aggtgggtga tgtcttcctg tgctaaaagg tgaataaata    240

agctcctcac ctctcgcgga acactcggga acacatcaac aggggtccaa gccgccctgc    300

tgggaggctt ctcttcaaga gttctgggtc ccagagtgga aggcattttc ccatcaactg    360

gagagagacg aaacatcaga gaccaggagg ctgtggagaa agcagctgtc ccaggtgcct    420

caactatcag agaagggtca gcgtcacgtg gctgccagca tctttgagaa aatcactggc    480

aatcggactt cagagctgcg ggcacaggtg tggttagaac tgagatacga cctgccccacc   540

tgggtcaggc ctaaagacaa gaagtcctga gttcttgcca ctgagtaggc cagggtcatt    600

tgtccagaaa actttgtgac tgtctttgag tgacctagtc tgggacccat tcattggtgg    660

gttctaaggt tagaagctca tccaggatat tttcaatatt aagtcagtgc atagctgcac    720

cactaacaaa ttggtgcctg tagagtcaga gtgggtcaat tcttaggaca atggcgctgg    780

cactgttaga ggactggtgc aggataatga gtgtggatga gcagaagtca ctgatggtta    840

cggggatacc ggcggacttt gaggaggctg agattcagga ggtccttcag gagactttaa    900

agtctctggg caggtataga ctgcttggca agatattccg gaagcaggag aatgccaatg    960

ctgtcttact agagcttctg gaagatactg atgtctcggc cattcccagt gaggtccagg   1020

gaaagggggg tgtctggaag gtgatcttta agacccctaa tcaggacact gagtttcttg   1080

aaagattgaa cctgtttcta gaaaaagagg ggcagacggt ctcgggtatg tttcgagccc   1140

tggggcagga gggcgtgtct ccagccacag tgccctgcat ctcaccagaa ttactggccc   1200

atttgttggg acaggcaatg gcacatgcgc ctcagcccct gctacccatg agataccgga   1260

aactgcgagt attctcaggg agtgctgtcc cagccccaga ggaagagtcc tttgaggtct   1320

ggttggaaca ggccacggag atagtcaaag agtggccagt aacagaggca gaaaagaaaa   1380

ggtggctggc ggaaagcctg cggggccctg ccctggacct catgcacata gtgcaggcag   1440

acaacccgtc catcagtgta gaagagtgtt tggaggcctt taagcaagtg tttgggagcc   1500
```

-continued

```
tagagagccg caggacagcc caggtgaggt atctgaagac ctatcaggag gaaggagaga   1560
aggtctcagc ctatgtgtta cggctagaaa ccctgctccg gagagcggtg gagaaacgcg   1620
ccatccctcg gcgtattgcg gaccaggtcc gcctggagca ggtcatggct ggggccactc   1680
ttaaccagat gctgtggtgc cggcttaggg agctgaagga tcagggcccg ccccccagct   1740
tccttgagct aatgaaggta atacgggaag aagaggagga agaggcctcc tttgagaatg   1800
agagtatcga agagccagag gaacgagatg gctatggccg ctggaatcat gagggagacg   1860
actgaaaacc acctgggggc aggacccaca gccagtgggc taagaccttt aaaaaatttt   1920
tttctttaat gtatgggact gaaatcaaac catgaaagcc aattattgac cttccttcct   1980
tccttccttc cctcccttcc tccttctctc cttctctcct cctctctcct ctcctctcct   2040
ctctttcctt ccttccttcc tttttttcttt ttctctttct tctttatttc ttgggtctca   2100
ctctcatcac ccaggctaga gtgcagtggc acaaaaatct cggctcactg cagccttgac   2160
ttcccaggct caggctcagg tgatcctcac accttagcct cccaagtacc tgggactaca   2220
ggcacgcacc accatgccta gctattcttt tgtatttttg gtagagacag ggttttgctg   2280
tgttgctcag gctggtctgg aacccctagg ctcaaatgat gtgcccaact cggcctccca   2340
aagtgctggg attacaggca tgaaccgcca tgcctggccc ttgatttttc tttttaagaa   2400
aaaaatatct aggagtttct tagaccctat gtagattatt aatgaacaaa agattaaact   2460
ccaaatatta aatagtaagc ctgaaggaat ctgaaacact tgtacttcca attttcttta   2520
aataatccca aatagaccag aattggccca taccatagaa gaaagaattg gcagtcaaaa   2580
aaaaaaatac cttttgtaat gtttgaaaaa taaagctgtt tgacttgtca ggtgtttttcc   2640
tttctcaaat cagcaaattc tctctgagtg cctggctttg tgagacactg tacaaggagt   2700
tacaagacta cagctataac ctgcagttga gcagttataa acctacaaaa tgggccctgc   2760
cctcagagag gttccagtct agatgaggag ctgatctaga caggtaaaag gctaactaac   2820
cctttgtgta aataagttca tcaccccagt aaaagtgtca tcacccagtg aataggacca   2880
cctctgcctg cagatttttg ttgttgttgt tgtcattgtt gttgttgttt taacctggga   2940
agtgttcttc ctgcctttct gctaggtgtc agatagatgg tcccagagct aggtgctgtg   3000
tcaggccctg aagacacaga tgactcaacc taagctttac tttccagagg tccacagcct   3060
gagaggtgtc cccaaagaaa gggggacatg aggggactgc atgcttgaga gcagggttgt   3120
ttagggcagg tttggattta gtgagcaggc tggtttgctt agagaaggct tttagtggca   3180
acaaaggatg aagaggagag aaaaggaact cacatttatt gagggcctac tgtgtgcaaa   3240
gtgtttcatg tatatctcat tgaatgtata cagccaccct gttgtggtat aattttgctc   3300
tttataaaga gaaagaccga agctcagatg agttaagtgg tctcctcaac accaaaatgc   3360
caagaagtga tggagcctag acagaagccc agaactttct gactcacact agtccatcct   3420
ctaccatcac gatgactttc aaattgtgct ctgcagttct gcagattttc tagcagtgcc   3480
atctccaaaa tgtgttttaa actctttatt tttttaatta ttattagtat tattttgaga   3540
ctgagtcttg ctctatcacc caggctggag tgcagtggtg caatctcagc tcactgcaac   3600
ctccgcctcc caggttcaag cgatttcgtg cctcagcctc ccgagtagct gggattacag   3660
gcacccacca ccacgcccag ctaatttttg tatttttagt agaaatgggg tttcaccatg   3720
ttggccaggc tggtctcgaa ctcctgacct caagtgatcc actcacctcg gcctcccaaa   3780
gtgctgggat tacaggtgtg agccaccatg cctgggctaa actctttaag tctctagtaa   3840
```

```
atgcagctag attcaaatgg gctgataacc aaattttaac acatcagcat tcaccaccag   3900

gtttactttt attttcagat tggctcattt tgtgcagacc ttagagcaaa gtttccttta   3960

tggtatctgt gtacgtatcc aaacttcttt taattgttca cagattttaa aagcggtagc   4020

accacatggt tgtgtagatc agacctgtgt atttagatca gacctgtgta tcacgtaagt   4080

gtgtgagtgc agtgcagatg agcaccattt agttatatgt gctaggcaaa tctccaacac   4140

agttgatgtg tagtcttgtg gtagatttgt gcatactgta agcaaattgc ttagcttctc   4200

tagacatcag tttccacatc tgaaaaataa gaagatgaga gtacacggtt gttatgaaca   4260

aatgacttaa tgctttttaa gcacgttgca tgacatctgg aacacagaaa gccctcaata   4320

cattgaagct cttaggattt tcacgatgtt cctgtctgct caatgcatgc tttctttatt   4380

gttctgacag ttgtgtggta acaagctaat atgcttccag ttgacttcca gtctaccctg   4440

gtgttagaaa ccgtttcatc tcttattgta aatttgagtg cttgttgttt tttatatttg   4500

tgatgactct tccagcagtt gttgacaatt gttagaggtt tgacttttaa ataattactt   4560

atttttctg attgtggttc agtttaactg aagaatatcc tgagattgta agaaaagcat    4620

tttttaaaag gtatcacttg tgatcattta tctttctaaa ttctattttt aatactgttc   4680

caccaaagtg atgcagtggt taccatgaca ccctaatttc atgtgttttt gtatttatga   4740

aaatagtttc attgtcattt attggcggta tacaaagtaa aatgttataa atgtgaagtt   4800

ataaaataaa tatatgctaa taaaatcctg agtttttctg tttcct                  4846
```

<210> SEQ ID NO 21
<211> LENGTH: 4842
<212> TYPE: DNA
<213> ORGANISM: Homo sapiens

<400> SEQUENCE: 21

```
aagagcgcga gaggcgcggc gggaggagcc ggcggcgcgc gcctccctgg gcccggactc     60

ggccgcctcc cgccgcctcc cgcgcggcca tggactgagc gccgccggcc aggccgcggg    120

gatggggccg ccgctcccgc tgctgctgct gctactgctg ctgctgccgc cacgcgtcct    180

gcctgccgcc ccttcgtccg tcccccgcgg ccggcagctc ccggggcgtc tgggctgcct    240

gctcgaggag ggcctctgcg gagcgtccga ggcctgtgtg aacgatggag tgtttggaag    300

gtgccagaag gttccggcaa tggactttta ccgctacgag gtgtcgcccg tggccctgca    360

gcgcctgcgc gtggcgttgc agaagctttc cggcacaggt ttcacgtggc aggatgacta    420

tactcagtat gtgatggacc aggaacttgc agacctcccg aaaacctacc tgaggcgtcc    480

tgaagcatcc agcccagcca ggccctcaaa acacagcgtt ggcagcgaga ggaggtacag    540

tcgggagggc ggtgctgccc tggccaacgc cctccgacgc cacctgccct tcctggaggc    600

cctgtcccag gccccagcct cagacgtgct cgccaggacc catacggcgc aggacagacc    660

ccccgctgag ggtgatgacc gcttctccga gagcatcctg acctatgtgg cccacacgtc    720

tgcgctgacc taccctcccg ggtcccggac ccagctccgc gaggacctcc tgccgcggac    780

cctcggccag ctccagccag atgagctcag ccctaaggtg gacagtggtg tggacagaca    840

ccatctgatg gcggccctca gtgcctatgc tgcccagagg cccccagctc cccccgggga    900

gggcagcctg gagccacagt accttctgcg tgcaccctca agaatgccca ggcctttgct    960

ggcaccagcc gccccccaga agtggccttc acctctggga gattccgaag accccctccag  1020

cacaggcgat ggagcacgga ttcataccct cctgaaggac ctgcagaggc agccggctga   1080

ggtgaggggc ctgagtggcc tggagctgga cggcatggct gagctgatgg ctggcctgat   1140
```

-continued

```
gcaaggcgtg gaccatggag tagctcgagg cagccctggg agagcggccc tgggagagtc   1200
tggagaacag gcggatggcc ccaaggccac cctccgtgga gacagctttc cagatgacgg   1260
agtgcaggac gacgatgata gactttacca agaggtccat cgtctgagtg ccacactcgg   1320
gggcctcctg caggaccacg ggtctcgact cttacctgga gccctcccct ttgcaaggcc   1380
cctcgacatg gagaggaaga agtccgagca ccctgagtct tccctgtctt cagaagagga   1440
gactgccgga gtggagaacg tcaagagcca gacgtattcc aaagatctgc tggggcagca   1500
gccgcattcg gagcccgggg ccgctgcgtt tggggagctc caaaaccaga tgcctgggcc   1560
ctcgaaggag gagcagagcc ttccagcggg tgctcaggag gccctcagcg acggcctgca   1620
attggaggtc cagccttccg aggaagaggc gcggggctac atcgtgacag acagagaccc   1680
cctgcgcccc gaggaaggaa ggcggctggt ggaggacgtc gcccgcctcc tgcaggtgcc   1740
cagcagtgcg ttcgctgacg tggaggttct cggaccagca gtgaccttca aagtgagcgc   1800
caatgtccaa aacgtgacca ctgaggatgt ggagaaggcc acagttgaca acaaagacaa   1860
actggaggaa acctctggac tgaaaattct tcaaaccgga gtcgggtcga aaagcaaact   1920
caagttcctg cctcctcagg cggagcaaga agactccacc aagttcatcg cgctcaccct   1980
ggtctccctc gcctgcatcc tgggcgtcct cctggcctct ggcctcatct actgcctccg   2040
ccatagctct cagcacaggc tgaaggagaa gctctcggga ctagggggcg acccaggtgc   2100
agatgccact gccgcctacc aggagctgtg ccgccagcgt atggccacgc ggccaccaga   2160
ccgacctgag ggcccgcaca cgtcacgcat cagcagcgtc tcatcccagt tcagcgacgg   2220
gccgatcccc agcccctccg cacgcagcag cgcctcatcc tggtccgagg agcctgtgca   2280
gtccaacatg gacatctcca ccggccacat gatcctgtcc tacatggagg accacctgaa   2340
gaacaagaac cggctggaga aggagtggga agcgctgtgc gcctaccagg cggagcccaa   2400
cagctcgttc gtggcccaga gggaggagaa cgtgcccaag aaccgctccc tggccgtgct   2460
gacctatgac cactcccggg tcctgctgaa ggcggagaac agccacagcc actcagacta   2520
catcaacgct agccccatca tggatcacga cccgaggaac cccgcgtaca tcgccaccca   2580
gggaccgctg cccgccaccg tggctgactt ttggcagatg gtgtgggaga gcggctgcgt   2640
ggtgatcgtc atgctgacac ccctcgcgga gaacggcgtc cggcagtgct accactactg   2700
gccggatgaa ggctccaatc tctaccacat ctatgaggtg aacctggtct ccgagcacat   2760
ctggtgtgag gacttcctgg tgaggagctt ctatctgaag aacctgcaga ccaacgagac   2820
gcgcaccgtg acgcagttcc acttcctgag ttggtatgac cgaggagtcc cttcctcctc   2880
aaggtccctc ctggacttcc gcagaaaagt aaacaagtgc tacaggggcc gttcttgtcc   2940
aataattgtt cattgcagtg acggtgcagg ccggagcggc acctacgtcc tgatcgacat   3000
ggttctcaac aagatggcca aaggtgctaa agagattgat atcgcagcga ccctggagca   3060
cttgagggac cagagacccg gcatggtcca gacgaaggag cagtttgagt tcgcgctgac   3120
agccgtggct gaggaggtga acgccatcct caaggccctt ccccagtgag cggcagcctc   3180
aggggcctca ggggagcccc caccccacgg atgttgtcag gaatcatgat ctgactttaa   3240
ttgtgtgtct tctattataa ctgcatagta atagggccct tagctctccc gtagtcagcg   3300
cagtttagca gttaaaagtg tatttttgtt taatcaaaca ataataaaga gagatttgtg   3360
gaaaaatcca gttacgggtg gaggggaatc ggttcatcaa ttttcacttg cttaaaaaaa   3420
atacttttc ttaaagcacc cgttcacctt cttggttgaa gttgtgttaa caatgcagta   3480
```

-continued gccagcacgt tcgaggcggt ttccaggaag agtgtgcttg tcatctgcca ctttcgggag 3540
ggtggatcca ctgtgcagga gtggccgggg aagctggcag cactcagtga ggccgcccgg 3600
cacacaaggc acgtttggca tttctctttg agagagttta tcattgggag aagccgcggg 3660
gacagaactg aacgtcctgc agcttcgggg caagtgagac aatcacagct cctcgctgcg 3720
tctccatcaa cactgcgccg ggtaccatgg acggccccgt cagccacacc tgtcagccca 3780
agcagagtga ttcaggggct ccccgggggc agacacctgt gcaccccatg agtagtgccc 3840
acttgaggct ggcactcccc tgacctcacc tttgcaaagt tacagatgca ccccaacatt 3900
gagatgtgtt tttaatgtta aaatattgat ttctacgtta tgaaaacaga tgcccccgtg 3960
aatgcttacc tgtgagataa ccacaaccag gaagaacaaa tctgggcatt gagcaagcta 4020
tgagggtccc cgggagcaca cgaaccctgc caggcccccg ctggctcctc caggcacgtc 4080
ccggacctgt ggggccccag agaggggaca tttccctcct gggagagaag gagatcaggg 4140
caactcggag agggctgcga gcatttccct cccgggagag gagatcaggg cgacctgcac 4200
gcactgcgta gagcctggaa gggaagtgag aaaccagccg accggccctg cccctcttcc 4260
cgggatcact taatgaacca cgtgttttga catcatgtaa acctaagcac gtagagatga 4320
ttcggatttg acaaaataac atttgagtat ccgattcgcc atcacccccct accccagaaa 4380 taggacaatt cacttcattg accaagatga tcacatggaa ggcggcacag aggcagctgt 4440
gtgggctgca gatttcctgt gtggggttca gcgtagaaaa cgcacctcca tcccgccctt 4500
cccacagcat tcctccatct tagatagatg gtactctcca aaggccctac cagagggaac 4560
acggcctact gagcggacag aatgatgcca aaatattgct tatgtctcta catggtattg 4620
taatgaatat ctgctttaat atagctatca tttcttttcc aaaattactt ctctctatct 4680
ggaatttaat taatcgaaat gaatttatct gaatatagga agcatatgcc tacttgtaat 4740
ttctaactcc ttatgtttga agagaaacct ccggtgtgag atatacaaat atatttaatt 4800
gtgtcatatt aaacttctga tttcacaaaa aaaaaaaaaa aa 4842

<210> SEQ ID NO 22
<211> LENGTH: 3291
<212> TYPE: DNA
<213> ORGANISM: Homo sapiens

<400> SEQUENCE: 22
agaatcggag agccggtggc gtcgcaggtc gggaggacga gcaccgagtc gagggctcgc 60
tcgtctgggc cgcccgagag tcttaatcgc gggcgcttgg gccgccatct tagatggcgg 120
gagtaagagg aaaacgattg tgaggcggga acggctttct gctgcctttt ttgggccccg 180
aaaagggtca gctggccggg ctttggggcg cgtgccctga ggcgcggagc gcgtttgcta 240
cgatgcgggg gctgctcggg gctccgtccc ctgggctggg gacgcgccga atgtgaccgc 300
ctcccgctcc ctcacccgcc gcggggagga ggagcgggcg agaagctgcc gccgaacgac 360
aggacgttgg ggcggcctgg ctccctcagg tttaagaatt gtttaagctg catcaatgga 420
gcacatacag ggagcttgga agacgatcag caatggtttt ggattcaaag atgccgtgtt 480
tgatggctcc agctgcatct ctcctacaat agttcagcag tttggctatc agcgccgggc 540
atcagatgat ggcaaactca cagatccttc taagacaagc aacactatcc gtgttttctt 600
gccgaacaag caaagaacag tggtcaatgt gcgaaatgga atgagcttgc atgactgcct 660
tatgaaagca ctcaaggtga ggggcctgca accagagtgc tgtgcagtgt tcagacttct 720
ccacgaacac aaaggtaaaa aagcacgctt agattggaat actgatgctg cgtctttgat 780

-continued

```
tggagaagaa cttcaagtag atttcctgga tcatgttccc ctcacaacac acaactttgc    840
tcggaagacg ttcctgaagc ttgccttctg tgacatctgt cagaaattcc tgctcaatgg    900
atttcgatgt cagacttgtg gctacaaatt tcatgagcac tgtagcacca aagtacctac    960
tatgtgtgtg gactggagta acatcagaca actcttattg tttccaaatt ccactattgg   1020
tgatagtgga gtcccagcac taccttcttt gactatgcgt cgtatgcgag agtctgtttc   1080
caggatgcct gttagttctc agcacagata ttctacacct cacgccttca cctttaacac   1140
ctccagtccc tcatctgaag gttccctctc ccagaggcag aggtcgacat ccacacctaa   1200
tgtccacatg gtcagcacca ccctgcctgt ggacagcagg atgattgagg atgcaattcg   1260
aagtcacagc gaatcagcct caccttcagc cctgtccagt agccccaaca atctgagccc   1320
aacaggctgg tcacagccga aaacccccgt gccagcacaa agagagcggg caccagtatc   1380
tgggacccag gagaaaaaca aaattaggcc tcgtggacag agagattcaa gctattattg   1440
ggaaatagaa gccagtgaag tgatgctgtc cactcggatt gggtcaggct cttttggaac   1500
tgtttataag ggtaaatggc acggagatgt tgcagtaaag atcctaaagg ttgtcgaccc   1560
aaccccagag caattccagg ccttcaggaa tgaggtggct gttctgcgca aaacacggca   1620
tgtgaacatt ctgcttttca tggggtacat gacaaaggac aacctggcaa ttgtgaccca   1680
gtggtgcgag ggcagcagcc tctacaaaca cctgcatgtc caggagacca agtttcagat   1740
gttccagcta attgacattg cccggcagac ggctcaggga atggactatt tgcatgcaaa   1800
gaacatcatc catagagaca tgaaatccaa caatatattt ctccatgaag gcttaacagt   1860
gaaaattgga gattttggtt tggcaacagt aaagtcacgc tggagtggtt ctcagcaggt   1920
tgaacaacct actggctctg tcctctggat ggccccagag gtgatccgaa tgcaggataa   1980
caacccattc agtttccagt cggatgtcta ctcctatggc atcgtattgt atgaactgat   2040
gacgggggag cttccttatt ctcacatcaa caaccgagat cagatcatct tcatggtggg   2100
ccgaggatat gcctccccag atcttagtaa gctatataag aactgcccca aagcaatgaa   2160
gaggctggta gctgactgtg tgaagaaagt aaaggaagag aggcctcttt ttccccagat   2220
cctgtcttcc attgagctgc tccaacactc tctaccgaag atcaaccgga gcgcttccga   2280
gccatccttg catcgggcag cccacactga ggatatcaat gcttgcacgc tgaccacgtc   2340
cccgaggctg cctgtcttct agttgacttt gcacctgtct tcaggctgcc aggggaggag   2400
gagaagccag caggcaccac ttttctgctc cctttctcca gaggcagaac acatgttttc   2460
agagaagctg ctgctaagga ccttctagac tgctcacagg gccttaactt catgttgcct   2520
tcttttctat ccctttgggc cctgggagaa ggaagccatt tgcagtgctg gtgtgtcctg   2580
ctccctcccc acattcccca tgctcaaggc ccagccttct gtagatgcgc aagtggatgt   2640
tgatggtagt acaaaaagca ggggcccagc cccagctgtt ggctacatga gtatttagag   2700
gaagtaaggt agcaggcagt ccagccctga tgtggagaca catgggattt tggaaatcag   2760
cttctggagg aatgcatgtc acaggcggga ctttcttcag agagtggtgc agcgccagac   2820
attttgcaca taaggcacca aacagcccag gactgccgag actctggccg cccgaaggag   2880
cctgctttgg tactatggaa cttttcttag ggacacgtcc ctcctttcac agcttctaag   2940
gtgtccagtg cattgggatg gttttccagg caaggcactc ggccaatccg catctcagcc   3000
ctctcaggga gcagtcttcc atcatgctga attttgtctt ccaggagctg cccctatggg   3060
gcggggccgc agggccagcc ttgtttctct aacaaacaaa caaacaaaca gccttgtttc   3120
```

```
tctagtcaca tcatgtgtat acaaggaagc caggaataca ggttttcttg atgatttggg   3180

ttttaatttt gtttttattg cacctgacaa aatacagtta tctgatggtc cctcaattat   3240

gttattttaa taaaataaat taaatttagg tgtaaaaaaa aaaaaaaaaa a           3291
```

<210> SEQ ID NO 23
<211> LENGTH: 1244
<212> TYPE: DNA
<213> ORGANISM: Homo sapiens

<400> SEQUENCE: 23

```
gcggagctaa gatgcggagg agggtgacgc actagctctc cagttcgccc gttcctggcc     60

tgacccccac caaggcccat accgcagtag gctcctcggg ctgcccctcg gttgacaatg    120

gtctccagga tggtctctac catgctatct ggcctactgt tttggctggc atctggatgg    180

actccagcat ttgcttacag cccccggacc cctgaccggg tctcagaagc agatatccag    240

aggctgcttc atggtgttat ggagcaattg ggcattgcca ggccccgagt ggaatatcca    300

gctcaccagg ccatgaatct tgtgggcccc cagagcattg aaggtggagc tcatgaagga    360

cttcagcatt tgggtccttt tggcaacatc cccaacatcg tggcagagtt gactggagac    420

aacattccta aggactttag tgaggatcag ggtacccag accctccaaa tccctgtcct    480

gttggaaaaa cagcagatga tggatgtcta gaaaacaccc ctgacactgc agagttcagt    540

cgagagttcc agttgcacca gcatctcttt gatccggaac atgactatcc aggcttgggc    600

aagtggaaca agaaactcct ttacgagaag atgaagggag gagagagacg aaagcggagg    660

agtgtcaatc catatctaca aggacagaga ctggataatg ttgttgcaaa gaagtctgtc    720

ccccattttt cagatgagga taaggatcca gagtaaagag aagatgctag acgaaaaccc    780

acattacctg ttaggcctca gcatggctta tgtgcacgtg taaatggagt ccctgtgaat    840

gacagcatgt ttcttacata gataattatg gatacaaagc agctgtatgt agatagtgta    900

ttgtcttcac accgatgatt ctgctttttg ctaaattaga ataagagctt ttttgtttct    960

tgggttttta aaatgtgaat ctgcaatgat cataaaaatt aaaatgtgaa tgtcaacaat   1020

aaaaagcaag actatgaaag gctcagattt cttgcagttt aaaatggtgt ctgaggttgt   1080

actattttgg ccaagtctgt agaaagctgt catttgattt tgattatgta gttcatccag   1140

cccttgggca ttgttataca ccagtaaaga aggctgtact caagaggagg agctgacaca   1200

tttcacttgg ctgcgtctta ataaacatga atgcaagcat tggc                   1244
```

<210> SEQ ID NO 24
<211> LENGTH: 4841
<212> TYPE: DNA
<213> ORGANISM: Homo sapiens

<400> SEQUENCE: 24

```
agcacatcgc tgcgggctca caaagcggcc agacgctcgg cggcggcgtg tggcaggagc     60

gcaggggcgc gagccggcga tcagccttcc cggcgaccgt gccgcgggag ctcgagcaac    120

tcggactagg ggacccgggc cggcccccaa gatgccggcg atcgcggtgt tggcggcggc    180

cgccgcggcg tggtgcttcc tccaagtcga gagccggcac ctggacgcgc tcgccggagg    240

cgcgggcccc aaccacggca atttcctaga caatgaccag tggctgagca ccgtctccca    300

gtacgaccgg gacaagtact ggaaccgctt tcgagacgat gattatttca gaaactggaa    360

tcccaacaag ccctttgacc aagccctgga cccatccaag gacccctgcc tgaaggtaaa    420

atgcagccct cacaaagtgt gtgtgaccca ggactaccag accgccctgt gtgtcagccg    480
```

-continued

```
caagcacctg ctccccaggc aaaagaaggg gaacgtggcc cagaaacact gggttggacc    540
ttcgaatttg gtcaagtgca agccctgtcc cgtggcacag tcagccatgg tctgcggctc    600
agatggccac tcctacacat ccaagtgcaa attggagttc catgcttgtt ctactggcaa    660
aagcctcgcc accctctgtg atgggccctg tccctgtctc ccagagcctg agccaccaaa    720
gcacaaggca gaaaggagtg cctgcacaga caaggagttg cggaaccttg cctcccggct    780
gaaggattgg tttggagctc tccacgagga tgcgaacaga gtcatcaagc ccaccagctc    840
caacacagcc caaggcaggt ttgacactag catcctgccc atctgcaagg actccctggg    900
ctggatgttc aacaagttgg acatgaacta tgacctcctg cttgaccctt cagagatcaa    960
tgccatctac ctggataagt acgagccctg tatcaagcct cttttcaact cgtgtgactc   1020
cttcaaggat ggcaagcttt ctaacaatga gtggtgctac tgcttccaga agcctggagg   1080
tctcccttgc cagaatgaaa tgaacagaat tcagaagctg agtaagggga aaagcctgtt   1140
gggggccttc atacctcggt gtaatgagga gggctattac aaagccacac agtgccacgg   1200
cagcacgggg cagtgctggt gtgtggacaa atatgggaat gagttggctg gctccaggaa   1260
acagggtgct gtgagctgtg aagaggagca ggaaacctca ggggattttg gcagtggtgg   1320
gtccgtggtc ctgctggatg acctagaata tgaacgggag ctgggaccaa aggacaaaga   1380
ggggaagctg agggtgcaca cccgagccgt gacagaggat gatgaggatg aggatgatga   1440
caaagaggat gaggtcgggt acatatggta gtgcccacaa gaaagaggac acaagttttg   1500
cacaaaattg caagtcactt cctattcctg catttgtatc taagactcca aggcaccaag   1560
gtctcttctc cattgttgct ctctataccc gacctaaggt ttggaagaca actgcttgtt   1620
cccagaggat tctgattttg catatgtttg tatgggagaa agggtgttgt gttttttttt   1680
tgttgttgtt tattttttgg atagggaagt cattggctta attagagcct ccttcctttc   1740
tgtgagattt ttccaacaag catgtgattt acgtggaatt ctgacagtgc agggagcccc   1800
aaccctctta aatgtcaaag acccttttg attacccaca ctggtggtta ttacagcatg   1860
gttcccagcc ttacagtgtc taagtgcttc tcttgtgtcc tgtagatgtt gtgaaaaaga   1920
aaaaaacaaa aaatacacca cactgtactt tttccccctg cccccgttac tgccggtgat   1980
tattattaaa aattagtttt tttcacatca ttatatctgg cttcctataa acaacagcct   2040
taattcagtc aagactccct ttggggaatt cattttatta aaaattggtg tctggatact   2100
tccctgtaca tgcataaata tgcatgcatg tacagaaaga ctgtatgtgt gtgccttgca   2160
cacacaccca tacctctcag aaaaagtgtt tgggtatctt aaaaactcga aaaacaatga   2220
taaatttctc agcttgtcca gacctggaac aaaatttctg gaataagaaa tttgtattaa   2280
agtccttttt tgcactaaca gttggctctt gtagcctgca ggctgaggaa gtctcttctc   2340
tgtgcatcag cagagttact gaaagcctct gattgagaaa aaacctccgt ctgcctaaat   2400
cacttttctc gcagaagcca tgcgactccc acacgacacg ggcagcttca caagccatct   2460
ctttcatttc tgcttgaagc cccttggctg cagcaatcct gtctgccata ggtttcttcc   2520
ttccttacct actcaagggc tttttctaag gcatgcacac atatctcctg ttctctgaga   2580
gtaccatggt gttccttaaa agaagaaaat ttctaattct gaactcaatg ttttgctttt   2640
actccctttc tactgacaaa tcatgataag ggcacaaaag ctgtacagat tttttttttt   2700
aaccactcaa tcccaaatgg aggcctacaa agaacatcgt aataacacat ggaagcaaac   2760
cctgggtttt taagagcaaa ttctgtcccc ccctcactcc cccaagtgac aagatactaa   2820
```

tgaagaaagt tcttcaccat agtgtttgtt ttaactaaac tcattggagt ctagttccaa 2880
atttggtagg gtcatcatct ctacattcct taggatttct ctccctatca agctggccca 2940
gatacaagta ccaaacagta gtctctgaag ttcccccatt tccttcagta ccagtctata 3000
agctactgtc cgccactgat tttcatttat cagggtgtcc taatcagaat cagccaccca 3060
agcaagcctc tctggcccac atatctatct cttgccttcc cccatgaact tcagcctgtc 3120
cacacaaaag ccacataaac tcaagcaaga aatatgttca gccaaaacat gattatagtg 3180
gcagctgacc aatcccccat cccaaattga ccatttagat gtaccaactc accttaaatt 3240
agcatgttcc aatccagtcg gcattgcctg aatacagtag catcatacct atagttggtc 3300
ttagataaga aatgaactac ttgatatagc aaagtccttt ggcttcgtaa ataaccctga 3360
ggttttgtac ttactttccc cataggaaga cagaccatag gcaaactctg ttttgggatc 3420
tcaactccat cacctttgtt tcaatatttt ttttctctct tgaacaaaac tgagataatt 3480
tagaaaacag gtgcttaatt gcaataaaat tactatgaag tatattaaaa atcacgacat 3540
tgtaaaatct cactttagat catcaaagaa aaccattgtt actatctcct ttgagcttag 3600
gaaaatgtac aagagaacaa attaaaattg aaaaattgat ttcacttaga aaaacttcta 3660
ggaacagggt gaaccactga ttttaatttg cctaattatc ttatgacaag tatcaaatta 3720
agatgacact taaagatcct tagcattaac ttaatgatgg agaagagtgc tcaatagaca 3780
gttcccagta aggtaatgag atgccatttt cagagacatt ctaagaagat attttgattc 3840
attaaaacat taaataaaaa gccctcctca gattggaacc cccaaatcga tggagccaca 3900
ttaataatac ttttcatgcc tcactttgac atgacagcat tcgatttttt taaagatctt 3960
taatactttc catgagtact aaagattgta atgagttacc ttatccttag aagtagaatg 4020
tttgctttct tcttcttgga aatagtcctc caaaaagtcc acttgtacca gtgacaagaa 4080
gtcacttgta tagtgaccaa gtacacataa aatactgatt ataaaaatat tgtaataaac 4140
cacttcctca tttgatacag gtattaagct gaatcctcac taattcactt ttgaaaagtt 4200
cttaatgaac agttttattc ttattccatg aacagctctt ttaatacaat ttccttggta 4260
tccaacttaa atcccagaat tttgttccac catggttagt tatttgccat atgaatgtat 4320
tcttgtttct accaatattc taggcatgag aataccttaa tactgagttg gagattttgt 4380
atctgtttct cctcctttac gcccattttc ctacccacag cagcaaatga caacgtgtct 4440
gtccaggtct gtccccctgc tcatcccagg atgccactca cattttttttc ttcttgttac 4500 cttgaccacg ctgtacagta acatccaaga gcccattcta cagtgggtgg ttttggtctt 4560
tttataactt tttctcaaag tcactgatgt ttgttcctgt taaatgtata gcattgtaat 4620
gagagcccat caaatcctga gtgtcagttt gttgtcccta ttgtagatga aatagtgatg 4680
tagcaaaaac ctagtaaatt ctgaatgctt ttccacgtag acttatctgg aatgtgaaca 4740
caactctttg gttaatagta aatgcttaac tgtagtcctg agtaggtgca tttctgtctg 4800
tctcaataaa ttttactttg tctgcaaaaa aaaaaaaaaa a 4841

<210> SEQ ID NO 25
<211> LENGTH: 2655
<212> TYPE: DNA
<213> ORGANISM: Homo sapiens

<400> SEQUENCE: 25
cccagaaggc cgcgggggt ggaccgccta agagggcgtg cgctcccgac atgccccgcg 60
gcgcgccatt aaccgccaga tttgaatcgc gggacccgtt ggcagaggtg gcggcggcgg 120

-continued

```
catgggtgcc ccgacgttgc cccctgcctg gcagcccttt ctcaaggacc accgcatctc    180
tacattcaag aactggccct tcttggaggg ctgcgcctgc accccggagc ggatggccga    240
ggctggcttc atccactgcc ccactgagaa cgagccagac ttggcccagt gtttcttctg    300
cttcaaggag ctggaaggct gggagccaga tgacgacccc atagaggaac ataaaaagca    360
ttcgtccggt tgcgctttcc tttctgtcaa gaagcagttt gaagaattaa cccttggtga    420
atttttgaaa ctggacagag aaagagccaa gaacaaaatt gcaaaggaaa ccaacaataa    480
gaagaaagaa tttgaggaaa ctgcggagaa agtgcgccgt gccatcgagc agctggctgc    540
catggattga ggcctctggc cggagctgcc tggtcccaga gtggctgcac cacttccagg    600
gtttattccc tggtgccacc agccttcctg tgggcccctt agcaatgtct taggaaagga    660
gatcaacatt ttcaaattag atgtttcaac tgtgctcttg ttttgtcttg aaagtggcac    720
cagaggtgct tctgcctgtg cagcgggtgc tgctggtaac agtggctgct tctctctctc    780
tctctctttt ttgggggctc atttttgctg ttttgattcc cgggcttacc aggtgagaag    840
tgagggagga agaaggcagt gtcccttttg ctagagctga cagctttgtt cgcgtgggca    900
gagccttcca cagtgaatgt gtctggacct catgttgttg aggctgtcac agtcctgagt    960
gtggacttgg caggtgcctg ttgaatctga gctgcaggtt ccttatctgt cacacctgtg   1020
cctcctcaga ggacagtttt tttgttgttg tgtttttttg tttttttttt tttggtagat   1080
gcatgacttg tgtgtgatga gagaatggag acagagtccc tggctcctct actgtttaac   1140
aacatggctt tcttattttg tttgaattgt taattcacag aatagcacaa actacaatta   1200
aaactaagca caaagccatt ctaagtcatt ggggaaacgg ggtgaacttc aggtggatga   1260
ggagacagaa tagagtgata ggaagcgtct ggcagatact ccttttgcca ctgctgtgtg   1320
attagacagg cccagtgagc cgcggggcac atgctggccg ctcctccctc agaaaaaggc   1380
agtggcctaa atcctttta aatgacttgg ctcgatgctg tgggggactg gctgggctgc   1440
tgcaggccgt gtgtctgtca gcccaacctt cacatctgtc acgttctcca cacgggggag   1500
agacgcagtc cgcccaggtc cccgctttct ttggaggcag cagctcccgc agggctgaag   1560
tctggcgtaa gatgatggat ttgattcgcc ctcctccctg tcatagagct gcagggtgga   1620
ttgttacagc ttcgctggaa acctctggag gtcatctcgg ctgttcctga gaaataaaaa   1680
gcctgtcatt tcaaacactg ctgtggaccc tactgggttt ttaaaatatt gtcagttttt   1740
catcgtcgtc cctagcctgc caacagccat ctgcccagac agccgcagtg aggatgagcg   1800
tcctggcaga gacgcagttg tctctgggcg cttgccagag ccacgaaccc cagacctgtt   1860
tgtatcatcc gggctccttc cgggcagaaa caactgaaaa tgcacttcag acccacttat   1920
ttctgccaca tctgagtcgg cctgagatag acttttccct ctaaactggg agaatatcac   1980
agtggttttt gttagcagaa aatgcactcc agcctctgta ctcatctaag ctgcttattt   2040
ttgatatttg tgtcagtctg taaatggata cttcacttta ataactgttg cttagtaatt   2100
ggctttgtag agaagctgga aaaaaatggt tttgtcttca actcctttgc atgccaggcg   2160
gtgatgtgga tctcggcttc tgtgagcctg tgctgtgggc agggctgagc tggagccgcc   2220
cctctcagcc cgcctgccac ggcctttcct taaaggccat ccttaaaacc agaccctcat   2280
ggctaccagc acctgaaagc ttcctcgaca tctgttaata aagccgtagg cccttgtcta   2340
agtgcaaccg cctagacttt ctttcagata catgtccaca tgtccatttt tcaggttctc   2400
taagttggag tggagtctgg gaagggttgt gaatgaggct tctgggctat gggtgaggtt   2460
```

-continued ccaatggcag gttagagccc ctcgggccaa ctgccatcct ggaaagtaga gacagcagtg 2520
cccgctgccc agaagagacc agcaagccaa actggagccc ccattgcagg ctgtcgccat 2580
gtggaaagag taactcacaa ttgccaataa agtctcatgt ggttttatct aaaaaaaaaa 2640
aaaaaaaaaa aaaaa 2655

<210> SEQ ID NO 26
<211> LENGTH: 1814
<212> TYPE: DNA
<213> ORGANISM: Homo sapiens

<400> SEQUENCE: 26
ttttagagaa ttactccaaa ttcatcatga ttgaagacaa taaggagaac aaagaccatt 60
ccttagaaag gggaagagca agtctcattt tttccttaaa gaatgaagtt ggaggactta 120
taaaagccct gaaaatcttt caggagaagc atgtgaatct gttacatatc gagtcccgaa 180
aatcaaaaag aagaaactca gaatttgaga tttttgttga ctgtgacatc aacagagaac 240
aattgaatga tatttttcat ctgctgaagt ctcataccaa tgttctctct gtgaatctac 300
cagataattt tactttgaag gaagatggta tggaaactgt tccttggttt ccaaagaaga 360
tttctgacct ggaccattgt gccaacagag ttctgatgta tggatctgaa ctagatgcag 420
accatcctgg cttcaaagac aatgtctacc gtaaacgtcg aaagtatttt gcggacttgg 480
ctatgaacta taaacatgga gaccccattc caaaggttga attcactgaa gaggagatta 540
agacctgggg aaccgtattc caagagctca acaaactcta cccaacccat gcttgcagag 600
agtatctcaa aaacttacct ttgctttcta aatattgtgg atatcgggag gataatatcc 660
cacaattgga agatgtctcc aacttttttaa aagagcgtac aggtttttcc atccgtcctg 720
tggctggtta cttatcacca agagatttct tatcaggttt agcctttcga gtttttcact 780
gcactcaata tgtgagacac agttcagatc ccttctatac cccagagcca gatacctgcc 840
atgaactctt aggtcatgtc ccgcttttgg ctgaacctag ttttgcccaa ttctcccaag 900
aaattggctt ggcttctctt ggcgcttcag aggaggctgt tcaaaaactg gcaacgtgct 960
actttttcac tgtggagttt ggtctatgta aacaagatgg acagctaaga gtctttggtg 1020
ctggcttact ttcttctatc agtgaactca aacatgcact ttctggacat gccaaagtaa 1080
agccctttga tcccaagatt acctgcaaac aggaatgtct tatcacaact tttcaagatg 1140
tctactttgt atctgaaagt tttgaagatg caaaggagaa gatgagagaa tttaccaaaa 1200
caattaagcg tccatttgga gtgaagtata atccatatac acggagtatt cagatcctga 1260
aagacaccaa gagcataacc agtgccatga atgagctgca gcatgatctc gatgttgtca 1320
gtgatgccct tgctaaggtc agcaggaagc cgagtatcta acagtagcca gtcatccagg 1380
aacatttgag catcaattcg gaggtctggg ccatctcttg ctttccttga acacctgatc 1440
ctggagggac agcatcttct ggccaaacaa tattatcgaa ttccactact taaggaatca 1500
ctagtctttg aaaatttgta cctggatatt ctatttacca cttatttttt tgtttagttt 1560
tatttctttt tttttttggt agcagcttta atgagacaat ttatatacca tacaagccac 1620
tgaccaccca tttttaatag agaagttgtt tgacccaata gatagatcta atctcagcct 1680
aactctattt tccccaatcc tccttgagta aaatgaccct ttaggatcgc ttagaataac 1740
ttgaggagta ttatggcgct gactcatatt gttacctaag atccccttat ttctaaagta 1800
tctgttactt attg 1814

<210> SEQ ID NO 27
<211> LENGTH: 2974
<212> TYPE: DNA
<213> ORGANISM: Homo sapiens

<400> SEQUENCE: 27

```
cacacacaca catacacaga atcctcagat aacaggaggc aataaatcca acagcacatc     60
cacgttcaga gaacagtgtc cctgctgtct tgctaacagc tgccaatacc tcactgagtg    120
cctcacacca acatgggctc caagatgaag gcatctttct gatcaggggt ttgtagctca    180
aacaaaagaa tgagcgtgct tctagaacca cagagcaagg gaacatggta gaggataagc    240
tggcaagttg aaaagcgtgg gatttcatcc cagtttgaca ctaactgtgc aaccccaaac    300
aaatctccta accttcagag gctcggattt cttgtctatg agatgaagtg agtttccttc    360
gtctgggcag actccctccc ctcttccata aaggctgcag gagacctgta gctgtcacag    420
gaccttccct aagagcccgc aggggaagac tgccccagtc cggccatcac catgctccgg    480
accattctgg atgctcccca gcggttgctg aaggagggga gagcgtcccg gcagctggtg    540
ctggtggtgg tattcgtcgc tttgctcctg gacaacatgc tgtttactgt ggtggtgcca    600
attgtgccca ccttcctata tgacatggag ttcaaagaag tcaactcttc tctgcacctc    660
ggccatgccg gaagttcccc acatgccctc gcctctcctg ccttttccac catcttctcc    720
ttcttcaaca acaacaccgt ggctgttgaa gaaagcgtac ctagtggaat agcatggatg    780
aatgacactg ccagcaccat cccacctcca gccactgaag ccatctcagc tcataaaaac    840
aactgcttgc aaggcacagg tttcttggag gaagagatta cccgggtcgg ggttctgttt    900
gcttcaaagg ctgtgatgca acttctggtc aacccattcg tgggccctct caccaacagg    960
attggatatc atatccccat gtttgctggc tttgttatca tgtttctctc cacagttatg   1020
tttgcttttt ctgggaccta tactctactc tttgtggccc gaacccttca aggcattgga   1080
tcttcatttt catctgttgc aggtcttgga atgctggcca gtgtctacac tgatgaccat   1140
gagagaggac gagccatggg aactgctctg gggggcctgg ccttggggtt gctggtggga   1200
gctccctttg gaagtgtaat gtacgagttt gttgggaagt ctgcaccctt cctcatcctg   1260
gccttcctgg cactactgga tggagcactc cagctttgca tcctacagcc ttccaaagtc   1320
tctcctgaga gtgccaaggg gactcccctc tttatgcttc tcaaagaccc ttacatcctg   1380
gtggctgcag ggtccatctg ctttgccaac atgggggtgg ccatcctgga gcccacactg   1440
cccatctgga tgatgcagac catgtgctcc cccaagtggc agctgggtct agctttcttg   1500
cctgccagtg tgtcctacct cattggcacc aacctctttg gtgtgttggc caacaagatg   1560
ggtcggtggc tgtgttccct aatcgggatg ctggtagtag gtaccagctt gctctgtgtt   1620
cctctggctc acaatatttt tggtctcatt ggccccaatg cagggcttgg ccttgccata   1680
ggcatggtgg attcttctat gatgcccatc atggggcacc tggtggatct acgccacacc   1740
tcggtgtatg ggagtgtcta cgccatcgct gatgtggctt tttgcatggg ctttgctata   1800
ggtccatcca ccggtggtgc cattgtaaag gccatcggtt ttccctggct catggtcatc   1860
actggggtca tcaacatcgt ctatgctcca ctctgctact acctgcggag ccccccggca   1920
aaggaagaga agcttgctat tctgagtcag gactgcccca tggagacccg gatgtatgca   1980
acccagaagc ccacgaagga atttcctctg gggggaggaca gtgatgagga gcctgaccat   2040
gaggagtagc agcagaaggt gctccttgaa ttcatgatgc ctcagtgacc acctctttcc   2100
ctgggaccag atcaccatgg ctgagcccac ggctcagtgg gcttcacata cctctgcctg   2160
```

ggaatcttct ttcctcccct cccatggaca ctgtccctga tactcttctc acctgtgtaa 2220
cttgtagctc ttcctctatg ccttggtgcc gcagtggccc atcttttatg ggaagacaga 2280
gtgatgcacc ttcccgctgc tgtgaggttg attaaacttg agctgtgacg ggttctgcaa 2340
ggggtgactc attgcataga ggtggtagtg agtaatgtgc ccctgaaacc agtggggtga 2400
ctgacaagcc tctttaatct gttgcctgat tttctctggc atagtcccaa cagatcggaa 2460
gagtgttacc ctcttttcct caacgtgttc tttcccgggt tttcccagcc gagttgagaa 2520
aatgttctca gcattgtctt gctgccaaat gccagcttga agagttttgt tttgtttttt 2580
ttcatttatt ttttttttta ataaagtgag tgattttttct gtggctaaat ctagagctgc 2640
taaaagggct ttaccctcag tgaaaagtgt cttctatttt cattatcttt cagaaacagg 2700
agcccatttc tcttctgctg gagttattga cattctcctg acctcccctg tgtgttccta 2760
ccttttctga acctcttaga ctcttagaaa taaaagtaga agaaagacag aaaaaataac 2820
tgattagacc caagatttca tgggaagaag ttaaaagaaa ctgccttgaa atccctcctg 2880
attgtagatt tcctaacagg aggggtgtaa tgtgacattg ttcatacttg ctaataaata 2940
cattattgcc taattcaaaa aaaaaaaaaa aaaa 2974

<210> SEQ ID NO 28
<211> LENGTH: 1894
<212> TYPE: DNA
<213> ORGANISM: Homo sapiens

<400> SEQUENCE: 28
cgcaagcgac cccgagcgga gccccggagc catggccctg agcgagctgg cgctggtccg 60
ctggctgcag gagagccgcc gctcgcggaa gctcatcctg ttcatcgtgt tcctggcgct 120
gctgctggac aacatgctgc tcactgtcgt ggtccccatc atcccaagtt atctgtacag 180
cattaagcat gagaagaatg ctacagaaat ccagacggcc aggccagtgc acactgcctc 240
catctcagac agcttccaga gcatcttctc ctattatgat aactcgacta tggtcaccgg 300
gaatgctacc agagacctga cacttcatca gaccgccaca cagcacatgg tgaccaacgc 360
gtccgctgtt ccttccgact gtcccagtga agacaaagac ctcctgaatg aaaacgtgca 420
agttggtctg ttgtttgcct cgaaagccac cgtccagctc atcaccaacc ctttcatagg 480
actactgacc aacagaattg gctatccaat tcccatattt gcgggattct gcatcatgtt 540
tgtctcaaca attatgtttg ccttctccag cagctatgcc ttcctgctga ttgccaggtc 600
gctgcagggc atcggctcgt cctgctcctc tgtggctggg atgggcatgc ttgccagtgt 660
ctacacagat gatgaagaga gaggcaacgt catgggaatc gccttgggag gcctggccat 720
gggggtctta gtgggccccc ccttcgggag tgtgctctat gagtttgtgg ggaagacggc 780
tccgttcctg gtgctggccg ccctggtact cttggatgga gctattcagc tctttgtgct 840
ccagccgtcc cgggtgcagc cagagagtca gaaggggaca cccctaacca cgctgctgaa 900
ggacccgtac atcctcattg ctgcaggctc catctgcttt gcaaacatgg gcatcgccat 960
gctggagcca gccctgccca tctggatgat ggagaccatg tgttcccgaa agtggcagct 1020
gggcgttgcc ttcttgccag ctagtatctc ttatctcatt ggaaccaata tttttgggat 1080
acttgcacac aaaatgggga ggtggctttg tgctcttctg ggaatgataa ttgttggagt 1140
cagcatttta tgtattccat ttgcaaaaaa catttatgga ctcatagctc cgaactttgg 1200
agttggtttt gcaattggaa tggtggattc gtcaatgatg cctatcatgg gctacctcgt 1260
agacctgcgg cacgtgtccg tctatgggag tgtgtacgcc attgcggatg tggcattttg 1320
tatggggtat gctataggtc cttctgctgg tggtgctatt gcaaaggcaa ttggatttcc 1380
atggctcatg acaattattg ggataattga tattcttttt gcccctctct gctttttttct 1440 tcgaagtcca cctgccaaag aagaaaaaat ggctattctc atggatcaca actgccctat 1500
taaaacaaaa atgtacactc agaataatat ccagtcatat ccgataggtg aagatgaaga 1560
atctgaaagt gactgagatg agatcctcaa aaatcatcaa agtgtttaat tgtataaaac 1620
agtgtttcca gtgacacaac tcatccagaa ctgtcttagt cataccatcc atccctggtg 1680
aaagagtaaa accaaaggtt attatttcct ttccatggtt atggtcgatt gccaacagcc 1740
ttataaagaa aaagaagctt ttctaggggt ttgtataaat agtgttgaaa ctttatttta 1800
tgtatttaat tttattaaat atcatacaat atattttgat gaaataggta ttgtgtaaat 1860
ctataaatat ttgaatccaa accaaatata attt 1894

<210> SEQ ID NO 29
<211> LENGTH: 2467
<212> TYPE: DNA
<213> ORGANISM: Homo sapiens

<400> SEQUENCE: 29
ctggagtggg gtaagaggcg aattatagac acaaggggct cctctgcagg aaggaggcca 60
agggaaagag gcttgaaagg cttgatattt cacccaccac cactcactgc cggagtaagc 120
aggtctcccc ttcccagggc tgaggggagg cagggatgtg tgctgtccca gggctgagaa 180
gtggcaggtg agctggtgat tccttactgc ccaggttctg tctaggaagg tgcgtcctca 240
ccatgctgga tggtgtccta gtccaggagc accccctgag ctcctggcct agactccaaa 300
gggttgggta gatgagcaaa gactttacaa agaccttagg cgatatatgt ccaggagcac 360
ccaggaatta ctgggctacc actgcagact gcaggacaag ctccaagaac aggaaggaag 420
tcttgcagct gaagggaggc actccttggc ctccgcagcc gatcacatga aggtggtgcc 480
aagtctcctg ctctccgtcc tcctggcaca ggtgtggctg gtacccggct tggcccccag 540
tcctcagtcg ccagagaccc cagcccctca gaaccagacc agcagggtag tgcaggctcc 600
caaggaggaa gaggaagatg agcaggaggc cagcgaggag aaggccagtg aggaagagaa 660
agcctggctg atggccagca ggcagcagct tgccaaggag acttcaaact tcggattcag 720
cctgctgcga aagatctcca tgaggcacga tggcaacatg gtcttctctc catttggcat 780
gtccttggcc atgacaggct tgatgctggg ggccacaggg ccgactgaaa cccagatcaa 840
gagagggctc cacttgcagg ccctgaagcc caccaagccc gggctcctgc cttccctctt 900
taagggactc agagagaccc tctcccgcaa cctggaactg ggcctcacac aggggagttt 960
tgccttcatc cacaaggatt ttgatgtcaa agagactttc ttcaatttat ccaagaggta 1020
ttttgataca gagtgcgtgc ctatgaattt tcgcaatgcc tcacaggcca aaaggctcat 1080
gaatcattac attaacaaag agactcgggg gaaaattccc aaactgtttg atgagattaa 1140
tcctgaaacc aaattaattc ttgtggatta catcttgttc aaagggaaat ggttgacccc 1200
atttgaccct gtcttcaccg aagtcgacac tttccacctg gacaagtaca agaccattaa 1260
ggtgcccatg atgtacggtg caggcaagtt tgcctccacc tttgacaaga attttcgttg 1320
tcatgtcctc aaactgccct accaaggaaa tgccaccatg ctggtggtcc tcatggagaa 1380
aatgggtgac cacctcgccc ttgaagacta cctgaccaca gacttggtgg agacatggct 1440
cagaaacatg aaaaccagaa acatggaagt tttctttccg aagttcaagc tagatcagaa 1500

-continued

```
gtatgagatg catgagctgc ttaggcagat gggaatcaga agaatcttct caccctttgc   1560

tgaccttagt gaactctcag ctactggaag aaatctccaa gtatccaggg ttttacaaag   1620

aacagtgatt gaagttgatg aaaggggcac tgaggcagtg gcaggaatct tgtcagaaat   1680

tactgcttat tccatgcctc ctgtcatcaa agtggaccgg ccatttcatt tcatgatcta   1740

tgaagaaacc tctggaatgc ttctgtttct gggcagggtg gtgaatccga ctctcctata   1800

attcaggaca cgcataagca cttcgtgctg tagtagatgc tgaatctgag gtatcaaaca   1860

cacacaggat accagcaatg gatggcaggg gagagtgttc cttttgttct taactagttt   1920

agggtgttct caaataaata cagtagtccc cacttatctg agggggatac attcaaagac   1980

ccccagcaga tgcctgaaac ggtggacagt gctgaacctt atatatattt tttcctacac   2040

atacatacct atgataaagt ttaatttata aattaggcac agtaagagat taacaataat   2100

aacaacatta agtaaaatga gttacttgaa tgcaagcact gcaataccat aacagtcaaa   2160

ctgattatag agaaggctac taagtgactc atgggcgagg agcatagaca gtgtggagac   2220

attgggcaag ggagaattc acatcctggg tgggacagag caggacaatg caagattcca   2280

tcccactact cagaatggca tgctgcttaa gacttttaga ttgtttattt ctggaatttt   2340

tcatttaatg tttttggacc atggttgacc atggttaact gagactgcag aaagcaaaac   2400

catggataag ggaggactac tacaaaagca ttaaattgat acatattttt taaaaaaaaa   2460

aaaaaaa                                                             2467
```

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
tacctggttg atcctgccag 20

<210> SEQ ID NO 31
<211> LENGTH: 20
<212> TYPE: DNA
<213> ORGANISM: Artificial Sequence
<220> FEATURE:
<223> OTHER INFORMATION: primer

<400> SEQUENCE: 31
cgcccgtcgg catgtattag 20

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
atttggtcgt attgggcgcc 20

<210> SEQ ID NO 33
<211> LENGTH: 20
<212> TYPE: DNA
<213> ORGANISM: Artificial Sequence
<220> FEATURE:
<223> OTHER INFORMATION: primer

<400> SEQUENCE: 33
gaatcatatt ggaacatgta 20

<210> SEQ ID NO 34
<211> LENGTH: 429
<212> TYPE: DNA
<213> ORGANISM: Homo sapiens

<400> SEQUENCE: 34
atgggtgccc cgacgttgcc ccctgcctgg cagccctttc tcaaggacca ccgcatctct 60
acattcaaga actggccctt cttggagggc tgcgcctgca ccccggagcg gatggccgag 120
gctggcttca tccactgccc cactgagaac gagccagact tggcccagtg tttcttctgc 180
ttcaaggagc tggaaggctg ggagccagat gacgacccca tagaggaaca taaaaagcat 240
tcgtccggtt gcgctttcct ttctgtcaag aagcagtttg aagaattaac ccttggtgaa 300
tttttgaaac tggacagaga aagagccaag aacaaaattg caaaggaaac caacaataag 360
aagaaagaat ttgaggaaac tgcgaagaaa gtgcgccgtg ccatcgagca gctggctgcc 420
atggattga 429

<210> SEQ ID NO 35
<211> LENGTH: 6158
<212> TYPE: DNA
<213> ORGANISM: Homo sapiens

<400> SEQUENCE: 35
gtcttttgtc cctcggcgga caccgtttgc cagccaaagc tatgtctgcg cgctcaccga 60
cttcataggg tgccgaattc ttttttcccc aggcttgcca tggctagtcg aggggctcgg 120
cagcgcctga agggcagcgg ggccagcagt ggggatacgg ccccggctgc ggacaagctg 180
cgggagctgc tgggcagccg agaggcgggc ggcgcggagc accggaccga gttatctggg 240
aacaaagcag gacaagtctg ggcacctgaa ggatctactg ctttcaagtg tctgctttca 300
gcaaggttat gtgctgctct cctgagcaac atctctgact gtgatgaaac attcaactac 360
tgggagccaa cacactacct catctatggg gaagggtttc agacttggga atattcccca 420
gcatatgcca ttcgctccta tgcttacctg ttgcttcatg cctggccagc tgcatttcat 480
gcaagaattc tacaaactaa taagattctt gtgttttact ttttgcgatg tcttctggct 540
tttgtgagct gtatttgtga actttacttt tacaaggctg tgtgcaagaa gtttgggttg 600
cacgtgagtc gaatgatgct agccttcttg gttctcagca ctggcatgtt ttgctcatca 660
tcagcattcc ttcctagtag cttctgtatg tacactacgt tgatagccat gactggatgg 720
tatatggaca agacttccat tgctgtgctg ggagtagcag ctggggctat cttaggctgg 780
ccattcagtg cagctcttgg tttacccatt gcctttgatt tgctggtcat gaaacacagg 840
tggaagagtt tctttcattg gtcgctgatg gccctcatac tatttctggt gcctgtggtg 900
gtcattgaca gctactatta tgggaagttg gtgattgcac cactcaacat tgttttgtat 960
aatgtcttta ctcctcatgg acctgatctt tatggtacag aaccctggta tttctattta 1020
attaatggat ttctgaattt caatgtagcc tttgctttgg ctctcctagt cctaccactg 1080
acttctctta tggaatacct gctgcagaga tttcatgttc agaatttagg ccacccgtat 1140
tggcttacct tggctccaat gtatatttgg tttataattt tcttcatcca gcctcacaaa 1200
gaggagagat ttcttttccc tgtgtatcca cttatatgtc tctgtggcgc tgtggctctc 1260
tctgcacttc agcacagttt tctgtacttc cagaaatgtt accactttgt gtttcaacga 1320

-continued

```
tatcgcctgg agcactatac tgtgacatcg aattggctgg cattaggaac tgtcttcctg   1380
tttgggctct tgtcattttc tcgctctgtg gcactgttca gaggatatca cgggcccctt   1440
gatttgtatc cagaatttta ccgaattgct acagacccaa ccatccacac tgtcccagaa   1500
ggcagacctg tgaatgtctg tgtgggaaaa gagtggtatc gatttcccag cagcttcctt   1560
cttcctgaca attggcagct tcagttcatt ccatcagagt tcagaggtca gttaccaaaa   1620
ccttttgcag aaggacctct ggccacccgg attgttccta ctgacatgaa tgaccagaat   1680
ctagaagagc catccagata tattgatatc agtaaatgcc attatttagt ggatttggac   1740
accatgagag aaacaccccg ggagccaaaa tattcatcca ataaagaaga atggatcagc   1800
ttggcctata gaccattcct tgatgcttct agatcttcaa agctgctgcg ggcattctat   1860
gtccccttcc tgtcagatca gtatacagtg tacgtaaact acaccatcct caaaccccgg   1920
aaagcaaagc aaatcaggaa gaaaagtgga ggttagcaac acacctgtgg ccccaaagga   1980
caaccatctt gttaactatt gattccagtg acctgactcc ctgcaagtca tcgcctgtaa   2040
catttgtaat aaaggtcttc tgacatgaat actggaatct gggtgctctg ggctagtcaa   2100
agtctatttc aaagtctaat caaagtcaca tttgctccct gtgtgtgtct ctgttctgca   2160
tgtaaacttt ttgcagctag gcagagaaag gccctaaagc acagatagat atattgctcc   2220
acatctcatt gtttttcctc tgttcaatta tttactagac cggagaagag cagaaccaac   2280
ttacaggaag aattgaaaat cctggtactg gatggctgtg ataagctgtt ctccacactc   2340
tggcctggca tctgagaact agcaagcctc tcttaggcca tatgggcttc tccaccaaag   2400
ctgtttggca gctcctagca gaccttctta ttgaaatcct catgctgaaa atgaacacag   2460
cctagttgcc aacccacatg tccttttcac ctccagcaag actaagcttc tttaaagcac   2520
ttcacaggac taggaccctg tcctggagct atctcaggaa aaaggtgacc atttgaggaa   2580
ctgtgaccta attttattat aatgatgcct ctaattttca tttcctttac aaccaactgt   2640
aactataagg ttgtattgct tttttgttca gttttagcat gctatttttt gaattctaga   2700
ctcctccatg tgaagatatc aacagacaaa actacaactg tataggacat atttggagaa   2760
aattctatca attgatacat ttggatgaca tcacattttt aagtaatgta atctgaggcc   2820
attgctgagg aaattaagaa ttttcctttt tttttaacca cccccagtga aaaggatcag   2880
tgtatattta tagcacctat tttttagttc tgtctgttgt gaggcacatc ctgcatgggg   2940
cacttctagt caaataggca atgataagga cctaattaaa atgtgataag tgtatactat   3000
tactttaaaa gcctttacag tcagtacttc agtttacaag gcactttcac agcatctcgt   3060
ttgatcctca cagtcacaac atgtggtaga caaggcaggt gatttttatc cccattttac   3120
agataaggaa acaggctgcg ggtggggagt gaggggaggt aaagatagtt agttgcctaa   3180
ggtcacacag ccagtaagta atagagctgg gactggaacc caggtttcct tactctcatc   3240
tattgctcct ccatattcct cactcaacca tgaaaacatt acttgaaagg actgatgagg   3300
ttaaccagag acctaactga tattgtaact ttctatttta aggaagaatt gtgtctgtat   3360
ttgagttctt tggagcctcc agtctgcctg tgtgttagac cagcacagca gtgctgtgtg   3420
atgcagcctg acctgtggca ggaaagtagt gcttctgttt ggaagtcatg ttcttttgca   3480
gccacacagg atccaaatat cagtactatt cctgtagtca atctggggtc acattatagg   3540
tgccttattt ccctaagggt aactgatctg aatatctgca aataggatga atctattttt   3600
cagaagttcc atctttcatt tttctttttt tttttgagac agagtctcat tctgtcgccc   3660
atgctggagt gcagtggcgc gatctcggct cgctgcaacc tctgcctccc aggttgaagc   3720
```

-continued

```
aattctcatg cctcagccac ccgagtagct gggattacag gcatgcgcca tcatgcccag   3780
ctaatttatg tatttttagt agagttggag tttcaccatg ttggccaggc tggtcttgga   3840
ctcctgacct caggtcatcc acccgcctca gcctcccaaa gtgctggtat tacaggcgtg   3900
agccaccgca cccagcccca tctttcattt tcaaagagaa gggcattcta ataggaactg   3960
gtgccaagag agaagaaaag aagtgataac agaagaaatg gctagttaca atattaaaaa   4020
gctcctcttt gagatctcct ctgcaggaat atcagagacg gagttgaagc gctggagagg   4080
taataggtct agacagtaca gaacaataac tggggagtgt gtgaggatag actgggctcc   4140
cccttgcttg aaagatctct ggcatttaat tctcaattct tgattactat tttccagtgt   4200
aaaactagca catatgatct gactacagga cagagaattt taagtgaaac atttgcctta   4260
cttgcagtaa taatgtgctg ttcttcacag tagctaaggc cctctatgtt tcccagaggt   4320
aaataagaat ccaggaatgg aggtccatct gtgatgaatg gctttttttct aatcaaagta   4380
gtataatgct gttttatctg ttttgtcatc ttgttttttt tttttttaa aaaaacaaaa   4440
ccttaattat aatatagcgc aaagaaaggc caggactgat gcagggattc cttggaaata   4500
tcagttccta tcacttttaa aacctgattt tggatctctc tgttctatgt atgtctttag   4560
tgagagcaca atacatggca gaacgctgtg ccaaatgtta taggtaagga atatagaaat   4620
gaatgttttt tgttgtgaag gtgttttcat gtgatatttt ataaacacat tttaaaaaat   4680
ctccatcact ttttagtata ggaaggatag ctttgcctgg gaaaaacagt ttcaacacac   4740
ctgctcagag tagcagttct ccctcaaaaa agcagtgttc agcctgcact gactgttctg   4800
cttgccaaaa ggaggaagca tgcaagatac ttatttctcc atagattgtg gagtatagag   4860
ggatgtggga ctacagatta ttattttttt tccccgagac agagtcttgc tctgtcgccc   4920
aggttggaac acaatggcac gacctcagct cactgcaacc tctgtctccc gggttcaagc   4980
aattctcctg cttcagcctc ctgagtagct gggattacag gcacacacca ccaccgcact   5040
cagctaattt ttgtattttt agtagaggtg gggttttacc atgttggcca ggctggtctt   5100
aaactcctga ccttgtaatc atcccgcctc ggcctcctaa agtgctagga ttacaggcat   5160
gagccaccgc acccggccca gataattttt aatagccttt gatcatgggg tgagtgaggg   5220
agtaggtata cttggcaaat gcatggttct ctgatttcta gctctaaagc agccttatct   5280
gaatccccaa atcttgtgat gctgagtacc attactgaac cagtctgcac ggtaggcatc   5340
tgctaccaaa atttacctcc tacctggtag gtgtcatctg ataagaaaga agacaggtta   5400
ttttaatttt ttgagataat cacagaaaat tgcagcccat actctttatt accgaattca   5460
agtttggaaa tagacccttt gttttaaatc atgatgggtc tttatcccaa tcatttatct   5520
gggtcatttt tccaactttg gagttctagg aaagaacctt gaaaacctga tatgattctg   5580
cagcatgagg tctacggtga ccatttgggc aaagctccag tggcaatcat ttattgtgtt   5640
ttgcatttcc tgggatttat tgaaataaga attcactgtg attatgtagt cttctggcta   5700
gtatcaggca gctctgcttt taatttggtt aattttattt tctctgaaga gggagaagag   5760
gtacaattta atcttggcct ccacaagcat attaaagctc acgtgttaat cagtgcattc   5820
ttatgctcct acattaaatg ccttgggtaa atggataaat ggacatgtgc ccagctttaa   5880
ttttttttgc aacagaaaga tcagacttcc gtatggcatc gttggatttc agaggctttc   5940
tggtgtatct gtaaatctga atgttgcctt ctgccagtct gtataaccag gtgattcatg   6000
ctgcaaatga aatcaggaag cagtaaagtg ttaaagcaag agtattgtcc aattcacttg   6060
```

-continued tcttcctgat ccttgtactt tatttcacgt gtcggtgttt acattacata cttatatttc 6120
ctgtgaaaga aagagttaaa taaattgtag cagtttga 6158

<210> SEQ ID NO 36
<211> LENGTH: 3715
<212> TYPE: DNA
<213> ORGANISM: Homo sapiens

<400> SEQUENCE: 36
gacgtcatgt tcgccgggca ggcgaggaaa gaggacgcca tgattggttg gcgctggggc 60
ggcggacggt ggaagggcct ggcgagtcta ggttttacgc ctgtgctgga ctttctcctt 120
ccatgtttcc aggccgtggg gggctacaga gggcgagaag tcggctcagc ggaaacctgg 180
atttggttct aagccgtggg gttgagaagg ggtgaccgga agtgatcgtg ggactgaccg 240
gaagcgaggc ctggagggga aagagagagc gagacctggg agggaggggg cctccagcag 300
aaaggggcgg gggaaaaggt gcaaaagcag cgtgggagcg ccgggctggc ttcctgcggc 360
tgctgctggt ctgactggga agcagcaagc caccactacg aactctcaag aggagtggga 420
gtgcgggagt ccagagctgc ctctgggaag tctgcagtag ttgagcaaag ggtcctcac 480 gttcctgaga gctgggcagg ggggatttg gaacctgggg cagccaagaa cgagcagcca 540
agggtacggg agattagttg tgcacagagc agtgctggtc gggcttgggg gtggctggtg 600
ggcactgcgt gggaaacctt ggtttgtagt tttcttggtt tgcgttactc ctgttgggta 660
gaattaccct ccgcgccttt gtacaagaca cggtgtctcc tggggcaagg aaggagccag 720
gatggcctgg gctctgaagc tgcctctggc cgacgaagtg attgaatccg ggttggtgca 780
ggactttgat gctagcctgt ccgggatcgg ccaggaactg ggtgctggtg cctatagcat 840
gagtgatgtc cttgcattgc ccatttttaa gcaagaagag tcgagtttgc ctcctgataa 900
tgagaataaa atcctgcctt ttcaatatgt gctttgtgct gctacctctc cagcagtgaa 960
actccatgat gaaaccctaa cgtatctcaa tcaaggacag tcttatgaaa ttcgaatgct 1020
agacaatagg aaacttggag aacttccaga aattaatggc aaattggtga agagtatatt 1080
ccgtgtggtg ttccatgaca gaaggcttca gtacactgag catcagcagc tagagggctg 1140
gaggtggaac cgacctggag acagaattct tgacatagat atcccgatgt ctgtgggtat 1200
aatcgatcct agggctaatc caactcaact aaatacagtg gagttcctgt gggaccctgc 1260
aaagaggaca tctgtgttta ttcaggtgca ctgtattagc acagagttca ctatgaggaa 1320
acatggtgga gaaaaggggg tgccattccg agtacaaata gataccttca aggagaatga 1380
aaacggggaa tatactgagc acttacactc ggccagctgc cagatcaaag ttttcaagcc 1440
caaaggtgca gacagaaagc aaaaaacgga tagggaaaaa atggagaaac gaacacctca 1500
tgaaaaggag aaatatcagc cttcctatga gacaaccata ctcacagagt gttctccatg 1560
gcccgagatc acgtatgtca ataactcccc atcacctggc ttcaacagtt cccatagcag 1620
tttttctctt ggggaaggaa atggttcacc aaaccaccag ccagagccac cccctccagt 1680
cacagataac ctcttaccaa caaccacacc tcaggaagct cagcagtggt tgcatcgaaa 1740
tcgtttttct acattcacaa ggcttttcac aaacttctca ggggcagatt tattgaaatt 1800
aactagagat gatgtgatcc aaatctgtgg ccctgcagat ggaatcagac tttttaatgc 1860
attaaaaggc cggatggtgc gtccaaggtt aaccatttat gtttgtcagg aatcactgca 1920
gttgagggag cagcaacaac agcagcagca acagcagcag aagcatgagg atggagactc 1980
aaatggtact ttcttcgttt accatgctat ctatctagaa gaactaacag ctgttgaatt 2040
gacagaaaaa attgctcagc ttttcagcat ttccccttgc cagatcagcc agatttacaa 2100
gcaggggcca acaggaattc atgtgctcat cagtgatgag atgatacaga actttcagga 2160
agaagcatgt tttattctgg acacaatgaa agcagaaacc aatgatagct atcatatcat 2220
actgaagtag gagtgcggcg tttcgtgccc agtggctgct ccttccttca cctctgaaaa 2280
cggccctctt gaagggggat atgaatggag atttgaaggt ctgcaagaac ctgactcgtc 2340
tgactgtgtg tggaggagtc caggccatgg aggcagaatc ctggccctct gtgttggccc 2400
aagctcttgt ggtacacaca gattactgcc caatatgcag ttctgcagct gttttagtta 2460
aatttctgga ccttgttgtt gttaaatatc agtagaaact ctacataatt tagagtgtat 2520
gtagggcata atgatgatgg gaattgtgtg atgtttaaca ggaagatctt aaattttgtg 2580
atatggagcc ctgtaatttt tttcttatat aaaaatgggt atctatattc ataagactag 2640
gtcttcaatc tctttgtact ggtctcaaat gtactggtat ctctgctttt tgccacagtt 2700
tgtccctgaa aactttatca gtgaggagaa atacagaatt ttccttttgg ttcccctgta 2760
ataccacaac taatagtatt ttcagctaac atttattgac caggcagtgt gataaatttt 2820
ttgaatgacc atcttgttta accccctaat cacactatct gaagtaggtg ctatagtgac 2880
ccccaaccga agatgaggaa atggagacac acagtggcta agtagcttgc taggtgccag 2940
gagctggcag gcagtgatgc tgaaatccaa accaggcaat ctggccctcc ttattcaccc 3000
tctcatacca ccagtgctac ccattataac ctgtgttcac ttcgcttatt actgtggccc 3060
ttctggtgac tacaacataa cactgagtat gaactgagga attaaccact gaaagagaca 3120
aagcacacct aaataatgat gaacaaatca agacctacaa gaaatgaaca catagatgct 3180
ttttaagtgt cattagttat cggaatcaaa gaatttgagg tggtgacaac tggggattat 3240
ctgtaactcc ccaaatttac tgttcttgaa tgacattctc aaactattta ttaatgagtt 3300
agtctcatcc ctgctttctg tttcctctct ctgcatcttc tcttggcata ggaagttatt 3360
ttactcatgc tatgtttttt aatagaagct ttacaaaaaa agatgcattc ccttcctgtt 3420
cacactctta ccatgttttt gttcttcctt aagaatgatt gtgtgtgtgt gtgtgtgtgt 3480
gtgtaagtgt gtaagtgtaa catcatgggt tttctttctt cacttgtaaa gttttatcta 3540
gaaatacttt tacaggttat gttgaggtac acaaagataa tgttctaaga ttgtgtattg 3600
gatttggatt tgtgtgtgtg tgtgtgtgtg tgtgtgttta aagcatttga taaggtttaa 3660
atgtttttta tacagagatt tttgttcatt aaactcaatc tgcatcatgg tctaa 3715

<210> SEQ ID NO 37
<211> LENGTH: 2207
<212> TYPE: DNA
<213> ORGANISM: Homo sapiens

<400> SEQUENCE: 37
actgacggcc ggccggcttc ccggaactgg aaggttacat tgattaccca cctagtacaa 60
catcttacgg gaagagcata gtatttccta gaggaatatg aacataacag gaaggtatca 120
ttggctctga attaaatttg aacttgtccc ctgaatagct acaggttttg gaagctgaat 180
caatgttatc agatgagtta gaatccaaac cagagctcct ggtacagttt gttcagaata 240
cgtccatccc attgggacag gggcttgtag aatcagaagc taaagatatt acttgcttgt 300
ccctccttcc cgtgactgaa gcctcagaat gcagtcggct aatgttacca gatgatacta 360
caaatcattc taactcctcc aaggaggtcc cttcctcagc tgttttgaga agccttcggg 420

-continued

```
tgaatgtggg tccagacgga gaggagacga gagctcagac tgtacagaaa tccccggagt    480
ttttgtccac ttcagagtct tctagcttgt tgcaagatct acagccaagt gatagcactt    540
cttttattct tcttaaccta acaagagcag gtctgggctc ttcagctgag cacttagtgt    600
ttgtacagga tgaggcagaa gattcaggga atgatttcct ctccagtgag agcacagaca    660
gtagcattcc atggttcctc cgggttcagg agttggccca tgacagtttg attgctgcta    720
ctcgtgcaca actggcaaag aatgcaaaaa ccagcagcaa tggagaaaat gtccaccttg    780
gttctggtga tgggcagtca aaagattctg ggccccttcc tcaagtggaa aagaagctca    840
agtgtacagt tgaaggttgt gaccggacat ttgtatggcc agctcacttt aaataccacc    900
tcaagactca tcgaaatgac cgctccttca tctgtcctgc agaaggttgt gggaaaagct    960
tctatgtgct gcagaggctg aaggtgcaca tgaggaccca caatggagag aagcccttta   1020
tgtgccatga gtctggctgt ggtaagcagt ttactacagc tggaaacctg aagaaccacc   1080
ggcgcatcca cacaggagag aaacctttcc tttgtgaagc ccaaggatgt ggccgttcct   1140
ttgctgagta ttctagcctc cgaaaacatc tggtggttca ctcaggagag aagcctcatc   1200
agtgccaagt ctgtgggaag accttctctc agagtggaag caggaatgtg catatgagaa   1260
agcatcacct gcagctggga gcagctggga gtcaagagca ggagcaaact gctgagccac   1320
taatgggcag tagtttgctt gaagaggctt cagtacccag taaaaacctg gtgtctatga   1380
attcccagcc cagccttggt ggagagtcct tgaacctacc aaataccaat tctatcctgg   1440
gagttgatga tgaggtgctt gctgaaggat ccccacgttc cctgtcttca gtgcctgatg   1500
tgacacatca cctggtgacc atgcagtcag ggaggcaatc atatgaagtt tctgtcttaa   1560
ctgcagtaaa tccacaagag ttactaaacc aaggagattt aactgaaaga cggacatgag   1620
cgtgggtgct gactcctgga agagcaactc tatctgatct caaaatgcgt atactgggaa   1680
caggatgcct tagcccacaa cagaaccaga atgaatcttt gaaggcacaa gactctgctt   1740
ttgccactct tcctctttcc tggtatagaa gatggatgta ggagagcttc ttttctaact   1800
accatctgat cagacaagga atgaagcaat gactgtgggc tgggaaactg tacctacctc   1860
tcttcccact gcaaatttct gggatagacc aaaagtgaat ttgattatgt gttggctgaa   1920
gttcttcatt ctgactgttg aggggaggtt ttcctttgaa gagttttcat cccagactca   1980
gctgtctttt cacatggatg aaataattcc tgctaccaac aacagagctt caccaggaag   2040
ttgagttttc aagatgcctt gttgctttga agaagggagt gatgtcaatt ctcttgttac   2100
attctccctt tagcaacctg agtaagagac tctctgccac tgggctgcaa aaaaataaat   2160
tacttgaatc tccccttgaa aaaaaaaaaa aaaaaaaaaa aaaaaaa                 2207
```

<210> SEQ ID NO 38
<211> LENGTH: 1310
<212> TYPE: DNA
<213> ORGANISM: Homo sapiens

<400> SEQUENCE: 38

```
aaattgagcc cgcagcctcc cgcttcgctc tctgctcctc ctgttcgaca gtcagccgca     60
tcttcttttg cgtcgccagc cgagccacat cgctcagaca ccatggggaa ggtgaaggtc    120
ggagtcaacg gatttggtcg tattgggcgc ctggtcacca gggctgcttt taactctggt    180
aaagtggata ttgttgccat caatgacccc ttcattgacc tcaactacat ggtttacatg    240
ttccaatatg attccaccca tggcaaattc catggcaccg tcaaggctga gaacgggaag    300
cttgtcatca atggaaatcc catcaccatc ttccaggagc gagatccctc caaaatcaag    360
```

-continued tggggcgatg ctggcgctga gtacgtcgtg gagtccactg gcgtcttcac caccatggag 420
aaggctgggg ctcatttgca ggggggagcc aaaagggtca tcatctctgc cccctctgct 480
gatgccccca tgttcgtcat gggtgtgaac catgagaagt atgacaacag cctcaagatc 540
atcagcaatg cctcctgcac caccaactgc ttagcacccc tggccaaggt catccatgac 600
aactttggta tcgtggaagg actcatgacc acagtccatg ccatcactgc cacccagaag 660
actgtggatg gcccctccgg gaaactgtgg cgtgatggcc gcggggctct ccagaacatc 720
atccctgcct ctactggcgc tgccaaggct gtgggcaagg tcatccctga gctgaacggg 780
aagctcactg gcatggcctt ccgtgtcccc actgccaacg tgtcagtggt ggacctgacc 840
tgccgtctag aaaaacctgc caaatatgat gacatcaaga aggtggtgaa gcaggcgtcg 900
gagggccccc tcaagggcat cctgggctac actgagcacc aggtggtctc ctctgacttc 960
aacagcgaca cccactcctc cacctttgac gctggggctg gcattgccct caacgaccac 1020
tttgtcaagc tcatttcctg gtatgacaac gaatttggct acagcaacag ggtggtggac 1080
ctcatggccc acatggcctc caaggagtaa gacccctgga ccaccagccc cagcaagagc 1140
acaagaggaa gagagagacc ctcactgctg gggagtccct gccacactca gtcccccacc 1200
acactgaatc tcccctcctc acagttgcca tgtagacccc ttgaagaggg gaggggccta 1260
gggagccgca ccttgtcatg taccatcaat aaagtaccct gtgctcaacc 1310

<210> SEQ ID NO 39
<211> LENGTH: 1869
<212> TYPE: DNA
<213> ORGANISM: Homo sapiens

<400> SEQUENCE: 39
tacctggttg atcctgccag tagcatatgc ttgtctcaaa gattaagcca tgcatgtcta 60
agtacgcacg gccggtacag tgaaactgcg aatggctcat taaatcagtt atggttcctt 120
tggtcgctcg ctcctctccc acttggataa ctgtggtaat tctagagcta atacatgccg 180
acgggcgctg accccccttcg cggggggggat gcgtgcattt atcagatcaa aaccaacccg 240
gtcagcccct ctccggcccc ggccgggggg cgggcgccgg cggctttggt gactctagat 300
aacctcgggc cgatcgcacg ccccccgtgg cggcgacgac ccattcgaac gtctgcccta 360
tcaactttcg atggtagtcg ccgtgcctac catggtgacc acgggtgacg gggaatcagg 420
gttcgattcc ggagagggag cctgagaaac ggctaccaca tccaaggaag gcagcaggcg 480
cgcaaattac ccactcccga cccggggagg tagtgacgaa aaataacaat acaggactct 540
ttcgaggccc tgtaattgga atgagtccac tttaaatcct ttaacgagga tccattggag 600
ggcaagtctg gtgccagcag ccgcggtaat tccagctcca atagcgtata ttaaagttgc 660
tgcagttaaa aagctcgtag ttggatcttg ggagcgggcg ggcggtccgc cgcgaggcga 720
gccaccgccc gtccccgccc cttgcctctc ggcgcccccct cgatgctctt agctgagtgt 780
cccgcggggc ccgaagcgtt tactttgaaa aaattagagt gttcaaagca ggcccgagcc 840
gcctggatac cgcagctagg aataatggaa taggaccgcg gttctatttt gttggttttc 900
ggaactgagg ccatgattaa gagggacggc cgggggcatt cgtattgcgc cgctagaggt 960
gaaattcttg gaccggcgca agacggacca gagcgaaagc atttgccaag aatgttttca 1020
ttaatcaaga acgaaagtcg gaggttcgaa gacgatcaga taccgtcgta gttccgacca 1080
taaacgatgc cgaccggcga tgcggcggcg ttattcccat gacccgccgg gcagcttccg 1140

```
ggaaaccaaa gtctttgggt tccgggggga gtatggttgc aaagctgaaa cttaaaggaa   1200

ttgacggaag ggcaccacca ggagtggagc ctgcggctta atttgactca acacgggaaa   1260

cctcacccgg cccggacacg gacaggattg acagattgat agctctttct cgattccgtg   1320

ggtggtggtg catggccgtt cttagttggt ggagcgattt gtctggttaa ttccgataac   1380

gaacgagact ctggcatgct aactagttac gcgacccccg agcggtcggc gtcccccaac   1440

ttcttagagg gacaagtggc gttcagccac ccgagattga gcaataacag gtctgtgatg   1500

cccttagatg tccggggctg cacgcgcgct acactgactg gctcagcgtg tgcctaccct   1560

acgccggcag gcgcgggtaa cccgttgaac cccattcgtg atggggatcg ggattgcaa   1620

ttattcccca tgaacgagga attcccagta agtgcgggtc ataagcttgc gttgattaag   1680

tccctgccct ttgtacacac cgcccgtcgc tactaccgat tggatggttt agtgaggccc   1740

tcggatcggc cccgccgggg tcggcccacg gccctggcgg agcgctgaga agacggtcga   1800

acttgactat ctagaggaag taaaagtcgt aacaaggttt ccgtaggtga acctgcggaa   1860

ggatcatta                                                           1869
```

<210> SEQ ID NO 40
<211> LENGTH: 1435
<212> TYPE: DNA
<213> ORGANISM: Homo sapiens

<400> SEQUENCE: 40

```
ggcggggcct gcttctcctc agcttcaggc ggctgcgacg agccctcagg cgaacctctc     60

ggctttcccg cgcggcgccg cctcttgctg cgcctccgcc tcctcctctg ctccgccacc    120

ggcttcctcc tcctgagcag tcagcccgcg cgccggccgg ctccgttatg gcgacccgca    180

gccctggcgt cgtgattagt gatgatgaac caggttatga ccttgattta ttttgcatac    240

ctaatcatta tgctgaggat ttggaaaggg tgtttattcc tcatggacta attatggaca    300

ggactgaacg tcttgctcga gatgtgatga aggagatggg aggccatcac attgtagccc    360

tctgtgtgct caagggggc tataaattct ttgctgacct gctggattac atcaaagcac    420

tgaatagaaa tagtgataga tccattccta tgactgtaga ttttatcaga ctgaagagct    480

attgtaatga ccagtcaaca ggggacataa aagtaattgg tggagatgat ctctcaactt    540

taactggaaa gaatgtcttg attgtggaag atataattga cactggcaaa acaatgcaga    600

ctttgctttc cttggtcagg cagtataatc caaagatggt caaggtcgca agcttgctgg    660

tgaaaaggac cccacgaagt gttggatata agccagactt tgttggattt gaaattccag    720

acaagtttgt tgtaggatat gcccttgact ataatgaata cttcagggat ttgaatcatg    780

tttgtgtcat tagtgaaact ggaaaagcaa aatacaaagc ctaagatgag agttcaagtt    840

gagtttggaa acatctggag tcctattgac atcgccagta aaattatcaa tgttctagtt    900

ctgtggccat ctgcttagta gagctttttg catgtatctt ctaagaattt tatctgtttt    960

gtactttaga aatgtcagtt gctgcattcc taaactgttt atttgcacta tgagcctata   1020

gactatcagt tccctttggg cggattgttg tttaacttgt aaatgaaaaa attctcttaa   1080

accacagcac tattgagtga aacattgaac tcatatctgt aagaaataaa gagaagatat   1140

attagttttt taattggtat tttaattttt atatatgcag gaaagaatag aagtgattga   1200

atattgttaa ttataccacc gtgtgttaga aaagtaagaa gcagtcaatt ttcacatcaa   1260

agacagcatc taagaagttt tgttctgtcc tggaattatt ttagtagtgt ttcagtaatg   1320

ttgactgtat tttccaactt gttcaaatta ttaccagtga atctttgtca gcagttccct   1380
```

tttaaatgca aatcaataaa ttcccaaaaa tttaaaaaaa aaaaaaaaaa aaaaa 1435

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
cggtgccgaa gagaaagtga 20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
ctctctcggc attgaaaatc 20

<210> SEQ ID NO 43
<211> LENGTH: 20
<212> TYPE: DNA
<213> ORGANISM: Artificial Sequence
<220> FEATURE:
<223> OTHER INFORMATION: primer

<400> SEQUENCE: 43
ctcatcgacg tggcccggca 20

<210> SEQ ID NO 44
<211> LENGTH: 20
<212> TYPE: DNA
<213> ORGANISM: Artificial Sequence
<220> FEATURE:
<223> OTHER INFORMATION: primer

<400> SEQUENCE: 44
gtggatgatg ttcttggcat 20

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
cctcttcggc tgcggaccct 20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gtgtcaactt aatcatttgt 20

<210> SEQ ID NO 47
<211> LENGTH: 20
<212> TYPE: DNA

<213> ORGANISM: Artificial Sequence
<220> FEATURE:
<223> OTHER INFORMATION: primer

<400> SEQUENCE: 47
ggctgctgct cgtcctggct 20

<210> SEQ ID NO 48
<211> LENGTH: 20
<212> TYPE: DNA
<213> ORGANISM: Artificial Sequence
<220> FEATURE:
<223> OTHER INFORMATION: primer

<400> SEQUENCE: 48
ttgggttagg acagttgtag 20

<210> SEQ ID NO 49
<211> LENGTH: 20
<212> TYPE: DNA
<213> ORGANISM: Artificial Sequence
<220> FEATURE:
<223> OTHER INFORMATION: primer

<400> SEQUENCE: 49
aacggatcct ttccattctg 20

<210> SEQ ID NO 50
<211> LENGTH: 20
<212> TYPE: DNA
<213> ORGANISM: Artificial Sequence
<220> FEATURE:
<223> OTHER INFORMATION: primer

<400> SEQUENCE: 50
ctgagagttc atcttcaaaa 20

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
tgcgaagctg acctggaaga 20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
ttttgggagt acggatgcac 20

<210> SEQ ID NO 53
<211> LENGTH: 20
<212> TYPE: DNA
<213> ORGANISM: Artificial Sequence
<220> FEATURE:
<223> OTHER INFORMATION: primer

<400> SEQUENCE: 53
aagcgcttca tcaagtggta 20

<210> SEQ ID NO 54
<211> LENGTH: 20
<212> TYPE: DNA
<213> ORGANISM: Artificial Sequence
<220> FEATURE:
<223> OTHER INFORMATION: primer

<400> SEQUENCE: 54
tgaggttttt caccctattc 20

<210> SEQ ID NO 55
<211> LENGTH: 20
<212> TYPE: DNA
<213> ORGANISM: Artificial Sequence
<220> FEATURE:
<223> OTHER INFORMATION: primer

<400> SEQUENCE: 55
gatgcgggac cccggcgcgg 20

<210> SEQ ID NO 56
<211> LENGTH: 20
<212> TYPE: DNA
<213> ORGANISM: Artificial Sequence
<220> FEATURE:
<223> OTHER INFORMATION: primer

<400> SEQUENCE: 56
cagcagcgcc agcaccaggg 20

<210> SEQ ID NO 57
<211> LENGTH: 20
<212> TYPE: DNA
<213> ORGANISM: Artificial Sequence
<220> FEATURE:
<223> OTHER INFORMATION: primer

<400> SEQUENCE: 57
aagtttgcat acctctatga 20

<210> SEQ ID NO 58
<211> LENGTH: 21
<212> TYPE: DNA
<213> ORGANISM: Artificial Sequence
<220> FEATURE:
<223> OTHER INFORMATION: primer

<400> SEQUENCE: 58
tttcagcagc agaatccagc a 21

<210> SEQ ID NO 59
<211> LENGTH: 20
<212> TYPE: DNA
<213> ORGANISM: Artificial Sequence
<220> FEATURE:
<223> OTHER INFORMATION: primer

<400> SEQUENCE: 59
ccagatttac ccctggatgc 20

<210> SEQ ID NO 60
<211> LENGTH: 20
<212> TYPE: DNA
<213> ORGANISM: Artificial Sequence
<220> FEATURE:

<223> OTHER INFORMATION: primer

<400> SEQUENCE: 60
cgagtagatc tggcggccgc 20

<210> SEQ ID NO 61
<211> LENGTH: 20
<212> TYPE: DNA
<213> ORGANISM: Artificial Sequence
<220> FEATURE:
<223> OTHER INFORMATION: primer

<400> SEQUENCE: 61
gcacgtcgtg tctcaagatc 20

<210> SEQ ID NO 62
<211> LENGTH: 20
<212> TYPE: DNA
<213> ORGANISM: Artificial Sequence
<220> FEATURE:
<223> OTHER INFORMATION: primer

<400> SEQUENCE: 62
gacacacgcc ttcttttcaa 20

<210> SEQ ID NO 63
<211> LENGTH: 20
<212> TYPE: DNA
<213> ORGANISM: Artificial Sequence
<220> FEATURE:
<223> OTHER INFORMATION: primer

<400> SEQUENCE: 63
gtggcctctg tggggaattc 20

<210> SEQ ID NO 64
<211> LENGTH: 20
<212> TYPE: DNA
<213> ORGANISM: Artificial Sequence
<220> FEATURE:
<223> OTHER INFORMATION: primer

<400> SEQUENCE: 64
ctccccgggg gccaggaggc 20

<210> SEQ ID NO 65
<211> LENGTH: 20
<212> TYPE: DNA
<213> ORGANISM: Artificial Sequence
<220> FEATURE:
<223> OTHER INFORMATION: primer

<400> SEQUENCE: 65
tcaggactta gcaagaagtt 20

<210> SEQ ID NO 66
<211> LENGTH: 20
<212> TYPE: DNA
<213> ORGANISM: Artificial Sequence
<220> FEATURE:
<223> OTHER INFORMATION: primer

<400> SEQUENCE: 66
tcatcttttc tttatgtttt 20

<210> SEQ ID NO 67
<211> LENGTH: 20
<212> TYPE: DNA
<213> ORGANISM: Artificial Sequence
<220> FEATURE:
<223> OTHER INFORMATION: primer

<400> SEQUENCE: 67
gaatcaggat actcggccca 20

<210> SEQ ID NO 68
<211> LENGTH: 20
<212> TYPE: DNA
<213> ORGANISM: Artificial Sequence
<220> FEATURE:
<223> OTHER INFORMATION: primer

<400> SEQUENCE: 68
actctgatca ctgctgccat 20

<210> SEQ ID NO 69
<211> LENGTH: 20
<212> TYPE: DNA
<213> ORGANISM: Artificial Sequence
<220> FEATURE:
<223> OTHER INFORMATION: primer

<400> SEQUENCE: 69
ggcggtacgc aagccgctgg 20

<210> SEQ ID NO 70
<211> LENGTH: 21
<212> TYPE: DNA
<213> ORGANISM: Artificial Sequence
<220> FEATURE:
<223> OTHER INFORMATION: primer

<400> SEQUENCE: 70
ggacacgctt ttcacggggt c 21

<210> SEQ ID NO 71
<211> LENGTH: 20
<212> TYPE: DNA
<213> ORGANISM: Artificial Sequence
<220> FEATURE:
<223> OTHER INFORMATION: primer

<400> SEQUENCE: 71
ggtctacctt ctgcttccct 20

<210> SEQ ID NO 72
<211> LENGTH: 20
<212> TYPE: DNA
<213> ORGANISM: Artificial Sequence
<220> FEATURE:
<223> OTHER INFORMATION: primer

<400> SEQUENCE: 72
tcttgtaaga actaaaattg 20

<210> SEQ ID NO 73
<211> LENGTH: 20
<212> TYPE: DNA
<213> ORGANISM: Artificial Sequence
<220> FEATURE:
<223> OTHER INFORMATION: primer

<400> SEQUENCE: 73
aaggaacatg aagaggagcc 20

<210> SEQ ID NO 74
<211> LENGTH: 21
<212> TYPE: DNA
<213> ORGANISM: Artificial Sequence
<220> FEATURE:
<223> OTHER INFORMATION: primer

<400> SEQUENCE: 74
ccgccttgca gtctccggcc g 21

<210> SEQ ID NO 75
<211> LENGTH: 21
<212> TYPE: DNA
<213> ORGANISM: Artificial Sequence
<220> FEATURE:
<223> OTHER INFORMATION: primer

<400> SEQUENCE: 75
agccctctac ttttcaagac a 21

<210> SEQ ID NO 76
<211> LENGTH: 21
<212> TYPE: DNA
<213> ORGANISM: Artificial Sequence
<220> FEATURE:
<223> OTHER INFORMATION: primer

<400> SEQUENCE: 76
agccagcatc tttggaattc a 21

<210> SEQ ID NO 77
<211> LENGTH: 21
<212> TYPE: DNA
<213> ORGANISM: Artificial Sequence
<220> FEATURE:
<223> OTHER INFORMATION: primer

<400> SEQUENCE: 77
ctggaggaag actggacaaa g 21

<210> SEQ ID NO 78
<211> LENGTH: 21
<212> TYPE: DNA
<213> ORGANISM: Artificial Sequence
<220> FEATURE:
<223> OTHER INFORMATION: primer

<400> SEQUENCE: 78
caccatcatg aagaagctga a 21

<210> SEQ ID NO 79
<211> LENGTH: 20
<212> TYPE: DNA
<213> ORGANISM: Artificial Sequence
<220> FEATURE:
<223> OTHER INFORMATION: primer

<400> SEQUENCE: 79
gggtccaagc cgccctgctg 20

<210> SEQ ID NO 80
<211> LENGTH: 20

<212> TYPE: DNA
<213> ORGANISM: Artificial Sequence
<220> FEATURE:
<223> OTHER INFORMATION: primer

<400> SEQUENCE: 80
ccttccactc tgggacccag 20

<210> SEQ ID NO 81
<211> LENGTH: 20
<212> TYPE: DNA
<213> ORGANISM: Artificial Sequence
<220> FEATURE:
<223> OTHER INFORMATION: primer

<400> SEQUENCE: 81
gcagcgcctg cgcgtggcgt 20

<210> SEQ ID NO 82
<211> LENGTH: 20
<212> TYPE: DNA
<213> ORGANISM: Artificial Sequence
<220> FEATURE:
<223> OTHER INFORMATION: primer

<400> SEQUENCE: 82
tcacatactg agtatagtca 20

<210> SEQ ID NO 83
<211> LENGTH: 21
<212> TYPE: DNA
<213> ORGANISM: Artificial Sequence
<220> FEATURE:
<223> OTHER INFORMATION: primer

<400> SEQUENCE: 83
gacatccaca cctaatgtcc a 21

<210> SEQ ID NO 84
<211> LENGTH: 21
<212> TYPE: DNA
<213> ORGANISM: Artificial Sequence
<220> FEATURE:
<223> OTHER INFORMATION: primer

<400> SEQUENCE: 84
ctgattcgct gtgacttcga a 21

<210> SEQ ID NO 85
<211> LENGTH: 20
<212> TYPE: DNA
<213> ORGANISM: Artificial Sequence
<220> FEATURE:
<223> OTHER INFORMATION: primer

<400> SEQUENCE: 85
ctcctttacg agaagatgaa 20

<210> SEQ ID NO 86
<211> LENGTH: 20
<212> TYPE: DNA
<213> ORGANISM: Artificial Sequence
<220> FEATURE:
<223> OTHER INFORMATION: primer

<400> SEQUENCE: 86
acattatcca gtctctgtcc 20

<210> SEQ ID NO 87
<211> LENGTH: 20
<212> TYPE: DNA
<213> ORGANISM: Artificial Sequence
<220> FEATURE:
<223> OTHER INFORMATION: primer

<400> SEQUENCE: 87
cctgtgtgtc agccgcaagc 20

<210> SEQ ID NO 88
<211> LENGTH: 20
<212> TYPE: DNA
<213> ORGANISM: Artificial Sequence
<220> FEATURE:
<223> OTHER INFORMATION: primer

<400> SEQUENCE: 88
gtgtttctgg gccacgttcc 20

<210> SEQ ID NO 89
<211> LENGTH: 21
<212> TYPE: DNA
<213> ORGANISM: Artificial Sequence
<220> FEATURE:
<223> OTHER INFORMATION: primer

<400> SEQUENCE: 89
ctggactttc ctccaggagt t 21

<210> SEQ ID NO 90
<211> LENGTH: 20
<212> TYPE: DNA
<213> ORGANISM: Artificial Sequence
<220> FEATURE:
<223> OTHER INFORMATION: primer

<400> SEQUENCE: 90
ccgcagtttc ctcaaattct 20

<210> SEQ ID NO 91
<211> LENGTH: 22
<212> TYPE: DNA
<213> ORGANISM: Artificial Sequence
<220> FEATURE:
<223> OTHER INFORMATION: primer

<400> SEQUENCE: 91
gaagagcaag tctcattttt tc 22

<210> SEQ ID NO 92
<211> LENGTH: 20
<212> TYPE: DNA
<213> ORGANISM: Artificial Sequence
<220> FEATURE:
<223> OTHER INFORMATION: primer

<400> SEQUENCE: 92
aacaaaaatc tcaaattctg 20

<210> SEQ ID NO 93
<211> LENGTH: 21
<212> TYPE: DNA
<213> ORGANISM: Artificial Sequence
<220> FEATURE:
<223> OTHER INFORMATION: primer

<400> SEQUENCE: 93
ctaacagctg ccaatacctc a 21

<210> SEQ ID NO 94
<211> LENGTH: 21
<212> TYPE: DNA
<213> ORGANISM: Artificial Sequence
<220> FEATURE:
<223> OTHER INFORMATION: primer

<400> SEQUENCE: 94
ctgcagcctt tatggaagag g 21

<210> SEQ ID NO 95
<211> LENGTH: 20
<212> TYPE: DNA
<213> ORGANISM: Artificial Sequence
<220> FEATURE:
<223> OTHER INFORMATION: primer

<400> SEQUENCE: 95
ctgaaggacc cgtacatcct 20

<210> SEQ ID NO 96
<211> LENGTH: 21
<212> TYPE: DNA
<213> ORGANISM: Artificial Sequence
<220> FEATURE:
<223> OTHER INFORMATION: primer

<400> SEQUENCE: 96
gcgatgccca tgtttgcaaa g 21

<210> SEQ ID NO 97
<211> LENGTH: 20
<212> TYPE: DNA
<213> ORGANISM: Artificial Sequence
<220> FEATURE:
<223> OTHER INFORMATION: primer

<400> SEQUENCE: 97
gtgaactctc agctactgga 20

<210> SEQ ID NO 98
<211> LENGTH: 20
<212> TYPE: DNA
<213> ORGANISM: Artificial Sequence
<220> FEATURE:
<223> OTHER INFORMATION: primer

<400> SEQUENCE: 98
tgcccctttc atcaacttca 20

<210> SEQ ID NO 99
<211> LENGTH: 20
<212> TYPE: DNA
<213> ORGANISM: Artificial Sequence
<220> FEATURE:
<223> OTHER INFORMATION: primer

<400> SEQUENCE: 99
tttgtgagct gtatttgtga 20

<210> SEQ ID NO 100
<211> LENGTH: 20
<212> TYPE: DNA
<213> ORGANISM: Artificial Sequence
<220> FEATURE:
<223> OTHER INFORMATION: primer

<400> SEQUENCE: 100
caacccaaac ttcttgcaca 20

<210> SEQ ID NO 101
<211> LENGTH: 21
<212> TYPE: DNA
<213> ORGANISM: Artificial Sequence
<220> FEATURE:
<223> OTHER INFORMATION: primer

<400> SEQUENCE: 101
aatctgtggc cctgcagatg g 21

<210> SEQ ID NO 102
<211> LENGTH: 21
<212> TYPE: DNA
<213> ORGANISM: Artificial Sequence
<220> FEATURE:
<223> OTHER INFORMATION: primer

<400> SEQUENCE: 102
gattcctgac aaacataaat g 21

<210> SEQ ID NO 103
<211> LENGTH: 20
<212> TYPE: DNA
<213> ORGANISM: Artificial Sequence
<220> FEATURE:
<223> OTHER INFORMATION: primer

<400> SEQUENCE: 103
cgttcctttg ctgagtattc 20

<210> SEQ ID NO 104
<211> LENGTH: 22
<212> TYPE: DNA
<213> ORGANISM: Artificial Sequence
<220> FEATURE:
<223> OTHER INFORMATION: primer

<400> SEQUENCE: 104
ccactctgag agaaggtctt cc 22

<210> SEQ ID NO 105
<211> LENGTH: 2122
<212> TYPE: DNA
<213> ORGANISM: Homo sapiens

<400> SEQUENCE: 105
gggctgcaaa gctgaagctt tggtttctgc tctaaatgaa ggacttttcc aggacccaag 60
gccacacact ggaagtcttg cagctgaagg gaggcactcc ttggcctccg cagccgatca 120
catgaaggtg gtgccaagtc tcctgctctc cgtcctcctg gcacaggtgt ggctggtacc 180
cggcttggcc cccagtcctc agtcgccaga gaccccagcc cctcagaacc agaccagcag 240
ggtagtgcag gctcccaagg aggaagagga agatgagcag gaggccagcg aggagaaggc 300
cagtgaggaa gagaaagcct ggctgatggc cagcaggcag cagcttgcca aggagacttc 360
aaacttcgga ttcagcctgc tgcgaaagat ctccatgagg cacgatggca acatggtctt 420
ctctccattt ggcatgtcct tggccatgac aggcttgatg ctgggggcca cagggccgac 480
tgaaacccag atcaagagag ggctccactt gcaggccctg aagcccacca agcccgggct 540
cctgccttcc ctctttaagg gactcagaga gaccctctcc cgcaacctgg aactgggcct 600
cacacagggg agttttgcct tcatccacaa ggattttgat gtcaaagaga ctttcttcaa 660
tttatccaag aggtattttg atacagagtg cgtgcctatg aattttcgca atgcctcaca 720
ggccaaaagg ctcatgaatc attacattaa caaagagact cgggggaaaa ttcccaaact 780
gtttgatgag attaatcctg aaaccaaatt aattcttgtg gattacatct tgttcaaagg 840
gaaatggttg accccatttg accctgtctt caccgaagtc gacactttcc acctggacaa 900
gtacaagacc attaaggtgc ccatgatgta cggtgcaggc aagtttgcct ccacctttga 960
caagaatttt cgttgtcatg tcctcaaact gccctaccaa ggaaatgcca ccatgctggt 1020
ggtcctcatg gagaaaatgg gtgaccacct cgcccttgaa gactacctga ccacagactt 1080
ggtggagaca tggctcagaa acatgaaaac cagaaacatg gaagttttct ttccgaagtt 1140
caagctagat cagaagtatg agatgcatga gctgcttagg cagatgggaa tcagaagaat 1200
cttctcaccc tttgctgacc ttagtgaact ctcagctact ggaagaaatc tccaagtatc 1260
cagggtttta caaagaacag tgattgaagt tgatgaaagg ggcactgagg cagtggcagg 1320
aatcttgtca gaaattactg cttattccat gcctcctgtc atcaaagtgg accggccatt 1380
tcatttcatg atctatgaag aaacctctgg aatgcttctg tttctgggca gggtggtgaa 1440
tccgactctc ctataattca ggacacgcat aagcacttcg tgctgtagta gatgctgaat 1500
ctgaggtatc aaacacacac aggataccag caatggatgg caggggagag tgttcctttt 1560
gttcttaact agtttagggt gttctcaaat aaatacagta gtccccactt atctgagggg 1620
gatacattca aagaccccca gcagatgcct gaaacggtgg acagtgctga accttatata 1680
tattttttcc tacacataca tacctatgat aaagtttaat ttataaatta ggcacagtaa 1740
gagattaaca ataataacaa cattaagtaa aatgagttac ttgaatgcaa gcactgcaat 1800
accataacag tcaaactgat tatagagaag gctactaagt gactcatggg cgaggagcat 1860
agacagtgtg gagacattgg gcaaggggag aattcacatc ctgggtggga cagagcagga 1920
caatgcaaga ttccatccca ctactcagaa tggcatgctg cttaagactt ttagattgtt 1980
tatttctgga atttttcatt taatgttttt ggaccatggt tgaccatggt taactgagac 2040
tgcagaaagc aaaaccatgg ataagggagg actactacaa aagcattaaa ttgatacata 2100
ttttttaaaa aaaaaaaaaa aa 2122

<210> SEQ ID NO 106
<211> LENGTH: 20
<212> TYPE: DNA
<213> ORGANISM: Artificial Sequence
<220> FEATURE:
<223> OTHER INFORMATION: primer

<400> SEQUENCE: 106
gaagcatctg aagaccatgg 20

<210> SEQ ID NO 107
<211> LENGTH: 20
<212> TYPE: DNA
<213> ORGANISM: Artificial Sequence
<220> FEATURE:

<223> OTHER INFORMATION: primer

<400> SEQUENCE: 107
atgagggagg acttcttgga 20

<210> SEQ ID NO 108
<211> LENGTH: 20
<212> TYPE: DNA
<213> ORGANISM: Artificial Sequence
<220> FEATURE:
<223> OTHER INFORMATION: primer

<400> SEQUENCE: 108
caggtccgct ataatgctct 20

<210> SEQ ID NO 109
<211> LENGTH: 20
<212> TYPE: DNA
<213> ORGANISM: Artificial Sequence
<220> FEATURE:
<223> OTHER INFORMATION: primer

<400> SEQUENCE: 109
ggcagcggtc tggggctgct 20

<210> SEQ ID NO 110
<211> LENGTH: 20
<212> TYPE: DNA
<213> ORGANISM: Artificial Sequence
<220> FEATURE:
<223> OTHER INFORMATION: primer

<400> SEQUENCE: 110
cagagtagtt ccagaggcag 20

<210> SEQ ID NO 111
<211> LENGTH: 21
<212> TYPE: DNA
<213> ORGANISM: Artificial Sequence
<220> FEATURE:
<223> OTHER INFORMATION: primer

<400> SEQUENCE: 111
aaacatgatc tgcccatctt c 21

<210> SEQ ID NO 112
<211> LENGTH: 20
<212> TYPE: DNA
<213> ORGANISM: Artificial Sequence
<220> FEATURE:
<223> OTHER INFORMATION: primer

<400> SEQUENCE: 112
attactgtgc ccgtggaaat 20

<210> SEQ ID NO 113
<211> LENGTH: 20
<212> TYPE: DNA
<213> ORGANISM: Artificial Sequence
<220> FEATURE:
<223> OTHER INFORMATION: primer

<400> SEQUENCE: 113
gaaagaccaa aggaatggag 20

<210> SEQ ID NO 114
<211> LENGTH: 20
<212> TYPE: DNA
<213> ORGANISM: Artificial Sequence
<220> FEATURE:
<223> OTHER INFORMATION: primer

<400> SEQUENCE: 114
ctcaaaaacc tgctgacaaa 20

<210> SEQ ID NO 115
<211> LENGTH: 20
<212> TYPE: DNA
<213> ORGANISM: Artificial Sequence
<220> FEATURE:
<223> OTHER INFORMATION: primer

<400> SEQUENCE: 115
gtggcagaga gatctgattt 20

<210> SEQ ID NO 116
<211> LENGTH: 21
<212> TYPE: DNA
<213> ORGANISM: Artificial Sequence
<220> FEATURE:
<223> OTHER INFORMATION: primer

<400> SEQUENCE: 116
gctggacaat tgtgctaaat g 21

<210> SEQ ID NO 117
<211> LENGTH: 20
<212> TYPE: DNA
<213> ORGANISM: Artificial Sequence
<220> FEATURE:
<223> OTHER INFORMATION: primer

<400> SEQUENCE: 117
aaatggatgc atactaggca 20

<210> SEQ ID NO 118
<211> LENGTH: 20
<212> TYPE: DNA
<213> ORGANISM: Artificial Sequence
<220> FEATURE:
<223> OTHER INFORMATION: primer

<400> SEQUENCE: 118
tcagcgaggg cgaacaagag 20

<210> SEQ ID NO 119
<211> LENGTH: 20
<212> TYPE: DNA
<213> ORGANISM: Artificial Sequence
<220> FEATURE:
<223> OTHER INFORMATION: primer

<400> SEQUENCE: 119
tccgcgatgg caaactgctc 20

<210> SEQ ID NO 120
<211> LENGTH: 20
<212> TYPE: DNA
<213> ORGANISM: Artificial Sequence
<220> FEATURE:
<223> OTHER INFORMATION: primer

<400> SEQUENCE: 120
acacaaactg gagaatggtc 20

<210> SEQ ID NO 121
<211> LENGTH: 20
<212> TYPE: DNA
<213> ORGANISM: Artificial Sequence
<220> FEATURE:
<223> OTHER INFORMATION: primer

<400> SEQUENCE: 121
tgttccagag gctgctgcag 20

<210> SEQ ID NO 122
<211> LENGTH: 20
<212> TYPE: DNA
<213> ORGANISM: Artificial Sequence
<220> FEATURE:
<223> OTHER INFORMATION: primer

<400> SEQUENCE: 122
aacttcctca gcttgagcag 20

<210> SEQ ID NO 123
<211> LENGTH: 20
<212> TYPE: DNA
<213> ORGANISM: Artificial Sequence
<220> FEATURE:
<223> OTHER INFORMATION: primer

<400> SEQUENCE: 123
atttgggaca aagtctatag 20

<210> SEQ ID NO 124
<211> LENGTH: 20
<212> TYPE: DNA
<213> ORGANISM: Artificial Sequence
<220> FEATURE:
<223> OTHER INFORMATION: primer

<400> SEQUENCE: 124
gcagaagcaa taccagcagc 20

<210> SEQ ID NO 125
<211> LENGTH: 20
<212> TYPE: DNA
<213> ORGANISM: Artificial Sequence
<220> FEATURE:
<223> OTHER INFORMATION: primer

<400> SEQUENCE: 125
tgcttcagtt gttcaataga 20

<210> SEQ ID NO 126
<211> LENGTH: 20
<212> TYPE: DNA
<213> ORGANISM: Artificial Sequence
<220> FEATURE:
<223> OTHER INFORMATION: primer

<400> SEQUENCE: 126
aggaagacaa tttagcatag 20

<210> SEQ ID NO 127
<211> LENGTH: 20

<212> TYPE: DNA
<213> ORGANISM: Artificial Sequence
<220> FEATURE:
<223> OTHER INFORMATION: primer

<400> SEQUENCE: 127
gatgtaatct gtgggattca 20

<210> SEQ ID NO 128
<211> LENGTH: 20
<212> TYPE: DNA
<213> ORGANISM: Artificial Sequence
<220> FEATURE:
<223> OTHER INFORMATION: primer

<400> SEQUENCE: 128
ggaaggcgag gagtccatca 20

<210> SEQ ID NO 129
<211> LENGTH: 20
<212> TYPE: DNA
<213> ORGANISM: Artificial Sequence
<220> FEATURE:
<223> OTHER INFORMATION: primer

<400> SEQUENCE: 129
gagctttatc ttcttctgat 20

<210> SEQ ID NO 130
<211> LENGTH: 20
<212> TYPE: DNA
<213> ORGANISM: Artificial Sequence
<220> FEATURE:
<223> OTHER INFORMATION: primer

<400> SEQUENCE: 130
gcaaagaatt ctgcatctct 20

<210> SEQ ID NO 131
<211> LENGTH: 20
<212> TYPE: DNA
<213> ORGANISM: Artificial Sequence
<220> FEATURE:
<223> OTHER INFORMATION: primer

<400> SEQUENCE: 131
aattttacaa gaaaaagact 20

<210> SEQ ID NO 132
<211> LENGTH: 20
<212> TYPE: DNA
<213> ORGANISM: Artificial Sequence
<220> FEATURE:
<223> OTHER INFORMATION: primer

<400> SEQUENCE: 132
ccgtgttggc ctccaggtcc 20

<210> SEQ ID NO 133
<211> LENGTH: 20
<212> TYPE: DNA
<213> ORGANISM: Artificial Sequence
<220> FEATURE:
<223> OTHER INFORMATION: primer

<400> SEQUENCE: 133
ggcgtttccg ctcgcggtcg 20

<210> SEQ ID NO 134
<211> LENGTH: 20
<212> TYPE: DNA
<213> ORGANISM: Artificial Sequence
<220> FEATURE:
<223> OTHER INFORMATION: primer

<400> SEQUENCE: 134
tggcagcagt tcgtgaagtc 20

<210> SEQ ID NO 135
<211> LENGTH: 20
<212> TYPE: DNA
<213> ORGANISM: Artificial Sequence
<220> FEATURE:
<223> OTHER INFORMATION: primer

<400> SEQUENCE: 135
aactaatctt cccaatgtcc 20

<210> SEQ ID NO 136
<211> LENGTH: 20
<212> TYPE: DNA
<213> ORGANISM: Artificial Sequence
<220> FEATURE:
<223> OTHER INFORMATION: primer

<400> SEQUENCE: 136
ctcccaccct gagcagagcc 20

<210> SEQ ID NO 137
<211> LENGTH: 18
<212> TYPE: DNA
<213> ORGANISM: Artificial Sequence
<220> FEATURE:
<223> OTHER INFORMATION: primer

<400> SEQUENCE: 137
gtgcctgcag cactggag 18

<210> SEQ ID NO 138
<211> LENGTH: 20
<212> TYPE: DNA
<213> ORGANISM: Artificial Sequence
<220> FEATURE:
<223> OTHER INFORMATION: primer

<400> SEQUENCE: 138
agtacgagat atttatggag 20

<210> SEQ ID NO 139
<211> LENGTH: 20
<212> TYPE: DNA
<213> ORGANISM: Artificial Sequence
<220> FEATURE:
<223> OTHER INFORMATION: primer

<400> SEQUENCE: 139
ctggccaggt cctctttact 20

<210> SEQ ID NO 140
<211> LENGTH: 20
<212> TYPE: DNA
<213> ORGANISM: Artificial Sequence
<220> FEATURE:
<223> OTHER INFORMATION: primer

<400> SEQUENCE: 140
ggaagaagca attccatggc 20

<210> SEQ ID NO 141
<211> LENGTH: 20
<212> TYPE: DNA
<213> ORGANISM: Artificial Sequence
<220> FEATURE:
<223> OTHER INFORMATION: primer

<400> SEQUENCE: 141
ttgtcgttct tgttttaaat 20

<210> SEQ ID NO 142
<211> LENGTH: 20
<212> TYPE: DNA
<213> ORGANISM: Artificial Sequence
<220> FEATURE:
<223> OTHER INFORMATION: primer

<400> SEQUENCE: 142
agcctgaccg tgtggaaggc 20

<210> SEQ ID NO 143
<211> LENGTH: 20
<212> TYPE: DNA
<213> ORGANISM: Artificial Sequence
<220> FEATURE:
<223> OTHER INFORMATION: primer

<400> SEQUENCE: 143
gccttgcagg acacacactc 20

<210> SEQ ID NO 144
<211> LENGTH: 20
<212> TYPE: DNA
<213> ORGANISM: Artificial Sequence
<220> FEATURE:
<223> OTHER INFORMATION: primer

<400> SEQUENCE: 144
accctcacca acaatgacac 20

<210> SEQ ID NO 145
<211> LENGTH: 16
<212> TYPE: DNA
<213> ORGANISM: Artificial Sequence
<220> FEATURE:
<223> OTHER INFORMATION: primer

<400> SEQUENCE: 145
cggacgttca cgccct 16

<210> SEQ ID NO 146
<211> LENGTH: 20
<212> TYPE: DNA
<213> ORGANISM: Artificial Sequence
<220> FEATURE:
<223> OTHER INFORMATION: primer

<400> SEQUENCE: 146
caagagaggc atcctcaaac 20

-continued

<210> SEQ ID NO 147
<211> LENGTH: 20
<212> TYPE: DNA
<213> ORGANISM: Artificial Sequence
<220> FEATURE:
<223> OTHER INFORMATION: primer

<400> SEQUENCE: 147
cgtcatagtc ctcggcaatg 20

<210> SEQ ID NO 148
<211> LENGTH: 20
<212> TYPE: DNA
<213> ORGANISM: Artificial Sequence
<220> FEATURE:
<223> OTHER INFORMATION: primer

<400> SEQUENCE: 148
gaacagggaa cctgcccccc 20

<210> SEQ ID NO 149
<211> LENGTH: 20
<212> TYPE: DNA
<213> ORGANISM: Artificial Sequence
<220> FEATURE:
<223> OTHER INFORMATION: primer

<400> SEQUENCE: 149
gttacatcat accccatgtc 20

<210> SEQ ID NO 150
<211> LENGTH: 20
<212> TYPE: DNA
<213> ORGANISM: Artificial Sequence
<220> FEATURE:
<223> OTHER INFORMATION: primer

<400> SEQUENCE: 150
aaaaatgtgg ccttccaaac 20

<210> SEQ ID NO 151
<211> LENGTH: 16
<212> TYPE: DNA
<213> ORGANISM: Artificial Sequence
<220> FEATURE:
<223> OTHER INFORMATION: primer

<400> SEQUENCE: 151
cactatcgca agagtc 16

<210> SEQ ID NO 152
<211> LENGTH: 20
<212> TYPE: DNA
<213> ORGANISM: Artificial Sequence
<220> FEATURE:
<223> OTHER INFORMATION: primer

<400> SEQUENCE: 152
gtgattggtc tattcaccat 20

<210> SEQ ID NO 153
<211> LENGTH: 22
<212> TYPE: DNA
<213> ORGANISM: Artificial Sequence
<220> FEATURE:
<223> OTHER INFORMATION: primer

<400> SEQUENCE: 153
aactgattgg ttcaccaacc cc 22

<210> SEQ ID NO 154
<211> LENGTH: 20
<212> TYPE: DNA
<213> ORGANISM: Artificial Sequence
<220> FEATURE:
<223> OTHER INFORMATION: primer

<400> SEQUENCE: 154
gctgcaggac tcccatgaca 20

<210> SEQ ID NO 155
<211> LENGTH: 20
<212> TYPE: DNA
<213> ORGANISM: Artificial Sequence
<220> FEATURE:
<223> OTHER INFORMATION: primer

<400> SEQUENCE: 155
ggctgtgagg cgctggggaa 20

<210> SEQ ID NO 156
<211> LENGTH: 20
<212> TYPE: DNA
<213> ORGANISM: Artificial Sequence
<220> FEATURE:
<223> OTHER INFORMATION: primer

<400> SEQUENCE: 156
tgcaagagga ctaagcatgg 20

<210> SEQ ID NO 157
<211> LENGTH: 20
<212> TYPE: DNA
<213> ORGANISM: Artificial Sequence
<220> FEATURE:
<223> OTHER INFORMATION: primer

<400> SEQUENCE: 157
aaataggcac ggtggaccat 20

<210> SEQ ID NO 158
<211> LENGTH: 20
<212> TYPE: DNA
<213> ORGANISM: Artificial Sequence
<220> FEATURE:
<223> OTHER INFORMATION: primer

<400> SEQUENCE: 158
acggcatgga ggagccaggg 20

<210> SEQ ID NO 159
<211> LENGTH: 20
<212> TYPE: DNA
<213> ORGANISM: Artificial Sequence
<220> FEATURE:
<223> OTHER INFORMATION: primer

<400> SEQUENCE: 159
atgaaagaga tcaggatggc 20

<210> SEQ ID NO 160

<211> LENGTH: 20
<212> TYPE: DNA
<213> ORGANISM: Artificial Sequence
<220> FEATURE:
<223> OTHER INFORMATION: primer

<400> SEQUENCE: 160
gcagggctgg ccgtcagtgg 20

<210> SEQ ID NO 161
<211> LENGTH: 20
<212> TYPE: DNA
<213> ORGANISM: Artificial Sequence
<220> FEATURE:
<223> OTHER INFORMATION: primer

<400> SEQUENCE: 161
gaccagcgag ttacccagca 20

<210> SEQ ID NO 162
<211> LENGTH: 20
<212> TYPE: DNA
<213> ORGANISM: Artificial Sequence
<220> FEATURE:
<223> OTHER INFORMATION: primer

<400> SEQUENCE: 162
cgggggcgag gaagggctgg 20

<210> SEQ ID NO 163
<211> LENGTH: 20
<212> TYPE: DNA
<213> ORGANISM: Artificial Sequence
<220> FEATURE:
<223> OTHER INFORMATION: primer

<400> SEQUENCE: 163
cccgcgcgtc cccgggcccc 20

<210> SEQ ID NO 164
<211> LENGTH: 20
<212> TYPE: DNA
<213> ORGANISM: Artificial Sequence
<220> FEATURE:
<223> OTHER INFORMATION: primer

<400> SEQUENCE: 164
cctctgggga gcgacttttc 20

<210> SEQ ID NO 165
<211> LENGTH: 20
<212> TYPE: DNA
<213> ORGANISM: Artificial Sequence
<220> FEATURE:
<223> OTHER INFORMATION: primer

<400> SEQUENCE: 165
caagcgcttt cgggtgtctt 20

<210> SEQ ID NO 166
<211> LENGTH: 20
<212> TYPE: DNA
<213> ORGANISM: Artificial Sequence
<220> FEATURE:
<223> OTHER INFORMATION: primer

<400> SEQUENCE: 166
aggcgagcag tggaagtgtg 20

<210> SEQ ID NO 167
<211> LENGTH: 20
<212> TYPE: DNA
<213> ORGANISM: Artificial Sequence
<220> FEATURE:
<223> OTHER INFORMATION: primer

<400> SEQUENCE: 167
ttatgcagac gggttctaaa 20

<210> SEQ ID NO 168
<211> LENGTH: 22
<212> TYPE: DNA
<213> ORGANISM: Artificial Sequence
<220> FEATURE:
<223> OTHER INFORMATION: primer

<400> SEQUENCE: 168
cttacccaca atctgctgag ct 22

<210> SEQ ID NO 169
<211> LENGTH: 20
<212> TYPE: DNA
<213> ORGANISM: Artificial Sequence
<220> FEATURE:
<223> OTHER INFORMATION: primer

<400> SEQUENCE: 169
ggcagatacg gacctcggtg 20

<210> SEQ ID NO 170
<211> LENGTH: 20
<212> TYPE: DNA
<213> ORGANISM: Artificial Sequence
<220> FEATURE:
<223> OTHER INFORMATION: primer

<400> SEQUENCE: 170
aagtttaagg gccaggttgt 20

<210> SEQ ID NO 171
<211> LENGTH: 20
<212> TYPE: DNA
<213> ORGANISM: Artificial Sequence
<220> FEATURE:
<223> OTHER INFORMATION: primer

<400> SEQUENCE: 171
cagggaacat tgcacctggt 20

<210> SEQ ID NO 172
<211> LENGTH: 20
<212> TYPE: DNA
<213> ORGANISM: Artificial Sequence
<220> FEATURE:
<223> OTHER INFORMATION: primer

<400> SEQUENCE: 172
aagtcctaga aatgcaggaa 20

<210> SEQ ID NO 173
<211> LENGTH: 20
<212> TYPE: DNA

<213> ORGANISM: Artificial Sequence
<220> FEATURE:
<223> OTHER INFORMATION: primer

<400> SEQUENCE: 173
cttctgaatc actgctgtcc 20

<210> SEQ ID NO 174
<211> LENGTH: 20
<212> TYPE: DNA
<213> ORGANISM: Artificial Sequence
<220> FEATURE:
<223> OTHER INFORMATION: primer

<400> SEQUENCE: 174
gaggagcttg ctaaggacca 20

<210> SEQ ID NO 175
<211> LENGTH: 20
<212> TYPE: DNA
<213> ORGANISM: Artificial Sequence
<220> FEATURE:
<223> OTHER INFORMATION: primer

<400> SEQUENCE: 175
gaatctgtca gctccttctc 20

<210> SEQ ID NO 176
<211> LENGTH: 20
<212> TYPE: DNA
<213> ORGANISM: Artificial Sequence
<220> FEATURE:
<223> OTHER INFORMATION: primer

<400> SEQUENCE: 176
gcgcccttac aagtgtgact 20

<210> SEQ ID NO 177
<211> LENGTH: 20
<212> TYPE: DNA
<213> ORGANISM: Artificial Sequence
<220> FEATURE:
<223> OTHER INFORMATION: primer

<400> SEQUENCE: 177
gaaaacaggg cactcactgt 20

<210> SEQ ID NO 178
<211> LENGTH: 20
<212> TYPE: DNA
<213> ORGANISM: Artificial Sequence
<220> FEATURE:
<223> OTHER INFORMATION: primer

<400> SEQUENCE: 178
gaaagtggat ttgtgcaaca 20

<210> SEQ ID NO 179
<211> LENGTH: 20
<212> TYPE: DNA
<213> ORGANISM: Artificial Sequence
<220> FEATURE:
<223> OTHER INFORMATION: primer

<400> SEQUENCE: 179
tggatgggtt ctatgccaca 20

<210> SEQ ID NO 180
<211> LENGTH: 20
<212> TYPE: DNA
<213> ORGANISM: Artificial Sequence
<220> FEATURE:
<223> OTHER INFORMATION: primer

<400> SEQUENCE: 180
accgccgaga ccgcgtccgc 20

<210> SEQ ID NO 181
<211> LENGTH: 20
<212> TYPE: DNA
<213> ORGANISM: Artificial Sequence
<220> FEATURE:
<223> OTHER INFORMATION: primer

<400> SEQUENCE: 181
gcccgggggg catcgtcgcc 20

<210> SEQ ID NO 182
<211> LENGTH: 20
<212> TYPE: DNA
<213> ORGANISM: Artificial Sequence
<220> FEATURE:
<223> OTHER INFORMATION: primer

<400> SEQUENCE: 182
ggagaccccg cctagcatag 20

<210> SEQ ID NO 183
<211> LENGTH: 20
<212> TYPE: DNA
<213> ORGANISM: Artificial Sequence
<220> FEATURE:
<223> OTHER INFORMATION: primer

<400> SEQUENCE: 183
tgaccatgca gaattgatcg 20

<210> SEQ ID NO 184
<211> LENGTH: 20
<212> TYPE: DNA
<213> ORGANISM: Artificial Sequence
<220> FEATURE:
<223> OTHER INFORMATION: primer

<400> SEQUENCE: 184
gagctccttg gcggtccaca 20

<210> SEQ ID NO 185
<211> LENGTH: 20
<212> TYPE: DNA
<213> ORGANISM: Artificial Sequence
<220> FEATURE:
<223> OTHER INFORMATION: primer

<400> SEQUENCE: 185
ctgcaggaaa cgcagtggcg 20

<210> SEQ ID NO 186
<211> LENGTH: 20
<212> TYPE: DNA
<213> ORGANISM: Artificial Sequence
<220> FEATURE:

<223> OTHER INFORMATION: primer

<400> SEQUENCE: 186
cacgttttgg atacactcat 20

<210> SEQ ID NO 187
<211> LENGTH: 20
<212> TYPE: DNA
<213> ORGANISM: Artificial Sequence
<220> FEATURE:
<223> OTHER INFORMATION: primer

<400> SEQUENCE: 187
ttggtccgct gctgtgtgaa 20

<210> SEQ ID NO 188
<211> LENGTH: 20
<212> TYPE: DNA
<213> ORGANISM: Artificial Sequence
<220> FEATURE:
<223> OTHER INFORMATION: primer

<400> SEQUENCE: 188
gtgctgtgag gtctgcgggc 20

<210> SEQ ID NO 189
<211> LENGTH: 20
<212> TYPE: DNA
<213> ORGANISM: Artificial Sequence
<220> FEATURE:
<223> OTHER INFORMATION: primer

<400> SEQUENCE: 189
tcaggcactg ccagctctac 20

<210> SEQ ID NO 190
<211> LENGTH: 20
<212> TYPE: DNA
<213> ORGANISM: Artificial Sequence
<220> FEATURE:
<223> OTHER INFORMATION: primer

<400> SEQUENCE: 190
gcacacaagg cgggagctag 20

<210> SEQ ID NO 191
<211> LENGTH: 20
<212> TYPE: DNA
<213> ORGANISM: Artificial Sequence
<220> FEATURE:
<223> OTHER INFORMATION: primer

<400> SEQUENCE: 191
ctctgccttc ttcaggtttc 20

<210> SEQ ID NO 192
<211> LENGTH: 20
<212> TYPE: DNA
<213> ORGANISM: Artificial Sequence
<220> FEATURE:
<223> OTHER INFORMATION: primer

<400> SEQUENCE: 192
ctggttattg gctctcttca 20

-continued

<210> SEQ ID NO 193
<211> LENGTH: 18
<212> TYPE: DNA
<213> ORGANISM: Artificial Sequence
<220> FEATURE:
<223> OTHER INFORMATION: primer

<400> SEQUENCE: 193
catgcccatc ctgatact 18

<210> SEQ ID NO 194
<211> LENGTH: 20
<212> TYPE: DNA
<213> ORGANISM: Artificial Sequence
<220> FEATURE:
<223> OTHER INFORMATION: primer

<400> SEQUENCE: 194
ctaggatgtc ttccagcctc 20

<210> SEQ ID NO 195
<211> LENGTH: 20
<212> TYPE: DNA
<213> ORGANISM: Artificial Sequence
<220> FEATURE:
<223> OTHER INFORMATION: primer

<400> SEQUENCE: 195
gcaatatatt taaaactaag 20

<210> SEQ ID NO 196
<211> LENGTH: 20
<212> TYPE: DNA
<213> ORGANISM: Artificial Sequence
<220> FEATURE:
<223> OTHER INFORMATION: primer

<400> SEQUENCE: 196
gaactcagta tagtgccaac 20

<210> SEQ ID NO 197
<211> LENGTH: 20
<212> TYPE: DNA
<213> ORGANISM: Artificial Sequence
<220> FEATURE:
<223> OTHER INFORMATION: primer

<400> SEQUENCE: 197
gtgccacccc ctaggctcaa 20

<210> SEQ ID NO 198
<211> LENGTH: 20
<212> TYPE: DNA
<213> ORGANISM: Artificial Sequence
<220> FEATURE:
<223> OTHER INFORMATION: primer

<400> SEQUENCE: 198
atggtcagta ggacagaagg 20

<210> SEQ ID NO 199
<211> LENGTH: 20
<212> TYPE: DNA
<213> ORGANISM: Artificial Sequence
<220> FEATURE:
<223> OTHER INFORMATION: primer

<400> SEQUENCE: 199
atggttcatg acaatatcga 20

<210> SEQ ID NO 200
<211> LENGTH: 1852
<212> TYPE: DNA
<213> ORGANISM: Homo sapiens

<400> SEQUENCE: 200
accgccgaga ccgcgtccgc cccgcgagca cagagcctcg cctttgccga tccgccgccc 60
gtccacaccc gccgccagct caccatggat gatgatatcg ccgcgctcgt cgtcgacaac 120
ggctccggca tgtgcaaggc cggcttcgcg ggcgacgatg ccccccgggc cgtcttcccc 180
tccatcgtgg ggcgccccag gcaccagggc gtgatggtgg gcatgggtca gaaggattcc 240
tatgtgggcg acgaggccca gagcaagaga ggcatcctca ccctgaagta ccccatcgag 300
cacggcatcg tcaccaactg ggacgacatg gagaaaatct ggcaccacac cttctacaat 360
gagctgcgtg tggctcccga ggagcacccc gtgctgctga ccgaggcccc cctgaacccc 420
aaggccaacc gcgagaagat gacccagatc atgtttgaga ccttcaacac cccagccatg 480
tacgttgcta tccaggctgt gctatccctg tacgcctctg gccgtaccac tggcatcgtg 540
atggactccg gtgacggggt cacccacact gtgcccatct acgaggggta tgccctcccc 600
catgccatcc tgcgtctgga cctggctggc cgggacctga ctgactacct catgaagatc 660
ctcaccgagc gcggctacag cttcaccacc acggccgagc gggaaatcgt gcgtgacatt 720
aaggagaagc tgtgctacgt cgccctggac ttcgagcaag agatggccac ggctgcttcc 780
agctcctccc tggagaagag ctacgagctg cctgacggcc aggtcatcac cattggcaat 840
gagcggttcc gctgccctga ggcactcttc cagccttcct tcctgggcat ggagtcctgt 900
ggcatccacg aaactacctt caactccatc atgaagtgtg acgtggacat ccgcaaagac 960
ctgtacgcca acacagtgct gtctggcggc accaccatgt accctggcat tgccgacagg 1020
atgcagaagg agatcactgc cctggcaccc agcacaatga agatcaagat cattgctcct 1080
cctgagcgca agtactccgt gtggatcggc ggctccatcc tggcctcgct gtccaccttc 1140
cagcagatgt ggatcagcaa gcaggagtat gacgagtccg gcccctccat cgtccaccgc 1200
aaatgcttct aggcggacta tgacttagtt gcgttacacc ctttcttgac aaaacctaac 1260
ttgcgcagaa aacaagatga gattggcatg gctttatttg ttttttttgt tttgttttgg 1320 ttttttttt ttttttggct tgactcagga tttaaaaact ggaacggtga aggtgacagc 1380
agtcggttgg agcgagcatc ccccaaagtt cacaatgtgg ccgaggactt tgattgcaca 1440
ttgttgtttt tttaatagtc attccaaata tgagatgcgt tgttacagga agtcccttgc 1500
catcctaaaa gccaccccac ttctctctaa ggagaatggc ccagtcctct cccaagtcca 1560
cacaggggag gtgatagcat tgctttcgtg taaattatgt aatgcaaaat ttttttaatc 1620
ttcgccttaa tactttttta ttttgtttta ttttgaatga tgagccttcg tgcccccccct 1680 tccccctttt ttgtccccca acttgagatg tatgaaggct tttggtctcc ctgggagtgg 1740
gtggaggcag ccagggctta cctgtacact gacttgagac cagttgaata aaagtgcaca 1800
ccttaaaaat gaaaaaaaaa aaaaaaaaaa aaaaaaaaaa aaaaaaaaaa aa 1852

<210> SEQ ID NO 201
<211> LENGTH: 2136
<212> TYPE: DNA
<213> ORGANISM: Homo sapiens

<400> SEQUENCE: 201
gtgtgtggag gggaccctgt ggttagcagc agctatcgca gcgtcggatg ttcagagcag 60
cagaagccgg cgtcgtcgga tgttgtgttg cccgccacca tgagctacac aggctttgtc 120
cagggatctg aaaccacttt gcagtcgaca tactcggata ccagcgctca gcccacctgt 180
gattatggat atggaacttg gaactctggg acaaatagag gctacgaggg ctatggctat 240
ggctatggct atggccagga taacaccacc aactatgggt atggtatggc cacttcacac 300
tcttgggaaa tgcctagctc tgacacaaat gcaaacacta gtgcctcggg tagcgccagt 360
gccgattccg ttttatccag aattaaccag cgcttagata tggtgccgca tttggagaca 420
gacatgatgc aaggaggcgt gtacggctca ggtggagaaa ggtatgactc ttatgagtcc 480
tgcgactcga gggccgtcct gagtgagcgc gacctgtacc ggtcaggcta tgactacagc 540
gagcttgacc ctgagatgga aatggcctat gagggccaat acgatgccta ccgcgaccag 600
ttccgcatgc gtggcaacga caccttcggt cccagggcac agggctgggc ccgggatgcc 660
cggagcggcc ggccaatggc ctcaggctat gggcgcatgt gggaagaccc catgggggcc 720
cggggccagt gcatgtctgg tgcctctcgg ctgccctccc tcttctccca gaacatcatc 780
cccgagtacg gcatgttcca gggcatgcga ggtgggggcg ccttcccggg cggctcccgc 840
tttggtttcg ggtttggcaa tggcatgaag cagatgaggc ggacctggaa gacctggacc 900
acagccgact tccgaaccaa gaagaagaag agaaagcagg gcggcagtcc tgatgagcca 960
gatagcaaag ccacccgcac ggactgctcg gacaacagcg actcagacaa tgatgagggc 1020
accgaggggg aagccacaga gggccttgaa ggcaccgagg ctgtggagaa gggctccaga 1080
gtggacggag aggatgagga gggaaaagag gatgggagag aagaaggcaa agaggatcca 1140
gagaaggggg ccctaaccac ccaggatgaa aatggccaga ccaagcgcaa gttgcaggca 1200
ggcaagaaga gtcaggacaa gcagaaaaag cggcagcgag accgcatggt ggaaaggatc 1260
cagtttgtgt gttctctgtg caaataccgg accttctatg aggacgagat ggccagccat 1320
cttgacagca agttccacaa ggaacacttt aagtacgtag gcaccaagct ccctaagcag 1380
acggctgact ttctgcagga gtacgtcact aacaagacca agaagacaga ggagctccga 1440
aaaaccgtgg aggaccttga tggcctcatc caccaaatct acagagacca ggatctgacc 1500
caggaaattg ccatggagca ttttgtgaag aaggtggagg cagcccattg tgcagcctgc 1560
gacctcttca ttcccatgca gtttgggatc atccagaagc atctgaagac catggatcac 1620
aaccggaacc gcaggctcat gatggagcag tccaagaagt cctccctcat ggtggcccgc 1680
agtattctca acaacaagct catcagcaag aagctggagc gctacctgaa gggcgagaac 1740
cctttcaccg acagccccga ggaggagaag gagcaggagg aggctgaggg cggtgccctg 1800
gacgaggggg cgcagggcga agcggcaggg atctcggagg gcgcagaggg cgtgccggcg 1860
cagcctcccg tgcccccaga gccagccccc ggggccgtgt cgccgccacc gccgccgccc 1920
ccagaggagg aggaggaggg cgccgtgccc ttgctgggag ggcgctgca acgccagatc 1980
cgcggcatcc cgggcctcga cgtggaggac gacgaggagg gcggcggggg cgccccgtga 2040
cccgagctcg gggcgggcgg agcccgcgtg gccgaagctg gaaaccaaac ctaataaagt 2100
tttcccatcc caccaaaaaa aaaaaaaaaa aaaaaa 2136

<210> SEQ ID NO 202
<211> LENGTH: 1986
<212> TYPE: DNA

<213> ORGANISM: Homo sapiens

<400> SEQUENCE: 202
ccttacccgg cgtgccccgc gcccggaggc gctgacgtgg ccgccgtcag agccgccatc 60
ttgtgggagc aaaaccaacg cctggctcgg agcagcagcc tctgaggtga gggcgagggg 120
cgcgggccgg tgtgggccgc agagacgttg gagccggcgg gggctgggga ctggcctcgg 180
ggcgacttga ggtgtccctg gccagtgtcc ttccacctgt ccacaagcat ggggaacatc 240
ttcgccaacc tcttcaaggg cctttttggc aaaaaagaaa tgcgcatcct catggtgggc 300
ctggatgctg cagggaagac cacgatcctc tacaagctta agctgggtga gatcgtgacc 360
accattccca ccataggctt caacgtggaa accgtggagt acaagaacat cagcttcact 420
gtgtgggacg tgggtggcca ggacaagatc cggcccctgt ggcgccacta cttccagaac 480
acacaaggcc tgatcttcgt ggtggacagc aatgacagag agcgtgtgaa cgaggcccgt 540
gaggagctca tgaggatgct ggccgaggac gagctccggg atgctgtcct cctggtgttc 600
gccaacaagc aggacctccc caacgccatg aatgcggccg agatcacaga caagctgggg 660
ctgcactcac tacgccacag gaactggtac attcaggcca cctgcgccac cagcggcgac 720
gggctctatg aaggactgga ctggctgtcc aatcagctcc ggaaccagaa gtgaacgcga 780 ccccccctccc tctcactcct cttgccctct gctttactct catgtggcaa acgtgcggct 840
cgtggtgtga gtgccagaag ctgcctccgt ggtttggtca ccgtgtgcat cgcaccgtgc 900
tgtaaatgtg gcagacgcag cctgcggcca ggctttttat ttaatgtaaa tagtttttgt 960
ttccaatgag gcagtttctg gtactcctat gcaatattac tcagcttttt ttattgtaaa 1020
aagaaaaatc aactcactgt tcagtgctga gaggggatgt aggcccatgg gcacctggcc 1080
tccaggagtc gctgtgttgg gagagccggc cacgcccttg gctttagagc tgtgttgaaa 1140
tccattttgg tggttggttt ttaacccaaa ctcagtgcat tttttaaaat agttaagaat 1200
ccaagtcgag aacacttgaa cacacagaag ggagaccccg cctagcatag atttgcagtt 1260
acggcctgga tgccagtcgc cagcccagct gttcccctcg ggaacatgag gtggtggtgg 1320
cgcagcagac tgcgatcaat tctgcatggt cacagtagag atccccgcaa ctcgcttgtc 1380
cttgggtcac cctgcattcc atagccatgt gcttgtccct gtgctcccac ggttcccagg 1440
ggccaggctg ggagcccaca gccaccccac tatgccgcag gccgccctac ccaccttcag 1500
gcagcctatg ggacgcaggg ccccatctgt ccctcggtcg ccgtgtggcc agagtgggtc 1560
cgtcgtcccc aacactcgtg ctcgctcaga cactttggca ggatgtctgg ggcctcacca 1620
gcaggagcgc gtgcaagccg ggcaggcggt ccacctagac ccacagcccc tcgggagcac 1680
cccacctctg tgtgtgatgt agctttctct ccctcagcct gcaagggtcc gatttgccat 1740
cgaaaaagac aacctctact tttttctttt gtattttgat aaacactgaa gctggagctg 1800
ttaaatttat cttggggaaa cctcagaact ggtctatttg gtgtcgtgga acctcttact 1860
gctttcaata cacgattagt aatcaactgt tttgtatact tgttttcagt tttcatttcg 1920
acaaacaagc actgtaatta tagctattag aataaaatct cttaactatt tcaaaaaaaa 1980
aaaaaa 1986

<210> SEQ ID NO 203
<211> LENGTH: 2886
<212> TYPE: DNA
<213> ORGANISM: Homo sapiens

<400> SEQUENCE: 203

-continued

```
gcgccggcac acctattggc ccccgcggcg tcccgtcgcc gcgtcgcgtt gctggcccgt     60
cggagcgacg ccgctcgggt cagtcggcgg ccggactggg aagatggacg cagctactct    120
gacctacgac actctccggt ttgctgagtt tgaagatttt cctgagacct cagagcccgt    180
ttggatactg ggtagaaaat acagcatttt cacagaaaag gacgagatct tgtctgatgt    240
ggcatctaga ctttggttta catacaggaa aaactttcca gccattgggg ggacaggccc    300
cacctcggac acaggctggg gctgcatgct gcggtgtgga cagatgatct ttgcccaagc    360
cctggtgtgc cggcacctag gccgagattg gaggtggaca caaaggaaga ggcagccaga    420
cagctacttc agcgtcctca acgcattcat cgacaggaag gacagttact actccattca    480
cagatagcga aatgggagtg gcgaaggcaa gtccatagcc agtggtacgg gcccaacact    540
gtcgcccagg tcctgaagaa gcttgctgtc ttcgatacgt ggagctcctt ggcggtccac    600
attgcaatgg acaacactgt tgtgatggag gaaatcagaa ggttgtgcag gaccagcgtt    660
ccctgtgcag gcgccactgc gtttcctgca gattccgacc ggcactgcaa cggattccct    720
gccggagctg aggtcaccaa caggccgtcg ccatggagac ccctggtact tctcattccc    780
ctgcgcctgg ggctcacgga catcaacgag gcctacgtgg agacgctgaa gcactgcttc    840
atgatgcccc agtccctggg cgtcatcgga gggaagccca acagcgccca ctacttcatc    900
ggctacgttg gtgaggagct catctacctg gacccccaca ccacgcagcc agccgtggag    960
cccactgatg gctgcttcat cccggacgag agcttccact gccagcaccc gccgtgccgc   1020
atgagcatcg cggagcttga cccgtccatc gctgtggggt ttttctgtaa gactgaagat   1080
gacttcaatg attggtgcca gcaagtcaaa aagctgtctc tgcttggagg tgccctgccc   1140
atgtttgagc tggtggagct gcagccttca catctggcct gccccgacgt cctgaacctg   1200
tccctagatt cttctgatgt agagcgactg gaaagattct tcgactcaga agatgaagac   1260
tttgaaatcc tgtccctttg aaaatcctgg ggtcgggggt ggcacctgtg agagcctggg   1320
gctcctggtg ccgctgcgtt tcatccatcc cgcccgctcg cctgccgagg gctgcgcccc   1380
gtgctgcctc cccccagagg gccacccgct gtgctcgtgg actgaggctg cgctgcccgg   1440
gaggccttac tgcttggtgt cagactgccc agctcagagt gcccgtcagg gcctgtgcat   1500
ccgcacgcgg agccgtctgt taggagcttc cagagtgttc tctcgacact gccagccccg   1560
tgttagcacc tgggcctcag tcccacttgc tcccaggcgc cggttctgtg gttggtttgg   1620
aattaaagtc ctgtttgaag ttgtcagaca cagacatgaa tttctgggcg ctccctgagt   1680
cagagtctca gaagacctgt gcaggctggc gtgagaggag cggcagccac actgcggccc   1740
cacgcccaag gactgggctg ctctcgaggg gggcgcgccc accgctgtgt cctctctgcc   1800
cagcctggct taccaagggc tacctcagtg ggagatgagg ttggaggaac gaaggcgagg   1860
ttcctccttg ctttggggag aaaagtattc aggaagtggg tgtgtgggaa acctgaagat   1920
ggcgtgcaca ggacacagcg tgggcggcct gggcagaagg gcggctggct gtcctggagc   1980
tgctgctgga gcctgccctc agagtgtccc tttccagtgc tgtggcattc tgtggcagct   2040
tccccaggtg tggtgacggg gggggggcgg ggcctccacc tgtgacagcc aggcttgagg   2100
gtggacggcg tgcctctccc aggagccttc cccatgtcct tgccttgctg agaattgccc   2160
tcccatgccg ctgaggtgtt aggtggttta gggccaaaag gggaaaacca cttgagtctt   2220
gtggtgtgtg gtgggcagac accacagggt ggcatcacct ggtggcattt ccagaacctc   2280
agccccgatt ccagcaccca ccaccgcctg accctgtgta acctgctgtc ccgggtccca   2340
```

gagtgcactc tgccccgctg ctctgctgcc tgtcctggga aagtatcttt gccccactag 2400
gaaatgtaaa caggagggct tggggagcgt gggcactttt ctcatgagca gctactgcgg 2460
cgttggcagg actcgctgct gctgctgctg cttgtgtagg tcggggagcc agagatcccc 2520
gaggacgcgc gccggacagt cggcactgac cggcccacct ggtagcagag gacaccccca 2580
gccccccaag cattgaagac atagtgattt cctcgtatcc tttctccctt gggtgtagtt 2640
ggggtgggga agcagggaag gctggtgcga tctccattcc ttgggctcca cgtccgagtt 2700
catggtgcgc cgctgtgctg ggagctgcag tggtaatgtg tgggacacct tgaccaaagg 2760
ggagctttgt ctcgtgtgtt ttgaaaaagg cttaatgaag agaatgttgt tcattcttag 2820
tagtatagtt tgcaattctt aatggcaaat aataagtttc agtagaaaac aaaaaaaaaa 2880
aaaaaa 2886

<210> SEQ ID NO 204
<211> LENGTH: 2165
<212> TYPE: DNA
<213> ORGANISM: Homo sapiens

<400> SEQUENCE: 204
acgtgaccgg cgcctctgtc attctactgc ggccgccctg gcttccttct acctgtgcgg 60
ccctcaacgt ctccttggtg cgggacccgc ttcactttcg gctcccggag tctccctcca 120
ctgctcagac ctctggacct gacaggagac gcctacttgg ctctgacgcg gcgccccagc 180
ccggctgtgt ccccggcgcc ccggaccacc ctccctgccg gctttgggtg cgttgtgggg 240
tcccgaggat tcgcgagatt tgttgaaaga cattcaagat tacgaagttt agatgaccaa 300
aatggatatc cgaggtgctg tggatgctgc tgtccccacc aatattattg ctgccaaggc 360
tgcagaagtt cgtgcaaaca aagtcaactg gcaatcctat cttcagggac agatgatttc 420
tgctgaagat tgtgagttta ttcagaggtt tgaaatgaaa cgaagccctg aagagaagca 480
agagatgctt caaactgaag gcagccagtg tgctaaaaca tttataaatc tgatgactca 540
tatctgcaaa gaacagaccg ttcagtatat actaactatg gtggatgata tgctgcagga 600
aaatcatcag cgtgttagca ttttctttga ctatgcaaga tgtagcaaga acactgcgtg 660
gccctacttt ctgccaatgt tgaatcgcca ggatcccttc actgttcata tggcagcaag 720
aattattgcc aagttagcag cttggggaaa agaactgatg gaaggcagtg acttaaatta 780
ctatttcaat tggataaaaa ctcagctgag ttcacagaaa ctgcgtggta gcggtgttgc 840
tgttgaaaca ggaacagtct cttcaagtga tagttcgcag tatgtgcagt gcgtggccgg 900
gtgtttgcag ctgatgctcc gggtcaatga gtaccgcttt gcttgggtgg aagcagatgg 960
ggtaaattgc ataatgggag tgttgagtaa caagtgtggc tttcagctcc agtatcaaat 1020 gatttttttca atatggctcc tggcattcag tcctcaaatg tgtgaacacc tgcggcgcta 1080
taatatcatt ccagttctgt ctgatatcct tcaggagtct gtcaaagaga aagtaacaag 1140
aatcattctt gcagcatttc gtaacttttt agaaaaatca actgaaagag aaactcgcca 1200
agaatatgcc ctggctatga ttcagtgcaa agttctgaaa cagttggaga acttggaaca 1260
gcagaagtac gatgatgaag atatcagcga agatatcaaa tttcttttgg aaaaacttgg 1320
agagagtgtc caggacctta gttcatttga tgaatacagt tcagaactta aatctggaag 1380
gttggaatgg agtcctgtgc acaaatctga gaaatttttgg agagagaatg ctgtgaggtt 1440
aaatgagaag aattatgaac tcttgaaaat cttgacaaaa cttttggaag tgtcagatga 1500
tccccaagtc ttagctgttg ctgctcacga tgttggagaa tatgtgcggc attatccacg 1560
aggcaaacgg gtcatcgagc agctcggtgg gaagcagctg gtcatgaacc acatgcatca 1620
tgaagaccag caggtccgct ataatgctct gctggccgtg cagaagctca tggtgcacaa 1680
ctgggaatac cttggcaagc agctccagtc cgagcagccc cagaccgctg ccgccccgaag 1740 ctaagcctgc ctctggcctt cccctccgcc tcaatgcaga accagtagtg ggagcactgt 1800
gtttagagtt aagagtgaac actgtttgat tttacttgga atttcctctg ttatatagct 1860
tttcccaatg ctaatttcca aacaacaaca acaaaataac atgtttgcct gttaagttgt 1920
ataaaagtag gtgattctgt atttaaagaa aatattactg ttacatatac tgcttgcaat 1980
ttctgtattt attgttctct ggaaataaat atagttatta aaggattctc actccaaaca 2040
tggcctctct ctttacttgg actttgaaca aaagtcaact gttgtctctt ttcaaaccaa 2100
attgggagaa ttgttgcaaa gtagtgaatg gcaaataaat gttttaaaat ctaaaaaaaa 2160
aaaaa 2165

<210> SEQ ID NO 205
<211> LENGTH: 3505
<212> TYPE: DNA
<213> ORGANISM: Homo sapiens

<400> SEQUENCE: 205
cgtcaggggc aggggaggga cggcgcaggc gcagaaaagg gggcggcgga ctcggcttgt 60
tgtgttgctg cctgagtgcc ggagacggtc ctgctgctgc cgcagtcctg ccagctgtcc 120
gacaatgtcg tcccacctag tcgagccgcc gccgccccctg cacaacaaca acaacaactg 180
cgaggaaaat gagcagtctc tgcccccgcc ggccggcctc aacagttcct gggtggagct 240
acccatgaac agcagcaatg gcaatgataa tggcaatggg aaaaatgggg ggctggaaca 300
cgtaccatcc tcatcctcca tccacaatgg agacatggag aagattcttt tggatgcaca 360
acatgaatca ggacagagta gttccagagg cagttctcac tgtgacagcc cttcgccaca 420
agaagatggg cagatcatgt ttgatgtgga aatgcacacc agcagggacc atagctctca 480
gtcagaagaa gaagttgtag aaggagagaa ggaagtcgag gctttgaaga aaagtgcgga 540
ctgggtatca gactggtcca gtagacccga aaacattcca cccaaggagt tccacttcag 600
acaccctaaa cgttctgtgt ctttaagcat gaggaaaagt ggagccatga agaaaggggg 660
tattttctcc gcagaatttc tgaaggtgtt cattccatct ctcttccttt ctcatgtttt 720
ggctttgggg ctaggcatct atattggaaa gcgactgagc acaccctctg ccagcaccta 780
ctgagggaaa ggaaaagccc ctggaaatgc gtgtgacctg tgaagtggtg tattgtcaca 840
gtagcttatt tgaacttgag accattgtaa gcatgaccca acctaccacc ctgtttttac 900
atatccaatt ccagtaactc tcaaattcaa tattttattc aaactctgtt gaggcatttt 960
actaacctta taccctttttt ggcctgaaga cattttagaa tttcctaaca gagtttactg 1020
ttgtttagaa atttgcaagg gcttcttttc cgcaaatgcc accagcagat tataattttg 1080
tcagcaatgc tattatctct aattagtgcc accagactag acctgtatca ttcatggtat 1140
aaattttact cttgcaacat aactaccatc tctctcttaa aacgagatca ggttagcaaa 1200
tgatgtaaaa gaagctttat tgtctagttg ttttttttcc cccaagacaa aggcaagttt 1260
ccctaagttt gagttgatag ttattaaaaa gaaaacaaaa caaaaaaaaa aggcaaggca 1320
caacaaaaaa atatcctggg caataaaaaa aatattttaa accagctttg gagccacttt 1380
tttgtctaag cctcctaata gcgtctttta atttatagga ggcaaactgt ataaatgata 1440

```
ggtatgaaat agaataagaa gtaaaataca tcagcagatt ttcatactag tatgttgtaa   1500
tgctgtcttt tctatggtgt agaatctttc tttctgataa ggaacgtctc aggcttagaa   1560
atatatgaaa ttgcttttg agatttttgc gtgtgtgttt gatattttt acgataatta   1620
gctgcatgtg aatttttcat gaccttcttt acatttttta tttttattt ctttattttt   1680
ttttctctaa gaagaggctt tggaatgagt tccaatttgt gatgttaata caggcttctt   1740
gttttaggaa gcatcaccta tactctgaag cctttaaact ctgaagagaa ttgtttcaga   1800
gttattccaa gcacttgtgc aacttggaaa aacagacttg ggttgtggga acagttgaca   1860
gcgttctgaa aagatgccat ttgtttcctt ctgatctctc actgaataat gtttactgta   1920
cagtcttccc aaggtgattc ctgcgactgc aggcactggt cattttctca tgtagctgtc   1980
ttttcagtta tggtaaactc ttaaagttca gaacactcaa cagattcctt cagtgatata   2040
cttgttcgtt catttctaaa atgtgaagct ttaggaccaa attgttagaa agcatcagga   2100
tgaccagtta tctcgagtag atttcttgg atttcagaac atctagcatg actctgaagg   2160
ataccacatg ttttatatat aaataattac tgtttatgat atagacattg atattgacta   2220
tttagagaac cgttgttaat tttaaaacta gcaatctata aagtgcacca ggtcaacttg   2280
aataaaaaca ctatgacaga caggtttgcc agtttgcaga aactaactct tttctcacat   2340
caacatttgt aaaattgatg tgttatagtg gaaaataaca tatagattaa acaaaatttt   2400
tatcttttt caagaatata gctggctatc tttaagaaag atgatatatc ctagttttga   2460
aagtaatttt ctttttcttt tctagcattt gatgtctaaa taattttgga catcttttc   2520
ctagaccatg tttctgtctt actcttaaac ctggtaacac ttgatttgcc ttctataacc   2580
tatttatttc aagtgttcat atttgaattt ctttgggaag aaagtaaatc tgatggctca   2640
ctgattttg aaaagcctga ataaaattgg aaagactgga aagttaggag aactgactag   2700
ctaaactgct acagtatgca atttctatta caattggtat tacaggggggg aaaagtaaaa   2760
ttacacttta cctgaaagtg acttcttaca gctagtgcat tgtgctcttt ccaagttcag   2820
cagcagttct atcagtggtg ccactgaaac tgggtatatt tatgatttct ttcagcgtta   2880
aaaagaaaca tagtgttgcc ctttttctta aagcatcagt gaaattatgg aaaattactt   2940
aaaacgtgaa tacatcatca cagtagaatt tattatgaga gcatgtagta tgtatctgta   3000
gccctaacac atgggatgaa cgttttactg ctacacccag atttgtgttg aacgaaaaca   3060
ttgtggtttg gaaaggagaa ttcaacaatt aatagttgaa attgtgaggt taatgtttaa   3120
aaagctttac acctgtttac aatttgggga caaaaaggca ggcttcattt ttcatatgtt   3180
tgatgaaaac tggctcaaga tgtttgtaaa tagaatcaag agcaaaactg cacaaacttg   3240
cacattggaa agtgcaacaa gttcccgtga ttgcagtaaa aatatttact attctaaaaa   3300
aatgagaatt gaagacttag ccagtcagat aagtttttc atgaacccgt tgtggaaatt   3360
attggaatta actgagccaa agtgattatg cattcttcat ctattttagt tagcactttg   3420
tatcgttata tacagtttac aatacatgta taacttgtag ctataaacat tttgtgccat   3480
taaagctctc acaaaacttt aaaaa                                         3505
```

<210> SEQ ID NO 206
<211> LENGTH: 1997
<212> TYPE: DNA
<213> ORGANISM: Homo sapiens

<400> SEQUENCE: 206

```
atgtacaagg gcagccgtgg ggctggcaac agcttcgtaa tcctggcttc ctgctttctg     60
```

-continued

```
ggtcaaagcc ctggtggtgt gttcttgata tcggtccatc tagtggcgtt gtttgattcc    120

tcccaccttg ctgatcattc gtagtgtagc ccccaaggtg tggaataacc cttaagccct    180

taccggggtc cttctggact gagaattgtt gtaaagtaat actgctcagg tgaaagacaa    240

cttgagtggt taaattactg tcatgcaaag cgactagatg gttcagctga ttgcaccttt    300

agaagttatg tggaacgagg cagcagatct taagcccctt gctctgtcac gcaggctgga    360

atgcagtggt ggaatcatgg ctcactacag ccctgacctc ctgggcccag agatggagtc    420

tcgctatttt gcccaggttg gtcttgaaca cctggcttca agcagtcctc ctgcttttgg    480

cttcttgaag tgcttggatt acagtatttc agttttatgc tctgcaacaa gtttggccat    540

gttggaggac aatccaaagg tcagcaagtt ggctactggc gattggatgc tcactctgaa    600

gccaaagtct attactgtgc ccgtggaaat ccccagctcc cctctggatg atacaccccc    660

tgaagactcc attcctttgg tctttccaga attagaccag cagctacagc ccctgccgcc    720

ttgtcatgac tccgaggaat ccatggaggt gttcaaacag cactgccaaa tagcagaaga    780

ataccatgag gtcaaaaagg aaatcaccct gcttgagcaa aggaagaagg agctcattgc    840

caagttagat caggcagaaa aggagaaggt ggatgctgct gagctggttc gggaattcga    900

ggctctgacg gaggagaatc ggacgttgag gttggcccag tctcaatgtg tggaacaact    960

ggagaaactt cgaatacagt atcagaagag gcagggctcg tcctaacttt aaatttttca   1020

gtgtgagcat acgaggctga tgactgccct gtgctggcca aaagattttt attttaaatg   1080

aatagtgagt cagatctatt gcttctctgt attacccaca tgacaactgt ctataatgag   1140

tttactgctt gccagcttct agcttgagag aagggatatt ttaaatgaga tcattaacgt   1200

gaaactatta ctagtatatg tttttggaga tcagaattct tttccaaaga tatatgtttt   1260

tttctttttt aggaagatat gatcatgctg tacaacaggg tagaaaatga taaaaataga   1320

ctattgactg acccagctaa gaatcgtggg ctgagcagag ttaaaccatg ggacaaaccc   1380

ataacatgtt caccatagtt tcacgtatgt gtatttttaa atttcatgcc tttaatattt   1440

caaatatgct caaatttaaa ctgtcagaaa cttctctgca tgtatttata tttgccagag   1500

tataaacttt tatactctga tttttatcct tcaatgattg attatactaa gaataaatgg   1560

tcacatatcc taaaagcttc ttcatgaaat tattagcaga aaccatgttt gtaaccaaag   1620

cacatttgcc aatgctaact ggctgttgta ataataaaca gataaggctg catttgcttc   1680

atgccatgtg acctcacagt aaacatctct gcctttgcct gtgtgtgttc tgggggaggg   1740

gggacatgga aaaatattgt ttggacatta cttgggtgag tgcccatgaa aacatcagtg   1800

aacttgtaac tattgttttg ttttggattt aaggagatgt tttagatcag taacagctaa   1860

taggaatatg cgagtaaatt cagaattgaa acaatttctc cttgttctac ctatcaccac   1920

attttctcaa attgaactct ttgttatatg tccatttcta ttcatgtaac ttctttttca   1980

ttaaacatgg atcaaaa                                                  1997
```

```
<210> SEQ ID NO 207
<211> LENGTH: 2880
<212> TYPE: DNA
<213> ORGANISM: Homo sapiens

<400> SEQUENCE: 207
```

```
gcttccctgg gtgccacggt catgtgactt cggcaagatg gctgccctga cagcggagca     60

ttttgcagca ctccagagcc tgctcaagct gctccaggct ctgcaccgcc tcactaggct    120
```

-continued

```
ggtggcattc cgtgacctgt cctctgccga ggcaattctg gctctctttc cagaaaattt    180
ccaccaaaac ctcaaaaacc tgctgacaaa gatcatccta gaacatgtgt ctacttggag    240
aaccgaagcc caggcaaatc agatctctct gccacgcctg gtcgatctgg actggagagt    300
ggatatcaaa acctcctcag acagcatcag ccgcatggcc gtccccacct gcctgctcca    360
gatgaagatc caagaagatc ccagcctatg cggagacaaa ccctccatct cagctgtcac    420
cgtggagctg agcaaagaaa cactggacac catgttagat ggcctgggcc gcatccgaga    480
ccaactctct gccgtggcca gtaaatgatc cagccagctg ccagggccac tgccatgacc    540
cagctgctca tgagtgataa atgtctcccc atatgcaggc tgcccttgca gctgcagctg    600
acaacaggca ggatggtggg gacagcaggg ggctactgcc atccagaagt tacagttgga    660
ttgggaagaa gcagccagat cccccgctgt tctcactcat cttctttctc tttctgaagc    720
tggagagcag aagcccccat ctttgaaaag ctcctgagtg caacttaatt accaccatgg    780
cagggtgagg gaacatttgc atcgtcagct gcctctgcat agctgtttga gaaattcagg    840
cccaaatcat gcagcctatc caataagtaa gtttatttcc aacattagct ctaattagtt    900
catttccaat cccagaacac atggagggaa tcggacaggt gatgccagca gttcctgctc    960
ctctgtcagg gaagccaggc agagcccaca gagcatggtc catccagagt gttccctgag   1020
ccccctccac catactggaa cccctcttca gtgtaggaag tctgaaatgg gtgctaattc   1080
ccttcttcat gaaaccaggg ccctcttcct tcatctaatg cagccactcc taggtgaaga   1140
agtgggaata attggaaata aacaacagtt ctaaaacttc catgattttt gtagcttctt   1200
ttgtccccaa gttgaagctt ttggccagta ccttctctag tttttaaaga tgatcccaac   1260
ttcctaattc ccagctaagc ccttgaccca tggtgtgaca tgaaatcagg caattgaatc   1320
gcaccacttt ctgtgttttc acctgttacg tagaacaaaa ggaagcaagg tggccaggcg   1380
caatggctca cgcctgtaat cccagcactt tgggaggccg aggcaggcag atcatgaggt   1440
caggagatcg agaccatggt gaaaccccat ctctactaaa aatacaaaaa attagctggg   1500
cgcggtggcg ggcatctgta gtcccagctc ctcgggaggc tgaggcagga gaatggcgtg   1560
aacctgggag gcagagcttg cagtgagccg agatcgtgcc actgcactcc agtctgggtg   1620
acagagaagg actcgtctca aaaaataaaa ataaataaaa aggaagcaag gctaatcatc   1680
agtatgtgct tgttacaaga gctatgatga aggcactcct tcgagtttaa ccaaatgaga   1740
tcatctctgt catgtgcctc acgcctcaca gggactccat gtgtgaagat tccccccttca   1800
ctcaccagat catctccatg gcaacagctt gcagcctgct cttggagtgc tttgttttgg   1860
cagcttctct gctagtttgt gtatggagtg aatggaggag gtaaatccac agattaagaa   1920
tatgctgtca ggagtcaggc agccaaggtc agaagccagc tctgcttctc agtggtaagg   1980
tgcttgactt ctacatctca attttcaccc actttgtact tttttcctaa attaaatgag   2040
tataatagta gtacctactt gataggactt ttgtgaaaat taaatgatat aatgcaccta   2100
aaaacagtac tgttacaact aataggaaag gctttgatta ttaatggatg agagtagaaa   2160
gcttggtgca tttattgtct catctactat aacagagttg gtgtgagaat tagtattatc   2220
atcctccctt tattgaccag gaaaccagct cattgagatt gagtcatctg ctggtaaatg   2280
gtctcattaa gaggtggacc catatttctc tagctttctc tttacaacac aggactttgc   2340
aaggaacata taattctgtg actagcgcca tttggaaaat gttgaaactg aagtagagat   2400
gagagatctt acgtctgcct acccagtgag atacgaggaa ggtcaaggga aaaaaaattc   2460
caagctcttc tttatctgct ataggaaatg aacattcaat tttttgcatg caacgacaag   2520
```

```
aggtcaagga ccccagaagc cagcccgcta cttccaagtt gagagcccct ggtcataccc   2580

tccagttgag ctcagatttg tcacaaattt accccctctcc tttccttcca ttccccatga   2640

cctgcagaga gagatgtcag ataccttcct cttggcctcc catgggcatc cataagaaac   2700

ttacttgaag caagaagccc agtataggtg tctgggcagt tggacatttc ctctagccag   2760

atctgtccga atagagccat ctgggtacat gacgcagagg gcatttgata aataactgga   2820

aaagtcaata aatctttgct acccttcaaa aaaaaaaaaa aaaaaaaaaa aaaaaaaaaa   2880


<210> SEQ ID NO 208
<211> LENGTH: 4697
<212> TYPE: DNA
<213> ORGANISM: Homo sapiens

<400> SEQUENCE: 208

agacgctcgc ctggcagctg cgcacactcg gagcgccccg agcggcgcag atagggacgt     60

tggggctgtg ccccgcggcg cggcgcctgc cactgcgcag gcgcctcagg aagagctcgg    120

catcgcccct cttcctccag gtccccccttc cccgcaactt cccacgagtg ccaggtgccg    180

cgagcgccga gttccgcgca ttggaaagaa gcgaccgcgg cggctggaac cctgattgct    240

gtccttcaac gtgttcatta tgaagttatt agtaatactt ttgttttctg gacttataac    300

tggttttaga agtgactctt cctctagttt gccacctaag ttactactag tatcctttga    360

tggcttcaga gctgattatc tgaagaacta tgaatttcct catctccaga attttatcaa    420

agaaggtgtt ttggtagagc atgttaaaaa tgtttttatc acaaaaacat ttccaaacca    480

ctacagtatt gtgacaggct tgtatgaaga aagccatggc attgtggcta attccatgta    540

tgatgcagtc acaaagaaac acttttctga ctctaatgac aaggatcctt tttggtggaa    600

tgaggcagta cctatttggg tgaccaatca gcttcaggaa aacagatcaa gtgctgctgc    660

tatgtggcct ggtactgatg tacccattca cgataccatc tcttcctatt ttatgaatta    720

caactcctca gtgtcatttg aggaaagact aaataatatt actatgtggc taaacaattc    780

gaacccacca gtcacctttg caacactata ttgggaagaa ccagatgcaa gtggccacaa    840

atacggacct gaagataaag aaaacatgag cagagtgttg aaaaaaatag atgatcttat    900

cggtgactta gtccaaagac tcaagatgtt agggctatgg gaaaatctta atgtgatcat    960

tacaagtgat catgggatga cccagtgttc tcaggacaga ctgataaacc tggattcctg   1020

catcgatcat tcatactaca ctcttataga tttgagccca gttgctgcaa tacttcccaa   1080

aataaataga acagaggttt ataacaaact gaaaaactgt agccctcata tgaatgttta   1140

tctcaaagaa gacattccta acagatttta ttaccaacat aatgatcgaa ttcagcccat   1200

tattttggtt gccgatgaag gctggacaat tgtgctaaat gaatcatcac aaaaattagg   1260

tgaccatggt tatgataatt ctttgcctag tatgcatcca tttctagctg cccacggacc   1320

tgcatttcac aaaggctaca agcatagcac aattaacatt gtggatattt atccaatgat   1380

gtgccacatc ctgggattaa aaccacatcc caataatggg acctttggtc atactaagtg   1440

cttgttagtt gaccagtggt gcattaatct cccagaagcc atcgcgattg ttatcggttc   1500

actcttggtg ttaaccatgc taacatgcct cataataatc atgcagaata gactttctgt   1560

acctcgtcca ttttctcgac ttcagctaca agaagatgat gatgatcctt taattgggtg   1620

acatgtgcta gggcttatac aaagtgtctt tgattaatca caaaactaag aatacatcca   1680

aagaatagtg ttgtaactat gaaaaagaat actttgaaag acaaagaact tagactaagc   1740
```

-continued

```
atgttaaaat tattactttg ttttccttgt gttttgtttc ggtgcatttg ctaataagat   1800
aacgctgacc atagtaaaat tgttagtaaa tcattaggta acatcttgtg gtaggaaatc   1860
attaggtaac atcaatccta actagaaata ctaaaaatgg cttttgagaa aaatacttcc   1920
tctgcttgta ttttgcgatg aagatgtgat acatctttaa atgaaaatat accaaaattt   1980
agtaggcatg tttttctaat aaatttatat atttgtaaag aaaacaacag aaatctttat   2040
gcaatttgtg aattttgtat attagggagg aaaagcttcc tatattttta tatttacctt   2100
taattagttt gtatctcaag taccctcttg aggtaggaaa tgctctgtga tggtaaataa   2160
aattggagca gacagaaaag atatagcaaa tgaagaaata ttttaaggaa acctatttga   2220
aaaaaaaagc aaagaccatt tgataaaagc ctgagttgtc accattatgt cttaagctgt   2280
tagtcttaaa gattattgtt aaaaaattca gaagaaaaga gagacaagtg ctcttctctc   2340
tatctatgct taatgccttt atgtaagtta cttagttgtt tgcgtgtgcc tgtgcaagtg   2400
tgtttgtgtg tggttgtgtg gacattatgt gatttactat ataaggaggt cagagatgga   2460
ctgtggccag gcttccacat tcctgaagca cacagatctc aggaaaggtt atttttgcac   2520
ttcatatttg tttactttct cctaactcac aagttaaaat cataacttaa tttcattaac   2580
ttttatcatt taactctctc atgtttgttg taacctgagg tatccaaatg ctacagaaaa   2640
atttatgacc caaatacaaa tctcaatttg actgggacag aatgaggaat ggagattttt   2700
gtatttatct ttgggacttt atgccttact ttttaggcta tagaatagtt aagaaatttt   2760
aaacaaaatt tagtatcttt tggtctttca caccattcat atgttaagtg gcagaatagc   2820
cttagtgcta cctccacttt tttctccagt atttgcatca cagaaataat ccctctgttt   2880
aacatgtttg ttcagagcca agggtttatt gtgaagaact gtcatcctgc ctttgctagc   2940
tggtaccttc tagtaatcaa aattaatatg aagaaactag gttgtgacag actagattat   3000
atttagtagg ggaaaaattg ggctcaagaa ccattcatca gtacgtgaga caagcagtta   3060
atagtatgat ctttaaagtt ttgacaatat aaaataaact tggtaactgt tttacaaata   3120
taaaagtata ataaatatgc agcccagtta aatattgatt atctgtgatg gtaaagaaca   3180
acagtggtgc cagtcatcaa acatacagtg cgtcctattg agtcactgct aatttcttga   3240
gcctggtatt tgctgcctat tgtatttgtg gttgttgaga ggcattttca aaccctgtat   3300
aaataatcca tgctgttggt cataagttaa ctgtattaag aacagtaaaa taaataaaaa   3360
ccaatagtac taattttgct ttaaaaaaat ttctaatttt tttcacataa aacaattatc   3420
ctaaaggtta atagttgatc gaaacagaat aatagaaaaa ttctacttta atttccatta   3480
aaaagcaaat agcattgaca catttaaagc ttttcattta aagtagtgga tgtttttgaa   3540
gtatctaaaa tagtagcaga atattttata cttggtcctt gcaatggtgt gagttttaat   3600
gattgcatta tcgtgattgg tggttatgag tttcagaaat ctatacttgg catccaactc   3660
atgagtggat tttatatagg atggaacagg aaggtatgtc ctgtcagtat cttaaccctt   3720
tcaacaagac atttacctat ttgtctttcc ttacgttctc aaaatattaa ctcgaattgt   3780
aaattaagca aaaatttaaa aagtatatgt tgatgggaca agaagaatag tatttattta   3840
ataaaacata tattatattg aactatgtgt taattcattt gtatctttta aaaaattatc   3900
actgttaaag ccattgactc ctttagtaca ctgagaaaaa tcttatagta aaactagcct   3960
ttcacattaa ggttttggtg tgtattttgt taaataacta acatgctgct ctattttctg   4020
ggtgtagaaa gtatttggct ctaggaaaca tttacttgtt tgtgaaaaca ataccccaag   4080
gtaataggaa aagtttgagt taagtgtttt taattcagtc agtgaattca gaataagtac   4140
```

```
attcatgtat aacataggga cagttctgct gctgttattt atatgcaatt cttctggtaa   4200

atagcaatag aataaaacat atttcaatgt ttgtgtatag gttttatatt attattccac   4260

taggaatggc ataagaattt atagataaat tcttgtaaca ttaaaggatt aaaatgtttt   4320

tacattgttt ttgggtgtct ccttcttgtg cccatatctg ataagcttta tggattattg   4380

catttaattc cttttatttg gagggtttta cttccttgtt aacatataaa gttataaatg   4440

aaggacaagg aggagatgga aaatgtgtat ttattgttaa ttcttaaaat agtgtgtaaa   4500

taaaataaca tcagtgtgct ttaaagaaat gtgtatgtag tgccttaatt taaattaaaa   4560

tatttttgac tgttacttga gttcagaatt aatgactttg ttcatgattt ttaaaatgtg   4620

tgtgaataaa atctaccaaa aaattcttac tgtaattatt aaatataaag ttcagtgtca   4680

aaaaaaaaaa aaaaaaa                                                  4697
```

<210> SEQ ID NO 209
<211> LENGTH: 2448
<212> TYPE: DNA
<213> ORGANISM: Homo sapiens

<400> SEQUENCE: 209

```
accggcccgg ttccctctcc ggggagcggc ggcggacgcg cggctcccac ccctcccctc     60

tcacgggctc tcccctcccc agtgtggccg cgaccctacc ctctgcaagg cgatggcccg    120

cgccccgagc gcaggctagc gtgcctgggt gcccggccat gggctgtatc ggctctcgga    180

gcccggcggg tcaggcattt ctggggacca acagctggcc gaggctcagg gatagagacg    240

gctgctccag ctaaaggtga atgttggaga cacagtcgcg atgctgccca agtcccggcg    300

agccctaact atccaggaga tcgctgcgct ggccaggtcc tccctgcatg gtatttccca    360

ggtggtgaag gaccacgtga ccaagcctac cgccatggcc cagggccgag tggctcacct    420

cattgagtgg aagggctgga gcaagccgag tgactcacct gctgccctgg aatcagcctt    480

ttcctcctat tcagacctca gcgagggcga acaagaggct cgctttgcag caggagtggc    540

tgagcagttt gccatcgcgg aagccaagct ccgagcatgg tcttcggtgg atggcgagga    600

ctccactgat gactcctatg atgaggactt tgctggggga atggacacag acatggctgg    660

gcagctgccc ctggggccgc acctccagga cctgttcacc ggccaccggt tctcccggcc    720

tgtgcgccag ggctccgtgg agcctgagag cgactgctca cagaccgtgt ccccagacac    780

cctgtgctct agtctgtgca gcctggagga tgggttgttg ggctccccgg cccggctggc    840

ctcccagctg ctgggcgatg agctgcttct cgccaaactg ccccccagcc gggaaagtgc    900

cttccgcagc ctgggcccac tggaggccca ggactcactc tacaactcgc ccctcacaga    960

gtcctgcctt tcccccgcgg aggaggagcc agccccctgc aaggactgcc agccactctg   1020

cccaccacta acgggcagct gggaacggca gcggcaagcc tctgacctgg cctcttctgg   1080

ggtggtgtcc ttagatgagg atgaggcaga gccagaggaa cagtgaccca catcatgcct   1140

ggcagtggca tgcatccccc ggctgctgcc aggggcagag cctctgtgcc caagtgtggg   1200

ctcaaggctc ccagcagagc tccacagcct agagggctcc tgggagcgct cgcttctccg   1260

ttgtgtgttt tgcatgaaag tgtttggaga ggaggcaggg gctgggctgg gggcgcatgt   1320

cctgccccca ctcccggggc ttgccggggg ttgcccgggg cctctggggc atggctacag   1380

ctgtggcaga cagtgatgtt catgttctta aaatgccaca cacacatttc ctcctcggat   1440

aatgtgaacc actaaggggg ttgtgactgg gctgtgtgag ggtggggtgg gagggggccc   1500
```

```
agcaaccccc caccctcccc atgcctctct cttctctgct tttcttctca cttccgagtc   1560
catgtgcagt gcttgataga atcaccccca cctggagggg ctggctcctg ccctcccgga   1620
gcctatgggt tgagccgtcc ctcaagggcc cctgcccagc tgggctcgtg ctgtgcttca   1680
ttcacctctc catcgtctct aaatcttcct ctttttttcct aaagacagaa ggtttttggt   1740
ctgtttttttc agtcggatct tctcttctct gggaggcttt ggaatgatga aagcatgtac   1800
cctccaccct tttcctggcc ccctaatggg gcctgggccc tttcccaacc cctcctagga   1860
tgtgcgggca gtgtgctggc gcctcacagc cagccgggct gcccattcac gcagagctct   1920
ctgagcggga ggtggaagaa aggatggctc tggttgccac agagctggga cttcatgttc   1980
ttctagagag ggccacaaga gggccacagg ggtggccggg agttgtcagc tgatgcctgc   2040
tgagaggcag gaattgtgcc agtgagtgac agtcatgagg gagtgtctct tcttggggag   2100
gaaagaaggt agagcctttc tgtctgaatg aaaggccaag gctacagtac agggccccac   2160
cccagccagg gtgttaatgc ccacgtagtg gaggcctctg gcagatcctg cattccaagg   2220
tcactggact gtacgttttt atggttgtgg gaagggtggg tggctttaga attaagggcc   2280
ttgtaggctt tggcaggtaa gagggcccaa ggtaagaacg agagccaacg ggcacaagca   2340
ttctatatat aagtggctca ttaggtgttt attttgttct atttaagaat ttgttttatt   2400
aaattaatat aaaaatcttt gtaaatctct aaaaaaaaaa aaaaaaaa               2448
```

<210> SEQ ID NO 210
<211> LENGTH: 5458
<212> TYPE: DNA
<213> ORGANISM: Homo sapiens

<400> SEQUENCE: 210

```
aagcgtcgga cgcggcccgg cgccgagcca tggagcctga gccagtggag gactgtgtgc     60
agagcactct cgccgccctg tatccaccct ttgaggcaac agcccccacc ctgttgggcc    120
aggtgttcca ggtggtggag aggacttatc gggaggacgc actgaggtac acgctggact    180
tcctggtacc agccaagcac ctgcttgcca aggtccagca ggaagcctgt gcccaataca    240
gtggattcct cttcttccat gaggggtggc cgctctgcct gcatgaacag gtggtggtgc    300
agctagcagc cctaccctgg caactgctgc gcccaggaga cttctatctg caggtggtgc    360
cctcagctgc ccaagcaccc cgactagcac tcaagtgtct ggcccctggg ggtgggcggg    420
tgcaggaggt tcctgtgccc aatgaggctt gtgcctacct attcacacct gagtggctac    480
aaggcatcaa caaggaccgg ccaacaggtc gcctcagtac ctgcctactg tctgcgccct    540
ctgggattca gcggctgccc tgggctgagc tcatctgtcc acgatttgtg cacaaagagg    600
gcctcatggt tggacatcag ccaagtacac tgcccccaga actgccctct ggacctccag    660
ggcttcccag ccctccactt cctgaggagg cgctgggtac ccggagtcct ggggatgggc    720
acaatgcccc tgtggaagga cctgagggcg agtatgtgga gctgttagag gtgacgctgc    780
ccgtgagggg gagcccaaca gatgctgaag gctccccagg cctctccaga gtccggacgg    840
tacccacccg caagggcgct ggagggaagg gccgccaccg gagacaccgg gcgtggatgc    900
accagaaggg cctggggcct cggggccagg atggagcacg cccacccggc gaggggagca    960
gcaccggagc ctcccctgag tctcccccag gagctgaggc tgtcccagag gcagcagtct   1020
tggaggtgtc tgagccccca gcagaggctg tgggagaagc ctccggatct tgcccccctga   1080
ggccagggga gcttagagga ggaggaggag gaggccaggg ggctgaagga ccacctggta   1140
cccctcggag aacaggcaaa ggaaacagaa gaaagaagcg agctgcaggt cgagggggctc   1200
```

```
ttagccgagg aggggacagt gccccactga gccctgggga caaggaagat gccagccacc   1260
aagaagccct tggcaatctg ccctcaccaa gtgagcacaa gcttccagaa tgccacctgg   1320
ttaaggagga atatgaaggc tcagggaagc cagaatctga gccaaaagag ctcaaaacag   1380
caggcgagaa agagcctcag ctctctgaag cctgtgggcc tacagaagag ggggccggag   1440
agagagagct ggaggggcca ggcctgctgt gtatggcagg acacacaggc ccagaaggcc   1500
ccctgtctga cactccaaca cctccgctgg agactgtgca ggaaggaaaa ggggacaaca   1560
ttccagaaga ggcccttgca gtctccgtct ctgatcaccc tgatgtagct tgggacttga   1620
tggcatctgg attcctcatc ctgacgggag gggtggacca gagtgggcga gctctgctga   1680
ccattacccc accgtgccct cctgaggagc cccaccctc ccgagacacg ctgaacacaa   1740
ctcttcatta cctccactca ctgctcaggc ctgatctaca gacactgggg ctgtccgtcc   1800
tgctggacct tcgtcaggca cctccactgc ctccagcact cattcctgcc ttgagccaac   1860
ttcaggactc aggagatcct ccccttgttc agcggctgct gattctcatt catgatgacc   1920
ttccaactga actctgtgga tttcagggtg ctgaggtgct gtcagagaat gatctgaaaa   1980
gagtggccaa gccagaggag ctgcagtggg agttaggagg tcacagggac ccctctccca   2040
gtcactgggt agagatacac caggaagtgg taaggctatg tcgcctgtgc caaggtgtgc   2100
tgggctcggt acggcaggcc attgaggagc tggagggagc agcagagcca gaggaagagg   2160
aggcagtggg aatgcccaag ccactgcaga aggtgctggc agatccccgg ctgacggcac   2220
tgcagaggga tgggggggcc atcctgatga ggctgcgctc cactcccagc agcaagctgg   2280
agggccaagg cccagctaca ctgtatcagg aagtggacga ggccattcac cagcttgtgc   2340
gcctctccaa cctgcacgtg cagcagcaag agcagcggca gtgcctgcgg cgactccagc   2400
aggtgttgca gtggctctcg ggcccagggg aggagcagct ggcaagcttt gctatgcctg   2460
gggacacctt gtctgccctg caggagacag agctgcgatt ccgtgctttc agcgctgagg   2520
tccaggagcg cctggcccag gcacgggagg ccctggctct ggaggagaat gccacctccc   2580
agaaggtgct ggatatcttt gaacagcggc tggagcaggt tgagagtggc ctccatcggg   2640
ccctgcggct acagcgcttc ttccagcagg cacatgaatg ggtggatgag ggctttgctc   2700
ggctggcagg agctgggccg ggtcgggagg ctgtgctggc tgcactggcc ctgcggcggg   2760
ccccagagcc cagtgccggc accttccagg agatgcgggc cctggccctg gacctgggca   2820
gcccagcagc cctgcgagaa tggggccgct gccaggcccg ctgccaagag ctagagagga   2880
ggatccagca acacgtggga gaggaggcga gcccacgggg ctaccgacga cggcgggcag   2940
acggtgccag cagtggaggg gcccagtggg ggccccgcag cccctcgccc agcctcagct   3000
ccttgctgct ccccagcagc cctgggccac ggccagcccc atcccattgc tccctggccc   3060
catgtggaga ggactatgag gaagagggcc ctgagctggc tccagaagca gagggcaggc   3120
ccccaagagc tgtgctgatc cgaggcctgg aggtcaccag cactgaggtg gtagacagga   3180
cgtgctcacc acgggaacac gtgctgctgg gccgggctag gggggccagac ggaccctggg   3240
gagtaggcac cccccggatg gagcgcaagc gaagcatcag tgcccagcag cggctggtgt   3300
ctgagctgat tgcctgtgaa caagattacg tggccacctt gagtgagcca gtgccacccc   3360
ctgggcctga gctgacgcct gaacttcggg gcacctgggc tgctgccctg agtgcccggg   3420
aaaggcttcg cagcttccac cggacacact ttctgcggga gcttcagggc tgcgccaccc   3480
accccctacg cattggggcc tgcttccttc gccacgggga ccagttcagc ctttatgcac   3540
```

agtacgtgaa gcaccgacac aaactggaga atggtctggc tgcgctcagt cccttaagca 3600
agggctccat ggaggctggc ccttacctgc cccgagccct gcagcagcct ctggaacagc 3660
tgactcggta tgggcggctc ctggaggagc tcctgaggga agctgggcct gagctcagtt 3720
ctgagtgccg ggcccttggg gctgctgtac agctgctccg ggaacaagag gcccgtggca 3780
gagacctgct ggccgtggag gcggtgcgtg gctgtgagat agatctgaag gagcagggac 3840
agctcttgca tcgagacccc ttcactgtca tctgtggccg aaagaagtgc cttcgccatg 3900
tctttctctt cgagcatctc ctcctgttca gcaagctcaa gggccctgaa ggggggtcag 3960
agatgtttgt ttacaagcag gcctttaaga ctgctgatat ggggctgaca gaaaacatcg 4020
gggacagcgg actctgcttt gagttgtggt ttcggcggcg gcgtgcacga gaggcataca 4080
ctctgcaggc aacctcacca gagatcaaac tcaagtggac aagttctatt gcccagctgc 4140
tgtggagaca ggcagcccac aacaaggagc tccgagtgca gcagatggtg tccatgggca 4200
ttgggaataa acccttcctg gacatcaaag cccttgggga gcggacgctg agtgccctgc 4260
tcactggaag agccgcccgc acccgggcct ccgtggccgt gtcatccttt gagcatgccg 4320
gcccctccct tcccggcctt tcgccgggag cctgctccct gcctgcccgc gtcgaggagg 4380
aggcctggga tctggacgtc aagcaaattt ccctggcccc agaaacactt gactcttctg 4440
gagatgtgtc cccaggacca agaaacagcc ccagcctgca acccccccac cctgggagca 4500
gcactcccac cctggccagt cgagggatct tagggctatc ccgacagagt catgctcgag 4560
ccctgagtga ccccaccacg cctctgtgac ctggagaaga tccagaactt gcgtgcagct 4620
tctcctctca gcacactttg ggctgggatg gcagtggggc ataatggagc cctgggcgat 4680
cgctgaattt cttccctctg cttcctggac acagaggagg tctaacgacc agagtattgc 4740
cctgccacca ctatctctag tctccctagc ttggtgcctt ctcctgcagg agtcagagca 4800
gccacattgc ttgccttcat accctggagg tggggaagtt atccctcttc cggtgctttc 4860
ccatcctggg ccactgtatc caggacatca ctcccatgcc agccctccct ggcagcccat 4920
gttctcctct tttctcaccc cctgactttc cctgagaaga atcatctctg ccaggtcaac 4980
tggagtccct ggtgactcca ttctgaggtg tcacaagcaa tgaagctatg caaacaatag 5040
gagggtgtga caggggaacc gtagacttta tatatgtaat tactgttatt ataatactat 5100
tgttatatta aatgtattta ctcacacttt gcctctaagg agctagagta gtcctctgga 5160
ttaaggtgat aaataacttg agcactttcc ctcaaccagc ccttaactag aacacagaaa 5220
ataaaaccaa gactggaagg tcccctctac ccctcccagg cccagagcta gctgactgtg 5280
tatgagcctg ggagaatgtg tctcctccac agtggctccc agaggttcca cacactctct 5340
gaagctcctt ctcccacact gcacctactc cttgaggctg aactggtcac agacaaactg 5400
ggatccagca cagtccagca gttctcaaaa tgaggtcctc aggccacagt gcgtgaga 5458

<210> SEQ ID NO 211
<211> LENGTH: 2347
<212> TYPE: DNA
<213> ORGANISM: Homo sapiens

<400> SEQUENCE: 211
gcgcttttgc cgcgccgtgc tgcccgcgag ggcagctgag gtggtggtgg cggccgcctt 60
gtcgaggcat cgcgcgcccg tgaagtgttc gccgtcagtg ctgttgggtg cctggagccg 120
cgtcccccgt cccgaaaact gtccttgaca gtacttgcgc ggcccaacgg ccgccggcgc 180
ccccgcgtct ccatggcgac ggccttttc cctgcgagga ccccggcggc agggctgccc 240

```
cgcggcgcct gcttggcgcg acgctctagc ggttaccgct gcgggctggc tgggcgtagt    300
ggggctgcgc ggctgccacg gagctagagg gcaagtgtgc tcggcccagc gtgcagggaa    360
cgcgggcggc cagacaacgg gctgggctcc ggggcctgcg gcgcgggcgc tgagctggca    420
gggcgggtcg gggcgcgggc tgcatccgca tctcctccat cgcctgcagt aagggcggcc    480
gcggcgagcc tttgagggga acgacttgtc ggagccctaa ccaggggtat ctctgagcct    540
ggtgggatcc ccggagcgtc acatcacttt ccgatcactt caaagtacag cagaccgagg    600
acacggttgt taccaagacc aggctgttgc cttggaagag cccagagcgt gtcaagggag    660
acagccacat cacgccagaa atacatgaca gctggattag ccctgggaga gggaggccca    720
gatgtgggag ctcaggggag gtgcagctca acgtggagtt tggaggaggc taccttgacc    780
tttgaatgcc aagtgggagc cagccagatg aaaggggtta aaaactaata tttatatgac    840
agaagaaaaa gatgtcattc cgtaaagtaa acatcatcat cttggtcctg gctgttgctc    900
tcttcttact ggttttgcac cataacttcc tcagcttgag cagtttgtta aggaatgagg    960
ttacagattc aggaattgta gggcctcaac ctatagactt tgtcccaaat gctctccgac   1020
atgcagtaga tgggagacaa gaggagattc ctgtggtcat cgctgcatct gaagacaggc   1080
ttgggggggc cattgcagct ataaacagca ttcagcacaa cactcgctcc aatgtgattt   1140
tctacattgt tactctcaac aatacagcag accatctccg gtcctggctc aacagtgatt   1200
ccctgaaaag catcagatac aaaattgtca attttgaccc taaacttttg gaaggaaaag   1260
taaaggagga tcctgaccag gggggaatcca tgaaaccttt aacctttgca aggttctact   1320
tgccaattct ggttcccagc gcaaagaagg ccatatacat ggatgatgat gtaattgtgc   1380
aaggtgatat tcttgccctt tacaatacag cactgaagcc aggacatgca gctgcatttt   1440
cagaagattg tgattcagcc tctactaaag ttgtcatccg tggagcagga aaccagtaca   1500
attacattgg ctatcttgac tataaaaagg aaagaattcg taagctttcc atgaaagcca   1560
gcacttgctc atttaatcct ggagtttttg ttgcaaacct gacggaatgg aaacgacaga   1620
atataactaa ccaactggaa aaatggatga aactcaatgt agaagaggga ctgtatagca   1680
gaaccctggc tggtagcatc acaacacctc ctctgcttat cgtattttat caacagcact   1740
ctaccatcga tcctatgtgg aatgtccgcc accttggttc cagtgctgga aaacgatatt   1800
cacctcagtt tgtaaaggct gccaagttac tccattggaa tggacatttg aagccatggg   1860
gaaggactgc ttcatatact gatgtttggg aaaaatggta tattccagac ccaacaggca   1920
aattcaacct aatccgaaga tataccgaga tctcaaacat aaagtgaaac agaatttgaa   1980
ctgtaagcaa gcatttctca ggaagtcctg gaagatagca tgcgtgggaa gtaacagttg   2040
ctaggcttca atgcctatcg gtagcaagcc atggaaaaag atgtgtcagc taggtaaaga   2100
tgacaaactg ccctgtctgg cagtcagctt cccagacaga ctatagacta taaatatgtc   2160
tccatctgcc ttaccaagtg ttttcttact acaatgctga atgactggaa agaagaactg   2220
atatggctag ttcagctagc tggtacagat aattcaaaac tgctgttggt tttaattttg   2280
taacctgtgg cctgatctgt aaataaaact tacatttttc aataaaaaaa aaaaaaaaaa   2340
aaaaaaa                                                             2347
```

<210> SEQ ID NO 212
<211> LENGTH: 4463
<212> TYPE: DNA
<213> ORGANISM: Homo sapiens -continued

<400> SEQUENCE: 212
gcagcgcgca ccgagccggc cgcgccgcgc ccgccgctct cgccgctttc gccgcggtct 60
cctcctctag cgcccgccgc ggccggtaaa tctcggctgg aggagcagcg gcggcccccg 120
agtcaacttt cattcccttt ttgcttctgc ctcaccattc tcttctcctc ctcgaaagat 180
ggctgtttgg agaaggggga gaagttaaga ggtcgccagc gcggagcgaa ggagggcgcg 240
atagcctcag caggagcggg cggaggtttc tcctctgcca acccctcctg gaccattgtc 300
agcagttgaa cgacaaaggc tgtgaatctg catcctagtc ttagcagtcc ctctgattct 360
catgatgagc tcacctgcac agcctgacct catgtggaac cttgtaccat gggtgctatt 420
ctgtggctgc tgtaggatct tcccagatgg ggtggctgga cgagagcagc tcttggctca 480
gcaaagaatg cacagtatga tcagctcagt ggatgtgaag tcagaagttc ctgtgggcct 540
ggagcccatc tcacctttag acctaaggac agacctcagg atgatgatgc ccgtggtgga 600
ccctgttgtc cgtgagaagc aattgcagca ggaattactt cttatccagc agcagcaaca 660
aatccagaag cagcttctga tagcagagtt tcagaaacag catgagaact tgacacggca 720
gcaccaggct cagcttcagg agcatatcaa ggaacttcta gccataaaac agcaacaaga 780
actcctagaa aaggagcaga aactggagca gcagaggcaa gaacaggaag tagagaggca 840
tcgcagagaa cagcagcttc ctcctctcag aggcaaagat agaggacgag aaagggcagt 900
ggcaagtaca gaagtaaagc agaagcttca agagttccta ctgagtaaat cagcaacgaa 960
agacactcca actaatggaa aaaatcattc cgtgagccgc catcccaagc tctggtacac 1020
ggctgcccac cacacatcat tggatcaaag ctctccaccc cttagtggaa catctccatc 1080
ctacaagtac acattaccag gagcacaaga tgcaaaggat gatttccccc ttcgaaaaac 1140
tgaatcctca gtcagtagca gttctccagg ctctggtccc agttcaccaa acaatgggcc 1200
aactggaagt gttactgaaa atgagacttc ggttttgccc cctacccctc atgccgagca 1260
aatggtttca cagcaacgca ttctaattca tgaagattcc atgaacctgc taagtcttta 1320
tacctctcct tctttgccca acattacctt ggggcttccc gcagtgccat cccagctcaa 1380
tgcttcgaat tcactcaaag aaaagcagaa gtgtgagacg cagacgctta ggcaaggtgt 1440
tcctctgcct gggcagtatg gaggcagcat cccggcatct tccagccacc ctcatgttac 1500
tttagaggga aagccaccca acagcagcca ccaggctctc ctgcagcatt tattattgaa 1560
agaacaaatg cgacagcaaa agcttcttgt agctggtgga gttcccttac atcctcagtc 1620
tcccttggca acaaaagaga gaatttcacc tggcattaga ggtacccaca aattgccccg 1680
tcacagaccc ctgaaccgaa cccagtctgc acctttgcct cagagcacgt tggctcagct 1740
ggtcattcaa cagcaacacc agcaattctt ggagaagcag aagcaatacc agcagcagat 1800
ccacatgaac aaactgcttt cgaaatctat tgaacaactg aagcaaccag gcagtcacct 1860
tgaggaagca gaggaagagc ttcagggggga ccaggcgatg caggaagaca gagcgccctc 1920
tagtggcaac agcactagga gcgacagcag tgcttgtgtg gatgacacac tgggacaagt 1980
tggggctgtg aaggtcaagg aggaaccagt ggacagtgat gaagatgctc agatccagga 2040
aatggaatct ggggagcagg ctgcttttat gcaacaggta ataggcaaag atttagctcc 2100
aggatttgta attaaagtca ttatctgaac atgaaatgca ttgcaggttt ggtaaatgga 2160
tatgatttcc tatcagttta tatttctcta tgatttgagt tcagtgttta aggattctac 2220
ctaatgcaga tatatgtata tatctatata gaggtctttc tatatactga tctctatata 2280
gatatcaatg tttcattgaa aatccactgg taaggaaata cctgttatac taaaattatg 2340

```
atacataata tctgagcagt taataggctt taaatttatc ccaaagcctg ctacaccaat   2400
tacttctaaa gaaaacaaat tcactgttat tttgagttta tgtgttgaga tcagtgactg   2460
ctggatagtc tcccagtctg atcaatgaag cattcgatta gtttttgatt ttttgcaaca   2520
tctagaattt aattttcaca tcactgtaca taatgtatca tactatagtc ttgaacactg   2580
ttaaaggtag tctgcccctt ccttcctctc tcttttttta gttaagtaga aatgttctgg   2640
tcaccatgcc agtagtccta ggttattgtg taggttgcaa ttgaacatat taggaataca   2700
ggtggtttta aatatataga tgcaaattgc agcactactt taaatattag attatgtctc   2760
acatagcact gctcatttta cttttatttt gtgtaatttg atgacactgt ctatcaaaaa   2820
agagcaaatg aagcagatgc aaatgttagt gagaagtaat gtgcagcatt atggtccaat   2880
cagatacaat attgtgtcta caattgcaaa aaacacagta acaggatgaa tattatctga   2940
tatcaagtca aaatcagttt gaaaagaagg tgtatcatat tttatattgt cactagaatc   3000
tcttaagtat aattccataa tgacatgggc atataccgta acattctggc aaataacaat   3060
tagaaaagat aggtttaaca aaaaaattta cttgtatata atgcaccttc aggaggacta   3120
tgtcctttga tgctataaaa tacaaacaac tttgaaggca acagaagaca ctgtttattc   3180
aagtcagttc tttgtcaggt tcctgctgtt ctcctacaga aaagtgattc tgtgagggtg   3240
aacaggaaat gccttgtgga aacaggaagt ccaagtgatt catgtactga ggaatgtagg   3300
aaaaaaaatc tgaggatagt gctttactct ttctgttttt aaagggcact ctatgaattg   3360
atttattgtc taagaaaata acaccacaag tagggaaatt gttacggaag cttttcactg   3420
gaacatttcc ttcatattcc cttttgatat gtttaccttg ttttataggt ttacttttgt   3480
taagctagtt aaaggttcgt tgtattaaga ccccttttaat atggataatc caaattgacc   3540
tagaatcttt gtgaggtttt ttctattaaa atatttatat ttctaaatcc gaggtatttc   3600
aaggtgtagt atcctatttc aaaggagata tagcagtttt gccaaatgta gacattgttc   3660
aactgtatgt tattggcacg tgttgtttac attttgctgt gacatttaaa aatatttctt   3720
taaaaatgtt actgctaaag atacattatc cttttttaaa aagtctccat tcaaattaaa   3780
ttaacataac tagaagttag aaagtttaaa agttttccac ataatgaaag tccttctgat   3840
aatttgacaa atagctataa taggaacact ccctatcacc aacatatttt ggttagtata   3900
ttccttcata ttaaaatgac tttttgtcag ttgttttgca ttaaaaatat ggcatgccta   3960
agataaaatt gtatattttt tccatctcat aaatattcat tttcttcaaa gtctttttc   4020
aatctcataa aaaagggata gtgcatcttt taaaatacat tttatttggg gaggaacatg   4080
tggctgagca gacttttgta taatattact tcaaagatat gtaatcacaa acaaaaaaaa   4140
ctattttttta taatgtcatt tgagagagtt tcatcagtac agttggtgga cgttaattgt   4200
ttgaatttga tagtctttga atttaatcaa gaaactacct ggaaccagtg aaaaggaaag   4260
ctggacttaa ataatcttag aattaattga taaatgtctc ttttaaaatc tactgtattt   4320
attataattt acacccttga aggtgatctc ttgttttgtg ttgtaaatat attgtttgta   4380
tgtttccctt cttgccttct gttataagtc tcttcctttc tcaaataaag ttttttttaa   4440
aagaaaaaaa aaaaaaaaaa aaa                                          4463
```

<210> SEQ ID NO 213
<211> LENGTH: 2697
<212> TYPE: DNA
<213> ORGANISM: Homo sapiens

<400> SEQUENCE: 213

```
acttgtccgt cacgtgcggc cgcccggcct ctcggccttg ccgcgcgcct ggcggggttg     60
ggggggcggg gaccaagatc tgctgcgcct gcgttgtggg cgttctcggg gagctgctgc    120
cgtagctgcc gccgccgcta ccaccgcgtt cgggtgtaga atttggaatc cctgcgccgc    180
gttaacaatg aagcagagtt cgaacgtgcc ggctttcctc agcaagctgt ggacgcttgt    240
ggaggaaacc cacactaacg agttcatcac ctggagccag aatggccaaa gttttctggt    300
cttggatgag caacgatttg caaaagaaat tcttcccaaa tatttcaagc acaataatat    360
ggcaagcttt gtgaggcaac tgaatatgta tggtttccgt aaagtagtac atatcgactc    420
tggaattgta aagcaagaaa gagatggtcc tgtagaattt cagcatcctt acttcaaaca    480
aggacaggat gacttgttgg agaacattaa aaggaaggtt tcatcttcaa aaccagaaga    540
aaataaaatt cgtcaggaag atttaacaaa aattataagt agtgctcaga aggttcagat    600
aaaacaggaa actattgagt ccaggctttc tgaattaaaa agtgagaatg agtccctttg    660
gaaggaggtg tcagaattac gagcaaagca tgcacaacag caacaagtta ttcgaaagat    720
tgtccagttt attgttacat tggttcaaaa taaccaactt gtgagtttaa aacgtaaaag    780
gcctctactt ctaaacacta atggagccca aaagaagaac ctgtttcagc acatagtcaa    840
agaaccaact gataatcatc atcataaagt tccacacagt aggactgaag gtttaaagcc    900
aagggagagg atttcagatg acatcattat ttatgatgtt actgatgata atgcagatga    960
agaaaatatc ccagttattc cagaaactaa tgaggatgtt atatctgatc cctccaactg   1020
tagccagtac cctgatattg tcatcgttga agatgacaat gaagatgagt atgcacctgt   1080
cattcagagt ggagagcaga atgaaccagc cagagaatcc ctaagttcag gcagtgatgg   1140
cagcagccct ctcatgtcta gtgctgtcca gctaaatggc tcatccagtc tgacctcaga   1200
agatccagtg accatgatgg attccatttt gaatgataac atcaatcttt tgggaaaggt   1260
tgagctgttg gattatcttg acagtattga ctgcagttta gaggacttcc aggccatgct   1320
atcaggaaga caatttagca tagacccaga tctcctggtt gatcttttca ctagttctgt   1380
gcagatgaat cccacagatt acatcaataa tacaaaatct gagaataaag gattagaaac   1440
taccaagaac aatgtagttc agccagtttc ggaagaggga agaaaatcta aatccaaacc   1500
agataagcag cttatccagt ataccgcctt tccacttctt gcattcctcg atgggaaccc   1560
tgcttcttct gttgaacagg cgagtacaac agcatcatca gaagttttgt cctctgtaga   1620
taaacccata gaagttgatg agcttctgga tagcagccta gacccagaac caacccaaag   1680
taagcttgtt cgcctggagc cattgactga agctgaagct agtgaagcta cactgtttta   1740
tttatgtgaa cttgctcctg cacctctgga tagtgatatg ccacttttag atagctaaat   1800
ccccaggaag tggactttac atgtatatat tcatcaaaat gatgaactat ttattttaaa   1860
gtatcatttg gtactttttt tgtaaattgc tttgttttgt ttaatcagat actgtggaat   1920
aaaagcacct tttgcttttc tcactaacca cacactcttg cagagctttc aggtgttact   1980
cagctgcata gttacgcaga tgtaatgcac attattggcg tatctttaag ttggattcaa   2040
atggccattt ttctccaatt ttggtaaatt ggatatcttt tttttacaaa tacgaccatt   2100
aacctcagtt aaattttgt ttgttttcct gtttgatgct gtctatttgc attgagtgta    2160
agtcatttga actaatggta taactcctaa agctttctct gctccagtta tttttattaa   2220
atatttttca cttggcttat ttttaaaact gggaacataa agtgcctgta tcttgtaaaa   2280
cttcatttgt ttcttttggt tcagagaagt tcatttatgt tcaaagacgt ttattcatgt   2340
```

tcaacaggaa agacaaagtg tacgtgaatg ctcgctgtct gatagggttc cagctccata 2400
tatatagaaa gatcgggggt gggatgggat ggagtgagcc ccatccagtt agttggacta 2460
gttttaaata aaggttttcc ggtttgtgtt tttttgaacc atactgttta gtaaaataaa 2520
tacaatgaat gttgagtact agtgtctgtt atgtgtcttc tttagaggtg acactcacat 2580
gaaacaattt tttcttctca taggaagcag tagctttaaa ctgtctgtgg ttcattattc 2640
tcaatatgaa tcataccaag atatttgtgc ctcatctcga aaatatattg tatattg 2697

<210> SEQ ID NO 214
<211> LENGTH: 14734
<212> TYPE: DNA
<213> ORGANISM: Homo sapiens

<400> SEQUENCE: 214
gaggctttcg actgagggct agcgagggga gcacggctgg agcagggctg gagcagggct 60
ggagcagggc tggagcaggg ctgaagcagg gccgcggacc ccgcacgctc ctgcgggccc 120
cgcggagcca ttgcggccga ggcctcggca ggcgccagcg gagagctagc cgcatcttcg 180
ggggcagccc ggcagctgcc ggcggcgcgg cgagagagcg gctgacagag gggatgcgag 240
gtcctccagc agcctgacct gagtgggtta gtgatccaga gaaaccagca ggccaacttg 300
gtcaggaagg ttcgggaagc tgttggagca gtgtggggaa tttcccacca ggatgagtat 360
gattggctgt gattttagat cgtaaagctg aaaattgaaa tcatgaaagt agacaggact 420
aaactgaaga agacacctac tgaggctcct gcagactgca gagccttaat agacaaactc 480
aaagtttgta atgatgagca acttctcttg gaactgcagc agatcaaaac atggaacatt 540
ggaaagtgcg agttatatca ctgggtggac ctgttggacc gcttcgatgg aatactggca 600
gatgctggac agacagtgga gaatatgtca tggatgctcg tatgtgatag gccagaaaga 660
gagcaactga aaatgcttct cttggctgtg ttgaacttca cagccttgct cattgagtac 720
agcttttccc ggcatctgta cagttccata gagcatttga caactttatt ggcttcctct 780
gatatgcaag tggtgctggc agtcctcaat ctcctatatg tatttagcaa aagatcaaac 840
tacatcactc gtctgggatc tgacaagagg accccgctgc taactcggct acaacatttg 900
gcagagagct ggggtggaaa ggagaatggc tttggacttg cagaatgttg cagagacttg 960
catatgatga aatatccacc cagtgcaact acactacact ttgaattcta tgcagatcct 1020
ggggccgagg tcaaaattga gaaaaggaca actagtaaca cactacatta tattcacata 1080
gagcaacttg acaagatttc agaaagccct tctgaaatca tggaatctct taccaaaatg 1140
tacagcattc ctaaggataa gcagatgctg ttatttacac acatacgact ggcccatggc 1200
ttttctaatc acaggaagcg attgcaggca gttcaggcca gactgcatgc aatatctata 1260
ttagtgtatt ccaatgcctt gcaggaatca gcaaacagta tcttgtataa tggcttgata 1320
gaggagttgg tagatgtcct tcagataacg gataagcagc ttatggagat taaagcagct 1380
tctttacgaa cattaacatc aattgtccac ttggagagaa ctcccaaact cagcagtatt 1440
attgactgta ctggaactgc ctcctaccat ggatttttgc cagtgcttgt aaggaactgt 1500
atccaggcca tgattgatcc ttccatggat ccataccctc accagtttgc cactgctctc 1560
ttctcttttt tataccatct ggccagctac gatgctggtg gtgaagcctt ggtctcctgt 1620
ggaatgatgg aagccttatt gaaggtcata aagtttcttg gcgatgaaca ggaccagata 1680
acatttgtca ccagagccgt cagagtggtt gaccttatca ccaacctgga tatggcagct 1740

-continued

```
tttcaatccc atagtggact ttctatcttc atttatagac ttgagcatga agtagatttg   1800
tgccgaaaag aatgtccgtt tgtgatcaag ccaaagatcc agagacccaa tactacacaa   1860
gaaggagagg aaatggaaac tgatatggat ggagtccagt gtattccaca acgagcagca   1920
cttctgaaat ccatgttgaa tttcctcaag aaggccatcc aagaccctgc tttctcagat   1980
ggcatacgac atgtgatgga tggttctctg cctacctccc tgaaacacat catcagcaat   2040
gcagaatact atggcccatc actcttcctc ctagctactg aagtggtgac tgtgtttgta   2100
tttcaagaac catcactgct ctcctcactc caggacaatg gattgacaga tgtcatgctg   2160
catgcactgc ttatcaaaga tgttcctgct acccgtgaag tccttggctc cctcccaaat   2220
gtattcagtg cactctgttt gaatgcccga ggtcttcagt cttttgttca gtgtcagcct   2280
tttgaacgcc tcttcaaagt tcttctgtct ccagattacc tcccagccat gcggaggagg   2340
agaagttctg atccccttgg ggatactgca tccaacctgg ggagtgctgt cgatgagctc   2400
atgagacatc agcccaccct taaaacagat gcaacgactg ccatcatcaa gttacttgaa   2460
gaaatctgta atcttggaag ggaccccaaa tacatctgtc agaagccatc aatccagaag   2520
gcagatggca ctgccactgc tcctcccccca aggtctaatc atgccgcaga agaagcctct   2580
agtgaggatg aggaggaaga ggaagtacag gccatgcaga gctttaattc tacccagcaa   2640
aatgaaactg agcctaatca gcaggttgtt ggtacagagg aacgtattcc tattcccctc   2700
atggattaca tccttaatgt gatgaaattt gtggaatcta ttctgagcaa caatacaaca   2760
gatgaccact gccaggaatt tgtgaatcag aaaggactgt tgcctttggt taccattttg   2820
ggtcttccca atctgcccat tgactttccc acatctgctg cctgtcaggc tgttgcaggt   2880
gtctgcaaat ccatattgac actgtcacat gaacccaaag tccttcaaga gggtctcctt   2940
cagttggact ccatcctctc ctccctggag cccttacacc gccccattga atcccctggg   3000
ggctcagtgt tgttgcgaga actggcttgc gcaggcaatg ttgctgatgc taccctctca   3060
gcccaggcca cacctctgct gcatgcactc actgctgccc atgcctacat catgatgttt   3120
gttcatactt gcagagttgg acagagtgaa attcgttcca tctccgtaaa ccagtggggc   3180
tctcaattgg gtctgagtgt tttgagcaag ctgagccagt tatactgttc cctggtgtgg   3240
gaaagcactg tcctcctctc tctgtgtacc ccaaacagcc taccatctgg gtgtgaattt   3300
ggccaggcag atatgcagaa actggttcca aaggatgaga aggcaggtac gacccagggc   3360
ggaaaaagat cagatgggga acaggatgga gcagctggaa gtatggatgc ttctacccag   3420
ggcttattag aaggcattgg gctagatggt gacacattgg ctcccatgga gacagatgaa   3480
cctactgctt cagactctaa gggcaaatct aaaatcacac cagcaatggc tgccagaatt   3540
aagcaaatca agcctttgtt atcagcttcc tccagattag gccgagcact tgctgagcta   3600
tttggacttc ttgttaaact ttgtgtggga tctcctgtcc gccagagaag gagccatcat   3660
gctgccagca ccactacagc accgacacct gccgcgcgat caacagcctc agctctcact   3720
aagctcttga ctaaggggtt atcttggcag cccccaccat atacacctac tccccgattc   3780
aggctgacat tcttcatctg ttcagttggt ttcacatccc caatgctgtt tgatgagagg   3840
aagtatccct accacctcat gctgcaaaaa tttctctgct ccggaggcca caatgctctt   3900
tttgaaactt tcaactgggc tctgtccatg ggaggtaaag ttcctgtttc tgagggattg   3960
gaacactcag acttgcctga tggcacagga gaattcctag atgcctggct tatgctggtg   4020
gagaagatgg tgaatcccac cacggtgctt gaatctccac attcgctgcc tgccaaattg   4080
cctggaggtg tccagaactt tccccagttc agtgcactgc gcttccttgt ggtaactcag   4140
```

-continued

```
aaagcagcct ttacttgcat caaaaactta tggaaccgga aacccctgaa ggtatatggt   4200
ggacgaatgg ctgaatcgat gctggccatt ctatgccaca tcctccgagg agaacctgtg   4260
attcgagaga gactaagcaa ggagaaggag gggtctcgag gagaagagga tacagggcaa   4320
gaggaaggtg gctcccgccg ggaacctcaa gtcaaccagc aacaactgca acagctcatg   4380
gacatgggct tcacaaggga acatgcaatg gaggcactgt tgaacaccag caccatggag   4440
caggccacag agtacctttt aacccaccct cctccaatca tgggaggagt tgttcgggat   4500
ctcagcatgt ctgaagagga ccagatgatg agagcaattg ctatgtctct gggacaggat   4560
attccaatgg atcaaagggc agagtcacct gaggaagttg cttgccggaa ggaggaagag   4620
gaacggaaag ctcgggaaaa gcaggaggag gaagaggcta aatgtctaga gaagttccag   4680
gatgctgacc cgttggaaca agatgagctc cacactttca cagatactat gttgccaggc   4740
tgcttccacc ttcttgatga gctgccagac acagtatacc gtgtgtgtga cctgatcatg   4800
acagcaatca aacgtaatgg agcagattat cgtgacatga ttctgaagca agtagtcaat   4860
caggtgtggg aagctgctga tgtattgatc aaagctgctc ttcccctgac aacaagtgac   4920
acaaaaaccg tgtcagagtg gataagtcag atggccacac tgccccaggc ctccaatttg   4980
gctactagaa tcttgctttt aacgctactt tttgaggagt tgaagctacc ttgtgcttgg   5040
gtggttgaat caagtggcat ccttaatgtc ctaatcaaac tcttggaagt ggttcagccc   5100
tgcctccagg cagccaagga gcagaaggaa gtccagaccc caaagtggat cacaccagtg   5160
ttgctcctga ttgatttcta tgaaaagaca gccatctcct caaaaaggag agcccagatg   5220
actaagtacc tgcaatccaa cagcaacaac tggcgctggt ttgatgatcg ctctgggcgt   5280
tggtgtagtt acagtgcaag caacaatagc actattgatt ctgcctggaa atctggagag   5340
acaagcgtgc gattcactgc aggccgaaga agatacacgg tccaattcac tacaatggtg   5400
caggttaatg aggaaacagg gaaccgacgc cctgtgatgc tgactctcct cagggtacct   5460
cggctgaata aaaattcaaa aaacagcaat ggacaggaac tagagaagac gctggaagaa   5520
agcaaagaaa tggatatcaa acgtaaagaa aataaaggca atgataccccc tttggcccta   5580
gagagtacaa acactgaaaa ggagacaagc ctggaggaaa caaaaaatcgg ggagatcctg   5640
atccagggct tgacagaaga tatggtgact gttttaatcc gggcctgcgt gagcatgctg   5700
ggagtccctg tggacccaga tactttgcat gccacccttc gtctctgtct gaggctcacc   5760
cgggaccaca aatatgccat gatgtttgca gaactgaaga gtacccgcat gatcttgaat   5820
ttgacccaga gctcaggctt caatgggttt actcccctgg tcacccttct cttaagacac   5880
atcattgagg acccctgtac ccttcgtcat accatggaaa aggttgttcg ctcagcagct   5940
acaagtggag ctggtagcac tacctctggt gttgtgtctg gcagcctcgg ctctcgggag   6000
atcaactaca tccttcgtgt ccttgggcca gccgcatgcc gcaatccaga catattcaca   6060
gaagtggcca actgctgtat ccgcatcgcc cttcctgccc ctcgaggctc aggaactgct   6120
tcagatgatg aatttgagaa tcttagaatt aaaggcccta atgctgtaca gctggtgaag   6180
accacccctt tgaagccctc acctctgcct gtcatccctg atactatcaa ggaagtgatc   6240
tatgatatgc tgaatgctct ggctgcatac catgctccag aggaagcaga taaatctgat   6300
cctaaacctg ggggttatgac ccaagaggtt ggccagctcc tgcaagacat gggtgatgat   6360
gtataccagc agtaccggtc acttacgcgt cagagcagtg actttgatac gcagtcaggt   6420
ttttccatta atagtcaggt ctttgctgca gatggtgcct ccactgagac ttccgcatct   6480
```

-continued

```
gggacctccc aaggagaggc ttcaactcca gaggagtctc gagatgggaa gaaagataaa   6540
gaaggggacc gggcctctga ggaaggcaaa cagaaaggca agggcagcaa acctttaatg   6600
cctacctcca ctatccttcg tcttctggca gagttggtga ggtcctatgt tggtattgct   6660
accctgattg ccaactacag ctacactgtg ggccagtctg aactgatcaa agaggactgc   6720
agtgtgctag cttttgttct ggaccacctg ctcccacata cccagaatgc agaagacaag   6780
gacacccctg ccttggcccg cctgttcctc gcaagcctgg ctgctgcagg gagtggcaca   6840
gatgcccagg tggccctagt gaatgaagta aaagcagccc ttggacgggc actggctatg   6900
gctgagagta cagagaaaca tgccaggctt caggcagtga tgtgtatcat cagtactatc   6960
atggagtcct gcccctccac ctccagcttc tacagcagtg ccacagcgaa gacccagcac   7020
aatggcatga acaacatcat tcggcttttc ctgaagaagg gactggttaa tgacctggcc   7080
agagtacctc acagcttaga cctgtccagt cccaacatgg ccaacacagt caatgctgct   7140
ctgaagcctt tggaaacact ttcccggatt gtgaaccagc ccagtagcct tttggcagc    7200
aagagtgctt ctagcaagaa caagtctgag caggatgccc aaggagcctc tcaagattcc   7260
agtagcaacc agcaggaccc aggcgagcct ggggaagcag aagtgcagga ggaggatcat   7320
gatgtcactc agacagaggt ggcagatggg gatatcatgg atggggaggc tgaaaccgac   7380
tcagtggtga ttgctgggca gcctgaggtg ctcagttcac aagagatgca ggttgagaat   7440
gagctggagg acctgataga tgagttgctt gagagggatg gcggatctgg gaacagtaca   7500
attatagtga gcagaagtgg agaggatgaa tcacaagagg acgtgctgat ggatgaagct   7560
ccttccaacc tcagccaagc ttccaccttg caggccaacc gagaagattc catgaatatc   7620
ctggaccctg aggatgagga ggagcacact caggaagagg acagcagtgg cagtaacgag   7680
gatgaggatg atagtcagga tgaagaggag gaggaggagg aagatgagga agatgatcag   7740
gaggatgatg aaggtgaaga gggagatgaa gacgatgacg acgatggctc tgagatggaa   7800
ttggatgagg attatcctga tatgaacgct tctcccttgg tccgatttga gcgctttgac   7860
cgggaggatg atctcatcat tgagtttgac aacatgttct ccagtgctac agacatcccc   7920
ccatccccag gaaatatccc taccacccat ccactgatgg tgcgccatgc agaccacagt   7980
tctctgacac tgggcagtgg ctcttcaaca actcgtctca cccagggcat cgggcgcagt   8040
cagaggaccc taaggcagct gacggccaat actggccaca ccattcatgt tcactaccct   8100
gggaatcgcc agcccaaccc tcctcttata ctgcagaggt tgcttggtcc ctcagctgct   8160
gctgacatcc ttcagctgag cagcagcctt cccctacaaa gccggggtcg ggcccgcctc   8220
ctggtaggca acgatgacgt ccacatcatc gcccgttctg atgatgagct gctggatgac   8280
tttttccatg atcagagcac agctaccagc caagcaggaa ccctgtccag catccccaca   8340
gccctgaccc gctggacaga agaatgcaaa gttctcgatg ctgagagcat gcatgactgt   8400
gtttcagtgg ttaaagtgtc cattgtcaat cacctggaat tcctgaggga tgaggagctg   8460
gaagaaaggc gagagaagcg caggaaacaa ctggctgagg aagaaacaaa gataactgat   8520
aaaggcaaag aagataagga gaacagggat cagagtgcac agtgtactgc atctaagtca   8580
aatgactcca ctgaacagaa tctctcagat gggacgccta tgcctgacag ctacccaaca   8640
accccatctt caactgatgc agctacatct gagtccaagg agacccttgg cactctgcaa   8700
tcctcacaac agcaaccaac actcccaacc ccaccagctt tgggagaggt tcctcaggag   8760
ctgcagtctc cagctggaga agggggcagc tctacacagc tattgatgcc tgtagagcca   8820
gaggaattgg gtcccacaag gccaagtggg gaagcagaaa caactcagat ggagttatcc   8880
```

```
ccagctccca ctataacctc actttcccca gagagagctg aggattctga tgcactgacg   8940
gctgtcagca gtcagctaga aggctctcct atggatacaa gcagcctggc ttcctgtacc   9000
ttagaggagg ctgtgggtga cacttcagca gctggcagtt ctgagcagcc cagagcaggc   9060
agctccactc ctggggatgc cccaccagct gtggcggaag tgcaaggcag gagtgatggg   9120
tcaggggaat ctgcccagcc acctgaggac agctccccac ctgcatcctc tgagagctct   9180
tccaccagag attctgccgt ggccatttct ggagcagatt cccgaggaat cctagaagag   9240
ccgttgcctt caacaagcag tgaagaagaa gatccccttg cgggtatcag tctccctgaa   9300
ggtgtggacc cctcttttct ggctgccctg cctgatgaca tccgtcggga agttctacag   9360
aaccagctag gcattcgtcc accaacccgg actgcccccct ccacaaatag ctcagcgcct   9420
gcagtggtgg ggaatcctgg tgtgactgaa gtgagccctg agtttctggc tgccctgcct   9480
ccagccattc aggaggaagt actggcacag cagagagctg agcagcagcg acgagaacta   9540
gcacagaatg ccagctcaga caccccctatg gaccctgtga ccttcatcca gactctgccc   9600
tcagacctgc gccgtagtgt cctagaggat atggaggaca gtgtgttagc tgtgatgcca   9660
cctgacattg cagctgaggc tcaagccctg agacgagagc aagaagcccg gcagcgacag   9720
ctcatgcatg agcgtctgtt tgggcacagt agcacctccg cactctctgc tattctccga   9780
agcccggctt tcaccagtcg cttaagtggc aaccgtgggg tccagtatac tcgccttgct   9840
gtgcagagag gtggcacctt ccagatgggg ggtagcagca gccataacag gccttctggc   9900
agtaatgtag atactctcct ccgcctccga ggacggctcc ttctggacca cgaagccctt   9960
tcttgtctct tggtcctact ttttgtggat gagccaaagc tcaatactag ccgtctacac  10020
cgagtactga gaaatctctg ctaccatgcc cagacccgcc actgggtcat ccgcagtctg  10080
ctctccatct tgcagcgcag cagtgagagt gagctatgca ttgaaacacc caaactcact  10140
acaagtgagg aaaagggcaa aaagtcgagc aagagctgtg ggtcaagtag ccatgagaac  10200
cgtcccctgg acctgctaca caagatggag tcaaagagct ccaaccagct ttcctggctc  10260
tcagtatcca tggatgcagc cctaggctgc aggactaata tatttcagat ccagcgttca  10320
ggggggcgta aacataccga gaagcatgca agcggtggct ccaccgtcca catccatccc  10380
caagctgctc ctgttgtctg cagacacgtt ttggatacac tcattcaatt ggccaaggta  10440
tttcccagcc acttcacaca gcagcggacc aaagaaacaa actgtgagag tgatcgggaa  10500
aggggcaata aggcctgtag cccatgctcc tcacagtcct ccagcagtgg catttgcaca  10560
gacttctggg acttattggt aaaactggac aacatgaatg tcagccggaa aggcaagaac  10620
tccgtgaagt cagtgccagt gagcgctggc ggtgaggggg aaacctctcc atacagcctc  10680
gaggcctctc cactggggca gctcatgaac atgttgtcac acccagtcat ccgccggagc  10740
tctctcttaa ctgagaaact cctcagactc ctttctctca tctcaattgc tctcccagaa  10800
aacaaggtgt cagaagcaca ggctaattct ggcagcggtg cttcctccac caccactgcc  10860
acctcaacca catctaccac caccaccact gccgcctcca ccacgcccac accccctact  10920
gcacccaccc ctgtcacttc tgctccagcc ctggttgctg ccacggctat ttccaccatt  10980
gtcgtagctg cttcgaccac agtgactacc cccacgactg ctaccactac tgtttcaatt  11040
tctcccacta ctaagggcag caaatctcca gcgaaggtga gtgatggggg cagcagcagt  11100
acagacttta agatggtgtc ctctggcctc actgaaaacc agctacagct ctctgtagag  11160
gtgttgacat cccactcttg ttctgaggaa ggcttagagg atgcagccaa cgtactactg  11220
```

cagctctccc ggggggactc tgggacccgg gacactgttc tcaagctgct actgaatgga 11280
gcccgccatc tgggttatac cctttgtaaa caaataggta ccctgctggc cgagctgcgg 11340
gaatacaacc tcgagcagca gcggcgagcc caatgtgaaa ccctctctcc tgatggcctg 11400
cctgaggagc agccacagac caccaagctg aagggcaaaa tgcagagcag gtttgacatg 11460
gctgagaatg tggtaattgt ggcatctcag aagcgacctt tgggtggccg ggagctccag 11520
ctgccttcta tgtccatgtt gacatccaag acatctaccc agaagttctt cttgagggta 11580
ctacaggtca tcatccagct ccgggacgac acgcgccggg ctaacaagaa agccaagcag 11640
acaggcaggc taggttcctc cggtttaggc tcagctagca gcatccaggc agctgttcgg 11700
cagctggagg ctgaggctga tgccattata caaatggtac gtgagggtca aagggcgcgg 11760
agacagcaac aagcagcaac gtcggagtct agccagtcag aggcgtctgt ccggagggag 11820
gaatcaccca tggatgtgga ccagccatct cccagtgctc aagatactca atccattgcc 11880
tccgatggaa ccccacaggg ggagaaggaa aaggaagaaa gaccacctga gttacccctg 11940
ctcagcgagc agctgagttt ggacgagctg tgggacatgc ttggggagtg tctaaaggaa 12000
ctagaggaat cccatgacca gcatgcggtg ctagtgctac agcctgctgt cgaggccttc 12060
tttctggtcc atgccacaga gcgggagagc aagcctcctg tccgagacac ccgtgagagc 12120
cagctggcac acatcaagga cgagcctcct ccactctccc ctgcccccttt aaccccagcc 12180
acgccttcct cccttgaccc attcttctcc cgggagccct catctatgca catctcctca 12240
agcctgcccc ctgacacaca gaagttcctt cgctttgcag agactcaccg cactgtgtta 12300
aaccagatcc tacggcagtc cacgacccac cttgctgatg ggccttttgc tgtcctggta 12360
gactacattc gtgtcctcga ctttgatgtc aagcgcaaat atttccgcca agagctggag 12420
cgtttagatg aggggctccg gaaagaagac atggctgtgc atgtccgtcg tgaccatgtg 12480
tttgaagact cctatcgtga gctgcatcgc aaatcccccg aagaaatgaa gaatcgattg 12540
tatatagtat ttgaaggaga agaagggcag gatgctggtg ggctcctgcg ggagtggtat 12600
atgatcatct ctcgagagat gtttaaccct atgtatgcct tgttccgtac ctcacctggt 12660
gatcgagtca cctacaccat caatccatct tcccactgca accccaacca cctcagctac 12720
ttcaagtttg tcggacgcat tgtggccaaa gctgtatatg acaaccgtct tctggagtgc 12780
tactttactc gatcctttta caaacacatc ttgggcaagt cagtcagata tacagatatg 12840
gagagtgaag attaccactt ctaccaaggt ctggtttatc tgctggaaaa tgatgtctcc 12900
acactaggct atgacctcac cttcagcact gaggtccaag agtttggagt ttgtgaagtt 12960
cgtgacctca aacccaatgg ggccaacatc ttggtaacag aggagaataa gaaggagtat 13020
gtacacctgg tatgccagat gagaatgaca ggagccatcc gcaagcagtt ggcggctttc 13080
ttagaaggct tctatgagat cattccaaag cgcctcattt ccatcttcac tgagcaggag 13140
ttagagctgc ttatatcagg actgcccacc attgacatcg atgatctgaa atccaacact 13200
gaataccaca agtaccagtc caactctatt cagatccagt ggttctggag agcattgcgt 13260
tctttcgatc aagctgaccg tgccaagttc ctccagtttg tcacgggtac ttccaaggta 13320
cccctgcaag gctttgctgc cctcgaaggc atgaatggca ttcagaagtt tcagatccat 13380
cgagatgaca ggtccacaga tcgcctgcct tcagctcaca catgttttaa tcagctggat 13440
ctgcctgcct atgagagctt tgagaagctc cgccacatgc tactgttggc tatccaggag 13500
tgctctgaag gctttgggct ggcctaataa ggccctgccc aactccgtgg ggttttttt 13560
accattgttg gacctgggga ggggggagtt aaaaaaagaa ccagaaagaa attgtcaaaa 13620

```
accaataaat gaaatccacc aactcaccgt gtgtgtccca gctgccccat cttccccagc  13680
gcatacctgt tcctcttctc attctctccc cgccgcctgt ttcctcacct tctctcccct  13740
ttccatgccg tccatgatcc ccaccccatg tgttttaaaa aggcagtagc ctttgcaggg  13800
acctgtctgt cccaactgtt tgaacagtgt gctcctcaga ttctgtgttc agaaggattt  13860
gctgcattga gacttgaaac ctttggatag gggaaaaaat tatatatata tatatttttt  13920
tgttctgttt gcatttctta atttgtgctt ggaatgtgtt gatgtgcaca gctaatgatt  13980
caatgcgaga caagattggc gtctgtgttg tggaggtttc aaataaagag cactcttcat  14040
aactcacttt tcacaatgga gttttttttca aacttaaaaa aaaaaacaaa aaactcttaa  14100
gcacatgcta ggcatctgga gaaaagatgg attctccagg aaaccatccc tgccctaccc  14160
gcttgcccac ctgcctccac cactggtgca acttcctcct tcagagtcag tttctgcagt  14220
caggagagat gagcagttca ccaggaattg ggggtggggg catctgtttt tttttttag  14280
aatgggagct gcacttgggg atggtgatgg tgttagagat tgcagcccag gacaaagcat  14340
caccttgctc aaggggaaca aactgcagca ggttgtacaa aacattcaga gagctcactt  14400
gacccaaccg agggttttac ttggtgagcc tttctagtag tcttgagtct ggggctcagt  14460
tttagatttt tatttcatta atgtttgttt atttctaata aattttaata agcgagtaat  14520
ttaactaggt cgccagaaga ccattatttt tgtttgtcta tttttgttgt cgtcactccc  14580
tctctcgtca tctgtctgcc agtctgttca cagatcacct tgtagtccct tgtggttttt  14640
actccatcca gtgcttaaag ctgatctaag gacttcgatg gttccagcct tcaaagaaaa  14700
aataatttaa taaaaattta gttagaaaaa ataa                              14734
```

<210> SEQ ID NO 215
<211> LENGTH: 2162
<212> TYPE: DNA
<213> ORGANISM: Homo sapiens

<400> SEQUENCE: 215

```
gcggacgtga gcgataatgg cggatatgga ggatctcttc gggagcgacg ccgacagcga    60
agctgagcgt aaagattctg attctggatc tgactcagat tctgatcaag agaatgctgc   120
ctctggcagt aatgcctctg gaagtgaaag tgatcaggat gaaagaggtg attcaggaca   180
accaagtaat aaggaactgt ttggagatga cagtgaggac gagggagctt cacatcatag   240
tggtagtgat aatcactctg aaagatcaga caatagatca gaagcttctg agcgttctga   300
ccatgaggac aatgacccct cagatgtaga tcagcacagt ggatcagaag cccctaatga   360
tgatgaagac gaaggtcata gatcggatgg agggagccat cattcagaag cagaaggttc   420
tgaaaaagca cattcagatg atgaaaaatg gggcagagaa gataaaagtg accagtcaga   480
tgatgaaaag atacaaaatt ctgatgatga ggagagggca caaggatctg atgaagataa   540
gctgcagaat tctgacgatg atgagaaaat gcagaacaca gatgatgagg agaggcctca   600
gctttccgat gatgagagac aacagctatc tgaggaggaa aaggctaatt ctgatgatga   660
acggccggta gcttctgata atgatgatga gaaacagaat tctgatgatg aagaacaacc   720
acagctgtct gatgaagaga aaatgcaaaa ttctgatgat gaaaggccac aggcctcaga   780
tgaagaacac aggcattcag atgatgaaga ggaacaggat cataaatcag aatctgcaag   840
aggcagtgat agtgaagatg aagttttacg aatgaaacgc aagaatgcga ttgcatctga   900
ttcagaagcg gatagtgaca ctgaggtgcc aaaagataat agtggaacca tggatttatt   960
```

tggaggtgca gatgatatct cttcagggag tgatggagaa gacaaaccac ctactccagg 1020
acagcctgtt gatgaaaatg gattgcctca ggatcaacag gaagaggagc caattcctga 1080
gaccagaata gaagtagaaa tacccaaagt aaacactgat ttaggaaacg acttatattt 1140
tgttaaactg cccaactttc tcagtgtaga gcccagacct tttgatcctc agtattatga 1200
agatgaattt gaagatgaag aaatgctgga tgaagaaggt agaaccaggt taaaattaaa 1260
ggtagaaaat actataagat ggaggatacg ccgagatgaa gaaggaaatg aaattaaaga 1320
aagcaatgct cggatagtca agtggtcaga tggaagcatg tccctgcatt taggcaatga 1380
agtgtttgat gtgtacaaag ccccactgca gggcgaccac aatcatcttt ttataagaca 1440
aggtactggt ctacagggac aagcagtctt taaaacgaaa ctcaccttca gacctcactc 1500
tacggacagt gccacacata gaaagatgac tctgtcactt gcagataggt gttcaaagac 1560
acagaagatt agaatcttgc caatggctgg tcgtgatcct gaatgccaac gcacagaaat 1620
gattaagaaa gaagaagaac gtttgagggc ttccatacgt agggaatctc agcagcgccg 1680
aatgagagag aaacagcacc agcgggggct gagcgccagt tacctggaac ctgatcgata 1740
cgatgaggag gaggaaggcg aggagtccat cagcttggct gccattaaaa accgatataa 1800
agggggcatt cgagaggaac gagccagaat ctattcatca gacagtgatg agggatcaga 1860
agaagataaa gctcaaagat tactcaaagc aaagaaactt accagtgatg aggaaggtga 1920
accttccgga aagagaaaag cagaagatga tgataaagca aataaaaagc ataagaagta 1980
tgtgatcagc gatgaagagg aagaagatga tgattgaagt atgaaatatg aaaacatttt 2040
atatatttta ttgtacagtt ataaatatgt aaacatgagt tattttgatt gaaatgaatc 2100
gatttgcttt tgtgtaattt taattgtaat aaaacaattt aaaagcaaaa aaaaaaaaaa 2160
aa 2162

<210> SEQ ID NO 216
<211> LENGTH: 1852
<212> TYPE: DNA
<213> ORGANISM: Homo sapiens

<400> SEQUENCE: 216
gtcgttggct ggagcagcgg ctgcgcgggt cgcggtgctg tgaggtctgc gggcgctggc 60
aaatccggcc caggatgtag agctggcagt gcctgacggc gcgtctgacg cggagttggg 120
tggggtagag agtagggggc ggtagtcggg ggtggtggga gaaggaggag gcggcgaatc 180
acttataaat ggcgccgaag caggacccga agcctaaatt ccaggagggt gagcgagtgc 240
tgtgctttca tgggcctctt ctttatgaag caaagtgtgt aaaggttgcc ataaaggaca 300
aacaagtgaa atacttcata cattacagtg gttggaataa aaattgggat gaatgggttc 360
cggagagcag agtactcaaa tacgtggaca ccaatttgca gaaacagcga gaacttcaaa 420
aagccaatca ggagcagtat gcagagggga agatgagagg ggctgcccca ggaaagaaga 480
catctggtct gcaacagaaa aatgttgaag tgaaaacgaa aaagaacaaa cagaaaacac 540
ctggaaatgg agatggtggc agtaccagtg agacccctca gcctcctcgg aagaaaaggg 600
cccgggtaga tcctactgtt gaaaatgagg aaacattcat gaacagagtt gaagttaaag 660
taaagattcc tgaagagcta aaaccgtggc ttgttgatga ctgggactta attaccaggc 720
aaaaacagct cttttatctt cctgccaaga agaatgtgga ttccattctt gaggattatg 780
caaattacaa gaaatctcgt ggaaacacag ataataagga gtatgcggtt aatgaagttg 840
tggcagggat aaaagaatac ttcaacgtaa tgttgggtac ccagctactc tataaatttg 900

-continued agagaccaca gtatgctgaa attcttgcag atcatcccga tgcacccatg tcccaggtgt 960
atggagcgcc acatctcctg agattatttg tacgaattgg agcaatgttg gcttatacac 1020
ctctggatga gaagagcctt gctttattac tcaattatct tcacgatttc ctaaagtacc 1080
tggcaaagaa ttctgcaact ttgttcagtg ccagcgatta tgaagtggct cctcctgagt 1140
accatcggaa agctgtgtga gaggcactct cactcactta tgtttggatc tccgtaaaca 1200
catttttgtt cttagtctat ctcttgtaca aacgatgtgc tttgaagatg ttagtgtata 1260
acaattgatg tttgttttct gtttgatttt aaacagagaa aaaataaaag gggtaatag 1320
ctcctttttt cttctttctt ttttttttc atttcaaaat tgctgccagt gttttcaatg 1380
atggacaaca gagggatatg ctgtagagtg ttttattgcc tagttgacaa agctgctttt 1440
gaatgctggt ggttctattc ctttgacact acgcactttt ataatacatg ttaatgctat 1500
atgacaaaat gctctgattc ctagtgccaa aggttcaatt cagtgtatat aactgaacac 1560
actcatccat ttgtgctttt gttttttttt atggtgctta aagtaaagag cccatccttt 1620
gcaagtcatc catgttgtta cttaggcatt ttatcttggc tcaaattgtt gaagaatggt 1680
ggcttgtttc atggtttttg tatttgtgtc taatgcacgt tttaacatga tagacgcaat 1740
gcattgtgta gctagtttc tggaaaagtc aatcttttag gaattgtttt tcagatcttc 1800
aataaatttt ttctttaaat ttcaaaaaaa aaaaaaaaaa aaaaaaaaaa aa 1852

<210> SEQ ID NO 217
<211> LENGTH: 2047
<212> TYPE: DNA
<213> ORGANISM: Homo sapiens

<400> SEQUENCE: 217
ttgattatgg aacattctaa aacttagaca agacgattgt gattggctga agggcatacg 60
ccctcctcca gggtgacgtg tctgcctatg gatatcagtt gccagagaaa cctggcttta 120
ctatggcggt tggaggaacg gcagtgatca cacgtcggct gctgggaaga tctggattct 180
cgtttcaggt caccatcaga aaagctaagt ttgctgtata gtgaggatca ggagatctga 240
tcctgattgc agaaccttcc ctgattacag aatcttggga ttgttgagag gattacatgt 300
aaagtaccag gacagtgcat ggcacatatg atttcacaaa agttcatctt cattgcagat 360
acctgccttt ctttctaggt tgtatctccc acttcaccct tctagaccat cccagaagat 420
ctataagatt tcatctggga aatcactagg agttcttgga agggaaagaa ggaagattgt 480
tggttggaat aaaaacaggg ttgaatgagt tccagaaagc agggttctca acctcgtgga 540
cagcaatctg cagaagaaga gaacttcaaa aaaccaacta gaagcaacat gcagagaagt 600
aaaatgagag gggcctcctc aggaaagaag acagctggtc cacagcagaa aaatcttgaa 660
ccagctctcc caggaagatg gggtggtcgc tctgcagaga accccccttc aggatccgtg 720
aggaagacca gaaagaacaa gcagaagact cctggaaacg gagatggtgg cagtaccagc 780
gaagcacctc agccccctcg gaagaaaagg gcccgggcag accccactgt tgaaagtgag 840
gaggcgttta agaatagaat ggaggttaaa gtgaagattc ctgaagaatt aaaaccatgg 900
cttgttgagg actgggactt agttaccagg cagaagcagc tgtttcaact ccctgccaag 960
aaaaatgtag atgcaattct ggaggagtat gcaaattgca agaaatcgca gggaaatgtt 1020
gataataagg aatatgcggt taatgaagtt gtggcaggaa taaaagaata tttcaatgtg 1080
atgttgggca ctcagctgct ctacaaattt gagaggcccc agtatgctga aatcctcttg 1140

-continued

```
gctcaccctg atgctccaat gtcccaggtt tatggagcac cacacctact gagattattt   1200

gtaagaattg gagcaatgtt ggcctatacg ccccttgatg agaaaagcct tgcattattg   1260

ttgggctatt tgcatgattt cctaaaatat ctggcaaaga attctgcatc tctctttact   1320

gccagtgatt acaaagtggc ttctgctgag taccaccgca aagccctgtg agcgtctaca   1380

gacagctcac catttttgtc ctgtatctgt aaacactttt tgttcttagt ctttttcttg   1440

taaaattgat gttctttaaa atcgttaatg tataacaggg cttatgtttc agtttgtttt   1500

ccgttctgtt ttaaacagaa aataaaagga gtgtaagctc cttttctcat ttcaaagttg   1560

ctaccagtgt atgcagtaat tagaacaaag aagaaacatt cagtagaaca ttttattgcc   1620

tagttgacaa cattgcttga atgctggtgg ttcctatccc tttgacacta cacaattttc   1680

taatatgtgt taatgctatg tgacaaaacg ccctgattcc tagtgccaaa ggttcaactt   1740

aatgtatata cctgaaaacc catgcatttg tgctcttttt tttttttat ggtgcttgaa   1800

gtaaaacagc ccatcctctg caagtccatc tatgttgttc ttaggcattc tatctttgct   1860

caaattgttg aaggatggtg atttgtttca tggtttttgt atttgagtct aatgcacgtt   1920

ctaacatgat agaggcaatg cattattgtg tagccacggt tttctggaaa agttgatatt   1980

ttaggaattg tatttcagat cttaaataaa atttgtttct aaatttcaaa gcaaaaaaaa   2040

aaaaaaa                                                             2047
```

<210> SEQ ID NO 218
<211> LENGTH: 1496
<212> TYPE: DNA
<213> ORGANISM: Homo sapiens

<400> SEQUENCE: 218

```
agagtagatg ccagtcctgg gaaaggcagg ggaggagagg agagccacgg ctgacgcttg     60

gggacagaag gaggagcctg aggaggagac aggacagagc gtctggagag gcaggaggac    120

accgagttcc ccgtgttggc ctccaggtcc tgtgcttgcg gagccgtccg gcggctggga    180

tcgagccccg acaatgggca acgcgcagga gcggccgtca gagactatcg accgcgagcg    240

gaaacgcctg gtcgagacgc tgcaggcgga ctcgggactg ctgttggacg cgctgctggc    300

gcggggcgtg ctcaccgggc cagagtacga ggcattggat gcactgcctg atgccgagcg    360

cagggtgcgc cgcctactgc tgctggtgca gggcaagggc gaggccgcct gccaggagct    420

gctacgctgt gcccagcgta ccgcgggcgc gccggacccc gcttgggact ggcagcacgc    480

taccgggacc gcagctatga ccctccatgc ccaggccact ggacgccgga ggcacccggc    540

tcggggacca catgccccgg gttgcccaga gcttcagacc ctgacgaggc cgggggccct    600

gagggctccg aggcggtgca atccgggacc ccggaggagc cagagccaga gctggaagct    660

gaggcctcta aagaggctga accggagccg gagccagagc cagagctgga acccgaggct    720

gaagcagaac cagagccgga actggagcca gaaccggacc cagagcccga gcccgacttc    780

gaggaaaggg acgagtccga agattcctga aggccagagc tctgacaggc ggtgccccgc    840

ccatgctgga taggacctgg gatgctgctg gagctgaatc ggatgccacc aaggctcggt    900

ccagcccagt accgctggaa gtgaataaac tccggagggt cggacgggac ctgggctctc    960

tccacgattc tggctgtttg cccaggaact tagggtgggt acctctgagt cccagggacc   1020

tgggcaggcc caagcccacc acgagcatca tccagtcctc agccctaatc tgcccttagg   1080

agtccaggct gcaccctgga gatcccaaac ctagcccccct agtgggacaa ggacctgacc   1140

ctcctgcccg catacacaac ccatttcccc tggtgagcca cttggcagca tatgtaggta   1200
```

ccagctcaac cccacgcaag ttcctgagct gaacatggag caaggggagg gtgacttctc 1260
tccacatagg gagggcttag agctcacagc cttgggaagt gagactagaa gaggggagca 1320
gaaagggacc ttgagtagac aaaggccaca cacatcattg tcattactgt tttaattgtc 1380
tggcttctct ctggactggg agctcagtga ggattctgac cagtgactta cacaaaaggc 1440
gctctataca tattataata tattcgctta ctaaatgaat aaggactttc caactg 1496

<210> SEQ ID NO 219
<211> LENGTH: 2410
<212> TYPE: DNA
<213> ORGANISM: Homo sapiens

<400> SEQUENCE: 219
ggtgcagcct tacgccgctg acgcatcgcg cccaagatgg cggcgcggtc gtcgtcgggg 60
gtggcggcgg cagagggggc ggcggccctg gcggcagcgg agacggcagc cgtgacggtg 120
gcagcggcgg cgcgggacct gggcctgggg gaatgaggcg gccgcggcgg gccagcggcg 180
gagccgtgta gcggagaagc tccccctccc tgcttccctt ggccgagccg ggggcgcgcg 240
cgcacgcggc cgtccagagc gggctcccca cccctcgact cctgcgaccc gcaccgcacc 300
cccacccggg cccggaggat gatgaagctc aagtcgaacc agacccgcac ctacgacggc 360
gacggctaca agaagcgggc cgcatgcctg tgtttccgca gcgagagcga ggaggaggtg 420
ctactcgtga gcagtagtcg ccatccagac agatggattg tccctggagg aggcatggag 480
cccgaggagg agccaagtgt ggcagcagtt cgtgaagtct gtgaggaggc tggagtaaaa 540
gggacattgg gaagattagt tggaattttt gagaaccagg agaggaagca caggacgtat 600
gtctatgtgc tcattgtcac tgaagtgctg gaagactggg aagattcagt taacattgga 660
aggaagaggg aatggtttaa aatagaagac gccataaaag tgctgcagta tcacaaaccc 720
gtgcaggcat catattttga aacattgagg caaggctact cagccaacaa tggcacccca 780
gtcgtggcca ccacatactc ggtttctgct cagagctcga tgtcaggcat cagatgactg 840
aagacttcct gtaagagaaa tggaaattgg aaactagact gaagtgcaaa tcttccctct 900
caccctggct ctttccactt ctcacaggcc tcctctttca aataaggcat ggtgggcagc 960
aaagaaaggg tgtattgata atgttgctgt ttggtgttaa gtgatggggc tttttcttct 1020
gtttttattg agggtggggg ttgggtgtgt aatttgtaag tacttttgtg catgatctgt 1080
ccctccctct tcccacccct gcagtcctct gaagagaggc caacagcctt cccctgcctt 1140
ggattctgaa gtgttcctgt ttgtcttatc ctggccctgg ccagacgttt tctttgattt 1200
ttaatttttt ttttttatta aaagatacca gtatgagatg aaaacttcca ataatttgtc 1260
ctataatgtg ctgtacagtt cagtagagtg gtcactttca ctgcagtata catttatcta 1320
cacattatat atcggacata taatatgtaa ataaatgact tctagaaaga gaaatttgtt 1380
taatttttca aggttttttt ctcttttaat ttgggcattt ctagaattga gagcctcaca 1440
attaacatac ctttttgttt tcgatgctag tggctgggca ggttgccctg tcctttctct 1500
atttcccagt cattgactgt agatatggga agagtttagc taccttcata gtgctcccag 1560
gactcatggc ctttccttct ttaagctgta tttccctgcc cagaaagaaa caggaagaaa 1620
ccttttttta ttttttattt tttttttaac caagcaagga gcaaatggcc tcagcccaga 1680
tctgtaaaaa caatgataga aattgaattc tgccccacat gttgacagta gagttggaac 1740
tggattcttg ggattactta tctaaaaaac tggagcatca ggtccatttc tgttctgctg 1800

-continued gtttggaatc ttttccgtaa tgctatttat tgccaacaat ggcctctctt tgtgtccata 1860
tatgccttac accgtgctga cctgggtatc atccatgtgc tctgaagcat ccaactttac 1920
tttgcaggtg catcaatgta gtcctgtccc tgaactgagt aaccgtgttc ctgaaaagta 1980
cactagggaa attcacctgc ttgcttgtct ttgtattggc atggcacttg tgattgcacc 2040
atggagcatg ctcagagcta ttaaattggt ctcccatctc ccaccaggat atgaaaggtc 2100
catatgggag gccacgtaat cacttattac agtggttaca taatacactg gctcactgca 2160
gactctcttg tttttgata cagtttcgtg ctggcttcat ttgccaattg tgttgtttag 2220
ttcggaagta agagggtctt gagattgagg ggtagggagg gctacactga ctgatccgtg 2280
gcttaagaca ggagattatc tctgtactcc agtggcatct ccttagccaa gatgtgaaat 2340
taaaatcata gttcgcctca tttaaaaatt ctaataaagc actcaaactt tgaaaaaaaa 2400
aaaaaaaaaa 2410

<210> SEQ ID NO 220
<211> LENGTH: 1936
<212> TYPE: DNA
<213> ORGANISM: Homo sapiens

<400> SEQUENCE: 220
ggggcggggc ggcggcggcg gcggcggcgg tggcggccgg ggagggtcag ttggaggcag 60
gcgctcgctg aggcaaaagg aggcgctcgg cccgcggcct gacagggact tagcccgcag 120
agatcgaccc cgcgcgcgtg accccacacc cacccactca tccatctatc cactccctgc 180
gccgcctcct cccaccctga gcagagccgc cgaggatgat aaacacccag gacagtagta 240
ttttgccttt gagtaactgt ccccagctcc agtgctgcag gcacattgtt ccagggcctc 300
tgtggtgctc ctgatgcccc tcacccactg tcgaagatcc ccggtgggcg agggggcggc 360
agggatcctt ctctctcagc tctaatatat aaggacgaga agctcactgt gacccaggac 420
ctccctgtga atgatggaaa acctcacatc gtccacttcc agtatgaggt caccgaggtg 480
aaggtctctt cttgggatgc agtcctgtcc agccagagcc tgtttgtaga aatcccagat 540
ggattattag ctgatgggag caaagaagga ttgttagcac tgctagagtt tgctgaagag 600
aagatgaaag tgaactatgt cttcatctgc ttcaggaagg gccgagaaga cagagctcca 660
ctcctgaaga ccttcagctt cttgggcttt gagattgtac gtccaggcca tccctgtgtc 720
ccctctcggc cagatgtgat gttcatggtt tatcccctgg accagaactt gtccgatgag 780
gactaatagt catagaggat gctttaccca agagccacag tgggggaaga ggggaagtta 840
ggcagccctg ggacagacga gagggctcct cgctgtctag ggaaggacac tgaggggctc 900
agggtgaggg ttgcctattg tgttctcgga gttgactcgt tgaaattgtt ttccataaag 960
aacagtataa acatattatt cacatgtaat caccaatagt aaatgaagat gtttatgaac 1020
tggcattaga agctttctaa actgcgctgt gtgatgtgtt ctatctagcc taggggagga 1080
cattgcctag agggggaggg actgtctggg ttcaggggca tggcctggag ggctggtggg 1140
cagcactgtc aggctcaggt ttccctgctg ttggctttct gttttggtta ttaagacttg 1200
tgtattttct ttctttgctt cctgtcaccc caggggctcc tgagtatagg cttttcagtc 1260
cctgggcagt gtccttgagt tgttttttga cactcttacc tgggcttctc tgtgtgcatt 1320
tgcgtctggc ctggagtaag caggtccgac ccctccttct ttacagctta gtgttattct 1380
ggcatttggt taagctggct taatctgttt aatgttatca gtacatttta aataggggca 1440
ttgaaattta ctcccaccac cagggctttt ttgggggatg cctgggcctt taaaacacta 1500

```
gccaaactct aattaattct caaatcactg ccaggagttc ttgctcctgg ctgcaggccc   1560

aggccccaag gtctccttct tggggtcaca aacagcagta aggaagagga atatatagca   1620

actcagggcc tgggaattgt ggggcaatcc gttcttaggg actggatact tctggctggc   1680

tgagtatagt actagctgcc tccccaccag gttccgagta gtgtctgaga ctctgctctg   1740

cagggcctag ggtagcgctg ggagtgtaga agtggcctgc ccttaactgt tttcactaaa   1800

cagcttttc taaggggaga gcaaggggga gagatctaga ttgggtgagg gggacgggga   1860

tgtcagggag gcaagtgtgt tgtgttactg tgtcaataaa ctgatttaaa gttgtgaaaa   1920

aaaaaaaaaa aaaaaa                                                    1936


<210> SEQ ID NO 221
<211> LENGTH: 1712
<212> TYPE: DNA
<213> ORGANISM: Homo sapiens

<400> SEQUENCE: 221

atgctggggg aggggctggc ggcctcgacg gcagctgcgg aactaggccg agggacaaag     60

gctaagtttt tccatggttt ggactggata tcggtggaac tctggtcaag ctggtatatt    120

ttgaacccaa agacatcact gctgaagaag aagaggaaga agtggaaagt cttaaaagca    180

ttcggaagta cctgacctcc aatgtggctt atgggtctac aggcattcgg gacgtgcacc    240

tcgagctgaa ggacctgact ctgtgtggac gcaaaggcaa tctgcacttt atacgctttc    300

ccactcatga catgcctgct tttattcaaa tgggcagaga taaaaacttc tcgagtctcc    360

acactgtctt ttgtgccact ggaggtggag cgtacaaatt tgagcaggat tttctcacaa    420

taggtgatct tcagctttgc aaactggatg aactagattg cttgatcaaa ggaattttat    480

acattgactc agtcggattc aatggacggt cacagtgcta ttactttgaa aaccctgctg    540

attctgaaaa gtgtcagaag ttaccatttg atttgaaaaa tccgtatcct ctgcttctgg    600

tgaacattgg ctcaggggtt agcatcttag cagtatattc caaagataat tacaaacggg    660

tcacaggtac tagtcttgga ggaggaactt tttttggtct ctgctgtctt cttactggct    720

gtaccacttt tgaagaagct cttgaaatgg catctcgtgg agatagcacc aaagtggata    780

aactagtacg agatatttat ggaggggact atgagaggtt tggactgcca ggctgggctg    840

tggcttcaag ctttggaaac atgatgagca aggagaagcg agaggctgtc agtaaagagg    900

acctggccag agcgactttg atcaccatca ccaacaacat tggctcaata gcaagaatgt    960

gtgcccttaa tgaaaacatt aaccaggtgg tatttgttgg aaatttcttg agaattaata   1020

cgatcgccat gcggcttttg gcatatgctt tggattattg gtccaagggg cagttgaaag   1080

cactttttc ggaacacgag ggttattttg gagctgttgg agcactcctt gagctgttga   1140

agatcccgtg atcattacct ggggaggggt tcctgaaacc ttccacaatg ggatctgtgg   1200

actttcattt ttttaagaga cttactcaat ttcatgactg tactacctga aacaaagtga   1260

gaaaggacag gtgtattttt ctaagtcatc aagataaatc cttaagaatt cagtctaaat   1320

tagcaaccag gaaggaaaaa tatattaaaa acaacaaaaa agtggcacat gtccaggcag   1380

tgtgaggatt tgctgtatat aagttgcctg ctttgtattt ttgaaatctc tgcatcactc   1440

attggaagtg cttctgaaga gagctgctct gtgttcagtt gactggtttt gtgtcctgtt   1500

tgaacttgct gaatgtaagg caggctacta tgcgttataa tctaatcaca atttgtcaat   1560

atggtcttgg caatcatctg tgcattactc tggtttgcat taagcctgtg tgtgaactta   1620
```

```
ctgtaaaaca tgttttattt caaggttctg caaaattaat tgggcaggtt aattgtgtac   1680

ctgaaactta acaagcagtt tttggaaggg ca                                 1712


<210> SEQ ID NO 222
<211> LENGTH: 7332
<212> TYPE: DNA
<213> ORGANISM: Homo sapiens

<400> SEQUENCE: 222

ggtgaatggg ctggtggtgc tcgctgctgc tgctgagagg aggaggagga tgaagagttg     60

ggcttgtttg tctcctacag tttctctcct gctgctctga ttccccctc ccgattccgg    120

cccggggcct gtgtgtgtcc ctcctggagg aggaggagga tccagttcct ccccccaacc    180

ccctcctccc cacccccccct tgcctgggga agaggaggaa agaaacagcc cagagagaga    240

gagagagaga gagtgagtga gagagagagg agaggagagg aggaggagga ggagggagaa    300

gggaacaacc taccatctta acacactaat atctaaaaag tgcgagaggc ccagagcagc    360

agcagaagca gcagcagcag ctccagcttc ttccctccct ccccatgaag aagagttccc    420

tcctcctcct cctcctgctt ctcctgctca gagttcctgc ctccagctgc caggggggac    480

agccagccag cagcaggagg ggggctagag agctgaagga gagccagttt ccccaaaatt    540

gctgcagtga gaagaggagt ttgttacttt aaacagaggc tgaagaaact atagaattag    600

cagagaaagt ggagaaggta gaggatggag ttgcagactc tacaggaggc tcttaaagtg    660

gaaattcagg ttcaccagaa actggttgct caaatgaagc aggatccaca gaatgctgac    720

ttaaagaaac agcttcatga actccaagcc aaaatcacag ctttgagtga gaaacagaaa    780

agagtagttg aacagctacg gaagaacctg atagtaaagc aagaacaacc ggacaagttc    840

caaatacagc cattgccaca atctgaaaac aaactacaaa cagcacagca gcaaccacta    900

cagcaactac aacaacagca gcagtaccac caccaccacg cccagcagtc agctgcagcc    960

tctcccaacc tgactgcttc acagaagact gtaactacag cttctatgat taccacaaag   1020

acactacctc tcgtcttgaa agcagcaact gcgaccatgc ctgcctctgt ggtgggccag   1080

agacctacca ttgctatggt gaccgccatc aacagtcaga aggctgtgct cagcactgat   1140

gtgcagaaca caccagtcaa cctccagacg tctagtaagg tcactgggcc tggggcagag   1200

gctgtccaaa ttgtggcaaa aaacacagtc actctggttc aggcaacacc tcctcagccc   1260

atcaaagtac cacagtttat ccccccctcct agactcactc cacgtccaaa ctttcttcca   1320

caggttcgac ccaagcctgt ggcccagaat aacattccta ttgccccagc accacctccc   1380

atgctcgcag ctcctcagct tatccagagg cccgtcatgc tgaccaagtt cacccccaca   1440

acccttccca catcccagaa ttccatccac cccgtccgtg tcgtcaatgg gcagactgca   1500

accatagcca aaacgttccc catggcccag ctcaccagca ttgtgatagc tactccaggg   1560

accagactcg ctggacctca aactgtacag cttagcaagc caagtcttga aaaacagaca   1620

gttaaatctc acacagaaac agatgagaaa caaacagaga gccgcaccat caccccacct   1680

gctgcaccca aaccaaaacg ggaggagaac cctcagaaac ttgccttcat ggtgtctcta   1740

gggttggtaa cacatgacca tctagaagaa atccaaagca agaggcaaga gcgaaaaaga   1800

agaacaacag caaatccggt ctacagtgga gcagtctttg agccagagcg taagaagagt   1860

gcagtgacat acctaaacag cacaatgcac cctgggaccc ggaagagagg tcgtcctcca   1920

aaatacaatg cagtgctggg gtttggagcc cttaccccaa catcccccca atccagtcat   1980

cctgactccc ctgaaaatga aaagacagag accacattca ctttccctgc acctgttcag   2040
```

-continued

```
cctgtgtccc tgcccagccc cacctccaca gacggtgata ttcatgagga tttttgcagc   2100
gtttgcagaa aaagtggcca gttactgatg tgcgacacat gttcccgtgt atatcatttg   2160
gactgcttag acccccctct gaaaacaatt cccaagggca tgtggatctg tcccagatgt   2220
caggaccaga tgctgaagaa ggaagaagca attccatggc ctggaacttt agcaattgtt   2280
cattcctata ttgcctacaa agcagcaaaa gaagaagaga aacagaagtt acttaaatgg   2340
agttcagatt taaaacaaga acgagaacaa ctagagcaaa aggtgaaaca gctcagcaat   2400
tccataagta aatgcatgga aatgaagaac accatcctgg cccggcagaa ggagatgcac   2460
agctccctgg agaaggtaaa acagctgatt cgcctcatcc acggcatcga cctctccaaa   2520
cctgtagact ctgaggccac tgtgggggcc atctccaatg gcccggactg caccccccct   2580
gccaatgccg ccacctccac gccggcccct tccccctcct cccagagctg cacagcgaac   2640
tgtaaccagg gggaagagac taaataacag agcccctcta ggagaagcca cgggatcccg   2700
gcggcaagga gaacagaaca ctgaagactc tagaaaagca aagccggatt tctggaaagt   2760
gcagaattct tttggttctt tggttccaga gagagagaag atgcttgtgc caggtggcac   2820
cagagtttgc caattgatcc ttcttattct gtgtgtacat gcaaagattg gaccatgtta   2880
catgaaatag tgccagctgg aggttctttg ccagcaccat gccaagtgaa ataatatatt   2940
tactctctct attatacacc agtgtgtgcc tgcagcagcc tccacagcca cgatgggttt   3000
gtttctgttt tcttgggtgg ggagcaggga cgggcggagg gaggagagca ggtttcagat   3060
ccttacttgc cgagccgttt gtttaggtag agaagacaag tccaaagagt gtgtgggctt   3120
tcctgtttct aaactttcgc tactataaaa ccaaaaaaag gaattgagat ttcaccaacc   3180
ccagtgccca gaagagggaa ggggagtggc tggagggagc agggggtggg acagtgtatc   3240
aaataagcag tatttaatca cctctggcgg gggcctcgtg caaggggaga ctgacaccaa   3300
gaacagccag taggttcttc tcccctgcac tctgctccct gcgcggtaac cccaccactc   3360
ctgaagcctg cccagtctcc ttccttccct gcttggtgag tcgcgcatct ccgtggttat   3420
cccgctgtct cctctccaag aacaagcaga gcccgggcca ctggcccttg cccaaggcag   3480
ggaagaagga tgtgtgtgtc caggaaggaa aaaaaggtgg atcagtgatt ttacttgaaa   3540
acaagctcca tccctttct atatttataa gaagagaaga tcttgagtga agcagcacgc   3600
gacccaggtg tgtgtgaatt gaatggagac gtttcttttc tctttcttta atttttgttt   3660
ttgttctttt tttctttaag gaaagtttta ttttactgtt cattttactt tcttggtaac   3720
aaaaactaaa ataaggaata gaaaagctgt ttttcaggct gacagtccaa ttaagggtag   3780
ccaagacctt gcatggtaga gtaggaatca tagtgtcagt gaggtcccgt gagtctttgt   3840
gagtccttgt gtcatcgttc gggcactgtt tttttatgca agggcaaaaa tctttgtatc   3900
tggggaaaaa aaactttttt ttaaattaaa aaggaaaata aaagatattg aggtcttcct   3960
agtgttactt aaattaagat caaggtaaga aacattgtaa aaaaaaatta caaaagtgct   4020
atttgtttcc taaaaacagt gatttctatt aaaaaggtgt cagaactgga gaaaatgccg   4080
tgtagttata attttttagc acagaccctg ctgatcacga tgacattttg ccgtgtgtgt   4140
gtctctagac tggtgggcca gtctccttga aggacagagg cggagctccc caccccttctc  4200
tctcctcaga aaagaccgtg ctctcttctt ggtgcaggga tcttgtctcc tgttgtgaag   4260
cccaaatgga agcgtggatg gtatcagggc cctacccgtg gtcttctcag attctgctag   4320
agcaaaaggc tggtgcctaa ataagatccc ttcctttggt gctgcttttg gtctttcagc   4380
```

-continued

```
caccagcatt atgagtgcct gggggacacc tccgagggaa ctggccagcg gagctctgtg   4440
gtgcgcacgc accctggccg tgacaggagg gtgcgggagt acaggctggc tgcatcagcc   4500
cttggtgctt agaacagagg aggagtgaca tgttttgagg gtacgtctct gagacagagc   4560
cccagcgtgg ccttcgctct gtcttgcctt tggggagagg tctgaagctc ccactccttt   4620
ctctgcctgt tggctccagg caccagaaat ttactccact ccacccaccc acaagcctcc   4680
tgggtgaccc tgggctagaa ttgctgcgct tgcctcggct tggccggttg tggcctctcc   4740
ttgagaaaac cagggttgtg aaagactcag accattctct catcttgcct tgtcagaagt   4800
aaattgtgtc agatttgtgc tctcgctgga gacctttgcc ccttgcgtgc ccctggccga   4860
tgggagggcg gtggaggctc tgtaccctgg ccctgctgga gcatctcccc caagcccact   4920
ccaggccctg ggaatggcca gagtctagga gaggtagaaa cgatcctatc agcttctctc   4980
ccacccaatt aggcccagag agacaaagac agatctgaaa gcaaatgcaa cagagaagag   5040
acacttctta gagtaaaatg tgtctcatct ctatcagcca tcgcctttca tcttcccagg   5100
ggcctcagaa gaaggaatta agttaggctg aacaggcctc agagttaggc cctggctgct   5160
tgattggctg agggggaaag agttcccttt tctcattcag aaaccaaggt gctgtgtcta   5220
gtcagggagc cttggagatg cctggactag ttggaggaat cgttggcaga ggatcagaga   5280
ccagcagcag gctgtctgcc ctgtctagag ctcttcccct caacttgtct gggcccatct   5340
gggggttgcc acacaacacc taacttacct tttcctgaaa gaagttggga aaccatcatc   5400
actagaggcc tttgctcaga gaggagctgc cttaggagtc ttgggtcgga ggacggggct   5460
aggaattgac cagggctttg cctgccgccc tcagcagtgt cgggtacatt ctgacctcgc   5520
ctgcagctgg gctgtggatt cttcctgaca ttcagatgtg agctgttttg ggagtcagct   5580
agtatggagt acgagatgca acccagcccc caaacctaca ttctgcactc aaattccaaa   5640
acactgcttt actgtaaaga agaggcccct ggcacccaat ctccctgtcc ttcactgtcc   5700
cctcagacct gggcggggag ggggggggc ctgtgaccac ctgagacata cgctcgtgac    5760
actgccccac cccagccacc tccacttgct tcctcctcct tccctccgct gctctttccc   5820
cacggcccag aatttagctg ctctgacagc cacttttgag accagctggc tttgtagtca   5880
cttcagagag ctggagcggc tgcccactgg gccctgactg ggagtcccct gccagctcct   5940
gatcaggcgc tgcgccctgg tggcagtgat gactgggagt cccctgccag ctcctgtcca   6000
ggcgctgcat cctggtaaca gtgaggccat gttgctgtca tctccacctc tgcattcttg   6060
ctgcctgtgg gtcctttttc tttcatggag cctgctgggt cttgtctcac ctgtgctgag   6120
ctcctctggg gttttgattt cttccttcct tatcaggccc tttggggtaa gcctgctggt   6180
tgtacctgac atagggaggc agttaggggc agtccctggt ggggccgccc tggcagcctc   6240
cagctggcac catcgtgtgc ctggtttccc tgcaacacct gcctctctgt ccctgctgct   6300
gcttggctca ggcccaacag gcagcgtgca tggaggtggt tacacacagc tgtttccgtg   6360
agggtgaccg tgtctgcagc acgcttccgt ctccgcatgc acggctgcct ctccagccac   6420
ctctgatact tctctcttgg ggccatcaga gcctcccttg ggctgtcacc tcccagctca   6480
cacacactct tcagtggttt cctctcttca ttctcttata gggcgtggtc cttcttattt   6540
atctaaaggg ctgaatttag gagacttttt acccaggggc aaaaggctct tagggtaatg   6600
agatggatgg tggcccaggt gcattttcca gggcctgggt tctccagatc ccgtggcttc   6660
tgttgagtgg aggcaacttt gctctgtgtg aacctcgccc ctgtccctct gccgggcacc   6720
cctggcagga agcaggactc ccatcctcac cctgacttag actgtcctct gagtcagctc   6780
```

```
ctctccaaga caggagtggg cagccctggg cagtcttctg gccccttgct aaagtgaggg   6840
gcaggaagct ggggctgccc tccagaaagc cggggtagga actctgaaaa atacctcctc   6900
taaacggaag cagggctctc cagttccact tggcgccccc tcccacaagg cccttcctcc   6960
ctgaggaccc caccccccta cccccttcccc agcagccttt ggaccctcac ctctctccgg   7020
tgtccgtggg tcctcagccc agggtgagct gcagtcaggc gggatgggac gggcaggcca   7080
gaggtcagcc agctcctagc agagaagagc cagccagacc ccaaccctgt ctcttgtcca   7140
tgccctttgt gatttcagtc ttggtagact tgtatttgga gttttgtgct tcaaagtttt   7200
tgtttttgtt tgtttggttt ttgttttgag gggtggggg gggatacaga gcagctgatc   7260
aatttgtatt tatttatttt aacattttac taaataaagc caaataaagc ctctcaaaaa   7320
aaaaaaaaaa aa                                                       7332
```

<210> SEQ ID NO 223
<211> LENGTH: 14135
<212> TYPE: DNA
<213> ORGANISM: Homo sapiens

<400> SEQUENCE: 223

```
gcactgcagc gccagcgtcc gagcgggcgg ccgagctccc ggagcggcct ggccccgagc     60
cccgagcggg cgtcgctcag cagcaggtcg cggccgcagc cccatccagc cccgcgcccg    120
ccatgccgtc cgcgggcccc gcctgagctg cggcctccgc gcgcgggcgg gcctggggac    180
ggcggggcca tgcgcgcgct gccctaacga tgccgcccgc cgcgcccgcc cgcctggcgc    240
tggccctggg cctgggcctg tggctcgggg cgctggcggg gggccccggg cgcggctgcg    300
ggccctgcga gcccccctgc ctctgcggcc cagcgcccgg cgccgcctgc cgcgtcaact    360
gctcgggccg cgggctgcgg acgctcggtc ccgcgctgcg catccccgcg gacgccacag    420
cgctagacgt ctcccacaac ctgctccggg cgctggacgt tgggctcctg gcgaacctct    480
cggcgctggc agagctggat ataagcaaca acaagatttc tacgttagaa gaaggaatat    540
ttgctaattt atttaattta agtgaaataa acctgagtgg gaacccgttt gagtgtgact    600
gtggcctggc gtggctgccg cgatgggcgg aggagcagca ggtgcgggtg gtgcagcccg    660
aggcagccac gtgtgctggg cctggctccc tggctggcca gcctctgctt ggcatcccct    720
tgctggacag tggctgtggt gaggagtatg tcgcctgcct ccctgacaac agctcaggca    780
ccgtggcagc agtgtccttt tcagctgccc acgaaggcct gcttcagcca gaggcctgca    840
gcgccttctg cttctccacc ggccagggcc tcgcagccct ctcggagcag ggctggtgcc    900
tgtgtggggc ggcccagccc tccagtgcct cctttgcctg cctgtccctc tgctccggcc    960
ccccgccacc tcctgccccc acctgtaggg gccccaccct cctccagcac gtcttccctg   1020
cctccccagg ggccaccctg gtggggcccc acggacctct ggcctctggc cagctagcag   1080
ccttccacat cgctgccccg ctccctgtca ctgccacacg ctgggacttc ggagacggct   1140
ccgccgaggt ggatgccgct gggccggctg cctcgcatcg ctatgtgctg cctgggcgct   1200
atcacgtgac ggccgtgctg gccctggggg ccggctcagc cctgctgggg acagacgtgc   1260
aggtggaagc ggcacctgcc gccctggagc tcgtgtgccc gtcctcggtg cagagtgacg   1320
agagccttga cctcagcatc cagaaccgcg gtggttcagg cctggaggcc gcctacagca   1380
tcgtggccct gggcgaggag ccggcccgag cggtgcaccc gctctgcccc tcggacacgg   1440
agatcttccc tggcaacggg cactgctacc gcctggtggt ggagaaggcg gcctggctgc   1500
```

aggcgcagga gcagtgtcag gcctgggccg gggccgccct ggcaatggtg gacagtcccg 1560
ccgtgcagcg cttcctggtc tcccgggtca ccaggagcct agacgtgtgg atcggcttct 1620
cgactgtgca gggggtggag gtgggcccag cgccgcaggg cgaggccttc agcctggaga 1680
gctgccagaa ctggctgccc ggggagccac acccagccac agccgagcac tgcgtccggc 1740
tcgggcccac cgggtggtgt aacaccgacc tgtgctcagc gccgcacagc tacgtctgcg 1800
agctgcagcc cggaggccca gtgcaggatg ccgagaacct cctcgtggga gcgcccagtg 1860
gggacctgca gggacccctg acgcctctgg cacagcagga cggcctctca gccccgcacg 1920
agcccgtgga ggtcatggta ttcccgggcc tgcgtctgag ccgtgaagcc ttcctcacca 1980
cggccgaatt tgggacccag gagctccggc ggcccgccca gctgcggctg caggtgtacc 2040
ggctcctcag cacagcaggg accccggaga acggcagcga gcctgagagc aggtccccgg 2100
acaacaggac ccagctggcc cccgcgtgca tgccaggggg acgctggtgc cctggagcca 2160
acatctgctt gccgctggac gcctcctgcc acccccaggc ctgcgccaat ggctgcacgt 2220
cagggccagg gctacccggg gcccccctatg cgctatggag agagttcctc ttctccgttc 2280
ccgcggggcc ccccgcgcag tactcggtca ccctccacgg ccaggatgtc ctcatgctcc 2340
ctggtgacct cgttggcttg cagcacgacg ctggccctgg cgccctcctg cactgctcgc 2400
cggctcccgg ccaccctggt ccccaggccc cgtacctctc cgccaacgcc tcgtcatggc 2460
tgccccactt gccagcccag ctggagggca cttgggcctg ccctgcctgt gccctgcggc 2520
tgcttgcagc cacggaacag ctcaccgtgc tgctgggctt gaggcccaac cctggactgc 2580
ggctgcctgg gcgctatgag gtccgggcag aggtgggcaa tggcgtgtcc aggcacaacc 2640
tctcctgcag ctttgacgtg gtctccccag tggctgggct gcgggtcatc taccctgccc 2700
cccgcgacgg ccgcctctac gtgcccacca acggctcagc cttggtgctc caggtggact 2760
ctggtgccaa cgccacggcc acggctcgct ggcctggggg cagtgtcagc gcccgctttg 2820
agaatgtctg ccctgccctg gtggccacct tcgtgcccgg ctgcccctgg gagaccaacg 2880
ataccctgtt ctcagtggta gcactgccgt ggctcagtga gggggagcac gtggtggacg 2940
tggtggtgga aaacagcgcc agccgggcca acctcagcct gcgggtgacg gcggaggagc 3000
ccatctgtgg cctccgcgcc acgcccagcc ccgaggcccg tgtactgcag ggagtcctag 3060
tgaggtacag ccccgtggtg gaggccggct cggacatggt cttccggtgg accatcaacg 3120
acaagcagtc cctgaccttc cagaacgtgg tcttcaatgt catttatcag agcgcggcgg 3180
tcttcaagct ctcactgacg gcctccaacc acgtgagcaa cgtcaccgtg aactacaacg 3240
taaccgtgga gcggatgaac aggatgcagg gtctgcaggt ctccacagtg ccggccgtgc 3300
tgtcccccaa tgccacgcta gcactgacgg cgggcgtgct ggtggactcg gccgtggagg 3360
tggccttcct gtggaccttt ggggatgggg agcaggccct ccaccagttc cagcctccgt 3420
acaacgagtc cttcccggtt ccagacccct cggtggccca ggtgctggtg gagcacaatg 3480
tcatgcacac ctacgctgcc ccaggtgagt acctcctgac cgtgctggca tctaatgcct 3540
tcgagaacct gacgcagcag gtgcctgtga gcgtgcgcgc ctccctgccc tccgtggctg 3600
tgggtgtgag tgacggcgtc ctggtggccg gccggcccgt caccttctac ccgcacccgc 3660
tgccctcgcc tgggggtgtt ctttacacgt gggacttcgg ggacggctcc cctgtcctga 3720
cccagagcca gccggctgcc aaccacacct atgcctcgag gggcacctac cacgtgcgcc 3780
tggaggtcaa caacacggtg agcggtgcgg cggcccaggc ggatgtgcgc gtctttgagg 3840
agctccgcgg actcagcgtg gacatgagcc tggccgtgga gcagggcgcc cccgtggtgg 3900

-continued

```
tcagcgccgc ggtgcagacg ggcgacaaca tcacgtggac cttcgacatg gggacggca   3960
ccgtgctgtc gggcccggag gcaacagtgg agcatgtgta cctgcgggca cagaactgca   4020
cagtgaccgt gggtgcggcc agccccgccg gccacctggc ccggagcctg cacgtgctgg   4080
tcttcgtcct ggaggtgctg cgcgttgaac ccgccgcctg catccccacg cagcctgacg   4140
cgcggctcac ggcctacgtc accgggaacc cggcccacta cctcttcgac tggaccttcg   4200
gggatggctc ctccaacacg accgtgcggg ggtgcccgac ggtgacacac aacttcacgc   4260
ggagcggcac gttcccctg gcgctggtgc tgtccagccg cgtgaacagg gcgcattact   4320
tcaccagcat ctgcgtggag ccagaggtgg gcaacgtcac cctgcagcca gagaggcagt   4380
ttgtgcagct cggggacgag gcctggctgg tggcatgtgc ctggcccccg ttcccctacc   4440
gctacacctg ggactttggc accgaggaag ccgccccac ccgtgccagg ggccctgagg   4500
tgacgttcat ctaccgagac ccaggctcct atcttgtgac agtcaccgcg tccaacaaca   4560
tctctgctgc caatgactca gccctggtgg aggtgcagga gcccgtgctg gtcaccagca   4620
tcaaggtcaa tggctccctt gggctggagc tgcagcagcc gtacctgttc tctgctgtgg   4680
gccgtgggcg ccccgccagc tacctgtggg atctgggga cggtgggtgg ctcgagggtc   4740
cggaggtcac ccacgcttac aacagcacag gtgacttcac cgttagggtg gccggctgga   4800
atgaggtgag ccgcagcgag gcctggctca atgtgacggt gaagcggcgc gtgcgggggc   4860
tcgtcgtcaa tgcaagccgc acggtggtgc ccctgaatgg gagcgtgagc ttcagcacgt   4920
cgctggaggc cggcagtgat gtgcgctatt cctgggtgct ctgtgaccgc tgcacgccca   4980
tccctggggg tcctaccatc tcttacacct tccgctccgt gggcaccttc aatatcatcg   5040
tcacggctga gaacgaggtg ggctccgccc aggacagcat cttcgtctat gtcctgcagc   5100
tcatagaggg gctgcaggtg gtgggcggtg gccgctactt ccccaccaac cacacggtac   5160
agctgcaggc cgtggttagg gatggcacca acgtctccta cagctggact gcctggaggg   5220
acaggggccc ggccctggcc ggcagcggca aaggcttctc gctcaccgtg ctcgaggccg   5280
gcacctacca tgtgcagctg cgggccacca acatgctggg cagcgcctgg gccgactgca   5340
ccatggactt cgtggagcct gtggggtggc tgatggtggc cgcctccccg aacccagctg   5400
ccgtcaacac aagcgtcacc ctcagtgccg agctggctgg tggcagtggt gtcgtataca   5460
cttggtcctt ggaggagggg ctgagctggg agacctccga gccatttacc acccatagct   5520
tccccacacc cggcctgcac ttggtcacca tgacggcagg gaacccgctg ggctcagcca   5580
acgccaccgt ggaagtggat gtgcaggtgc ctgtgagtgg cctcagcatc agggccagcg   5640
agcccggagg cagcttcgtg gcggccgggt cctctgtgcc cttttggggg cagctggcca   5700
cgggcaccaa tgtgagctgg tgctgggctg tgcccggcgg cagcagcaag cgtggccctc   5760
atgtcaccat ggtcttcccg gatgctggca ccttctccat ccggctcaat gcctccaacg   5820
cagtcagctg ggtctcagcc acgtacaacc tcacggcgga ggagcccatc gtgggcctgg   5880
tgctgtgggc cagcagcaag gtggtggcgc ccgggcagct ggtccatttt cagatcctgc   5940
tggctgccgg ctcagctgtc accttccgcc tgcaggtcgg cggggccaac cccgaggtgc   6000
tccccgggcc ccgtttctcc cacagcttcc cccgcgtcgg agaccacgtg gtgagcgtgc   6060
ggggcaaaaa ccacgtgagc tgggcccagg cgcaggtgcg catcgtggtg ctggaggccg   6120
tgagtgggct gcaggtgccc aactgctgcg agcctggcat cgccacgggc actgagagga   6180
acttcacagc ccgcgtgcag cgcggctctc gggtcgccta cgcctggtac ttctcgctgc   6240
```

agaaggtcca gggcgactcg ctggtcatcc tgtcgggccg cgacgtcacc tacacgcccg 6300
tggccgcggg gctgttggag atccaggtgc gcgccttcaa cgccctgggc agtgagaacc 6360
gcacgctggt gctggaggtt caggacgccg tccagtatgt ggccctgcag agcggcccct 6420
gcttcaccaa ccgctcggcg cagtttgagg ccgccaccag ccccagcccc cggcgtgtgg 6480
cctaccactg ggactttggg gatgggtcgc cagggcagga cacagatgag cccagggccg 6540
agcactccta cctgaggcct ggggactacc gcgtgcaggt gaacgcctcc aacctggtga 6600
gcttcttcgt ggcgcaggcc acggtgaccg tccaggtgct ggcctgccgg gagccggagg 6660
tggacgtggt cctgcccctg caggtgctga tgcggcgatc acagcgcaac tacttggagg 6720
cccacgttga cctgcgcgac tgcgtcacct accagactga gtaccgctgg gaggtgtatc 6780
gcaccgccag ctgccagcgg ccggggcgcc cagcgcgtgt ggccctgccc ggcgtggacg 6840
tgagccggcc tcggctggtg ctgccgcggc tggcgctgcc tgtggggcac tactgctttg 6900
tgtttgtcgt gtcatttggg gacacgccac tgacacagag catccaggcc aatgtgacgg 6960
tggcccccga gcgcctggtg cccatcattg agggtggctc ataccgcgtg tggtcagaca 7020
cacgggacct ggtgctggat gggagcgagt cctacgaccc caacctggag gacggcgacc 7080
agacgccgct cagtttccac tggggcctgtg tggcttcgac acagagggag gctggcgggt 7140
gtgcgctgaa ctttgggccc cgcgggagca gcacggtcac cattccacgg gagcggctgg 7200
cggctggcgt ggagtacacc ttcagcctga ccgtgtggaa ggccggccgc aaggaggagg 7260
ccaccaacca gacggtgctg atccggagtg gccgggtgcc cattgtgtcc ttggagtgtg 7320
tgtcctgcaa ggcacaggcc gtgtacgaag tgagccgcag ctcctacgtg tacttggagg 7380
gccgctgcct caattgcagc agcggctcca agcgagggcg gtgggctgca cgtacgttca 7440
gcaacaagac gctggtgctg gatgagacca ccacatccac gggcagtgca ggcatgcgac 7500
tggtgctgcg gcggggcgtg ctgcgggacg gcgagggata caccttcacg ctcacggtgc 7560
tgggccgctc tggcgaggag gagggctgcg cctccatccg cctgtccccc aaccgcccgc 7620
cgctgggggg ctcttgccgc ctcttcccac tgggcgctgt gcacgccctc accaccaagg 7680
tgcacttcga atgcacgggc tggcatgacg cggaggatgc tggcgccccg ctggtgtacg 7740
ccctgctgct gcggcgctgt cgccagggcc actgcgagga gttctgtgtc tacaagggca 7800
gcctctccag ctacggagcc gtgctgcccc cgggtttcag gccacacttc gaggtgggcc 7860
tggccgtggt ggtgcaggac cagctgggag ccgctgtggt cgccctcaac aggtctttgg 7920
ccatcaccct cccagagccc aacggcagcg caacggggct cacagtctgg ctgcacgggc 7980
tcaccgctag tgtgctccca gggctgctgc ggcaggccga tccccagcac gtcatcgagt 8040
actcgttggc cctggtcacc gtgctgaacg agtacgagcg ggccctggac gtggcggcag 8100
agcccaagca cgagcggcag caccgagccc agatacgcaa gaacatcacg gagactctgg 8160
tgtccctgag ggtccacact gtggatgaca tccagcagat cgctgctgcg ctggcccagt 8220
gcatggggcc cagcagggag ctcgtatgcc gctcgtgcct gaagcagacg ctgcacaagc 8280
tggaggccat gatgctcatc ctgcaggcag agaccaccgc gggcaccgtg acgcccaccg 8340
ccatcggaga cagcatcctc aacatcacag gagacctcat ccacctggcc agctcggacg 8400
tgcgggcacc acagccctca gagctgggag ccgagtcacc atctcggatg gtggcgtccc 8460
aggcctacaa cctgacctct gccctcatgc gcatcctcat gcgctcccgc gtgctcaacg 8520
aggagcccct gacgctggcg ggcgaggaga tcgtggccca gggcaagcgc tcggacccgc 8580
ggagcctgct gtgctatggc ggcgccccag ggcctggctg ccacttctcc atccccgagg 8640
ctttcagcgg ggccctggcc aacctcagtg acgtggtgca gctcatcttt ctggtggact 8700
ccaatccctt tccctttggc tatatcagca actacaccgt ctccaccaag gtggcctcga 8760
tggcattcca gacacaggcc ggcgcccaga tccccatcga gcggctggcc tcagagcgcg 8820
ccatcaccgt gaaggtgccc aacaactcgg actgggctgc ccggggccac cgcagctccg 8880
ccaactccgc caactccgtt gtggtccagc cccaggcctc cgtcggtgct gtggtcaccc 8940
tggacagcag caaccctgcg gccgggctgc atctgcagct caactatacg ctgctggacg 9000
gccactacct gtctgaggaa cctgagccct acctggcagt ctacctacac tcggagcccc 9060
ggcccaatga gcacaactgc tcggctagca ggaggatccg cccagagtca ctccagggtg 9120
ctgaccaccg gccctacacc ttcttcattt ccccggggag cagagaccca gcggggagtt 9180
accatctgaa cctctccagc cacttccgct ggtcggcgct gcaggtgtcc gtgggcctgt 9240
acacgtccct gtgccagtac ttcagcgagg aggacatggt gtggcggaca gaggggctgc 9300
tgcccctgga ggagacctcg ccccgccagg ccgtctgcct cacccgccac ctcaccgcct 9360
tcggcgccag cctcttcgtg cccccaagcc atgtccgctt tgtgtttcct gagccgacag 9420
cggatgtaaa ctacatcgtc atgctgacat gtgctgtgtg cctggtgacc tacatggtca 9480
tggccgccat cctgcacaag ctggaccagt tggatgccag ccggggccgc gccatccctt 9540
tctgtgggca gcggggccgc ttcaagtacg agatcctcgt caagacaggc tggggccggg 9600
gctcaggtac cacggcccac gtgggcatca tgctgtatgg ggtggacagc cggagcggcc 9660
accggcacct ggacggcgac agagccttcc accgcaacag cctggacatc ttccggatcg 9720
ccaccccgca cagcctgggt agcgtgtgga agatccgagt gtggcacgac aacaaagggc 9780
tcagccctgc ctggttcctg cagcacgtca tcgtcaggga cctgcagacg gcacgcagcg 9840
ccttcttcct ggtcaatgac tggctttcgg tggagacgga ggccaacggg ggcctggtgg 9900
agaaggaggt gctggccgcg agcgacgcag cccttttgcg cttccggcgc ctgctggtgg 9960
ctgagctgca gcgtggcttc tttgacaagc acatctggct ctccatatgg gaccggccgc 10020
ctcgtagccg tttcactcgc atccagaggg ccacctgctg cgttctcctc atctgcctct 10080
tcctgggcgc caacgccgtg tggtacgggg ctgttggcga ctctgcctac agcacggggc 10140
atgtgtccag gctgagcccg ctgagcgtcg acacagtcgc tgttggcctg gtgtccagcg 10200
tggttgtcta tcccgtctac ctggccatcc tttttctctt ccggatgtcc cggagcaagg 10260
tggctgggag cccgagcccc acacctgccg ggcagcaggt gctggacatc gacagctgcc 10320
tggactcgtc cgtgctggac agctccttcc tcacgttctc aggcctccac gctgaggcct 10380
ttgttggaca gatgaagagt gacttgtttc tggatgattc taagagtctg gtgtgctggc 10440
cctccggcga gggaacgctc agttggccgg acctgctcag tgacccgtcc attgtgggta 10500
gcaatctgcg gcagctggca cggggccagg cgggccatgg gctgggccca gaggaggacg 10560
gcttctccct ggccagcccc tactcgcctg ccaaatcctt ctcagcatca gatgaagacc 10620
tgatccagca ggtccttgcc gagggggtca gcagcccagc ccctacccaa gacacccaca 10680
tggaaacgga cctgctcagc agcctgtcca gcactcctgg ggagaagaca gagacgctgg 10740
cgctgcagag gctgggggag ctggggccac ccagcccagg cctgaactgg gaacagcccc 10800
aggcagcgag gctgtccagg acaggactgg tggagggtct gcggaagcgc ctgctgccgg 10860
cctggtgtgc ctccctggcc cacgggctca gcctgctcct ggtggctgtg gctgtggctg 10920
tctcagggtg ggtgggtgcg agcttccccc cgggcgtgag tgttgcgtgg ctcctgtcca 10980

-continued

```
gcagcgccag cttcctggcc tcattcctcg gctgggagcc actgaaggtc ttgctggaag  11040
ccctgtactt ctcactggtg gccaagcggc tgcacccgga tgaagatgac accctggtag  11100
agagcccggc tgtgacgcct gtgagcgcac gtgtgccccg cgtacggcca ccccacggct  11160
ttgcactctt cctggccaag gaagaagccc gcaaggtcaa gaggctacat ggcatgctgc  11220
ggagcctcct ggtgtacatg ctttttctgc tggtgaccct gctggccagc tatggggatg  11280
cctcatgcca tgggcacgcc taccgtctgc aaagcgccat caagcaggag ctgcacagcc  11340
gggccttcct ggccatcacg cggtctgagg agctctggcc atggatggcc cacgtgctgc  11400
tgccctacgt ccacgggaac cagtccagcc cagagctggg gcccccacgg ctgcggcagg  11460
tgcggctgca ggaagcactc tacccagacc ctcccggccc cagggtccac acgtgctcgg  11520
ccgcaggagg cttcagcacc agcgattacg acgttggctg ggagagtcct cacaatggct  11580
cggggacgtg ggcctattca gcgccggatc tgctgggggc atggtcctgg ggctcctgtg  11640
ccgtgtatga cagcgggggc tacgtgcagg agctgggcct gagcctggag gagagccgcg  11700
accggctgcg cttcctgcag ctgcacaact ggctggacaa caggagccgc gctgtgttcc  11760
tggagctcac gcgctacagc ccggccgtgg ggctgcacgc cgccgtcacg ctgcgcctcg  11820
agttcccggc ggccggccgc gccctggccg ccctcagcgt ccgcccccttt gcgctgcgcc  11880
gcctcagcgc gggcctctcg ctgcctctgc tcacctcggt gtgcctgctg ctgttcgccg  11940
tgcacttcgc cgtggccgag gcccgtactt ggcacaggga agggcgctgg cgcgtgctgc  12000
ggctcggagc ctgggcgcgg tggctgctgg tggcgctgac ggcggccacg gcactggtac  12060
gcctcgccca gctgggtgcc gctgaccgcc agtggacccg tttcgtgcgc ggccgcccgc  12120
gccgcttcac tagcttcgac caggtggcgc agctgagctc cgcagcccgt ggcctggcgg  12180
cctcgctgct cttcctgctt ttggtcaagg ctgcccagca gctacgcttc gtgcgccagt  12240
ggtccgtctt tggcaagaca ttatgccgag ctctgccaga gctcctgggg gtcaccttgg  12300
gcctggtggt gctcggggta gcctacgccc agctggccat cctgctcgtg tcttcctgtg  12360
tggactccct ctggagcgtg gcccaggccc tgttggtgct gtgccctggg actgggctct  12420
ctaccctgtg tcctgccgag tcctggcacc tgtcacccct gctgtgtgtg gggctctggg  12480
cactgcggct gtggggcgcc ctacggctgg gggctgttat tctccgctgg cgctaccacg  12540
ccttgcgtgg agagctgtac cggccggcct gggagcccca ggactacgag atggtggagt  12600
tgttcctgcg caggctgcgc ctctggatgg gcctcagcaa ggtcaaggag ttccgccaca  12660
aagtccgctt tgaagggatg gagccgctgc cctctcgctc ctccaggggc tccaaggtat  12720
ccccggatgt gcccccaccc agcgctggct ccgatgcctc gcacccctcc acctcctcca  12780
gccagctgga tgggctgagc gtgagcctgg gccggctggg gacaaggtgt gagcctgagc  12840
cctcccgcct ccaagccgtg ttcgaggccc tgctcaccca gtttgaccga ctcaaccagg  12900
ccacagagga cgtctaccag ctggagcagc agctgcacag cctgcaaggc cgcaggagca  12960
gccgggcgcc cgccggatct tcccgtggcc catccccggg cctgcggcca gcactgccca  13020
gccgccttgc ccgggccagt cggggtgtgg acctggccac tggccccagc aggacacccc  13080
ttcgggccaa gaacaaggtc caccccagca gcacttagtc ctccttcctg gcgggggtgg  13140
gccgtggagt cggagtggac accgctcagt attactttct gccgctgtca aggccgaggg  13200
ccaggcagaa tggctgcacg taggttcccc agagagcagg caggggcatc tgtctgtctg  13260
tgggcttcag cactttaaag aggctgtgtg gccaaccagg acccagggtc cctccccag  13320
ctcccttggg aaggacacag cagtattgga cggtttctag cctctgagat gctaatttat  13380
```

```
ttccccgagt cctcaggtac agcgggctgt gcccggcccc accccctggg cagatgtccc  13440
ccactgctaa ggctgctggc ttcagggagg gttagcctgc accgccgcca ccctgcccct  13500
aagttattac ctctccagtt cctaccgtac tccctgcacc gtctcactgt gtgtctcgtg  13560
tcagtaattt atatggtgtt aaaatgtgta tatttttgta tgtcactatt ttcactaggg  13620
ctgaggggcc tgcgcccaga gctggcctcc cccaacacct gctgcgcttg gtaggtgtgg  13680
tggcgttatg gcagcccggc tgctgcttgg atgcgagctt ggccttgggc cggtgctggg  13740
ggcacagctg tctgccaggc actctcatca ccccagaggc cttgtcatcc tcccttgccc  13800
caggccaggt agcaagagag cagcgcccag gcctgctggc atcaggtctg ggcaagtagc  13860
aggactaggc atgtcagagg accccagggt ggttagagga aaagactcct cctgggggct  13920
ggctcccagg gtggaggaag gtgactgtgt gtgtgtgtgt gtgcgcgcgc gcacgcgcga  13980
gtgtgctgta tggcccaggc agcctcaagg ccctcggagc tggctgtgcc tgcttctgtg  14040
taccacttct gtgggcatgg ccgcttctag agcctcgaca cccccccaac ccccgcacca  14100
agcagacaaa gtcaataaaa gagctgtctg actgc                             14135
```

<210> SEQ ID NO 224
<211> LENGTH: 2200
<212> TYPE: DNA
<213> ORGANISM: Homo sapiens

<400> SEQUENCE: 224

```
gcatcctctc accgccggaa gctgaactga ctcgtccgcg gccgctctac cccaacaggc     60
cgccaccagc gagagtgcgg ccataaccat cacgtgaccg cccaccgaca ccagcgagag    120
tgcagtcgta accgtcacgt gaccgcccac cgtcggcccg gcgctcccct ccgcccgaag    180
ctagcaagcg gcgcggccaa tgagaaaggc gcatgcctgg cccccgccgg cctgcagtct    240
agccgtagtg cgcctgcgcg cggctaggag gggccgtcag gcggggatac agcctggaag    300
gtaatgcatg tccatggtac acaaattcac aagtttggag accctgacac acccaccttc    360
tcacctgggc tctgcgtatc cccagccttg gagggaagat gaagcctaaa ctgatgtacc    420
aggagctgaa ggtgcctgca gaggagcccg ccaatgagct gcccatgaat gagattgagg    480
cgtggaaggc tgcggaaaag aaagcccgct gggtcctgct ggtcctcatt ctggcggttg    540
tgggcttcgg agccctgatg actcagctgt ttctatggga atacggcgac ttgcatctct    600
ttgggcccaa ccagcgccca gccccctgct atgacccttg cgaagcagtg ctggtggaaa    660
gcattcctga gggcctggac ttccccaatg cctccacggg gaacccttcc accagccagg    720
cctggctggg cctgctcgcc ggtgcgcaca gcagcctgga catcgcctcc ttctactgga    780
ccctcaccaa caatgacacc cacacgcagg agccctctgc ccagcagggt gaggaggtcc    840
tccggcagct gcagaccctg gcaccaaagg gcgtgaacgt ccgcatcgct gtgagcaagc    900
ccagcgggcc ccagccacag gcggacctgc aggctctgct gcagagcggt gcccaggtcc    960
gcatggtgga catgcagaag ctgacccatg gcgtcctgca taccaagttc tgggtggtgg   1020
accagaccca cttctacctg ggcagtgcca acatggactg gcgttcactg acccaggtca   1080
aggagctggg cgtggtcatg tacaactgca gctgcctggc tcgagacctg accaagatct   1140
ttgaggccta ctggttcctg ggccaggcag gcagctccat cccatcaact tggccccggt   1200
tctatgacac ccgctacaac caagagacac caatggagat ctgcctcaat ggaacccctg   1260
ctctggccta cctggcgagt gcgcccccac ccctgtgtcc aagtggccgc actccagacc   1320
```

```
tgaaggctct actcaacgtg gtggacaatg cccggagttt catctacgtc gctgtcatga   1380

actacctgcc cactctggag ttctcccacc ctcacaggtt ctggcctgcc attgacgatg   1440

ggctgcggcg ggccacctac gagcgtggcg tcaaggtgcg cctgctcatc agctgctggg   1500

gacactcgga gccatccatg cgggccttcc tgctctctct ggctgccctg cgtgacaacc   1560

atacccactc tgacatccag gtgaaactct ttgtggtccc cgcggatgag gcccaggctc   1620

gaatcccata tgcccgtgtc aaccacaaca agtacatggt gactgaacgc gccacctaca   1680

tcggaacctc caactggtct ggcaactact tcacggagac ggcgggcacc tcgctgctgg   1740

tgacgcagaa tgggaggggc ggcctgcgga gccagctgga ggccattttc ctgagggact   1800

gggactcccc ttacagccat gaccttgaca cctcagctga cagcgtgggc aacgcctgcc   1860

gcctgctctg aggcccgatc cagtgggcag gccaaggcct gctgggcccc cgcggaccca   1920

ggtgctctgg gtcacggtcc ctgtccccgc gcccccgctt ctgtctgccc cattgtggct   1980

cctcaggctc tctcccctgc tctcccacct ctacctccac ccccaccggc ctgacgctgt   2040

ggccccggga cccagcagag ctgggggagg gatcagcccc caaagaaatg gggggtgcatg  2100

ctgggcctgg ccccctggcc cacccccact ttccagggca aaaagggccc agggttataa   2160

taagtaaata acttgtctgt aaaaaaaaaa aaaaaaaaaa                         2200
```

```
<210> SEQ ID NO 225
<211> LENGTH: 1014
<212> TYPE: DNA
<213> ORGANISM: Homo sapiens

<400> SEQUENCE: 225

tgcctcctga gcgtagtcca gttactttca ggctcgggga gtgaaggcct cgttgagaga     60

aggtctcatt cggtgttttg ggaagagagt cgtgtgggcc caggtctgtc tgctatcagc    120

tatgccgctg cccgttgcgc tgcagacccg cttggccaag agaggcatcc tcaaacatct    180

ggagcctgaa ccagaggaag agatcattgc cgaggactat gacgatgatc ctgtggacta    240

cgaggccacc aggttggagg gcctaccacc aagctggtac aaggtgttcg acccttcctg    300

cgggctccct tactactgga atgcagacac agaccttgta tcctggctct ccccacatga    360

ccccaactcc gtggttacca aatcggccaa gaagctcaga agcagtaatg cagatgctga    420

agaaaagttg gaccggagcc atgacaagtc ggacaggggc catgacaagt cggaccgcag    480

ccatgagaaa ctagacaggg gccacgacaa gtcagaccgg ggccacgaca agtctgacag    540

ggatcgagag cgtggctatg acaaggtaga cagagagaga gagcgagaca gggaacggga    600

tcgggaccgc gggtatgaca aggcagaccg ggaagagggc aaagaacggc gccaccatcg    660

ccgggaggag ctggctccct atcccaagag caagaaggca gtaagccgaa aggatgaaga    720

gttagacccc atggacccta gctcatactc agacgccccc cggggcacgt ggtcaacagg    780

actccccaag cggaatgagg ccaagactgg cgctgacacc acagcagctg ggcccctctt    840

ccagcagcgg ccgtatccat ccccaggggc tgtgctccgg gccaatgcag aggcctcccg    900

aaccaagcag caggattgaa gcttcggcct ccctggccct gggttaaaat aaaagctttc    960

tggtgatcct gcccaccaaa aaaaaaaaaa aaaaaaaaaa aaaaaaaaaa aaaa         1014
```

```
<210> SEQ ID NO 226
<211> LENGTH: 1926
<212> TYPE: DNA
<213> ORGANISM: Homo sapiens

<400> SEQUENCE: 226
```

```
gtggatgagc tgtgagtgcg cgcgcgtgcg cggggccgcg acctgtgccg gctcgagccc     60
gctgggcact cggaggcgcg cacgtcgttc cccgccctcc cgccgccgcc cgccctcgct    120
ctctcgcgct accctcccgc cgcccgcggt cctccgtcgg ttctctcgtt agtccacggt    180
ctggtcttca gctacccgcc ttcgtctccg agtttgcgac tcgcggaccg gcgtccccgg    240
cgcgaagagg ctggactcgg attcgttgcc tgagcaatgg ctgccatccg gaagaaactg    300
gtgattgttg gtgatggagc ctgtggaaag acatgcttgc tcatagtctt cagcaaggac    360
cagttcccag aggtgtatgt gcccacagtg tttgagaact atgtggcaga tatcgaggtg    420
gatggaaagc aggtagagtt ggctttgtgg gacacagctg ggcaggaaga ttatgatcgc    480
ctgaggcccc tctcctaccc agataccgat gttatactga tgtgtttttc catcgacagc    540
cctgatagtt tagaaaacat cccagaaaag tggaccccag aagtcaagca tttctgtccc    600
aacgtgccca tcatcctggt tgggaataag aaggatcttc ggaatgatga gcacacaagg    660
cgggagctag ccaagatgaa gcaggagccg gtgaaacctg aagaaggcag agatatggca    720
aacaggattg gcgcttttgg gtacatggag tgttcagcaa agaccaaaga tggagtgaga    780
gaggtttttg aaatggctac gagagctgct ctgcaagcta gacgtgggaa gaaaaaatct    840
gggtgccttg tcttgtgaaa ccttgctgca agcacagccc ttatgcggtt aatttgaag     900
tgctgtttat taatcttagt gtatgattac tggccttttt catttatcta taatttacct    960
aagattacaa atcagaagtc atcttgctac cagtatttag aagccaacta tgattattaa   1020
cgatgtccaa cccgtctggc ccaccagggt ccttttgaca ctgctctaac agccctcctc   1080
tgcactccca cctgacacac caggcgctaa ttcaaggaat ttcttaactt cttgcttctt   1140
tctagaaaga gaaacagttg gtaacttttg tgaattaggc tgtaactact ttataactaa   1200
catgtcctgc ctattatctg tcagctgcaa ggtactctgg tgagtcacca cttcagggct   1260
ttactccgta acagatttg ttggcatagc tctggggtgg gcagtttttt gaaaatgggc    1320
tcaaccagaa aagcccaagt tcatgcagct gtggcagagt tacagttctg tggtttcatg   1380
ttagttacct tatagttact gtgtaattag tgccacttaa tgtatgttac caaaaataaa   1440
tatatctacc ccagactaga tgtagtattt tttgtataat tggatttcct aatactgtca   1500
tcctcaaaga aagtgtattg gtttttttaaa aaagaaagtg tatttggaaa taaagtcaga   1560
tggaaaattc attttttaaa ttcccgtttt gtcacttttt ctgataaaag atggccatat   1620
taccccttt cggccccatg tatctcagta ccccatggag ctgggctaag taaataggaa    1680
ttggtttcac gcctgaggca attagacact ttggaagatg gcataacctg tctcacctgg   1740
acttaagcat ctggctctaa ttcacagtgc tcttttctcc tcactgtatc caggttccct   1800
cccagaggag ccaccagttc tcatgggtgg cactcagtct ctcttctctc cagctgacta   1860
aactttttt ctgtaccagt taatttttcc aactactaat agaataaagg cagttttcta    1920
aaaaaa                                                              1926
```

<210> SEQ ID NO 227
<211> LENGTH: 5216
<212> TYPE: DNA
<213> ORGANISM: Homo sapiens

<400> SEQUENCE: 227

```
gatgtcccag gggtattggg gcggggggtt gaaataactg gggttcagga ggagggatgg     60
tggtagagat aaaaatgtga gaagggagca gcactggcga ggagtcggga gagtactcct    120
```

-continued gattgtgaca tcacattcat cccctgggcg atggagcttg tcactgggaa ggaatactca 180
gtcggagaat agccaacaag atgggttact gggagaatct cttcagtggc actgagtgga 240
ggcatcaggg ggttggagcc ttgtgaacag ggaacctgcc ccccaacact tggaaggacc 300
tgggtttcag tgatgagaca tggggtatga tgtaacccgt ttccaggggg atgttgacga 360
agatcttatc tgccctattt gcagtggagt cttggaggag ccagtacagg cacctcattg 420
tgaacatgct ttctgcaacg cctgcatcac ccagtggttc tctcagcaac agacatgtcc 480
agtggaccgt agtgttgtga cggtcgccca tctgcgccca gtacctcgga tcatgcggaa 540
catgttgtca aagctgcaga ttgcctgtga caacgctgtg ttcggctgta gtgccgttgt 600
ccggcttgac aacctcatgt ctcacctcag cgactgtgag cacaacccga agcggcctgt 660
gacctgtgaa cagggctgtg gcctggagat gcccaaagat gagctgccca accataactg 720
cattaagcac ctgcgctcag tggtacagca gcagcagaca cgcatcgcag agctggagaa 780
gacgtcagct gaacacaaac accagctggc ggagcagaag cgagacatcc agctgctaaa 840
ggcatacatg cgtgcaatcc gcagtgtcaa ccccaacctt cagaacctgg aggagacaat 900
tgaatacaac gagatcctag agtgggtgaa ctcccttcag ccagcaagag tgacccgctg 960
gggagggatg atctcgactc ctgatgctgt gctccaggct gtaatcaagc gctccctggt 1020
ggagagtggc tgtcctgctt ctattgtcaa cgagctgatt gaaaatgccc acgagcgtag 1080
ctggccccag ggtctggcca cactagagac tagacagatg aaccgacgct actatgagaa 1140
ctacgtggcc aagcgcatcc ctggcaagca ggctgttgtc gtgatggcct gtgagaacca 1200
gcacatgggg gatgacatgg tgcaagagcc aggccttgtc atgatatttg cgcatggcgt 1260
ggaagagata taagagaact cgactggcta tcaggaagag atggaaatca gaaaatccca 1320
tcactccagc agctgggacc tgagtcctac ccaccattct taatactgtg gcttatacct 1380
gagccacaca tctccctgcc cttctggcac tgaagggcct tggggtagtt tgctcagcct 1440
ttcaggtggg aaacccagat ttcctccctt tgccatattc ccctaaaatg tctataaatt 1500
atcagtctgg gtgggaaagc cccacctcc atccattttc ctgcttaggg tccctggttc 1560
cagttatttt cagaaagcac aaagagattc aatttccctg gaggatcagg acagaggaag 1620
gaatctctaa tcgtccctct cctccaaaac cagggaatca gagcagtcag gcctgttgac 1680
tctaagcagc agacatcctg aagaaatggt aagggtggag ccaaatctct agaaataagt 1740
agtgaggccg ttaattggcc atcactgatg gcccttaggg aaagactgga cctctgtgcc 1800
aagcagtatc cctgttcagc ccaccttaaa ggtgtaggca ccccactgggt ctaccagtat 1860 gcaggttggg atactgaaaa tttccagatg agctcttctt tcctacaagt tttcataatt 1920
agggaatgcc agggtttagg gtaggggtta atctgttggg ggttgatgtg tttagcaaga 1980
agctactcct agcttttgct aaaatatggt tggcactgcc tcttgtggca caggccataa 2040
ttgttccata gacccctctc tagccctgtg actgtagtta gttactttga taattttctt 2100
tggccattgt ttgtttatat ttcacaaact ccacctactg cccccccccc tcttttttt 2160 aagaatggcc tgatcatggc tatctcagcc acattgttgg caatttaatt tatttacttc 2220
cttttttttt ttttaagaaa ggaaaaaaga aaaaaaaatc aaacttgaaa cttttctttt 2280
gatgttccta ttgtgggggt tctggatagg gtgggacagg gatgggggtg tgttttatat 2340
tttttccttt tcagcacaac ctttggcttt aatataggaa gagccaaggg agtcctcggc 2400
tgaacttacg atatctgccc caaacctctg taaccccaac tgaaatgagg agcttcctct 2460
cttcctgtga aggatatgac agtccagcat cgatgcctgt gccctctgga aaaatttcct 2520

-continued

```
cctagccctt ccagggcctt atcataaaac tctggattta gagtattcat tttgaaggca   2580
actccccctt ccccaagttt ccttggagct gtatagctgg gttctaagct tcaccatgca   2640
aatcagaaat tttatctcta agtacaggct gtgccgtgtc tcacccacac ccccctgggg   2700
acttcagttc catttcaggt tacctggggt ataccttgat ccctagagtg actggcagag   2760
taagagaagg ggagagataa taggtgtgat tattttaata tggaggtggg agtgtggttg   2820
gagatagaaa ggctcctccc caccatgtaa tggcttcctc tcagaatttt attccaggct   2880
agcttgctgc aggtctgggt agttggatca tggctccact gggattgggg tggaaagctt   2940
gaggggagta gggttccagc tctgggacat tgtgctcagg aatttgaaaa cgctgctata   3000
cttactctgg ttactacatt tcttccactc ccctttcccc tacctgcctt aaccaaggct   3060
catactgtcc tgtccttacc ctcagatgga gccaggaagc tcagtgaaag gcttccctac   3120
cctttgcact agtgtctctg caggttgctg gttgtgttgt atgtgctgtt ccatggtgtt   3180
gactgcacta ataataaacc ttttactcaa ctctctaaat tcttcagcat tactcccttt   3240
cttgagaagg tttcccctct gcttttgcct ttctctcacc ttaattccct ttcttcctta   3300
ctttgttacc taccctatc ttagtgctaa cttctctttc aggaggatgt ctgggagtag   3360
tgtgcacttc acagctgctt tcccatgtac cctcctgcat tcttccctcc tatctcctgt   3420
tctgtagcag ccaaagctct ctagtgatct gaactgtgtg cttcccaggg tctgccttta   3480
tcctaaattc catgtcttcc ctgagtggtc ctgagttttt gggataattt ctacagaaga   3540
tatgtatata tctttttcct ttgtcccaca agcaactttg ctttagaatc tagaattcct   3600
ttgcaggcag agaagtctct acctcccagt gtttcctagc taagaacgta aatgtgagga   3660
gggaaatgta cttgcagagg tttcataatt atttacttat aaaaatagtc ttcatagccg   3720
ggcgcggtgg ctcacgcctg taatcccagc actttgggag gccgaggtgg gtggatcaca   3780
aggtcaggag ttcgagacca tcctggctaa cacagtgaaa ccccgtctct actaaaaata   3840
caaaaaatta gccgggcgtg gtggcaggca cctgtagtcc cagctactta ggaggctgag   3900
gcaggagaat ggcgtgaacc cgggaggcag agcttgcagt gagcagagat tgggccactg   3960
cattccagcc tgggcgacag agcaaggctc cgtctaaaaa aaaaaaaaaa aaaaaaagtc   4020
ttcataggcc gggcacggtg gctcacgtct gtaatcccag cactttggga ggccaaggtg   4080
ggtggatcac aacgtcagga gatcgagacc atcctggcta acatggtgaa accctgtctc   4140
tactaaaaat ataaataaat tagccggaca ggcgcctgtc ctcccagcta ctcaggaggc   4200
tgaggcagga gaatggtgtg aacctgggag gcggagcttg cagtgagctg agatcacgcc   4260
actgcactcc agcctgggca acagagcaag actccgtctc aaaaaaaaaa aaaaaaaaac   4320
cagtcttcat aagtatttgc tgctaccttt ccctgtcata agaaaaagga tagccagaca   4380
tggtgggacg ccactatgat cccagctcct tggaaggcta aggcacaaga atcgcttgaa   4440
cctgggaggt ggaggttgca gtgagctgag atcatgccac tgcactccag cctggtgaca   4500
gagcaagagc ctgtctcaaa aaaaaaaaag aaaagaaaag aaaaagggat atcttttcct   4560
cctcccagaa gtttgtttta aatttgagca tttatcatgc acctgatgta aacctaatag   4620
tactcttgat actctagtgg cttgaaaaaa aaaaaaaagg catttctgtg ctgagtctgc   4680
gcttctatgc acacaaggta tgtttataaa atactgataa gcatgtcaca gtatagagca   4740
taagaggcaa tgtatgtatc ctagtgacat tagcagtgct tttccccccct taaactcctt   4800
taaaattact tttagaactt gctgctcatt cttgtgaatg ttatgaatgg tgtcatattg   4860
```

-continued tcctttttaca gaagatacga tttttagaaa caaatattca ttgaatgtct gccctgtgag 4920
atactcacta gagtgaacat gaggaggctt atgtagcaaa atggcaccta cctgcaaaga 4980
acttagtccc taatggagat gaatatataa taagggatca taaatgtgct aagtggattt 5040
actagtaata tgtgagccaa ggacgataaa gctcctgatt ctgatgggta tcaggaaagg 5100
cttttcagga agtgttactt gttataggtc agaggtcagc aaactacagg ttacaacccc 5160
actgcctgct tttgtaaaaa actttattgg aatacagtta tgcccacttg tttata 5216

<210> SEQ ID NO 228
<211> LENGTH: 5138
<212> TYPE: DNA
<213> ORGANISM: Homo sapiens

<400> SEQUENCE: 228
gatccgcaga ggagcccact tgagagcgcc tcctgtcgtc tgtaaggttg ccttgccatc 60
cctcggcacc ccaacttccc ccgccccccc atcgcctcct cctccatcct ccagttcaaa 120
atggcgacgg cggcggcagc ggcggcggtg atggctcctc cgggctgccc gggttcgtgc 180
cccaacttcg ccgtagtctg ctccttcttg gagcgctacg ggccgctgct agacctgcct 240
gagttgccgt tccctgagct ggagcgggtg ctgcaggcgc cgccgccgga cgtcggcaac 300
ggagaagtac caaaagaatt ggtggagctc catttgaagc tgatgaggaa aattggcaaa 360
tctgttactg cagacagatg ggaaaaatat ttgatcaaga tatgccaaga gtttaacagt 420
acctgggcat gggagatgga gaagaagggc tatcttgaaa tgagtgttga atgcaaacta 480
gcactcttaa agtacctctg tgagtgtcag tttgatgaca atctcaaatt caagaatatt 540
attaatgagg aggatgccga tactatgcgt ctccagccaa ttggtcgaga caaagatggc 600
ctcatgtact ggtaccaatt ggatcaagat cacaatgtca gaatgtacat agaagaacaa 660
gatgatcaag atggctcttc atggaaatgc attgtcagaa atcgaaacga gttggctgag 720
actcttgcac tcctgaaagc acaaattgat cctgtactat tgaaaaactc tagccaacaa 780
gacaactctt ctcgggaaag tcccagctta gaggatgagg agactaaaaa agaggaagaa 840
acacctaaac aagaggaaca gaaagaaagt gaaaagatga aaagtgagga gcagcctatg 900
gatttagaaa accgttctac agccaatgtt ctagaagaga ctactgtgaa aaaagaaaaa 960
gaagatgaaa aggaacttgt gaaactgcca gtcatagtga agctagaaaa acctttgcca 1020
gaaaatgaag aaaaaaagat tatcaaagaa gaaagtgatt ccttcaagga aaatgtcaaa 1080
cccattaaag ttgaggtgaa ggaatgtaga gcagatccta aagataccaa aagtagcatg 1140
gagaagccag tggcacagga gcctgaaagg atcgaatttg gtggcaatat taaatcttct 1200
cacgaaatta ctgagaaatc tactgaagaa actgagaaac ttaaaaatga ccagcaggcc 1260
aagataccac taaaaaaacg agaaattaaa ctgagtgatg attttgacag tccagtcaag 1320
ggacctttgt gtaaatcagt tactccaaca aaagagtttt tgaaagatga aataaaacaa 1380
gaggaagaga cttgtaaaag gatctctaca atcactgctt tgggtcatga agggaaacag 1440
ctggtaaatg gagaagttag tgatgaaagg gtagctccaa attttaagac agaaccaata 1500
gagacaaagt tttatgagac aaaggaagag agctatagcc cctctaagga cagaaatatc 1560
atcacggagg gaaatggaac agagtcctta aattctgtca taacaagtat gaaaacaggt 1620
gagcttgaga aagaaacagc ccctttgagg aaagatgcag atagttcaat atcagtctta 1680
gagatccata gtcaaaaagc acaaatagag gaacccgatc ctccagaaat ggaaacttct 1740
cttgattctt ctgagatggc aaaagatctc tcttcaaaaa ctgctttatc ttccaccgag 1800
tcgtgtacca tgaaaggtga agagaagtct cccaaaacta agaaggataa gcgcccacca 1860
atcctagaat gtcttgaaaa gttagagaag tccaaaaaga cttttcttga taaggacgca 1920
caaagattga gtccaatacc agaagaagtt ccaaagagta ctctagagtc agaaaagcct 1980
ggctctcctg aggcagctga aacttctcca ccatctaata tcattgacca ctgtgagaaa 2040
ctagcctcag aaaaagaagt ggtagaatgc cagagtacaa gtactgttgg tggccagtct 2100
gtgaaaaaag tagacctaga aaccctaaaa gaggattctg agttcacaaa ggtagaaatg 2160
gataatctgg acaatgccca gacctctggc atagaggagc cttctgagac aaagggttct 2220
atgcaaaaaa gcaaattcaa atataagttg gttcctgaag aagaaaccac tgcctcagaa 2280
aatacagaga taacctctga aaggcagaaa gagggcatca aattaacaat caggatatca 2340
agtcggaaaa agaagcccga ttctcccccc aaagttctag aaccagaaaa caagcaagag 2400
aagacagaaa aggaagagga gaaaacaaat gtgggtcgta ctttaagaag atctccaaga 2460
atatctagac ccactgcaaa agtggctgag atcagagatc agaaagctga taaaaaaaga 2520
ggggaaggag aagatgaggt ggaagaagag tcaacagctt tgcaaaaaac tgacaaaaag 2580
gaaattttga aaaaatcaga gaaagataca aattctaaag taagcaaggt aaaacccaaa 2640
ggcaaagttc gatggactgg ttctcggaca cgtggcagat ggaaatattc cagcaatgat 2700
gaaagtgaag ggtctggcag tgaaaaatca tctgcagctt cagaagagga ggaagaaaag 2760
gaaagtgaag aagccatcct agcagatgat gatgaaccat gcaaaaaatg tggccttcca 2820
aaccatcctg agctaattct tctgtgtgac tcttgcgata gtggatacca tactgcctgc 2880
cttcgccctc ctctgatgat catcccagat ggagaatggt tctgcccacc ttgccaacat 2940
aaactgctct gtgaaaaatt agaggaacag ttgcaggatt tggatgttgc cttaaagaag 3000
aaagagcgtg ccgaacgaag aaaagaacgc ttggtgtatg ttggtatcag tattgaaaac 3060
atcattcctc cacaagagcc agacttttct gaagatcaag aagaaaagaa aaaagattca 3120
aaaaaatcca aagcaaactt gcttgaaagg aggtcaacaa gaacaaggaa atgtataagc 3180
tacagatttg atgagtttga tgaagcaatt gatgaagcta ttgaagatga catcaaagaa 3240
gccgatggag gaggagttgg ccgaggaaaa gatatctcca ccatcacagg tcatcgtggg 3300
aaagacatct ctactatttt ggatgaagaa agaaaagaaa ataaacgacc ccagagggca 3360
gctgctgctc gaaggaagaa acgccggcga ttaaatgatc tggacagtga tagcaacctg 3420
gatgaagaag agagcgagga tgaattcaag atcagtgatg gatctcaaga tgagtttgtt 3480
gtgtctgatg aaaacccaga tgaaagtgaa gaagatccgc catctaatga tgacagtgac 3540
actgactttt gtagccgtag actgaggcga caccccctctc ggccaatgag gcagagcagg 3600
cgtttgcgaa gaaagacccc aaagaaaaaa tattccgatg atgatgaaga ggaggaatct 3660
gaggagaata gtagagactc tgaaagtgac ttcagtgatg attttagtga tgattttgta 3720
gaaactcggc gaaggcggtc aaggagaaat cagaaaagac aaattaacta caaagaagac 3780
tcagaaagtg acggttccca gaagagtttg cgacgtggta aagaaataag gcgagtacac 3840
aagcgaagac tttccagctc agagagtgaa gagagctatt tgtccaagaa ctctgaagat 3900
gatgagctag ctaaagaatc aaagcggtca gttcgaaagc ggggccgaag cacagacgag 3960
tattcagaag cagatgagga ggaggaggaa gaggaaggca aaccatcccg caaacggcta 4020
caccggattg agacggatga ggaggagagt tgtgacaatg ctcatggaga tgcaaatcag 4080
cctgcccgtg acagccagcc tagggtcctg ccctcagaac aagagagcac caagaagccc 4140

```
taccggatag aaagtgatga ggaagaggac tttgaaaatg taggcaaagt ggggagccca   4200
ttggactata gcttagtgga cttaccttca accaatggac agagccctgg caaagccatt   4260
gagaacttga ttggcaagcc tactgagaag tctcagaccc ccaaggacaa cagcacagcc   4320
agtgcaagcc tagcctccaa tgggacaagt ggtgggcagg aggcaggagc accagaagag   4380
gaggaagatg agcttttgag agtgactgac cttgttgatt atgtctgtaa cagtgaacag   4440
ttataagact ttttttccat ttttgtgcta atttattcca cggtagctct cacaccagcg   4500
ggccagttat taaaagctgt ttaatttttc ctagaaaact ccactacaga atgactttta   4560
gaagaaaaat ttcaacaaat cctgaagtct ttctgtgaag tgaccagttc tgaactttga   4620
agataaataa ttgctgtaaa ttccttttga ttttcttttt ccaggttcat ggtccttggt   4680
aatttcattc atggaaaaaa atcttattat aataacaaca aagatttgta tatttttgac   4740
tttatatttc ctgagctctc ctgactttgt gaaaaagggt ggatgaaaat gcattccgaa   4800
tctgtgaggg cccaaaacag aatttagggg tgggtgaaag cacttgtgct ttagcttttt   4860
catattaaat atatattata tttaaacatt catggcatag atgatgattt acagacaatt   4920
taaaagttca agtctgtact gttacagttt gagaattgta gataacatca tacataagtc   4980
atttagtaac agcctttgtg aaatgaactt gtttactatt ggagataacc acacttaata   5040
aagaagagac agtgaaagta ccatcataat taacctaaat ttttgttata gcagagtttc   5100
ttgtttaaaa aaaaataaaa tcatctgaaa agcaaaaa                           5138
```

<210> SEQ ID NO 229
<211> LENGTH: 2317
<212> TYPE: DNA
<213> ORGANISM: Homo sapiens

<400> SEQUENCE: 229

```
cgcgctgcag tgccttcccc acctcggccc cgcccgcccc cgccgagccg agcaccaggg     60
cggcggcggc ggcggcggcg gcggcggcgg ctggagcagc ccgggaggag gaggcggcga    120
gaatggcagc ggcgtcgtgg gcgcggcgga gatgagcgcc cgcgaccccg ggcccagggc    180
ggcacagccg gagtgggcgg gggtcccgat gcaggcccga ggggggccat ggggcaggtc    240
ctgccggtct tcgcccactg caaagaagct ccgtctacag cctcctcaac tcctgattcc    300
acagaaggag ggaacgacga ctctgatttt cgagagctgc acacagcccg ggaattctca    360
gaggaggacg aggaggagac cacgtcgcag gactggggca ccccccggga gctgaccttc    420
tcctacatcg cctttgatgg tgtagtgggc tccgggggcc gcagggattc aactgcccgc    480
cgcccccgcc cccagggccg ctcagtctcg gaaccacgag accagcaccc tcagcccagc    540
ctgggcgaca gcttggagag catccccagc ctgagccaat ccccggagcc tggacgacgg    600
ggtgatcctg acaccgcgcc tccatccgag cgccctctgg aagacctgag gcttcggttg    660
gaccatctgg gctgggtggc ccggggaacg ggatccgggg aggactcttc caccagcagc    720
tccaccccgc tggaagacga agaaccccaa gaacccaaca gattggagac aggagaagct    780
ggggaagaac tggacctacg actccgactt gctcagccct catcgcccga ggtcttgact    840
ccccagctca gtccgggctc tgggacaccc caggccggta ctccgtcccc atcccgatcg    900
cgagattcga actctgggcc cgaagagcca ttgctggaag aggaagaaaa gcagtggggg    960
ccactggagc gagagccagt aaggggacag tgcctcgata gcacggacca attagaattc   1020
acggtggagc cacgccttct aggaacagct atggaatggt taaagacatc attgcttttg   1080
gctgtttaca agacggttcc aattttggaa ttgtccccac ctctgtggac agccattggc   1140
```

-continued

```
tgggtccaaa ggggccccac ccccccctact cctgtcctcc gggttctact gaagtgggca   1200

aaatccccga gaagcagcgg tgtccccagc ctctcactcg gagccgatat ggggagtaaa   1260

gtggcggacc tgctgtactg gaaggacacg aggacgtcag gagtggtctt cacaggcctg   1320

atggtctccc tcctctgcct cctgcacttt agcatcgtgt ccgtggccgc gcacttggct   1380

ctgttgctgc tctgcggcac catctctctc agggtttacc gcaaagtgct gcaggccgtg   1440

caccgggggg atggagccaa ccctttccag gcctacctgg atgtggacct caccctgact   1500

cgggagcaga cggaacgttt gtcccaccag atcacctccc gcgtggtctc ggcggccacg   1560

cagctgcggc acttcttcct ggtagaagac ctcgtggatt ccctcaagct ggccctcctc   1620

ttctacatct tgaccttcgt gggtgccatc ttcaatggtt tgactcttct cattctggga   1680

gtgattggtc tattcaccat ccccctgctg taccggcagc accaggctca gatcgaccaa   1740

tatgtggggt tggtgaccaa tcagttgagc cacatcaaag ctaagatccg agctaaaatc   1800

ccagggaccg gagccctggc ctctgcagca gccgcagtct ccggatccaa agccaaagcc   1860

gaatgagaac ggtgtctctg cccgcaggac gcctgccccc agcccccgca gccctctggc   1920

cccctccatc tcttgtccgt tcccacccac cccccctcctc ggcccgagcc ttttcccggt   1980

gggtgtcagg atcactccca ctagggactc tgcgctaatt acctgagcga ccaggactac   2040

atttcccaag aggctctgct ccaggagtcc aggaaagacg aggcaccttg gccgcggggc   2100

ctgctgggac ttgtagttgc ctagacaggg caccaccctg cacttccgga cccgccgctg   2160

gaggcgccgt gaggcgttgg tgtctcctgg atgctactag ccccaacgcc ggggctttgc   2220

atggggccca ggggaggcct gagcttggat ttacactgta ataaagactc ctgtggaaaa   2280

ccaaaaaaaa aaaaaaaaaa aaaaaaaaaa aaaaaaa                             2317
```

<210> SEQ ID NO 230
<211> LENGTH: 3181
<212> TYPE: DNA
<213> ORGANISM: Homo sapiens

<400> SEQUENCE: 230

```
aaacgcgcac gcgcaaatct agggcgacgc ttgacagagc ttgggagggt gcgcctgctt     60

tcgccctcct tctccagcgg gaggggcgcg cacttccgcg gggcggagtc cgtctagtgc    120

tgacgttggc agccgaaccc aaagtagatc gaggcggcgg gctgcacatt cccgttgttg    180

cgttgcgttt ccttcctctt tcactccgcg ctcacggcgg cggccaaagc ggcggcgacg    240

gcggcgcgag aacgacccgg cggccagttc tcttcctcct gcgcacctgc cccgctcggt    300

cagtcagtcg gcggccggcg cccggcttgt gctcagacct cgcgcttgcg gcgcccaggc    360

ccagcggccg tagctagcgt ctggcctgag aacctcggcg ctccggcggc gcgggcacca    420

cgagccgagc ctcgcagcgg ctccagagga ggcaggcgag tgagcgagtc cgaggggtgg    480

ccggggcagg tggtggcgcc gcgaagatgg tcgccaagca aaggatccgt atggccaacg    540

agaagcacag caagaacatc acccagcgcg gcaacgtcgc caagacctcg agaaatgccc    600

ccgaagagaa ggcgtctgta ggaccctggt tattggctct cttcattttt gttgtctgtg    660

gttctgcaat tttccagatt attcaaagta tcaggatggg catgtgaagt gactgacctt    720

aagatgtttc cattctcctg tgaattttaa cttgaactca ttcctgatgt ttgataccct    780

ggttgaaaac aattcagtaa agcatcctgc ctcagaatga ctttcctatc atgcttcatg    840

tgtcattcca aggtttcttc atgagtcatt ccaagttttc tagtccatac cacagtgcct    900
```

-continued

```
tgcaaaaaac accacatgaa taaagcaata aaatttgatt gttaagatac agtagtggac    960
cctacttatt cagtcaatta agagtaagtt tttttatgtg gttattaaaa cagtatgaac   1020
aattagtcta actctgcata gacagggtct agattttgtt aacccaaatg tataactgca   1080
gttagcttaa attacaattt gaagtcttgt ggtttttata tagctaggca ctttattact   1140
cttttgaact gaaagcacac tcccttatag gttcatgtaa ctgtcctgta ataaggtgct   1200
tataaatgga acaactacac agcctagttt tgccacaacc tttagcatct aaaaagtttt   1260
aaaagcttct aaatgtctaa tataaaggga gatgcttata gccacaacat ctattttacc   1320
aatattgttt ccattacact accttggatt ttgcatgagt gagtatagta acccaagatg   1380
ccataaaaaa aaaacttgat cgttttctga cttaatcagt tactgtggtt tcactaaaag   1440
ctaccgtggt ggagtgaagt cagtcaggga aggtttgttt atgttacatt tatttcacca   1500
gaactatttt aatatatcaa aggggtttac tatgccaaac aaaattctag ggaaaaatac   1560
tgctaaaaat ggatgcctca tcagaacatg ctgttgagtc caatgtgcca taagacattt   1620
tagcatgtta aatagcactt ttaatagcaa aaaaaggcac atcaactgcg aagttatcct   1680
tagtttgcaa atgctttttc tagattaatg atttttcaat cattagggta ctagacacat   1740
cagcctaaag tggcatctgg aattgaatgg atttactgat aatgatcagt ctttagtctt   1800
ccctttgtta tatgacttta taggttatga ttgatcaaat ttacgtttta ctaatggtaa   1860
gggtgagggt catagggcag gttttgggtt ttctagtact gttgaaaact gcaagtattg   1920
gctatttgta tacttagcca taacttggtg aaaaaaaacc tgagcagtgt ctatgtatta   1980
atgcgttgga aagaaagctg cttgtgtttg ctttgttaat tgcctcagga tatttctttt   2040
aaaataagct gttttaagag gaacagaagg gaaatctgct acctagtcta tacacagcgt   2100
gaacctcaca gggggcttct gataccctca aacatggaga acagtaaggg agcagagtgg   2160
ttaaggactt tcaggaactt aactattctg gaataaggaa tgaatcaact gaccttgggc   2220
cagcaggttt ttaactaaat tgttacttgc ctttctcacc cagttaatca gtctctgtac   2280
ttgtttccct ttttgaaaca agtgtcttgg ttaactaatt ctgttttatg gttgtgctaa   2340
attcatagca ggtgccttat tctttgcttt tagtcaaacc attccatatc agaattttcc   2400
ttggtttact atagatattt ggctttaagt tgttgtttgt gttttttaat gtacaatgtt   2460
ctgataaatt tgactgttaa attgctatag ctagcaatca ttttacatat gtaaaattgc   2520
attccctttg tatttcatgt gtaattcacc aattaagtgc agtttatatt caggttggat   2580
tatgcatgtt taggtaaacg aaagctgtgt cttacttgat ttattcttta aaaataaagt   2640
tccctgaata tttgatgctt ttcttctaaa cggaaatgat tttacagtta tctgagtgta   2700
ccttttatag ttagtagaaa atgattttaa agaatgttta gtattgtact taaatggtat   2760
gcagaggcac agatgtaagg tttataactg gaaataggtg gtaagaaaaa tatatagaaa   2820
gcacaatgat ttgaatattt ttccacttag gatttcctaa tctccttgtc atccaattca   2880
agctcaagat gaagcacaat tctttgatct ccctttgcca gttgaatttt atagatcatc   2940
taatgttgag cacagtatga gaataaatat tggggttgtc aacattactc agttactctt   3000
tgtggtttaa ctctaacatt tcaacaagtt gtcaattaat tgtatctgtt gggttgtata   3060
taatgttgct caaaataatt aagtggactt ccaaaaataa gatttccatt gtaacaggat   3120
gcattgtgat gggctttgac ttacattaaa gaaatgtgga tagtcaactg caaaaaaaaa   3180
a                                                                   3181
```

<210> SEQ ID NO 231
<211> LENGTH: 2714
<212> TYPE: DNA
<213> ORGANISM: Homo sapiens

<400> SEQUENCE: 231
agccgcgatg tgacgccgcg cgccccgggg tcctcggcgc ctgcgccctc tcctataaag 60
cagacgccgc gccgcgctgc gacgctgtag tggcttcgtc ttcggttttt ctcttccttc 120
gctaacgcct cccggctctc gtcagcctcc cgccggccgt ctccttaaca ccgaacacca 180
tgccttcaat taagttgcag agttctgatg gagagatatt tgaagttgat gtggaaattg 240
ccaaacaatc tgtgactatt aagaccatgt tggaagattt gggaatggat gatgaaggag 300
atgatgaccc agttcctcta ccaaatgtga atgcagcaat attaaaaaag gtcattcagt 360
ggtgcaccca ccacaaggat gaccctcctc ctcctgaaga tgatgagaac aaagaaaagc 420
gaacagatga tatccctgtt tgggaccaag aattcctgaa agttgaccaa ggaacacttt 480
ttgaactcat tctggctgca aactacttag acatcaaagg tttgcttgat gttacatgca 540
agactgttgc caatatgatc aaggggaaaa ctcctgagga gattcgcaag accttcaata 600
tcaaaaatga ctttactgaa gaggaggaag cccaggtagg tagcacacag ttttgtcttt 660
gatcacatgc tcttaaaaag ggagtaacac ctataacatg ccagcaaaag aggtgactgt 720
atcaagtagt cttgatactt tagggataat atgtacttaa tgtgtcttaa acatactctt 780
actgttctgt ctttatgaat ctgaacactt agatgatact gcattttaag cataagaaca 840
attagttttc aatgagaaga gctcttgtta atgtattaac agttactagt tttggcacct 900
gcaactttct gtatagacca tacatatctg acatcagaaa agcaggccct agagagaagt 960
atatactagg gtactttaga gcaacttaat gaggggagga aatgaaagaa tagatcagaa 1020
tgattttgtt gacatgacta cagactgaaa taatgtgaat gaattaactg aatttgctct 1080
gtcaacttta gtaaattgcc cattgccttt gctttgttca taatttcagc agggcagaat 1140
aaaaaccatg ggaggcaaag aaaggaaatc cggaaatata gtcttaacct ggtgttgttc 1200
taattttcca tctgttcttc tgactcaact cactggctat cgatgaatca gtaggtagta 1260
tttataagtc ttaggaaaga ctactcaagt taaggtactt ccctatatcc atctctttta 1320
ggtacgcaaa gagaaccagt ggtgtgaaga gaagtgaaat gttgtgcctg acactgtaac 1380
actgtaagga ttgttccaaa tactagttgc actgctctgt ttataattgt taatattaga 1440
caaacagtag acaaatgcag cagcaagtca attgtattag cagaatattg tcctcattgc 1500
atgtgtagtt tgagcacaga tcccaaacct tacggccaag tttcttctag tatgatggaa 1560
agtttctttt ttctttgctc tgaataaaac tgaactgtgg gttctctata agtggcattt 1620
tgggctttcc ctcttttttg taaagcaatg tctgcctagt ttattgtcca gttaacttta 1680
gtgacctttt aaaagttggc attgtaaata aaacaacttg caaaaaagtt ttctggaata 1740
gaattaacaa aatattatct ttattcatga gttggaaact ggaaaaaggc ttcttgaagt 1800
aaatgttctg agtggagcta ctaggatgtc ttccagcctc ctgcagtcaa ggagtaccac 1860
tgtattgatt agcctgtatg tagcagggct cccttcattg catctgagga cttgttttct 1920
ttttctttat ttttaatcct cttagtttta aatatattgc ctagagactc agttactacc 1980
cagtttgtgg ttttttggga gaaatgtaac tggacagtta gcttttcaat taaaaagaca 2040
cttaacccat gtgggatgtc atctttttat aattagtgtt cccatgtgga gaaaattatt 2100
cacactactt gcatgtaaag aataatttaa cttttaacat taaaatatgt ggtaaaaccc 2160
agaaagcatc catcatgaat gcaagatact ttcaataaaa agtaagttat atagtaggta 2220
gttaagtttg cttttgtgga cttaaatgtg tctcttcact taaatgggtt gaatgtgtat 2280
atatttgttc agcttgaaaa gacttagttt atatcctagc tcactggagg ctgctgacat 2340
aaccataact tctgtccctt ctaattgtca tttatatgcc taactggagc tagtacttta 2400
attcttaaca caaaattact ctgccattgt ttccagcttc cctcctacaa tagaatgaag 2460 ttttttgat ggcttgagat ggctcacaaa ttttgatttt tttttcttcc ttgtgctccc 2520
tttttttctc cttgcttttc cagttaacat ctatattcac atgtaatctt gttttctctt 2580
cacattcact gagttgttca ggctcagatc atcccttgac agtagtttgc cttcatctca 2640
cctttcattt gtcccaaatt caccttattt aataaagtcc catatgttgt ctcacttaaa 2700
aaaaaaaaaa aaaa 2714

<210> SEQ ID NO 232
<211> LENGTH: 1700
<212> TYPE: DNA
<213> ORGANISM: Homo sapiens

<400> SEQUENCE: 232
agcaggactc agaggggaga gttggaggaa aaaaaaaggc agaaaaggga aagaaagagg 60
aagagagaga gagagtgaga ggagccgctg agcccacccc gatggccgcg gacgaagttg 120
ccggaggggc gcgcaaagcc acgaaaagca aactttttga gtttctggtc catggggtgc 180
gccccgggat gccgtctgga gcccggatgc cccaccaggg ggcgcccatg ggccccccgg 240
gctccccgta catgggcagc cccgccgtgc gacccggcct ggcccccgcg ggcatggagc 300
ccgcccgcaa gcgagcagcg cccccgcccg ggcagagcca ggcacagagc cagggccagc 360
cggtgcccac cgcccccgcg cggagccgca gtgccaagag gaggaagatg gctgacaaaa 420
tcctccctca aaggattcgg gagctggtcc ccgagtccca ggcttacatg gacctcttgg 480
catttgagag gaaactggat caaaccatca tgcggaagcg ggtggacatc caggaggctc 540
tgaagaggcc catgaagcaa aagcggaagc tgcgactcta tatctccaac acttttaacc 600
ctgcgaagcc tgatgctgag gattccgacg gcagcattgc ctcctgggag ctacgggtgg 660
aggggaagct cctggatgat cccagcaaac agaagcggaa gttctcttct ttcttcaaga 720
gtttggtcat cgagctggac aaagatcttt atggccctga caaccacctc gttgagtggc 780
atcggacacc cacgacccag gagacggacg gcttccaggt gaaacggcct ggggacctga 840
gtgtgcgctg cacgctgctc ctcatgctgg actaccagcc tccccagttc aaactggatc 900
cccgcctagc ccggctgctg gggctgcaca cacagagccg ctcagccatt gtccaggccc 960
tgtggcagta tgtgaagacc aacaggctgc aggactccca tgacaaggaa tacatcaatg 1020
gggacaagta tttccagcag atttttgatt gtccccggct gaagttttct gagattcccc 1080
agcgcctcac agccctgcta ttgcccccctg acccaattgt catcaaccat gtcatcagcg 1140
tggacccttc agaccagaag aagacggcgt gctatgacat tgacgtggag gtggaggagc 1200
cattaaaggg gcagatgagc agcttcctcc tatccacggc caaccagcag gagatcagtg 1260
ctctggacag taagatccat gagacgattg agtccataaa ccagctcaag atccagaggg 1320
acttcatgct aagcttctcc agagacccca aaggctatgt ccaagacctg ctccgctccc 1380
agagccggga cctcaaggtg atgacagatg tagccggcaa ccctgaagag gagcgccggg 1440
ctgagttcta ccaccagccc tggtcccagg aggccgtcag tcgctacttc tactgcaaga 1500
tccagcagcg caggcaggag ctggagcagt cgctggttgt gcgcaacacc taggagccca 1560
aaaataagca gcacgacgga actttcagcc gtgtcccggg ccccagcatt ttgccccggg 1620
ctccagcatc actcctctgc caccttgggg tgtggggctg gattaaaagt cattcatctg 1680
acaaaaaaaa aaaaaaaaaa 1700

<210> SEQ ID NO 233
<211> LENGTH: 1935
<212> TYPE: DNA
<213> ORGANISM: Homo sapiens

<400> SEQUENCE: 233
acaatagcga ctcactggac ccagccctta gcaacggcct ggcgacggtt tccctgctgc 60
tgcagccccc gtcggctcct cttttccagt cctccactgc cggggctggg cccggccgcg 120
ggaaggaccg aaggggatac agcgtgtccc tgcggcggct gcaagaggac taagcatgga 180
tggcagccgg agagtcagag caacctctgt ccttcccaga tatggtccac cgtgcctatt 240
taaaggacac ttgagcacca aaagtaatgc tgcagtagac tgctcggttc cagtaagcgt 300
gagtaccagc ataaagtatg cagaccaaca acgaagagag aaactcaaaa aggaattagc 360
acaatgtgaa aaagagttca aattaactaa aactgcaatg cgagccaatt ataaaaataa 420
ttccaagtca ctttttaata ccttacaaaa gccctcaggc gaaccgcaaa ttgaggatga 480
catgttaaaa gaagaaatga atggattttc atcctttgca aggtcactag taccctcttc 540
agagagacta cacctaagtc tacataaatc cagtaaagtc atcacaaatg gtcctgagaa 600
gaactccagt tcctccccgt ccagtgtgga ttatgcagcc tccgggcccc ggaaactgag 660
ctctggagcc ctgtatggca gaaggcccag aagcacattc ccaaattccc accggtttca 720
gttagtcatt tcgaaagcac ccagtgggga tcttttggat aaacattctg aactcttttc 780
taacaaacaa ttgccattca ctcctcgcac tttaaaaaca gaagcaaaat ctttcctgtc 840
acagtatcgc tattatacac ctgccaaaag aaaaaaggat tttacagatc aacggataga 900
agctgaaacc cagactgaat taagctttaa atctgagttg gggacagctg agactaaaaa 960
catgacagat tcagaaatga acataaagca ggcatctaat tgtgtgacat atgatgccaa 1020
agaaaaaata gctcctttac ctttagaagg gcatgactca acatgggatg agattaagga 1080
tgatgctctt cagcattcct caccaagggc aatgtgtcag tattccctga agcccccttc 1140
aactcgtaaa atctactctg atgaagaaga actgttgtat ctgagtttca ttgaagatgt 1200
aacagatgaa attttgaaac ttggtttatt ttcaaacagg tttttagaac gactgttcga 1260
gcgacatata aaacaaaata aacatttgga ggaggaaaaa atgcgccacc tgctgcatgt 1320
cctgaaagta gacttaggct gcacatcgga ggaaaactcg gtaaagcaaa atgatgttga 1380
tatgttgaat gtatttgatt ttgaaaaggc tgggaattca gaaccaaatg aattaaaaaa 1440
tgaaagtgaa gtaacaattc agcaggaacg tcaacaatac caaaaggctt tggatatgtt 1500
attgtcggca ccaaaggatg agaacgagat attcccttca ccaactgaat tttcatgcc 1560 tatttataaa tcaaagcatt cagaaggggt tataattcaa caggtgaatg atgaaacaaa 1620
tcttgaaact tcaactttgg atgaaaatca tccaagtatt tcagacagtt taacagatcg 1680
ggaaacttct gtgaatgtca ttgaaggtga tagtgaccct gaaaaggttg agatttcaaa 1740
tggattatgt ggtcttaaca catcaccctc ccaatctgtt cagttctcca gtgtcaaagg 1800
cgacaataat catgacatgg agttatcaac tcttaaaatc atggaaatga gcattgagga 1860
ctgccctttg gatgtttaat cttcattaat aaatacctca aatggccagt aactcaaaaa 1920

-continued

```
aaaaaaaaaa aaaaa                                                  1935


<210> SEQ ID NO 234
<211> LENGTH: 4343
<212> TYPE: DNA
<213> ORGANISM: Homo sapiens

<400> SEQUENCE: 234

tggtcatcgc acggcggcag ctcctcacct ggatttagaa gagctggcgt ccccgcccgc     60

ccaagccttt aaactctcgt ctgccagaac ccgccaactc tccaggctta gggccagttt    120

ccgcgattct aagagtaatt gcgtgggcac ctgtgctggg gccaggcgca aagaagggag    180

ttggtctgcg cgaagatcgt caacctgcta acagaccgca catgcacttt gcaccgacca    240

tctacgtctc agtctggagg ttgcgcactt tggctgctga cgcgctggtg gtgcctatta    300

atcatttacc agtccagagc cgcgccagtt aatggctgtg ccgtgcggtg ctcccacatc    360

ctggcctctc ctctccacgg tcgcctgtgc ccgggcaccc cggagctgca aactgcagag    420

cccaggcaac cgctgggctg tgcgccccgc cggcgccggt aggagccgcg ctccccgcag    480

cggttgcgct ctacccggag gcgctgggcg gctgtgggct gcaggcaagc ggtcgggtgg    540

ggagggaggg cgcaggcggc gggtgcgcga ggagaaagcc ccagccctgg cagccccact    600

ggccccccctc agctgggatg ttccccaatg gcaccgcctc ctctccttcc tcctctccta    660

gccccagccc gggcagctgc ggcgaaggcg gcggcagcag gggccccggg gccggcgctg    720

cggacggcat ggaggagcca gggcgaaatg cgtcccagaa cgggaccttg agcgagggcc    780

agggcagcgc catcctgatc tctttcatct actccgtggt gtgcctggtg gggctgtgtg    840

ggaactctat ggtcatctac gtgatcctgc gctatgccaa gatgaagacg gccaccaaca    900

tctacatcct aaatctggcc attgctgatg agctgctcat gctcagcgtg cccttcctag    960

tcacctccac gttgttgcgc cactggccct tcggtgcgct gctctgccgc ctcgtgctca   1020

gcgtggacgc ggtcaacatg ttcaccagca tctactgtct gactgtgctc agcgtggacc   1080

gctacgtggc cgtggtgcat cccatcaagg cggcccgcta ccgccggccc accgtggcca   1140

aggtagtaaa cctgggcgtg tgggtgctat cgctgctcgt catcctgccc atcgtggtct   1200

tctctcgcac cgcggccaac agcgacggca cggtggcttg caacatgctc atgccagagc   1260

ccgctcaacg ctggctggtg ggcttcgtgt tgtacacatt tctcatgggc ttcctgctgc   1320

ccgtgggggc tatctgcctg tgctacgtgc tcatcattgc taagatgcgc atggtggccc   1380

tcaaggccgg ctggcagcag cgcaagcgct cggagcgcaa gatcacctta atggtgatga   1440

tggtggtgat ggtgtttgtc atctgctgga tgcctttcta cgtggtgcag ctggtcaacg   1500

tgtttgctga gcaggacgac gccacggtga gtcagctgtc ggtcatcctc ggctatgcca   1560

acagctgcgc caaccccatc ctctatggct ttctctcaga caacttcaag cgctctttcc   1620

aacgcatcct atgcctcagc tggatggaca acgccgcgga ggagccggtt gactattacg   1680

ccaccgcgct caagagccgt gcctacagtg tggaagactt ccaacctgag aacctggagt   1740

ccggcggcgt cttccgtaat ggcacctgca cgtcccggat cacgacgctc tgagcccggg   1800

ccacgcaggg gctctgagcc cgggccacgc aggggccctg agccaaaaga gggggagaat   1860

gagaagggaa ggccgggtgc gaaagggacg gtatccaggg cgccagggtg ctgtcgggat   1920

aacgtggggc taggacactg acagcctttg atggaggaac ccaagaaagg cgcgcgacaa   1980

tggtagaagt gagagctttg cttataaact gggaaggctt tcaggctacc tttttctggg   2040

tctcccactt tctgttcctt cctccactgc gcttactcct ctgaccctcc ttctattttc   2100
```

```
cctaccctgc aacttctatc ctttcttccg caccgtcccg ccagtgcaga tcacgaactc   2160
attaacaact cattctgatc ctcagcccct ccagtcgtta tttctgtttg tttaagctga   2220
gccacggata ccgccacggg tttccctcgg cgttagtccc tagccgcgcg gggccgctgt   2280
ccaggttctg tctggtgccc ctactggagt cccgggaatg accgctctcc ctttgcgcag   2340
ccctacctta aggaaagttg gacttgagaa agatctaagc agctggtctt ttctcctact   2400
cttgggtgaa ggtgcatctt tccctgccct cccctgtccc cctctcgccg cccgcccgcc   2460
accaccactc tcactccacc cagagtagag ccaggtgctt agtaaaatag gtcccgcgct   2520
tcgaactcca ggctttctgg agttcccacc caagccctcc tttggagcaa agaaggagct   2580
gagaacaagc cgaatgagga gtttttataa gattgcgggg tcggagtgtg ggcgcgtaat   2640
aggaatcacc ctcctactgc gcgttttcaa agaccaagcg ctgggcgctc ccgggccgcg   2700
cgtctgcgtt aggcagggca gggtagtgca gggcacacct tccccggggt tcggggttcg   2760
gggttcggtt gcagggctgc agcccgcctt ggctttctcc ctcacccaag tttccggagg   2820
agccgaccta aaagtaacaa tagataaggt ttcctgctcc agtgtatctc aaaagaccgg   2880
gcgccagggg cgggggacct agggcgacgt cttcagagtc cgccagtgtt ggcggtgtcg   2940
ccgcaacctg caggctcccg agtggggcct gcctggtctc tagagggttg ctgcctttca   3000
agcggtgcct aagaagttat tttcttgttt aacatatata tttattaatt tatttgtcgt   3060
gttggaaaat gtgtctctgc tttccttttc tctgcttgcc tagccccagg tcttttcttt   3120
gggaccctgg gggcgggcat ggaagtggaa gtaggggcaa gctcttgccc cactccctgg   3180
ccatctcaac gcctctcctc aatgctgggc cctcttatct catcctttcc tctagctttt   3240
ctatttttga ttgtgttgag tgaagtttgg agatttttca tacttttctt actatagtct   3300
cttgtttgtc ttattaggat aatacataaa tgataatgtg ggttatcctc ctctccatgc   3360
acagtggaaa gtcctgaact cctggctttc caggagacat atatagggga acatcaccct   3420
atatataatt tgagtgtata tatatttata tatatgatgt ggacatatgt atacttatct   3480
tgctccattg tcatgagtcc atgagtctaa gtatagccac tgatggtgac aggtgtgagt   3540
ctggctggaa cactttcagt ttcaggagtg caagcagcac tcaaacctgg agctgaggaa   3600
tctaattcag acagagactt taatcactgc tgaagatgcc cctgctccct ctgggttcca   3660
gcagaggtga ttcttacata tgatccagtt aacatcatca cttttttga ggacattgaa   3720
agtgaaataa tttgtgtctg tgtttaatat taccaactac attggaagcc tgagcagggc   3780
gaggaccaat aattttaatt atttatattt cctgtattgc tttagtatgc tggcttgtac   3840
atagtaggca ctaaatacat gtttgttggt tgattgttta agccagagtg tattacaaca   3900
atctggagat actaaatctg ggttctcag gttcactcat tgacatgata tacaatggtt   3960
aaaatcacta ttgaaaaata cgttttgtgt atatttgctt caacaacttt gtgctttcct   4020
gaaagcagta accaagagtt aagatatccc taatgttttg cttaaactaa tgaacaaata   4080
tgctttgggt cataaatcag aaagtttaga tctgtccctt aataaaaata tatattacta   4140
ctcctttgga aaatagattt ttaatggtta agaactgtga aatttacaaa tcaaaatctt   4200
aatcattatc cttctaagag gatacaaatt tagtgctctt aacttgttac cattgtaata   4260
ttaactaaat aaacagatgt attatgctgt taaaaaaaaa aaaaaaaaaa aaaaaaaaaa   4320
aaaaaaaaaa aaaaaaaaaa aaa                                           4343
```

<210> SEQ ID NO 235

<211> LENGTH: 2123
<212> TYPE: DNA
<213> ORGANISM: Homo sapiens

<400> SEQUENCE: 235
cgcatctctc atcactcccc ctcattctgc ctttcctcct actcacggtc tcctctccct 60
ctccctctct ctctctcccc ctccctcttt ctctctctct ctctttctcc acctcctccc 120
gacccccttt cccctctatt tctattggct tctgtgtccc ttgctcccct cttctcttcc 180
tcaccctggg aagcttctcc cccctatcct tgcccctgcc cccccaggat gtgtcctgga 240
gatggggggt gacgtaccag gctctggttg ggaagtcagg gccggagacc agatgggaga 300
ggctctgtgg acagccgtgg ccgagggcct gggagggaac ctgagcccgc aagcggtcta 360
gaagtgggtg ccgtgtgggg accctagtta ggagtgccct gggggcacct ggggactggg 420
cagggagagg ggacagcaga atgataacca gcctggcggc aaggagggaa gccctcaccc 480
catgggcagg caaatagctg actgctgacc accctcccct cagccatgga catgcttcat 540
ccatcatcgg tgtccacgac ctcagaacct gagaatgcct cctcggcctg gcccccagat 600
gccaccctgg gcaacgtgtc ggcgggccca agcccggcag ggctggccgt cagtggcgtt 660
ctgatccccc tggtctacct ggtggtgtgc gtggtgggcc tgctgggtaa ctcgctggtc 720
atctatgtgg tcctgcggca cacggccagc ccttcagtca ccaacgtcta catcctcaac 780
ctggcgctgg ccgacgagct cttcatgctg gggctgccct tcctggccgc ccagaacgcc 840
ctgtcctact ggcccttcgg ctccctcatg tgccgcctgg tcatggcggt ggatggcatc 900
aaccagttca ccagcatatt ctgcctgact gtcatgagcg tggaccgcta cctggccgtg 960
gtacatccca cccgctcggc ccgctggcgc acagctccgg tggcccgcac ggtcagcgcg 1020
gctgtgtggg tggcctcagc cgtggtggtg ctgcccgtgg tggtcttctc gggagtgccc 1080
cgcggcatga gcacctgcca catgcagtgg cccgagccgg cggcggcctg gcgagccggc 1140
ttcatcatct acacggccgc actgggcttc ttcgggccgc tgctggtcat ctgcctctgc 1200
tacctgctca tcgtggtgaa ggtgcgctca gctgggcgcc gggtgtgggc accctcgtgc 1260
cagcggcggc ggcgctccga acgcagggtc acgcgcatgg tggtggccgt ggtggcgctc 1320
ttcgtgctct gctggatgcc cttctacgtg ctcaacatcg tcaacgtggt gtgcccactg 1380
cccgaggagc ctgccttctt tgggctctac ttcctggtgg tggcgctgcc ctatgccaac 1440
agctgtgcca accccatcct ttatggcttc ctctcctacc gcttcaagca gggcttccgc 1500
agggtcctgc tgcggccctc ccgccgtgtg cgcagccagg agcccactgt ggggcccccg 1560
gagaagactg aggaggagga tgaggaggag gaggatgggg aggagagcag ggagggggc 1620 aaggggaagg agatgaacgg ccgggtcagc cagatcacgc agcctggcac cagcgggcag 1680
gagcggccgc ccagcagagt ggccagcaag gagcagcagc tcctacccca agaggcttcc 1740
actggggaga agtccagcac gatgcgcatc agctacctgt agggcctggg gaaagccagg 1800
atggcccgag gaagaggcag aagccgtggg tgtgcctagg gcctacttcc caaggtgcca 1860
caggcccatg atgggatgtt gaggggcctg gactttgatg ctattgctgc caggtcttgc 1920
tgtgtgacct tgggtaggtt gcttctactc tctgggcctt gttttctcct ctgtgactca 1980
gggataggag tcatcagcct ggatgagcta tgtcagatga gaggtttgga gggcactgtt 2040
gctgggctga cctggctgag caggcaaaag gtgggtgcag actggcctcc ccccagggat 2100
ggagtgtctt ggggcatcaa cta 2123

<210> SEQ ID NO 236
<211> LENGTH: 1258
<212> TYPE: DNA
<213> ORGANISM: Homo sapiens

<400> SEQUENCE: 236
ccgagctctc tggcgcagcg ctagctccgc cgcgctcagc tgccctgcgc cggcacccct 60
ggtcatgagc gccccctcga cgctgccccc cgggggcgag gaagggctgg ggacggcctg 120
gccctctgca gccaatgcca gtagcgctcc ggcggaggcg gaggaggcgg tggcggggcc 180
cggggacgcg cgggcggcgg gcatggtcgc tatccagtgc atctacgcgc tggtgtgcct 240
ggtggggctg gtgggcaacg ccctggtcat cttcgtgatc cttcgctacg ccaagatgaa 300
gacggctacc aacatctacc tgctcaacct ggccgtagcc gacgagctct tcatgctgag 360
cgtgcccttc gtggcctcgt cggccgccct gcgccactgg cccttcggct ccgtgctgtg 420
ccgcgcggtg ctcagcgtcg acggcctcaa catgttcacc agcgtcttct gtctcaccgt 480
gctcagcgtg gaccgctacg tggccgtggt gcaccctctg cgcgcggcga cctaccggcg 540
gcccagcgtg gccaagctca tcaacctggg cgtgtggctg gcatccctgt tggtcactct 600
ccccatcgcc atcttcgcag acaccagacc ggctcgcggc ggccaggccg tggcctgcaa 660
cctgcagtgg ccacacccgg cctggtcggc agtcttcgtg gtctacactt tcctgctggg 720
cttcctgctg cccgtgctgg ccattggcct gtgctacctg ctcatcgtgg gcaagatgcg 780
cgccgtggcc ctgcgcgctg gctggcagca gcgcaggcgc tcggagaaga aaatcaccag 840
gctggtgctg atggtcgtgg tcgtctttgt gctctgctgg atgcctttct acgtggtgca 900
gctgctgaac ctcttcgtga ccagccttga tgccaccgtc aaccacgtgt cccttatcct 960
tagctatgcc aacagctgcg ccaaccccat tctctatggc ttcctctccg acaacttccg 1020
ccgattcttc cagcgggttc tctgcctgcg ctgctgcctc ctggaaggtg ctggaggtgc 1080
tgaggaggag cccctggact actatgccac tgctctcaag agcaaaggtg gggcagggtg 1140
catgtgcccc ccactcccct gccagcagga agccctgcaa ccagaacccg gccgcaagcg 1200
catccccctc accaggacca ccaccttctg aggagccctt cccctaccca ccctgcgt 1258

<210> SEQ ID NO 237
<211> LENGTH: 2674
<212> TYPE: DNA
<213> ORGANISM: Homo sapiens

<400> SEQUENCE: 237
atgcctgcat gtgctggttc agggactcac caccctggcg tcctcccttc ttctcttgca 60
gagcctgacg caccccaggg ctgccgccat ggagcccctg ttcccagcct ccacgcccag 120
ctggaacgcc tcctccccgg gggctgcctc tggaggcggt gacaacagga cgctggtggg 180
gccggcgccc tcggcagggg cccgggcggt gctggtgccc gtgctgtacc tgctggtgtg 240
tgcggccggg ctgggcggga acacgctggt catctacgtg gtgctgcgct tcgccaagat 300
gaagaccgtc accaacatct acattctcaa cctggcagtg gccgacgtcc tgtacatgct 360
ggggctgcct ttcctggcca cgcagaacgc cgcgtccttc tggcccttcg gccccgtcct 420
gtgccgcctg gtcatgacgc tggacggcgt caaccagttc accagtgtct tctgcctgac 480
agtcatgagc gtggaccgct acctggcagt ggtgcacccg ctgagctcgg cccgctggcg 540
ccgcccgcgt gtggccaagc tggcgagcgc cgcggcctgg gtcctgtctc tgtgcatgtc 600
gctgccgctc ctggtgttcg cggacgtgca ggagggcggt acctgcaacg ccagctggcc 660
ggagcccgtg gggctgtggg gcgccgtctt catcatctac acggccgtgc tgggcttctt 720
cgcgccgctg ctggtcatct gcctgtgcta cctgctcatc gtggtgaagg tgagggcggc 780
gggcgtgcgc gtgggctgcg tgcggcggcg ctcggagcgg aaggtgacgc gcatggtgtt 840
ggtggtggtg ctggtgtttg cgggatgttg gctgcccttc ttcaccgtca acatcgtcaa 900
cctggccgtg gcgctgcccc aggagcccgc ctccgccggc ctctacttct tcgtggtcat 960
cctctcctac gccaacagct gtgccaaccc cgtcctctac ggcttcctct ctgacaactt 1020
ccgccagagc ttccagaagg ttctgtgcct ccgcaagggc tctggtgcca aggacgctga 1080
cgccacggag ccgcgtccag acaggatccg gcagcagcag gaggccacgc cacccgcgca 1140
ccgcgccgca gccaacgggc ttatgcagac cagcaagctg tgagagtgca ggcgggggt 1200 gggcggcccc gtgtcacccc caggagcgga ggttgcactg cggtgacccc cacccatgac 1260
ctgccagtca ggatgctccc cggcggtggt gtgaggacag agctggctga agccaggctg 1320
gggtagacac agggcagtag gttccccacc gtgaccgacc atcccctcta accgtctgcc 1380
acacagcggg ggctcccggg aggtagggga ggtggccaga ccggtggggg gctccgccat 1440
gccgtgcaag tgctcagggc cgcctcaccc tccatctggc cccagcccat gccggccttc 1500
cctctgggga gcgacttttc cagaaggccg gccaggcgag agggtcttcc tgacggcgga 1560
gctgacctgc ccggcccacc agctgcatgt cagctccgag ccaccgggtc cccgtccaag 1620
gctgctctgc taagttaaag acacccgaaa gcgcttgact caggtccccg gagtccctgg 1680
ccagggcccc agcccctcgc ttgccctgca ctgtgtggac tctggggatg caggtgtaag 1740
gggagtgtgg ctgggcagcc cctggtcagc cagggtcacg cctgtcctgg gggccccacc 1800
ctgctgcccg acaccccca tgggaggctg cgggcggcag ttgctgtctc agagagggga 1860
gtgtgggggc ttgggcgctg gcctagccag gggcgaggtg gggaggcggc tggtgcagag 1920
gagagctggg ggctgaggtt ggggtgaagg ctgcagccct ccaggctgct gggggtgcag 1980
atggctgtgc cgtgctgaga ttggctctgt ctggaggggt ccagtgtggg gtgcctgagg 2040
gcactaggga gaggtgctcc tgctgcagga ggacctgagg gtcagggctt ggagaggaca 2100
gggaacctgc ggccgtctct tctgctttgg ggcaggggct ctggcccggg agagggaacg 2160
gggacaggag cagaggacgg tcatccaggc gcagcgggga gctgctcccc aggccacagc 2220
agacagcact gctgagaggc agcggccgcg cgggtgacgc aaatggcagg ccctgggaat 2280
cccgccgcct cccacctaga attgtcctac ctcccccacc ccaaacacca gcttttcctg 2340
gcgccccagg cccagaacgt gggcccagag agccttgctg gggtctctgg ggcaccttgg 2400
ccttgctctg aggctggaag gagaaggacc agggtgcggc atcactcggc ctcagggacc 2460
cctctgccct gcccagcact ggccccgacc cgtgctcccg ccgtctgccc agagcaggac 2520
ctcaacctcc tggagggcac agggagcggc tgagtgggca caaatcctgg caggagaaag 2580
gcccaggctg aggccaggcc tgggaaacat ccaagcagtg aggacacgcg tgtttgacaa 2640
ctgctcccct gaataaatgc gaggataaat gttt 2674

<210> SEQ ID NO 238
<211> LENGTH: 4427
<212> TYPE: DNA
<213> ORGANISM: Homo sapiens

<400> SEQUENCE: 238
cccccggcgg agccagctgc tgctcttcgg tgctggcccc ggtgccggcc ccgttgccca 60
gggaacaggc tcccggcagc cccgcggcc cggagtccat cccgcctcct ccggcccggc 120

```
ggggccgacg agtccggagg ggctgccgcg ggagccccca ggtttcccta gatgacaaat    180
aaacattcct tttcctgcgt gaagatagtc tgtggaaacc ttggccatgg catcgatatc    240
agagcctgtt acattcagag agttctgccc gttgtactat ctcctcaatg ccattccgac    300
aaagatccag aagggtttcc gctctatcgt ggtctatctc acggccctcg acaccaacgg    360
ggactacatc gcggtgggca gcagcatcgg catgctctat ctgtactgcc ggcacctcaa    420
ccagatgagg aagtacaact ttgaggggaa gacggaatct atcactgtgg tgaagctgct    480
gagctgcttt gatgacctgg tggcagcagg cacagcctct ggcagggttg cagtttttca    540
acttgtatct tcattgccag ggagaaataa acagcttcgg agatttgatg tcactggtat    600
tcacaaaaat agcattacag ctctggcttg gagccccaat ggaatgaaat tgttctctgg    660
agatgacaaa ggcaaaattg tttattcttc tctggatcta gaccaggggc tctgtaactc    720
ccagctggtg ttggaggagc catcttccat tgtgcagctg gattatagcc agaaagtgct    780
gctggtctct actctgcaaa gaagtctgct cttttacact gaagaaaagt ctgtaaggca    840
aattggaaca caaccaagga aaagtactgg gaaatttggt gcttgtttta taccaggact    900
ctgtaagcaa agtgatctaa ccttgtatgc gtcacggccc gggctccggc tatggaaggc    960
tgatgtccac gggactgttc aagccacgtt tatcttaaaa gatgcttttg ccgggggagt   1020
caagcctttt gaactgcacc cgcgtctgga atcccccaac agtggaagtt gcagcttacc   1080
tgagaggcac ctggggcttg tttcatgttt ctttcaagaa ggctgggtgc tgagttggaa   1140
tgaatatagt atctatctcc tagacacagt caaccaggcc acagttgctg gtttggaagg   1200
atccggtgat attgtgtctg tttcgtgcac agaaaatgaa atatttttct tgaaaggaga   1260
taggaacatt ataagaattt caagcaggcc tgaaggatta acatcaacag tgagagatgg   1320
tctggagatg tctggatgct cagagcgtgt ccacgtgcag caagcggaga agctgccagg   1380
ggccacagtt tctgagacga ggctcagagg ctcttccatg gccagctccg tggccagcga   1440
gccaaggagc aggagcagct cgctcaactc caccgacagc ggctccgggc tcctgccccc   1500
tgggctccag gccacccctg agctgggcaa gggcagccag cccctgtcac agagattcaa   1560
cgccatcagc tcagaggact ttgaccagga gcttgtcgtg aagcctatca aagtgaaaag   1620
gaagaagaag aagaagaaga cagaaggtgg aagcaggagc acctgtcaca gctccctgga   1680
atcgacaccc tgctccgaat ttcctgggga cagtccccag tccttgaaca cagacttgct   1740
gtcgatgacc tcaagtgtcc tgggcagtag cgtggatcag ttaagtgcag agtctccaga   1800
ccaggaaagc agcttcaatg gtgaagtgaa cggtgtccca caggaaaata ctgaccccga   1860
aacgtttaat gtcctggagg tgtcaggatc aatgcctgat tctctggctg aggaagatga   1920
cattagaact gaaatgccac actgtcacca tgcacatggg cgggagctgc tcaatggagc   1980
gagggaagat gtgggaggca gtgatgtcac gggactcgga gatgagccgt gtcctgcaga   2040
tgatggacca aatagcacac agttaccctt ccaagaacag gacagctctc ctggggcgca   2100
tgatggggaa gacatccaac ccattggccc ccaaagcact ttttgtgaag tcccccctcct   2160
gaactcactc actgtgcctt ccagcctcag ctgggcccca agtgctgaac agtggctgcc   2220
tgggaccaga gctgatgaag gcagccccgt ggagcccagc caagagcagg acatcctaac   2280
cagcatggag gcctctggcc acctcagcac aaatctctgg catgctgtca ctgatgatga   2340
cacaggtcag aaagaaatac ccatttctga acgtgtcttg gggagtgtgg gaggacagct   2400
gactccggtc tctgccttgg cagccagcac tcacaagccc tggcttgagc agcctccacg   2460
```

ggatcagaca ttgacgtcca gcgatgagga ggacatctat gcccacgggc ttccttcttc 2520
atcctcagag acgagtgtga cagagctcgg acctagttgc tcccagcagg acctgagccg 2580
gctgggtgca gaggacgccg ggctgctcaa gccagatcag tttgcagaaa gctggatggg 2640
ctactcgggt cccggctatg gcatcctcag cttggtggtc tccgagaagt atatctggtg 2700
cctggactac aaaggcggcc tgttctgcag cgcgttgccg ggcgccgggc tgcgctggca 2760
gaagtttgaa gatgctgtcc agcaggtggc agtctcgccc tcaggagccc ttctctggaa 2820
gattgaacag aaatctaacc gggcttttgc ttgtgggaaa gtcaccatca aggggaagcg 2880
gcactggtac gaagccctgc cccaggcagt gtttgtggcc ctgagcgatg acacggcctg 2940
gatcatcagg accagtgggg acctatactt gcagacaggt ctgagcgtgg atcgcccttg 3000
tgccagagcc gtaaaggtgg actgtcccta cccgctgtcc cagatcacag cccggaacaa 3060
tgtggtgtgg gcgctgacag agcagagggc cctcctgtac cgggagggcg tgagcagctt 3120
ctgtccggaa ggcgagcagt ggaagtgtga cattgtcagc gaaaggcaag ctttagaacc 3180
cgtctgcata acgctcgggg atcagcagac tctctgggcc ctggacatcc atgggaacct 3240
gtggttcaga actggcatta tttccaagaa gccccaagga gatgacgacc attggtggca 3300
agtgagcatc acggactatg tggtgtttga ccagtgcagc ttatttcaga cgataatcca 3360
tgccactcac tcggtggcca cagcagccca agcccccgta gaaaaggtgg cagataagct 3420
gcgcatggcg ttttggtccc agcagcttca gtgccagcca agccttctcg ggtcaataa 3480 cagcggtgtc tggatctcct cgggcaagaa tgaattccac gtcgctaagg gaagtctcat 3540
aggcacctac tggaatcatg tggttccccg tgggacagct tctgctacaa aatgggcctt 3600
tgtgttggct tctgcagctc ccacgaagga aggaagcttc ctgtggctgt gccagagcag 3660
caaggacctg tgcagcgtca gcgcccagag cgcacagtcg cggccctcca cggtgcagct 3720
gcctcccgaa gccgagatgc gcgcctatgc cgcctgccag gatgcgctgt gggcgctgga 3780
cagcctcggc caggtgttca tcaggacgct ctccaagagc tgccccacgg gcatgcactg 3840
gaccaggctg gacctctccc agctaggagc tgtaaaattg acaagcttgg catgtggaaa 3900
tcagcacatc tgggcctgtg attccagggg tggagtttac ttccgtgtag ggactcagcc 3960
tctcaatccc agtctcatgc ttccagcctg gataatgatt gagccacctg tccaggtaag 4020
cagaagttag ctggtggaac tcactcttca gtaagacaga aactgtgagg atgctggtac 4080
tgggaaaaag gatctgcaca gcctctagag gcctcccagc aaatgcgggg agccatgccc 4140
ccagggtcta cacactctcg ttcatcaaca tcacaactgg aattcgggat ttgtgaagtt 4200
tagagctgaa cagactgtta cagattatga gtcaacacgt atattttctc tttcaaaata 4260
ataatatttc gtttttgact ttttactaag tgaatattat tttttaaatc tgcctatata 4320
ttggaacctc tattttataa taataatgat aataaatcag tacccagaag tataaagaag 4380
gtaaaagtta ctttgaaaaa aaaaaaaaaa aaaaaaaaaa aaaaaaa 4427

<210> SEQ ID NO 239
<211> LENGTH: 4538
<212> TYPE: DNA
<213> ORGANISM: Homo sapiens

<400> SEQUENCE: 239
agcagagaga acacacgtcc ttgcggaagt gacggcagtt ccgagtccag tgggggcggt 60
gggagcgatg agggtctgag acggtgggag cggttgtgtg aagatggagt ttcccggagg 120
aaatgacaat tacctgacga tcacagggcc ttcgcacccc ttcctgtcag ggccgagac 180

```
attccataca ccaagcttgg gtgatgagga atttgaaatc ccacctatct ccttggattc    240
tgatccctca ttggctgtct cagatgtggt tggccacttt gatgacctgg cagacccttc    300
ctcttcacag gatggcagtt tttcagccca gtatggggtc cagacattgg acatgcctgt    360
gggcatgacc catggcttga tggagcaggg cggggggctc ctgagtgggg gcttgaccat    420
ggacttggac cactctatag gaactcagta tagtgccaac ccacctgtta caattgatgt    480
accaatgaca gacatgacat ctggcttgat ggggcatagc cagttgacca ccattgatca    540
gtcagaactg agttcccagc tgggtttgag cctagggggt ggcaccatcc tgccacctgc    600
ccagtcacct gaagatcgtc tttcaaccac cccttcacct actagttcac ttcacgagga    660
tggtgttgag gatttccgga ggcaacttcc cagccagaag acagtcgtgg tggaagcagg    720
gaaaaagcag aaggccccaa agaagagaaa aaagaaagat cctaatgaac ctcagaaacc    780
agtttcagca tatgctttat tctttcgtga tacacaggct gccatcaagg gacagaatcc    840
taatgccact tttggtgagg tttcaaaaat tgtggcctcc atgtgggata gtcttggaga    900
ggagcaaaaa caggtatata agaggaaaac tgaggctgcc aagaaagagt atctgaaggc    960
actggctgct tacaaagaca accaggagtg tcaggccact gtggaaacag tggaattgga   1020
tccagcacca ccatcacaaa ctccttctcc acctcctatg gctactgttg acccagcatc   1080
tccagcacca gcttcaatag agcccctgc cctgtcccca tccattgttg ttaactccac   1140
cctttcatcc tatgtggcaa accaggcatc ttctggagct gggggtcagc ccaatatcac   1200
caagttgatt attaccaaac aaatgttgcc ctcttctatt actatgtctc aaggagggat   1260
ggttactgtt atcccagcca cagtggtgac ctcccggggg ctccaactag gccaaaccag   1320
tacagctact atccagccca gtcaacaagc ccagattgtc actcggtcag tgttgcaggc   1380
agcagcagct gctgctgctg ctgcttctat gcaactgcct ccaccccgac tacagccccc   1440
tccattacaa cagatgccac agcccccgac tcagcagcaa gttaccattc tgcagcagcc   1500
tcctccactc caggccatgc aacagcctcc acctcagaaa gttcgaatca atttacagca   1560
acagcctcct cctctgcaga tcaagagtgt gcctctaccc actttgaaaa tgcagactac   1620
cttagtccca ccaactgtgg aaagtagtcc tgagcggcct atgaacaaca gccctgaggc   1680
ccatacagtg gaggcacctt ctcctgagac tatctgtgag atgatcacag atgtagttcc   1740
tgaggttgag tctccttctc agatggatgt tgaattggtg agtgggtctc ctgtggcact   1800
ctcaccccag cctcgatgtg tgaggtctgg ttgtgagaac cctcccattg tgagtaagga   1860
ctgggacaat gaatactgca gcaatgagtg tgtggtgaag cactgcaggg atgtattctt   1920
ggcctgggta gcctctagaa attcaaacac agtggtgttt gtgaaatagt ccttcctgtt   1980
ctccaagcca gtgaagagtt atctgctggg aaagtgtcca agagcctgtt tttgaaacac   2040
aagctgggct tctggtagtg cctcatcaca acccatgatg gctgttcatg tttcacccct   2100
tttcttcctt cagcagaggc caggctatgg agcagggcca ctgaatttgc tgtaatctgg   2160
agatgctttt tactttcaac cataagcggt aatagcagag gaaagggtga agggagtctg   2220
ggcaagcaaa gcatagagat ggtggggtgg tggtggggtt gaagaaactt gttggtataa   2280
ttgtcatagg acttgcctaa aatattatta aaattacggg agtgtactca gctttgagcc   2340
taggagaaaa tgccactgtg tgcatccatt ttaaagggtt ccctcataaa aaaatgttat   2400
tccccattat cacatcagta cactgctttg aaaacaaaac ttttcaacat gggcatactg   2460
ggctacatgg aaaatgacat cacccaggag tgatttctct ttatatatat tatttctgca   2520
```

```
gttaccatcc ttatctgagt tatcacagtt catgaatcta agaggcggaa ctctacatca   2580
ttagtaagag gttccaccaa agtctaaagt tgtattcact tgtgtttgat gaactatctt   2640
taaaagacca taggtctatc attatttctt agacataatc taaagaaaaa cagactagag   2700
aagccacctg gttgtaacag aataagcaga agtttacagc atgatagtcc aagtggtgat   2760
aactttaaat aaaactcaaa tttttactgt ttgtagacag gaatgctgtc ctagagaacc   2820
tcctcctcaa ccagctacgt acatagtttt atcctatgca ttcctgtttt ctgtgttttt   2880
tgtttttttt ttttgagaca gagtctcgct ctgtcaccca ggctggagtg cagtggtgcg   2940
acctcagctc actgaaacct ctgcctcccg ggttcaagcg attctcctgc atcagcctcc   3000
cgagtagcta ggattacagg cgcccgccac tacgcccagc taatttgtgg tatttttagt   3060
agagacaggg tttcaccatg ttggccaggc tggtctcgaa ctcctgacct catgatccgc   3120
ccgccttgac ctcccaaagt gctgggatta caggcatgag ccaccgcacc cagcctgcat   3180
tcctgttttt ttaatggttt tggagggtag cagtagagat ggggtctcac tatgttgccc   3240
agtctagtct tgaactcctg ggctacagtt accctcctac ctcggcttcc caaagtgctc   3300
ggattacagg tgtgagccac tgtgcctagc ctataatgat cattttaatg tttcccatgc   3360
actcatttag tttgaacctt cacagcaacc caatgaggta atactcccat ttcacatata   3420
atactgagag atgagttgca caagattata cactgttaag tagcagagcc agaatggact   3480
tcagaatccc aactacaata caaatgttta tttaaataaa gaagaaagct attgtacaaa   3540
tatcactctt caggtttagc ttacagagcc atggctatgg attcttagct ctgtaaggaa   3600
gtgcttctat aaattcttag gtttagagat gataccatct gggtaccttt gcttgaaccg   3660
tgcaaccaca tctgggtcta gtaggtggat cccatccagt tggtttccaa gggtgatcct   3720
gaaacagtgt aaaaggaggg gcaaaccaga aatcctggaa ttagagggtt taatattgtt   3780
aaaaaatgca taccaaatga agactgccta tcatcatatc aaatatgcca attctaaaaa   3840
gagcttaaca ttagaatagt atatggtaga attactagtt cagaattggc atagattctg   3900
gtgttaaaat agactggatc tgtattatct gagggttagt aactaatgct tagccaggcc   3960
tgcttcacag agttgctacc agggagtatt ctttggataa gcaaaatgct agcagcatgt   4020
gttttaagct ctgttaaggg gtgaaagatg taattattga cagattaaat agataacttc   4080
gtaaccacca gggggcagat tcaatacatc acagaatggc tgaggaagat ccttgggttg   4140
tgaagagagt agaaacccta gggagcagtg cttttgggtc ctagaacctg ttgagtttct   4200
aatgaatatt tgtagaatct cataaaacag tttaaataca agcttaagtg gcttatgaat   4260
cctgtgaagc tcatttatgg actagtgtaa aacaatgtga agctctacta agttctgtcc   4320
ttaatcataa ataatagccc cttgaggact agcctgttct ctggtcacct taccagttgg   4380
gttgcacatt gtgtggtcgt ccaaataact caatcttgcg agtgccagga gatagtcttt   4440
caatcatgcc atagatttca tctggtttat gactggtgga acgaacctag gaaataaaaa   4500
ctagctgctt tttaagttac acaaaaaaaa aaaaaaaa                            4538
```

<210> SEQ ID NO 240
<211> LENGTH: 829
<212> TYPE: DNA
<213> ORGANISM: Homo sapiens

<400> SEQUENCE: 240

```
ccccccgagc gccgctccgg ctgcaccgcg ctcgctccga gtttcaggct cgtgctaagc     60
tagcgccgtc gtcgtctccc ttcagtcgcc atcatgatta tctaccggga cctcatcagc    120
```

```
cacgatgaga tgttctccga catctacaag atccgggaga tcgcggacgg gttgtgcctg    180

gaggtggagg ggaagatggt cagtaggaca gaaggtaaca ttgatgactc gctcattggt    240

ggaaatgcct ccgctgaagg ccccgagggc gaaggtaccg aaagcacagt aatcactggt    300

gtcgatattg tcatgaacca tcacctgcag gaaacaagtt tcacaaaaga agcctacaag    360

aagtacatca aagattacat gaaatcaatc aaagggaaac ttgaagaaca gagaccagaa    420

agagtaaaac cttttatgac aggggctgca gaacaaatca agcacatcct tgctaatttc    480

aaaaactacc agttctttat tggtgaaaac atgaatccag atggcatggt tgctctattg    540

gactaccgtg aggatggtgt gaccccatat atgatttttct ttaaggatgg tttagaaatg    600

gaaaaatgtt aacaaatgtg gcaattattt tggatctatc acctgtcatc ataactggct    660

tctgcttgtc atccacacaa caccaggact taagacaaat gggactgatg tcatcttgag    720

ctcttcattt attttgactg tgatttattt ggagtggagg cattgttttt aagaaaaaca    780

tgtcatgtag gttgtctaaa aataaaatgc atttaaactc atttgagag                829
```

<210> SEQ ID NO 241
<211> LENGTH: 612
<212> TYPE: DNA
<213> ORGANISM: Homo sapiens

<400> SEQUENCE: 241

```
tccggttccg gcctggcgag agtttgtgcg gcgacatgaa actgcttacc cacaatctgc     60

tgagctcgca tgtgcggggg gtggggtccc gtggcttccc cctgcgcctc caggccaccg    120

aggtccgtat ctgccctgtg gaattcaacc ccaacttcgt ggcgcgtatg atacctaaag    180

tggagtggtc ggcgttcctg gaggcggccg ataacttgcg tctgatccag gtgccgaaag    240

ggccggttga gggatatgag gagaatgagg agtttctgag gaccatgcac cacctgctgc    300

tggaggtgga agtgatagag ggcaccctgc agtgcccgga atctggacgt atgttcccca    360

tcagccgcgg gatccccaac atgctgctga gtgaagagga aactgagagt tgattgtgcc    420

aggcgccagt tttcttgtt atgactgtgt atttttgttg atctataccc tgtttccgaa    480

ttctgccgtg tgtatcccca acccttgacc caatgacacc aaacacagtg tttttgagct    540

cggtattata tatttttttc tcattaaagg tttaaaacca aaaaaaaaaa aaaaaaaaaa    600

aaaaaaaaaa aa                                                        612
```

<210> SEQ ID NO 242
<211> LENGTH: 14607
<212> TYPE: DNA
<213> ORGANISM: Homo sapiens

<400> SEQUENCE: 242

```
ccggaggggc tgtcatttgc agcgctggtc gcagccctca gctgcgccgg gcggttccgg     60

ctcctccctc tccttgtgcc tcagcgccac catggtgctg gagtcggtgg tcgcggactt    120

gctgaaccgc ttcctggggg actatgtgga gaacctgaac aagtcccagc tgaagctggg    180

catctggggc ggaaatgtgg ctttagataa tctacagata aaagaaaatg ccctgagtga    240

attggatgtt ccttttaaag tcaaggctgg ccaaattgat aaattaactt tgaagattcc    300

ttggaagaac ctttatggag aagcagttgt tgcgaccctg gaaggattat acctgcttgt    360

tgtccctgga gcaagtatta agtatgatgc tgtaaaagaa gaaaaatcct tgcaggatgt    420

taaacagaaa gagctatccc gaattgaaga agcccttcaa aaagcagcag aaaaaggcac    480
```

-continued

```
acattcaggg gagttcatat atggcttgga gaactttgtt tacaaggaca tcaagcctgg    540
acgtaaacgt aaaaagcaca aaaaacattt taagaaacct tttaaaggtc ttgatcgttc    600
aaaagataag ccaaaagaag ccaaaaagga tacatttgtg gaaaaattgg caactcaagt    660
aataaaaaat gtacaagtaa aaatcacaga tattcacatt aaatatgaag atgatgtcac    720
tgatccaaag cggcctcttt catttggtgt cacactggga gagcttagtc tactgactgc    780
aaatgaacac tggactccat gcatattaaa tgaagcagac aaaattatat acaagcttat    840
acgacttgat agtcttagcg cctactggaa tgtaaattgc agcatgtctt accagagatc    900
aagggaacag attttggatc agctgaaaaa tgaaattctt acaagtggaa atatacccccc   960
aaattatcaa tacattttcc agccaatatc agcctctgca aaactctaca tgaatcctta   1020
tgcagaatca gagctcaaaa cgcccaaact ggattgcaac atagaaatac aaaatattgc   1080
cattgaactg accaaacctc agtacttaag tatgattgac cttttggagt cagtggatta   1140
tatggttagg aatgcgcctt ataggaaata caagccttat ttaccacttc ataccaatgg   1200
tcgacgatgg tggaaatatg caattgattc tgttcttgaa gttcatataa gaaggtatac   1260
acagatgtgg tcatggagta acataaaaaa gcacaggcag ttactcaaga gttataaaat   1320
tgcctacaaa aacaagttaa cacagtctaa agtctcagaa gaaatacaga aagaaattca   1380
ggacttggag aagactctag atgtttttaa cataatttta gcaaggcaac aagcacaagt   1440
tgaggtgatt cggtctgggc aaaaattaag gaaaaagtct gctgacacag gcgagaaacg   1500
tggaggctgg tttagtgggt tgtggggtaa gaaagagtct aagaaaaagg acgaagaatc   1560
attgattcct gaaactattg atgaccttat gactccagag gaaaaagata aactcttcac   1620
tgccattggt tatagtgaga gtacccacaa cctaacttta cctaagcagt atgttgccca   1680
tattatgacc ctgaagttag taagcacctc tgttacgata agagaaaaca agaatattcc   1740
agaaatacta aaaattcaga taattggcct gggcactcaa gtatctcagc gaccaggagc   1800
acaagcactt aaggtagaag cgaaattaga acactggtat ataacaggtt tgagacagca   1860
ggatattgtg ccatcacttg tggcttcaat tggtgacact acatcatcct tgcttaaaat   1920
taaatttgaa accaatccgg aggatagtcc tgctgaccag actctgattg ttcagtccca   1980
gcctgtggag gtcatctatg atgctaaaac tgtcaatgca gtggttgaat tctttcaatc   2040
aaataaggga ttggatcttg agcaaataac atcagcaaca ttgatgaagc tggaagaaat   2100
taaggagaga acagctacag gacttacaca tattattgaa actcgaaaag tccttgattt   2160
aaggataaat ctgaagcctt cttatctagt agttccacag acgggtttcc accatgaaaa   2220
gtcagatctt ctgattttag attttggtac atttcagctc aacagtaaag atcaaggttt   2280
acagaagact actaattcat ctctggaaga aataatggat aaggcatatg acaagtttga   2340
tgttgaaata aaaaatgtac aactactttt tgcaagagca gaggaaacct ggaaaaagtg   2400
tcgatttcag catccatcaa ctatgcatat attgcaaccc atggatattc atgttgagtt   2460
ggctaaggcc atggtagaaa aagacattag aatggccaga tttaaagtgt caggaggact   2520
tcctttgatg catgtgagaa tttctgacca gaagatgaaa gatgtgctat atttgatgaa   2580
cagtatacct ttgccacaga aatcatcagc ccagtctcca gagagacagg tatcctcaat   2640
tcctattatt tcaggtggta caaaaggtct acttggtact tcactattgc tagacactgt   2700
ggaatcagag tctgatgatg agtattttga tgctgaagat ggagaaccac agacttgtaa   2760
aagtatgaaa ggatcagaac ttaaaaaagc tgcagaggtc ccaaatgagg agctcatcaa   2820
tcttctactc aagtttgaaa ttaaagaagt gattttggaa tttactaaac agcagaaaga   2880
```

-continued

```
agaagataca attctagtat ttaatgttac tcagttagga acagaggcca caatgagaac   2940
atttgactta actgtggtat cttatttaaa gaaaatcagc ttggattatc atgaaattga   3000
aggatccaaa aggaagcccc ttcacttgat tagctcttct gacaaacctg gattagatct   3060
tttgaaagtg gagtatatta aggctgataa gaatggacct agttttcaaa ctgcttttgg   3120
aaaaactgaa caaacagtta aggtggcctt ttcatcttta aatctgttgc tgcaaacaca   3180
agctcttgtc gcttctatta attacctcac aaccattatt ccatctgatg atcaaagcat   3240
aagtgttgct aaggaggtac aaatttcaac tgaaaaacaa caaaaaaatt caactctgcc   3300
aaaagcgatt gtatcctcca gagatagtga cattattgat ttcaggctat ttgccaagtt   3360
gaatgctttc tgtgtcattg tttgcaacga aaagaacaat atcgccgaaa tcaagattca   3420
aggactggat tcctcccttt ctctccagtc aagaaagcag tcactttttg cccgactaga   3480
aaatattatt gtcacagatg ttgatccaaa gacagttcat aagaaagctg tgtcaataat   3540
gggaaatgaa gttttccgtt ttaatttgga tttgtatcca gatgctactg agggggattt   3600
gtatactgac atgtccaaag tggatggtgt gctgtctctg aatgttggct gtattcagat   3660
tgtctatctt cataaattcc ttatgtcact tctgaacttc ctgaataatt tccagacagc   3720
caaagagtct ctgagtgctg ccactgccca ggctgcagaa agggctgcca caagtgtgaa   3780
agatcttgcc cagaggagtt ttcgtgtttc catcaatatt gatttgaaag caccggttat   3840
agtcatccca cagtcttcta tttccaccaa tgcagtagtg gtagatcttg ggttaatcag   3900
agttcataat cagttcagtc tggtgtctga tgaagactac ttaaatcctc cagtaattga   3960
tagaatggat gtgcagctaa caaagcttac actttatagg acagtgatcc agccaggcat   4020
ctaccatcct gatattcagc tgttgcaccc aattaacttg gaatttcttg taaatcggaa   4080
tctagctgca tcttggtacc acaaggtgcc tgttgtggaa attaaaggac atcttgattc   4140
aatgaatgtt agtctaaatc aagaagatct taatctttta tttaggatac taacagaaaa   4200
tctctgtgag ggtactgaag acttggataa agtgaaacca agagtacaag agacaggtga   4260
aattaaagag ccccttgaaa tctctatatc acaagatgta catgattcaa aaaatacttt   4320
aacaactgga gtggaagaaa ttaggtctgt agacatcatt aatatgctgc tgaattttga   4380
aattaaagag gttgtggtta ctttgatgaa aaaatcagaa aagaaaggaa ggcctttaca   4440
tgagctaaat gtcctgcaac ttggaatgga agctaaagtt aaaacctatg acatgactgc   4500
taaagcttat ctaaaaaaaa ttagtatgca gtgctttgat ttcactgact ctaaagggga   4560
acctcttcac attattaact cttctaatgt gactgacgaa ccccttctga aaatgttact   4620
gacaaaggca gacagtgatg gaccagaatt taaaactatt catgacagta ccaaacagag   4680
actgaaggtt tcatttgcat ccttagactt agtacttcat ttggaagctt tactttcctt   4740
catggatttt ttatcatctg ctgctccatt ctctgagcct tcctcttctg agaaggaatc   4800
cgagctgaaa ccacttgtgg gggagtccag aagtatcgct gtcaaagctg tatccagcaa   4860
catttcccaa aaggatgtgt ttgatttaaa gatcacagct gaattaaatg catttaatgt   4920
ctttgtctgt gatcagaagt gtaacattgc agatattaaa atacatggaa tggatgcctc   4980
tatttctgtg aagcctaagc agactgatgt gtttgccaga cttaaagata ttatagttat   5040
gaatgtagat ttgcagtcca ttcacaaaaa ggctgtctct attttgggag atgaagtctt   5100
taggttccaa ctgactcttt atccagatgc cacagaagga gaggcctatg ctgatatgtc   5160
caaagtagac ggcaaactta gttttaaagt gggttgtatt cagattgttt atgttcataa   5220
```

attcttcatg tctcttttga acttcctcaa caatttccaa actgctaaag aagctttgag 5280
tacagccaca gtccaggctg cagaaagagc tgcttccagc atgaaagact tggctcaaaa 5340
gagtttccgc cttttgatgg atattaattt gaaagcacca gttattatta ttcctcagtc 5400
ttcagtatca cctaatgctg ttatagcaga tctgggttta atcagagttg aaaacaagtt 5460
tagcttggtt cctatggaac attattctct tcctccagtc attgataaaa tgaacatcga 5520
actcactcag ttgaagctgt caagaactat tttgcaggct agcttgccac aaaatgacat 5580
tgaaatttta aaaccagtca acatgctttt gtccatacag cgaaacttag cagcagcatg 5640
gtatgtgcaa attccaggga tggagataaa aggaaaacta aaacctatgc aggttgctct 5700
cagtgaagat gacttgacag ttttaatgaa aattttgcta gaaaatcttg gagaagcttc 5760
ctcacaacca agccctacac agtctgtgca ggagactgta agagtgagaa aagttgatgt 5820
ttcaagtgta cctgaccatc tcaaagaaca agaagattgg acagactcaa agctctctat 5880
gaaccagatt gtcagtctcc aatttgactt tcactttgaa tctctttcca ttatccttta 5940
taacaatgat atcaaccagg aatctggagt tgcatttcat aatgacagtt tccaacttgg 6000
tgaactcaga ctacatctta tggcctcctc agggaagatg tttaaggatg gctcaatgaa 6060
tgtcagcgtt aaacttaaga catgcaccct tgatgatctc agagaaggaa ttgagagagc 6120
aacatcgaga atgattgaca gaaagaatga ccaagataac aacagttcta tgattgatat 6180
aagttacaaa caagacaaaa atggaagtca aattgatgct gttcttgaca agctgtatgt 6240
atgtgccagt gtggaatttc tgatgactgt ggcagatttc tttatcaaag ctgtgcctca 6300
gagtccagaa aatgtggcaa aagaaacaca gattttacca agacagactg ccacagggaa 6360
ggtcaagata gagaaagatg actctgttag accaaatatg actttaaagg ccatgatcac 6420
agatccagaa gtggtatttg ttgccagcct gacaaaggct gatgctcctg ctctgacagc 6480
ctcgtttcag tgcaaccttt ctctgtcaac atccaaactc gaacagatga tggaagcttc 6540
tgtgagagat ctgaaagtgc tcgcttgccc ttttctcaga gaaaagagag ggaaaaacat 6600
taccacagtc ttgcagccct gttctttatt tatggaaaaa tgtacgtggg cttcaggaaa 6660
gcaaaatata aatattatgg ttaaagaatt tataattaag atttcaccca taattcttaa 6720
tactgtgttg acaatcatgg ctgcattgtc tccaaaaaca aaagaagatg gatccaaaga 6780
tacgtctaag gaaatggaaa atctttgggg tatcaaatcg attaatgatt ataacacttg 6840
gtttcttggt gttgacacgg caacagaaat aacggaaagc ttcaaaggca ttgaacattc 6900
actgatagag gaaaattgtg gtgttgttgt agaatccatt caagttacct tagaatgtgg 6960
ccttggacat cgaactgtac ctttattatt ggcagagtct aagttttcag gaaatattaa 7020
aaattggact tctctaatgg ctgctgttgc tgacgtgaca ctacaggtgc actattacaa 7080
tgagatccat gctgtctggg agccactgat tgagagagtg gaggggaaga gacaatggaa 7140
tttaaggctt gatgtaaaga agaacccagt tcaggataaa agtttgctgc caggagatga 7200
ttttattcct gagccacaaa tggcaattca tatttcttca ggaaatacaa tgaatataac 7260
aatatccaaa agttgtctta atgttttcaa caatttagca aaaggttttt cagagggcac 7320
tgcttctact tttgactact ctttaaagga cagagctcct tttacggtaa aaaatgctgt 7380
aggtgttccc attaaggtga agcccaattg taatctcaga gtaatgggct tccctgagaa 7440
aagtgatatt tttgatgttg atgctggcca gaatttggaa ctggagtatg ccagcatggt 7500
accttcaagt caagggaacc tatctatatt gagccgtcaa gaaagctcct tcttcactct 7560
gaccattgta cctcatggat atacagaagt tgcaaatatc cctgtggcca gacctggacg 7620
gcgattgtat aatgtacgga atcccaatgc cagtcattct gactctgtct tggtacaaat 7680
tgatgcaact gaagggaata aagtaattac ccttcgctct cctctacaga tcaaaaacca 7740
tttctccatt gcatttatca tctataaatt tgttaagaat gttaagctat tggagcgcat 7800
tgggatagcc agacctgaag aggagttcca tgttccttta gattcatata gatgtcaatt 7860
gtttatccag ccagctggaa tcttagagca tcagtacaaa gaatctacca cttatatttc 7920
ctggaaggaa gaacttcata ggagcaggga agtcagatgc atgttgcagt gtccatcagt 7980
agaagtcagc ttcttacctc tcatagtgaa tacagttgct ctgcctgatg aattgagcta 8040
catatgtaca catggggaag actgggatgt agcttacatt attcatcttt atccttctct 8100
cactttgcgg aatcttctcc catattccct aagatattta cttgagggaa cagcagaaac 8160
tcatgagctg gcagaaggca gtactgctga tgttctgcat tcgagaatca gtggtgaaat 8220
aatggaatta gtcctggtga aataccaggg caaaaactgg aatggacatt tccgcatacg 8280
tgatacacta ccagaattct ttcctgtgtg tttttcttct gactccacag aagtgacgac 8340
agtcgacctg tcagtccacg tcaggagaat tggcagccgg atggtgctgt ctgtctttag 8400
tccctattgg ttaatcaaca agactacccg ggttctccag tatcgttcag aagatattca 8460
tgtgaaacat ccagctgatt tcagggatat tattttattt tctttcaaga agaagaacat 8520
ttttactaaa aataaggtac aattaaaaat ttcaaccagt gcctggtcca gtagtttctc 8580
attggataca gtgggaagtt atgggtgtgt gaagtgtcct gccaacaata tggagtacct 8640
ggttggtgtt agcatcaaaa tgagcagttt caacctttca cgaatagtta ccctgactcc 8700
cttttgtacc attgcaaaca agtcatcatt agaactagaa gttggcgaga ttgcatctga 8760
tggctcaatg ccaactaata aatggaacta tattgcttct tcagagtgcc ttccattttg 8820
gccagaaagt ttgtcaggca aactttgtgt gagagtggtg ggctgtgaag gatcttccaa 8880
accattcttt tataaccgac aggataatgg cactttattg agcttagaag atctgaatgg 8940
gggtatcttg gtggatgtaa acactgccga acattcaact gtcataactt tttctgatta 9000
ccatgaggga tctgcacctg ccttgataat gaaccataca ccatgggaca tcctcacata 9060
caaacagagt gggtcaccag aagaaatggt cttgctgcca agacaggctc gactttttgc 9120
ctgggcagat cctactggta ccagaaaact tacatggaca tatgcagcaa atgttgggga 9180
acatgatctg ttaaaggatg gatgtggaca gtttccatat gatgcaaaca tccagataca 9240
ctgggtatca tttctggatg ggcgccagag agttttgctt ttcaccgatg atgttgcctt 9300
ggtttccaaa gcactgcagg cagaagaaat ggaacaggct gattatgaaa taaccttgtc 9360
tctccacagt cttgggcttt cactggttaa caatgaaagc aagcaggaag tttcctatat 9420
tgggataacc agttctggtg ttgtttggga ggtgaaacca aagcagaaat ggaagccatt 9480
tagtcaaaag cagataatct tattggaaca atcctatcag aaacatcaaa tatcaagaga 9540
ccatggctgg attaagctag ataataattt tgaggtcaat tttgataaag atccaatgga 9600
aatgcgcctc cctattcgta gccctattaa acgagacttt ttatcaggaa ttcagattga 9660
atttaagcag tcttctcacc agagaagttt aagggccagg ttgtactggc ttcaggttga 9720
taatcagtta ccaggtgcaa tgttccctgt tgtatttcat cctgttgccc ctccaaaatc 9780
tattgcttta gattcagagc ccaagccttt cattgatgtg agtgtcatca caagatttaa 9840
tgagtacagt aaagtcttac agttcaagta ttttatggtc ctcattcagg aaatggcctt 9900
aaaaattgat caagggtttc taggagctat tattgcactg tttaccccaa caacagaccc 9960

```
tgaagctgaa agaagacgga caaagttaat ccaacaagat attgatgctc taaatgcaga  10020
attaatggag acttcaatga ctgatatgtc aattcttagt ttctttgaac atttccatat  10080
ttctcctgtg aagttgcatt tgagtttgtc tttgggttcc ggaggtgaag aatcagacaa  10140
agaaaaacag gaaatgtttg cagttcattc tgtcaacttg ctgttgaaaa gcataggtgc  10200
tactctgact gatgtggatg accttatatt caaacttgct tattatgaaa ttcgatatca  10260
gttctacaag agagatcagc ttatatggag tgttgttagg cattacagtg aacagttctt  10320
gaaacagatg tatgtccttg tattggggtt agatgtactt ggaaacccat ttggattaat  10380
tagaggtctg tctgaaggag ttgaagcttt attctatgaa cccttccagg gtgctgttca  10440
aggccctgaa gaatttgcag aggggttagt gattggagtg agaagcctct ttggacacac  10500
agtaggtggt gcagcaggag ttgtatctcg aatcaccggt tctgttggga aaggtttggc  10560
agcaattaca atggacaagg aatatcagca aaaaagaaga gaagagttga gtcgacagcc  10620
cagagatttt ggagacagcc tggccagagg aggaaagggc tttctgcgag gagttgttgg  10680
tggagtgact ggaataataa caaaacctgt ggaaggtgcc aaaaaggaag gagctgctgg  10740
attctttaaa ggaattggaa aagggcttgt gggtgctgtg gcccgtccaa ctggtggaat  10800
cgtagatatg gccagtagta ccttccaagg cattcagagg gcagcagaat caactgagga  10860
agtatctagc ctccgtcccc ctcgcctgat ccatgaagat ggcatcattc gtccttatga  10920
cagacaggaa tctgagggct ctgacttact tgagcaagaa ctggaaatac aggaataaat  10980
gtttcctaaa ctactacttg atttcatcct taaaaatcaa aacaaactgt ggtgttaatt  11040
gactgtgtgt gaattccatt gtcaatttta atgaaatttt ctttaaaact ctcacctcca  11100
tctgaacttt tcatagtagt gggattgact acaaataaaa acttgtggta ttcctggtaa  11160
tactgtccag aaataagaga ttagtataaa atattaaagg atgcagagaa tcagctctct  11220
tctgcgttta atagatgaaa gcctttattg agctcagaag cagatactgt tactatcatt  11280
tcgaaaattt tatcttatgg tgttcatgtg catttcaggt aaaattgaaa aacaggacaa  11340
ttattatgtc caattaatat gtttatgttt gtgagtcttg atgatggaat tacatagctt  11400
tctgtttcac aaatggctct aaatttgctt aagttacggg actattacct ggagcatctg  11460
ctttaataat tgaattgtca gttgctctga gcctgccctt agacctcaag taataaatag  11520
ttggcacatg aattttgagg atatgtttcc tcttccctct ttttcctatt taaccccttg  11580
gtactgttgc taaataaatg atagccattt tataattatg ttatatacat tttcagcctt  11640
tagcatttct gcttttcaaa aattgaatct ccttgttggt tatgcttatt tcataattat  11700
tagttttaat taatgtagat agaagttgaa catgtaatta ggcaaattgc tgtgtggcac  11760
ttgaatacat agatttcttt attttcaaaa accaaccttt tgcttttaaa tccttagaga  11820
gggtttatta tcttagagaa aaaataatta taatcattat ttttgaaatt agtatcctct  11880
taattctcaa cataagttat gtttcaattt cttttttttg taataaatga tggaaatgtt  11940
taacaatgtc ttatctagca actttcatgc ttctcctcag aaatgaagcc aaagtataaa  12000
cttagattta atgtgttgta tatttgaaga gaatgaaact attaacatat aattgttcag  12060
ttggattatg tattttaagg attgcagtta tcaaaataat aaattgaatg ttttatgttt  12120
aaccacttta aagaagaaag actgacatcc aaaaaccagc gtgtgctaga tatacaaagg  12180
aaattacttc tgtccttaag ggaccaagta taacaaaaca tgtaactgtt aaaagtagct  12240
gacaaacctt tcttgtgcct agataattta gcattggcaa aatgtcacc acatgcagtt  12300
ttctaggaga gtcaagcaca aataactaat tcaagatgct gacttaaatc atctccaata  12360
```

gttacccttc ctgagattct aaagtaacaa tttttaattt tactggttat attgctgttt 12420
tactgagact tacttttaag aacccctgta acttaagatt ttttcttaat tgttttgttt 12480
agctctgtta ttaatttttt ccttgtgata tctttttata actctctgtc aaaaagcaca 12540
aaacttcaag aaacttttaa ttattttgtc tgaacatata atcttgtctg atttcttagt 12600
ttttattaag atatcagaca acttttaaaa ctttagtgca ttattataat tactggaaga 12660
aaaagaatga ttatacacta atgagaggac ttggtagttt ttgtcgtgga tgtcaagtgt 12720
gggcatggat aattgaaata tttaggctat ttcattcttt gcccatcttg ctgtgatcag 12780
ttagttgggt aaaaatattt attgattatt tagactgtac tggatataca aaagaagcct 12840
tctgtcctta agggaccgag taaaacaaaa catggaaata ttaaagagta ttagagtata 12900
aaagtatatc tttttagccc tttgtaatat ggccaaattc taaataattt atttggggat 12960
cttttgatcc tcatgttcct ttttctccta agtactactt tgtattcttt aatatgcagc 13020
tttgagagtt actgaatcat atattatatt tccatgagat gtactattct acttatcctc 13080
taatcttcat atatatatac acacacacat atatatacac atacatatat acacacgtac 13140
atatatgtac acatacagat atacatacac acaaacacat atatacacac atacatatac 13200
acacatatat atacacatac aaatatacac atatatacac atacatatat atacacacat 13260
acaaatatac ccatatgtac acatacatat atacacatac atatatacac acacatatac 13320
acacatatat acgcaaacat acacatattt acacatacat atatacatac attatatgta 13380
tgtatatata gtcatttaat actcattttg gttcacatac ttatgatcat gcaacgttta 13440
aaacagcatt tcttgctttt tagttttagt tatatttttc catgttctta gaaatgcctc 13500
attaacattt ttaattcttg tattgccatc tattgaggtg acattacatt gtgtttttat 13560
ctcgtcttaa ttcatgacat taaattattc tactaacagt aataatgctg taataaacat 13620
cattatagat tttgcttttt tatatcttgt ttgctttttc atatttcctt agaatttact 13680
tgaaaaaatt gaattactgg gtaaagggct tttgcaaagt attgttaaat tcctcgagtt 13740
gcatttttgg aaaggggacg tgaatatttt atcaactaat ttggtctccc tgctgccatt 13800
agtgactgaa tatcttaatc tgaatctcag agtgtagtgg gtttttagta gtgctgaaga 13860
caagttttct aaagtgtatt atggtgataa attatatttt aaaaactgtc aatggcttga 13920
agcacaatag cctaataact aacgaaaata catacaagat agaaagtggg tagtatttct 13980
tgtacttgca tttcagatct aaatatttta acatatttaa atttcaagct gcagataaat 14040
gcattacatt attaaattca tttcccattt tctctttgaa gaaattaagg caaaagtgtt 14100
aaaagatttt aactaattcg cacaagtgaa ttgtgaaaca agtagctatt gctgtgaaat 14160
ctgcactcct ctctgagact cattctgaag atgagatccc agttctttgt ggattcctct 14220
tccttattca tggctttttg caattgtcaa ggaatgacta ggtaccaagc aactttaaaa 14280
aatgtatatt taagcattga aataatatca aatgtgattt ctctgcttgt ggttatattg 14340
attatattat ccttttaata atattggcat tatattcttg gtcgtaaaat gtcaaggtct 14400
tatttattca gtatatttat gttctgtatt ttcatatata ttatctattt tcagccatgc 14460
attatatata atgtcagtaa tagtatttca ttagcattca ttataaaaaa actcgttttt 14520
aatatttgac taattcaagt cacagtactt ttgagatagc tgaaaaggaa aataaatgtg 14580
ttttaatgtg ctactaaaaa aaaaaaa 14607

<210> SEQ ID NO 243

<211> LENGTH: 14329
<212> TYPE: DNA
<213> ORGANISM: Homo sapiens

<400> SEQUENCE: 243
gcggccgcag aatcgagctc gggccccggc ccccggcccg cggcgcgggg ctcccgggcc 60
ccgccgcgga cgtcgcgccg gtcgcccctt ccccgtagcc cgtgcgccct cggcgcggag 120
ccccggcccg ccgcggtccc gtctcctggg cctgtcccgc ccgcgccctc cgccggccct 180
caggtataat acttctccac gtctgcttca ggaagaaagt gcctgccatt cttatcattt 240
ctaagcaggt tcatgccagc ccagaacaga gaatcagctg gagcccagat ttcaagtttt 300
gagtaaaata ccttcaagcg aatgggccct attgtgctca cacattcaga acctgttacc 360
caaggaattc cctaaagaat tagaagtgcg tctcaccaac cagccaagat gaacatggtg 420
aagaggatca tggggcggcc gaggcaggag gagtgcagcc cacaagacaa cgccttagga 480
ctgatgcacc tccgccggct cttcacggag ttgtgccatc ctccccggca catgactcag 540
aaggaacaag aagagaaact gtatatgatg ctgccagtgt ttaacagggt ttttggaaat 600
gctccgccga atacaatgac agaaaaattt tctgatcttc tgcagttcac aacacaagtc 660
tcacgactaa tggtgacaga aattcgaagg agagcatcaa acaaatccac agaggctgca 720
agtcgggcca tagttcagtt cctagagatt aatcagagtg aagaagccag tagaggctgg 780
atgcttctaa cgacaattaa tttgttagct tcctctggtc agaaaaccgt ggactgcatg 840
acaacaatgt cagtgccttc caccctggtt aaatgtttat atctgttttt tgaccttcca 900
catgtgcctg aggcagttgg aggtgcacag aatgagctac ctctagcaga acgtcgagga 960
ctactccaga aagtttttgt acagatctta gtgaaactgt gcagttttgt ttcccctgcg 1020
gaggagctgg ctcagaaaga tgatctccag cttctattca gtgcaataac ctcttggtgc 1080
cctccctata acctgccttg gagaaagagt gctggagaag tcctcatgac catatctcgt 1140
catggtctta gtgtcaatgt agtgaagtat attcatgaga aagagtgttt atctacatgt 1200
gttcagaata tgcagcaatc agatgacctg tctcccctag aaattgtcga aatgtttgct 1260
gggctttctt gtttcctcaa agattccagc gatgtttccc aaacacttct ggatgatttt 1320
cggatatggc aaggatataa ttttctttgt gatctcttgc ttagattgga acaagcaaaa 1380
gaggcagaat ccaaagatgc cttgaaagat ctggttaatc tgataacttc cctaacaaca 1440
tatggtgtca gtgaactaaa accagctggt attaccacag gggcaccctt tttattgcct 1500
ggatttgcag tacctcagcc tgcaggcaaa ggtcacagtg tgagaaacgt ccaggccttt 1560
gcagttcttc agaatgcatt tttaaaagca aaaaccagct tccttgccca aatcatcctt 1620
gatgctatca caaatattta catggctgac aatgccaatt acttcatcct agagtcacag 1680
cacacattgt cacagtttgc agagaagatt tctaaactcc cagaagtaca aaacaaatac 1740
tttgagatgc tggagtttgt tgtttttagc ttaaattata taccttgtaa agaacttatt 1800
agtgtcagta tcctcttaaa atctagctct tcttatcact gtagcattat tgcaatgaaa 1860
acacttctta agtttacaag acatgactac atatttaaag acgtgttcag ggaggttggc 1920
cttttggagg tcatggtaaa ccttttgcat aaatatgctg ccctgttgaa ggatccaact 1980
caggcactaa atgaacaagg ggactcaaga aataatagtt cagttgaaga ccaaaaacac 2040
ctggctttat tggttatgga gaccttgaca gtgcttcttc aaggatcaaa cacaaatgca 2100
ggaatttttc gagaatttgg aggtgcaaga tgtgcacata atatagtaaa gtaccctcaa 2160
tgccggcagc atgccttgat gactatccaa cagctggtgc tctccccaaa tggggacgat 2220

-continued

```
gacatgggca ctctcctggg gctaatgcat tcagccccac cgacggaatt gcagttgaag   2280
actgatattt taagggccct cctgtcggtc cttcgagaaa gccatcgttc aagaacagtt   2340
tttaggaaag ttggaggatt tgtgtacatt acatccttgc tcgttgctat ggaaagatct   2400
ttgagctgtc cacccaagaa tggctgggag aaagtgaacc agaatcaagt gtttgaactt   2460
cttcacactg tgttctgcac gttgactgca gcaatgcgct atgagccagc caactctcat   2520
ttcttcaaaa cagagattca gtatgagaag ttggcagatg ctgttcgatt tcttggctgc   2580
ttctcagacc taagaaaaat aagcgccatg aatgtcttcc cctcaaatac acagccattt   2640
caaagacttt tagaggaaga tgtaatctca atagaatcag tgtcacccac gttacggcac   2700
tgcagtaaac tttttattta tctttacaaa gtagccacag attcttttga cagtcgtgca   2760
gaacagatcc ctccttgcct gacaagtgag tcttctctcc cctctccttg ggtacacca   2820
gctttgtcca ggaaaaggca tgcatatcat tctgtttcaa ctccccctgt ttaccctcct   2880
aaaaatgttg ccgacctgaa actacatgtg acaacttcat ctctgcagag ttctgatgca   2940
gtcatcattc atcctggagc catgcttgcc atgctggacc tactggcctc tgttgggtca   3000
gtgacacagc cagaacatgc tttggatctt caacttgccg tggcaaatat tttacaatcc   3060
ctggtgcaca cagaaaggaa ccagcaagtc atgtgtgaag ctggtcttca tgcacgactg   3120
ctgcagaggt gcagtgctgc attggctgat gaggaccact cactgcaccc gcccctgcag   3180
cggatgtttg aacgattagc ctctcaggct ctggaaccca tggtgttgag ggagtttta   3240
cgtttggcaa gtcctttaaa ttgtggtgcc tgggacaaaa aactgctaaa acaatatagg   3300
gtccacaaac caagttcact gagttatgaa ccagaaatga gaagtagtat gatcacatct   3360
ctggaaggtc tgggtactga taatgttttt agcttacatg aagataacca ttaccggata   3420
agcaagagcc tggtaaaatc tgcggaagga agtactgtac cctgaccag ggtgaagtgt   3480
ctggtctcca tgacaacccc acatgacatc agacttcatg ggtcatcagt tactccagct   3540
tttgttgaat ttgacacatc acttgaaggg tttggatgtc ttttttgcc cagtttggcc   3600
cctcataatg ctcctacaaa taataccgtc acaacaggtc ttattgatgg ggctgtggtc   3660
agtggcattg gttctggtga aagattcttc cctcctccct ccggcttaag ttactctagc   3720
tggttttgta ttgaacattt tagttctcct ccaaataacc accctgtcag acttcttact   3780
gttgtgcgcc gagcaaattc ttctgagcaa cattacgtgt gccttgcaat agttctatca   3840
gcaaaagacc gatctctgat tgtttccacc aaagaggaac tcctccaaaa ttatgttgat   3900
gattttagtg aagagtcctc attttatgaa attctcccat gctgtgctcg ctttcgatgt   3960
ggagagctta tcattgaggg acagtggcat catttggtcc tggtaatgag caaaggcatg   4020
ttgaaaaaca gtactgcagc cctttatatt gatggacagc ttgttaacac tgtaaagctt   4080
cattatgtcc acagtactcc agggggttca ggttcggcaa atccaccagt ggtgagcacg   4140
gtctatgcct acattggtac tccacctgcc caacgccaaa ttgcctcatt ggtttggcgc   4200
ctgggaccca cacattttct agaagaagtt ttaccttctt caaatgttac taccatttat   4260
gaacttggac caaattatgt tggaagcttt caggctgtat gtatgccatg taaagatgca   4320
aaatccgaag ggtggtgcc atcccctgtg tcattagtac cagaggagaa agtgtcattt   4380
ggcctctatg cactctctgt gtcgtctcta acagtggcaa gaatccggaa agtgtataac   4440
aaattggata gcaaagccat tgctaagcag ttaggcattt cctcacatga gaatgccact   4500
cctgtgaagt tgatacacaa ttcagcagga catcttaatg gatctgcacg gacaattggg   4560
```

-continued

```
gccgctctga ttggatactt gggagtaaga acatttgtcc ctaagcctgt tgccactact   4620
ttgcagtacg ttggtggagc tgcagccatc ctgggcctgg tggccatggc ctctgatgtg   4680
gaagggttat atgcagcagt caaggccctg gtttgtgtgg tcaagagtaa cccactagcc   4740
agcaaagaaa tggaaagaat caagggctac cagttgctgg caatgttgct taagaagaaa   4800
cgttcccttc ttaacagcca catcctccat ctaacttttt ctttggtggg aactgttgat   4860
agtggacatg agacctccat tattccaaat tcaactgctt tccaggacct cctctgtgat   4920
tttgaagtct ggctccatgc accatatgaa cttcatcttt ccttatttga acactttatt   4980
gaactgctca cagagtccag tgaagcctca aagaatgcca aattaatgag agaattccag   5040
ttaatcccaa agctgctcct gactcttcga gatatgtctt tatcccagcc tactattgct   5100
gctattagta atgtcctgag cttcttactg caaggttttc ctagcagcaa tgatctgctc   5160
agatttgggc agtttatttc ttctactttg ccaacctttg cggtttgtga gaaatttgta   5220
gtaatggaaa taaataatga agagaagctt gacactggaa ctgaagagga gtttggaggt   5280
cttgtatcag ctaatcttat acttttgagg aacagacttc tggatatctt gctaaaacta   5340
atttatacat ctaaagaaaa gacaagcatt aatttgcaag cttgtgaaga actggtgaag   5400
acactgggtt ttgactggat catgatgttt atggaggaac acttacattc caccacagtt   5460
acagcagcca tgaggattct tgttgtccta ctaagtaatc agtctattct catcaagttt   5520
aaagaaggac tcagtggtgg aggatggctt gaacagacag attctgtctt aactaataag   5580
attggaactg tattaggatt caacgtgggc agaagtgctg gtgggagatc gacggtcagg   5640
gagattaacc gagatgcttg tcattttcct ggttttccag tccttcagtc attccttcct   5700
aaacacacta atgtccctgc cctctatttt ctcctcatgg ccttgtttct gcagcagcca   5760
gttagtgagc tgcctgagaa cctgcaggtc agtgtgcctg tcatcagctg ccggagtaag   5820
cagggttgcc agtttgattt ggattccatt tggacattca tctttggagt tcctgcctcc   5880
agcggaactg tggtctcttc tatccataac gtatgcacag aagctgtttt tttattattg   5940
ggaatgctcc gcagcatgct gacttcacct tggcaatcag aagaagaggg atcttggctc   6000
cgagaatatc ctgtgaccct gatgcagttc ttcagatatt tgtatcacaa cgtgccagac   6060
cttgcctcca tgtggatgag ccctgacttc ctgtgtgcat tagcagccac cgtcttcccc   6120
ttcaatattc gcccttactc agagatggtg actgaccttg atgatgaagt tggatctcca   6180
gcagaagagt ttaaagcgtt tgcagcagac acagggatga acaggagcca atcagagtac   6240
tgcaatgtgg gcaccaagac atatctgacc aatcacccgg ctaaaaagtt cgtttttgac   6300
ttcatgcggg tcttaatcat agacaacctc tgtctcactc ctgccagcaa gcaaactcca   6360
ctaattgatc ttttgttgga ggcttcccct gaaaggtcta caagaactca gcaaaaagaa   6420
tttcaaactt acattttgga tagcgtgatg gaccatttgc ttgcagctga tgtgttatta   6480
ggggaagatg catctctgcc tattaccagt ggaggaagct accaggtatt ggtgaacaat   6540
gtgttttatt tcacacagcg tgtggtggac aagctttggc aaggcatgtt caacaaagaa   6600
tctaaacttc ttatagattt tataattcaa ctaattgcac agtcaaagag aagatcacag   6660
ggattgtcac tggatgcagt gtatcattgc ctcaatagga ccatcttgta ccagttctca   6720
cgggcacaca aaaccgttcc tcagcaagta gctctgcttg attcactcag ggtcctcact   6780
gtaaacagaa acttgatcct gggacctggg aaccatgacc aagaattcat tagctgtctg   6840
gcccactgct tgataaatct acatgttgga agcaacgtgg atggatttgg actggaagca   6900
gaagcccgca tgaccacatg gcacattatg atcccctcgg acattgaacc agatggtagt   6960
```

tacagccaag atattagtga agggcgtcag cttctcataa aagctgtcaa cagagtttgg 7020
actgaactga tacatagtaa gaaacaagtc ttagaggaac ttttcaaagt aactctacct 7080
gtgaatgaaa ggggccacgt ggacatagct acagcaaggc cactcattga agaagctgcc 7140
ctgaagtgct ggcagaatca tttggcccat gaaaagaaat gcataagtcg aggagaagct 7200
ttagcgccca ccacacagtc caaattatcc cgtgtcagca gtggctttgg tctttccaag 7260
ttaacaggat caagaaggaa tcgaaaagaa agtggtctta ataaacacag tctttccacc 7320
caggagattt cgcagtggat gtttactcac attgctgttg ttcgtgactt agtagataca 7380
caatataaag aatatcagga gcgtcagcag aatgccctga agtacgtgac agaagagtgg 7440
tgtcagatcg agtgcgagct gttgagggag cgggggctgt ggggccctcc catcggctcc 7500
cacctcgaca agtggatgct ggagatgaca gaagggccct gcaggatgag gaaaaagatg 7560
gtgcgaaatg atatgtttta taaccattac ccttacgtgc cagaaactga gcaagagaca 7620
aatgtggcgt ctgagatccc aagtaaacag cctgagacac ccgatgatat tcctcaaaag 7680
aaacctgctc gatatagaag agccgtaagt tatgacagta aagagtacta catgcgactg 7740
gcctctggca atcccgccat tgtccaagac gccattgtgg agagttcaga aggtgaagct 7800
gctcagcaag aaccagagca tggggaagac actattgcta aagtcaaagg tttggtcaag 7860
cctcctctaa aacgctcccg atctgcacct gatggaggag atgaggagaa ccaggagcag 7920
ctacaagacc agattgctga gggcagctcc atagaagagg aggagaaaac agataatgct 7980
accttactgc gcctgttaga ggaaggagaa aagatccaac acatgtaccg ctgtgctcga 8040
gtccagggcc tagataccag tgaggggctc cttctttttg gtaaagagca tttttatgtg 8100
attgatggat ttaccatgac agcaaccagg gaaataagag atattgaaac cttacctcca 8160
aatatgcatg agcctattat tcctagagga gccaggcaag gccctagtca actcaagaga 8220
acatgcagca tttttgcata tgaagatatc aaggaagttc ataaaaggag atatctcctg 8280
cagcctattg ctgtggaagt ttctctggga gatggacgga attacctcct tgcttttcag 8340
aaaggaatca gaaacaaagt ctatcaaagg tttttggctg tagtgccatc tctaacggac 8400
agttcagaat ctgtatctgg gcaacgacca aacacgagtg tggagcaggg atctgggtta 8460
cttagcactt tggttggaga gaagtctgtg actcagagat gggagagagg tgaaatcagc 8520
aacttccaat atttgatgca tttgaacact ttggctggca gatcatataa tgatctcatg 8580
cagtatcctg tcttcccctg gatccttgca gattatgact cagaggaggt ggatcttact 8640
aatcccaaga cgtttagaaa cctggctaag ccaatgggag cacaaacaga tgaacgatta 8700
gctcagtata agaagcggta taaagactgg gaggatccta atggagaaac tcctgcatac 8760
cactatggga cccactattc atctgcaatg attgtggcct catacttgt aaggatggag 8820 cctttcacac agatattctt aaggctacag ggtggccact ttgacctggc tgaccggatg 8880
tttcacagtg tgcgcgaggc ctggtattca gcgtcaaagc acaatatggc agatgtaaaa 8940
gaacttatcc cagagttctt ttatttacca gaattcctgt tcaattccaa caactttgat 9000
ctaggctgta aacaaaatgg caccaagctt ggagatgtta tccttccacc ctgggcaaaa 9060
ggggacccac gagaattcat cagagtccat cgtgaggctt tggagtgtga ttacgtgagt 9120
gcccatctac atgagtggat tgacttaatc ttcggttata aacagcaagg ccctgctgca 9180
gtagaagctg taaatgtctt ccatcatctt ttttatgagg gtcaagtgga tatctacaac 9240
atcaatgacc cactaaagga gacagccaca attgggttca ttaataactt cggtcagatc 9300

-continued

```
cctaaacagt tatttaaaaa acctcatcca ccaaagcgag tgagaagtcg actcaatgga   9360
gacaatgcag gaatctctgt cctaccagga tctacaagtg acaagatctt ttttcatcat   9420
ctagacaact tgaggccttc tctaacacct gtaaaagaac tcaaagaacc tgtaggacaa   9480
atcgtatgta cagataaagg tattcttgcg gtggaacaga ataaggttct tatcccacca   9540
acctggaata aaacttttgc ttggggctat gcagacctca gttgcagact gggaacctat   9600
gagtcagaca aggccatgac tgtttatgaa tgcttgtctg agtggggcca gattctctgt   9660
gcaatctgcc ccaaccccaa gctggtcatc acgggtggaa caagcacggt tgtgtgtgtg   9720
tgggagatgg gcacctccaa agaaaaggcc aagaccgtca ccctcaaaca ggccttactg   9780
ggccacactg ataccgtcac ctgcgccaca gcatcattag cctatcacat aattgtcagt   9840
gggtcccgtg atcgaacctg tatcatttgg gatttgaaca aactgtcatt tctaacccag   9900
cttcgagggc atcgagctcc agtttctgct ctttgtatca atgaattaac aggggacatt   9960
gtgtcctgcg ctggcacata tatccatgtg tggagcatca atgggaaccc tatcgtgagt  10020
gtcaacacgt tcacaggtag gagccagcag atcatctgct gctgcatgtc ggagatgaac  10080
gaatgggaca cgcagaacgt catagtgaca ggacactcag atggagtggt tcggttttgg  10140
agaatggaat ttttgcaagt tcctgaaaca ccagctcctg agcctgctga agtcctagaa  10200
atgcaggaag actgtccaga agcacaaata gggcaggaag cccaagacga ggacagcagt  10260
gattcagaag cagatgagca gagcatcagc caggacccta aggacactcc aagccaaccc  10320
agcagcacca gccacaggcc ccgggcagcc tcctgccgcg caacagccgc ctggtgtact  10380
gacagtggct ctgacgactc cagacgctgg tccgaccagc tcagtctaga tgagaaagac  10440
ggcttcatat ttgtgaacta ttcagagggc cagaccagag cccatctgca gggccccctt  10500
agccaccccc accccaatcc cattgaggtg cggaattaca gcagattgaa acctgggtac  10560
cgatgggaac ggcagctggt gttcaggagt aagctgacta tgcacacagc ctttgatcga  10620
aaggacaatg cacacccagc tgaggtcact gccttgggca tctccaagga tcacagtagg  10680
atcctcgttg gtgacagtcg aggccgagtt ttcagctggt ctgtgagtga ccagccaggc  10740
cgttctgctg ctgatcactg ggtgaaggat gaaggtggtg acagctgctc aggctgctcg  10800
gtgaggtttt cactcacaga aagacgacac cattgcagga actgtggtca gctcttctgc  10860
cagaagtgca gtcgctttca atctgaaatc aaacgcttga aaatctcatc cccggtgcgt  10920
gtttgtcaga actgttatta taacttacag catgagagag gttcagaaga tgggcctcga  10980
aattgttgaa gattcaacaa gctgagtgga gaccatggtc tgtagacccc ttcccgattc  11040
tcctgtccca gcttggaagg cattgaaaac agtctccgtt tacacatctc ttcataccac  11100
gtgtttgaag tgttaaaatt caaagggatc attgaataaa acgggtgtag agtacaggaa  11160
tggggcagac gcgattcagg tgaacagcac aagaagaata tgaggtggtt cctaggagca  11220
acactttcga cctccagttc tccctgatga cagtagctgt ctccaagaga aaaatcctca  11280
cttattaact ctcttttctt gcatctcatt tttatagagc tactcatcct tatttggaaa  11340
aaccaacaac aaaaaaggct tttagaaaat ggttgtaaat ctgacttctt tgcaagtaac  11400
tatgtatatt gtaaatagat ataaaaggcc ttttttctaa ataaggactt aactgcctgt  11460
aacatgaaac ttcaaactaa accactaact caatgaacta cttatggttt gtctgacatc  11520
cctcacttac caattaatta taaatatgtt tttttaaatc cccaaagaca ttatctgtgg  11580
tctttttttc ctttcaagct cagcctgtgt gcctgatgtc atttctttca agttgcccac  11640
agtatctcca cttaaactag gctagtaacc aaaataatgt ggaccttctt taggaaacag  11700
```

tgtgggagaa taggagtcca gccgtaagat aaactggaaa tatttgggcg tcttgtacct 11760
ggctacgcac cacctcagtg ttgttcctac ataaacaggg ccccttttaa acttgtatgt 11820
ggactgctgt ttggtcaaag aataccttct tagcattgca gaaaggtggt cagatgacca 11880
gtgtagtgca ggaaacagcc ctgtctcaac taatggaaat atatttgcat gtaacccaaa 11940
attagcttat cttgcataga acataataag tatgtgtctt tggtgacact aatgttctac 12000
tatagcttat tttcaaacaa ggggtaaaaa aaggaaagaa agaagtgtac agaattaaca 12060
tataaacttt gttgtaaaac tgaatcatgt cagaactgct taaaattaac ctttaccatt 12120
taatgtcatc tacctgaaaa cagtgagatt tatactgtat caatgtctat ttttttgttt 12180
ttgctatgaa tataattaca gtattttaat atttagttat ttaatttgtt ctactagttg 12240
gatacagaac acacaaatcc agggggatta aagctggaag gggctaagag attagtttac 12300
agagaaaagg cttggtggtg ggattttttt aaatgtgtgt tatgtacata tatatatata 12360
tataatatat attaaaaatg aaacaattaa tctagatttt aacattttca gaaacttagt 12420
gataacatta tgaacaattc taaaagccct gtgatttgaa aaatatagaa tcattaatgg 12480
cccaagatag gccttcacac cttcacaggt gcgaaaggaa aggccttcac accctcacag 12540
aggcatcatg caaaggacag cggctttggc ttttccaatt ttccatcttt aggccctggt 12600
gagaggcaca cttatgcact aaaatgcaca tatatgcaca tgcattcaaa aataggcatt 12660
tggtacaatg gtgatcttgt acctgatggg ctgaaaccag cttaagaaca aatttgttct 12720
tcctgatatg ataactaggt ctccaagaga aaatagaaag gctgctttag tgccttacgc 12780
ttactaaatt taaatcttta tttacctggg tttgagccta cagtctattt atgattacat 12840
atcaaaattg attaaaacac ttccatttct aaaagttcaa atatacttgt taataaaagg 12900
attatcggca ttaatacttt aatttaaaga aaagttgtgt tctgttttcc tttctgtgtc 12960
ttactccccc cacactctcc ctcccccatc accatcttca attctaataa ataatgctga 13020
tgttcaacag ttgcagaaat tgtgctatta tgtaactgtg ggccttgccc ctgtctggcc 13080
ctctagatga tttgtagcag tgttattcta cactttttaa aagaagcgtc ctccttttgt 13140
ccatgaatca tgtttacccc atacccagtg gcagaggtgt tctttaaaga cttgaatata 13200
tgaatgtgtg tgtgtagtta cttaaaggtt attcctcttt gtaataggaa actatatggg 13260
atgaacactt ttaaactttc cgacacaact tccattacta actttctaac agaacttcca 13320
taactagaag gtggaaacca aaaccctcat ggtagtattt cctctggcag ctggtgctgt 13380
gggcaactgt tttgttcaat cgggtttctt ttctttttgc ctctaatgca gaaatcaaca 13440
gaatcactca cacatacaag tacactcaca tacataaact aattatttct ctggatatct 13500
ttctgtgttc catgtaaatt tatttaccaa catctattgt caacatgtac atctacctta 13560
gtatggtctg cattcttttt ctgagagtac ctcatagggc tcctgcctga tctttgtagt 13620
ttgttcattc atccatccac ctgttcattt gttcatccat gtattctaac atttctatgt 13680
agtgtgcaac tctaatgtca tgcttttgaa gaagagaata gctgcccata gcagccatcc 13740
gtctggataa tagcaaaaca ctctagataa gttattttgc actttcttat gtataaagtt 13800
ggtagaaact tattttttgct ttgtatcatt taaatacatt ttgttttggt aaatgaactg 13860
tgtataaaat atttatgccg ttaaaactgt ttttagaaag tatttttaat ttcagcaagt 13920
ttggttactt gttgcatgac tcttaacaca gctgactttt tgtgtcagtg caatgtatat 13980
tttttgtcct gttattaact tgtaagccct agtaatggcc aattatttgt acagcaacag 14040

-continued

```
aagtaaattg aagatactgg ctaagactgg attgattgtg gacttttata ctatattgca  14100

gaaaccaata tctgtttctt ggtggttatg taaaagacct gaagaattac tatctagtgt  14160

gcagtctgtg atatctgaat gttcattgta tatttgtctc tgatgcaaaa aggtagagta  14220

acacaattac aatacatgat taaatgcaat agtccaggta cttaagtaat tttttttca   14280

tttcaaataa atacctattt accaccaaaa gaaagaaaaa aaaaaaaaa             14329
```

<210> SEQ ID NO 244
<211> LENGTH: 12778
<212> TYPE: DNA
<213> ORGANISM: Homo sapiens

<400> SEQUENCE: 244

```
cgcggcccga gcgcctcttt tcgggattaa aagcgccgcc agctcccgcc gccgccgccg     60

tcgccagcag cgccgctgca gccgccgccg ccggagaagc aaccgctggg cggtgagatc    120

cccctagaca tgcggctcgg gggcgggcag ctggtgtcag aggagctgat gaacctgggc    180

gagagcttca tccagaccaa cgacccgtcg ctgaagctct tccagtgcgc cgtctgcaac    240

aagttcacga cggacaacct ggacatgctg ggcctgcaca tgaacgtgga gcgcagcctg    300

tcggaggacg agtggaaggc ggtgatgggg gactcatacc agtgcaagct ctgccgctac    360

aacacccagc tcaaggccaa cttccagctg cactgcaaga cagacaagca cgtgcagaag    420

taccagctgg tggcccacat caaggagggc ggcaaggcca acgagtggag gctcaagtgt    480

gtggccatcg gcaaccccgt gcacctcaag tgcaacgcct gtgactacta caccaacagc    540

ctggagaagc tgcggctgca cacggtcaac tccaggcacg aggccagcct gaagttgtac    600

aagcacctgc agcagcatga gagtggtgta gaaggtgaga gctgctacta ccactgcgtt    660

ctgtgcaact actccaccaa ggccaagctc aacctcatcc agcatgtgcg ctccatgaag    720

caccagcgaa gcgagagcct gcgaaagctg cagcggctgc agaagggcct tccagaggag    780

gacgaggacc tggggcagat cttcaccatc cgcaggtgcc cctccacgga cccagaagaa    840

gccattgaag atgttgaagg acccagtgaa acagctgctg atccagagga gcttgctaag    900

gaccaagagg gcggagcatc gtccagccaa gcagagaagg agctgacaga ttctcctgca    960

acctccaaac gcatctcctt cccaggtagc tcagagtctc cctctcttc gaagcgacca   1020

aaaacagctg aggagatcaa accggagcag atgtaccagt gtccctactg caagtacagt   1080

aatgccgatg tcaaccggct ccgggtgcat gccatgacgc agcactcggt gcaacccatg   1140

cttcgctgcc ccctgtgcca ggacatgctc aacaacaaga tccacctcca gctgcacctc   1200

acccacctcc acagcgtggc acctgactgc gtggagaagc tcattatgac ggtgaccacc   1260

cctgagatgg tgatgccaag cagcatgttc ctcccagcag ctgttccaga tcgagatggg   1320

aattccaatt tggaagaggc aggaaagcag cctgaaacct cagaggatct gggaaagaac   1380

atcttgccat ccgcaagcac agagcaaagc ggagatttga aaccatcccc tgctgaccca   1440

ggctctgtga gagaagactc aggcttcatc tgctggaaga aggggtgcaa ccaggttttc   1500

aaaacttctg ctgcccttca gacgcatttt aatgaagtgc atgccaagag gcctcagctg   1560

ccggtgtcag atcgccatgt gtacaagtac cgctgtaatc agtgtagcct ggccttcaag   1620

accattgaaa agttgcagct ccattctcag taccatgtga tcagagctgc caccatgtgc   1680

tgtctttgtc agcgcagttt ccgaactttc caggctctga agaagcacct tgagacaagc   1740

cacctggagc tgagtgaggc tgacatccaa cagctttatg gtggcctgct ggccaatggg   1800

gacctcctgg caatgggaga ccccactctg gcagaggacc ataccataat tgttgaggaa   1860
```

-continued gacaaggagg aagagagtga cttggaagat aaacagagcc caacgggcag tgactctggg 1920
tcagtacaag aagactcggg ctcagagcca aagagagctc tgcctttcag aaaaggtccc 1980
aattttacta tggaaaagtt cctagaccct tctcgccctt acaagtgtac cgtctgcaag 2040
gaatctttca ctcaaaagaa tatcctgcta gtacactaca attctgtctc ccacctgcat 2100
aagttaaaga gagcccttca agaatcagca accggtcagc cagaacccac cagcagccca 2160
gacaacaaac cttttaagtg taacacttgt aatgtggcct acagccagag ttccactctg 2220
gagatccata tgaggtctgt gttacatcaa accaaggccc gggcagccaa gctggaggct 2280
gcaagtggca gcagcaatgg gactgggaac agcagcagta tttccttgag ctcctccacg 2340
ccaagtcctg tgagcaccag tggcagtaac acctttacca cctccaatcc aagcagtgct 2400
ggcattgctc caagctctaa cttactaagc caagtgccca ctgagagtgt agggatgcca 2460
cccctgggga atcctattgg tgccaacatt gcttcccctt cagagcccaa agaggccaat 2520
cggaagaaac tggcagatat gattgcatcc aggcagcagc aacaacagca gcagcaacag 2580
caacaacaac aacaacaaca acaacaacaa gcacaaacgc tggcccaggc ccaggctcaa 2640
gttcaagctc acctgcagca ggagctgcag caacaggctg ccctgatcca gtctcagctg 2700
tttaacccca ccctccttcc tcacttcccc atgacaactg agaccctgct gcaactacag 2760
cagcagcagc acctcctctt ccctttctac atccccagtg ctgagttcca gcttaacccc 2820
gaggtgagct tgccagtgac cagtggggca ctgacactga ctgggacagg cccaggcctg 2880
ctggaagatc tgaaggctca ggttcaggtc ccacagcaga gccatcagca gatcttgccg 2940
cagcagcagc agaaccaact ctctatagcc cagagtcact ctgccctcct tcagccaagc 3000
cagcaccccg aaaagaagaa caaattggtc atcaaagaaa aggaaaaaga aagccagaga 3060
gagagggaca gcgccgaggg gggagagggc aacaccggtc cgaaggaaac actgccagat 3120
gccttgaagg ccaaagagaa gaaagagttg gcaccagggg gtggttctga gccttccatg 3180
ctccctccac gcattgcttc agatgccaga gggaacgcca ccaaggccct gctggagaac 3240
tttggctttg agttggtcat ccagtataat gagaacaagc agaaggtgca gaaaaagaat 3300
gggaagactg accagggaga gaacctggaa aagctcgagt gtgactcctg cggcaagttg 3360
ttttccaaca tcttgatttt aaagagtcat caagagcacg ttcatcagaa ttactttcct 3420
ttcaaacagc tcgagaggtt tgccaaacag tacagagacc actacgataa actgtaccca 3480
ctgaggcccc agaccccaga gccaccacca cctccccctc cacccccctcc acccccactt 3540 ccggcagcgc cgcctcagcc ggcgtccaca ccagccatcc ccgcatcagc cccacccatc 3600
acctcaccta caattgcacc ggcccagcca tcagtgccgc tcacccagct ctccatgccg 3660
atggagctgc ccatcttctc gccgctgatg atgcagacga tgccgctgca gaccttgccg 3720
gctcagctac ccccgcagct gggacctgtg gagcctctgc ctgcggacct ggcccaactc 3780
taccagcatc agctcaatcc aaccctgctc cagcagcaga acaagaggcc tcgcaccagg 3840
atcacagatg atcagctccg agtcttgcgg caatattttg acattaacaa ctcccccagt 3900
gaagagcaaa taaaagagat ggcagacaag tccgggttgc cccagaaagt gatcaagcac 3960
tggttcagga acactctctt caaagagagg cagcgtaaca aggactcccc ttacaacttc 4020
agtaatcctc ctatcaccag cctggaggag ctcaagattg actcccggcc cccttcgccg 4080
gaacctccaa agcaggagta ctggggaagc aagaggtctt caagaacaag gtttacggac 4140
taccagctga gggtcttaca ggacttcttc gatgccaatg cttacccaaa ggatgatgaa 4200

-continued

```
tttgagcaac tctctaattt actgaacctt ccaacccgag tgatagtggt gtggtttcag   4260
aatgcccgac agaaggccag gaagaattat gagaatcagg gagagggcaa agatggagag   4320
cggcgtgagc ttacaaatga tagatacatt cgaacaagca acttgaacta ccagtgcaaa   4380
aaatgtagcc tggtgtttca gcgcatcttt gatctcatca agcaccagaa gaagctgtgt   4440
tacaaggatg aggatgagga ggggcaggac gacagccaaa atgaggattc catggatgcc   4500
atggaaatcc tgacgcctac cagctcatcc tgcagtaccc cgatgccctc acaggcttac   4560
agcgccccag caccatcagc caataataca gcttcctccg ctttcttgca gcttacagcg   4620
gaggctgagg aactggccac cttcaattca aaaacagagg caggcgatga gaaaccaaag   4680
ctggcggaag ctcccagtgc acagccaaac caaacccaag aaaagcaagg acaaccaaag   4740
ccagagctgc agcagcaaga gcagcccgag cagaagacca acactcccca gcagaagctc   4800
ccccagctgg tgtccctgcc ttcgttgcca cagcctcctc cacaagcgcc ccctccacag   4860
tgccccttac cccagtcgag ccccagtcct tcccagctct cccacctgcc cctcaagccc   4920
ctccacacat caactcctca acagctcgca aacctacctc ctcagctaat ccccctaccag   4980
tgtgaccagt gtaagttggc atttccgtca tttgagcact ggcaggagca tcagcagctc   5040
cacttcctga gcgcgcagaa ccagttcatc cacccccagt tttggacag gtccctggat   5100
atgcctttca tgctctttga tcccagtaac ccactcctgg ccagccagct gctctctggg   5160
gccataccto agattccagc aagctcagcc acttctcctt caactccaac ctccacaatg   5220
aacactctca agaggaagct ggaggaaaag gccagtgcaa gccctggcga aaacgacagt   5280
gggacaggag gagaagagcc tcagagagac aagcgtttga gaacaaccat cacaccggaa   5340
caactagaaa ttctctacca gaagtatcta ctggattcca atccgactcg aaagatgttg   5400
gatcacattg cacacgaggt gggcttgaag aaacgtgtgg tacaagtctg gtttcagaac   5460
acccgagctc gggaaaggaa aggacagttc cgggctgtag gcccagcgca ggcccacagg   5520
agatgccctt tttgcagagc gctcttcaaa gccaagactg ctcttgaggc tcatatccgg   5580
tcccgtcact ggcatgaagc caagagagct ggctacaacc taactctgtc tgcgatgctc   5640
ttagactgtg atgggggact ccagatgaaa ggagatattt ttgacggaac tagcttttcc   5700
cacctacccc caagcagtag tgatggtcag ggtgtccccc tctcacctgt gagtaaaacc   5760
atggaattgt cacccagaac tcttctaagc ccttcctcca ttaaggtgga agggattgaa   5820
gactttgaaa gcccctccat gtcctcagtt aatctaaact ttgaccaaac taagctggac   5880
aacgatgact gttcctctgt caacacagca atcacagata ccacaactgg agacgagggc   5940
aacgcagata acgacagtgc aacgggaata gcaactgaaa ccaaatcctc ttctgcaccc   6000
aacgaagggt tgaccaaagc ggccatgatg gcaatgtctg agtatgaaga tcggttgtca   6060
tctggtctgg tcagcccggc cccgagcttt tatagcaagg aatatgacaa tgaaggtaca   6120
gtggactaca gtgaaacctc aagccttgca gatccctgct ccccgagtcc tggtgcgagt   6180
ggatctgcag gcaaatctgg tgacagcgga gatcggcctg ggcagaaacg ttttcgcact   6240
caaatgacca atctgcagct gaaggtcctc aagtcatgct ttaatgacta caggacaccc   6300
actatgctag aatgtgaggt cctgggcaat gacattggac tgccaaagag agtcgttcag   6360
gtctggttcc agaatgcccg ggcaaaagaa aagaagtcca agttaagcat ggccaagcat   6420
tttggtataa accaaacgag ttatgaggga cccaaaacag agtgcacttt gtgtggcatc   6480
aagtacagcg ctcggctgtc tgtacgtgac catatctttt cccaacagca tatctccaaa   6540
gttaaagaca ccattggaag ccagctggac aaggagaaag aatactttga cccagccacc   6600
```

-continued gtacgtcagt tgatggctca acaagagttg gaccggatta aaaaggccaa cgaggtcctt 6660
ggactggcag ctcagcagca agggatgttt gacaacaccc ctcttcaggc ccttaacctt 6720
cctacagcat atccagcgct ccagggcatt cctcctgtgt tgctcccggg cctcaacagc 6780
ccctccttgc caggctttac tccatccaac acagctttaa cgtctcctaa gccgaacttg 6840
atgggtctgc ccagcacaac tgttccttcc cctggcctcc ccacttctgg attaccaaat 6900
aaaccgtcct cagcgtcgct gagctcccca accccagcac aagccacgat ggcgatgggc 6960
cctcagcaac ccccccagca gcagcagcag cagcagcaac cacaggtgca gcagcctccc 7020
ccgccgccag cagcccagcc gccacccaca ccacagctcc cactgcaaca gcagcagcaa 7080
cgcaaggaca aagacagtga gaaagtaaag gagaaggaaa aggcacacaa agggaaaggg 7140
gaacccctgc ctgtccccaa gaaggagaaa ggagaggccc ccacggcaac tgcagccacg 7200
atctcagccc cgctgcccac catggagtat gcggtagacc ctgcacagct gcaggccctg 7260
caggccgcgt tgacttcgga ccccacagca ttgctcacaa gccagttcct tccttacttt 7320
gtaccaggct tttctcctta ttatgctccc cagatccctg gcgccctgca gagcgggtac 7380
ctgcagccta tgtatggcat ggaaggcctg ttcccctaca gccctgcact gtcgcaggcc 7440
ctgatggggc tgtccccagg ctccctactg cagcagtacc agcaatacca gcagagtctg 7500
caggaggcaa ttcagcagca gcagcagcgg caactacagc agcagcagca gcaaaaagtg 7560
cagcagcagc agcccaaagc aagccaaacc ccagtccccc ccggggctcc ttccccagac 7620
aaagaccctg ccaaagaatc ccccaaacca gaagaacaga aaaacacccc ccgtgaggtg 7680
tccccccctcc tgccgaaact ccctgaagag ccagaagcag aaagcaaaag tgcggactcc 7740
ctctacgacc ccttcattgt tccaaaggtg cagtacaagt tggtctgccg caagtgccag 7800
gcgggcttca gcgacgagga ggcagcgagg agccacctga agtccctctg cttcttcggc 7860
cagtctgtgg tgaacctgca agagatggtg cttcacgtcc ccaccggcgg cggcggcggt 7920
ggcagtggcg gcggcggcgg cggtggcggc ggcggcggcg gcggcggctc gtaccactgc 7980
ctggcgtgcg agagcgcgct ctgtggggag gaagctctga gtcaacatct cgagtcggcc 8040
ttgcacaaac acagaacaat cacgagagca gcaagaaacg ccaaagagca ccctagttta 8100
ttacctcact ctgcctgctt ccccgatcct agcaccgcat ctacctcgca gtctgccgct 8160
cactcaaacg acagcccccc tcccccgtcg gccgccgccc cctcctccgc ttccccccac 8220
gcctccagga agtcttggcc gcaagtggtc tcccgggctt cggcagcgaa gcccccttct 8280
tttcctcctc tctcctcatc ttcaacggtt acctcaagtt catgcagcac ctcaggggtt 8340
cagccctcga tgccaacaga cgactattcg gaggagtctg acacggatct cagccaaaag 8400
tccgacggac cggcgagccc ggtggagggt cccaaagacc ccagctgccc caaggacagt 8460
ggtctgacca gtgtaggaac ggacaccttc agattgtaag ctttgaagat gaacaataca 8520
aacaaatgaa tttaaataca aaaattaata acaaaccaat ttcaaaaata gactaactgc 8580
aattccaaag cttctaacca aaaaacaaaa aaaaaaaaaa aaagaaaaaa aagaaaaagc 8640
gtgggttgtt ttcccatata cctatctatg ccggtgattt tacattcttg tctttttctt 8700
ttcttttaat attaaaaaaa aaaaaaaagc cctaaccctg ttacattgtg tccttttgaa 8760
ggtactattg gtctgggaaa cagaagtccg cagggcctcc ctaatgtctt tggagcttaa 8820
acccccttgta tatttgcccc ttttcaataa acgccccacg ctgatagcac agaggagccc 8880
ggcatgcact gtatgggaaa gcagtccacc ttgttacagt tttaaatttc ttgctatctt 8940

-continued

```
agcattcaga taccaatggc ttgctaaaag aaaaaaagaa atgtaatgtc tttttattct   9000
caggtcaatc gctcacactt tgttttcaga atcattgttt tatatattat tgtttttca   9060
gttttttttt tttttttgt tccagaaaag attttttgtt ttgttaactt aaaaatgggc   9120
agaaagtatt caagaaaaac aatgtgaact gctttagctt tctggggatt tttaaggata   9180
gcttttctgc tgaagccaat ttcaagggga aaagttaagc actcccactt tcaaaaaaaa   9240
aaaaaaataa taacccacac acacaaagag tgttgaggac ttgtagctta aaaaaaataa   9300
gttttaaaaa ctgactttct gtatttatga tagatatgac catttttggt gttgagtaga   9360
ttgttgcatt ggaaatgaac tgaagcagta tggtagattt aaaaggaaaa aaaaaaaaaa   9420
accttttgtg tacatttagc tttttgtatg gtccagctga cagctcctca tttgatgttg   9480
tcttgttcat tcctagcaga tgatagattg caatccgttg attcgcctaa gcttttctcc   9540
ccttgtccct taattccact ttctctttct tgtcccttaa ttccactttc tctttccttc   9600
tcccacctcc cgtcctataa tctcccactt aaggtagctg ccttcatttc ttagagggag   9660
ctgcagaatt attttataaa actaaagaaa gaatttcaag ggattctagg ggtcattagg   9720
atcctcacag attattttg gttggggagt tgaaactttt taaaggcata taattctagt   9780
tacctgtgtc tgttagcttt gtgcatttat tttttattta tccttctttt ggcttttttt   9840
tctttgtacc ccttcttttc ctccttgttt ggtaggagct tcaaatattc ttttttttc   9900
tatactaaag gatttgtttc catttgtgta attggctgtg tacttttctt ttctaaaaaa   9960
agtttttggt tagggatttg gtttttggtt ttgtgtttgt tttttctttc ctctctcaga  10020
aaaaaaaatt tcatgcttta aataaaatcc aaagacacac cctttcactg ctgatgcaga  10080
aaaaagggaa agggttcttg ttacttgaga atttgtttct gatttaaaca aacaagactt  10140
agtttaataa aagaaagaga aaaacaaaag attcccaggt tgttatgtgc ttcttctgca  10200
agcagagagg caaatgttaa tgacaattcc atataccaaa agacacattt tttacttcaa  10260
agttttgtcc ttgtgttagg cagtctgagc agcgagtgat ccagagcgca gccaacaaag  10320
cagcagatag cagtgtacag aaagcaaaaa aggaactgta tgtgaggcac ttgtttctgt  10380
taatatccat attcctgtta acacacaccc tttctcatgt aaaaagaaaa ataaataaat  10440
ggtctgaact ttgaaaactt tgtgctgcta aaacatagat tttggagaca aataaataga  10500
tgctttgctg tttcactttc atagctaaac atcaacagaa accatctccc cttgccccca  10560
aagtgtgaaa tccttcttcc cttcgttttc ttccttatgt ttcaaaaggg aactttgaag  10620
actgtgaata caggttccat tggtcacctt tcgggcttct ttccccagtg ctgaagccac  10680
tcatcgactt tgcaaaagac tggagcattc caagatctga aaatggattt tttttctttt  10740
tttctttttt agccgggact attttatttt tatgaatttg tttttagttt aatgaaatag  10800
tagatcctga aatgttgtac atatttctaa ctaggctgat gcacagtgca aattcctttt  10860
ttaattgttt tttttaagta gaaatactaa agaaagaata ccatctaact attcatacca  10920
gtatccagtt gtagcataag gtgtcaaaag caagtacgca aaacatttac tgttttaaca  10980
agctatttcc ttttaacaag aaatcttgta tttcttcctg tgtttgagat gaacattttt  11040
aaattttaaa gttgtacagt tttttgtttt ccattatttt atcttgtttg taactctatg  11100
aaatatatat atatatattt tttgccattt aactgttgta tgttactctg tgtctgtacc  11160
atatagaaaa aaaattgttt ttgtttttgg ttctctatgt gatatcagtt aacaatgtaa  11220
cactagcttt acctgtcaaa ttctgctagg tcttctctga aaacgttgtt tttaaaaatg  11280
atattgcttg gtaatagtgc aatttctatc cttttccctc ccccctcaac ttttaagttc  11340
```

```
ttttctttat aattttgctg ccccctccct gatggtttgg gtttttgttt ttgtttttgt  11400
ttttttttt catggagcta ctatgccatc ctccctctgt gaggcagagt gactgtcagt  11460
gttttgttat gccatgcctt gagctgtggg tgtttggcga caataaggtg gttgaataga  11520
ttggctgagc acacttccac ccacctagtg ttctcagagg ggttatgtga ttgtttcaac  11580
ctggagtggg ttgcaccctt aatgctttcc tctgcaacta aaccgcccac atatatgttc  11640
attgaaaaaa gtaagaataa ttctcagcac taacccagaa gtagcaaagc agtcagtgat  11700
ggtgaacatt agaggtcaaa catgagttag atgtttgtgg gctgacagcc atcgtggcta  11760
tgaccagtac tatttacaaa gcatgaattc actacaatgc tcaactgttt gtttagcttt  11820
atctcacttg gggaatttat tcctgtctgc tgcattgtag gtagctgggt aggatatatt  11880
tccacttgct ttttaaatta gttcttcacc tccattgaca ctcgtttttt ggtttttctcc 11940
ctatagtgtg ggttggtgct agacaccagt ctgacccaca gaatgggagt tatttcatcc  12000
atctttcctc catccttcca aaaaccacat atctacacaa ggaaaaaattt aatacatcta 12060
ggaatttttt ttttaattac aagctattta aagagatgaa tgtggccaaa gttttacaca  12120
attgaaaata aagtaaaaca gacggcatgt gtttaaacct gagtttatca ggcatggcag  12180
gaagttgcag gagagagagg cagtgaccca agccagtgca cttgatgttc atggacatat  12240
atttttttta aataataaat taaaacattt taaatagaag cataaattga gttgtttgtt  12300
ggcgctgaga tactgcccac tgtgaaacaa agctttgact agttttttgt ttgtttactt  12360
tcttcagggg ggaggggggc aagtttgggt aggaaagaaa gcataaatga acgtgaccct  12420
gaggtgaaga ggtatatgaa cagcctttgc aatgtacaaa aagaaaaaaa aacaaaaaac  12480
aacaaaaaaa atagagcaag tgaaaccaaa aatgatgttc ttggtgtttt tctataatgt  12540
agtcttgtta gctttttttgt tactgtaaca atgctgatct cgaactgtac caaaatacat 12600
ggagactaac aaacagaacc acatggaact ttcaaactga aaaaaaaatt tgtcacaaaa  12660
actttgttgt catagttaag ttgattgtag atggtaattg aatatactcc tttgaaaata  12720
tttcatcaag tatgtttcct gctcattgtg atacattaaa aaaaaaatat gagcaaaa    12778
```

<210> SEQ ID NO 245
<211> LENGTH: 12600
<212> TYPE: DNA
<213> ORGANISM: Homo sapiens

<400> SEQUENCE: 245

```
gggcgcgggc agctctgcgt ccgaagctgc tccgacgccg tcgctgggac caagatggac     60
ctcccggcgc tgctccccgc cccgactgcg cgcggagggc aacatggcgg cggccccggc    120
ccgctccgcc gagccccagc gccgctcggc gcgagccccg cgcgccgccg cctgctactg    180
gtgcggggcc ctgaagatgg cgggcccggg gcgcggcccg gggaggcctc cgggccaagc    240
ccgccgcccg ccgaggacga cagcgacggc gactctttct tggtgctgct ggaagtgccg    300
cacggcggcg ctgccgccga ggctgccgga tcacaggagg ccgagcctgg ctcccgtgtc    360
aacctggcga gccgccccga gcagggcccc agcggcccgg ccgccccccc cggccctggc    420
gtagccccgg cgggcgccgt caccatcagc agccaggacc tgctggtgcg tctcgaccgc    480
ggcgtcctcg cgctgtctgc gccgcccggc cccgcaaccg cgggcgccgc cgctccccgc    540
cgcgcgcccc aggcctccgg ccccagcacg cccggctacc gctgccccga gccgcagtgc    600
gcgctggcct tcgccaagaa gcaccagctc aaggtgcacc tgctcacgca cggcggcggt    660
```

-continued

```
cagggccggc ggcccttcaa gtgcccactg gagggctgtg gttgggcctt cacaacgtcc    720
tacaagctca agcggcacct gcagtcgcac gacaagctgc ggcccttcgg ctgtccagtg    780
ggcggctgtg gcaagaagtt cactacggtc tataacctca aggcgcacat gaagggccac    840
gagcaggaga gcctgttcaa gtgcgaggtg tgcgccgagc gcttccccac gcacgccaag    900
ctcagctccc accagcgcag ccacttcgag cccgagcgcc cttacaagtg tgactttccc    960
ggctgtgaga agacatttat cacagtgagt gccctgtttt cccataaccg agcccacttc   1020
agggaacaag agctcttttc ctgctccttt cctgggtgca gcaagcagta tgataaagcc   1080
tgtcggctga aaattcacct gcggagccat acaggtgaaa gaccatttat ttgtgactct   1140
gacagctgtg gctggacctt caccagcatg tccaaacttc taaggcacag aaggaaacat   1200
gacgatgacc ggaggtttac ctgccctgtc gagggctgtg ggaaatcatt caccagagca   1260
gagcatctga aaggccacag cataacccac ctaggcacaa agccgttcga gtgtcctgtg   1320
gaaggatgtt gcgcgaggtt ctccgctcgt agcagtctgt acattcactc taagaaacac   1380
gtgcaggatg tgggtgctcc gaaaagccgt tgcccagttt ctacctgcaa cagactcttc   1440
acctccaagc acagcatgaa ggcgcacatg gtcagacagc acagccggcg ccaagatctc   1500
ttacctcagc tagaagctcc gagttctctt actcccagca gtgaactcag cagcccaggc   1560
caaagtgagc tcactaacat ggatcttgct gcactcttct ctgacacacc tgccaatgct   1620
agtggttctg caggtgggtc ggatgaggct ctgaactccg gaatcctgac tattgacgtc   1680
acttctgtga gctcctctct gggagggaac ctccctgcta ataatagctc cctagggccg   1740
atggaacccc tggtcctggt ggcccacagt gatattcccc caagcctgga cagccctctg   1800
gttctcggga cagcagccac ggttctgcag cagggcagct tcagtgtgga tgacgtgcag   1860
actgtgagtg caggagcatt aggctgtctg gtggctctgc ccatgaagaa cttgagtgac   1920
gacccactgg ctttgacctc caatagtaac ttagcagcac atatcaccac accgacctct   1980
tcgagcaccc cccgagaaaa tgccagtgtc ccggaactgc tggctccaat caaggtggag   2040
ccggactcgc cttctcgccc aggagcagtt gggcagcagg aaggaagcca tgggctgccc   2100
cagtccacgt tgcccagtcc agcagagcag cacggtgccc aggacacaga gctcagtgca   2160
ggcactggca acttctattt ggtatgaagc actctattca gtcaccacca tataggtcac   2220
ttctctcata ctcggtcttg aggatattct ggattaatcc tttctatgca gacgtttctg   2280
gtttacaaaa ggacgcagcc ctggactaca agtctggaac tgacaagttc ttatgacctt   2340
gacaaatcac cttaacccat ctgagcctta aattctcatt tatttcctgc ataaggagat   2400
ttggctaaat gctttctgag gtcctttgga gtcctgtggc tccatggtaa tgtgctcctt   2460
tccttgaaga ttgggggttt tgtaatgttg agatactttg cctctatgct tgtcagctca   2520
tgaccagtcc tagaagagga gtcgagacat aagccacctt cagaggttca atggaaactt   2580
taaaaccata ccaaactctt ttttaaaatt agaattaaca agaaaaaaaa aaagggtggg   2640
gtttatgagc cttagttctt ggaggattat aagagtactt ccccagtttt gaggctggac   2700
agttaatata ctttatatca attatacatt taatataatt taatttaaaa taatttaaag   2760
attcttagga gatagtctga ctttcctgac ctagatggga atgatcagat agggattttt   2820
tttgtggcac aggctaaatt tgatggtgac atttatattg ttgagaatgt tacatcttat   2880
tttaccacaa cttttaaaaa atgttacatc ttttgcagta ggatcagttg tgaggcacat   2940
agtagctgag gctccatgga gccacctttc atttctttca gtcagagagg aggacagtct   3000
ctgtctctgc atttctggtg tcttgcttgt cggtggcaga gccatgcttg ccggcatttg   3060
```

-continued

```
cttaggcggc catagtagtt gctaagtgta caggtgactg ggcagggatg ggaggtggcc   3120
acaggtcaga gacaagtgct cagtcagtcc ctggtgccag gactgtgtgc ctcggtgcct   3180
tgggaaatgg aagctccctg gtgcagctgc agctgtgggt ggaggtagag aagccagcaa   3240
gaccttggtc ttaaccccgt gttcattttc ttgctagctg tgtgacgttg ggctacctcg   3300
cttctctgag tacaaatggt gtgtggtgaa tgggtcccag gtatgctacg agctttgagg   3360
gctgctcttt ttctcttcat agcgataagt gttaaactgt ctttcttagg aaacgttcac   3420
agacttgcaa cagctgatgt cctctgagta ctgtctgact ccctcaggca agttcctgaa   3480
ttcagtacca tcattattat ttttgtgtaa gactttgaca aagtatagcc cctgccacca   3540
gagcagcctg tacagtgggt ctctaaggtg ggacctgccc cgggcctgcc atgcacgtgt   3600
gtgaaacagc gtgaaaagtg tcgcggtaag gtgaccctgg gttacccagg caaggctcgg   3660
tgtttgtttc agaaagcaga gaagtatgta attgatttta aaagtttctg tttaaaatat   3720
ttggctatgt tttagactat gaaggaatga actttgcttc tctggataag aaagtcacat   3780
acattgttcc agctccaagt ttgttcggcc ctcgccacaa gtggatgtag cgtttggccc   3840
tttgtgtgcc ttgctggtga ctctggtttt gggagctcgg atatgtccca gaagcaggct   3900
tatggcactt ctgtagctcc cttgctaccc ttcctttgtg tctagataag tgactgacat   3960
gcttttcttt ggtctcagga aagtgggggc tcagcaagaa ctgattaccg agccattcaa   4020
ctagccaagg aaaaaaagca gagaggagcg gggagcaatg caggtgaggc cgtgtgtgct   4080
gcagccggac gagcaagggc ctgagggttc tctgtcactg ttactggcag aagaaacaca   4140
gcaggtgttt ctgtgctctt ggttttactt ttctgttcag aataccctttt tatcaactcc   4200
ttagttttat ttgaacttaa gggaaaaaat tagtaacaaa attcccagca tcagtatgaa   4260
catattttat ttgcctaaac aagctttgtg aaagttaagc gttcaaacac cagtgtcagt   4320
tacctggaag gctactaagg taaataagca aagcaggcca gttgtcagga aagcagagat   4380
tgtgcctggt gctgaatggc cttggggcct gatcttggca tggcagagac ctggggactg   4440
ccactgtccc caggtacgtg tacatggagc caaactgtgt gtcctgtggc attgtcagag   4500
ttatgttgaa atcttatttg aaaatgttag caacttactt gcatttttaa agaccaaaca   4560
agagctggta acctatggcc tcaagcatct gtccttccta aaaatggaat agtgggatgt   4620
agtgcttaat ggaaactgct aaatcttttt ctaaaaacta acagtggatt tttaaaatat   4680
attgtttttt gtgtatttca tttgtccttt gtatttatct aaaagggttg atatgatttt   4740
atatcttgct ctctattcct aatagtatta tgacttctta tttaaaataa ataacaattg   4800
ccggttttct gttaatcagt tttcttaaag ccagtgtttc actatagtgt atgcatcagt   4860
gtgaattgtg acttaggaag ggacacctca acagttcaca aagtaccaga atggaacttg   4920
cagagataat agaaggaagt gtggtggtga aatttgtaga aagagttgac catataccaa   4980
ggaaagttca tgaaggaaag cggatgcctt tattgaacct ggtagataat cttgaagaaa   5040
aaagagacaa acattcaagt atataacacg tgtcctattt attacattgc tttggagtac   5100
tatctataaa ggaggtttga tgttttcatt actgtttttg taaatatttc agcattatct   5160
ttaaaaagta aggacattgg ccaggtgcgg tggctcatac ctgtaatccc agcactttgg   5220
gaggccgagg tgggtggatc acctgaggtc aggagttcga gaccagcctg gccaacatgg   5280
tgaaacactg tttctactaa aacacaaaaa aattagccag gcgtggtggc acgtgtctgt   5340
aatcctagct acttgggagg ctgaggcagg agaatcgctt gaacccagga ggcagaggtt   5400
```

```
gcagtgagcc gagattgtgc cactgtgctc cagcctgggt gacagagtga gactccattt   5460
caaaaaaaaa aaaaaaaagt aaggacatta aaaaaaatta tagccatcta atgttgccac   5520
ttctttaaaa attaacagta ttttcttaat gtcagtatct agcaaatgtt caaattttca   5580
gttgtcccag atgcctcaaa tattttatgt aactgtctgt tggaatcaga atccagtggg   5640
gttcatatgt cactactggt tgatacatca tctcttgact gtttgacagc tgtagggttc   5700
tctgctaggt cttgcctggt ttttgttgaa gaaactgatt gttctttcga gtgtgccagt   5760
ctggacctta atgatcacat cactgtttta ataggttcct tcgttttttt tcttttcctg   5820
aaaattagta gttacgttta gtggttagat ctggttggtt ggtaaaactc cgctgcaggt   5880
gggagtgggc tcttgcagga gaccccccagc ctctggtggc aaccattgtg accagatact   5940
ggatccactc atttcttagg ggttactcta aacggtggta ctctaaatct gtcattcctt   6000
tcttacttat agctgggaca tgtctataaa gcgcagcttc tcgttttttt accctgaggt   6060
gcagttcatg atgtttgaat ctgtgtgagt ttcttagcat cctgcagtga tggtcagagt   6120
atttaatgc actcattggt ttaaatactt catacacttc taagggaaat ggaaacctgg   6180
tacctgctag gtctccgtgt gtgagtgcag caggagaatg tcctcgtgag ggtgaggctg   6240
ctgtcagtgc cacccacatc cttgaaaagc ccctccaggt gcctcagcca gtgcaggaag   6300
gccaccgtct cttttccaaa acatgcaggg cactggtgtc ttcccgcgcc catgggtctg   6360
ctgtggtttt agacacatat tcctgcacag cgctcctctg tgtgtcttgt cacagtgttg   6420
catcctctgg cggggatgcc tttgcccgcc tcccctcaaa gcagcatcct gcatactcat   6480
gctgcattta tcacagctga gagtcccctg tggccgcagt cctggcagct gaatggcaga   6540
cttgatgtga atgtgaccag actcccccag tgcccttccc tgttccaggt tccatgtgca   6600
tttaattgtc acccctcccc gtctcctctg gtctggttga gggccttggc cctcccttgt   6660
catgatgctt tcaaagagga tggcctatc gctctggacc gtcctccctg tgggcctgcc   6720
tgatgtcttc tggagatgag acccgggctg ggttgctgga gacgggggtg aggtgccctc   6780
cccacacatc ctccctgggc catgctgtcc acacggcaga tgtggtaacc tggatcactg   6840
gttagggtgg tagctgctag gtttcttcac catcaacttc ttgtttttcc ctttgtaatt   6900
aactatcttg cagtagatgc tttgagactg tatgtggggc ttgggggtcc ctaagaccac   6960
cttcacttct aatagcaact gcaagcttgg gggtcctcaa gaccaccctt aggtaattct   7020
ctagaaggac tcatggagct cactgatagc tgttgtactc acggctaagg cttattgcag   7080
caaaaggaca cagattaaag ccagctgagg gaaaaggggc ccaggcaagg cagggcccat   7140
gagagttcct agtgtgacgc ttcaagtgtc ctctcatgga ggtgtgaaca gtgccaactt   7200
ctcccagcat gtgacagcac ccagagacca ttgcccccca gggaagccca cctgagactc   7260
actgtctgga gttttgttgg gtctcagttg tgtggattgg ctggccttag tctccagccc   7320
tccagaggct gagctggcgc tgtgtgcccg aggcctccac cacagggtta gcacagactg   7380
tggaagtggc ccagggcacc cagttagaca gacattctta ccaggcagga ctttccaagg   7440
gtctagagat ctcccaggag ctgggggcag aggcgaggcc tctctggcag ggttaaccct   7500
ttgccttgca ctgcaagtgc cctgtttctc tttaagcttt cctctcatgt aacactcagc   7560
aggggctttt tgcctgtggg gtttaatggt gattttccat ttcccttatt cttgtgtact   7620
tattaatttt ataaggaaga gctgtctctt ctccctcatt tacttattcg cagtatggat   7680
tcaatgatac tgattctttt ttttttgttt ttttttgaga tggagtcttg ctctgtcgcc   7740
ccggctggag agcagtggcg cgatctcggc tcactgcaag ctccgcctcc caggttcacg   7800
```

ccattctcct gcctcagcct cccgagtagc tgggactaca ggcgctgccg tgcccagcta 7860
attttttttt tttgtatttt tagtagagac gggggtttca ccgtattagc caggatggtc 7920
tccatctcct gaccttgtga tccgcccgcc tcggcctccc aaagtgctgg gattacaggc 7980
gtgagccacc atgcccggcc tcaacgatat tgattctttg ggctgtagtc agtattggat 8040
tatgatcaat attatcacca tttattttgt tgctccagtt cttccagctg tggccaatcc 8100
ttcagttgga ttcttgtgcc ccatcaacat tctccatcct ggctttttgt tttgagcact 8160
tccttccttc ctagcaccac caggctcttg tattatccct gtccctgccc tggaatcgac 8220
tcctcctcca gagagccctg gtttcttttg ttagaggatg gtatatagaa tccaacatgc 8280
agacactcgg tggacttatt gttactgggg ttttgttata ctagggtttc agtggtcagt 8340
gctagtattt atgtatgtta acccacgctg tgctttggat tcaggctatt tcaaatttta 8400
gataatatgg tacatatatt attaatacca ctagttacta cattggtact tttcagcaaa 8460
atatatctaa gtgggatcaa atgagactgt aaatagcttt acatcagttc aggtcagtta 8520
tgttgctaaa ttacttttgg cattaagttt agggaaaaaa aattgggttt gggatttttt 8580
ggtttcaaca tttgtgattg agagactatg gacctgtaat aagtccaaga acagcagttg 8640
cagtgtaaca ggactgttaa tggaatcggg tcatttagaa acagtcaaga cttcgctgtt 8700
gtgcatgtgg ttaggagcca gtgcacacgt cagttcttag gaaatgtaca gtctgagcaa 8760
tagcatttga aatccaagac tcttcccatt gtgttgctgt tgagtgtaga aaataaaatg 8820
tgtgaatttc tttatcttga gtattgagat tctcccctta gaataaaaca agaatttttc 8880
tctcagtgta aaaatgtcaa gttttattct tgaaatgaat agcaaagtta agcttaaaaa 8940
cgtgaacagc ttcagaacta taaatgggta tgtatacctt tctgctgtct aagggcagag 9000
aagggaaaga aagtgtggtg cttatcagag gagacagcag caagacacat tgtgacagaa 9060
aaccaagggt atcctgtgtc acagtgaagt gtaatgaggg cacctctcct ttcaagagac 9120
gaagattgaa tacatgggaa gcacactctc cgctgtgtgt tgtctaggag aggtgcaccc 9180
tgtatggaaa tatttgggaa ggttaagatt aagacagggt aaaataaagc aaaggcaaat 9240
cacaaagcaa gggctaatgt taatatgaaa agtgcagaat tcaaggaaaa agcatgggga 9300
caaagaagat ttttcctctt tttggttgct gttcatgtgt agcctacaac agaactataa 9360
gacctataga catttatatg aatatttatt tgaaaacgta taatatcaaa caatgtaaaa 9420
gccaatagaa atctcagata attgaatgta tagaaactag cagtttgaaa gtgattagtt 9480
cattatttgc tgatcaagca gaaaaataag catatgaaag atatttaaaa tgggattaat 9540
aaagttgatt taacagatcc tattccatgt cctttgaata tttatagaaa ttaaatggaa 9600
caaattaggg catcaggaaa actatacaaa agtctttacc aaaaaaaaaa atatatatat 9660
atatgtgtag tactacctat atatatacat aatatatagt actgcttata tatatatatg 9720
cctatatgta cacatatata tatacatgta taggcagtac tatgttttct gatcataata 9780
tgttaaatta gtaaaaatta cttggaaaac aaaacctcta gacaatcagg tgaaagaaga 9840
aataaaagcg aggctgggcg cggtggctca tgcctgtaat cccagctcag ctactcagga 9900
ggctgaggca ggagaatcgc ttgaacccgg gaggcagagg ttgcagtgag ccaagatcgc 9960
accattgcac tgcagcctgg gcaacaagag cgaaactcct tcgccaaaaa aaaagaaaaa 10020
aaataaaagc taattacaaa tacaggaaaa tggataggcc atgtgtttat aagtttgagc 10080
tcttgagcca gtgacttccc tgcacgttca gctttctcct ttgtgaaatg gtaatagaag 10140

-continued

```
cacgctgcac ttgggattct tgtggattac atgtgagggt cttagaaaca cttgatgtgt  10200
aagccaacta ttatgtatta ctgtatatgg aacacaaggg atgtagccaa aactaaatgc  10260
aagtttgtgc ctcagatgtc ttcctatcag aacagagtca aatccagatt ttgatgctta  10320
aatgtgacag cttattcaga tttagaaaaa cttttggtat gggccaaaga aaacatatcc  10380
ttaaggggat atggccccta ggccctcatt ttccttttct gtctgagcaa ttaaaaaaag  10440
cattaagtaa attccacaaa ttctttggaa tacctagaga taaacagata tcatgttaac  10500
tgtatgataa taagttagaa tacttgcaac aaaatgcaga gttttctagg aaaacaagta  10560
atcattcaga aataagaata tgaatagttc ctcagttctc cccctttgtg gaatttgtgc  10620
agtaaatgct gctccaaagc tctgtggaaa acagaagctt cccatgaaaa atctgacaag  10680
ggtatctctc agaaagagag ctgtaatccc agcactgtgg gaggctgagg tgggagtatt  10740
gcttgaggcc aggagttcaa gaccagcctg ggcaacgtgg taagaccccc atctgtaaaa  10800
aaaataataa ttagccacgc gtggtggtgc acacctgtgg tcccaattac tggggagact  10860
gaggcggaag aatcgcttga gcccaggaga tggaggttgt cgtgagctag gatctgccac  10920
tgcactctag cctgggtgac agtaagaccc ttgtctcaaa aaaaaaaaaa agaaaaactg  10980
cagattggtg actcttacga agatagatgg aaatgttcta aataaaacac acttaggatc  11040
tggcaatata tatatttaat gtactattct gaccaaatgg agcttaatca gatagcttga  11100
gaatgattta atgttacgaa atctgttaat tgcattatct caataataga tcggtgaata  11160
actttattat tctctcaaca aatcctgtat ttgatttaca aaatggatgg gaggtttcag  11220
ggagagcagt tggaagcctg tgtgctcacc tgttaggaac gagagtggca acagcagtgg  11280
ggaggagtgc tcggctcctg cacctgtctc gatggcagag cccacaggct tggctgacag  11340
acgtgggatg aaggaaagag aagcctctca ctcttcccac agcattgtag tgcgatttca  11400
tgcagaagtc caagcaggtt ccaggacaat tgtgtaagaa gctatggaca agaacgtcta  11460
agaaaacgga aaatgacata gaggatttgc actgtagcta agacttcacg caaggctgtg  11520
gcagctgaaa gcatgttctg gtgctggggc tgcgtggcag agccaggagc ccaggatcca  11580
gcgcactggg caccgacctg ggacctggtc atctttgcgt gtggaaaaga tggcatttcc  11640
agttattgac aggtgaatgc tggcctttta gggaaaaaaa aatattagaa ttccatacag  11700
aataaagaat gaagatgaga ggttaaaggt ttttctaagg catgaagagc tgtgggggca  11760
gcctgccctt gttctttttg tcgtgtgtcc ttcacatgca gtaactctgt tcacgcctca  11820
caaaaaccct atgaggtgga gacctgccat caacccttcc tgcacgggtg ccactgaggc  11880
cccaaggtta aatcatttcc cagagtgtat cagcagaggc acagccacag agacacgtcc  11940
gcacagagag ctttccagat caccagtaac agcgtgagat catggtgcag aaggtcatga  12000
ggaggatggc aacgagcgag acacagccgg ttggtgctca caaggacatt ggtagatctg  12060
actgagggcc aggtcggcta ggccttccca ggtgacagga gcccagtgcc ggccttggtg  12120
cacacagcgc gtccttgtgc tttctcagga gagcttcact ggggacactc tgtgatgttt  12180
ttggagggtc atttggtaat gtgttcagga gccaaaaaat atgcataata ttcagtctta  12240
caattacatt ttttgaattt atctcaagga aatcccaggg atctgtgtga agctgcacat  12300
gctgctgctg ctcagtgcgg gactgtttat aatatttgta actcaaatgt ccagaagaac  12360
tgtacactct gtgcatgttt tcagtaagtt catatttgta agaaaaagtg ggtgtgttga  12420
gagacaaatt tttgtgtaca tttacctgga aacaagcagt agtacacata tgcatgcatg  12480
aagtggtgtt ttcctgagtg ttaagattgt gaatgtttta ttatgatcat ttctactttt  12540
```

tctattggaa aatactttgt gtaattaaaa catgaagatg gagctaccat caaaatggtg 12600

<210> SEQ ID NO 246
<211> LENGTH: 4344
<212> TYPE: DNA
<213> ORGANISM: Homo sapiens

<400> SEQUENCE: 246
gttggcagag cagttgtcct ggatggcgga gccttgggtt ccgggggcct gggacctgca 60
actctttcta caagatatca agttattcta gtacaaccat ataaataaat aatacctgaa 120
gtctcagtgt aacatggaca attaacagtg atgacagata aatacagacg catggggatc 180
aaatactagg caaaacgctt tttaaaagtg tatcaggctt ttaagaaaca ctgcaggatc 240
ctgtctatct taatgctgat agagctcagc taaaaattta ggaggttcta gtattcttca 300
tggctgaagc tgagagagtc tgaaaccctg atgcttaagc tccattctag atcatagctc 360
caactccttc aggatataag gaaaagagat tatatttcca caatgataga tctttggttg 420
tacaggtttc ccaatgagtg gatcatgatg accgtattgt agggacttgc catagtatgg 480
ctgcttcccg atctactcgt gttacaagat caacagtggg gttaaacggc ttggatgaat 540
ctttttgtgg tagaacttta aggaatcgta gcattgcgca tcctgaagaa atctcttcta 600
attctcaagt acgatcaaga tcaccaaaga agagaccaga gcctgtgcca attcagaaag 660
gaaataataa tgggagaacc actgatttaa aacagcagag tacccgagaa tcatgggtaa 720
gccctaggaa aagaggactt tcttcttcag aaaaggataa catagaaagg caggctatag 780
aaaattgtga gagaaggcaa acagaacctg tttcaccagt tttaaaaaga attaagcgtt 840
gtcttagatc tgaagcacca aacagttcag aagaagattc tcctataaaa tcagacaagg 900
agtcagtaga acagaggagt acagtagtgg acaatgatgc agattttcaa gggactaaac 960
gagcttgtcg atgtcttata ctggatgatt gtgagaaaag ggaaattaaa aaggtgaatg 1020
tcagtgagga agggccactt aattctgcag tagttgaaga aatcacaggc tatttggctg 1080
tcaatggtgt tgatgacagt gattcagctg ttataaactg tgatgactgt cagcctgatg 1140
ggaacactaa acaaaatagc attggttcct atgtgttaca ggaaaaatca gtagctgaaa 1200
atggggatac ggatacccaa acttcaatgt tccttgatag taggaaggag gacagttata 1260
tagaccataa ggtgccttgc acagattcac aagtgcaggt caagttggag gaccacaaaa 1320
tagtaactgc ctgcttgcct gtggaacatg ttaatcagct gactactgag ccagctacag 1380 ggccctttc tgaaactcag tcatctttaa gggattctga ggaggaagta gatgtggtgg 1440
gagatagcag tgcctcaaaa gagcagtgta aagaaaacac caataacgaa ctggacacaa 1500
gtcttgagag tatgccagcc tccggagaac ctgaaccatc tcctgttcta gactgtgttt 1560
cagctcaaat gatgtcttta tcagaacctc aagaacatcg ttatactctg agaacctcac 1620
cacgaagggc agcccctacc agaggtagtc ccactaaaaa cagttctcct tacagagaaa 1680
atggacaatt tgaggagaat aatcttagtc ctaatgaaac aaatgcaact gttagtgata 1740
atgtaagtca atctcctaca aatcctggtg aaatttctca aaatgaaaaa gggatatgtt 1800
gtgactctca aaataatgga agtgaaggag taagtaaacc accctcagag gcaagactca 1860
atattggaca tttgccatct gccaaagaga gtgccagtca gcacattaca gaagaggaag 1920
atgatgatcc tgatgtttat tactttgaat cagatcatgt ggcactgaaa cacaacaaag 1980
attatcagag actattacag acgattgctg tactcgaggc tcagcgttct caagcagtcc 2040

```
aagaccttga aagtttaggc aggcaccaga gagaagcact gaaaaatccc attggatttg   2100
tggaaaaact ccagaagaag gctgatattg ggcttccata tccacagaga gttgttcaat   2160
tgcctgagat cgtatgggac caatataccc atagccttgg gaattttgaa agagaattta   2220
aaaatcgtaa aagacatact agaagagtta agctagtttt tgataaagta ggtttacctg   2280
ctagaccaaa aagtccttta gatcctaaga aggatggaga gtccctttca tattctatgt   2340
tgcctttgag tgatggtcca gaaggctcaa gcagtcgtcc tcagatgata agaggacgct   2400
tgtgtgatga taccaaacct gaaacattta accagttgtg gactgttgaa gaacagaaaa   2460
agctggaaca gctactcatc aaataccctc ctgaagaagt agaatctcga cgctggcaga   2520
agatagcaga tgaattgggc aacaggacag caaaacaggt tgccagccga gtacagaagt   2580
atttcataaa gctaactaaa gctggcattc cagtaccagg cagaacacca aacttatata   2640
tatactccaa aaagtcttca acaagcagac gacagcaccc tcttaataag catctcttta   2700
agccttccac tttcatgact tcacatgaac cgccagtgta tatggatgaa gatgatgacc   2760
gatcttgttt tcatagccac atgaacactg ctgttgaaga tgcatcagat gacgaaagta   2820
ttcctatcat gtataggaat ttacctgaat ataaagaact attacagttt aaaaagttaa   2880
agaagcagaa acttcagcaa atgcaagctg aaagtggatt tgtgcaacat gtgggcttta   2940
agtgtgataa ctgtggcata gaacccatcc agggtgttcg gtggcattgc caggattgtc   3000
ctccagaaat gtctttggat ttctgtgatt cttgttcaga ctgtctacat gaaacagata   3060
ttcacaagga agatcaccaa ttagaaccta tttataggtc agagacattc ttagacagag   3120
actactgtgt gtctcagggc accagttaca attaccttga cccaaactac tttccagcaa   3180
acagatgaca tggaagagaa catcatttac tagtcctctt caacacatag caatggtatc   3240
attgttaatt atgtgcacag tttggaaaga ttctctgctt tcccagaaat gacactcaca   3300
gcatgagagc ttcctgagtg ttctcgtcaa gtacagctct gcaccgttgt ggctctagat   3360
cactgttcag cagctgaaca ttcctggtga gcaaaggttt ccctggtgaa tttttcacca   3420
ctgcgtttta ggtggtgatc ttaaatgggt gagatggaac gagagcacac attaaagaga   3480
gagtaaattc caaaggtttc aaagaacttg gtcataaata tgataatgag aagacaaagt   3540
atttatatta aaacagttta gtagccttca gttttgtgaa aatagttttc agcacagaaa   3600
ctgacttctt tagacaaagt tttaaccaat gatggtgttt gcttctagga tatacacttt   3660
aaaagaactc actgtcccag tggtggtcat tgatggcctt tagtaaattg gagctgctta   3720
atcatattga tatctaattt cttttaacca caatgaattg tccttaatta ccaacagtga   3780
agcactacag gaggcaactg tggcattgct tccttaacca gctcatggtg tgtgaatgtt   3840
ataaaattgt cactcagata tattttttaa atgtaatgtt atataagatg atcatgtgat   3900
gtgtacaaac tatggtgaaa agtgccagtg gtagtaactg tgtaaagttt ctaattcaca   3960
acattaattc ctttaaaata cacagccttc tgcctctgta tttggagttg tcagtacaac   4020
tcatcaaaga aaactgccta atataaaaat catatatatg gtaataattt ccctcttttg   4080
tagtctgcac aagatccata aaagattgta tttttattac tatttaaaca agtgattaaa   4140
tttagtctgc acagtgagca agggttcaca tgcattcttt tatactgctg gattttgttg   4200
tgcatcattt aaaacatttt gtatgtttct tcttatctgt gtatacagta tgttcttgaa   4260
tgatgttcat ttgtcaggag aactgtgaga aataaactat gtggatactg tctgtttata   4320
ttaaaagaaa aaaaaaaaaa aaaa                                          4344
```

<210> SEQ ID NO 247
<211> LENGTH: 1688
<212> TYPE: DNA
<213> ORGANISM: Homo sapiens

<400> SEQUENCE: 247
gtgtgcgtca cgccgacgac gcgcgaaggg cacacatctt aggacccgga ggacgtccgg 60
cctctgtgag ccgcaacctt tccaagggag tggttgtgtg atcgccatct tagggaaaag 120
atgttctcgt ccgtggcgca cctggcgcgg gcgaacccct tcaacacgcc acatctgcag 180
ctggtgcacg atggtctcgg ggacctccgc agcagctccc cagggcccac gggccagccc 240
cgccgccctc gcaacctggc agccgccgcc gtggaagagc agtatagctg tgactatgga 300
tctggcagat tctttatcct ttgtggactt ggaggaatta ttagctgtgg cacaacacat 360
acagcattgg ttcctctaga tctggttaaa tgcagaatgc aggtggaccc ccaaaagtac 420
aagggcatat ttaacggatt ctcagttaca cttaaagagg atggtgttcg tggtttggct 480
aaaggatggg ctccgacttt ccttggctac tccatgcagg gactctgcaa gtttggcttt 540
tatgaagtct ttaaagtctt gtatagcaat atgcttggag aggagaatac ttatctctgg 600
cgcacatcac tatatttggc tgcctctgcc agtgctgaat tctttgctga cattgccctg 660
gctcctatgg aagctgctaa ggttcgaatt caaacccagc caggttatgc caacactttg 720
agggatgcag ctcccaaaat gtataaggaa gaaggcctaa aagcattcta caagggggtt 780
gctcctctct ggatgagaca gataccatac accatgatga agttcgcctg ctttgaacgt 840
actgttgaag cactgtacaa gtttgtggtt cctaagcccc gcagtgaatg ttcaaagcca 900
gagcagctgg ttgtaacatt tgtagcaggt tacatagctg gagtcttttg tgcaattgtt 960
tctcaccctg ctgattctgt ggtatctgtg ttgaataaag aaaaaggtag cagtgcttct 1020
ctggtcctca agagacttgg atttaaaggt gtatggaagg gactgtttgc ccgtatcatc 1080
atgattggta ccctgactgc actacagtgg tttatctatg actccgtgaa ggtctacttc 1140
agacttcctc gccctcctcc acccgagatg ccagagtctc tgaagaagaa gcttgggtta 1200
actcagtagt tagatcaaag caaatgtgga ctgaatctgc ttgttgatca gtgttgaaga 1260
aagtgcaaaa ggaactttta tatatttgac agtgtaggaa attgtctatt cctgatataa 1320
ttactgtagt actcttgctt aaggcaagag tttcagattt actgttgaaa taaacccaac 1380
tcttcatgat ttgcctgtga cttattttta aaactttttt aaaaaagatt tagctttaaa 1440
atagttggaa agaatgaagt atataagtta aggaaaaaat acaaaactga ccatgaccat 1500
tgttggttga atattccagt tgctattcag aaattgtcat atgtctcaag ttttatcaca 1560
caaagttcct gtatttctag ggaagcagac tttaaatttc taaaaacttg atttaattat 1620
agttaaatat gtgtagtcat ttgtggttat tttggcaagt aaatgtcagt gtatacttac 1680
aaaaaaaa 1688

<210> SEQ ID NO 248
<211> LENGTH: 6994
<212> TYPE: DNA
<213> ORGANISM: Homo sapiens

<400> SEQUENCE: 248
agaagctccc ggccgggggc gcgcacgtag gcacgcagag gccgtcacgt gggtcgccga 60
ggctcgcaag tgcgcgtggc cgtggcggct ggtgtggggt tgagtcagtt gtgggacccg 120
gagctgctga cccagcgggt ggcccaccga accggtgaca cagcggcagg cgttagggct 180

-continued

```
cgggagccgc gagcctggcc tcgtcctaga gctcggccga gccgtcgccg ccgtcgtccc    240
ccgcccccag tcagcaaacc gccgccgcgg gcgcgccccc gctctgcgct gtctctccga    300
tggcgtccgc ctcaggggcc atggcgaagc acgagcagat cctggtcctc gatccgccca    360
cagacctcaa attcaaaggc cccttcacag atgtagtcac tacaaatctt aaattgcgaa    420
atccatcgga tagaaaagtg tgtttcaaag tgaagactac agcacctcgc cggtactgtg    480
tgaggcccaa cagtggaatt attgacccag ggtcaactgt gactgtttca gtaatgctac    540
agccctttga ctatgatccg aatgaaaaga gtaaacacaa gtttatggta cagacaattt    600
ttgctccacc aaacacttca gatatggaag ctgtgtggaa agaggcaaaa cctgatgaat    660
taatggattc caaattgaga tgcgtatttg aaatgcccaa tgaaaatgat aaattgggta    720
taactccacc agggaatgct ccgactgtca cttcaatgag cagcatcaac aacacagttg    780
caacacctgc cagttatcac acgaaggatg accccagggg actcagtgtg ttgaaacagg    840
agaaacagaa gaatgatatg gaacctagca aagctgttcc actgaatgca tctaagcaag    900
atggacctat gccaaaacca cacagtgttt cacttaatga taccgaaaca aggaaactaa    960
tggaagagtg taaaagactt cagggagaaa tgatgaagct atcagaagaa aatcggcacc   1020
tgagagatga aggtttaagg ctcagaaagg tagcacattc ggataaacct ggatcaacct   1080
caactgcatc cttcagagat aatgtcacca gtcctcttcc ttcacttctt gttgtaattg   1140
cagccatttt cattggattc tttctaggga aattcatctt gtagagtgaa gcatgcagag   1200
tgctgtttct tttttttttt ttctcttgac cagaaaaaga tttgtttacc taccatttca   1260
ttggtagtat ggcccacggt gaccattttt ttgtgtgtac agcgtcatat aggctttgcc   1320
tttaatgatc tcttacggtt agaaaacaca ataaaaacaa actgttcggc tactggacag   1380
gttgtatatt accagatcat cactagcaga tgtcagttgc acattgagtc ctttatgaaa   1440
ttcataaata aagaattgtt ctttctttgt ggttttaata agagttcaag aattgttcag   1500
agtcttgtaa atgttatttt aataatccct ttaaatttta tctgttgctg ttacctcttg   1560
aaatatgatt tatttagatt gctaatccca ctcattcagg aaatgccaag aggtattcct   1620
tggggaaatg gtgcctctta cagtgtaaat ttttcctcct ttacctttgc taatatcatg   1680
gcagaatttt tcttatccct tgtgaggcag ttgttgactg agtttttcat ccttacaatc   1740
ctgtcccatg gtatttaaca taaaaaaaaa taaaactgtt aacagattct tgctcgatag   1800
cttgtttgtg tctgtcgtgt tattagaggg aactccacta tatatggtca cttgaaatta   1860
tgatgcaaag gtttctcttg cattgaaacc ctcttggata ttacagtatt tttaattgaa   1920
agtcctaatt ctgttaagga aaggagttga ttaaatttta aggtaccact ggtattttgg   1980
gagattataa tcagtttgtt ttcaagataa tagaaaataa ggtccatgag aatagaagtt   2040
atgtgatttc agtgagttga tgtgtacagc atggctgtgc tccatctgat ttaccccatt   2100
cttaagttct gagagtatgt tctcaaggaa gatttaactc tctttggttt taaattactt   2160
tttaaccagc ctaataaata agtcttacta cttttcataa tatttcataa tagttaaaag   2220
taggtgtttt tttcgtgctc aatttggcac tcaaaataat gttcattatg gaagtttggt   2280
aatactgagc aagcctgtgg aattttcttt atgaaaaatg attttagcct ttgcaaatgt   2340
taaccatgtg aaacacattt tcagtataag tatgcgttac agggtttgat actttcctgc   2400
acttaggttt gtcctattct tcatttattc atactaggat agaaaatttt ggaatcagaa   2460
aatagatcca gtgtttagct acatacaatc tagtacaagt gaatttttat tcttaaacat   2520
aggtgtgttg gctctttttt taaaagatgc gctctacctg aaaaggaaat tggattttag   2580
```

aactggatgt ggtgcagtga agtattttag gcccaggtct gtgtacacat tttatagaag 2640
aatgaagtac tctgaagtat tttggttgcc ttttcatttc aactgtgttt tgaatttgtc 2700
agatcacaca tatattgtgt tattgggcgc tgtggtatct tttataaaac ctcttgcttg 2760
tgtgcaaaag ttcctaaaag gaaacacaag taatgcctat ccattactag catgctatgc 2820
tgcatgcttt actgccattg ctgtatgctt tactgtcttt gtaaaaatcc ccctctcccc 2880
ttttctggta actggaaaag catgctaaaa atagtcttat attttcaccc cataaatgca 2940
gaatcagtaa ttccttggct taaagctctt atataatcaa tattattggt ggtaaatacc 3000
aagtttggta tctcatagct atcttttttt aaagaaatta agttcttgaa aatttagcca 3060
aatcccgttt tatgggaatg ctctttagaa ttcattttgt tcagcccctt tgttctatgg 3120
ttgagaaatc tgaggcctta cgaaggttaa gagaactttc cccgtgtctc acaggtaggt 3180
agaggcagag ctggaactag atatctggtc tgttgactct agctcagtgt cttctggtaa 3240
ctgttgaaaa ttgtcttagt ttgagagatg gctgaaataa tgaacataaa atgctattta 3300
taataacaag tatatgtgaa atttcttatt gtaagactac taccggctta ctgttgaata 3360
gtttggttat agtgtttagg ctagaaatgc ctcccacatt ggtaataaac attacaaaat 3420
acaatgtatt tttaggtagg cattttataa aatgcattat gccatggttg cttttgagat 3480
agattgtagt ctgggtagca tctttaaaat gtatgtgggc ttaactgttg ttcatatcag 3540
gagatgctct gattgtatag gtgagactct gtttctgtta tttttaattg ctgtatgaaa 3600
tgtgatcaga ttattttact accaacagtt atagtttgaa agtccaactg tattaattga 3660
ctgataatat gataaatatag agattaaatt gtttgtcttc attccttata tgtttagaag 3720
tttttgcttt gtctgcctgc ttacttgtat atgtaagcat gagggaaata cactgttgct 3780
aatactgaaa ttacaatcaa gtaactaagg ccttgagttc atatgtgaca ctgaatgcac 3840
tagcttcctt cgttctataa ctaatgtacc ttaacttccc ccattcttat atttacaaga 3900
agctaagtca ttatgttctg agtgtgtggt atgttccctt aaaaaaaaat gacacttgga 3960
agaaaaatgt atgaaattca gaaattccga tcaaagaaaa gtaattcttt cttttttttt 4020
ttgagacaga gtcttgcttt gttgcccagg ctggagggca gtggtgtgat ctcacctcac 4080
tgcagcttcc gcctcctggg ttcaagtgat tctcatggct cagccgcctg agtagctggg 4140
attacaggtg tgagccaaca agcccggcta atttttgtat ttttagtaga gacaaggttt 4200
caccatgttg gtcaggctgg gctcaaactc ctgaatccgc ctgcctcggc ctcccaaagt 4260
gctgggatta caggtgtgag ctgccgcacc cagccaagaa aaataatact cttaaatact 4320
tagatgttca cctaaagttg atattatttg gtatgggaat tacttttgaa ctgtaatctt 4380
tcagattaca ccactttgaa aacaagtttt aacagtaggg taaaaatata gtttttgagg 4440
gtattcccaa cttgtgatct tctaccactt tagagacatt caagtaatag ttttcttaga 4500
gctttgcaca ttcctattca ctgagatttt aaaaatttca cctttattcg agggaaggat 4560
caatgcttat taccatttgg aaaaacgaag atcagaaggt aaatgatctt tattttctag 4620
ctttaaaggg aaattaaacc attcatgaat aaactttaaa aatgtgaagt gtccttttcc 4680
ttttcacaat acaaaaaaaa tttcaacaga ttgtgtggtt tgtgcattta tatcctgtta 4740
agcattaata gctaatcact gggacttgaa ttctgatggc agatagtctc ttgcttagtg 4800
agatggagtt aactattttt tagtaggaag tgagaacagc tgattttcat gccacgtttc 4860
atagccccac ttttggtaga ctaccaccac gcttcttcgc gtaagcagtg gcatcttggg 4920

```
aatgaatgcc cagccgctcg tgggttggtg caaagaagta taaacatata tcactaagga   4980
aaaagaaagt ttgtcttgcc cttctgacac agtgtgtgca cttcaggcaa tttttggaaa   5040
atataaaaaa ttccaaattc tgcctttcag cagcatcaat tgctaggaac atttcattca   5100
tttccctgta atattaatgt tctttaagca taatcactaa ttataagttg tatcctattt   5160
ttttccagct taatttctgt ggtttattga aaaccaagta taaatgtgac taaaagcatt   5220
ttgctttgtt tttatagtta actttcttaa ggttatggac attttataat gtaacatttg   5280
attggcctgg cctcttgaca attcccttct agttatgcat atcctcctgt tgccacattt   5340
cttgttttaa aactcagttt cttgttttcc agttgttgct atgtataaca cccatcttga   5400
aagagagtat ataggaagtt attcagataa cttttgtagt agtgatattc aactatagca   5460
gtaccttaac tcatgatgag cttaggaaca taaaagataa ttgttgcttg aatagcaccc   5520
ccagagatac tgacctaatt ggtctggggt ggagatctgg catggtagtt tttttcaagc   5580
tccaatcatc ggccagacag ttgctttatg taggttttta aatgccaaag gcagatatga   5640
agtagattta attaagactt gacttcagca atacagggga acttaaaata cttatttttc   5700
tttaaactgc aggagtcact gttaggtatt gcttaaaaaa aattgcataa aagctttgct   5760
tgtcaagtta ggattgctgg aataccacta aagatttttg acttgtgaat aaatgagctg   5820
tcatcgcaaa aaggcgattt gagaaatgtg ggcttcagta ttaattgcca ttttgctgac   5880
acccagtgta cctacctacc tgagaaattt attttgtcca tcatgtattt ctcaaagcaa   5940
aaggtggttt tcaagtataa tgtcgttttc aacatgctta ttacttagtt ttacgtcagc   6000
tcatttcatc atcattgata acttgtgaaa tacttatctc catcctatgg aataggggag   6060
acgggtttag acaggttcaa ttagctcaag tctacacagc tgaagtagca gagaaagtgg   6120
gatctagatg gtctgatcct agtgatctac catatgaagg acatagtttg tgtcctggtc   6180
caagtcaaat attgactcct cacaaacagt aagtatggca attttgtgat gcctttgatt   6240
ccactttaca tggagtacta ttatttgtga aatgtcttta agatttttgg tcttaaattt   6300
ttgaagactg ctttcccccct ttatctccca gaaaattgag aagaagtaaa ctcctgccca   6360
ctaacaatct cagtccgtga acaaaaccaa catgaacatt cctaaacaag agtgtgtgtt   6420
actctaagaa gaaggctata gaatttatgg aaatggctta tgtaacctac aagactggag   6480
aacagaatgt gactggcctt ttctaatggt cctttaagat ttaatgatta aagcaagagt   6540
tttttataat tgactttgtg gtctaaattc ttgatactgt ttataattct acaaagaaca   6600
aaaattgtta tgtactatag gcacttaaga accctgagga aaaataatac aatgtgtgtg   6660
tgtgagagag agagtgagtt actgacattg ttccaaaaaa aaaaaaaaaa aaaaaaaaaa   6720
tgtggagggt tgaaatggta aggaattgga atcttttgta ttttcgagca ataagaattc   6780
ctattcttgt ttcaaataga ggtttgttag gaattacagt tgtggggagc aaactttctt   6840
ttttgtgctg ttttaattca aaatgtatat ccttaattgt atataatatg tagataaata   6900
tatgagggta ttaagctact ttgaattaaa tttaaggata tatttcacat gaaaacaaat   6960
acaaacgaga atcaaaataa agttttgcaa agta                               6994
```

<210> SEQ ID NO 249
<211> LENGTH: 2953
<212> TYPE: DNA
<213> ORGANISM: Homo sapiens

<400> SEQUENCE: 249

```
atatagagac gtttccgcct cctgcttgaa actaacccct ctttttctcc aaaggagtgc     60
```

-continued

```
ttgtggagat cggatctttt ctccagcaat tgggggaaag aaggcttttt ctctgaattc    120
gcttagtgta accagcggcg tatatttttt aggcgccttt tcgaaaacct agtagttaat    180
attcatttgt ttaaatctta ttttattttt aagctcaaac tgcttaagaa taccttaatt    240
ccttaaagtg aaataatttt ttgcaaaggg gtttcctcga tttggagctt tttttttctt    300
ccaccgtcat ttctaactct taaaaccaac tcagttccat catggtgatg ttcaagaaga    360
tcaagtcttt tgaggtggtc tttaacgacc ctgaaaaggt gtacggcagt ggcgagaagg    420
tggctggccg ggtgatagtg gaggtgtgtg aagttactcg tgtcaaagcc gttaggatcc    480
tggcttgcgg agtggctaaa gtgctttgga tgcagggatc ccagcagtgc aaacagactt    540
cggagtacct gcgctatgaa gacacgcttc ttctggaaga ccagccaaca ggtgagaatg    600
agatggtgat catgagacct ggaaacaaat atgagtacaa gttcggcttt gagcttcctc    660
aggggcctct gggaacatcc ttcaaaggaa aatatgggtg tgtagactac tgggtgaagg    720
cttttcttga ccgcccgagc cagccaactc aagagacaaa gaaaaacttt gaagtagtgg    780
atctggtgga tgtcaatacc cctgatttaa tggcacctgt gtctgctaaa aaagaaaaga    840
aagtttcctg catgttcatt cctgatgggc gggtgtctgt ctctgctcga attgacagaa    900
aaggattctg tgaaggtgat gagatttcca tccatgctga ctttgagaat acatgttccc    960
gaattgtggt ccccaaagct gccattgtgg cccgccacac ttaccttgcc aatggccaga   1020
ccaaggtgct gactcagaag ttgtcatcag tcagaggcaa tcatattatc tcagggacat   1080
gcgcatcatg gcgtggcaag agccttcggg ttcagaagat caggccttct atcctgggct   1140
gcaacatcct tcgagttgaa tattccttac tgatctatgt tagcgttcct ggatccaaga   1200
aggtcatcct tgacctgccc ctggtaattg gcagcagatc aggtctaagc agcagaacat   1260
ccagcatggc cagccgaacc agctctgaga tgagttgggt agatctgaac atccctgata   1320
ccccagaagc tcctccctgc tatatggatg tcattcctga agatcaccga ttggagagcc   1380
caaccactcc tctgctagat gacatggatg gctctcaaga cagccctatc tttatgtatg   1440
cccctgagtt caagttcatg ccaccaccga cttatactga ggtggatccc tgcatcctca   1500
acaacaatgt gcagtgagca tgtggaagaa aagaagcagc tttacctact tgtttctttt   1560
tgtctctctt cctggacact cactttttca gagactcaac agtctctgca atggagtgtg   1620
ggtccacctt agcctctgac ttcctaatgt aggaggtggt cagcaggcaa tctcctgggc   1680
cttaaaggat gcggactcat cctcagccag cgcccatgtt gtgatacagg ggtgtttgtt   1740
ggatgggttt aaaaataact agaaaaactc aggcccatcc attttctcag atctccttga   1800
aaattgaggc cttttcgata gtttcgggtc aggtaaaaat ggcctcctgg cgtaagcttt   1860
tcaaggtttt ttggaggctt tttgtaaatt gtgataggaa ctttggacct tgaacttatg   1920
tatcatgtgg agaagagcca atttaacaaa ctaggaagat gaaaagggaa attgtggcca   1980
aaactttggg aaaaggaggt tcttaaaatc agtgtttccc ctttgtgcac ttgtagaaaa   2040
aaaagaaaaa ccttctagag ctgatttgat ggacaatgga gagagctttc cctgtgatta   2100
taaaaaagga agctagctgc tctacggtca tctttgctta agagtatact ttaacctggc   2160
ttttaaagca gtagtaactg ccccaccaaa ggtcttaaaa gccatttttg gagcctattg   2220
cactgtgttc tcctactgca aatattttca tatgggagga tggttttctc ttcatgtaag   2280
tccttggaat tgattctaag gtgatgttct tagcacttta attcctgtca aatttttttgt   2340
tctccccttc tgccatctta aatgtaagct gaaactggtc tactgtgtct ctagggttaa   2400
```

```
gccaaaagac aaaaaaaatt ttactacttt tgagattgcc ccaatgtaca gaattatata   2460
attctaacgc ttaaatcatg tgaaagggtt gctgctgtca gccttgccca ctgtgacttc   2520
aaacccaagg aggaactctt gatcaagatg ccgaaccctg tgttcagaac ctccaaatac   2580
tgccatgaga aactagaggg caggtcttca taaaagccct ttgaaccccc ttcctgccct   2640
gtgttaggag atagggatat tggcccctca ctgcagctgc cagcacttgg tcagtcactc   2700
tcagccatag cactttgttc actgtcctgt gtcagagcac tgagctccac ccttttctga   2760
gagttattac agccagaaag tgtgggctga agatggttgg tttcatgttt ttgtattatg   2820
tatctttttg tatggtaaag actatatttt gtacttaacc agatatattt ttaccccaga   2880
tggggatatt ctttgtaaaa aatgaaaata aagttttttt aatggaaaaa aaaaaaaaaa   2940
aaaaaaaaaa aaa                                                      2953
```

<210> SEQ ID NO 250
<211> LENGTH: 4454
<212> TYPE: DNA
<213> ORGANISM: Homo sapiens

<400> SEQUENCE: 250

```
gacgctcgag gggcgctcgg ctagtcccgc cagagcgcga gccgccagcc cgtaacggtc     60
gccagtgtga ggggcgggag ggaaagaaga ggggtttaaa ttagattttt taaaacacag    120
agcaagcgcc agaggcgtcg gcatcccagg tgtcgccgct tcctgctgca cagggctcgg    180
cgtacaggtc cctccctcct caagcccccct cccccttctcc cgccctaccc tctggggctc    240
tgcggcgctt aagaggcggc cgcagcggcg gatccggcgg ctgctgcagc ccgggcggct    300
gccgagaagg agggagggga aacacaaagc cggctacgcg ctgcgagata acaagagtaa    360
tccacagact taaaacatga gctcagatgc cagccaaggc gtgattacca ctcctcctcc    420
tcccagcatg cctcacaaag agagatattt tgaccgcatc aatgaaaatg acccagaata    480
cattagggag aggaacatgt ctcctgatct acgacaagac ttcaacatga tggagcagag    540
gaaacgagtt actcagatcc tgcaaagtcc tgcctttcgg gaagacttgg aatgccttat    600
tcaagaacag atgaagaaag gccacaaccc aactggatta ctagcattac agcagattgc    660
agattacatc atggccaatt ctttctcggg tttttcttca cctcctctca gtcttggcat    720
ggtcacacct atcaatgacc ttcctggtgc agatacatcc tcatatgtga agggagaaaa    780
acttactcgc tgtaaacttg ccagcctgta cagacttgta gacttgtttg gatgggcaca    840
cctggcaaat acctatatct cagtaagaat aagtaaggag caagaccaca ttataataat    900
tcccagaggc ctatcttttt ctgaagctac agcctccaat ttggtgaaag tcaatataat    960
aggagaagtg gttgaccagg gaagtaccaa tttgaaaatt gaccatacag gattcagtcc   1020
ccatgctgca atctattcaa cacgtcctga tgttaagtgt gtgatacaca tccataccct   1080
tgcaacagca gctgtatcct ccatgaaatg tgggatcctt ccaatttctc aagagtctct   1140
tcttctggga gatgttgcct attatgacta ccaagggtca cttgaagaac aggaggagag   1200
aattcaactg cagaaggttc tgggaccaag ttgtaaggtg ctggtactca ggaatcatgg   1260
tgtggttgca cttggagaaa cattagagga ggcttttcat tatattttta atgtgcaact   1320
agcctgtgag attcaggtgc aggccctagc aggtgcaggt ggagtagaca atctccatgt   1380
actggacttt cagaagtata aagctttcac ttacactgta gcagcgtctg gtggaggagg   1440
tgtgaatatg ggttcccatc aaaaatggaa ggttggcgaa attgagtttg aagggcttat   1500
gaggactctg gacaacttgg ggtatagaac aggctatgct tacaggcatc ctctcattcg   1560
```

-continued

```
agagaagcct aggcacaaga gtgatgtgga aatcccagca actgtgactg ctttttcctt   1620
tgaagacgat acagtgccac tctctcctct caaatacatg gcacagaggc aacagcgtga   1680
aaaaacaaga tggctgaact caccaaatac ttacatgaaa gtgaatgtgc ctgaggagtc   1740
tcggaacgga gaaaccagtc cccgaaccaa aatcacgtgg atgaaagcag aagactcatc   1800
taaagttagt ggtggaacac ctatcaaaat tgaagatcca aatcagtttg ttcctttaaa   1860
cacaaacccg aatgaggtac tagaaaagag aaataagatt cgggaacaaa atcgatatga   1920
cttgaaaaca gcaggaccac aatctcagtt gcttgctgga attgttgtgg ataagccacc   1980
ttctactatg caatttgaag atgatgatca tggcccacca gctcctccta acccatttag   2040
tcatctcaca gaaggagaac ttgaagagta taagaggaca atcgaacgta aacaacaagg   2100
cctagaagat gctgagcagg aattactctc agatgacgct tcatctgttt cacaaattca   2160
gtctcaaact cagtcaccgc aaaatgtccc tgaaaaatta gaagaaaacc atgagctgtt   2220
ttccaagagc ttcatctcca tggaagtgcc tgtcatggta gtaaatggca aggatgatat   2280
gcatgatgtt gaagatgagc ttgctaagcg agtgagtagg ttaagcacaa gtacaaccat   2340
agaaaacatc gagattacta ttaagtctcc agagaaaatc gaagaagtcc tgtcacctga   2400
aggctcccct tcaaaatcgc catccaagaa aaagaagaaa ttccgcactc cttcttttct   2460
gaaaaagaac aaaaaaaagg agaaagttga ggcctaaata aagtcttttt ataattatta   2520
ttataacaat gtgacattgc acatctaaat accacattta agttgatcat taatatgcaa   2580
tggtagatca gattggggga tgtagcaaac tggactttaa gaactggaaa gaggttttac   2640
aaaagaaaaa ctttcagatt catctctcat tttatatgtc cagaaatggc tttgaatttt   2700
aagcaattac tagttttaat tagctctgcc ctcatgaagt attattataa ttcaccataa   2760
acagctatct gtctgaatta cttcaggcct tctccataat atctgttaga aagaaattgc   2820
cagtgagcaa gtgagaattt ttatttctca atacctgctt cacttgataa tcatattata   2880
attttttatc atgattattg actatatttt tggagtccca ttgtttcagt gggcattaac   2940
agaatgcttt aaaaacttct aagacaagaa tctatagcat tagtatacac tggcacataa   3000
ttttttaaaa agttttaaga aaagattcat ttggaatttt attcacagta taaaatttcc   3060
tcacctgaag taactttgtt tgccaaaaaa gttgttttaa taaactataa tttttgaaaa   3120
cttccttttt tattagttta gaaagcccct tatttttcaa caaaggggat tttgtacaca   3180
taacatgggt tatttagttt aactctggca aaaaaaaaaa aaaaaatttt gtatgttgat   3240
gtttgtatac cgttcagtat aaaagtgtcc taagcatatt agccaatctt ttcacagtag   3300
agcatactta aggctgcttg gtactgagta tacttaaata taactccaga atccagggac   3360
ttggtgttaa aacaggatta gagcatgtaa aggtacatct agattcatat ttgaatctta   3420
aactgtattt ttctcttagt attgctaatg agtaaagaaa agtctcataa ggtagccaaa   3480
tgaaaaagaa tgaaagggaa agtgaaaaat taaggggaca aaagatggga tgtgaaaaga   3540
agaattctag tttgatggtg actcatattc acgataggat acaaagtgtg atttgttgga   3600
aacatgtccc aaatttctaa aattctgctt ctctgccaaa agcaatgtct ttcttggttg   3660
atatttgagt tttaaaaggg tcaaatcttt ctaatttttt gtatctttag agggcagcac   3720
tagaagaaat cagcaggtct aatcccacca gtaagaaaac taccacttct tgatttttac   3780
agatttaaaa aaatcttttc agtgaccttt ctttttaatg taaatacaaa tttaaaccta   3840
ggcttaatat aggcgtttcc cctttcaccc aagtgatgtc acagttcgat gcaaaatcaa   3900
```

```
tgatccagaa tgatcgtggg taaaaataac tcaaagtgtt tcttaagggt gagttggcat   3960

gcaaaaaatt acattgatta cagtgtgttt tggagctggc tctgtttgtg tgcatatgat   4020

aatgcagagt tgagccagag cctggaaatg tcattctaga tctcactaac tactggaatc   4080

agtgttttaa tctcttggtg gaaactttca gttgcttaac tctctattgg aagatttttt   4140

taatgttcta catcatttat gttgtattac aatgtatgta gaaatagtaa cctgtgaact   4200

atgcttttcc ataacttttt aaaaatatat atatctaaat gaatgcaatg tgcataaata   4260

ttttttaaac ataacagtga actattgcac cttttgctaa tgcctctatt tacttgcttt   4320

ggcataaaga atgagccaat gaacctctgt gtcctgtgga aaaatgtata aatgttatct   4380

gatattgctc ttagatgtaa tgctaattaa tgttaaatca caaataaaca gtattttaaa   4440

tataaaaaaa aaaa                                                     4454


<210> SEQ ID NO 251
<211> LENGTH: 2182
<212> TYPE: DNA
<213> ORGANISM: Homo sapiens

<400> SEQUENCE: 251

cggaccctcc cgcggccgac tggaggcccg gagcaggggc ggagtttccg gcggcagcgc     60

cactcgggcg tcgggtgacg ctaggcggac ggaccatcat gtgacacgga agtagctccg    120

aacaggaaga ggacgaaaaa aataaccgtc cgcgacgccg agacaaaccg gacccgcaac    180

caccatgaac agcaaaggtc aatatccaac acagccaacc taccctgtgc agcctcctgg    240

gaatccagta taccctcaga ccttgcatct tcctcaggct ccaccctata ccgatgctcc    300

acctgcctac tcagagctct atcgtccgag ctttgtgcac ccaggggctg ccacagtccc    360

caccatgtca gccgcatttc ctggagcctc tctgtatctt cccatggccc agtctgtggc    420

tgttgggcct ttaggttcca caatccccat ggcttattat ccagtcggtc ccatctatcc    480

acctggctcc acagtgctgg tggaaggagg gtatgatgca ggtgccagat ttggagctgg    540

ggctactgct ggcaacattc ctcctccacc tcctggatgc cctcccaatg ctgctcagct    600

tgcagtcatg cagggagcca acgtcctcgt aactcagcgg aaggggaact tcttcatggg    660

tggttcagat ggtggctaca ccatctggtg aggaaccaag gccacctctg tgccgggaaa    720

gacatcacat accttcagca cttctcacaa tgtaactgct ttagtcatat taacctgaag    780

ttgcagttta gacacatgtt gttggggtgt ctttctggtg cccaaacttt caggcacttt    840

tcaaatttaa taaggaacca tgtaatggta gcagtacctc cctaaagcat tttgaggtag    900

gggaggtatc cattcataaa atgaatgtgg gtgaagccgc cctaaggatt ttcctttaat    960

ttctctggag taatactgta ccatactggt ctttgctttt agtaataaaa catcaaatta   1020

ggtttggagg gaactttgat cttcctaaga attaaagttg ccaaattatt ctgattggtc   1080

tttaatctcc tttaagtctt tgatatatat tacttgttat aaatggaacg cattagttgt   1140

ctgccttttc ctttccatcc cttgccccac ccatcccatc tccaacccta gtcttccatt   1200

tcctcccgcc agtctccatt gaatcaatgg tgcaggacag aaagccagtc agactaattt   1260

ccttctttcc tcgcacttct ccccactcgt catcttttaa ctagtgtttc acaaggatcc   1320

tctgaaaccc tctctgtgcc ccaagtacag atgccattac ttctgctttc gtatctcctc   1380

aggcaaaagt ggagggtgcc ttatgggccc tcctcatagg ttgtctctgc atacacgaac   1440

ctaacccaaa tttgctttgg tgccagaaaa actgagctat gtttgaacaa agatgtcgtg   1500

caaactgtac tgtgaacaac agttggttta aaatatgagg ggcaaggagg aggatgcatt   1560
```

tcaaaagctt gattgatgtg ttcagagcta aattaagagg agttttcaga tcaaaaactg 1620
gttaccattt tttgtcagag tgtctgatgc ggccactcat tcggctcccc agaattccta 1680
gactgggtta atagggtcat attgtgaatg tctcactaca aaatgacttg agtccagtga 1740
aatctcatta gggtttaaga atatttcagg gatccttaat gttttgattt ttgttttctg 1800
aaattggatt ttattttatt ttatcttata atttcagttc atctaaattg tgtgttctgt 1860
acatgtgatg tttgactgta ccattgactg ttatggaagt tcagcgttgt atgtctctct 1920
ctacactgtg gtgcacttaa cttgtggaat ttttatacta aaaatgtaga ataaagacta 1980
ttttgaagat ttgaataaag tgatgaagtt gcattacacc tcactgcaag gattctttac 2040
ttagcttgtt tttagatttc ttctatatat attttattta tatcccatct agaattcagc 2100
taggtgctgc tgctgctctg tttcctttga tgacgctttg aaataaaggc aggagtacaa 2160
gcctaaaaaa aaaaaaaaaa aa 2182

<210> SEQ ID NO 252
<211> LENGTH: 2123
<212> TYPE: DNA
<213> ORGANISM: Homo sapiens

<400> SEQUENCE: 252
gcgcgccgcc gggccgcgcg ggcgcgccgc ttccgcttaa ataacggcgg gggaggccgc 60
ggtcggtctc agtcgccgct gccagctctc gcactctgtt cttccgccgc tccgccgtcg 120
cgtttctctg ccggtgagcg ccccgccccg gggcctgagc tggacgtcgc aggcctgcgc 180
cccccgaccc cggctggccc cgcttccagc tgccgaggcc tcgtcgcgcc ttccccggga 240
acaaaaggcg gggtcgcaat ggaagaagag atcgccgcgc tggtcattga caatggctcc 300
ggcatgtgca aagctggttt tgctggggac gacgctcccc gagccgtgtt tccttccatc 360
gtcgggcgcc ccagacacca gggcgtcatg gtgggcatgg gccagaagga ctcctacgtg 420
ggcgacgagg cccagagcaa gcgtggcatc ctgaccctga agtaccccat tgagcatggc 480
atcgtcacca actgggacga catggagaag atctggcacc acaccttcta caacgagctg 540
cgcgtggccc cggaggagca cccagtgctg ctgaccgagg ccccccctgaa ccccaaggcc 600 aacagagaga agatgactca gattatgttt gagaccttca acaccccggc catgtacgtg 660
gccatccagg ccgtgctgtc cctctacgcc tctgggcgca ccactggcat tgtcatggac 720
tctggagacg gggtcaccca cacggtgccc atctacgagg gctacgccct cccccacgcc 780
atcctgcgtc tggacctggc tggccgggac ctgaccgact acctcatgaa gatcctcact 840
gagcgaggct acagcttcac caccacggcc gagcgggaaa tcgtgcgcga catcaaggag 900
aagctgtgct acgtcgccct ggacttcgag caggagatgg ccaccgccgc atcctcctct 960
tctctggaga agagctacga gctgcccgat ggccaggtca tcaccattgg caatgagcgg 1020
ttccggtgtc cggaggcgct gttccagcct tccttcctgg gtatggaatc ttgcggcatc 1080
cacgagacca ccttcaactc catcatgaag tgtgacgtgg acatccgcaa agacctgtac 1140
gccaacacgg tgctgtcggg cggcaccacc atgtacccgg gcattgccga caggatgcag 1200
aaggagatca ccgccctggc gcccagcacc atgaagatca agatcatcgc accccccagag 1260 cgcaagtact cggtgtggat cggtggctcc atcctggcct cactgtccac cttccagcag 1320
atgtggatta gcaagcagga gtacgacgag tcgggcccct ccatcgtcca ccgcaaatgc 1380
ttctaaacgg actcagcaga tgcgtagcat ttgctgcatg ggttaattga gaatagaaat 1440

-continued

```
ttgcccctgg caaatgcaca cacctcatgc tagcctcacg aaactggaat aagccttcga   1500

aaagaaattg tccttgaagc ttgtatctga tatcagcact ggattgtaga acttgttgct   1560

gattttgacc ttgtattgaa gttaactgtt ccccttggta tttgtttaat accctgtaca   1620

tatctttgag ttcaaccttt agtacgtgtg gcttggtcac ttcgtggcta aggtaagaac   1680

gtgcttgtgg aagacaagtc tgtggcttgg tgagtctgtg tggccagcag cctctgatct   1740

gtgcagggta ttaacgtgtc agggctgagt gttctgggat ttctctagag gctggcaaga   1800

accagttgtt ttgtcttgcg ggtctgtcag ggttggaaag tccaagccgt aggacccagt   1860

ttcctttctt agctgatgtc tttggccaga acaccgtggg ctgttacttg ctttgagttg   1920

gaagcggttt gcatttacgc ctgtaaatgt attcattctt aatttatgta aggttttttt   1980

tgtacgcaat tctcgattct ttgaagagat gacaacaaat tttggttttc tactgttatg   2040

tgagaacatt aggccccagc aacacgtcat tgtgtaagga aaaataaaag tgctgccgta   2100

accaaaaaaa aaaaaaaaaa aaa                                           2123
```